United States Patent
Lalonde et al.

(10) Patent No.: US 9,681,664 B2
(45) Date of Patent: *Jun. 20, 2017

(54) MACROCYCLIC PICOLINAMIDES AS FUNGICIDES

(71) Applicant: Dow Agrosciences LLC, Indianapolis, IN (US)

(72) Inventors: Rebecca Lalonde, Portland, OR (US); Kevin G. Meyer, Zionsville, IN (US); Fangzheng Li, Carmel, IN (US); Jeremy Wilmot, Zionsville, IN (US); Karla Bravo-Altamirano, Carmel, IN (US); Chenglin Yao, Westfield, IN (US); Iain O'Callaghan, County Cork (IE); Jessica Herrick, Zionsville, IN (US); Kyle DeKorver, Lafayette, IN (US); Yu Lu, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 117 days.

This patent is subject to a terminal disclaimer.

(21) Appl. No.: 14/142,183

(22) Filed: Dec. 27, 2013

(65) Prior Publication Data

US 2014/0187588 A1 Jul. 3, 2014

Related U.S. Application Data

(60) Provisional application No. 61/747,723, filed on Dec. 31, 2012.

(51) Int. Cl.

| C07D 405/12 | (2006.01) |
|---|---|
| C07F 7/10 | (2006.01) |
| A01N 53/00 | (2006.01) |
| A01N 43/22 | (2006.01) |
| A01N 43/40 | (2006.01) |
| C07D 313/00 | (2006.01) |

(52) U.S. Cl.
CPC ............ *A01N 53/00* (2013.01); *A01N 43/22* (2013.01); *A01N 43/40* (2013.01); *C07D 313/00* (2013.01); *C07D 405/12* (2013.01)

(58) Field of Classification Search
CPC .................. C07D 405/12; C07F 7/10
USPC ..................... 546/14, 281.7; 514/63, 336
See application file for complete search history.

(56) References Cited

U.S. PATENT DOCUMENTS

| 6,355,660 B1 | 3/2002 | Ricks et al. |
| 6,521,622 B1 | 2/2003 | Ricks et al. |
| 6,706,740 B2 | 3/2004 | Ricks et al. |
| 6,861,390 B2 | 3/2005 | Meyer et al. |
| 6,927,225 B2 | 8/2005 | Ricks |
| 7,034,035 B2 | 4/2006 | Ricks |
| 7,183,278 B1 | 2/2007 | Imamura |
| 7,250,389 B1 | 7/2007 | Sakanaka et al. |
| 8,785,479 B2 | 7/2014 | Meyer |
| 8,835,462 B2 | 9/2014 | Meyer |
| 8,883,811 B2 | 11/2014 | Owen |
| 9,265,253 B2 | 2/2016 | Li et al. |
| 2002/0177578 A1 | 11/2002 | Ricks |
| 2003/0018012 A1 | 1/2003 | Ricks |
| 2003/0018052 A1 | 1/2003 | Ricks |
| 2003/0022902 A1 | 1/2003 | Ricks |
| 2003/0022903 A1 | 1/2003 | Ricks et al. |
| 2004/0034025 A1 | 2/2004 | Ricks |
| 2004/0048864 A1 | 3/2004 | Ricks |
| 2004/0171838 A1 | 9/2004 | Meyer et al. |
| 2004/0186296 A1 | 9/2004 | Nyaz |
| 2004/0192924 A1 | 9/2004 | Meyer et al. |
| 2005/0239873 A1 | 10/2005 | Hockenbery |
| 2006/0040995 A1 | 2/2006 | Bacque et al. |
| 2007/0060579 A1 | 3/2007 | Wachendorff-Neumann et al. |
| 2007/0066629 A1 | 3/2007 | Blasco et al. |
| 2008/0070985 A1 | 3/2008 | Derrer et al. |
| 2008/0293798 A1 | 11/2008 | Dietz |
| 2008/0318785 A1 | 12/2008 | Koltzenburg |
| 2009/0203770 A1 | 8/2009 | Hockenberry et al. |
| 2009/0306142 A1 | 12/2009 | Carson |
| 2011/0034493 A1 | 2/2011 | Boebel et al. |
| 2011/0053891 A1 | 3/2011 | Boebel |

(Continued)

FOREIGN PATENT DOCUMENTS

| CN | 102638989 | 8/2012 |
| CN | 102711477 A | 10/2012 |

(Continued)

OTHER PUBLICATIONS

Koyanagi et al., "Bioisoterism, etc.," Synthesis and Chemistry of Agrochemicals IV; Baker ,D et al., 1995, 15-24.*
K.Tani, et al. Journal of Antibiotics, vol. 55, No. 3, Mar. 2002, pp. 315-321.
Z.Hu, et al. Synthesis of Novel Analogues of Antimycin A3, Tetrahedron Letters 49 (2008) pp. 5192-5195.
Y. Usuki, et al. Journal of Antibiotics, vol. 55, No. 6, Jun. 2002, pp. 607-610.
Masashi Ueki, et al., Journal of Antibiotics, vol. 49, No. 7, Jul. 1996, pp. 639-643.
Search Report issued by State Intellectual Property Office of China for Chinese Patent Application No. 201380074059.9, Aug. 5, 2016, 4 pages (including English translation).

(Continued)

*Primary Examiner* — Patricia L Morris
(74) *Attorney, Agent, or Firm* — Charles W. Arnett; Faegre Baker Daniels LLP

(57) ABSTRACT

The disclosure relates to macrocyclic picolinamides of Formula (I) and to the use of these compounds as fungicides.

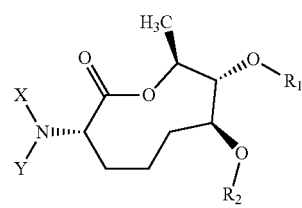

12 Claims, No Drawings

(56) References Cited

U.S. PATENT DOCUMENTS

| | | |
|---|---|---|
| 2011/0053966 A1 | 3/2011 | Klittich et al. |
| 2011/0082039 A1 | 4/2011 | Keeney et al. |
| 2011/0082160 A1 | 4/2011 | Owen et al. |
| 2011/0082162 A1 | 4/2011 | Lorsbach et al. |
| 2011/0306644 A1 | 12/2011 | Hoekstra et al. |
| 2012/0035054 A1 | 2/2012 | Ehr et al. |
| 2012/0245031 A1 | 9/2012 | Gewehr et al. |
| 2013/0090298 A1 | 4/2013 | Lee et al. |
| 2013/0296371 A1 | 11/2013 | Meyer |
| 2013/0296373 A1 | 11/2013 | Meyer |
| 2013/0296375 A1 | 11/2013 | Meyer et al. |
| 2014/0128411 A1 | 5/2014 | Ogawa et al. |
| 2014/0187587 A1 | 7/2014 | Ouimette et al. |
| 2014/0187588 A1 | 7/2014 | Lalonde |
| 2014/0275171 A1 | 9/2014 | Meyer |
| 2015/0065529 A1 | 3/2015 | Owen |

FOREIGN PATENT DOCUMENTS

| | | |
|---|---|---|
| EP | 1054011 | 11/2000 |
| EP | 1 516 874 | 3/2005 |
| WO | 01/14339 | 3/2001 |
| WO | WO 01/14365 | 3/2001 |
| WO | WO 03/011857 | 2/2003 |
| WO | WO 03/035617 | 5/2003 |
| WO | WO 2007017416 | 2/2007 |
| WO | WO 2009/040397 | 9/2008 |
| WO | WO 2011028657 | 3/2011 |
| WO | WO 2011044213 | 4/2011 |
| WO | WO 2011069893 | 6/2011 |
| WO | WO 2012/016972 | 2/2012 |
| WO | WO 2012016989 | 2/2012 |
| WO | WO 2012/070015 A1 | 5/2012 |
| WO | WO 2013/110002 | 7/2013 |
| WO | WO 2013/116251 | 8/2013 |
| WO | WO 2015/103161 | 7/2015 |

OTHER PUBLICATIONS

Huang, et al., Synergistic Interactions between Chitinase ChiCW and Fungicides Against Plant Fungal Pathogens, J. Microbiol. Biotechnol., 2008, 18(4) 784-787.
Backman, P., Fungicide Formulation: Relationship to Biological Activity, 1978, 16, 211-237.
Latin, et al, Re-Examining Fungicide Synergism for Dollar Spot Control, GCM, 2008, 84-87.
O'Sullivan, et al., Fungicide Resistance—an Increasing Problem, Proceedings of National Tillage Conference 2007, Published by Crop Research Centre Oak Park Carlow, date Jan. 31, 2007, 14 pages.
Anonymous, Synergistic Fungicidal Composition of Heterocyclic Aromatic Amides and Triazoles, ip.com Journal, ip.com, Inc., West Henrietta, NY, US, Jul. 2004, 10 pages.
Usuki, et al., "Semi-synthesis and biological evaluation of analogues of UK-2A, a novel antifungal antibiotic from *Steptomyces* sp. 517-02," Bioorganic & Medicinal Chemistry Letters, Pergamon, Amsterdam, KL, vol. 15, No. 8, Apr. 15, 2005, pp. 2011-2014, XP027801790.
Pubchem, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>.
International Search Report for Application No. PCT/US2013/077472, dated Apr. 16, 2014, 4 pages.
Written Opinion for Application No. PCT/US2013/077472, dated Apr. 16, 2014, 4 pages.
Anonymous, Synergistic Fungicidal Compositions of Heterocyclic Aromatic Amides and Triazoles, ip.com, Electronic Publication, 2004, 1-11.
Gisi, U., Synergistic Interaction of Fungicides in Mixtures, Symposium The American Phytopathological Society, 1996, 86(11), 1273-1279.
Science for a Better Life, Bayer Cropscience, Jun. 2008, p. 28.

* cited by examiner

MACROCYCLIC PICOLINAMIDES AS FUNGICIDES

CROSS REFERENCE TO RELATED APPLICATIONS

This application claims the benefit of U.S. Provisional Patent Application Ser. No. 61/747,723 filed Dec. 31, 2012, which is expressly incorporated by reference herein.

BACKGROUND AND SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to macrocyclic picolinamides and their use as fungicides. The compounds of the present disclosure may offer protection against ascomycetes, basidiomycetes, deuteromycetes and oomycetes.

One embodiment of the present disclosure may include compounds of Formula I:

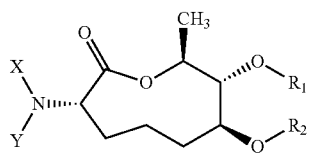

Formula I

X is H or $C(O)R_5$;
Y is H, $C(O)R_5$, or Q;
Q is

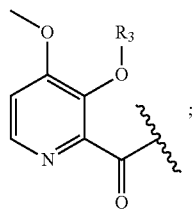

;

$R_1$ is H, alkyl, alkenyl, aryl, —$C(O)R_4$, each substituted with 0, 1 or multiple $R_4$;
$R_2$ is H, alkyl, alkenyl, aryl, —$C(O)R_4$, each substituted with 0, 1 or multiple $R_4$;
$R_3$ is H, —$C(O)R_6$ or —$CH_2OC(O)R_6$;
$R_4$ is alkyl, alkenyl, halo, haloalkyl, alkoxy, or aryl;
$R_5$ is alkyl, alkoxy, benzyl, benzyloxy, each substituted with 0, 1, or multiple $R_7$, wherein each $R_7$ may be substituted with 0, 1, or multiple $R_4$;
$R_6$ is alkyl or alkoxy, each substituted with 0, 1, or multiple $R^4$;
$R_7$ is alkyl, alkenyl, halo, haloalkyl, alkoxy, aryl, heteroaryl, carbocyclic, heterocyclic, —$Si(R_4)_3$, —$C(O)R_4$, —$S(O)_nR_4$, each substituted with 0, 1, or multiple $R_4$;
and with the proviso that when $R_1$ and $R_2$ are H then X and Y are $C(O)R_5$ and $R_5$ is tert-butoxy.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, an area adjacent to the plant, and the seed adapted to produce the plant.

The term "alkyl" refers to a branched or unbranched carbon chain, including methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched or unbranched carbon chain containing one or more double bonds including ethenyl, propenyl, butenyl, isopropenyl, isobutenyl, cyclopentenyl, cyclohexenyl, and the like.

The term "alkynyl" refers to a branched or unbranched carbon chain containing one or more triple bonds including propynyl, butyryl and the like.

The term "aryl" refers to any aromatic, mono- or bi-cyclic, containing 0 heteroatoms.

The term "heterocyclyl" refers to any aromatic or non-aromatic ring, mono- or bi-cyclic, containing one or more heteroatoms The term "cycloalkyl" refers to any monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

The term "cycloalkenyl" refers to any monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

The term "alkoxy" refers to an —OR substituent.

The term "alkoxycarbonyl" refers to a —C(O)—OR substituent.

The term "alkylcarbonyl" refers to a —C(O)—R substituent.

The term "alkylsulfonyl" refers to an —$SO_2$—R substituent.

The term "haloalkylsulfonyl" refers to an —$SO_2$—R substituent where R is fully or partially substituted with Cl, F, I, or Br or any combination thereof.

The term "alkylthio" refers to an —S—R substituent.

The term "haloalkylthio" refers to an alkylthio, which is substituted with Cl, F, I, or Br or any combination thereof.

The term "alkylaminocarbonyl" refers to a —C(O)—N(H)—R substituent.

The term "dialkylaminocarbonyl" refers to a —C(O)—$NR_2$ substituent.

The term "alkylcycloalkylamino" refers to a cycloalkylamino substituent that is substituted with an alkyl group.

The term "trialkylsilyl" refers to —$SiR_3$.

The term "cyano" refers to a —C≡N substituent.

The term "hydroxyl" refers to an —OH substituent.

The term "amino" refers to a —$NH_2$ substituent.

The term "alkylamino" refers to a —N(H)—R substituent.

The term "dialkylamino" refers to a —$NR_2$ substituent.

The term "alkoxyalkoxy" refers to —$O(CH_2)_nO(CH_2)_n$ where n is an integer selected from the list 1, 2, 3, 4, 5, or 6.

The term "alkoxyalkyl" refers to an alkoxy substitution on an alkyl.

The term "haloalkoxyalkyl" refers to an alkoxy substitution on an alkyl which may be partially substituted with halogen atoms.

The term "hydroxyalkyl" refers to an alkyl which is substituted with a hydroxyl group.

The term "haloalkoxy" refers to an —OR—X substituent, wherein X is Cl, F, Br, or I, or any combination thereof.

The term "haloalkyl" refers to an alkyl, which is substituted with Cl, F, I, or Br or any combination thereof.

The term "haloalkenyl" refers to an alkenyl, which is substituted with Cl, F, I, or Br or any combination thereof.

The term "haloalkynyl" refers to an alkynyl which is substituted with Cl, F, I, or Br or any combination thereof.

The term "halogen" or "halo" refers to one or more halogen atoms, defined as F, Cl, Br, and I.

The term "hydroxycarbonyl" refers to a —C(O)—OH substituent.

The term "nitro" refers to a —NO$_2$ substituent.

The term "optionally substituted with" a substituent means containing 0, 1, or more of that substituent.

Unless specifically noted or clearly implied otherwise the term "about" refers to a range of values of plus or minus 10 percent, e.g. about 1 refers to the range 0.9 to 1.1.

Throughout the disclosure, reference to the compounds of Formula I is read as also including diastereomers, enantiomers, and mixtures thereof. In another embodiment, Formula (I) is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, roots, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

In one embodiment, a compound of Formula (I) is provided:

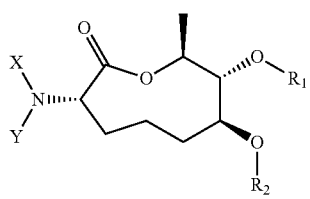

Formula (I)

wherein:

X is H or C(O)R$_5$;

Y is H, C(O)R$_5$, or Q;

Q is

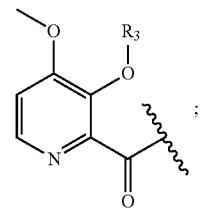

$R_1$ is H, alkyl, alkenyl, aryl, —C(O)R$_4$, each optionally substituted with one or more R$_4$;

$R_2$ is H, alkyl, alkenyl, aryl —C(O)R$_4$, each optionally substituted with one or more R$_4$;

$R_3$ is H, —C(O)R$_6$ or —CH$_2$OC(O)R$_6$;

$R_4$ is alkyl, alkenyl, halo, haloalkyl, alkoxy, or aryl;

$R_5$ is alkyl, alkoxy, benzyl, benzyloxy, each optionally substituted with one or more R$_7$, wherein each R$_7$ may be optionally substituted with one or more R$_4$;

$R^6$ is alkyl or alkoxy, each optionally substituted with one or more R$_4$;

$R^7$ is alkyl, alkenyl, halo, haloalkyl, alkoxy, aryl, heteroaryl, carbocyclic, heterocyclic, and —Si(R$_4$)$_3$, —C(O)R$_4$, —S(O)$_n$R$_4$, each optionally substituted with one or more R$^4$;

with the proviso that when R$_1$ and R$_2$ are H, X and Y are C(O)R$_5$ and R$_5$ is tert-butoxy.

In one more particular embodiment, X and Y are independently chosen from H or C(O)R$_5$. In an even more particular embodiment, X and Y are C(O)R$_5$ and R$_5$ is independently chosen from alkyl, alkoxy, benzyl, or benzyloxy, each optionally substituted with one or more R$_7$, wherein each R$_7$ may be optionally substituted with one or more R$^4$. In a still more particular embodiment, R$_1$ and R$_2$ are independently chosen from H, alkyl, alkenyl, aryl, or —C(O)R$_4$, each optionally substituted with one or more R$_4$.

In one embodiment, R$_5$ is alkoxy and R$_1$ and R$_2$ are H.

In one embodiment, R$_5$ is tert-butoxy. In one embodiment, X and Y are hydrogen. In a more particular embodiment, R$_1$ and R$_2$ are independently chosen from H, alkyl, alkenyl, aryl, or —C(O)R$_4$, each optionally substituted with one or more R$_4$.

In one embodiment, R$_1$ and R$_2$ are independently alkyl, alkenyl, aryl, or —C(O)R$_4$, each optionally substituted with one or more R$_4$.

In one embodiment, R$_1$ and R$_2$ are independently alkyl or aryl, each optionally substituted with one or more R$_4$.

In one embodiment, the amine is protonated to give an ammonium salt of a mineral acid independently chosen from hydrogen chloride, hydrogen bromide, or hydrogen iodide. In a more particular embodiment, the ammonium salt is the ammonium hydrochloride.

In one embodiment, X is H and Y is Q.

In one embodiment, R$_1$ and R$_2$ are independently chosen from H, alkyl, alkenyl, aryl, or —C(O)R$_4$, each optionally substituted with one or more R$_4$.

In one embodiment, R$_1$ and R$_2$ are independently alkyl, alkenyl, aryl, or —C(O)R$_4$, each optionally substituted one or more R$_4$.

In one embodiment, R$_1$ and R$_2$ are independently alkyl or aryl, each optionally substituted with one or more R$_4$.

In one embodiment, R$_3$ is H, —C(O)R$_6$ or —CH$_2$C(O)R$_6$. In a more particular embodiment, R$_3$ is H. In another more particular embodiment, R$_3$ is C(O)R$_6$. In a further particular embodiment, R$_6$ is alkyl or alkoxy, each optionally substituted with one or more R$_4$. In another further particular embodiment, $R_6$ is alkyl, optionally substituted with one or more $R_4$. In still another further particular embodiment, $R_6$ is —$CH_3$ or —$CH_2CH_2$—$R_4$ and $R_4$ is $OCH_3$. In another more particular embodiment, $R_3$ is —$CH_2OC(O)R_6$. In a further particular embodiment, $R_6$ is alkyl or alkoxy, each optionally substituted with one or more $R_4$. In another further particular embodiment, $R_6$ is alkyl, each optionally substituted with one or more $R_4$. In still another more particular embodiment, $R_6$ is —$CH_3$ or —$CH(CH_3)_2$.

In one embodiment, a composition is provided for the control of a fungal or fugal like pathogen. In one embodiment, the composition includes the compound of Formula I as defined by any of the above embodiments and a phytologically acceptable carrier material. The combination of Formula I and the carrier is useful for the control of fungal and fungal like pathogens. In a more particular embodiment, the fungal or fungal like pathogen is selected from the group consisting of: *Mycosphaerella graminicola*(*Septoria tritici*), *Puccinia triticina, Puccinia striiformis, Venturia inaequalis, Uncinula necator, Rhynchosporium secalis, Magnaporthe grisea, Phakopsora pachyrhizi, Leptosphaeria nodorum, Blumeria graminis* f. sp. *tritici, Blumeria graminis* f. sp. *hordei, Erysiphe cichoracearum, Glomerella lagenarium, Cercospora beticola*, and *Alternaria solani*. In a further particular embodiment, the fungal pathogen or fungal like pathogen is selected from the group consisting of: *Septoria tritici* and *Puccinia triticina*.

In one embodiment, a method for the control and prevention of plant disease is provided. The method includes applying a fungicidally effective amount of at least one of the compounds of Formula I as defined by any of the above embodiments to at least one surface selected from the group consisting of: at least one surface of a plant, an area adjacent to a plant, soil in contact with a plant, soil adjacent to a plant, seeds, and equipment for use in agriculture. In a more particular embodiment, the fungicidally effective amount Formula I is applied to a surface in the range of about 0.01 g/m² to about 0.45 g/m² of Formula I.

DESCRIPTION

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants. The materials may be applied in the form of any of the generally used formulation types, for example, as solutions, dusts, wettable powders, flowable concentrate, suspension concentrates, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations may be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG (400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzylaminobenzenesulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenylsuccinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyraflupyrole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, taufluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants.

When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Mycosphaerella graminicola*; impect stage: *Septoria tritici*), brown rust (*Puccinia triticina*), stripe rust (*Puccinia striiformis*), scab of apple (*Venturia inaequalis*), blister smut of maize (*Ustilago maydis*), powdery mildew of grapevine (*Uncinula necator*), leaf blotch of cereals (*Rhynchosporium secalis*), blast of rice (*Magnaporthe grisea*), downy mildew of cucurbits (*Pseudoperonospora cubensis*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe cichoracearum*), anthracnose of cucurbits (*Glomerella lagenarium*), leaf spot of beet (*Cercospora beticola*), early blight of eggplant (*Alternaria solani*), and net blotch of barley (*Pyrenophora teres*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$). Fungicidally effective amount of the compounds include amounts sufficient to kill or control true fungi, pseudo-fungi, and related organisms including water moulds.

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). It may be understood by those skilled in the art that $R_1$ and $R_2$ may be differentially substituted through sequential derivatizations, such as an arylation reaction followed by an allylation reaction. The following descriptions and examples are provided for illustrative purposes and should not be construed as limiting in terms of substituents or substitution patterns. The derivatizations that result in differential substitution at $R_1$ and $R_2$ are designated as "Derivatization Type", wherein n=1 or 2. For example, "Arylation[1]" indicates that the first derivatization performed is an arylation reaction and "Allylation[2]" denotes that the derivatization being performed second in the sequence is an allylation reaction. Additionally, this convention is applied to the structures throughout the schemes as well. For example, the structure below indicates that $R_1$ is an aryl substituent that was installed as the first derivatization of the diol, i.e. $R_1$ and $R_2$=H, and that $R_2$ is an allyl substituent that was installed as the second derivatization of a mono-substituted alcohol, i.e. $R_1$=aryl and $R_2$=H.

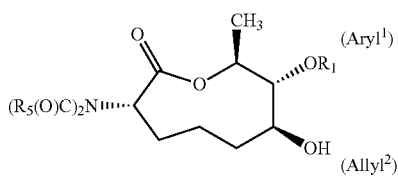

Compounds of Formulas 1.6, 1.7, 1.8, 1.9, 1.10, and 1.11 (shown below), wherein $R_5$ are previously defined within the scope of this disclosure, may be prepared as shown in Scheme 1. In step a of Scheme 1, treatment of a 3,4-dihydropyran of Formula 1.1, prepared as in Nicolaou, K. C. et al. *J. Am. Chem. Soc.*, 2004, 126, 6234-6235, with ozone in the presence of a base, such as sodium bicarbonate (NaHCO$_3$), in a mixture of a halogenated solvent such as dichloromethane (CH$_2$Cl$_2$) and an alcoholic solvent such as methanol (MeOH), followed by treatment with a biphasic mixture of an aqueous solution of a base, such as LiOH, and a polar aprotic solvent such as tetrahydrofuran (THF) provides the compound of Formula 1.2. In step b of Scheme 1, the compound of Formula 1.2 may be treated with an ylide, such as that which is generated from methyltriphenyl phosphonium bromide and a base such as n-butyl lithium, to produce a compound of Formula 1.3. In step c of Scheme 1, the compound of Formula 1.3 may be protected as an ester, such as an acetate, by treating with an acylating agent such as acetyl chloride or acetic anhydride in the presence of an organic base, such as triethylamine (TEA), in a halogenated solvent, such as CH$_2$Cl$_2$, to afford a compound of Formula 1.4. In step d of Scheme 1, the compound of Formula 1.4 may be treated with an alkylborane reagent, such as 9-borabicyclo[3.3.1]nonane (9-BBN), in a polar aprotic solvent such as THF, at a temperature between ambient temperature and 50° C. Treatment of the resulting mixture between ambient temperature and 55° C. with an aqueous solution of a base, such as potassium phosphate, a brominated olefin, such as the compound of Formula 1.5, wherein R5 is tert-butoxy, prepared as in Singh, Janak et al. *Organic Letters*, 2003, 5(17), 3155-3158, and a catalyst, such as [1,1-bis(diphenylphosphino)ferrocene]dichloropalladium (II) (PdCl$_2$(dppf) affords the compound of Formula 1.6. In step e of Scheme 1, treatment of the compound of Formula 1.6 with hydrogen (15-200 psi) in the presence of a catalyst, such as 1,2-bis[(2S,5S)-2,5-diethyl-phospholano]benzene(1,5-cyclooctadiene)rhodium(I) trifluoromethanesulfonate ((S,S)-Et-DUPHOS-Rh), in an alcoholic solvent such as MeOH, afforded a compound of Formula 1.7. In step f of Scheme 1, treatment of the compound of Formula 1.7 with a base such as lithium hydroxide (LiOH) in a mixture of water and an alcoholic solvent such as MeOH produced a compound of Formula 1.8. In step g of Scheme 1, a solution of a compound of Formula 1.8 in a halogenated solvent such as CH$_2$Cl$_2$ or an aromatic solvent such as toluene may be added over a period of 4-12 hours (h) to a mixture of a base such as 4-dimethylaminopyridine (DMAP) and an anhydride such as 2-methyl-6-nitrobenzoic anhydride (MNBA) in either a halogenated solvent such as CH$_2$Cl$_2$ or an aromatic solvent such as toluene to generate a compound of Formula 1.9. In step h of Scheme 1, a compound of Formula 1.9 may be protected with a group such as a carbamate, for example a tert-butylcarbamate, by treating with an alkyl, alkylaryl, haloalkyl, or an aryl dicarbonate such as di-tert-butyl dicarbonate in the presence of a base, such as DMAP, in a polar aprotic solvent such as acetonitrile (CH$_3$CN), to afford a compound of Formula 1.10. In step i of Scheme 1, treatment of a solution of a compound of Formula 1.10 in a solvent such as ethyl acetate (EtOAc) with hydrogen gas (15-55 psi) in the presence of a palladium catalyst, such as 5% or 10% w/w palladium on carbon (Pd/C), affords a compound of Formula 1.11.

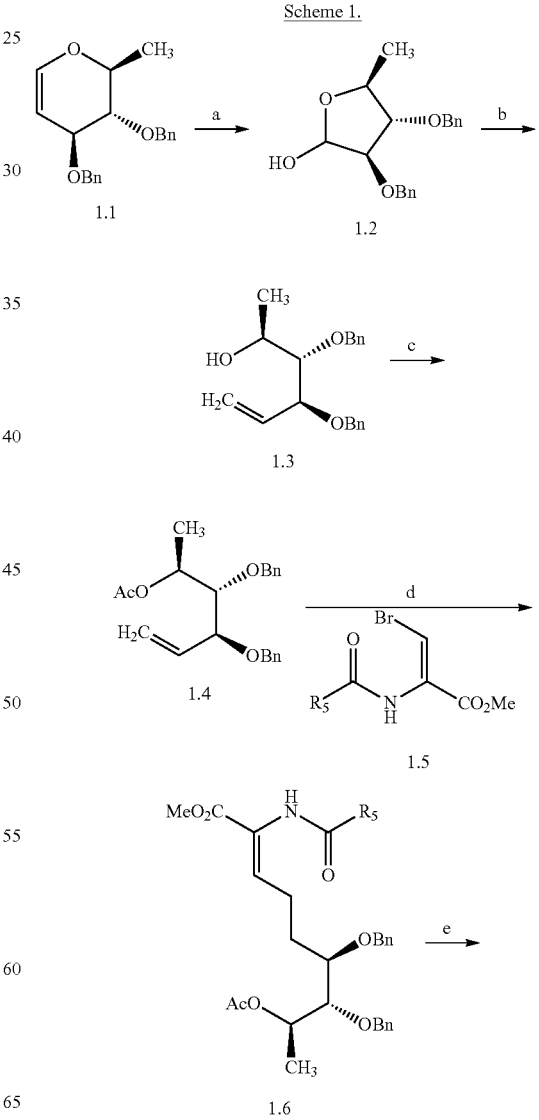

Scheme 1.

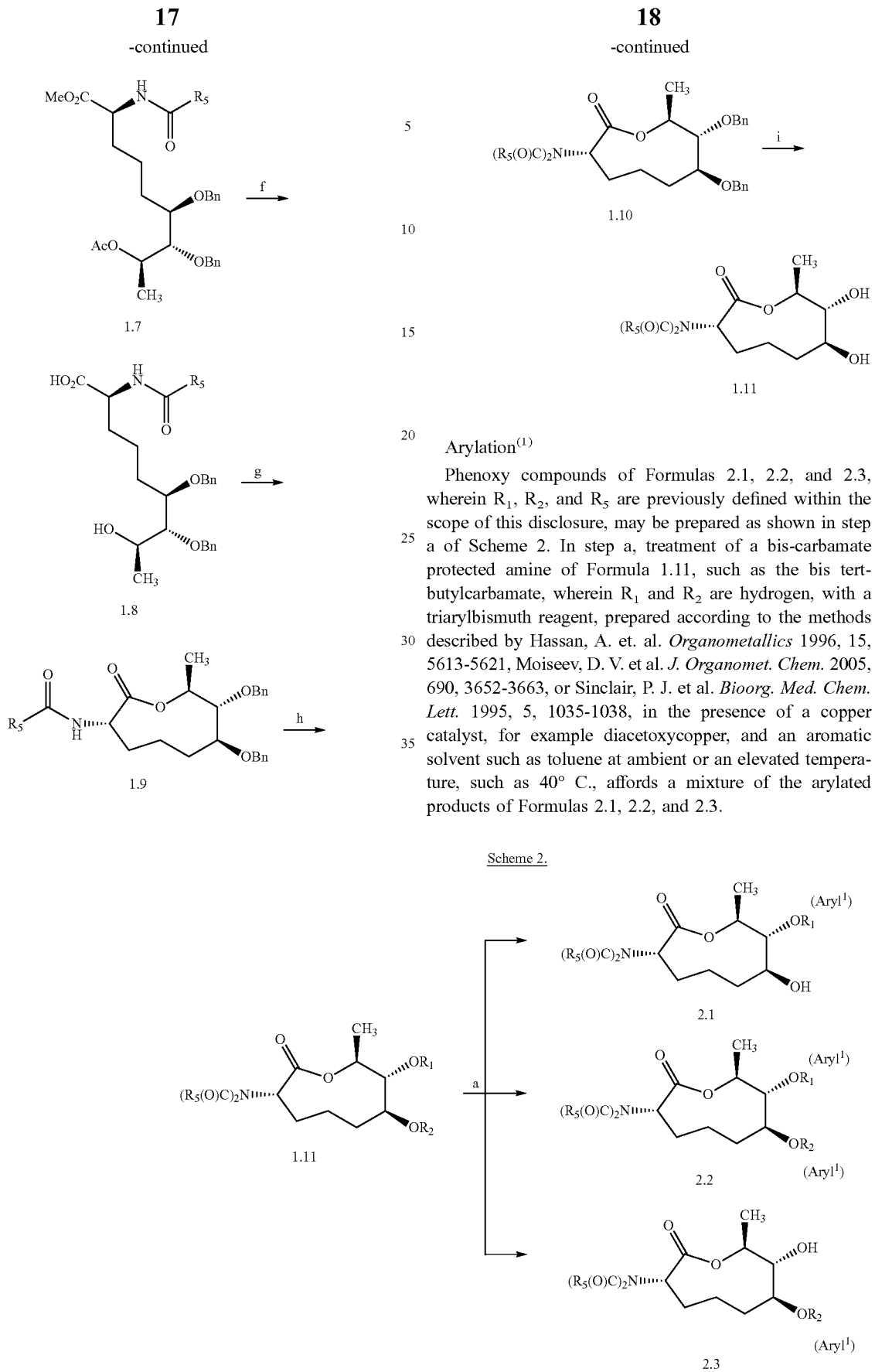

Arylation[(1)]

Phenoxy compounds of Formulas 2.1, 2.2, and 2.3, wherein $R_1$, $R_2$, and $R_5$ are previously defined within the scope of this disclosure, may be prepared as shown in step a of Scheme 2. In step a, treatment of a bis-carbamate protected amine of Formula 1.11, such as the bis tert-butylcarbamate, wherein $R_1$ and $R_2$ are hydrogen, with a triarylbismuth reagent, prepared according to the methods described by Hassan, A. et. al. *Organometallics* 1996, 15, 5613-5621, Moiseev, D. V. et al. *J. Organomet. Chem.* 2005, 690, 3652-3663, or Sinclair, P. J. et al. *Bioorg. Med. Chem. Lett.* 1995, 5, 1035-1038, in the presence of a copper catalyst, for example diacetoxycopper, and an aromatic solvent such as toluene at ambient or an elevated temperature, such as 40° C., affords a mixture of the arylated products of Formulas 2.1, 2.2, and 2.3.

Allylation[(1)]

Alkoxy compounds of Formulas 3.4, 3.5, and 3.6, wherein $R_1$, $R_2$, and $R_5$ are previously defined within the scope of this disclosure, may be prepared as shown in steps a and b of Scheme 3. In step a, treatment of a bis-carbamate protected amine of Formula 1.11, such as the bis tert-butylcarbamate, wherein $R_1$ and $R_2$ are hydrogen, with an allyl carbonate, such as a tert-butyl (allyl) carbonate or a symmetric (allyl) carbonate, such as bis(2-methallyl) carbonate, in the presence of a palladium catalyst and ligand, for example tris(dibenzylideneacetone)dipalladium(0) ($Pd_2(dba)_3$) and 1,1'-bis(diphenylphosphino)-ferrocene (dppf), in a polar aprotic solvent like THF at an elevated temperature, such as 60° C., affords a mixture of the allyloxy products of Formulas 3.1, 3.2, and 3.3. Subsequently, the allyloxy compounds may be reduced, as shown in step b, to the corresponding alkoxy compounds of Formulas 3.4, 3.5, and 3.6, wherein $R_1$, $R_2$, and $R_5$ are previously defined, under standard catalytic hydrogenation conditions. For example, stirring solutions of compounds of Formulas 3.1, 3.2, or 3.3 in a solvent like EtOAc with a palladium catalyst, such as 5% or 10% w/w Pd/C, under an atmosphere of hydrogen affords the alkoxy compounds of Formulas 3.4, 3.5, and 3.6. In step c, mono-substituted compounds of Formulas 3.3 or 3.6 may be treated with an alkylating reagent, such as trimethyloxonium tetrafluoroborate, in the presence of a base, such as Proton Sponge®, in a solvent such as $CH_2Cl_2$ to afford the di-substituted compounds of Formula 3.7, wherein $R_1$, $R_2$, and $R_5$ are as previously defined. Compounds of Formula 3.7, where $R_2$ is allyl, may be subsequently reduced under the conditions previously disclosed in step b to afford compounds of Formula 3.5.

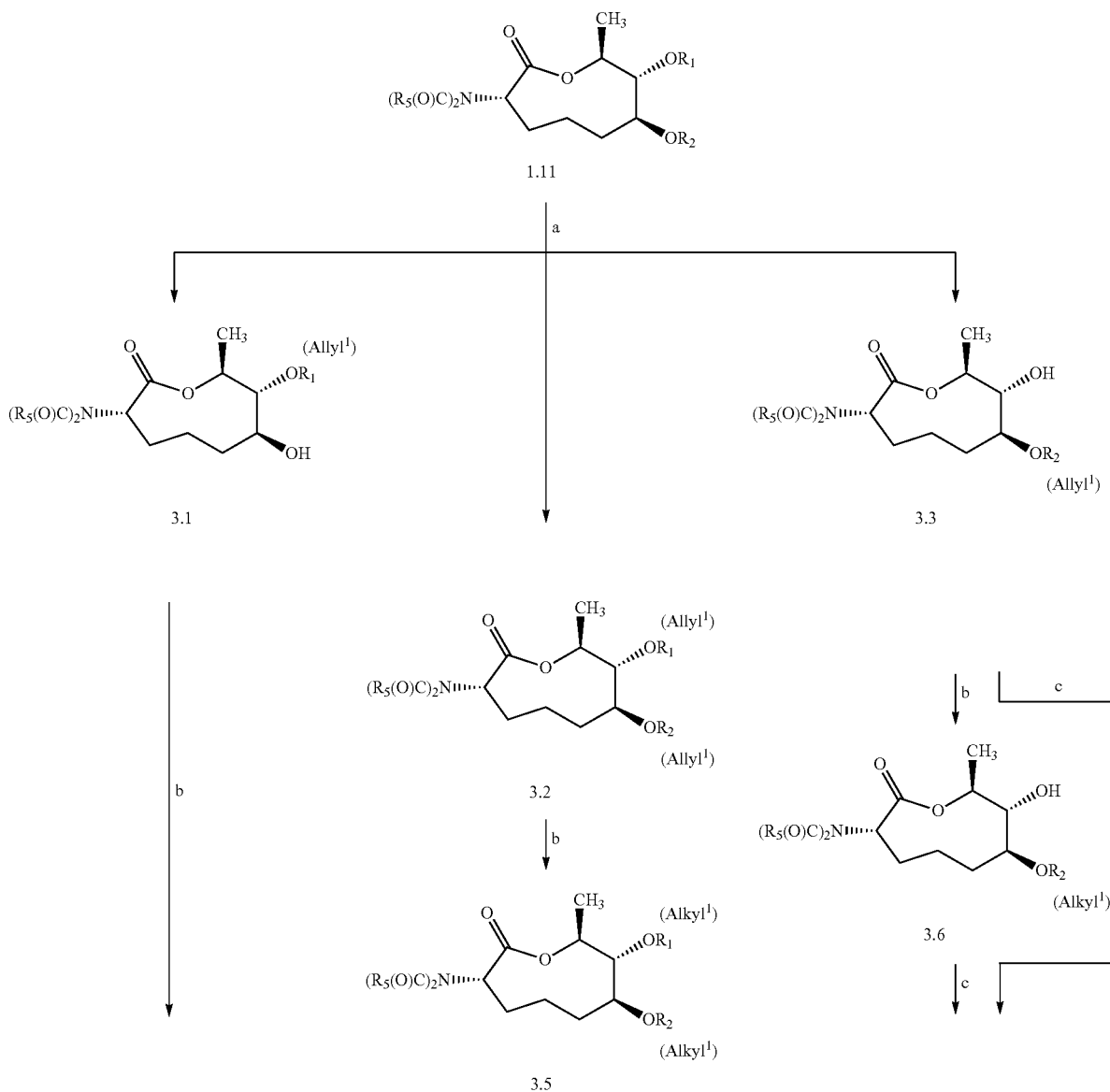

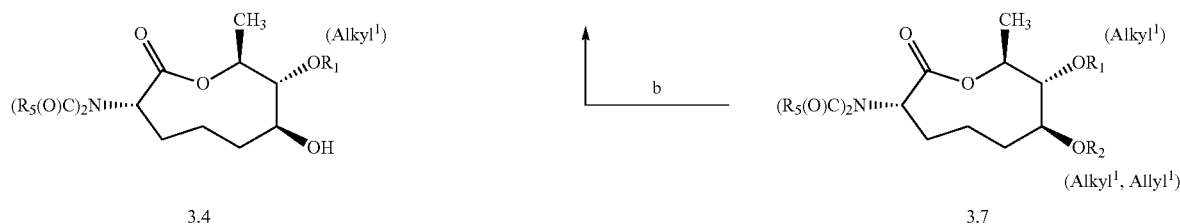

3.4 → b → 3.7

Acylation[1]

Acyloxy compounds of Formula 4.1, wherein $R_1$, $R_2$, and $R_5$ are previously defined herein, may be prepared as shown in step a of Scheme 4. In step a, treatment of a solution of a bis-carbamate protected amine of Formula 1.11, such as the bis tert-butylcarbamate, wherein $R_1$ and $R_2$ are hydrogen, with a base such as 4-dimethylaminopyridine (DMAP) in a solvent such as $CH_2Cl_2$, followed by treatment with an acid chloride affords the acyloxy compound of Formula 4.1.

Scheme 4.

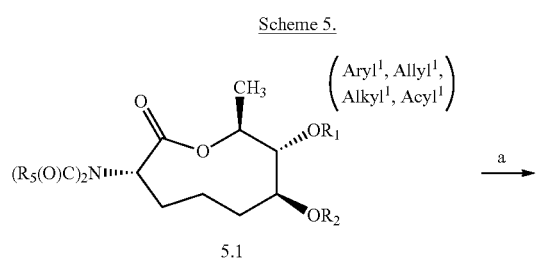

Arylation[2]

Disubstituted compounds of Formula 5.3 and 5.4, wherein $R_1$, $R_2$, and $R_5$ are previously defined within the scope of this disclosure, may be prepared as illustrated in step a of Scheme 5. Arylation of a bis-carbamate protected amine, such as the bis tert-butylcarbamate, of the isomeric mono-substituted compounds of Formulas 5.1 and 5.2, wherein $R_2$ is hydrogen and $R_1$ is hydrogen respectively, may be accomplished using the copper catalyzed triarylbismuth conditions previously disclosed in step a of Scheme 2.

Scheme 5.

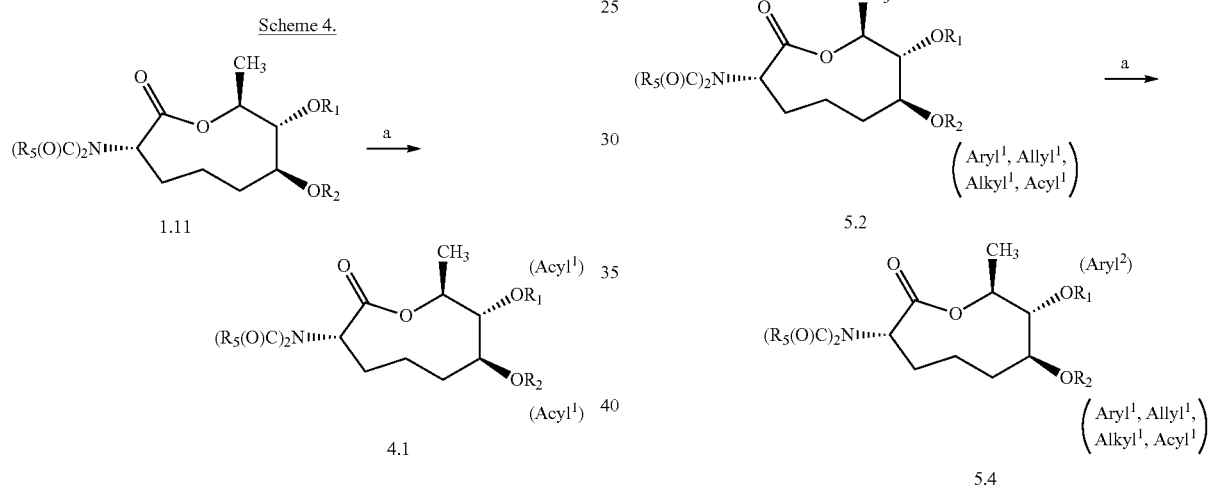

Allylation[2]

Disubstituted compounds of Formula 6.3, 6.4, 6.5, and 6.6, wherein $R_1$, $R_2$, and $R_5$ are previously defined within the scope of this disclosure, may be prepared as illustrated in steps a and b of Scheme 6. Allylation of a bis-carbamate protected amine, such as the bis tert-butylcarbamate, of the isomeric monosubstituted compounds of Formulas 6.1 and 6.2, wherein $R_2$ is hydrogen and $R_1$ is hydrogen respectively, may be accomplished using the palladium catalyzed allylation conditions previously disclosed in step a of Scheme 3 to give the disubstituted compounds of Formula 6.3 and 6.4, wherein $R_1$, $R_2$, and $R_5$ are previously defined. Subsequent palladium catalyzed hydrogenation of compounds of Formulas 6.3 and 6.4, as previously disclosed in step b of Scheme 3, affords compounds of Formulas 6.5 and 6.6. Alternatively, disubstituted compounds of Formula 6.5 and 6.6, wherein $R_1$, $R_2$, and $R_5$ are previously defined, can be obtained from monosubstituted compounds of Formulas 6.1 and 6.2, wherein $R_2$ is hydrogen and $R_1$ is hydrogen respectively, via direct alkylation as disclosed in step c of Scheme 3.

Scheme 6.

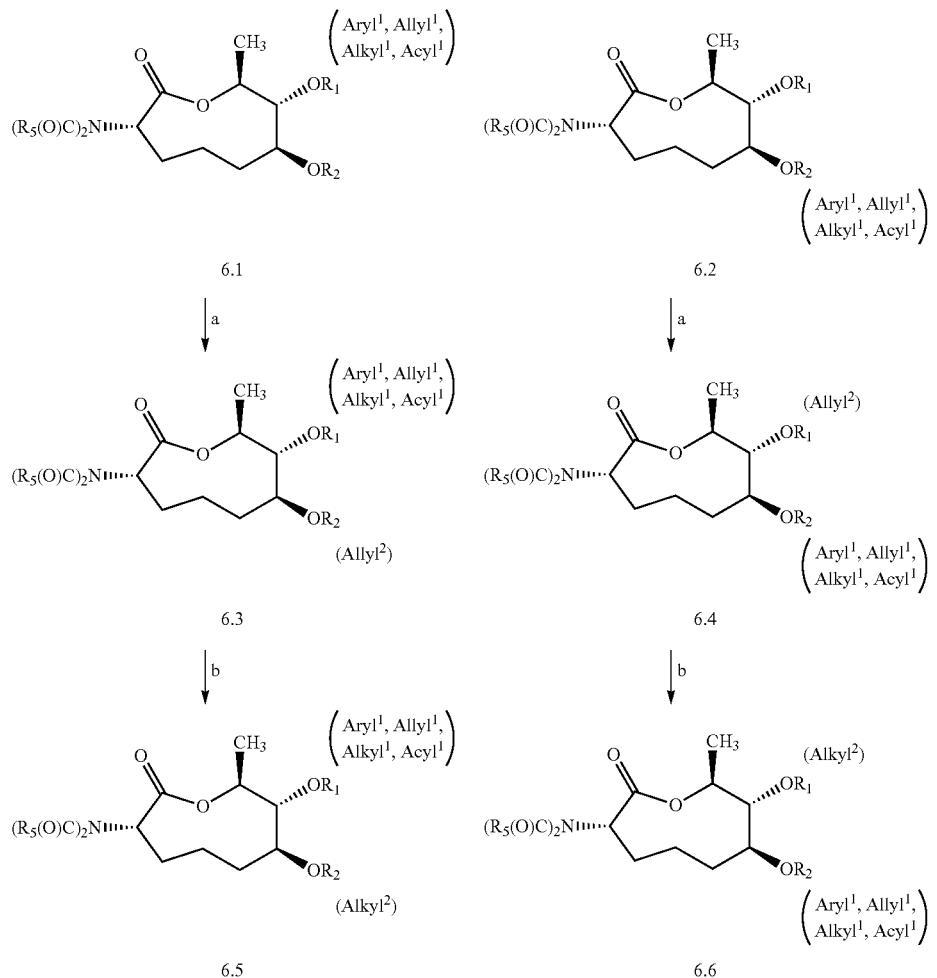

Acylation[(2)]

Disubstituted compounds of Formulas 7.3 and 7.4, wherein $R_1$, $R_2$, and $R_5$ are previously defined herein, may be prepared as illustrated in step a of Scheme 7. Acylation of a bis-carbamate protected amine, such as the bis tert-butylcarbamate, of the isomeric monosubstituted compounds of Formulas 7.1 and 7.2, wherein $R_2$ is hydrogen and $R_1$ is hydrogen respectively, may be accomplished by treating solutions of the compounds in $CH_2Cl_2$ with an organic base, such as pyridine, followed by treatment with an acid chloride to give the disubstituted compounds of Formulas 7.3 and 7.4, wherein $R_1$, $R_2$, and $R_5$ are previously defined.

-continued

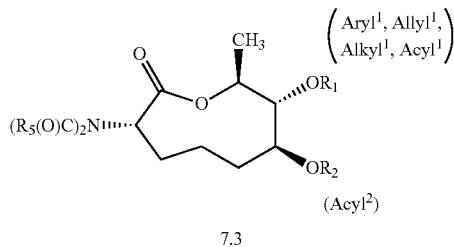

Scheme 7.

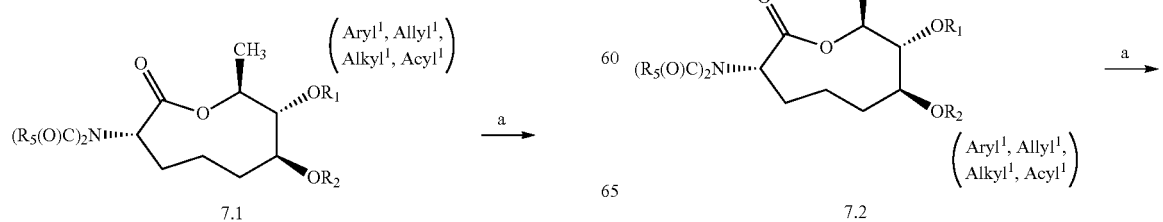

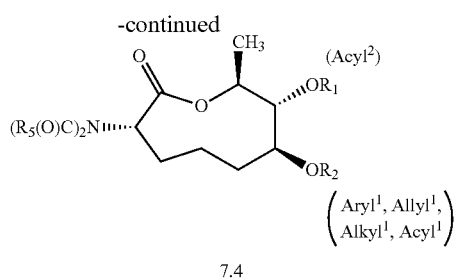

7.4

Conjugate Addition

Disubstituted compounds of Formulas 8.7 and 8.8, wherein $R_1$, $R_2$, and $R_5$ are previously defined within the scope of this disclosure, may be prepared as illustrated in steps a, b, and c of Scheme 8. Addition of a bis-carbamate protected amine, such as the bis tert-butylcarbamate, of the isomeric monosubstituted compounds of Formulas 8.1 and 8.2, wherein $R_2$ and $R_1$ are hydrogen respectively, into conjugated alkynes, such as but-3-yn-2-one, may be accomplished by treating solutions of the compounds in a solvent such as $CH_2Cl_2$ with a catalytic amount of 1,4-diazabicyclo[2.2.2]octane (DABCO), followed by addition of the conjugated alkyne at a reduced temperature, for example 0° C., to afford mixtures of E and Z isomers of the conjugate addition products of Formulas 8.3 and 8.4, as shown in step a. Subjecting the olefinic compounds of Formulas 8.3 and 8.4 to the catalytic hydrogenation conditions previously disclosed in step b of Schemes 3, as shown in step b, affords the alkoxy-ketones of Formulas 8.5 and 8.6, wherein $R_1$, $R_2$ and $R_5$ are previously defined within the scope of this application. Subsequent reduction of the ketones may be accomplished through treatment of the compounds of Formulas 8.5 or 8.6 in an alcohol, such as MeOH with a reducing agent, such as sodium borohydride ($NaBH_4$). Alkylation of the resulting diastereomeric mixtures of the hydroxyl intermediates may be achieved by treating the alcohols with an amine base, such as 1,8-Bis(dimethylamino)naphthalene (Proton Sponge®), in a solvent such as $CH_2Cl_2$, followed by an alkylating agent, for example trimethyloxonium tetrafluoroborate, to give compounds of Formulas 8.7 and 8.8, as shown in step c of Scheme 8.

Scheme 8.

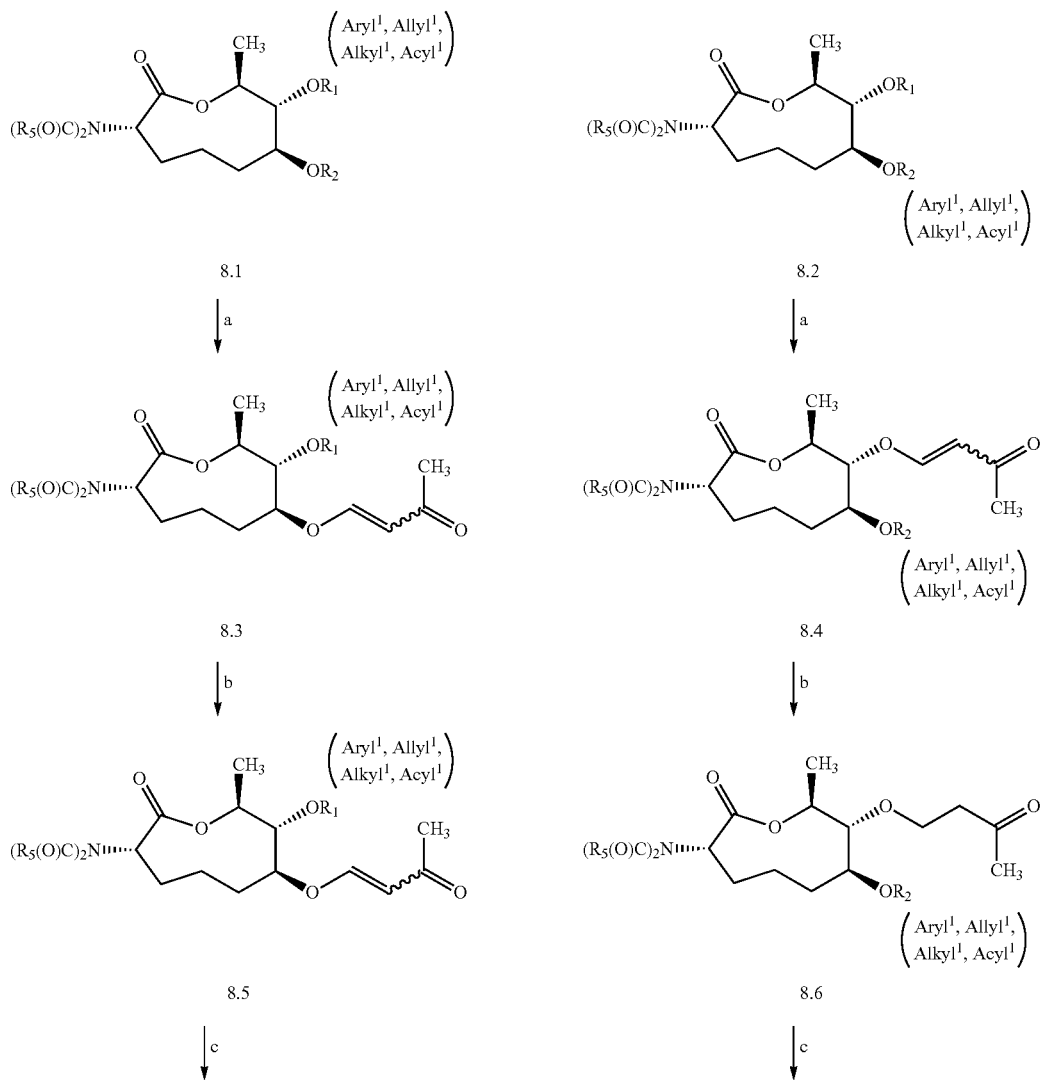

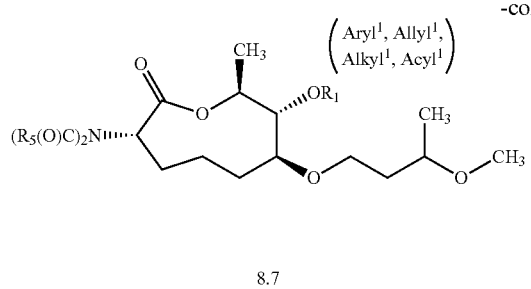

8.7

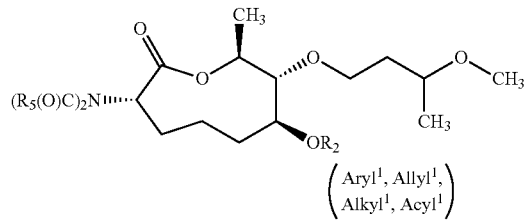

8.8

Deprotection and Amide Formation

Picolinamide compounds of Formula 9.3, wherein $R_1$, $R_2$, X, and Y are previously defined herein, may be prepared as illustrated in steps a and b of Scheme 9. Amine salts of Formula 9.2, may be prepared by treating a solution of a bis-carbamate protected amine of Formula 9.1, wherein R5 is tert-butoxy and $R_1$ and $R_2$ are previously defined within the scope of this disclosure, in a halogenated solvent, such as $CH_2Cl_2$ or chloroform ($CHCl_3$), or neat, with a solution of a mineral acid, for example hydrogen chloride (HCl) in a solvent such as dioxane, to give the HCl salts of compounds of Formula 9.2, as shown in step a. In step b, solutions of compounds of Formula 9.2, wherein $R_1$ and $R_2$ are previously defined, are treated with 3-methoxy-4-hydroxypicolinic acid and an excess of an organic base, such as diisopropylethyl amine or N-methylmorpholine, followed by a peptide coupling reagent, for example benzotriazol-1-yloxytripyrrolidinophosphonium hexafluorophosphate (PyBOP) or (dimethylamino)-N,N-dimethyl(3H-[1,2,3]triazolo[4,5-b]pyridin-3-yloxy)methaniminium hexafluorophosphate (HATU), in a halogenated solvent such as $CH_2Cl_2$ to give compounds of Formula 9.3, wherein X is hydrogen, Y is Q, and $R_1$ and $R_2$ are as defined within the scope of this disclosure.

Scheme 9.

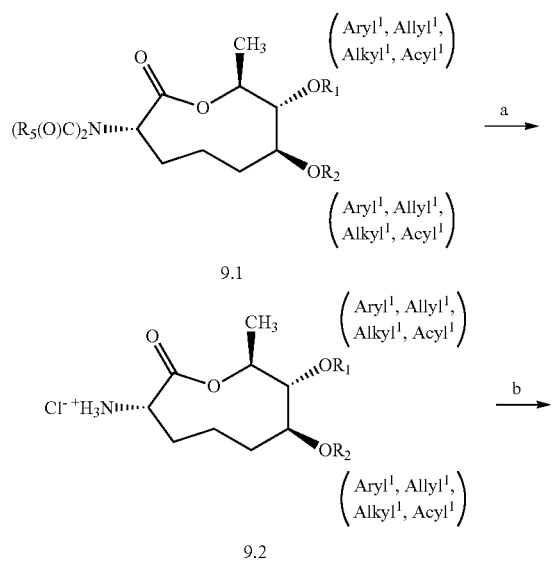

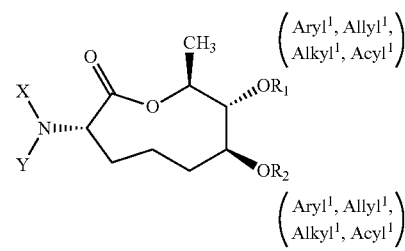

9.2

Hydroxypyridine Substitution

Picolinamide compounds of Formula 10.2, wherein $R_1$, $R_2$, and $R_3$ are previously defined herein, may be prepared as illustrated in methods a or b of Scheme 10. Treating picolinamide compounds of Formula 10.1, wherein $R_3$ is hydrogen and $R_1$ and $R_2$ are previously defined, with an organic base such as TEA and a catalyst, such as DMAP, in a halogenated solvent like $CH_2Cl_2$, followed by an acid chloride, for example acetyl chloride or 3-methoxypropanoyl chloride, affords compounds of Formula 10.2, as shown in method a. Alternatively, method b illustrates that treating picolinamide compounds of Formula 10.1, wherein $R_3$ is hydrogen and $R_1$ and $R_2$ are previously defined, with a carbonate base, such as sodium or potassium carbonate ($Na_2CO_3$ or $K_2CO_3$), with or without the addition of a catalytic amount of sodium iodide (NaI) in a solvent like acetone, followed by an alkyl halide, such as bromomethylacetate, chloromethylisobutyrate, or chloromethyl 2-ethoxyacetate (as prepared in Meyer, K. G.; Bravo-Altamirano, K.; Renga, J. M.; Herrick, J.; Nugent, B. M.; Boebel, T. A.; Li, F.; Wang, N. X.; Owen, W. J.; Graupner, P. R.; Yao, C.; Heemstra, R. J. Preparation of N-macrocyclyl picolinamides as fungicides. US 20130296375, Nov. 7, 2013) also affords picolinamide compounds of Formula 10.2, wherein $R_1$, $R_2$, and $R_3$ are previously defined within the scope of this disclosure.

Scheme 10.

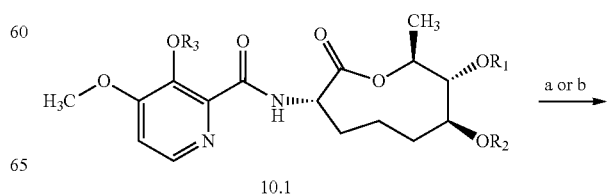

10.1

-continued

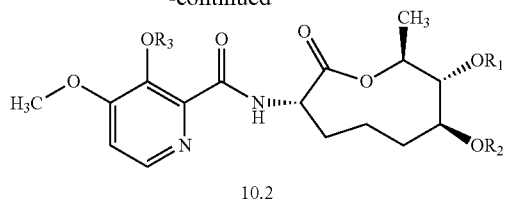

10.2

-continued

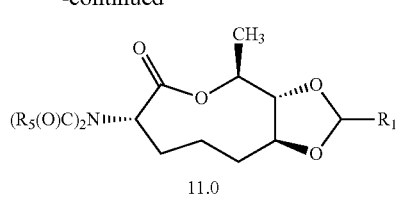

11.0

Acetal Formation

Acetal compounds of Formula 11.0, wherein $R_5$ is previously defined within the scope of this disclosure and $R_1$ is aryl, alkyl or alkenyl, may be prepared as shown in Scheme 11. In Scheme 11, treatment of a bis-carbamate protected amine of Formula 1.11, such as the bis tert-butylcarbamate, wherein $R_1$ and $R_2$ are hydrogen and $R_5$ is tert-butoxy, with an aldehyde, such as benzaldehyde, in the present of an acid catalyst, for example p-toluenesulfonic acid, and a dessicant, such as magnesium sulfate (MgSO$_4$), in a solvent such as CH$_2$Cl$_2$ or toluene at ambient temperature, affords the acetal product of Formula 11.0, where and $R_1$ and $R_5$ are as defined above.

Scheme 11.

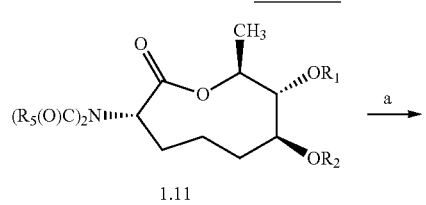

1.11

Aryl Functionalization

Functionalized compounds of Formula 12.2, wherein $R_1$ is aryl, $R_2$ is alkyl, and $R_5$ is as previously defined within the scope of this disclosure, and compounds of Formula 12.5, wherein $R_1$ is alkyl, $R_2$ is aryl, and $R_5$ is as previously defined within the scope of this disclosure, may be prepared as illustrated in Scheme 12, steps a and b. In step a, treatment of the aryl ethers of Formulas 12.0 and 12.3, wherein $R_1$, $R_2$, and $R_5$ are as defined above, with a halogenating agent, such as N-bromosuccinimide (NBS), in an aprotic solvent such as CH$_2$Cl$_2$ at ambient temperature affords the halogenated compounds of Formulas 12.1 and 12.4, wherein $R_1$, $R_2$, and $R_5$ are as defined above. In step b, the halogenated aryl ethers of Formulas 12.1 and 12.4, wherein $R_1$, $R_2$, and $R_5$ are as defined above, may be cross-coupled with a boronic acid or boronate ester, such as phenyl boronic acid, in the presence of a base, such as Na$_2$CO$_3$ and a palladium catalyst, such as tetrakis(triphenylphosphine)palladium(0) (Pd(PPh$_3$)$_4$), in a mixed solvent system, for example dioxane/water, at an elevated temperature, such as 80° C., to give compounds of Formulas 12.2 and 12.5, wherein $R_1$, $R_2$, and $R_5$ are as defined above and $R_4$ is alkyl, aryl, or alkenyl.

Scheme 12.

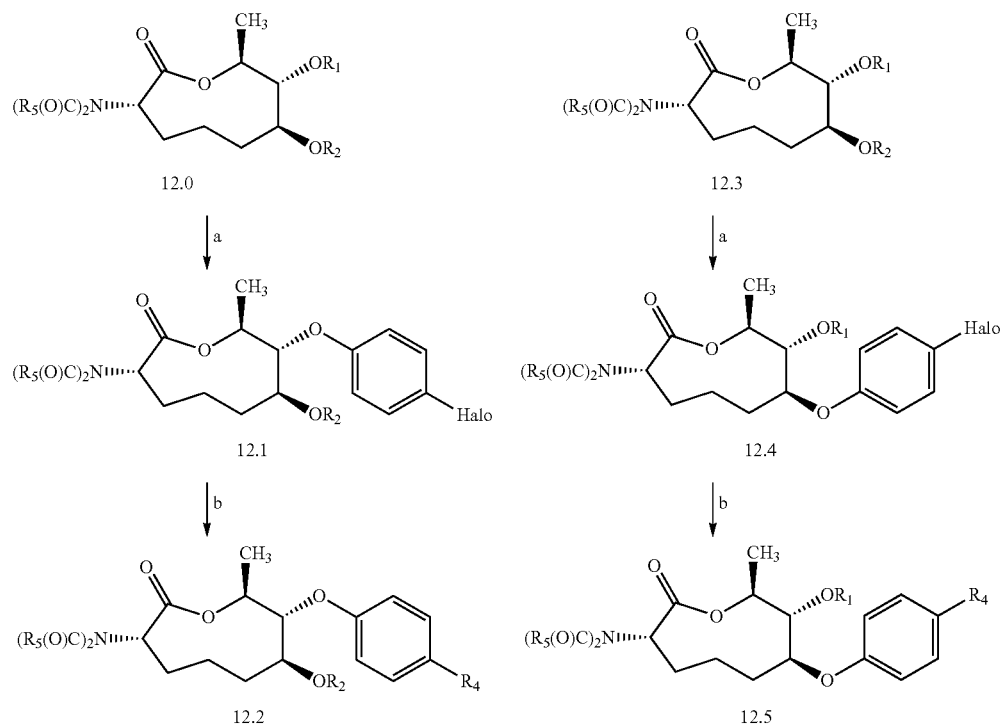

The following examples are presented to illustrate the various aspects of the compounds of the present disclosure and should not be construed as limitations to the claims.

EXAMPLES

Example 1

Preparation of (2S,3R,4S)-2-methyl-3,4-dihydro-2H-pyran-3,4-diol (C1)

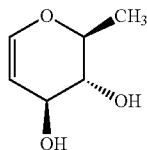

To a solution of (2S,3S,4S)-2-methyl-3,4-dihydro-2H-pyran-3,4-diyl diacetate (32.10 grams (g), 150 millimole (mmol)) in MeOH (150 milliliters (mL)) was added K$_2$CO$_3$ (2.07 g, 15.0 mmol). This mixture was stirred for 16 h at 20° C. The resulting yellow solution was filtered through a plug of silica gel, 6 centimeters (cm)×2 cm, that was flushed with EtOAc (500 mL). The solvent was concentrated to provide (2S,3R,4S)-2-methyl-3,4-dihydro-2H-pyran-3,4-diol (19.9 g, 102% yield with 95% purity resulting in 97% corrected yield) as a yellow solid, which was used without further purification: $^1$H NMR (400 MHz, CDCl$_3$) δ 6.31 (dd, J=6.0, 1.6 Hz, 1H), 4.70 (dd, J=6.0, 2.1 Hz, 1H), 4.21 (dt, J=7.4, 1.9 Hz, 1H), 3.85 (dq, J=9.9, 6.3 Hz, 1H), 3.41 (dd, J=9.9, 7.4 Hz, 1H), 1.38 (d, J=6.3 Hz, 3H); $^{13}$C NMR (101 MHz, CDCl$_3$) δ 144.82, 102.65, 75.64, 74.36, 70.34, 17.09; EIMS m/z 130 ([M$^+$]).

Example 2

Preparation of (2S,3S,4S)-3,4-bis(benzyloxy)-2-methyl-3,4-dihydro-2H-pyran (C2)

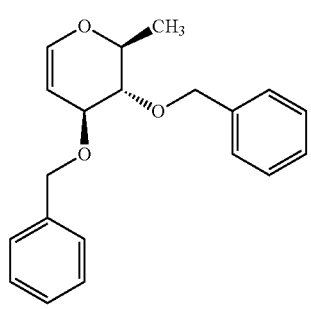 [SMILES: C[C@@H]1OC=C[C@H](OCc2ccccc2)[C@H]1OCc1ccccc1]

Sodium hydride, 60% dispersion in mineral oil, (NaH; 14.68 g, 367 mmol) was added to a 1 liter (L), 3-neck round bottomed flask under nitrogen. The NaH dispersion was washed with hexanes (100 mL and 50 mL) and then suspended in anhydrous N,N-dimethylformamide (DMF; 230 mL) and cooled to 0° C. in an ice water bath. The flask was fitted with a 125 mL addition funnel that was then charged with (2S,3R,4S)-2-methyl-3,4-dihydro-2H-pyran-3,4-diol (19.9 g, 153 mmol) as a solution in anhydrous DMF (70 mL). The diol solution was added to the NaH suspension dropwise with modification of the flow rate to mitigate the reaction rate and frothing. The addition took a total of 15 minutes (min). This mixture was then stirred at 0° C. for a further 30 min. The addition funnel was charged with benzyl bromide (40.0 ml, 336 mmol) that was added dropwise over 10 min. The mixture was then allowed to slowly warm to 20° C. over 16 h. The reaction was quenched by the slow and careful dropwise addition of saturated aqueous ammonium chloride (NH$_4$Cl) solution (20 mL), poured into methyl-t-butyl ether (MTBE; 900 mL), washed with water (600 mL) and saturated aqueous sodium chloride (NaCl, brine) solution (300 mL), dried over MgSO$_4$, filtered, and concentrated to provide a yellow oil (49.32 g, 99%; adjusted for 22 mol % residual DMF): IR (thin film) 3063, 3030, 2975, 2870, 1645, 1496, 1453, 1236, 1099, 1054, 733, 695 cm$^{-1}$; $^1$H NMR (400 MHz, CDCl$_3$) δ 7.54-7.26 (m, 10H), 6.36 (dd, J=6.1, 1.1 Hz, 1H), 4.95-4.80 (m, 2H), 4.80-4.62 (m, 2H), 4.57 (d, J=11.7 Hz, 1H), 4.21 (dt, J=6.5, 1.9 Hz, 1H), 3.95 (dq, J=8.9, 6.4 Hz, 1H), 3.49 (dd, J=8.9, 6.5 Hz, 1H), 1.38 (d, J=6.4 Hz, 3H); $^{13}$C NMR (101 MHz, CDCl$_3$) δ 144.82, 138.44, 138.29, 128.45, 128.00, 127.79, 127.67, 100.17, 79.55, 74.11, 74.00, 70.58, 17.54.

Example 3

Preparation of (3R,4S,5S)-3,4-bis(benzyloxy)-5-methyltetrahydrofuran-2-ol (C3)

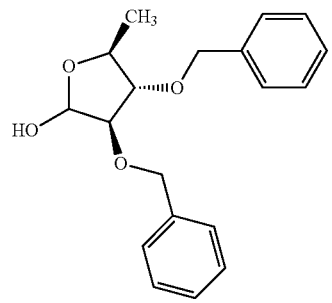 [SMILES: C[C@@H]1OC(O)[C@H](OCc2ccccc2)[C@H]1OCc1ccccc1]

To a solution of (2S,3S,4S)-3,4-bis(benzyloxy)-2-methyl-3,4-dihydro-2H-pyran (41.8 g, 135 mmol) in CH$_2$Cl$_2$ (405 mL) and MeOH (50 mL) was added NaHCO$_3$ (1.13 g, 13.5 mmol). This mixture was cooled to −78° C. (dry ice/acetone bath) and a stream of ozone was passed through the reaction until the solution took on a blue color (2 h). Oxygen was passed through until the blue color disappeared (10 min) and then dimethyl sulfide (19.9 ml, 269 mmol) was added. The solution was warmed to 20° C. and stirred overnight. The reaction was filtered through a plug of Celite® and concentrated to provide an oil. This oil was dissolved in THF (300 mL), a solution of LiOH (9.68 g, 404 mmol) in water (150 mL) was added, and the mixture was stirred vigorously at 20° C. for 2.5 h. The phases were separated and the aqueous phase was extracted with EtOAc (2×100 mL). The combined organic extracts were washed with saturated aqueous NaCl solution (100 mL), dried over MgSO$_4$, filtered, and concentrated to provide a yellow oil. Purification by automated silica gel column chromatography (5→30% acetone/hexanes) provided (3R,4S,5S)-3,4-bis(benzyloxy)-5-methyltetrahydrofuran-2-ol (34.1 g, 80%) as a yellow oil. The product exists as an inseparable mixture of isomers: IR (neat film) 3402, 3031, 2934, 1658, 1496, 1454, 1367, 1105, 1059, 989, 736, 697 cm$^{-1}$; $^1$H NMR (400 MHz, CDCl$_3$) δ 7.45-

7.25 (m, 42H), 5.37 (d, J=6.7 Hz, 3H), 5.30 (dd, J=8.5, 4.3 Hz, 1H), 4.66 (dd, J=5.3, 2.4 Hz, 1H), 4.64-4.47 (m, 16H), 4.35 (qd, J=6.4, 4.9 Hz, 3H), 3.98 (dd, J=2.5, 0.9 Hz, 3H), 3.97-3.89 (m, 2H), 3.80 (d, J=8.5 Hz, 1H), 3.77-3.72 (m, 1H), 3.66 (ddd, J=4.8, 2.5, 0.7 Hz, 3H), 3.40 (d, J=6.7 Hz, 3H), 1.34 (d, J=6.4 Hz, 3H), 1.31 (d, J=6.4 Hz, 9H); $^{13}$C NMR (101 MHz, CDCl$_3$) δ 137.73, 137.48, 137.42, 137.05, 128.63, 128.57, 128.52, 128.50, 128.24, 128.08, 127.98, 127.94, 127.91, 127.82, 127.81, 127.69, 127.00, 100.88, 95.90, 87.42, 87.31, 86.68, 83.14, 78.65, 76.43, 72.67, 72.19, 71.97, 65.37, 20.84, 19.38.

Example 4

Preparation of (2S,3S,4S)-3,4-bis(benzyloxy)hex-5-en-2-ol (C4)

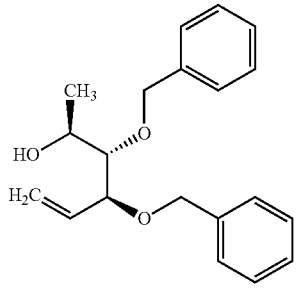 [SMILES: C=C[C@H](OCc1ccccc1)[C@@H](OCc1ccccc1)[C@H](C)O]

To a suspension of methyltriphenylphosphonium bromide (75.0 g, 211 mmol) in anhydrous THF (400 ml) under nitrogen at 0° C. (ice water bath) in a 1000 mL, 3-neck round bottom flask was added a 2.5 molar (M) solution of n-butyllithium in hexane (n-BuLi; 81.0 ml, 202 mmol) dropwise via syringe, keeping the internal temperature below 15° C. The resulting red solution was stirred at 0° C. for 45 min and then cooled to −78° C. (dry ice/acetone bath). A solution of (3R,4S,5S)-3,4-bis(benzyloxy)-5-methyltetrahydrofuran-2-ol (26.5 g, 84 mmol) in anhydrous THF (20 mL) was added via syringe and the solution was stirred for 30 min at −78° C., and then removed from the cold bath and stirred at 20° C. for 16 h. The reaction was quenched with saturated aqueous NH$_4$Cl solution (200 mL), diluted with water (200 mL) and diethyl ether (Et$_2$O; 400 mL). The phases were separated and the aqueous phase was extracted with Et$_2$O (2×200 mL). The combined organic phases were dried over MgSO$_4$, filtered, and concentrated to provide an orange oil. Purification by automated silica gel column chromatography (220% acetone/hexanes) provided (2S,3S,4S)-3,4-bis(benzyloxy)hex-5-en-2-ol (20.23 g, 77%) as a yellow oil: $^1$H NMR (400 MHz, CDCl$_3$) δ 7.45-7.25 (m, 10H), 5.92 (ddd, J=17.2, 10.6, 7.6 Hz, 1H), 5.44-5.25 (m, 2H), 4.75 (d, J=11.6 Hz, 1H), 4.70-4.54 (m, 2H), 4.38 (d, J=11.8 Hz, 1H), 4.12-3.99 (m, 1H), 3.91 (h, J=6.3 Hz, 1H), 3.50-3.35 (m, 1H), 2.73 (d, J=5.9 Hz, 1H), 1.17 (d, J=6.3 Hz, 3H); $^{13}$C NMR (101 MHz, CDCl$_3$) δ 138.31, 137.79, 134.47, 128.46, 128.37, 127.95, 127.94, 127.79, 127.72, 119.27, 83.70, 81.18, 74.07, 70.61, 67.37, 18.90; ESIMS m/z 313.5 ([M+Na]$^+$).

Example 5

Preparation of (2S,3S,4S)-3,4-bis(benzyloxy)hex-5-en-2-yl acetate (C5)

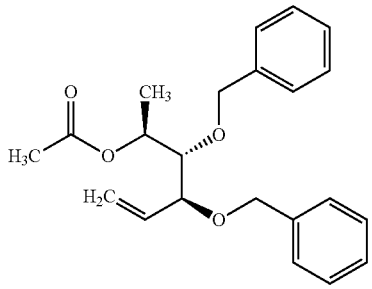 [SMILES: C=C[C@H](OCc1ccccc1)[C@@H](OCc1ccccc1)[C@H](C)OC(C)=O]

To a solution of (2S,3S,4S)-3,4-bis(benzyloxy)hex-5-en-2-ol (800 milligrams (mg), 2.56 mmol) in CH$_2$Cl$_2$ (10 mL) at room temperature was added TEA (1.07 ml, 7.68 mmol), acetic anhydride (0.48 ml, 5.12 mmol) and DMAP (62.6 mg, 0.512 mmol). The reaction mixture was stirred at room temperature for 2 h, concentrated and purified by column chromatography on SiO$_2$ (0→20% EtOAc/hexanes) to yield the title compound as a colorless oil (891 mg, 98%): $^1$H NMR (400 MHz, CDCl$_3$) δ 7.41-7.23 (m, 10H), 5.84 (ddd, J=17.2, 10.4, 8.2 Hz, 1H), 5.38-5.26 (m, 2H), 5.02 (qd, J=6.5, 3.7 Hz, 1H), 4.83-4.67 (m, 2H), 4.61 (d, J=11.8 Hz, 1H), 4.37 (d, J=11.8 Hz, 1H), 3.84 (ddt, J=8.0, 6.3, 0.8 Hz, 1H), 3.63 (dd, J=6.3, 3.7 Hz, 1H), 1.91 (s, 3H), 1.26 (d, J=6.5 Hz, 3H); $^{13}$C NMR (101 MHz, CDCl$_3$) δ 170.19, 138.64, 138.30, 135.07, 128.33, 128.25, 128.08, 127.94, 127.58, 127.52, 119.42, 82.90, 81.86, 74.98, 71.03, 70.48, 21.32, 14.75; ESIMS m/z 377.3 ([M+Na]$^+$).

Example 6

Preparation of (6S,7S,8S,Z)-methyl 8-acetoxy-6,7-bis(benzyloxy)-2-((tert-butoxycarbonyl)amino)non-2-enoate (C6)

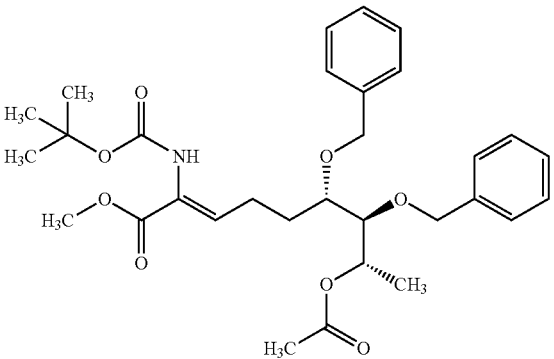 [SMILES: COC(=O)/C(=C/CC[C@H](OCc1ccccc1)[C@@H](OCc1ccccc1)[C@H](C)OC(C)=O)NC(=O)OC(C)(C)C]

To a solution of (2S,3S,4S)-3,4-bis(benzyloxy)oct-7-en-2-yl acetate (931 mg, 2.63 mmol) in THF (2 mL) was added 9-BBN (0.5 M solution in THF, 6.82 mL, 3.41 mmol). The reaction mixture was stirred at room temperature for 30 min, then warmed to 50° C. and stirred for 2 h. After the reaction mixture was cooled to room temperature, an aqueous solution of potassium phosphate (K$_3$PO$_4$; 3 M, 1.75 mL, 5.25 mmol), a solution of (Z)-methyl 3-bromo-2-((tert-butoxycarbonyl)amino)acrylate (736 mg, 2.63 mmol) in DMF (9 mL, degassed), and PdCl$_2$(dppf) (96 mg, 0.13 mmol) was added. The reaction mixture was heated to 55° C. and stirred overnight, and then quenched with saturated aqueous NaHCO$_3$ and extracted with Et$_2$O. The combined organic phase was dried over sodium sulfate (Na$_2$SO$_4$), filtered, concentrated, and purified by column chromatography on SiO$_2$ (0→30% EtOAc/hexanes) to yield the title compound as a light yellow oil (1.26 g, 86%): IR (thin film) 3341, 2930, 1717, 1367, 1241 cm$^{-1}$; $^1$H NMR (400 MHz, CDCl$_3$) δ 7.43-7.26 (m, 10H), 6.48 (t, J=7.3 Hz, 1H), 6.03 (s, 1H), 5.08 (qd, J=6.5, 3.1 Hz, 1H), 4.77-4.58 (m, 3H), 4.49 (d, J=11.2 Hz, 1H), 3.76 (s, 3H), 3.64 (dd, J=6.1, 3.1 Hz, 1H), 3.44 (ddd, J=7.9, 6.0, 4.2 Hz, 1H), 2.43-2.29 (m, 1H), 2.29-2.16 (m, 1H), 1.98 (s, 3H), 1.85-1.61 (m, 2H), 1.44 (s, 9H), 1.31 (d, J=6.5 Hz, 3H); $^{13}$C NMR (101 MHz, CDCl$_3$) δ 170.32, 165.29, 153.24, 138.41, 138.31, 135.67, 128.33, 128.04, 127.98, 127.68, 127.62, 81.82, 80.45, 79.30, 74.33, 73.15, 71.22, 70.56, 52.29, 29.54, 28.18, 24.66, 21.32, 15.09; HRMS-ESI (m/z) [M+H]$^+$ calcd for C$_{31}$H$_{42}$NO$_8$, 556.2905; found, 556.2903.

Example 7

Preparation of (2S,6S,7S,8S)-methyl-8-acetoxy-6,7-bis(benzyloxy)-2-((tert-butoxycarbonyl)amino)nonanoate (C7)

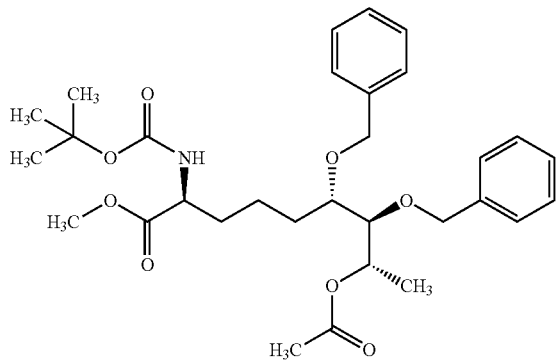 [SMILES: COC(=O)[C@H](CCC[C@H](OCc1ccccc1)[C@@H](OCc1ccccc1)[C@H](C)OC(C)=O)NC(=O)OC(C)(C)C]

A solution of (6S,7S,8S,Z)-methyl 8-acetoxy-6,7-bis(benzyloxy)-2-((tert-butoxycarbonyl)amino)non-2-enoate (120 mg, 0.216 mmol) in anhydrous MeOH (4.3 mL) was purged with N$_2$ for 15 min in a 250 mL stainless steel bomb. To the solution was added 1,2-bis[(2S,5S)-2,5-diethyl-phospholano]benzene(1,5-cyclooctadiene)rhodium(I) trifluoromethanesulfonate ((S,S)-Et-DUPHOS-Rh; 1.56 mg, 2.16 micromole (µmol)), and the vessel was sealed, purged twice with hydrogen (H$_2$; 200 psi), and then pressurized to 200 psi with H$_2$ and stirred at room temperature overnight. The reaction was concentrated and purified by column chromatography on SiO$_2$ (0→30% EtOAc/hexanes) to yield the title compound as a colorless oil (110 mg, 91%): $^1$H NMR (400 MHz, CDCl$_3$) δ 7.39-7.23 (m, 10H), 5.10-5.04 (m, 1H), 4.97 (d, J=8.4 Hz, 1H), 4.73 (d, J=11.6 Hz, 1H), 4.65 (d, J=7.7 Hz, 1H), 4.62 (d, J=7.4 Hz, 1H), 4.50 (d, J=11.4 Hz, 1H), 4.32-4.20 (m, 1H), 3.70 (s, 3H), 3.61 (dd, J=6.0, 3.1 Hz, 1H), 3.43-3.39 (m, 1H), 1.98 (s, 3H), 1.79-1.66 (m, 1H), 1.64-1.47 (m, 4H), 1.45 (s, 9H), 1.31 (d, J=6.5 Hz, 3H), 1.29-1.20 (m, 1H); $^{13}$C NMR (101 MHz, CDCl$_3$) δ 173.27, 170.24, 155.35, 138.51, 138.45, 128.33, 128.05, 128.01, 127.67, 127.63, 81.89, 79.82, 79.39, 74.30, 73.07, 71.28, 53.33, 52.21, 32.68, 30.52, 28.34, 21.34, 15.13; ESIMS m/z 580.4 ([M+Na]$^+$).

Example 8

Preparation of (2S,6S,7S,8S)-6,7-bis(benzyloxy)-2-((tert-butoxycarbonyl)amino)-8-hydroxynonanoic acid (C8)

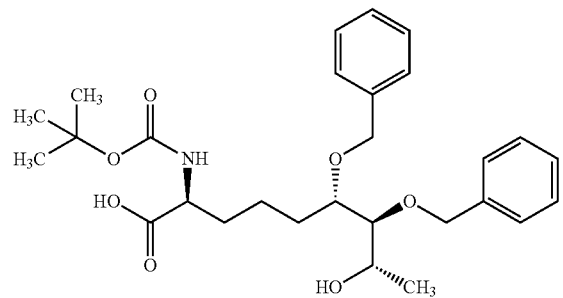 [SMILES: C[C@H](O)[C@H](OCc1ccccc1)[C@H](CCC[C@H](NC(=O)OC(C)(C)C)C(=O)O)OCc1ccccc1]

To a solution of (2S,6S,7S,8S)-methyl 8-acetoxy-6,7-bis(benzyloxy)-2-((tert-butoxycarbonyl)amino)nonanoate (110 mg, 0.20 mmol) in MeOH (2 mL) and water (2 mL) at room temperature was added LiOH.H$_2$O (33.1 mg, 0.789 mmol). The reaction mixture was stirred at room temperature for 3 h, quenched with 1 Normal (N) hydrochloric acid, and extracted with EtOAc. The combined organic phases were washed with saturated aqueous NaHCO$_3$, dried over Na$_2$SO$_4$, filtered, and concentrated to yield the title compound as a colorless oil (96 mg, 97%): IR (thin film) 3409, 2929, 1686, 1588; $^1$H NMR (400 MHz, CDCl$_3$) δ 7.33-7.21 (m, 10H), 5.40 (s, 1H), 4.56-4.48 (m, 4H), 3.96-3.81 (m, 2H), 3.57-3.51 (m, 1H), 3.31-3.23 (m, 1H), 1.81-1.41 (m, 6H), 1.37 (s, 9H), 1.19 (d, J=6.2 Hz, 3H); ESIMS m/z 524.4 ([M+Na]$^+$).

Example 9

Preparation of tert-butyl ((3S,7S,8S,9S)-7,8-bis(benzyloxy)-9-methyl-2-oxooxonan-3-yl)carbamate (C9)

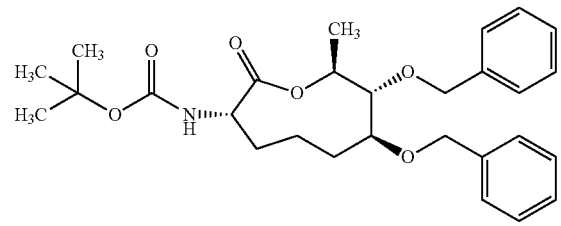 [SMILES: C[C@@H]1OC(=O)[C@@H](NC(=O)OC(C)(C)C)CCC[C@H](OCc2ccccc2)[C@H]1OCc1ccccc1]

To a solution of DMAP (137 mg, 1.12 mmol) and MNBA (129 mg, 0.375 mmol) in CH$_2$Cl$_2$ (30 mL) at room temperature was added a solution of (2S,6S,7S,8S)-6,7-bis(benzyloxy)-2-((tert-butoxycarbonyl)amino)-8-hydroxynonanoic acid (94 mg, 0.19 mmol) in CH$_2$Cl$_2$ (8 mL) over 4 h via syringe pump. The reaction mixture was stirred overnight, concentrated and purified by column chromatography on SiO$_2$ (0→20%, EtOAc/hexanes) to yield the title compound as a colorless oil (71 mg, 78%): $^1$H NMR (400

MHz, CDCl$_3$) δ 7.41-7.26 (m, 10H), 5.03 (d, J=8.3 Hz, 1H), 4.88 (d, J=10.8 Hz, 1H), 4.85-4.77 (m, 1H), 4.68 (d, J=10.8 Hz, 1H), 4.61 (d, J=11.4 Hz, 1H), 4.48 (d, J=11.4 Hz, 1H), 4.20 (dt, J=10.9, 7.7 Hz, 1H), 3.67-3.57 (m, 2H), 2.26 (dt, J=13.6, 6.7 Hz, 1H), 2.21-2.09 (m, 1H), 1.77-1.60 (m, 2H), 1.44 (s, 9H), 1.41 (d, J=6.4 Hz, 3H), 1.23-1.11 (m, 1H), 0.99-0.87 (m, 1H); $^{13}$C NMR (101 MHz, CDCl$_3$) δ 173.15, 154.91, 138.40, 138.31, 128.39, 128.37, 127.94, 127.80, 127.71, 127.64, 83.90, 83.70, 79.91, 75.77, 72.76, 71.20, 52.76, 33.88, 28.32, 28.00, 18.28, 18.10; ESIMS m/z 506.3 ([M+Na]$^+$).

Example 10

Preparation of tert-butyl N-tert-butoxycarbonyl-N-[(3S,7S,8S,9S)-7,8-dibenzyloxy-9-methyl-2-oxo-oxonan-3-yl]carbamate (C10)

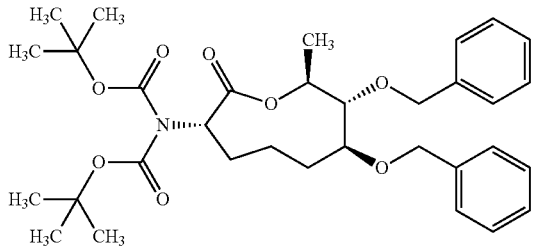 [SMILES: C[C@@H]1OC(=O)[C@@H](N(C(=O)OC(C)(C)C)C(=O)OC(C)(C)C)CCC[C@H](OCc2ccccc2)[C@H]1OCc1ccccc1]

A solution of tert-butyl ((3S,7S,8S,9S)-7,8-bis(benzyloxy)-9-methyl-2-oxooxonan-3-yl)carbamate (150 mg, 0.31 mmol), DMAP (19.0 mg, 0.155 mmol) and di-tert-butyl dicarbonate (271 mg, 1.24 mmol) in CH$_3$CN (2.1 mL) was stirred at room temperature for 18 h, concentrated, and purified by column chromatography on SiO$_2$ (0→15% EtOAc/hexanes) to yield the title compound (76 mg, 42%) as a colorless oil along with recovered starting material (72 mg, 48%) as a colorless oil: $^1$H NMR (400 MHz, CDCl$_3$) δ 7.35-7.27 (m, 10H), 4.88 (d, J=10.9 Hz, 1H), 4.83 (dd, J=10.4, 8.0 Hz, 1H), 4.75-4.59 (m, 3H), 4.49 (d, J=11.4 Hz, 1H), 3.69-3.57 (m, 2H), 2.42-2.33 (m, 1H), 2.24-2.14 (m, 1H), 2.08-2.00 (m, 1H), 1.79-1.65 (m, 2H), 1.51 (s, 18H), 1.41 (d, J=6.3 Hz, 3H), 1.01 (ddt, J=16.0, 7.7, 1.8 Hz, 1H); $^{13}$C NMR (101 MHz, CDCl$_3$) δ 170.86, 152.91, 138.52, 138.41, 128.39, 128.36, 127.95, 127.83, 127.68, 127.60, 84.08, 83.59, 82.71, 75.65, 72.95, 71.21, 57.43, 30.55, 28.50, 27.99, 19.28, 18.23; ESIMS m/z 606.4 ([M+Na]$^+$).

Example 11

Preparation of tert-butyl N-tert-butoxycarbonyl-N-[(3S,7S,8R,9S)-7,8-dihydroxy-9-methyl-2-oxo-oxonan-3-yl]carbamate (F1)

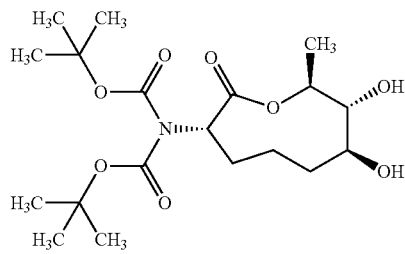 [SMILES: C[C@@H]1OC(=O)[C@@H](N(C(=O)OC(C)(C)C)C(=O)OC(C)(C)C)CCC[C@H](O)[C@H]1O]

A mixture of tert-butyl N-tert-butoxycarbonyl-N-[(3S,7S,8S,9S)-7,8-dibenzyloxy-9-methyl-2-oxo-oxonan-3-yl]carbamate (66.0 mg, 0.113 mmol) and Pd/C (5% w/w Pd, 24.1 mg, 0.011 mmol) in EtOAc (2.3 mL) was stirred under an H$_2$ balloon at room temperature for 7 h. The reaction mixture was filtered through Celite®, and concentrated to yield the title compound (44.0 mg, 96%) as a colorless oil: $^1$H NMR (400 MHz, CDCl$_3$) δ 4.83 (dd, J=10.1, 7.3 Hz, 1H), 4.72 (dq, J=9.1, 6.3 Hz, 1H), 3.58-3.42 (m, 2H), 2.84 (s, 1H), 2.45 (s, 1H), 2.35 (dtd, J=13.8, 9.8, 2.2 Hz, 1H), 2.14-2.02 (m, 1H), 1.96-1.67 (m, 3H), 1.51 (s, 18H), 1.42 (d, J=6.3 Hz, 3H), 1.31-1.21 (m, 1H); $^{13}$C NMR (101 MHz, CDCl$_3$) δ 170.77, 152.91, 82.81, 76.85, 73.86, 73.18, 57.69, 35.34, 30.93, 27.98, 20.03, 18.06; ESIMS m/z 426.3 ([M+Na]$^+$).

Example 12

Preparation of tert-butyl N-tert-butoxycarbonyl-N-[(3S,7S,8R,9S)-7-hydroxy-9-methyl-2-oxo-8-phenoxy-oxonan-3-yl]carbamate (C11)

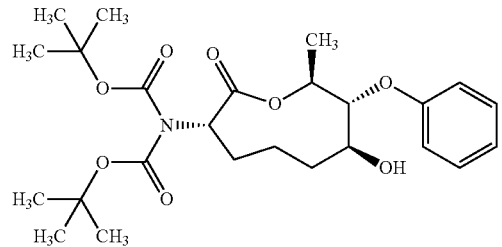 [SMILES: C[C@@H]1OC(=O)[C@@H](N(C(=O)OC(C)(C)C)C(=O)OC(C)(C)C)CCC[C@H](O)[C@H]1Oc1ccccc1]

A solution of tert-butyl N-tert-butoxycarbonyl-N-[(3S,7S,8R,9S)-7,8-dihydroxy-9-methyl-2-oxo-oxonan-3-yl]carbamate (1.845 g, 4.57 mmol), triphenylbismuth diacetate (3.06 g, 5.49 mmol) and diacetoxycopper (0.166 g, 0.915 mmol) in toluene (18.3 ml) was stirred at 40° C. for 1 h. The reaction mixture was filtered thru Celite®, the pad washed with toluene (2×40 mL), and the filtrate concentrated to yield 2.3 g light blue foam. Purification by column chromatography (SiO$_2$, 0→20% EtOAc/hexanes) yielded the title compound as a white foam (1.15 g, 52%), along with the 7-substituted and 7,8-disubstituted products: $^1$H NMR (400 MHz, CDCl$_3$) δ 7.33-7.24 (m, 2H), 7.03 (d, J=7.9 Hz, 2H), 6.98 (t, J=7.3 Hz, 1H), 4.96-4.80 (m, 2H), 4.29 (dd, J=9.4, 7.9 Hz, 1H), 3.86 (t, J=6.7 Hz, 1H), 2.47-2.27 (m, 2H), 2.15-1.95 (m, 2H), 1.91-1.71 (m, 2H), 1.59-1.40 (m, 19H), 1.31 (d, J=6.4 Hz, 3H); $^{13}$C NMR (101 MHz, CDCl$_3$) δ 170.73, 159.42, 152.85, 129.69, 121.92, 116.27, 83.73, 82.78, 73.98, 72.46, 57.56, 33.41, 30.90, 27.98, 19.79, 18.31; HRMS-ESI (m/z) [M+Na]$^+$ calcd for C$_{25}$H$_{37}$NNaO$_8$, 502.2411; found, 502.2344.

The following compounds were prepared and isolated using the appropriately substituted triphenylbismuth diacetate reagents and the methodology described in Example 12:

tert-Butyl N-tert-butoxycarbonyl-N-[(3S,7S,8S,9S)-8-hydroxy-9-methyl-2-oxo-7-phenoxy-oxonan-3-yl]carbamate (C12)

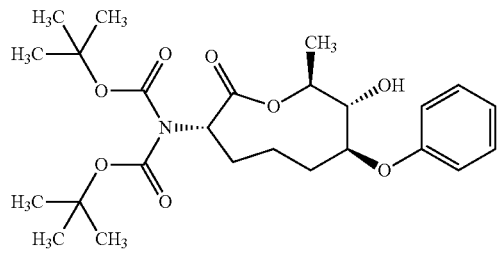 [SMILES: C[C@@H]1OC(=O)[C@@H](N(C(=O)OC(C)(C)C)C(=O)OC(C)(C)C)CCC[C@H](Oc2ccccc2)[C@H]1O]

Isolated as a white foam (520 mg, 24%): $^1$H NMR (400 MHz, CDCl$_3$) δ 7.35-7.27 (m, 2H), 7.03-6.95 (m, 1H), 6.92 (dd, J=8.7, 1.0 Hz, 2H), 4.95 (t, J=8.5 Hz, 1H), 4.84 (dq, J=9.6, 6.3 Hz, 1H), 4.24-4.12 (m, 1H), 3.86 (ddd, J=9.9, 7.8, 2.4 Hz, 1H), 2.63 (d, J=2.5 Hz, 1H), 2.38-2.20 (m, 1H), 2.13-1.98 (m, 2H), 1.89 (tt, J=11.1, 5.6 Hz, 1H), 1.65-1.54 (m, 2H), 1.51 (s, 18H), 1.47 (d, J=6.3 Hz, 3H); $^{13}$C NMR (101 MHz, CDCl$_3$) δ 170.56, 157.12, 152.90, 129.63, 121.65, 116.60, 82.78, 82.32, 75.72, 72.93, 57.26, 31.06, 30.37, 27.98, 20.17, 18.19; HRMS-ESI (m/z) [M+Na]$^+$ calcd for C$_{25}$H$_{37}$NNaO$_8$, 502.2411; found, 502.2399.

tert-Butyl N-tert-butoxycarbonyl-N-[(3S,7S,8S,9S)-9-methyl-2-oxo-7,8-diphenoxy-oxonan-3-yl]carbamate (C13)

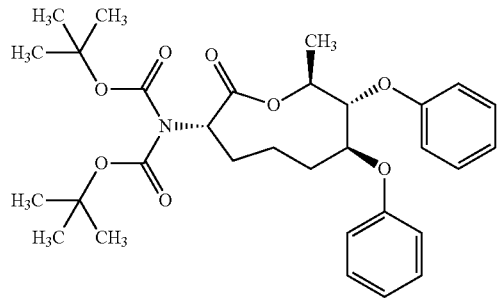 [SMILES: C[C@@H]1OC(=O)[C@@H](N(C(=O)OC(C)(C)C)C(=O)OC(C)(C)C)CCC[C@H](Oc2ccccc2)[C@H]1Oc1ccccc1]

Isolated as a white solid (172 mg, 7%): $^1$H NMR (400 MHz, CDCl$_3$) δ 7.30-7.14 (m, 4H), 7.04 (dd, J=8.8, 1.0 Hz, 2H), 6.97-6.86 (m, 2H), 6.86-6.77 (m, 2H), 4.98 (dd, J=9.5, 6.4 Hz, 1H), 4.91 (dd, J=10.0, 8.3 Hz, 1H), 4.62 (dd, J=9.5, 7.4 Hz, 1H), 4.52 (ddd, J=7.1, 5.2, 1.6 Hz, 1H), 2.46-2.18 (m, 2H), 2.08 (dd, J=13.5, 6.8 Hz, 1H), 1.91 (dt, J=13.0, 7.3 Hz, 1H), 1.72 (m, H), 1.52 (s, 18H), 1.41 (d, J=6.4 Hz, 3H), 1.20 (dt, J=7.7, 1.8 Hz, 1H); $^{13}$C NMR (101 MHz, CDCl$_3$) δ 170.71, 159.55, 157.64, 152.85, 129.39, 129.37, 121.54, 121.35, 116.72, 116.57, 82.81, 82.37, 82.21, 72.57, 57.25, 30.54, 28.98, 27.99, 19.32, 18.32; ESIMS m/z 578.8 ([M+Na]$^+$).

tert-Butyl N-tert-butoxycarbonyl-N-[(3S,7S,8R,9S)-8-(4-fluorophenoxy)-7-hydroxy-9-methyl-2-oxo-oxonan-3-yl]carbamate (C14)

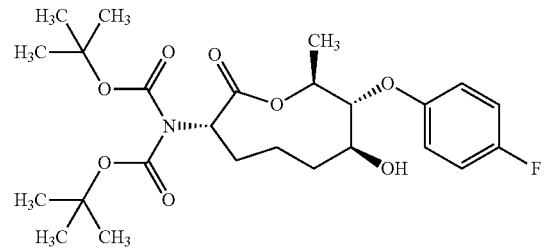 [SMILES: C[C@@H]1OC(=O)[C@@H](N(C(=O)OC(C)(C)C)C(=O)OC(C)(C)C)CCC[C@H](O)[C@H]1Oc1ccc(F)cc1]

Isolated as a colorless oil (150 mg, 0.30 mmol, 61%): $^1$H NMR (400 MHz, CDCl$_3$) δ 7.04-6.90 (m, 4H), 4.93-4.82 (m, 2H), 4.17 (dd, J=9.4, 7.9 Hz, 1H), 3.86 (ddd, J=8.1, 6.1, 2.4 Hz, 1H), 2.40 (dtd, J=13.7, 9.9, 3.5 Hz, 2H), 2.16-1.94 (m, 2H), 1.82 (dd, J=6.1, 3.1 Hz, 2H), 1.52 (s, 18H), 1.49-1.41 (m, 1H), 1.31 (d, J=6.4 Hz, 3H); $^{13}$C NMR (101 MHz, CDCl$_3$) δ 170.69, 157.76 (d, J=240.0 Hz), 155.62 (d, J=2.3 Hz), 152.85, 117.54 (d, J=8.0 Hz), 116.04 (d, J=23.2 Hz), 84.90, 82.82, 73.96, 72.30, 57.53, 33.52, 30.86, 27.97, 19.78, 18.35; ESIMS m/z 498.3 [(M+H)$^+$].

Example 12A

Preparation of [(3S,7S,8S,9S)-9-methyl-2-oxo-7,8-diphenoxy-oxonan-3-yl]ammonium chloride (F2)

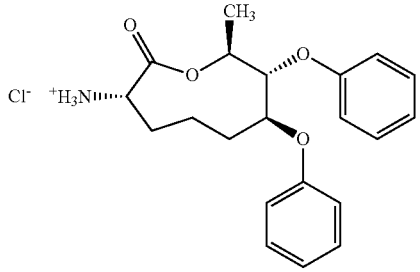 [SMILES: [Cl-] ; C[C@@H]1OC(=O)[C@@H]([NH3+])CCC[C@H](Oc2ccccc2)[C@H]1Oc1ccccc1]

A solution of tert-butyl N-tert-butoxycarbonyl-N-[(3S,7S,8S,9S)-9-methyl-2-oxo-7,8-diphenoxy-oxonan-3-yl]carbamate (650 mg, 1.17 mmol) and HCl (4M in dioxane; 5.85 mL, 23.4 mmol) in CHCl$_3$ (6 mL) was stirred at 23° C. for 1.5 h. The solution was concentrated to yield the title compound as a white foam (458 mg, 100%), which was used without further purification.

Example 12B

Step 1: Preparation of tert-butyl N-tert-butoxycarbonyl-N-[(3S,7S,8S,9S)-9-methyl-7-(2-methylallyloxy)-2-oxo-8-phenoxy-oxonan-3-yl]carbamate (C15)

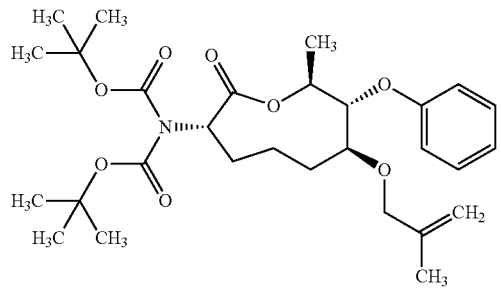 [SMILES: C=C(C)CO[C@H]1CCC[C@H](N(C(=O)OC(C)(C)C)C(=O)OC(C)(C)C)C(=O)O[C@@H](C)[C@@H]1Oc1ccccc1]

A solution of tert-butyl N-tert-butoxycarbonyl-N-[(3S,7S,8R,9S)-7-hydroxy-9-methyl-2-oxo-8-phenoxy-oxonan-3-yl]carbamate (1.075 g, 2.24 mmol), tert-butyl (2-methylallyl) carbonate (1.158 g, 6.70 mmol), dppf (0.025 g, 0.045 mmol) and Pd$_2$(dba)$_3$ (0.021 g, 0.022 mmol) in degassed THF (11.2 ml) was heated to 60° C. for 1.5 h. The solution was cooled to room temperature and purified by column chromatography (SiO$_2$; 0→5% EtOAc/Hex) to yield the title compound (1.0 g, 84%) as a white solid: $^1$H NMR (400 MHz, CDCl$_3$) δ 7.34-7.17 (m, 2H), 7.09-7.02 (m, 2H), 6.98-6.90 (m, 1H), 4.94-4.72 (m, 4H), 4.43 (dd, J=9.6, 7.4 Hz, 1H), 3.91 (d, 1H), 3.79 (d, 1H), 3.62 (ddd, J=7.0, 5.1, 1.7 Hz, 1H), 2.47-2.34 (m, 1H), 2.25-2.13 (m, 1H), 2.11-2.01 (m, 1H), 1.88-1.63 (m, 2H), 1.56 (s, 3H), 1.52 (s, 18H), 1.33 (d, J=6.4 Hz, 3H), 1.07 (dd, J=16.0, 7.7 Hz, 1H); $^{13}$C NMR (101 MHz, CDCl$_3$) δ 170.80, 159.58, 152.86, 142.36, 129.36, 121.24, 116.29, 112.34, 82.72, 82.53, 82.06, 73.50, 72.76, 57.39, 30.56, 28.61, 27.98, 19.40, 19.29, 18.19; HRMS-ESI (m/z) [M+Na]$^+$ calcd for C$_{29}$H$_{43}$NNaO$_8$, 556.2881; found, 556.2873.

The following compounds were prepared and isolated using the methodology described in Example 12B, Step 1:

tert-Butyl N-tert-butoxycarbonyl-N-[(3S,7S,8S,9S)-9-methyl-8-(2-methylallyloxy)-2-oxo-7-phenoxy-oxonan-3-yl]carbamate (C16)

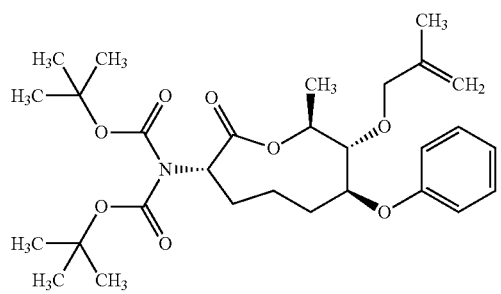 [SMILES: C=C(C)CO[C@H]1[C@H](C)OC(=O)[C@@H](N(C(=O)OC(C)(C)C)C(=O)OC(C)(C)C)CCC[C@@H]1Oc1ccccc1]

Isolated as a white solid (448 mg; 85%): $^1$H NMR (400 MHz, CDCl$_3$) δ 7.30-7.23 (m, 2H), 6.99-6.88 (m, 3H), 4.94-4.72 (m, 4H), 4.46-4.35 (m, 1H), 4.22-4.16 (m, 1H), 4.03 (d, J=11.6 Hz, 1H), 3.67 (dd, J=9.7, 7.1 Hz, 1H), 2.38-2.25 (m, 1H), 2.25-2.10 (m, 1H), 2.04-1.95 (m, 1H), 1.83 (m 1H), 1.65 (s, 3H), 1.63-1.57 (m, 1H), 1.49 (s, 18H), 1.46 (d, J=6.3 Hz, 3H), 1.08 (dd, J=16.0, 7.8 Hz, 1H); $^{13}$C NMR (101 MHz, CDCl$_3$) δ 170.75, 157.45, 152.86, 142.27, 129.49, 121.17, 116.55, 112.39, 83.08, 83.01, 82.73, 77.41, 72.73, 57.27, 30.44, 28.80, 27.98, 19.74, 19.18, 18.23; HRMS-ESI (m/z) [M+Na]$^+$ calcd for C$_{29}$H$_{43}$NNaO$_8$, 556.2881; found, 556.2875.

Example 12B, Step 2

Preparation of tert-butyl N-tert-butoxycarbonyl-N-[(3S,7S,8S,9S)-7-isobutoxy-9-methyl-2-oxo-8-phenoxy-oxonan-3-yl]carbamate (C17)

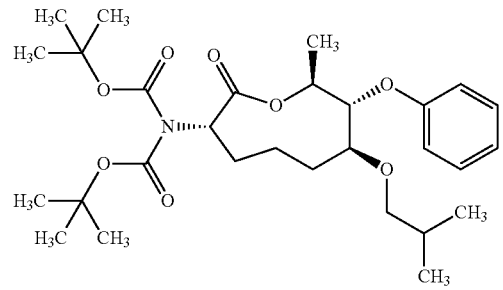

A suspension of Pd/C (5% w/w Pd; 199 mg) and tert-butyl N-tert-butoxycarbonyl-N-[(3S,7S,8S,9S)-9-methyl-7-(2-methylallyloxy)-2-oxo-8-phenoxy-oxonan-3-yl]carbamate (1.00 g, 1.87 mmol) in EtOAc (9.4 mL) was stirred rapidly at room temperature under one atmosphere (atm) of H$_2$ overnight. The suspension was filtered through Celite®, washed with EtOAc (3×30 mL), and the combined extracts were concentrated to yield the title compound as a clear oil (980 mg, 98%): $^1$H NMR (400 MHz, CDCl$_3$) δ 7.27-7.16 (m, 2H), 7.12-7.01 (m, 2H), 6.99-6.86 (m, 1H), 4.94-4.73 (m, 2H), 4.38 (dd, J=9.6, 7.3 Hz, 1H), 3.53 (ddd, J=7.1, 5.2, 1.7 Hz, 1H), 3.24 (dd, J=8.8, 6.6 Hz, 1H), 3.05 (dd, J=8.8, 6.3 Hz, 1H), 2.53-2.29 (m, 1H), 2.29-2.11 (m, 1H), 2.04 (s, 1H), 1.88-1.60 (m, 3H), 1.60-1.40 (m, 18H), 1.33 (d, J=6.4 Hz, 3H), 1.05 (dd, J=16.0, 7.8 Hz, 1H), 0.78 (d, J=6.7 Hz, 3H), 0.73 (d, J=6.7 Hz, 3H); $^{13}$C NMR (101 MHz, CDCl$_3$) δ 170.84, 159.72, 152.86, 129.27, 121.17, 116.42, 83.13, 82.72, 82.70, 76.40, 72.72, 57.41, 30.58, 28.70, 28.49, 27.98, 19.36, 19.24, 19.21, 18.20; HRMS-ESI (m/z) [M+Na]$^+$ calcd for C$_{29}$H$_{45}$NNaO$_8$, 558.3037; found, 558.3030.

The following compounds were prepared and isolated using the methodology described in Example 12B, Step 2:

tert-Butyl N-tert-butoxycarbonyl-N-[(3S,7S,8S,9S)-8-isobutoxy-9-methyl-2-oxo-7-phenoxy-oxonan-3-yl]carbamate (C18)

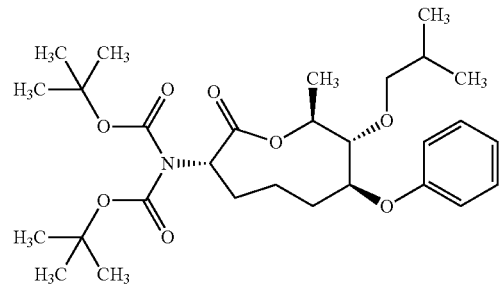 [SMILES: CC(C)CO[C@H]1[C@H](C)OC(=O)[C@@H](N(C(=O)OC(C)(C)C)C(=O)OC(C)(C)C)CCC[C@@H]1Oc1ccccc1]

Isolated as a white solid (430 mg; 100%): $^1$H NMR (400 MHz, CDCl$_3$) δ 7.32-7.22 (m, 2H), 6.99-6.86 (m, 3H), 4.86 (dd, J=10.2, 8.2 Hz, 1H), 4.75 (dq, J=9.7, 6.3 Hz, 1H), 4.43-4.26 (m, 1H), 3.66-3.50 (m, 2H), 3.36 (dd, J=8.7, 6.7 Hz, 1H), 2.44-2.24 (m, 1H), 2.24-2.08 (m, 1H), 2.04-1.91 (m, 1H), 1.89-1.56 (m, 3H), 1.53-1.46 (m, 18H), 1.44 (d, J=6.3 Hz, 3H), 1.06 (dd, J=16.0, 7.9 Hz, 1H), 0.82 (d, J=6.7 Hz, 3H), 0.78 (d, J=6.7 Hz, 3H); $^{13}$C NMR (101 MHz, CDCl$_3$) δ 170.78, 157.65, 152.86, 129.44, 121.06, 116.54, 83.33, 83.06, 82.71, 80.56, 72.93, 57.27, 30.46, 28.97, 28.85, 27.97, 19.39, 19.28, 19.17, 18.15; HRMS-ESI (m/z) [M+Na]$^+$ calcd for C$_{29}$H$_{45}$NNaO$_8$, 558.3037; found, 558.2994.

Example 12B, Step 3

Preparation of [(3S,7S,8S,9S)-7-isobutoxy-9-methyl-2-oxo-8-phenoxy-oxonan-3-yl]ammonium chloride (F3)

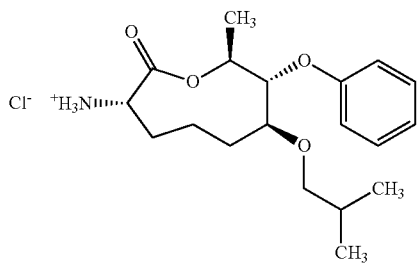 [SMILES: [Cl-] ; CC(C)CO[C@H]1CCC[C@H]([NH3+])C(=O)O[C@@H](C)[C@@H]1Oc1ccccc1]

Prepared according to the methods described in Example 12A.

The following compounds were prepared and isolated using the methodology described in Example 12B, Step 3:

[(3S,7S,8S,9S)-8-Isobutoxy-9-methyl-2-oxo-7-phenoxy-oxonan-3-yl]ammonium chloride (F4)

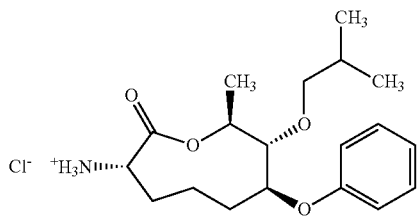 [SMILES: [Cl-] ; CC(C)CO[C@H]1[C@H](C)OC(=O)[C@@H]([NH3+])CCC[C@@H]1Oc1ccccc1]

Example 12C, Step 1

Preparation of tert-butyl N-tert-butoxycarbonyl-N-[(3S,7S,8S,9S)-8-(4-fluorophenoxy)-7-(4-methoxyphenoxy)-9-methyl-2-oxo-oxonan-3-yl]carbamate (C19)

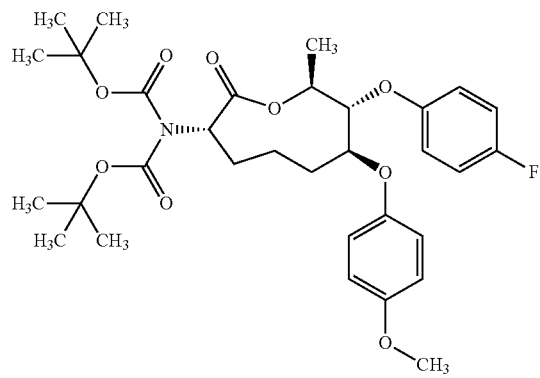 [SMILES: COc1ccc(O[C@H]2CCC[C@H](N(C(=O)OC(C)(C)C)C(=O)OC(C)(C)C)C(=O)O[C@@H](C)[C@@H]2Oc2ccc(F)cc2)cc1]

To a stirred solution of tert-butyl N-tert-butoxycarbonyl-N-[(3S,7S,8R,9S)-8-(4-fluorophenoxy)-7-hydroxy-9-methyl-2-oxo-oxonan-3-yl]carbamate (150 mg, 0.30 mmol) in toluene (1.51 mL) under N$_2$ was added tri(p-methoxyphenyl)bismuth diacetate (391 mg, 0.603 mmol) followed by diacetoxycopper (10.9 mg, 0.060 mmol) and N-cyclohexyl-N-methylcyclohexanamine (129 microliters (μL), 0.603 mmol). The reaction mixture was heated for 18 h at 43° C. The reaction was concentrated and purified by column chromatography (0→100% EtOAc/hex) to yield the title compound (75 mg, 41%) as a yellow oil: $^1$H NMR (400 MHz, CDCl$_3$) δ 7.07-6.97 (m, 2H), 6.96-6.85 (m, 2H), 6.81-6.69 (m, 4H), 4.99-4.85 (m, 2H), 4.47 (dd, J=9.6, 7.4 Hz, 1H), 4.34 (dt, J=5.5, 3.5 Hz, 1H), 3.73 (s, 3H), 2.37 (q, J=10.7 Hz, 1H), 2.22 (ddt, J=15.4, 9.6, 5.2 Hz, 1H), 2.12-1.98 (m, 1H), 1.95-1.80 (m, 1H), 1.73 (dd, J=14.5, 7.2 Hz, 1H), 1.51 (s, 18H), 1.40 (d, J=6.4 Hz, 3H), 1.15 (dd, J=16.0, 7.7 Hz, 1H); $^{19}$F NMR (376 MHz, CDCl$_3$) δ −122.84; HRMS-ESI (m/z) [M+Na]$^+$ calcd for C$_{32}$H$_{42}$FNNaO$_9$, 626.2736; found, 626.2739.

Example 12C, Step 2

Preparation of [(3S,7S,8S,9S)-8-(4-fluorophenoxy)-7-(4-methoxyphenoxy)-9-methyl-2-oxo-oxonan-3-yl]ammonium chloride (F5)

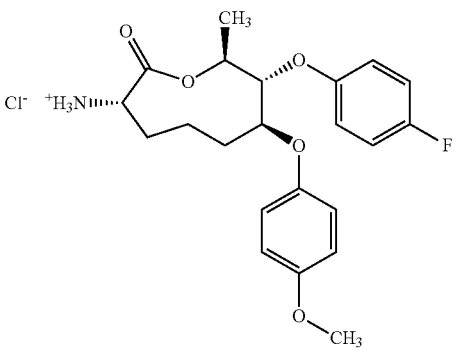 [SMILES: [Cl-] ; COc1ccc(O[C@H]2CCC[C@H]([NH3+])C(=O)O[C@@H](C)[C@@H]2Oc2ccc(F)cc2)cc1]

Prepared according to the methods described in Example 12A.

Example 13

Preparation of tert-butyl N-tert-butoxycarbonyl-N-[(3S,7S,8R,9S)-7-hydroxy-9-methyl-8-(2-methylallyloxy)-2-oxo-oxonan-3-yl]carbamate (C20)

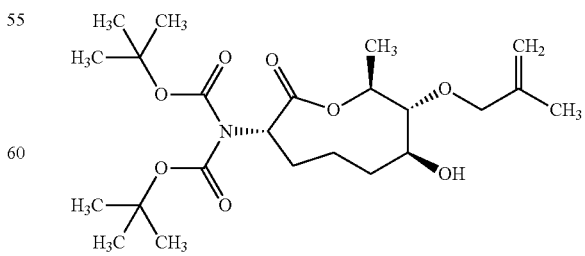

A solution of tert-butyl N-tert-butoxycarbonyl-N-[(3S,7S,8R,9S)-7,8-dihydroxy-9-methyl-2-oxo-oxonan-3-yl]carbamate (100 mg, 0.25 mmol), bis(2-methylallyl) carbonate (51 mg, 0.30 mmol), dppf (14 mg, 0.025 mmol) and Pd$_2$(dba)$_3$ (11.4 mg, 0.012 mmol) in degassed THF (1.24 mL) was heated to 60° C. for 1.5 h. The solution was cooled to room temperature and purified by column chromatography (SiO$_2$; 0→5% EtOAc/hexanes) to yield the title compound (61 mg, 54%) as a white solid: $^1$H NMR (400 MHz, CDCl$_3$) δ 5.03-4.97 (m, 1H), 4.90 (s, 1H), 4.82 (dd, J=10.4, 7.1 Hz, 1H), 4.74 (dq, J=9.5, 6.3 Hz, 1H), 4.09 (s, 2H), 3.64-3.56 (m, 1H), 3.23 (dd, J=9.4, 7.7 Hz, 1H), 2.53 (d, J=1.5 Hz, 1H), 2.43-2.30 (m, 1H), 2.12-2.00 (m, 1H), 1.92-1.80 (m, 1H), 1.77 (m, 5H), 1.61-1.45 (m, 19H), 1.42 (d, J=6.4 Hz, 3H); $^{13}$C NMR (101 MHz, CDCl$_3$) δ 170.73, 152.84, 141.85, 112.38, 85.49, 82.70, 77.62, 73.37, 72.70, 57.77, 34.76, 30.87, 27.96, 19.99, 19.67, 18.23; HRMS-ESI (m/z) [M+Na]$^+$ calcd for C$_{23}$H$_{39}$NNaO$_8$, 480.2568; found, 480.2572.

The following compounds were prepared and isolated using the appropriately substituted allyl carbonate and the methodology described in Example 13:

tert-Butyl N-tert-butoxycarbonyl-N-[(3S,7S,8S,9S)-8-hydroxy-9-methyl-7-(2-methylallyloxy)-2-oxo-oxonan-3-yl]carbamate (C21)

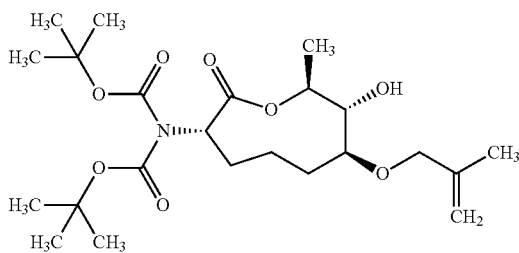 [SMILES: C=C(C)CO[C@H]1CCC[C@H](N(C(=O)OC(C)(C)C)C(=O)OC(C)(C)C)C(=O)O[C@@H](C)[C@@H]1O]

Isolated as a white solid (25 mg; 22%): $^1$H NMR (400 MHz, CDCl$_3$) δ 5.01-4.95 (m, 1H), 4.91 (s, 1H), 4.85 (dd, J=9.5, 7.6 Hz, 1H), 4.80-4.67 (m, 1H), 4.01 (d, J=12.2 Hz, 1H), 3.83 (d, J=12.2 Hz, 1H), 3.56 (ddd, J=9.5, 7.7, 2.0 Hz, 1H), 3.21 (td, J=7.6, 2.1 Hz, 1H), 2.85 (d, J=2.0 Hz, 1H), 2.40-2.23 (m, 1H), 2.13-2.00 (m, 1H), 1.93 (dt, J=14.0, 6.9 Hz, 1H), 1.84-1.73 (m, 4H), 1.70-1.56 (m, 1H), 1.51 (s, 18H), 1.46-1.38 (m, 4H); $^{13}$C NMR (101 MHz, CDCl$_3$) δ 170.74, 152.92, 141.77, 112.89, 82.69, 81.96, 75.76, 73.49, 73.25, 57.61, 31.12, 31.04, 27.98, 20.37, 19.67, 18.16; HRMS-ESI (m/z) [M+Na]$^+$ calcd for C$_{23}$H$_{39}$NNaO$_8$, 480.2568; found, 480.2576.

tert-Butyl N-tert-butoxycarbonyl-N-[(3S,7S,8S,9S)-9-methyl-7,8-bis(2-methylallyloxy)-2-oxo-oxonan-3-yl]carbamate (C22)

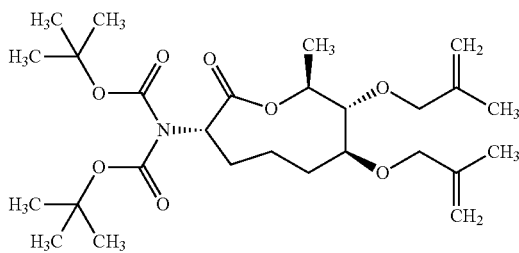 [SMILES: C=C(C)CO[C@H]1[C@H](C)OC(=O)[C@@H](N(C(=O)OC(C)(C)C)C(=O)OC(C)(C)C)CCC[C@@H]1OCC(=C)C]

Isolated as a white solid (200 mg; 5%): $^1$H NMR (400 MHz, CDCl$_3$) δ 5.03-4.91 (m, 2H), 4.90-4.75 (m, 3H), 4.67 (dq, J=9.0, 6.3 Hz, 1H), 4.25 (d, J=11.7 Hz, 1H), 3.99 (dd, J=21.0, 11.9 Hz, 2H), 3.90-3.79 (m, 1H), 3.56-3.35 (m, 2H), 2.44-2.27 (m, 1H), 2.12 (ddd, J=23.7, 9.0, 5.0 Hz, 1H), 2.02 (dt, J=13.3, 6.5 Hz, 1H), 1.74 (s, 3H), 1.75 (s, 3H), 1.72-1.54 (m, 3H), 1.51 (s, 18H), 1.40 (d, J=6.3 Hz, 3H), 1.03-0.91 (m, 1H); $^{13}$C NMR (101 MHz, CDCl$_3$) δ 170.86, 152.90, 142.54, 142.48, 112.09, 111.94, 83.62, 82.67, 73.10, 72.99, 57.43, 30.55, 28.52, 27.98, 19.80, 19.70, 19.24, 18.12; EIMS m/z 534.8 ([M+Na]$^+$)

tert-Butyl N-tert-butoxycarbonyl-N-[(3S,7S,8R,9S)-8-cyclopent-2-en-1-yloxy-7-hydroxy-9-methyl-2-oxo-oxonan-3-yl]carbamate (C23)

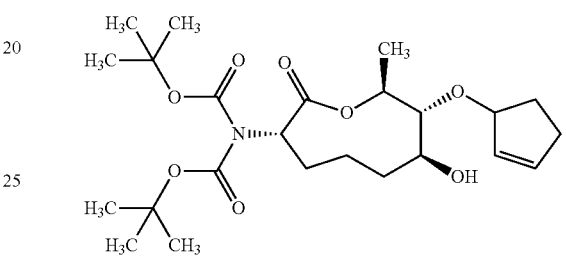

Isolated as a yellow foam (344 mg, 41%): IR (neat) 3520, 2978, 2928, 1744, 1704, 1358 cm$^{-1}$; $^1$H NMR (400 MHz, CDCl$_3$) δ 6.09-6.04 (m, 1H), 5.96 (dq, J=5.9, 2.1 Hz, 0.5H), 5.86 (dq, J=5.8, 2.2 Hz, 0.5H), 4.88-4.63 (m, 3H), 3.55-3.39 (m, 1H), 3.34-3.28 (m, 1H), 2.61-1.99 (m, 7H), 1.92-1.69 (m, 4H), 1.51 (s, 18H), 1.44 (d, J=6.4 Hz, 1.5H), 1.42 (d, J=6.4 Hz, 1.5H); ESIMS m/z 492.3 ([M+Na]$^+$).

Example 13A, Step 1

Preparation of tert-butyl N-tert-butoxycarbonyl-N-[(3S,7S,8S,9S)-7,8-diisobutoxy-9-methyl-2-oxo-oxonan-3-yl]carbamate (C24)

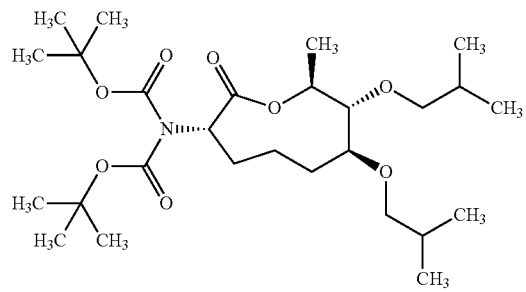 [SMILES: CC(C)CO[C@H]1[C@H](C)OC(=O)[C@@H](N(C(=O)OC(C)(C)C)C(=O)OC(C)(C)C)CCC[C@@H]1OCC(C)C]

To a solution of tert-butyl N-tert-butoxycarbonyl-N-[(3S,7S,8S,9S)-9-methyl-7,8-bis(2-methylallyloxy)-2-oxo-oxonan-3-yl]carbamate (333 mg, 0.651 mmol) in EtOAc (6.51 mL) was added Pd/C (10% w/w Pd, 34.6 mg, 0.033 mmol). The atmosphere was replaced with 1 atm hydrogen (balloon) and the reaction was stirred overnight at room temperature. The reaction mixture was filtered through Celite® and the pad was flushed with EtOAc. The filtrate was concentrated to provide the title compound (313 mg, 93%) as a white, crystalline solid: IR (thin film) 2957, 1742, 1724, 1470, 1366, 1347, 1245, 1104 cm$^{-1}$; $^1$H NMR (400 MHz, CDCl$_3$) δ 4.80 (dd, J=10.5, 8.0 Hz, 1H), 4.69-4.54 (m, 1H), 3.60 (dd, J=8.6, 6.2 Hz, 1H), 3.40-3.21 (m, 4H), 3.11 (dd, J=8.7, 6.3 Hz, 1H), 2.42-2.25 (m, 1H), 2.20-2.05 (m, 1H), 2.01 (m, 1H), 1.81 (tt, J=12.7, 6.3 Hz, 2H), 1.73-1.55 (m, 3H), 1.51 (s, 18H), 1.42-1.32 (m, 3H), 1.01-0.80 (m, 12H); $^{13}$C NMR (101 MHz, CDCl$_3$) δ 170.91, 152.89, 84.27, 83.65, 82.64, 80.41, 75.84, 73.15, 57.46, 30.53, 29.07, 28.89, 28.20, 27.98, 19.58, 19.54, 19.39, 19.18, 18.12.

Example 13A, Step 2

Preparation of [(3S,7S,8S,9S)-7,8-diisobutoxy-9-methyl-2-oxo-oxonan-3-yl]ammonium chloride (F6)

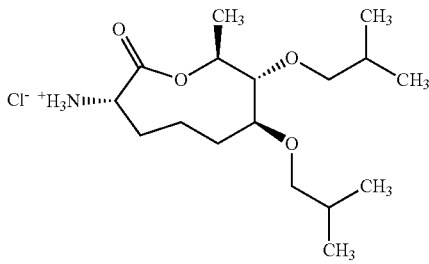 [SMILES: [Cl-] ; CC(C)CO[C@H]1[C@H](C)OC(=O)[C@@H]([NH3+])CCC[C@@H]1OCC(C)C]

Prepared according to the methods described in Example 12A.

Example 13B, Step 1

Preparation of tert-butyl N-tert-butoxycarbonyl-N-[(3S,7S,8S,9S)-8-hydroxy-7-isobutoxy-9-methyl-2-oxo-oxonan-3-yl]carbamate (C25)

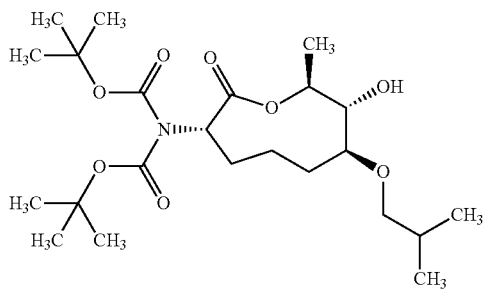 [SMILES: CC(C)CO[C@H]1CCC[C@H](N(C(=O)OC(C)(C)C)C(=O)OC(C)(C)C)C(=O)O[C@@H](C)[C@@H]1O]

To a solution of tert-butyl N-tert-butoxycarbonyl-N-[(3S,7S,8S,9S)-8-hydroxy-9-methyl-7-(2-methylallyloxy)-2-oxo-oxonan-3-yl]carbamate (1.00 g, 2.19 mmol) in EtOAc (4 mL) in a vial was added Pd/C (5% w/w Pd, 0.233 g). The vial was evacuated and backfilled with hydrogen (1 atm), then stirred vigorously at room temperature. After stirring overnight, the reaction mixture was filtered through a pad of Celite® and concentrated to yield a white solid (1.06 g, 95%): IR (thin film) 3448, 3224, 2960, 2934, 2877, 1752, 1742, 1723, 1139, 1119 cm$^{-1}$; $^1$H NMR (400 MHz, CDCl$_3$) δ 4.85 (dd, J=9.4, 7.4 Hz, 1H), 4.73 (dq, J=9.5, 6.3 Hz, 1H), 3.51 (ddd, J=9.5, 7.6, 1.8 Hz, 1H), 3.35 (dd, J=8.9, 6.7 Hz, 1H), 3.11 (dd, J=8.8, 6.3 Hz, 2H), 2.93 (d, J=1.8 Hz, 1H), 2.30 (dtd, J=14.0, 9.8, 1.9 Hz, 1H), 2.13-2.00 (m, 1H), 1.95-1.74 (m, 3H), 1.68-1.61 (m, 1H), 1.61-1.58 (m, 1H), 1.51 (s, 18H), 1.42 (d, J=6.3 Hz, 3H), 0.91 (dd, J=6.7, 1.2 Hz, 6H); $^{13}$C NMR (101 MHz, CDCl$_3$) δ 170.77, 152.92, 82.71, 82.40, 76.26, 75.85, 73.63, 57.69, 31.43, 31.22, 28.69, 27.99, 20.52, 19.41, 19.36, 18.19; HRMS-ESI (m/z) [M+Na]$^+$ calcd for C$_{23}$H$_{41}$NNaO$_8$, 482.2724; found, 482.2718.

The following compounds were prepared and isolated using the methodology described in Example 13B, Step 1:

tert-Butyl N-tert-butoxycarbonyl-N-[(3S,7S,8R,9S)-7-hydroxy-8-isobutoxy-9-methyl-2-oxo-oxonan-3-yl]carbamate (C26)

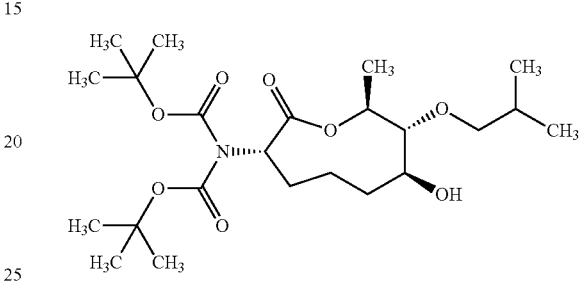

Isolated as a colorless oil (600 mg, 100%): $^1$H NMR (400 MHz, CDCl$_3$) δ 4.81 (dd, J=10.5, 6.9 Hz, 1H), 4.77-4.66 (m, 1H), 3.60-3.50 (m, 1H), 3.47 (dd, J=8.6, 6.3 Hz, 1H), 3.40 (dd, J=8.6, 6.7 Hz, 1H), 3.12 (dd, J=9.5, 7.7 Hz, 1H), 2.63-2.56 (m, 1H), 2.36 (ddt, J=13.7, 11.1, 4.9 Hz, 1H), 2.12-1.98 (m, 1H), 1.95-1.75 (m, 4H), 1.53-1.50 (m, 1H), 1.51 (s, 18H), 1.41 (d, J=6.3 Hz, 3H), 0.93 (dd, J=6.7, 3.3 Hz, 6H); $^{13}$C NMR (101 MHz, CDCl$_3$) δ 170.72, 152.82, 85.27, 82.67, 80.81, 72.95, 72.82, 57.87, 35.34, 30.89, 29.03, 27.95, 20.13, 19.33, 19.23, 18.26.

Example 13B, Step 2

Preparation of tert-butyl N-tert-butoxycarbonyl-N-[(3S,7S,8S,9S)-7-isobutoxy-8-(4-methoxyphenoxy)-9-methyl-2-oxo-oxonan-3-yl]carbamate (C27)

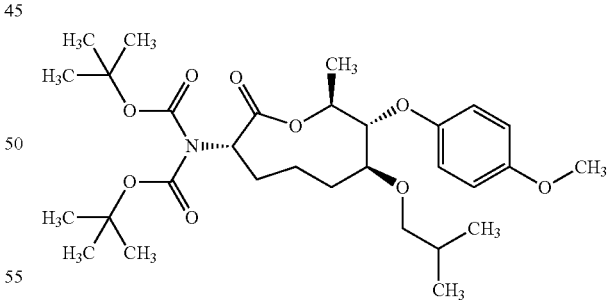

A vial was charged with tert-butyl N-tert-butoxycarbonyl-N-[(3S,7S,8S,9S)-8-hydroxy-7-isobutoxy-9-methyl-2-oxo-oxonan-3-yl]carbamate (50 mg, 0.11 mmol), tris(p-methoxyphenyl)bismuth diacetate (106 mg, 0.163 mmol), toluene (544 µl) and diacetoxycopper (2.0 mg, 11 µmol). N-cyclohexyl-N-methylcyclohexanamine (46.2 µl, 0.218 mmol) was added and the reaction was heated to 50° C. and stirred overnight. The heterogeneous mixture was filtered through a plug of Celite®, the filtrate concentrated, and the residue purified by automated flash chromatography (0→50% EtOAc/hexanes) to afford a colorless semi-solid (43 mg, 69%): $^1$H NMR (400 MHz, CDCl$_3$) δ 7.01 (d, J=9.1 Hz, 2H), 6.79 (d, J=9.1 Hz, 2H), 4.96-4.72 (m, 2H), 4.23 (dd, J=9.6, 7.3 Hz, 1H), 3.76 (s, 3H), 3.51 (ddd, J=7.1, 5.1, 1.8 Hz, 1H), 3.24 (dd, J=8.8, 6.7 Hz, 1H), 3.08 (dd, J=8.8, 6.2 Hz, 1H), 2.44-2.33 (m, 1H), 2.18 (dddd, J=15.5, 10.0, 8.1, 5.1 Hz, 1H), 2.05 (dddd, J=13.6, 8.2, 6.3, 1.7 Hz, 1H), 1.83-1.64 (m, 3H), 1.52 (s, 18H), 1.34 (d, J=6.3 Hz, 3H), 1.03 (ddt, J=15.8, 7.6, 1.9 Hz, 1H), 0.79 (dd, J=18.5, 6.7 Hz, 3H); $^{13}$C NMR (101 MHz, CDCl$_3$) δ 170.85, 154.09, 154.02, 152.86, 117.55, 114.37, 83.88, 83.14, 82.73, 76.36, 72.80, 57.40, 55.68, 30.57, 28.73, 28.38, 27.98, 19.43, 19.29, 19.21, 18.28; IR (thin film) 2977, 1744, 1704, 1506, 1140 cm$^{-1}$; HRMS-ESI (m/z) [M+Na]$^+$ calcd for C$_{30}$H$_{47}$NNaO$_9$, 588.3143; found, 588.3146.

Example 13B, Step 3

Preparation of [(3S,7S,8S,9S)-7-isobutoxy-8-(4-methoxyphenoxy)-9-methyl-2-oxo-oxonan-3-yl]ammonium chloride (F7)

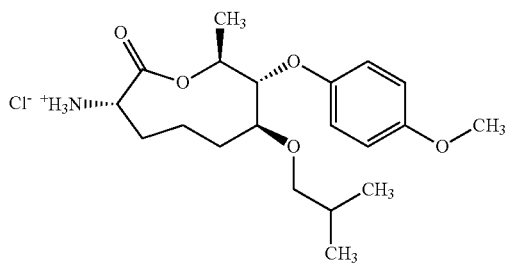 [SMILES: [Cl-] ; COc1ccc(O[C@H]2[C@H](C)OC(=O)[C@@H]([NH3+])CCC[C@@H]2OCC(C)C)cc1]

Prepared according to the methods described in Example 12A.

Example 13C, Step 1

Preparation of tert-butyl N-tert-butoxycarbonyl-N-[(3S,7S,8S,9S)-9-methyl-8-(2-methylallyloxy)-2-oxo-7-phenoxy-oxonan-3-yl]carbamate (An alternate method to prepare C16)

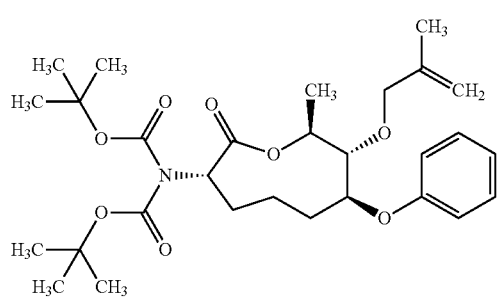 [SMILES: C=C(C)CO[C@H]1[C@H](C)OC(=O)[C@@H](N(C(=O)OC(C)(C)C)C(=O)OC(C)(C)C)CCC[C@@H]1Oc1ccccc1]

A solution of tert-butyl N-tert-butoxycarbonyl-N-[(3S,7S,8R,9S)-7-hydroxy-9-methyl-8-(2-methylallyloxy)-2-oxo-oxonan-3-yl]carbamate (56.0 mg, 0.122 mmol), triphenyl-bismuth diacetate (137 mg, 0.245 mmol) and diacetoxycopper (4.4 mg, 0.024 mmol) in toluene (1224 µl) was stirred at 40° C. overnight. The reaction mixture was filtered thru Celite®, the pad washed with toluene (2×10 mL), and the filtrate concentrated to yield a light blue foam. Purification by column chromatography (SiO$_2$; 0→20% EtOAc/hexanes) afforded the title compound (45 mg, 69%) as a white solid: See Compound 16 (Example 12B, Step 1) for analytical data.

Example 13C, Step 2

Preparation of tert-butyl N-tert-butoxycarbonyl-N-[(3S,7S,8S,9S)-8-isobutoxy-9-methyl-2-oxo-7-phenoxy-oxonan-3-yl]carbamate (An alternate method to prepare C18)

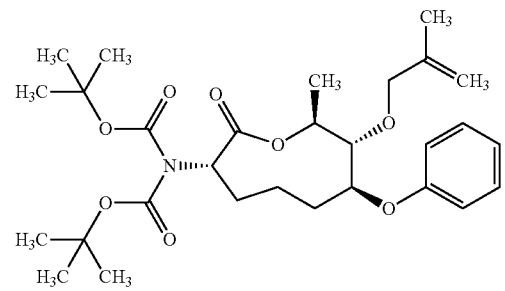 [SMILES: C=C(C)CO[C@H]1[C@H](C)OC(=O)[C@@H](N(C(=O)OC(C)(C)C)C(=O)OC(C)(C)C)CCC[C@@H]1Oc1ccccc1]

Prepared according to the procedure described for example 12B step 2 and isolated as a clear oil (430 mg; 100%): $^1$H NMR (400 MHz, CDCl$_3$) δ 7.32-7.22 (m, 2H), 6.99-6.86 (m, 3H), 4.86 (dd, J=10.2, 8.2 Hz, 1H), 4.75 (dq, J=9.7, 6.3 Hz, 1H), 4.43-4.26 (m, 1H), 3.66-3.50 (m, 2H), 3.36 (dd, J=8.7, 6.7 Hz, 1H), 2.44-2.24 (m, 1H), 2.24-2.08 (m, 1H), 2.04-1.91 (m, 1H), 1.89-1.56 (m, 3H), 1.53-1.46 (m, 18H), 1.44 (d, J=6.3 Hz, 3H), 1.06 (dd, J=16.0, 7.9 Hz, 1H), 0.82 (d, J=6.7 Hz, 3H), 0.78 (d, J=6.7 Hz, 3H); $^{13}$C NMR (101 MHz, CDCl$_3$) δ 170.78, 157.65, 152.86, 129.44, 121.06, 116.54, 83.33, 83.06, 82.71, 80.56, 72.93, 57.27, 30.46, 28.97, 28.85, 27.97, 19.39, 19.28, 19.17, 18.15; HRMS-ESI (m/z) [M+Na]$^+$ calcd for C$_{29}$H$_{45}$NNaO$_8$, 558.3037; found, 558.2994.

Example 13C, Step 3

Preparation of [(3S,7S,8S,9S)-8-isobutoxy-9-methyl-2-oxo-7-phenoxy-oxonan-3-yl]ammonium chloride (An alternative route to prepare F4)

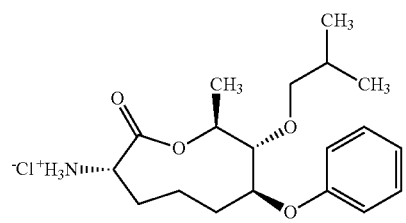

Prepared according to the methods described in Example 12B, Step 3.

Example 13D, Step 1

Preparation of [(2S,3S,4S,8S)-8-[bis(tert-butoxycarbonyl)amino]-3-isobutoxy-2-methyl-9-oxo-oxonan-4-yl]cyclopentanecarboxylate (C28)

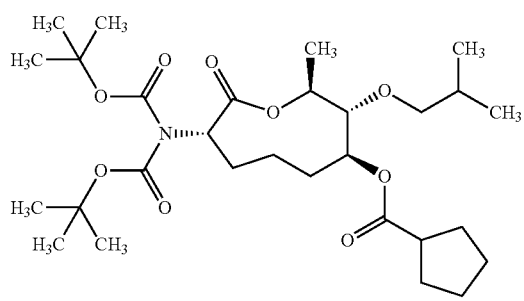 [SMILES: CC(C)CO[C@H]1[C@H](C)OC(=O)[C@@H](N(C(=O)OC(C)(C)C)C(=O)OC(C)(C)C)CCC[C@@H]1OC(=O)C1CCCC1]

To a 10 mL screw-cap vial were added tert-butyl N-tert-butoxycarbonyl-N-[(3S,7S,8R,9S)-7-hydroxy-8-isobutoxy-9-methyl-2-oxo-oxonan-3-yl]carbamate (200 mg, 0.44 mmol), pyridine (105 µl, 1.31 mmol) and CH$_2$Cl$_2$ (2176 µl), followed by cyclopentanecarbonyl chloride (79 µl, 0.65 mmol). The vial was sealed under N$_2$ and the reaction was magnetically stirred overnight. The crude mixture was purified by column chromatography (SiO$_2$, 1→25% acetone/hexanes) to yield the title compound (203 mg, 84%): $^1$H NMR (400 MHz, CDCl$_3$) δ 4.92 (ddd, J=7.4, 5.3, 1.9 Hz, 1H), 4.85 (dd, J=10.3, 8.0 Hz, 1H), 4.72 (dq, J=9.7, 6.3 Hz, 1H), 3.45 (dd, J=9.6, 7.6 Hz, 1H), 3.39-3.28 (m, 2H), 2.72 (p, J=7.9 Hz, 1H), 2.40-2.26 (m, 1H), 2.17-1.95 (m, 2H), 1.92-1.69 (m, 8H), 1.58 (ddd, J=10.7, 5.5, 3.0 Hz, 3H), 1.51 (s, 18H), 1.41 (d, J=6.3 Hz, 3H), 1.12-1.00 (m, 1H), 0.86 (t, J=7.0 Hz, 6H); $^{13}$C NMR (101 MHz, CDCl$_3$) δ 175.65, 170.57, 152.78, 82.78, 82.17, 80.05, 77.85, 72.95, 57.22, 44.14, 30.53, 30.22, 29.75, 29.58, 28.99, 27.97, 25.79, 19.36, 19.28, 18.04; ESIMS m/z 578.4 [(M+Na)$^+$].

The following compounds were prepared and isolated using the methodology described in Example 13D, Step 1:

[(2S,3S,4S,8S)-8-[bis(tert-butoxycarbonyl)amino]-4-isobutoxy-2-methyl-9-oxo-oxonan-3-yl]cyclopentanecarboxylate (C29)

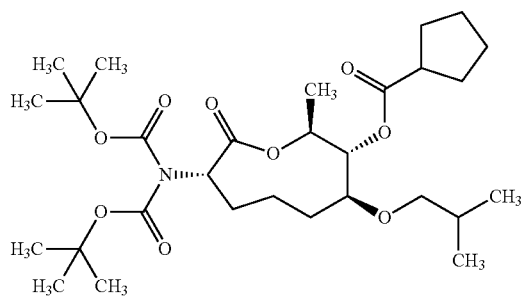 [SMILES: CC(C)CO[C@H]1CCC[C@H](N(C(=O)OC(C)(C)C)C(=O)OC(C)(C)C)C(=O)O[C@@H](C)[C@@H]1OC(=O)C1CCCC1]

Isolated as a white solid (98%): mp 101-106° C.; $^1$H NMR (400 MHz, CDCl$_3$) δ 5.12 (dd, J=9.7, 7.8 Hz, 1H), 4.88-4.73 (m, 2H), 3.36 (ddd, J=7.5, 5.2, 2.0 Hz, 1H), 3.26 (dd, J=8.7, 6.3 Hz, 1H), 2.97 (dd, J=8.7, 6.6 Hz, 1H), 2.72 (p, J=7.9 Hz, 1H), 2.36 (tdd, J=12.5, 10.3, 1.9 Hz, 1H), 2.22-1.98 (m, 2H), 1.95-1.55 (m, 10H), 1.51 (s, 18H), 1.26 (d, J=6.4 Hz, 3H), 1.02 (ddt, J=15.7, 7.3, 2.0 Hz, 1H), 0.84 (d, J=6.7 Hz, 6H); $^{13}$C NMR (101 MHz, CDCl$_3$) δ 175.60, 170.93, 152.83, 82.71, 81.23, 76.10, 75.21, 71.65, 57.37, 43.98, 30.58, 30.13, 29.74, 28.69, 28.36, 27.97, 25.81, 25.70, 19.38, 19.34, 18.96, 17.38; ESIMS m/z 578.5 ([M+Na]$^+$).

Example 13D, Step 2

Preparation of [(3S,7S,8S,9S)-7-(cyclopentanecarbonyloxy)-8-isobutoxy-9-methyl-2-oxo-oxonan-3-yl]ammonium chloride (F8)

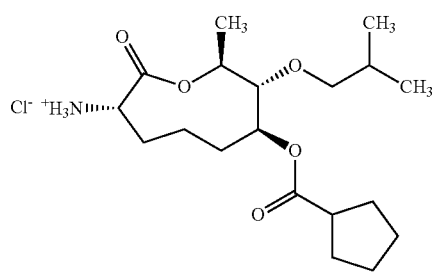 [SMILES: [Cl-] ; CC(C)CO[C@H]1[C@H](C)OC(=O)[C@@H]([NH3+])CCC[C@@H]1OC(=O)C1CCCC1]

Prepared according to the methods described in Example 12A.

The following compounds were prepared and isolated using the methodology described in Example 13D, Step 2:

[(3S,7S,8S,9S)-8-(cyclopentanecarbonyloxy)-7-isobutoxy-9-methyl-2-oxo-oxonan-3-yl]ammonium chloride (F9)

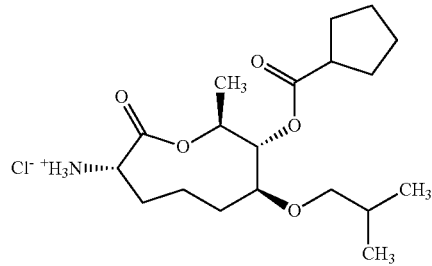 [SMILES: [Cl-] ; CC(C)CO[C@H]1CCC[C@H]([NH3+])C(=O)O[C@@H](C)[C@@H]1OC(=O)C1CCCC1]

Example 13E, Step 1

Preparation of (2S,3S,4S,8S)-8-((bis tert-butoxycarbonyl)amino)-2-methyl-4-((2-methylallyl)oxy)-9-oxooxonan-3-yl cyclopropanecarboxylate (C30)

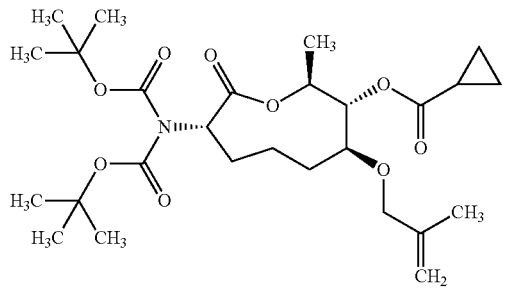 [SMILES: C=C(C)CO[C@H]1CCC[C@H](N(C(=O)OC(C)(C)C)C(=O)OC(C)(C)C)C(=O)O[C@@H](C)[C@@H]1OC(=O)C1CC1]

To a solution tert-butyl N-tert-butoxycarbonyl-N-[(3S,7S,8S,9S)-8-hydroxy-9-methyl-7-(2-methylallyloxy)-2-oxo-oxonan-3-yl]carbamate (500 mg, 1.09 mmol) in CH$_2$Cl$_2$ (2.2 mL) was added pyridine (0.265 mL, 3.28 mmol) and cyclopropanecarbonyl chloride (0.149 mL, 1.64 mmol). The resulting solution was stirred at room temperature for 16 h, then purified by automated silica gel column chromatography (0→100% EtOAc/hexanes) to provide a light yellow solid (599 mg, 99%): IR (thin film) 2979, 2938, 1737, 1703, 1355, 1159 cm$^-$; $^1$H NMR (400 MHz, CDCl$_3$) δ 5.14 (dd, J=9.7, 7.8 Hz, 1H), 4.95-4.66 (m, 4H), 3.94 (d, J=12.3 Hz, 1H), 3.76 (d, J=12.2 Hz, 1H), 3.46 (ddd, J=7.6, 5.3, 1.9 Hz, 1H), 2.37 (q, J=11.9, 11.3 Hz, 1H), 2.21-2.00 (m, 2H), 1.87-1.74 (m, 1H) 1.71 (s, 3H), 1.51 (s, 18H), 1.28 (d, J=6.3 Hz, 3H), 1.17 (dt, J=6.9, 4.2 Hz, 1H), 1.11-0.97 (m, 4H), 0.87 (dq, J=6.4, 3.7 Hz, 2H); $^{13}$C NMR (101 MHz, CDCl$_3$) δ 173.98, 170.89, 152.84, 142.11, 112.39, 82.73, 80.01, 75.46, 73.07, 71.66, 57.36, 30.57, 28.55, 27.97, 19.41, 19.03, 17.36, 12.89, 10.18, 8.49, 8.43.

Example 13E, Step 2

Preparation of (2S,3S,4S,8S)-8-((bis tert-butoxycarbonyl)amino)-4-isobutoxy-2-methyl-9-oxooxonan-3-yl cyclopropanecarboxylate (C31)

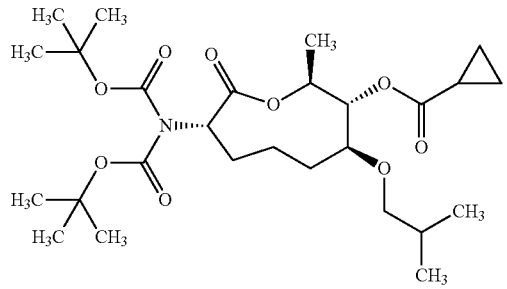 [SMILES: CC(C)CO[C@H]1CCC[C@H](N(C(=O)OC(C)(C)C)C(=O)OC(C)(C)C)C(=O)O[C@@H](C)[C@@H]1OC(=O)C1CC1]

Prepared according to the methodology described in Example 13B, Step 1 to give the title compound (424 mg, 89%) as a white solid: IR (thin film) 2978, 1739, 1706, 1162 cm$^{-1}$; $^1$H NMR (400 MHz, CDCl$_3$) δ 5.11 (dd, J=9.7, 7.8 Hz, 1H), 4.88-4.70 (m, 2H), 3.36 (ddd, J=7.6, 5.2, 2.0 Hz, 1H), 3.30 (dd, J=8.8, 6.1 Hz, 1H), 2.98 (dd, J=8.8, 6.8 Hz, 1H), 2.36 (dddd, J=13.9, 12.1, 10.1, 1.8 Hz, 1H), 2.22-1.97 (m, 2H), 1.85-1.69 (m, 2H), 1.70-1.55 (m, 2H), 1.51 (s, 18H), 1.27 (d, J=6.4 Hz, 3H), 1.12-0.96 (m, 3H), 0.91-0.82 (m, 8H); $^{13}$C NMR (101 MHz, CDCl$_3$) δ 173.94, 170.92, 152.84, 82.72, 81.25, 76.30, 75.50, 71.65, 57.37, 30.61, 28.63, 27.97, 19.32, 19.27, 19.00, 17.35, 12.89, 8.43, 8.36; HRMS-ESI (m/z) [M+H]$^+$ calcd for C$_2$H$_{46}$NO$_9$, 528.3167; found, 528.3167.

Example 13E, Step 3

Preparation of [(3S,7S,8S,9S)-8-(cyclopropanecarbonyloxy)-7-isobutoxy-9-methyl-2-oxo-oxonan-3-yl]ammonium chloride (F10)

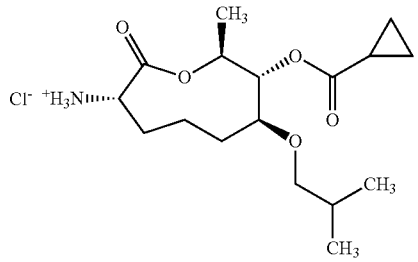 [SMILES: [Cl-] ; CC(C)CO[C@H]1CCC[C@H]([NH3+])C(=O)O[C@@H](C)[C@@H]1OC(=O)C1CC1]

Prepared according to the methods described in Example 12A.

Example 13F, Step 1

Preparation of tert-butyl N-tert-butoxycarbonyl-N-[(3S,7S,8S,9S)-9-methyl-7-(2-methylallyloxy)-2-oxo-8-[(E)-4,4,4-trifluorobut-2-enoxy]oxonan-3-yl]carbamate (C32)

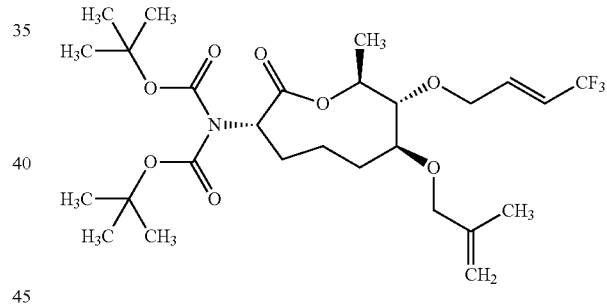

A solution of tert-butyl N-tert-butoxycarbonyl-N-[(3S,7S,8S,9S)-8-hydroxy-9-methyl-7-(2-methylallyloxy)-2-oxo-oxonan-3-yl]carbamate (499 mg, 1.09 mmol), (E)-bis tert-butyl (4,4,4-trifluorobut-2-en-1-yl) carbonate (493 mg, 2.18 mmol), dppf (60.5 mg, 0.109 mmol) and Pd$_2$(dba)$_3$ (49.9 mg, 0.055 mmol) in degassed THF (5453 µl) was heated to 60° C. for 1.5 h. The solution was cooled to room temperature and purified by automated flash chromatography (SiO2; 0→10% EtOAc/hexanes) to yield the title compound as a yellow semi-solid (292 mg, 73%): $^1$H NMR (400 MHz, CDCl$_3$) δ 6.44-6.36 (m, 1H), 5.96-5.78 (m, 1H), 4.96-4.92 (m, 1H), 4.88-4.85 (m, 1H), 4.82 (dd, J=10.3, 8.0 Hz, 1H), 4.73-4.64 (m, 1H), 4.46 (m, 1H), 4.30-4.21 (m, 1H), 3.96 (d, J=12.1 Hz, 1H), 3.79 (d, J=12.1 Hz, 1H), 3.50-3.39 (m, 2H), 2.36 (dd, J=12.0, 2.6 Hz, 1H), 2.19-1.98 (m, 2H), 1.72 (s, 3H), 1.70-1.59 (m, 2H), 1.51 (s, 18H), 1.38 (d, J=6.3 Hz, 3H), 0.97 (dd, J=16.3, 7.7 Hz, 1H); $^{13}$C NMR (101 MHz, CDCl$_3$) δ 170.79, 152.89, 142.25, 136.73, 118.34, 118.01, 112.25, 84.21, 83.30, 82.74, 77.21, 72.89, 72.49, 71.03, 57.31, 30.50, 28.23, 27.98, 19.59, 19.18, 18.04; ESIMS m/z 588.3 ([M+Na]$^+$).

Example 13F, Step 2

Preparation of tert-butyl N-tert-butoxycarbonyl-N-[(3S,7S,8S,9S)-7-isobutoxy-9-methyl-2-oxo-8-(4,4,4-trifluorobutoxy)oxonan-3-yl]carbamate (C33)

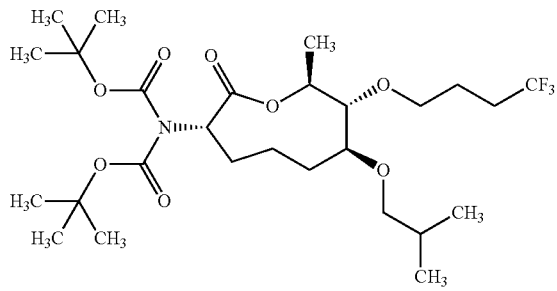 [SMILES: CC(C)CO[C@H]1CCC[C@H](N(C(=O)OC(C)(C)C)C(=O)OC(C)(C)C)C(=O)O[C@@H](C)[C@@H]1OCCCC(F)(F)F]

The tert-butyl N-tert-butoxycarbonyl-N-[(3S,7S,8S,9S)-9-methyl-7-(2-methylallyloxy)-2-oxo-8-[(E)-4,4,4-trifluorobut-2-enoxy]oxonan-3-yl]carbamate (451 mg, 0.80 mmol) was dissolved in EtOAc (4 mL) in a vial and Pd/C (5% w/w Pd, 85 mg, 0.040 mmol) was added. The vial was evacuated and backfilled with hydrogen (1 atm), then stirred vigorously at room temperature. After stirring for 16 h, the reaction mixture was filtered through a pad of Celite® and concentrated to provide a white solid (454 mg, 100%) $^1$H NMR (400 MHz, CDCl$_3$) δ 4.80 (dd, J=10.4, 8.0 Hz, 1H), 4.62 (pd, J=6.2, 2.0 Hz, 1H), 3.83 (dt, J=9.3, 6.0 Hz, 1H), 3.64 (dt, J=9.3, 6.1 Hz, 1H), 3.40-3.20 (m, 3H), 3.08 (dd, J=8.7, 6.2 Hz, 1H), 2.45-2.28 (m, 1H), 2.25-2.04 (m, 2H), 2.07-1.95 (m, 1H), 1.88-1.73 (m, 3H), 1.73-1.57 (m, 3H), 1.51 (s, 18H), 1.36 (d, J=6.4 Hz, 3H), 0.95-0.83 (m, 7H); $^{19}$F NMR (376 MHz, CDCl$_3$) δ −66.43; $^{13}$C NMR (101 MHz, CDCl$_3$) δ 170.88, 152.89, 84.07, 83.91, 82.70, 75.65, 72.75, 71.58, 57.39, 31.05, 30.76, 30.50, 28.88, 27.97, 23.07, 23.05, 19.55, 19.47, 19.11, 18.09; ESIMS m/z 592.3 ([M+Na]$^+$).

Example 13F, Step 3

Preparation of [(3S,7S,8S,9S)-7-isobutoxy-9-methyl-2-oxo-8-(4,4,4-trifluorobutoxy)oxonan-3-yl] ammonium chloride (F11)

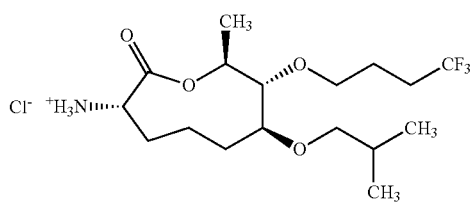 [SMILES: [Cl-] ; CC(C)CO[C@H]1CCC[C@H]([NH3+])C(=O)O[C@@H](C)[C@@H]1OCCCC(F)(F)F]

Prepared according to the methods described in Example 12A.

Example 13G, Step 1

Preparation of tert-butyl N-[(3S,7S,8S,9S)-7-allyloxy-8-cyclopent-2-en-1-yloxy-9-methyl-2-oxo-oxonan-3-yl]-N-tert-butoxycarbonyl-carbamate (C34)

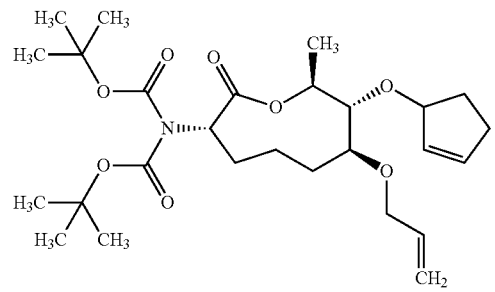 [SMILES: C=CCO[C@H]1CCC[C@H](N(C(=O)OC(C)(C)C)C(=O)OC(C)(C)C)C(=O)O[C@@H](C)[C@@H]1OC1C=CCC1]

To a solution of tert-butyl N-tert-butoxycarbonyl-N-[(3S,7S,8R,9S)-8-cyclopent-2-en-1-yloxy-7-hydroxy-9-methyl-2-oxo-oxonan-3-yl]carbamate (200 mg, 0.43 mmol), Pd$_2$(dba)$_3$ (39.0 mg, 0.043 mmol) and dppf (47.2 mg, 0.085 mmol) in THF (2.1 mL) at room temperature was added allyl tert-butyl carbonate (202 mg, 1.28 mmol). The reaction was stirred at 60° C. overnight. The reaction mixture was concentrated and purified by column chromatography on SiO$_2$ (5→25% EtOAc/hexanes) to yield the title compound as a yellow oil (160 mg, 74%): IR (thin film) 2978, 2933, 1742, 1703; $^1$H NMR (400 MHz, CDCl$_3$) δ 6.05-5.84 (m, 3H), 5.30-5.24 (m, 1H), 5.17-5.13 (m, 1H), 4.93-4.76 (m, 2H), 4.68-4.53 (m, 1H), 4.13-4.05 (m, 1H), 3.98-3.92 (m, 1H), 3.54-3.50 (m, 1H), 3.45-3.38 (m, 1H), 2.52-2.29 (m, 2H), 2.28-1.89 (m, 4H), 1.81-1.57 (m, 3H), 1.51 (s, 18H), 1.39 (d, J=6.4 Hz, 3H), 1.00-0.88 (m, 1H); ESIMS m/z 532.4 ([M+Na]$^+$).

Example 13G, Step 2

Preparation of tert-butyl N-tert-butoxycarbonyl-N-[(3S,7S,8S,9S)-8-(cyclopentoxy)-9-methyl-2-oxo-7-propoxy-oxonan-3-yl]carbamate (C35)

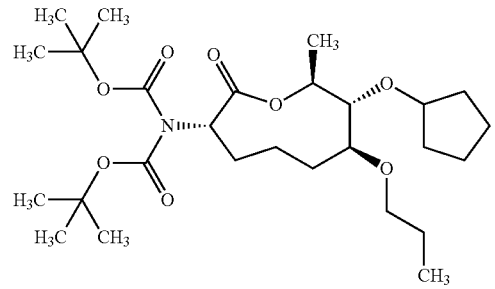 [SMILES: CCCO[C@H]1CCC[C@H](N(C(=O)OC(C)(C)C)C(=O)OC(C)(C)C)C(=O)O[C@@H](C)[C@@H]1OC1CCCC1]

Prepared according to the methodology described in Example 13F, Step 2 to give the title compound (286 mg, 95%) as a colorless oil): $^1$H NMR (400 MHz, CDCl$_3$) δ 4.79 (dd, J=10.6, 7.9 Hz, 1H), 4.57 (dq, J=9.5, 6.4 Hz, 1H), 4.32-4.25 (m, 1H), 3.53-3.37 (m, 2H), 3.35-3.27 (m, 2H), 2.42-2.28 (m, 1H), 2.19-1.95 (m, 2H), 1.83-1.53 (m, 12H), 1.51 (s, 18H), 1.37 (d, J=6.4 Hz, 3H), 0.92 (t, J=7.4 Hz, 3H), 0.90-0.87 (m, 1H); $^{13}$C NMR (101 MHz, CDCl$_3$) δ 170.93, 152.86, 84.28, 83.25, 82.60, 81.26, 73.34, 70.89, 57.47, 32.91, 32.35, 30.50, 28.36, 27.94, 23.33, 23.23, 23.19, 19.20, 18.20, 10.76; ESIMS m/z 536.5 ([M+Na]+).

Example 13G, Step 3

Preparation of [(3S,7S,8S,9S)-8-(cyclopentoxy)-9-methyl-2-oxo-7-propoxy-oxonan-3-yl]ammonium chloride (F11)

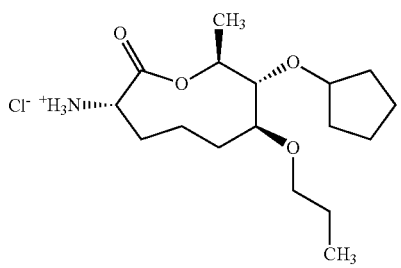 [SMILES: [Cl-] ; CCCO[C@H]1CCC[C@H]([NH3+])C(=O)O[C@@H](C)[C@@H]1OC1CCCC1]

Prepared according to the methods described in Example 12A.

Example 14

Preparation of (2S,3S,4S,8S)-8-((bis tert-butoxycarbonyl)amino)-2-methyl-9-oxooxonane-3,4-diyl dicyclopentanecarboxylate (C36)

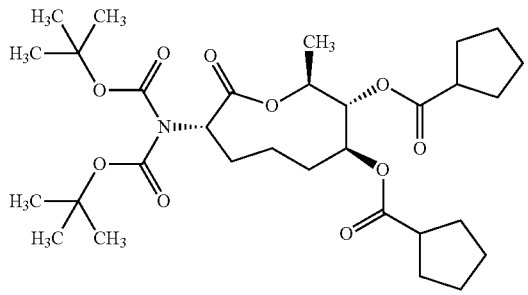 [SMILES: C[C@@H]1OC(=O)[C@@H](N(C(=O)OC(C)(C)C)C(=O)OC(C)(C)C)CCC[C@H](OC(=O)C2CCCC2)[C@H]1OC(=O)C1CCCC1]

A 20 mL vial was charged with tert-butyl N-tert-butoxycarbonyl-N-[(3S,7S,8R,9S)-7,8-dihydroxy-9-methyl-2-oxo-oxonan-3-yl]carbamate (300 mg, 0.74 mmol), CH$_2$Cl$_2$ (3.7 mL), and DMAP (182 mg, 1.49 mmol). Cyclopentanecarbonyl chloride (181 μL, 1.49 mmol) was added dropwise to the colorless solution, which then became dark brown. The reaction flask was placed in a room temperature water bath. The reaction mixture was stirred overnight, concentrated, and partially purified using automated flash chromatography (SiO$_2$; 0→100% EtOAc/hexanes) to give fractions that all contained an impurity derived from the cyclopentanecarbonyl chloride. The impure fractions were combined, washed with 1N HCl, then saturated NaHCO$_3$ and brine, and then concentrated to give a colorless oil (80.2 mg, 18%): IR (thin film) 2954, 1741, 1706, 1140 cm$^{-1}$; $^1$H NMR (400 MHz, CDCl$_3$) δ 5.24 (dd, J=9.9, 8.1 Hz, 1H), 5.00 (ddd, J=7.8, 5.2, 2.2 Hz, 1H), 4.92-4.81 (m, 2H), 2.83-2.72 (m, 2H), 2.36 (dddd, J=13.8, 12.1, 10.1, 1.8 Hz, 1H), 2.19-2.00 (m, 2H), 1.98-1.78 (m, 5H), 1.78-1.54 (m, 13H), 1.51 (s, 18H), 1.28 (d, J=6.3 Hz, 3H), 1.19 (ddt, J=16.2, 7.8, 2.2 Hz, 1H); $^{13}$C NMR (101 MHz, CDCl$_3$) δ 175.75, 175.55, 170.61, 152.75, 99.98, 82.86, 74.97, 73.67, 71.33, 57.12, 43.91, 43.80, 30.46, 30.07, 29.98, 29.93, 29.79, 29.62, 27.96, 25.76, 25.69, 19.08, 17.35; HRMS-ESI (m/z) [M+Na]+ calcd for C$_{31}$H$_{49}$NNaO$_{10}$, 618.3249; found, 618.3250.

Example 14A

Preparation of [(3S,7S,8S,9S)-7,8-bis(cyclopentanecarbonyloxy)-9-methyl-2-oxo-oxonan-3-yl]ammonium chloride (F12)

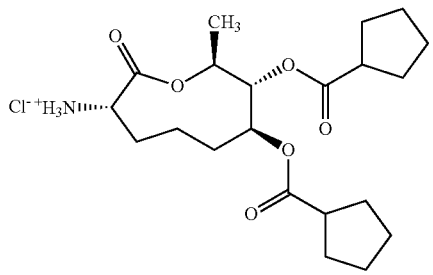 [SMILES: [Cl-] ; C[C@@H]1OC(=O)[C@@H]([NH3+])CCC[C@H](OC(=O)C2CCCC2)[C@H]1OC(=O)C1CCCC1]

Prepared according to the methods described in Example 12A.

Example 15, Step 1

Preparation of tert-butyl N-tert-butoxycarbonyl-N-[(3S,7S,8S,9S)-9-methyl-7-(2-methylallyloxy)-2-oxo-8-[3-oxobut-1-enoxy]oxonan-3-yl]carbamate (C37)

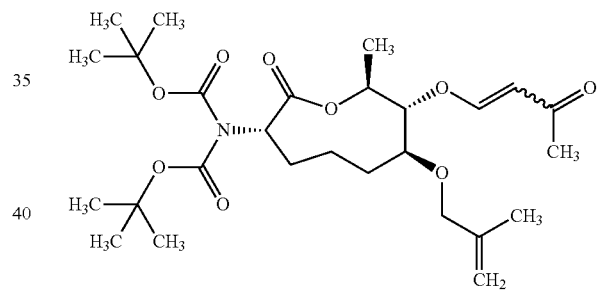

To a 100 mL round bottomed flask were charged tert-butyl N-tert-butoxycarbonyl-N-[(3S,7S,8S,9S)-8-hydroxy-9-methyl-7-(2-methylallyloxy)-2-oxo-oxonan-3-yl]carbamate (800 mg, 1.75 mmol), DABCO (9.8 mg, 0.087 mmol) and CH$_2$Cl$_2$ (8742 μl). The colorless solution was cooled to 0° C., then but-3-yn-2-one (163 μl, 2.10 mmol) was added dropwise over 10 min. The solution became dark brown. After stirring for 2 h, the reaction mixture was concentrated and purified by automated flash chromatography (SiO$_2$; 0→100% EtOAc/hexanes) to afford a white solid as an approximate 4:1 mixture of E/Z isomers (0.953 g, 100%): IR (thin film) 2976, 2937, 1742, 1727, 1632, 1139, 1119 cm$^{-1}$; $^1$H NMR (Major isomer; 400 MHz, CDCl$_3$) δ 7.50 (d, J=12.3 Hz, 1H), 5.67 (d, J=12.4 Hz, 1H), 4.95-4.76 (m, 4H), 3.94-3.86 (m, 2H), 3.76 (d, J=11.9 Hz, 1H), 3.46 (ddd, J=7.3, 4.9, 1.9 Hz, 1H), 2.49-2.32 (m, 1H), 2.21-2.11 (m, 1H), 2.16 (s, 3H), 2.10-2.01 (m, 1H), 1.75-1.64 (m, 5H), 1.52 (s, 18H), 1.35 (d, J=6.4 Hz, 3H), 1.07-0.96 (m, 1H); $^{13}$C NMR (101 MHz, CDCl$_3$) δ 197.43, 170.60, 164.05, 152.85, 141.82, 112.84, 108.78, 87.97, 82.88, 81.36, 73.01, 71.03, 57.12, 30.41, 27.97, 27.80, 27.50, 19.59, 19.07, 17.96; HRMS-ESI (m/z) [M+Na]+ calcd for C$_{27}$H$_{43}$NNaO$_9$, 548.2830; found, 548.2826.

Example 15, Step 2

Preparation of tert-butyl N-tert-butoxycarbonyl-N-[(3S,7S,8S,9S)-7-isobutoxy-9-methyl-2-oxo-8-(3-oxobutoxy)oxonan-3-yl]carbamate (C38)

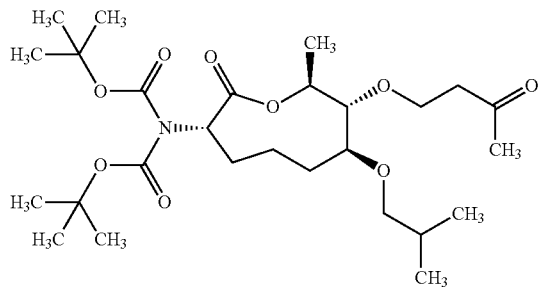 [SMILES: C=C(C)CO[C@H]1CCC[C@H](N(C(=O)OC(C)(C)C)C(=O)OC(C)(C)C)C(=O)O[C@@H](C)[C@@H]1OC=CC(C)=O]

A round bottomed flask was charged with tert-butyl N-tert-butoxycarbonyl-N-[(3S,7S,8S,9S)-9-methyl-7-(2-methylallyloxy)-2-oxo-8-[3-oxobut-1-enoxy]oxonan-3-yl]carbamate (954 mg, 1.82 mmol), Pd/C (5% w/w Pd, 193 mg, 0.091 mmol), and EtOAc (9 mL). The flask was evacuated and backfilled with $N_2$, then evacuated and backfilled with $H_2$. The reaction mixture was stirred vigorously at room temperature overnight. The crude reaction mixture was filtered through a plug of Celite® and the filtrate concentrated to give a crude solid. The solid was purified by automated flash chromatography ($SiO_2$; 0→100% EtOAc/hexanes) to give a white solid (785 mg, 82%): IR (thin film) 2977, 2937, 1743, 1704, 1356, 1141 $cm^{-1}$; $^1$H NMR (400 MHz, $CDCl_3$) δ 4.80 (dd, J=10.5, 8.0 Hz, 1H), 4.65-4.53 (m, 1H), 4.02 (dt, J=9.5, 6.0 Hz, 1H), 3.89 (ddd, J=9.5, 7.1, 5.7 Hz, 1H), 3.36-3.23 (m, 3H), 3.11 (dd, J=8.8, 6.2 Hz, 1H), 2.74-2.56 (m, 2H), 2.41-2.26 (m, 1H), 2.17 (s, 3H), 2.15-2.06 (m, 1H), 2.03-1.96 (m, 1H), 1.87-1.76 (m, 1H), 1.73-1.60 (m, 2H), 1.51 (d, J=2.4 Hz, 18H), 1.35 (d, J=6.3 Hz, 3H), 0.91 (dd, J=6.7, 1.4 Hz, 6H), 0.87 (dd, J=7.1, 1.9 Hz, 1H); $^{13}$C NMR (101 MHz, $CDCl_3$) δ 207.19, 170.86, 152.87, 84.02, 83.99, 82.67, 75.65, 72.76, 68.23, 57.39, 44.20, 30.49, 28.89, 28.06, 27.97, 19.56, 19.49, 19.13, 18.02; HRMS-ESI (m/z) [M+Na]$^+$ calcd for $C_{27}H_{47}NNaO_9$, 552.3143; found, 552.3158.

Example 15, Step 3

Preparation of tert-butyl N-tert-butoxycarbonyl-N-[(3S,7S,8S,9S)-7-isobutoxy-8-(3-methoxybutoxy)-9-methyl-2-oxo-oxonan-3-yl]carbamate (C39)

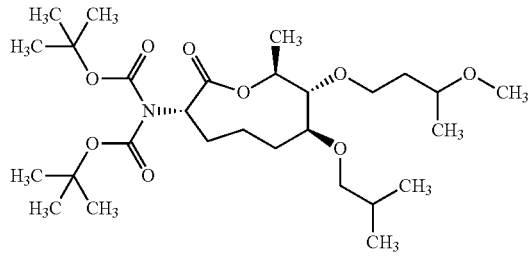 [SMILES: COC(C)CCO[C@H]1[C@H](C)OC(=O)[C@@H](N(C(=O)OC(C)(C)C)C(=O)OC(C)(C)C)CCC[C@@H]1OCC(C)C]

The tert-butyl N-tert-butoxycarbonyl-N-[(3S,7S,8S,9S)-7-isobutoxy-9-methyl-2-oxo-8-(3-oxobutoxy)oxonan-3-yl] carbamate (400 mg, 0.76 mmol) was dissolved in MeOH (3.8 mL) and cooled to 0° C. under $N_2$, and $NaBH_4$ (5 mg, 1.72 mmol) was added in one portion. The reaction was stirred for 2.5 h and then quenched by the addition of saturated aqueous $NH_4Cl$ solution. The mixture was extracted with EtOAc, and the extracts were washed with brine, dried over $Na_2SO_4$, filtered, and concentrated to afford tert-butyl N-tert-butoxycarbonyl-N-[(3S,7S,8S,9S)-8-(3-hydroxybutoxy)-7-isobutoxy-9-methyl-2-oxo-oxonan-3-yl] carbamate (382 mg, 95%) as a colorless oil, which was used without further purification. An oven-dried round bottom flask was charged with the diastereomeric mixture of the alcohol (405 mg, 0.762 mmol), Proton Sponge® (653 mg, 3.05 mmol), and $CH_2Cl_2$ (5 mL). Trimethyloxonium tetrafluoroborate (225 mg, 1.52 mmol) was added in one portion to the colorless solution. A white suspension formed, and the mixture was stirred at room temperature. After stirring for 6 h, the reaction was quenched by the addition of saturated aqueous $NaHCO_3$ (3 mL) and the phases were separated. The aqueous layer was extracted with $CH_2Cl_2$ and the combined organic layers were washed with brine, passed through a phase separator cartridge, concentrated, and purified by automated flash chromatography ($SiO_2$; 0→100% EtOAc/hexanes) to afford a light pink oil as a mixture of diastereomers (328 mg, 79%): IR (thin film) 2935, 1745, 1706, 1142 $cm^{-1}$; $^1$H NMR (400 MHz, $CDCl_3$) δ 4.91-4.75 (m, 1H), 4.71-4.51 (m, 1H), 4.02-3.93 (m, 1H), 3.91-3.78 (m, 1H), 3.74-3.59 (m, 1H), 3.50-3.36 (m, 1H), 3.36-3.31 (m, 2H), 3.30 (s, 2H), 3.29-3.22 (m, 1H), 3.13 (tt, J=8.7, 6.1 Hz, 1H), 2.43-2.27 (m, 1H), 2.18-1.92 (m, 2H), 1.90-1.75 (m, 1H), 1.75-1.59 (m, 4H), 1.51 (s, 18H), 1.43-1.33 (m, 3H), 1.18 (dd, J=6.2, 2.9 Hz, 1H), 1.14-1.12 (m, 2H), 0.96-0.85 (m, 7H); $^{13}$C NMR (101 MHz, $CDCl_3$) δ 170.92, 170.90, 152.89, 85.49, 84.82, 84.27, 84.14, 83.71, 82.68, 82.66, 82.61, 76.35, 75.95, 75.91, 75.53, 73.48, 73.11, 72.87, 61.27, 58.72, 57.44, 57.40, 56.51, 36.20, 32.47, 30.57, 30.54, 29.01, 28.87, 28.84, 28.29, 28.24, 19.63, 19.54, 19.49, 19.37, 19.15, 18.02, 17.92, 17.72, 15.73, 13.96; HRMS-ESI (m/z) [M+Na]$^+$ calcd for $C_{28}H_{51}NNaO_9$, 568.3456; found, 568.3453.

Example 15, Step 4

Preparation of [(3S,7S,8S,9S)-8-(3-methoxybutoxy)-7-isobutoxy-9-methyl-2-oxo-oxonan-3-yl] ammonium chloride (F13)

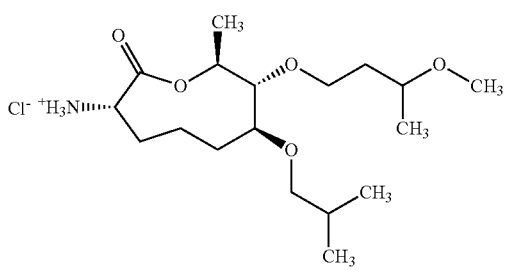 [SMILES: [Cl-] ; COC(C)CCO[C@H]1[C@H](C)OC(=O)[C@@H]([NH3+])CCC[C@@H]1OCC(C)C]

Prepared using the methodology described in Example 12A.

Example 16A

Preparation of 3-hydroxy-4-methoxy-N-((3S,7S,8S,9S)-9-methyl-7,8-bis((2-methylallyl)oxy)-2-oxooxonan-3-yl)pyridine-2-carboxamide (F14)

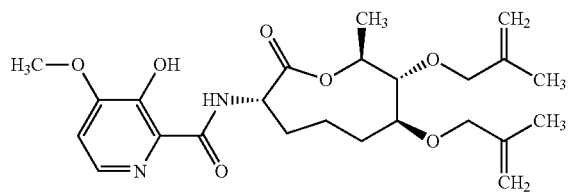 [SMILES: C=C(C)CO[C@H]1[C@H](C)OC(=O)[C@@H](NC(=O)c2nccc(OC)c2O)CCC[C@@H]1OCC(=C)C]

To a suspension of the [(3S,7S,8S,9S)-9-methyl-7,8-bis(2-methylallyloxy)-2-oxo-oxonan-3-yl]ammonium chloride (256 mg, 0.736 mmol) and 3-hydroxy-4-methoxypicolinic acid (137 mg, 0.809 mmol) in CH$_2$Cl$_2$ (6.0 ml) was added Hünig's base (0.422 ml, 2.42 mmol) followed by PyBOP (421 mg, 0.809 mmol). The reaction was stirred at room temperature for 90 min. The solvent was then removed and the resulting crude residue was purified by automated silica gel column chromatography (1→66% acetone/hexanes) to afford the title compound (246 mg, 72%) as a white foam.

Example 16B

Preparation of N-[(3S,7S,8S,9S)-7,8-dibenzyloxy-9-methyl-2-oxo-oxonan-3-yl]-3-hydroxy-4-methoxy-pyridine-2-carboxamide (F15)

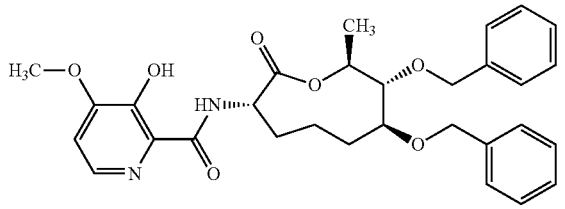 [SMILES: COc1ccnc(C(=O)N[C@H]2CCC[C@H](OCc3ccccc3)[C@@H](OCc3ccccc3)[C@H](C)OC2=O)c1O]

To a suspension of the [(3S,7S,8S,9S)-7,8-dibenzyloxy-9-methyl-2-oxo-oxonan-3-yl]ammonium chloride (220 mg, 0.52 mmol) and 3-hydroxy-4-methoxypicolinic acid (124 mg, 0.733 mmol) in CH$_2$Cl$_2$ (5.2 mL) was added N-methylmorpholine (0.346 mL, 3.14 mmol) followed by HATU (299 mg, 0.786 mmol). The mixture was stirred at room temperature for 5 h, then the solvent was removed and the crude residue was purified by automated silica gel column chromatography (5→20% acetone/hexanes) to afford the title compound (124 mg, 44.3%) as a hard white foam.

Example 17A

Preparation of [4-methoxy-2-[[(3S,7S,8S,9S)-9-methyl-7,8-bis(2-methylallyloxy)-2-oxo-oxonan-3-yl]carbamoyl]-3-pyridyl]oxymethyl acetate (F16)

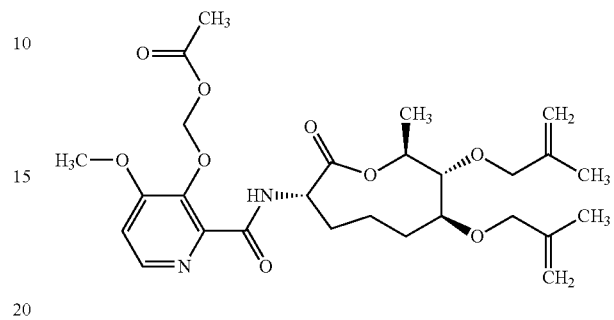

To a screw-cap vial were added 3-hydroxy-4-methoxy-N-((3S,7S,8S,9S)-9-methyl-7,8-bis((2-methylallyl)oxy)-2-oxooxonan-3-yl)pyridine-2-carboxamide (110 mg, 0.24 mmol) and K$_2$CO$_3$ (65.7 mg, 0.476 mmol), followed by acetone (2.38 ml). Then, bromomethyl acetate (33 µL, 0.34 mmol) was added dropwise and the reaction was heated to 50° C. for 1 h. The reaction mixture was cooled to room temperature, filtered through a plug of glass wool, and then the solvent was removed. The crude residue was purified by automated silica gel column chromatography (1-50% acetone/hexanes) to afford the title compound (98.9 mg, 78%) as a colorless oil.

Example 17B

Preparation of [4-methoxy-2-[[(3S,7S,8S,9S)-9-methyl-7,8-bis(2-methylallyloxy)-2-oxo-oxonan-3-yl]carbamoyl]-3-pyridyl]oxymethyl-2-methylpropanoate (F17)

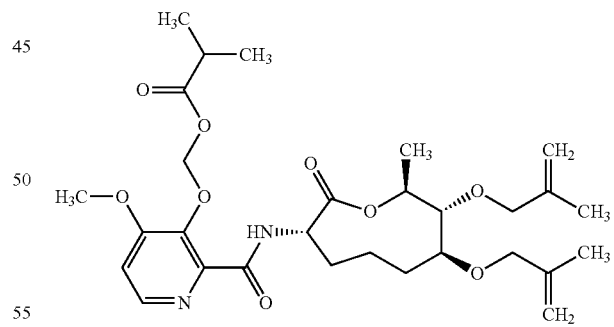

To a screw-cap vial were added 3-hydroxy-4-methoxy-N-((3S,7S,8S,9S)-9-methyl-7,8-bis((2-methylallyl)oxy)-2-oxooxonan-3-yl)pyridine-2-carboxamide (110 mg, 0.24 mmol), powdered Na$_2$CO$_3$ (50.4 mg, 0.476 mmol), and NaI (5.4 mg, 0.036 mmol) followed by acetone (2.38 ml). Then, chloromethyl isobutyrate (0.042 ml, 0.33 mmol) was added dropwise and the reaction was heated to 50° C. for 14 h. The reaction mixture was cooled to room temperature, filtered through a plug of glass wool, and then the solvent was evaporated. The crude residue was purified by automated silica gel column chromatography (1→50% acetone/hexanes) to afford the title compound (127.9 mg, 96%) as a colorless oil.

Example 17C

Preparation of [2-[[(3S,7S,8S,9S)-8-isobutoxy-9-methyl-7-(2-methylallyloxy)-2-oxo-oxonan-3-yl]carbamoyl]-4-methoxy-3-pyridyl]acetate (F18)

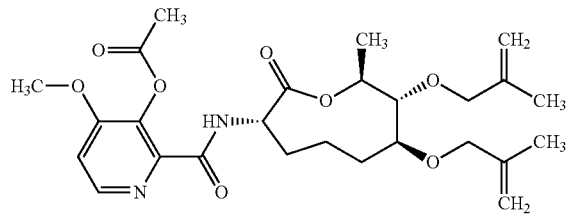 [SMILES: C=C(C)CO[C@H]1[C@H](C)OC(=O)[C@@H](NC(=O)c2nccc(OC)c2OC(C)=O)CCC[C@@H]1OCC(=C)C]

To a screw-cap vial were added 3-hydroxy-N-[(3S,7S,8S,9S)-8-isobutoxy-9-methyl-7-(2-methylallyloxy)-2-oxo-oxonan-3-yl]-4-methoxypyridine-2-carboxamide (17.0 mg, 0.037 mmol) and CH$_2$Cl$_2$ (0.52 mL), followed by DMAP (0.89 mg, 0.73 μmol) and TEA (10.2 μl, 0.073 mmol). Then, acetyl chloride (3.9 μl, 0.055 mmol) was added and the reaction was stirred at room temperature for 3 h. The mixture was diluted with CH$_2$Cl$_2$ and quenched by pouring into saturated aqueous NH$_4$Cl. The organic phase was separated and the aqueous phase was extracted with CH$_2$Cl$_2$ three times. The combined organic phases were passed through a phase separator and the solvent was then evaporated. The resulting crude residue was purified by automated silica gel column chromatography (1→50% acetone/hexanes) to afford the title compound (15.7 mg, 85%) as a colorless oil.

Example 17D

Preparation of [2-[[(3S,7S,8S,9S)-7-(cyclopentoxy)-9-methyl-2-oxo-8-propoxy-oxonan-3-yl]carbamoyl]-4-methoxy-3-pyridyl]3-methoxypropanoate (F19)

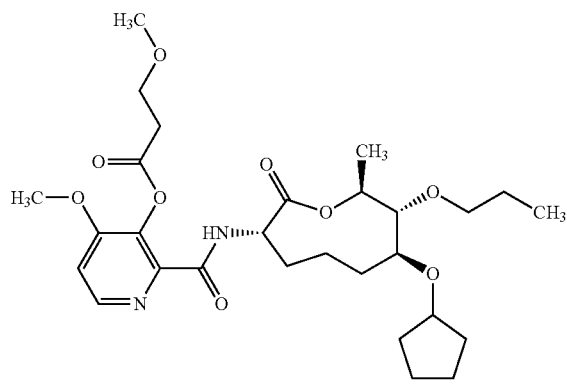 [SMILES: CCCO[C@H]1[C@H](C)OC(=O)[C@@H](NC(=O)c2nccc(OC)c2OC(=O)CCOC)CCC[C@@H]1OC1CCCC1]

To a screw-cap vial were added N-[(3S,7S,8S,9S)-7-(cyclopentoxy)-9-methyl-2-oxo-8-propoxy-oxonan-3-yl]-3-hydroxy-4-methoxypyridine-2-carboxamide (51.7 mg, 0.111 mmol) and CH$_2$Cl$_2$ (1.1 mL), followed by DMAP (6.8 mg, 0.056 mmol) and TEA (30.9 μl, 0.223 mmol). Then, 3-methoxypropanoyl chloride (24.1 μl, 0.223 mmol) was added dropwise and the reaction was stirred at room temperature for 3 h. The mixture was diluted with CH$_2$Cl$_2$ and quenched by pouring into saturated aqueous NH$_4$Cl. The organic phase was separated and the aqueous phase was extracted with CH$_2$Cl$_2$ three times. The combined organic phases were passed through a phase separator and the solvent was then evaporated. The resulting crude residue was purified by automated silica gel column chromatography (1→50% acetone/hexanes) to afford the title compound (58.7 mg, 96%) as a white solid.

Example 18

Preparation of tert-butyl ((3aS,4S,7S,10aS)-4-methyl-6-oxo-2-phenyloctahydro-[1,3]dioxolo[4,5-c]oxonin-7-yl)carbamate

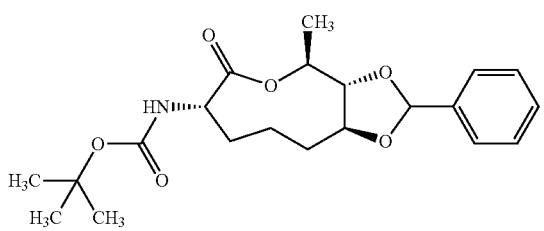

To a solution of tert-butyl N-tert-butoxycarbonyl-N-[(3S,7S,8R,9S)-7,8-dihydroxy-9-methyl-2-oxo-oxonan-3-yl]carbamate (250 mg, 0.620 mmol) in CH$_2$Cl$_2$ (3 mL) were added 4-methylbenzenesulfonic acid (21.34 mg, 0.124 mmol), benzaldehyde (315 μl, 3.10 mmol), and MgSO$_4$ (100 mg), and the reaction was stirred at ambient temperature for 2 h. The reaction mixture was filtered through a plug of Celite®, concentrated and purified via silica gel chromatography (gradient, hexanes/EtOAc) to afford the title compound (240 mg, 99%) as a white solid: $^1$H NMR (400 MHz, CDCl$_3$) δ 7.47 (tdd, J=5.2, 4.2, 2.8 Hz, 2H), 7.38 (dp, J=5.7, 1.5 Hz, 3H), 5.79 (s, 1H), 5.31-5.15 (m, 2H), 4.17 (ddd, J=12.4, 7.9, 5.0 Hz, 1H), 3.90 (ddd, J=11.4, 6.9, 3.0 Hz, 1H), 3.68 (dd, J=9.7, 6.9 Hz, 1H), 2.30 (ddd, J=17.7, 10.1, 4.5 Hz, 1H), 2.10-1.89 (m, 2H), 1.84-1.57 (m, 2H), 1.49 (d, J=6.3 Hz, 3H), 1.45 (s, 9H), 1.43-1.31 (m, 1H); $^{13}$C NMR (101 MHz, CDCl$_3$) δ 173.75, 154.81, 136.32, 129.69, 128.44, 126.79, 102.84, 83.62, 80.04, 79.70, 71.69, 54.23, 34.42, 32.94, 30.94, 28.33, 19.76, 18.33; ESIMS m/z 414 ([M+H]$^+$).

Example 19

Preparation of tert-butyl N-[(3aS,4S,7S,10aS)-2-ethyl-4-methyl-6-oxo-4,7,8,9,10,10a-hexahydro-3aH-[1,3]dioxolo[4,5-c]oxonin-7-yl]-N-tert-butoxycarbonyl-carbamate

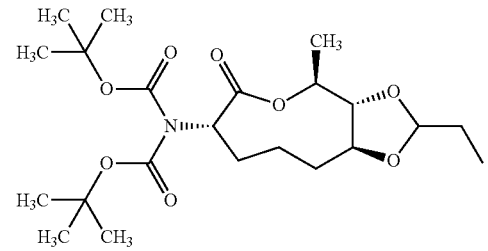

To a solution of tert-butyl N-tert-butoxycarbonyl-N-[(3S,7S,8R,9S)-7,8-dihydroxy-9-methyl-2-oxo-oxonan-3-yl]carbamate (250 mg, 0.620 mmol) in CH$_2$Cl$_2$ (3.1 mL) were added 4-methylbenzenesulfonic acid (21.34 mg, 0.124 mmol), propionaldehyde (225 μl, 3.10 mmol), and MgSO$_4$ (100 mg), and the reaction was stirred at ambient temperature for 2 h. The reaction mixture was filtered through a plug of Celite®, concentrated and purified via silica gel chromatography (gradient, hexanes/EtOAc) to afford the title compound (217 mg, 79%) as a sticky, colorless oil: $^1$H NMR (400 MHz, CDCl$_3$) δ 4.93 (dq, J=9.6, 6.3 Hz, 1H), 4.83 (t, J=4.6 Hz, 1H), 4.67 (dd, J=12.3, 4.8 Hz, 1H), 3.69 (ddd, J=11.3, 6.8, 2.7 Hz, 1H), 3.47 (dd, J=9.6, 6.9 Hz, 1H), 2.39 (dddd, J=13.9, 12.2, 6.6, 1.6 Hz, 1H), 2.16-1.91 (m, 3H), 1.80-1.59 (m, 4H), 1.51 (s, 18H), 1.43 (d, J=6.2 Hz, 3H), 0.94 (t, J=7.6 Hz, 3H); $^{13}$C NMR (101 MHz, CDCl$_3$) δ 171.36, 152.87, 104.15, 83.14, 82.76, 79.54, 72.13, 59.10, 34.45, 30.54, 27.97, 26.41, 21.04, 18.53, 7.93; ESIMS m/z 444 ([M+H]$^+$).

Example 20

Preparation of A) tert-butyl N-tert-butoxycarbonyl-N-[(3S,7S,8S,9S)-7-(3-fluorophenoxy)-8-hydroxy-9-methyl-2-oxo-oxonan-3-yl]carbamate and B) tert-butyl N-tert-butoxycarbonyl-N-[(3S,7S,8R,9S)-8-(3-fluorophenoxy)-7-hydroxy-9-methyl-2-oxo-oxonan-3-yl]carbamate

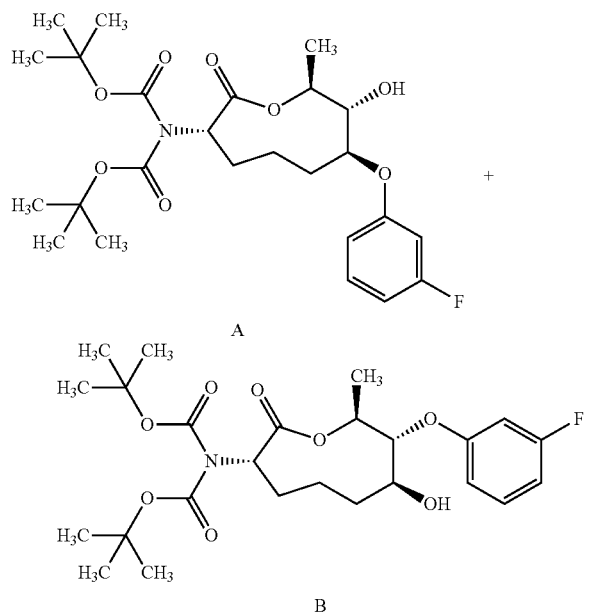

To a solution of tris(3-fluorophenyl)bismuthine (1.056 g, 2.137 mmol) in CH$_2$Cl$_2$ (7.12 mL) was added peracetic acid (0.503 mL, 2.421 mmol) at 0° C., and the solution was warmed to room temperature and stirred for 20 min. To the resulting solution were added tert-butyl N-tert-butoxycarbonyl-N-[(3S,7S,8R,9S)-7,8-dihydroxy-9-methyl-2-oxo-oxonan-3-yl]carbamate (575 mg, 1.42 mmol) and diacetoxycopper (52 mg, 0.28 mmol), and the resulting blue-green slurry was stirred at room temperature for 16 h, warmed to 40° C., and stirred at 40° C. for 4 h. The reaction mixture was filtered through a plug of Celite® and any peroxides in the filtrate were quenched by the addition of saturated aqueous sodium bisulfite (NaHSO$_3$). The biphasic mixture was passed through a phase separator cartridge and concentrated. The crude residue was purified by silica gel chromatography (gradient, petroleum ether/MTBE) to afford the title compounds A and B.

Compound A (117 mg, 16%) was isolated as a light yellow oil: $^1$H NMR (400 MHz, CDCl$_3$) δ 7.22 (td, J=8.2, 6.8 Hz, 1H), 6.74-6.61 (m, 3H), 4.95 (t, J=8.5 Hz, 1H), 4.84 (dq, J=9.5, 6.2 Hz, 1H), 4.17 (ddd, J=7.8, 6.0, 1.9 Hz, 1H), 3.86 (ddd, J=9.6, 7.6, 2.3 Hz, 1H), 2.64 (d, J=2.7 Hz, 1H), 2.29 (dddd, J=14.0, 11.2, 8.6, 1.7 Hz, 1H), 2.35-2.24 (m, 1H), 2.13-1.99 (m, 2H), 1.89 (dddd, J=17.3, 15.9, 8.6, 3.9 Hz, 1H), 1.68-1.55 (m, 1H), 1.52 (s, 18H), 1.47 (d, J=6.3 Hz, 3H); $^{19}$F NMR (376 MHz, CDCl$_3$) δ −111.22; ESIMS m/z 498 ([M+H]$^+$).

Compound B (214 mg, 30%) was isolated as a colorless oil: $^1$H NMR (400 MHz, CDCl$_3$) δ 7.23 (td, J=8.3, 6.7 Hz, 1H), 6.83 (ddd, J=8.4, 2.5, 0.9 Hz, 1H), 6.77 (dt, J=10.8, 2.4 Hz, 1H), 6.70 (dddd, J=8.3, 7.4, 2.4, 1.2 Hz, 1H), 4.95-4.83 (m, 2H), 4.27 (dd, J=9.5, 7.8 Hz, 1H), 3.88 (ddt, J=8.1, 5.3, 2.3 Hz, 1H), 2.45-2.33 (m, 1H), 2.16-2.13 (m, 1H), 2.13-1.97 (m, 2H), 1.83 (dtd, J=12.2, 9.4, 8.2, 6.1 Hz, 2H), 1.52 (s, 18H), 1.49-1.39 (m, 1H), 1.32 (d, J=6.4 Hz, 3H); $^{19}$F NMR (376 MHz, CDCl$_3$) δ −110.94; ESIMS m/z 498 ([M+H]$^+$).

Example 21

Preparation of tert-butyl N-[(3S,7S,8S,9S)-8-(4-bromophenoxy)-9-methyl-2-oxo-7-propoxy-oxonan-3-yl]-N-tert-butoxycarbonyl-carbamate

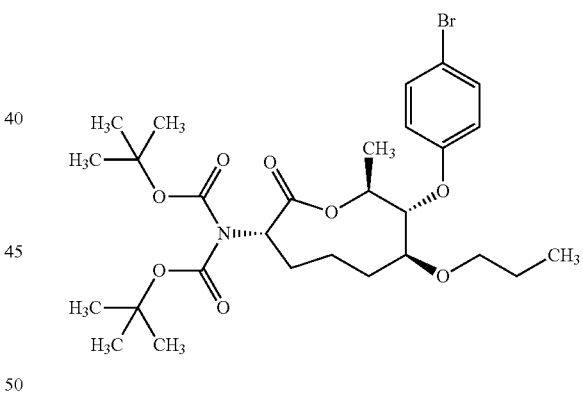

To a solution of tert-butyl N-tert-butoxycarbonyl-N-[(3S,7S,8S,9S)-9-methyl-2-oxo-8-phenoxy-7-propoxy-oxonan-3-yl]carbamate (523 mg, 1.003 mmol) in CH$_2$Cl$_2$ (5 mL) was added NBS (357 mg, 2.005 mmol). The vial was wrapped in aluminum foil and stirred at room temperature for 16 h. An additional portion of NBS (357 mg, 2 mmol) was added and the reaction was stirred at room temperature for an additional 3 h, concentrated, and the residue purified by silica gel chromatography (gradient, hexanes/EtOAc) to afford the title compound (567 mg, 94%): $^1$H NMR (400 MHz, CDCl$_3$) δ 7.39-7.30 (m, 2H), 7.00-6.91 (m, 2H), 4.90-4.78 (m, 2H), 4.28 (dd, J=9.7, 7.3 Hz, 1H), 3.52 (ddd, J=7.2, 5.2, 1.9 Hz, 1H), 3.44 (dt, J=9.0, 6.6 Hz, 1H), 3.20 (dt, J=9.0, 6.5 Hz, 1H), 2.48-2.33 (m, 1H), 2.23-2.11 (m, 1H), 2.12-2.00 (m, 1H), 1.82-1.65 (m, 2H), 1.52 (s, 18H), 1.47-1.36 (m, 2H), 1.31 (d, J=6.4 Hz, 3H), 1.12-0.99 (m, 1H), 0.77 (t, J=7.4 Hz, 3H); $^{13}$C NMR (101 MHz, CDCl$_3$) δ

170.80, 158.94, 152.87, 132.12, 118.28, 113.38, 83.31, 82.96, 82.76, 72.40, 71.28, 57.34, 30.53, 27.98, 23.15, 19.23, 18.17, 10.56; ESIMS m/z 622 ([M+H]$^+$).

Example 22

Preparation of tert-butyl N-tert-butoxycarbonyl-N-[(3S,7S,8S,9S)-9-methyl-2-oxo-8-(4-phenylphenoxy)-7-propoxy-oxonan-3-yl]carbamate

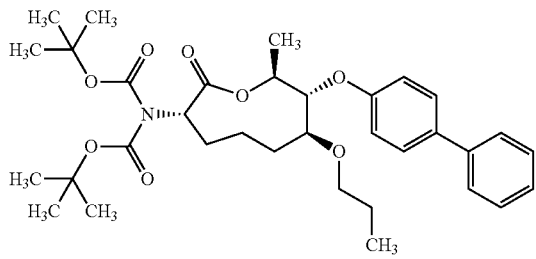 [SMILES: CCCO[C@H]1CCC[C@H](N(C(=O)OC(C)(C)C)C(=O)OC(C)(C)C)C(=O)O[C@@H](C)[C@@H]1Oc1ccc(-c2ccccc2)cc1]

A vial was charged with tert-butyl N-[(3S,7S,8S,9S)-8-(4-bromophenoxy)-9-methyl-2-oxo-7-propoxy-oxonan-3-yl]-N-tert-butoxycarbonyl-carbamate (34 mg, 0.057 mmol), phenylboronic acid (19 mg, 0.156 mmol), Na$_2$CO$_3$ (18.0 mg, 0.170 mmol) and Pd(PPh$_3$)$_4$ (6.54 mg, 5.66 μmol). The vial was evacuated and backfilled with N$_2$ (repeated 3×), dioxane (425 μl) and water (142 μl) were added, and the vial was fitted with an air condenser and the reaction mixture was heated at 80° C. for 3 h. The cooled reaction mixture was diluted with CH$_2$Cl$_2$, passed through a phase separator cartridge, concentrated, and the residue purified by silica gel chromatography (gradient, hexanes/EtOAc) to afford the title compound (25 mg, 74%) as a white solid: $^1$H NMR (400 MHz, CDCl$_3$) δ 7.59-7.53 (m, 2H), 7.51-7.46 (m, 2H), 7.47-7.37 (m, 2H), 7.36-7.26 (m, 1H), 7.18-7.09 (m, 2H), 4.94-4.79 (m, 2H), 4.40 (dd, J=9.6, 7.3 Hz, 1H), 3.56 (ddd, J=7.1, 5.1, 1.9 Hz, 1H), 3.47 (dt, J=9.0, 6.6 Hz, 1H), 3.26 (dt, J=9.1, 6.5 Hz, 1H), 2.49-2.35 (m, 1H), 2.25-2.12 (m, 1H), 2.13-2.01 (m, 1H), 1.86-1.66 (m, 2H), 1.52 (s, 18H), 1.48-1.39 (m, 2H), 1.37 (d, J=6.3 Hz, 3H), 1.08 (ddt, J=15.9, 7.5, 1.9 Hz, 1H), 0.77 (t, J=7.4 Hz, 3H); $^{13}$C NMR (101 MHz, CDCl$_3$) δ 170.86, 159.35, 152.89, 140.82, 134.28, 128.69, 127.99, 126.74, 126.66, 116.75, 83.07, 83.04, 82.75, 72.67, 71.42, 57.42, 30.59, 28.76, 27.99, 23.19, 19.30, 18.26, 10.57; ESIMS m/z 620 ([M+Na]$^+$).

Example 23

Preparation of tert-butyl N-tert-butoxycarbonyl-N-[(3S,7S,8S,9S)-8-methoxy-9-methyl-7-(2-methylallyloxy)-2-oxo-oxonan-3-yl]carbamate

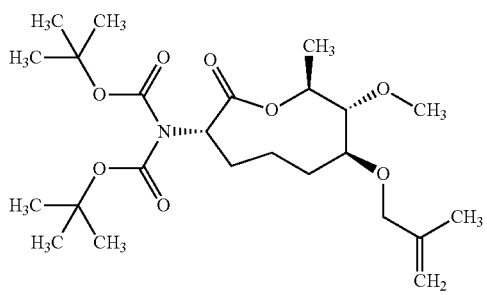 [SMILES: C=C(C)CO[C@H]1CCC[C@H](N(C(=O)OC(C)(C)C)C(=O)OC(C)(C)C)C(=O)O[C@@H](C)[C@@H]1OC]

To a solution of a tert-butyl N-tert-butoxycarbonyl-N-[(3S,7S,8S,9S)-8-hydroxy-9-methyl-7-(2-methylallyloxy)-2-oxo-oxonan-3-yl]carbamate (1.00 g, 2.19 mmol) in CH$_2$Cl$_2$ (21.86 ml) at 0° C. was added Proton Sponge® (0.937 g, 4.37 mmol) followed by trimethyloxonium tetrafluoroborate (0.485 g, 3.28 mmol). The mixture was stirred at 0° C. for 30 min, warmed to ambient temperature, stirred for an additional 30 min, and then poured into sat. aqueous NaHCO$_3$ (50 mL) and extracted with CH$_2$Cl$_2$ (3×50 mL). The combined organic extracts were washed with 10% NaHSO$_4$ (2×50 mL), washed with brine (50 mL), and dried by passing through a phase-separation cartridge. The filtrate was concentrated and the crude foam was purified via flash chromatography (SiO$_2$, 0→35% EtOAc/hexane) to afford the title product as a clear oil (1.03 g, 100%): $^1$H NMR (400 MHz, CDCl$_3$) δ 4.98 (dd, J=2.0, 0.9 Hz, 1H), 4.91-4.85 (m, 1H), 4.82 (dd, J=10.4, 8.1 Hz, 1H), 4.62 (dq, J=9.7, 6.3 Hz, 1H), 3.98 (d, J=12.1 Hz, 1H), 3.86 (d, J=12.1 Hz, 1H), 3.56 (s, 3H), 3.40 (ddd, J=7.0, 5.1, 1.7 Hz, 1H), 3.27 (dd, J=9.6, 7.3 Hz, 1H), 2.43-2.29 (m, 1H), 2.17-1.97 (m, 2H), 1.77 (s, 3H), 1.74-1.58 (m, 2H), 1.51 (s, 18H), 1.39 (d, J=6.3 Hz, 3H), 1.01-0.88 (m, 1H); $^{13}$C NMR (101 MHz, CDCl$_3$) δ 170.84, 152.88, 142.53, 112.15, 85.57, 83.24, 82.65, 73.03, 72.89, 61.32, 57.36, 30.55, 28.40, 27.96, 19.57, 19.17, 17.87; HRMS-ESI (m/z) [M+Na]$^+$ calcd for C$_{24}$H$_{41}$NNaO$_8$, 494.2734; found, 494.2724.

Example A

Evaluation of Fungicidal Activity: Leaf Blotch of Wheat (*Mycosphaerella graminicola*; Anamorph: *Septoria tritici*; Bayer Code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Example B

Evaluation of Fungicidal Activity: Wheat Brown Rust (*Puccinia triticina*; Synonym: *Puccinia recondite* f. sp. *tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C

Evaluation of Fungicidal Activity: Wheat Glume Blotch (*Leptosphaeria nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D

Evaluation of Fungicidal Activity: Apple Scab (*Venturia inaequalis*; Bayer Code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 hr after fungicide treatment and kept in a 22° C. dew chamber with 100% RH for 48 hr, and then moved to a greenhouse set at 20° C. for disease to develop. Fungicide formulation, application and disease assessment on the sprayed leaves followed the procedures as described in the Example A.

Example E

Evaluation of Fungicidal Activity: Grape Powdery Mildew (*Uncinula necator*; Bayer Code UNCINE)

Grape seedlings (variety Carignane) were grown in soil-less Metro mix, with one plant per pot, and used in the test when approximately one month old. Plants were inoculated 24 hr after fungicide treatment by shaking spores from infected leaves over test plants. Plants were maintained in a greenhouse set at 20° C. until disease was fully developed. Fungicide formulation, application and disease assessment on the sprayed leaves followed the procedures as described in the Example A.

Example F

Evaluation of Fungicidal Activity: Powdery Mildew of Cucumber (*Erysiphe cichoracearum*; Bayer Code ERYSCI)

Cucumber seedlings (variety Bush Pickle) were grown in soil-less Metro mix, with one plant per pot, and used in the test when 12 to 14 days old. Plants were inoculated with a spore suspension 24 hr following fungicide treatments. After inoculation the plants remained in the greenhouse set at 20° C. until disease was fully expressed. Fungicide formulation, application and disease assessment on the sprayed leaves followed the procedures as described in the Example A.

Example G

Evaluation of Fungicidal Activity: Leaf Spot of Sugar Beets (*Cercospora beticola*; Bayer Code CERCBE)

Sugar beet plants (variety HH88) were grown in soil-less Metro mix and trimmed regularly to maintain a uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example H

Evaluation of Fungicidal Activity: Asian Soybean Rust (*Phakopsora pachyrhizi*; Bayer Code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% RH then transferred to a growth room at 23° C. for disease to develop. Disease severity was assessed on the sprayed leaves.

Example I

Evaluation of Fungicidal Activity: Wheat Powdery Mildew (*Blumeria graminis* f. sp. *tritici*; Synonym: *Erysiphe graminis* f. sp. *tritici*; Bayer Code ERYSGT)

Wheat plants (variety Yuma) were grown from seed in a greenhouse in 50% mineral soil/50% soil-less Metro mix until the first leaf was fully emerged, with 7-10 seedlings per pot. These plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example J

Evaluation of Fungicidal Activity: Barley Powdery Mildew (*Blumeria graminis* f. sp. *hordei*; Synonym: *Erysiphe graminis* f. sp. *hordei*; Bayer Code ERYSGH)

Barley seedlings (variety Harrington) were propagated in soil-less Metro mix, with each pot having 8 to 12 plants, and used in the test when first leaf was fully emerged. Test plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example K

Evaluation of Fungicidal Activity: Barley Scald (*Rhyncosporium secalis*; Bayer Code RHYNSE)

Barley seedlings (variety Harrington) were propagated in soil-less Metro mix, with each pot having 8 to 12 plants, and used in the test when first leaf was fully emerged. Test plants were inoculated by an aqueous spore suspension of *Rhyncosporium secalis* 24 hr after fungicide treatments. After inoculation the plants were kept in a dew room at 20° C. with 100% relative humidity for 48 hr. The plants were then transferred to a greenhouse set at 20° C. for disease to develop. Fungicide formulation, application and disease assessment on the sprayed leaves followed the procedures as described in the Example A.

Example L

Evaluation of Fungicidal Activity: Rice Blast (*Magnaporthe grisea*; Anamorph: *Pyricularia oryzae*; Bayer Code PYRIOR)

Rice seedlings (variety Japonica) were propagated in soil-less Metro mix, with each pot having 8 to 14 plants, and used in the test when 12 to 14 days old. Test plants were inoculated with an aqueous spore suspension of *Pyricularia oryzae* 24 hr after fungicide treatments. After inoculation the plants were kept in a dew room at 22° C. with 100% relative humidity for 48 hr to permit spores to germinate and infect the leaf. The plants were then transferred to a greenhouse set at 24° C. for disease to develop. Fungicide formulation, application and disease assessment on the sprayed leaves followed the procedures as described in the Example A.

Example M

Evaluation of Fungicidal Activity: Tomato Early Blight (*Alternaria solani*; Bayer Code ALTESO)

Tomato plants (variety Outdoor girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a growth room at 22° C. for disease to develop. Fungicide formulation, application and disease assessment on the sprayed leaves followed the procedures as described in the Example A.

Example N

Evaluation of Fungicidal Activity: Cucumber Anthracnose (*Glomerella lagenarium*; Anamorph: *Colletotrichum lagenarium*; Bayer Code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

TABLE 1

Structure and Preparation Method for F Series Compounds

| Compound Number | Structure | Prepared According to Example |
|---|---|---|
| F1 | 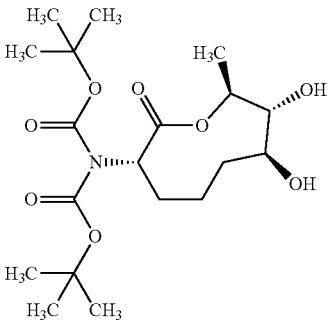 [SMILES: C[C@@H]1OC(=O)[C@@H](N(C(=O)OC(C)(C)C)C(=O)OC(C)(C)C)CCC[C@H](O)[C@H]1O] | 11 |

TABLE 1-continued

Structure and Preparation Method for F Series Compounds

| Compound Number | Structure | Prepared According to Example |
|---|---|---|
| F2 | 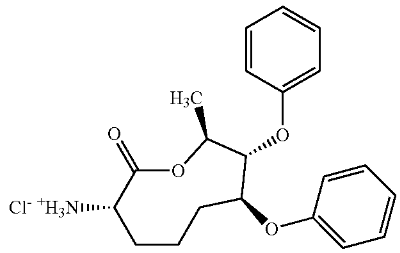 [SMILES: [Cl-] ; C[C@@H]1OC(=O)[C@@H]([NH3+])CCC[C@H](Oc2ccccc2)[C@H]1Oc1ccccc1] | 12, 12A |
| F3 | 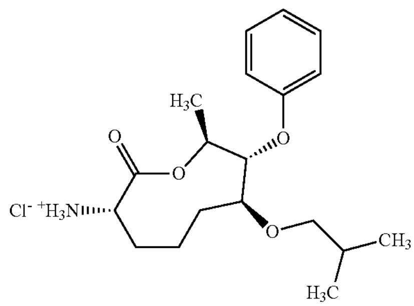 [SMILES: [Cl-] ; CC(C)CO[C@H]1CCC[C@H]([NH3+])C(=O)O[C@@H](C)[C@@H]1Oc1ccccc1] | 12, 12B (1-3) |
| F4 | 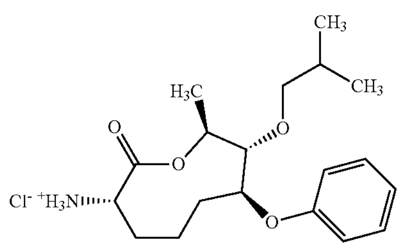 [SMILES: [Cl-] ; CC(C)CO[C@H]1[C@H](C)OC(=O)[C@@H]([NH3+])CCC[C@@H]1Oc1ccccc1] | 12, 12B (1-3) |
| F5 | 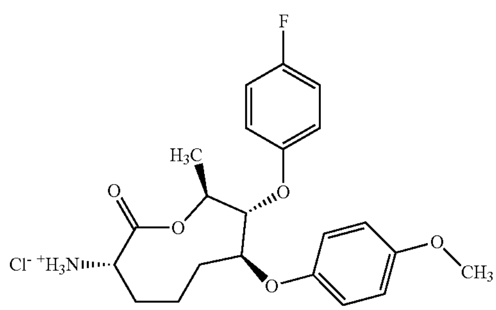 [SMILES: [Cl-] ; COc1ccc(O[C@H]2CCC[C@H]([NH3+])C(=O)O[C@@H](C)[C@@H]2Oc2ccc(F)cc2)cc1] | 12, 12C (1-2) |
| F6 | 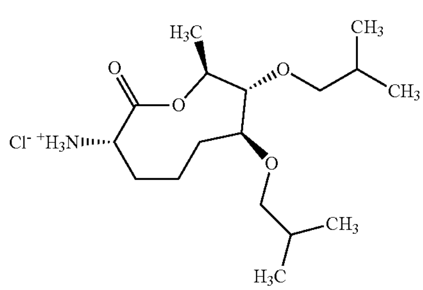 [SMILES: [Cl-] ; CC(C)CO[C@H]1[C@H](C)OC(=O)[C@@H]([NH3+])CCC[C@@H]1OCC(C)C] | 12, 12A |

TABLE 1-continued

Structure and Preparation Method for F Series Compounds

| Compound Number | Structure | Prepared According to Example |
|---|---|---|
| F7 | 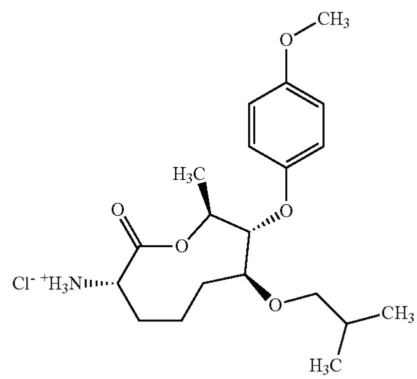 [SMILES: [Cl-] ; COc1ccc(O[C@H]2[C@H](C)OC(=O)[C@@H]([NH3+])CCC[C@@H]2OCC(C)C)cc1] | 13, 13B (1-3) |
| F8 | 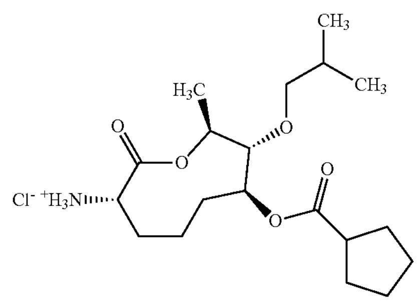 [SMILES: [Cl-] ; CC(C)CO[C@H]1[C@H](C)OC(=O)[C@@H]([NH3+])CCC[C@@H]1OC(=O)C1CCCC1] | 13, 13B (1) And 13D (1, 2) |
| F9 | 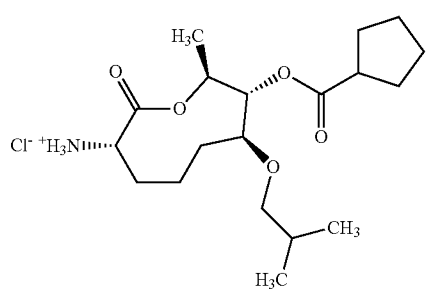 [SMILES: [Cl-] ; CC(C)CO[C@H]1CCC[C@H]([NH3+])C(=O)O[C@@H](C)[C@@H]1OC(=O)C1CCCC1] | 13, 13B (1) and 13D (1-2) |
| F10 | 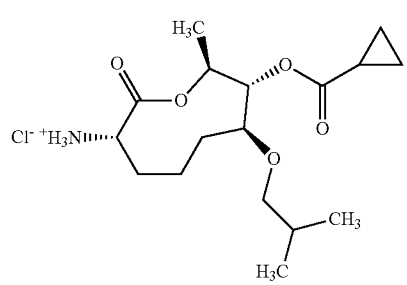 [SMILES: [Cl-] ; CC(C)CO[C@H]1CCC[C@H]([NH3+])C(=O)O[C@@H](C)[C@@H]1OC(=O)C1CC1] | 13, 13E (1-3) |

TABLE 1-continued

Structure and Preparation Method for F Series Compounds

| Compound Number | Structure | Prepared According to Example |
|---|---|---|
| F11 | 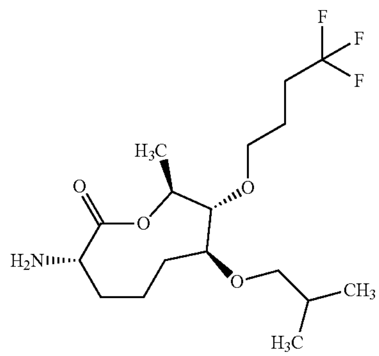 [SMILES: CC(C)CO[C@H]1CCC[C@H](N)C(=O)O[C@@H](C)[C@@H]1OCCCC(F)(F)F] | 13, 13F (1-3) |
| F12 | 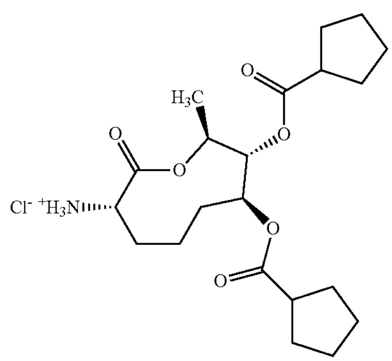 [SMILES: [Cl-] ; C[C@@H]1OC(=O)[C@@H]([NH3+])CCC[C@H](OC(=O)C2CCCC2)[C@H]1OC(=O)C1CCCC1] | 14, 14A |
| F13 | 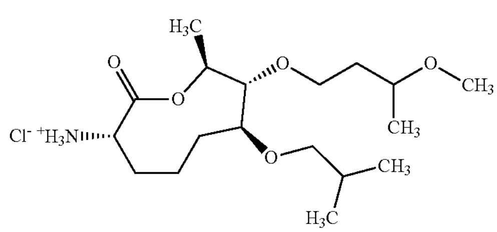 [SMILES: [Cl-] ; COC(C)CCO[C@H]1[C@H](C)OC(=O)[C@@H]([NH3+])CCC[C@@H]1OCC(C)C] | 15 (1-4) |
| F14 | 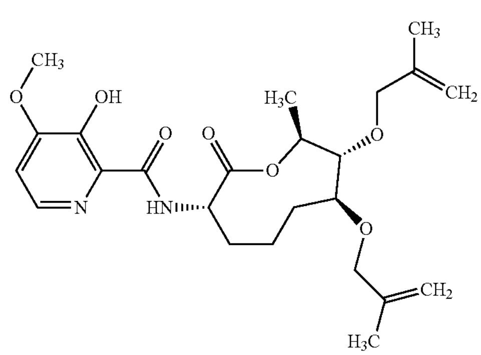 [SMILES: C=C(C)CO[C@H]1[C@H](C)OC(=O)[C@@H](NC(=O)c2nccc(OC)c2O)CCC[C@@H]1OCC(=C)C] | 16A |

TABLE 1-continued

Structure and Preparation Method for F Series Compounds

| Compound Number | Structure | Prepared According to Example |
|---|---|---|
| F15 | 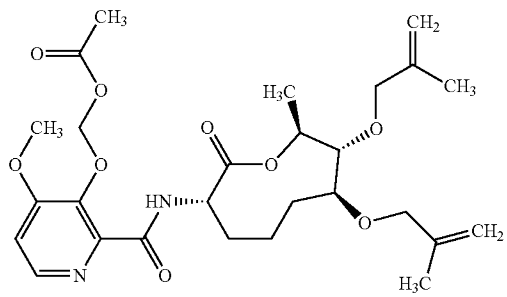 [SMILES: C=C(C)CO[C@H]1[C@H](C)OC(=O)[C@@H](NC(=O)c2nccc(OC)c2OCOC(C)=O)CCC[C@@H]1OCC(=C)C] | 17A |
| F16 | 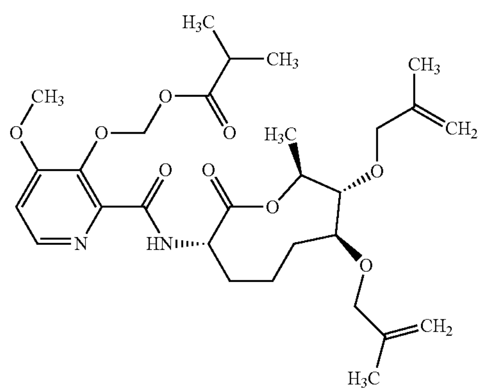 [SMILES: C=C(C)CO[C@H]1[C@H](C)OC(=O)[C@@H](NC(=O)c2nccc(OC)c2OCOC(=O)C(C)C)CCC[C@@H]1OCC(=C)C] | 17B |
| F17 | 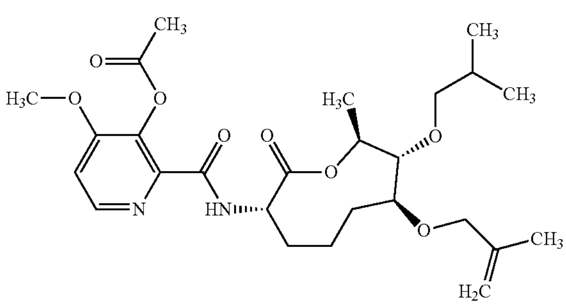 [SMILES: C=C(C)CO[C@H]1CCC[C@H](NC(=O)c2nccc(OC)c2OC(C)=O)C(=O)O[C@@H](C)[C@@H]1OCC(C)C] | 17C |
| F18 | 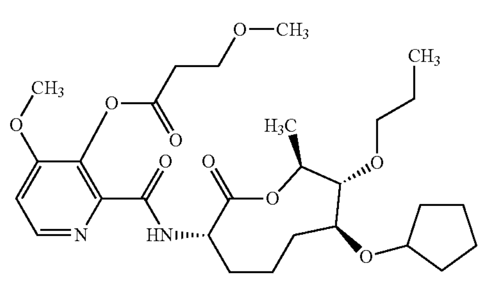 [SMILES: CCCO[C@H]1[C@H](C)OC(=O)[C@@H](NC(=O)c2nccc(OC)c2OC(=O)CCOC)CCC[C@@H]1OC1CCCC1] | 17D |

TABLE 1-continued

Structure and Preparation Method for F Series Compounds

| Compound Number | Structure | Prepared According to Example |
|---|---|---|
| F19 | 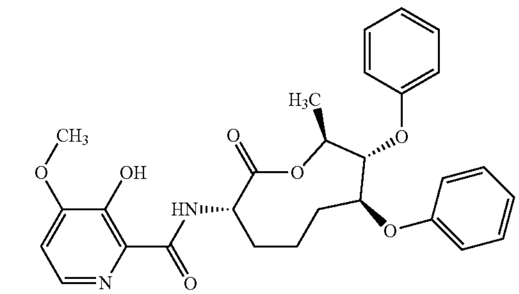 [SMILES: COc1ccnc(C(=O)N[C@H]2CCC[C@H](Oc3ccccc3)[C@@H](Oc3ccccc3)[C@H](C)OC2=O)c1O] | 16A |
| F20 | 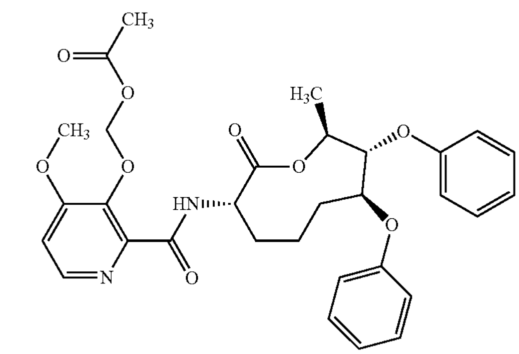 [SMILES: COc1ccnc(C(=O)N[C@H]2CCC[C@H](Oc3ccccc3)[C@@H](Oc3ccccc3)[C@H](C)OC2=O)c1OCOC(C)=O] | 17A |
| F21 | 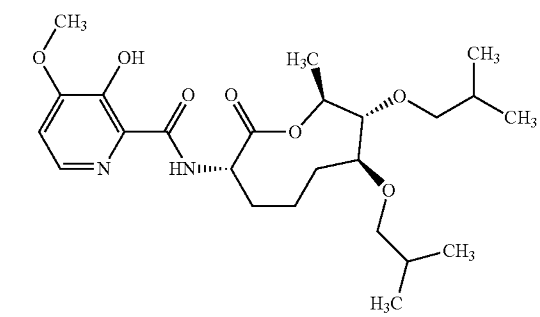 [SMILES: COc1ccnc(C(=O)N[C@H]2CCC[C@H](OCC(C)C)[C@@H](OCC(C)C)[C@H](C)OC2=O)c1O] | 16B |
| F22 | 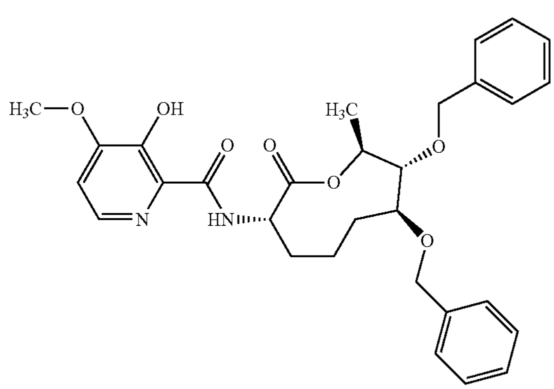 [SMILES: COc1ccnc(C(=O)N[C@H]2CCC[C@H](OCc3ccccc3)[C@@H](OCc3ccccc3)[C@H](C)OC2=O)c1O] | 16B |

TABLE 1-continued
Structure and Preparation Method for F Series Compounds
| Compound Number | Structure | Prepared According to Example |
|---|---|---|
| F23 | 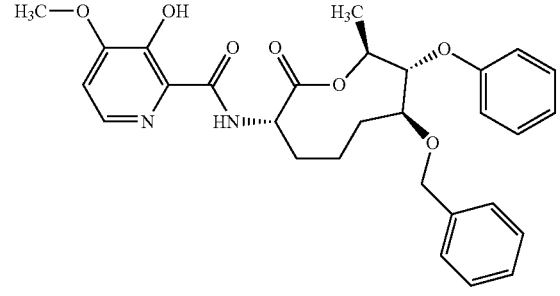 [SMILES: COc1ccnc(C(=O)N[C@H]2CCC[C@H](OCc3ccccc3)[C@@H](Oc3ccccc3)[C@H](C)OC2=O)c1O] | 16B |
| F24 | 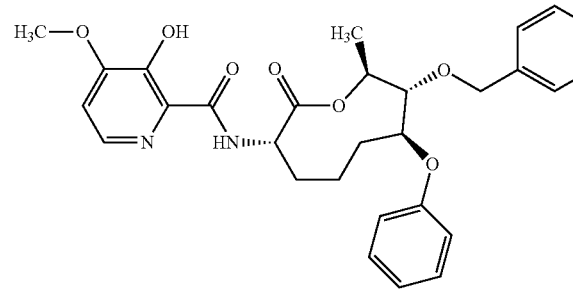 | 16B |
| F25 | 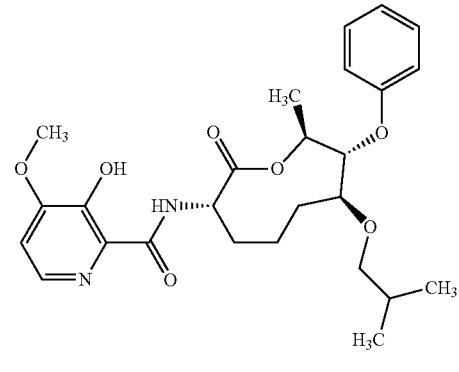 [SMILES: COc1ccnc(C(=O)N[C@H]2CCC[C@H](OCC(C)C)[C@@H](Oc3ccccc3)[C@H](C)OC2=O)c1O] | 16B |
| F26 | 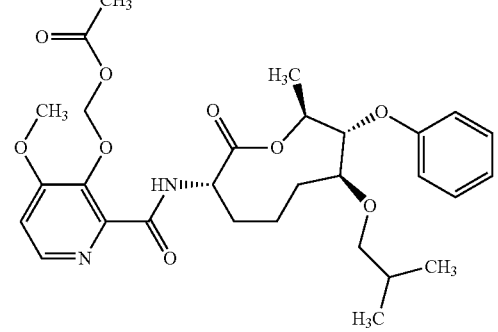 | 17A |

TABLE 1-continued

Structure and Preparation Method for F Series Compounds

| Compound Number | Structure | Prepared According to Example |
|---|---|---|
| F27 | 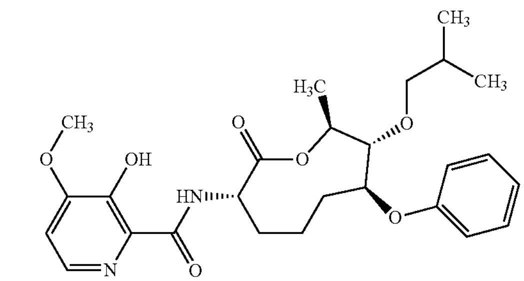 [SMILES: COc1ccnc(C(=O)N[C@H]2CCC[C@H](Oc3ccccc3)[C@@H](OCC(C)C)[C@H](C)OC2=O)c1O] | 16A |
| F28 | 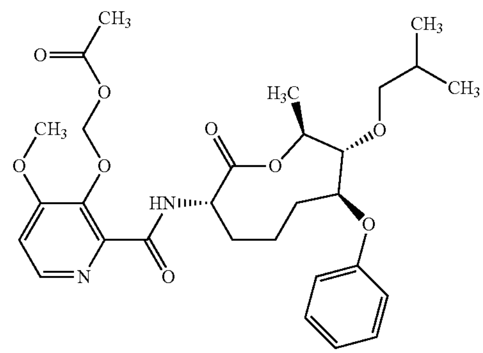 [SMILES: COc1ccnc(C(=O)N[C@H]2CCC[C@H](Oc3ccccc3)[C@@H](OCC(C)C)[C@H](C)OC2=O)c1OCOC(C)=O] | 17A |
| F29 | 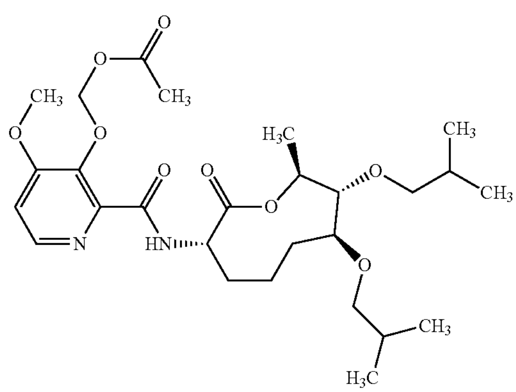 [SMILES: COc1ccnc(C(=O)N[C@H]2CCC[C@H](OCC(C)C)[C@@H](OCC(C)C)[C@H](C)OC2=O)c1OCOC(C)=O] | 17A |
| F30 | 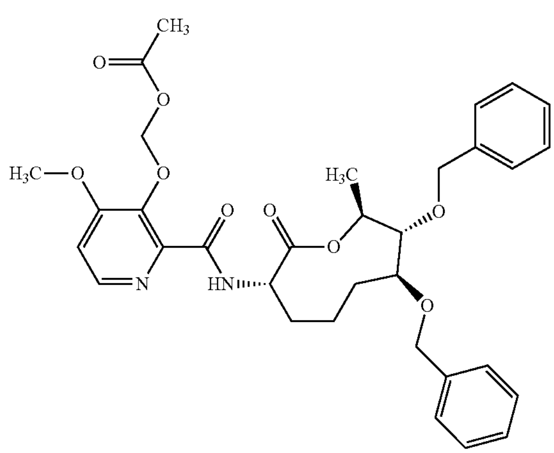 [SMILES: COc1ccnc(C(=O)N[C@H]2CCC[C@H](OCc3ccccc3)[C@@H](OCc3ccccc3)[C@H](C)OC2=O)c1OCOC(C)=O] | 17A |

TABLE 1-continued

Structure and Preparation Method for F Series Compounds

| Compound Number | Structure | Prepared According to Example |
|---|---|---|
| F31 | 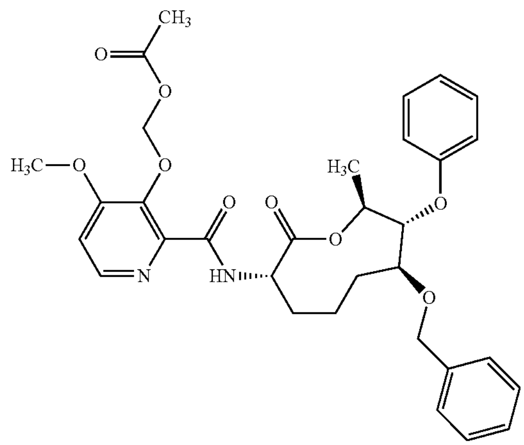 [SMILES: COc1ccnc(C(=O)N[C@H]2CCC[C@H](OCc3ccccc3)[C@@H](Oc3ccccc3)[C@H](C)OC2=O)c1OCOC(C)=O] | 17A |
| F32 | 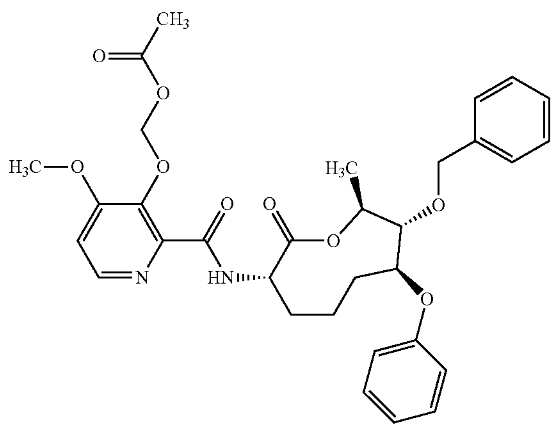 [SMILES: COc1ccnc(C(=O)N[C@H]2CCC[C@H](Oc3ccccc3)[C@@H](OCc3ccccc3)[C@H](C)OC2=O)c1OCOC(C)=O] | 17A |
| F33 | 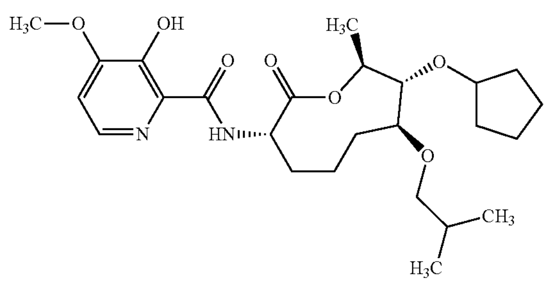 [SMILES: COc1ccnc(C(=O)N[C@H]2CCC[C@H](OCC(C)C)[C@@H](OC3CCCC3)[C@H](C)OC2=O)c1O] | 16A |
| F34 | 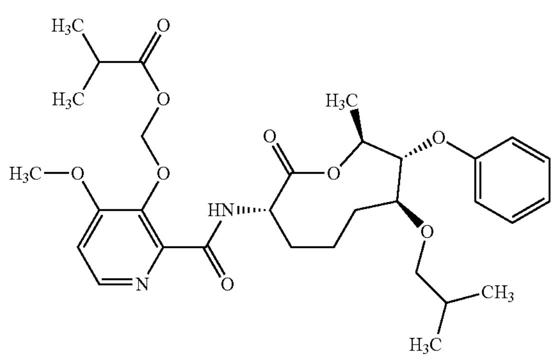 [SMILES: COc1ccnc(C(=O)N[C@H]2CCC[C@H](OCC(C)C)[C@@H](Oc3ccccc3)[C@H](C)OC2=O)c1OCOC(=O)C(C)C] | 17B |

TABLE 1-continued
Structure and Preparation Method for F Series Compounds
| Compound Number | Structure | Prepared According to Example |
|---|---|---|
| F35 | 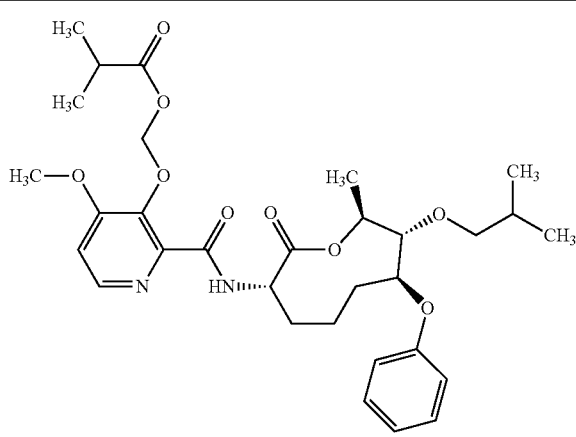 | 17B |
| F36 | 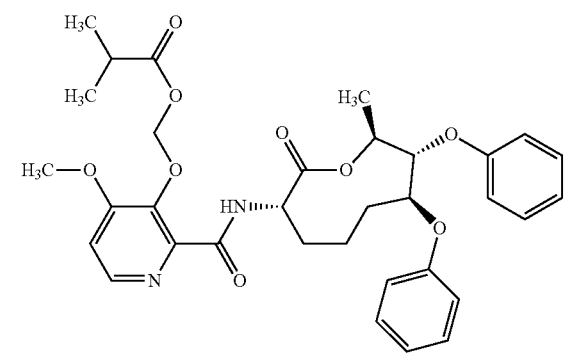 [SMILES: COc1ccnc(C(=O)N[C@H]2CCC[C@H](Oc3ccccc3)[C@@H](Oc3ccccc3)[C@H](C)OC2=O)c1OCOC(=O)C(C)C] | 17B |
| F37 | 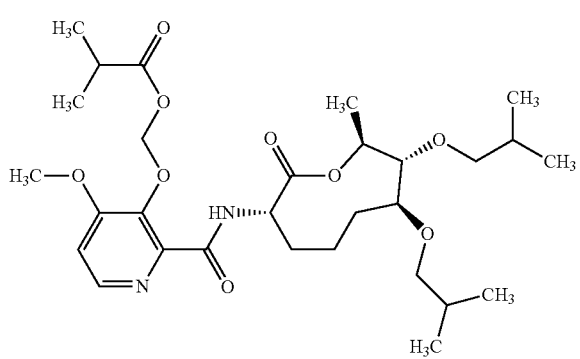 [SMILES: COc1ccnc(C(=O)N[C@H]2CCC[C@H](OCC(C)C)[C@@H](OCC(C)C)[C@H](C)OC2=O)c1OCOC(=O)C(C)C] | 17B |

TABLE 1-continued
Structure and Preparation Method for F Series Compounds
| Compound Number | Structure | Prepared According to Example |
|---|---|---|
| F38 | 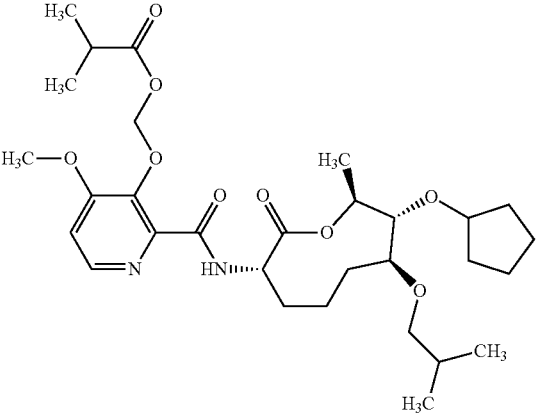 [SMILES: COc1ccnc(C(=O)N[C@H]2CCC[C@H](OCC(C)C)[C@@H](OC3CCCC3)[C@H](C)OC2=O)c1OCOC(=O)C(C)C] | 17B |
| F39 | 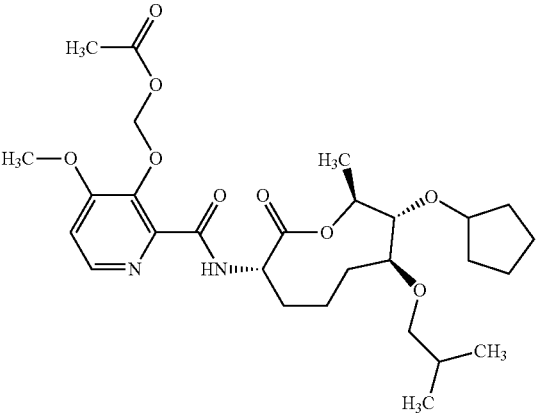 [SMILES: COc1ccnc(C(=O)N[C@H]2CCC[C@H](OCC(C)C)[C@@H](OC3CCCC3)[C@H](C)OC2=O)c1OCOC(C)=O] | 17A |
| F40 | 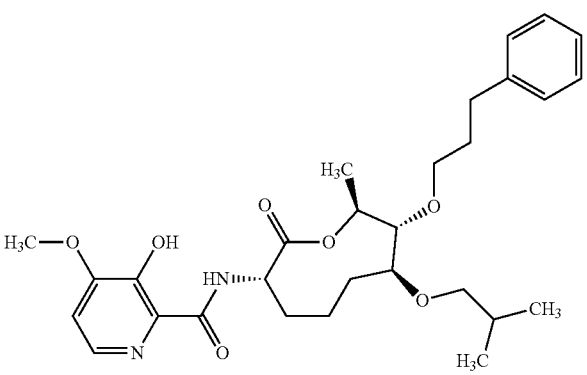 [SMILES: COc1ccnc(C(=O)N[C@H]2CCC[C@H](OCC(C)C)[C@@H](OCCCc3ccccc3)[C@H](C)OC2=O)c1O] | 16A |

TABLE 1-continued

Structure and Preparation Method for F Series Compounds

| Compound Number | Structure | Prepared According to Example |
|---|---|---|
| F41 | 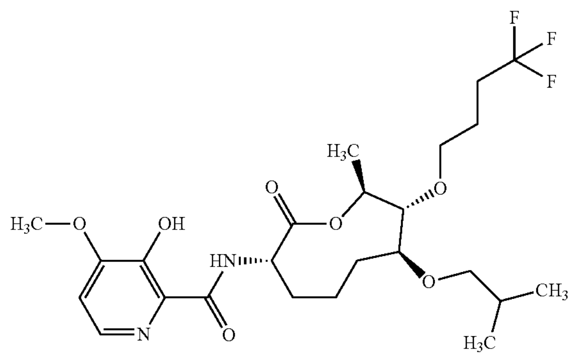 | 16A |
| F42 | 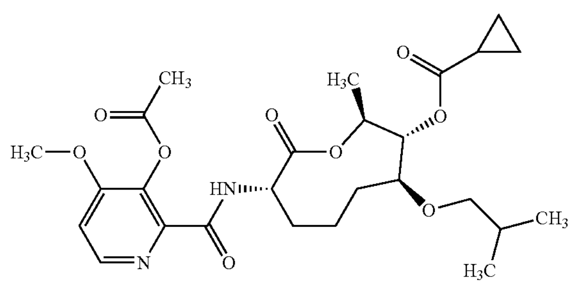 [SMILES: COc1ccnc(C(=O)N[C@H]2CCC[C@H](OCC(C)C)[C@@H](OC(=O)C3CC3)[C@H](C)OC2=O)c1OC(C)=O] | 17C |
| F43 | 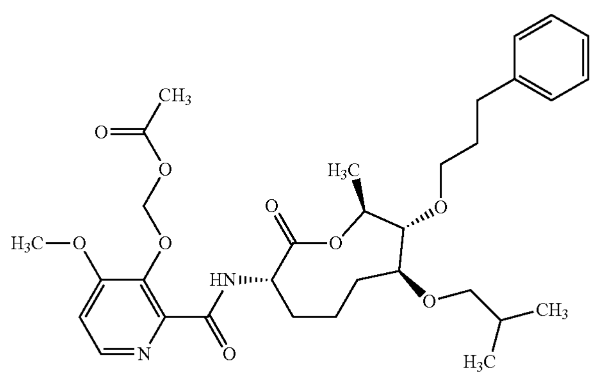 [SMILES: COc1ccnc(C(=O)N[C@H]2CCC[C@H](OCC(C)C)[C@@H](OCCCc3ccccc3)[C@H](C)OC2=O)c1OCOC(C)=O] | 17A |
| F44 | 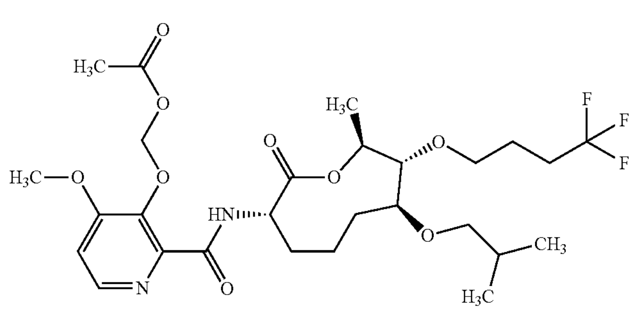 | 17A |

TABLE 1-continued

Structure and Preparation Method for F Series Compounds

| Compound Number | Structure | Prepared According to Example |
|---|---|---|
| F45 | 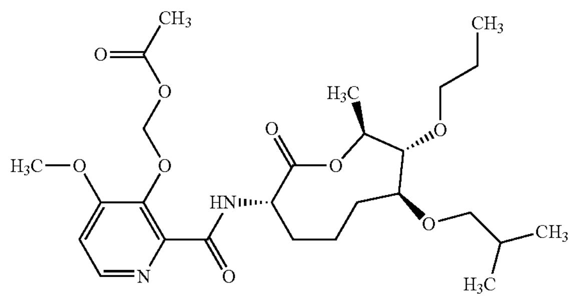 [SMILES: CCCO[C@H]1[C@H](C)OC(=O)[C@@H](NC(=O)c2nccc(OC)c2OCOC(C)=O)CCC[C@@H]1OCC(C)C] | 17A |
| F46 | 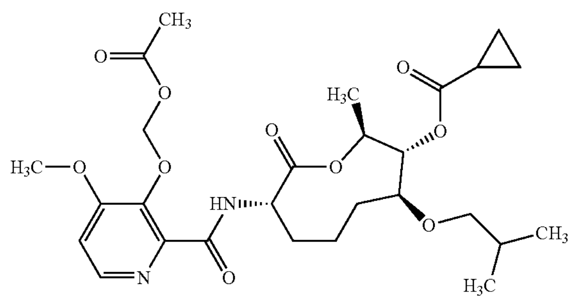 [SMILES: COc1ccnc(C(=O)N[C@H]2CCC[C@H](OCC(C)C)[C@@H](OC(=O)C3CC3)[C@H](C)OC2=O)c1OCOC(C)=O] | 17A |
| F47 | 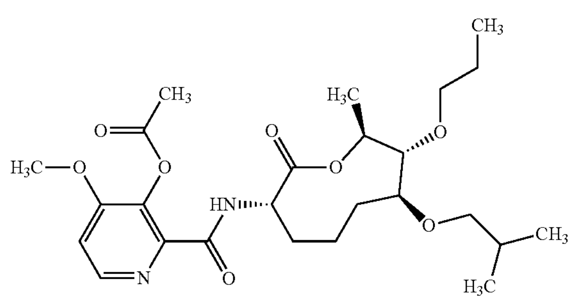 [SMILES: CCCO[C@H]1[C@H](C)OC(=O)[C@@H](NC(=O)c2nccc(OC)c2OC(C)=O)CCC[C@@H]1OCC(C)C] | 17C |
| F48 | 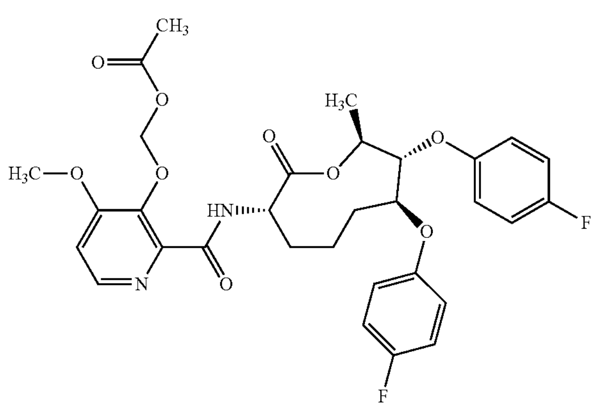 [SMILES: COc1ccnc(C(=O)N[C@H]2CCC[C@H](Oc3ccc(F)cc3)[C@@H](Oc3ccc(F)cc3)[C@H](C)OC2=O)c1OCOC(C)=O] | 17A |

TABLE 1-continued
Structure and Preparation Method for F Series Compounds
| Compound Number | Structure | Prepared According to Example |
|---|---|---|
| F49 | 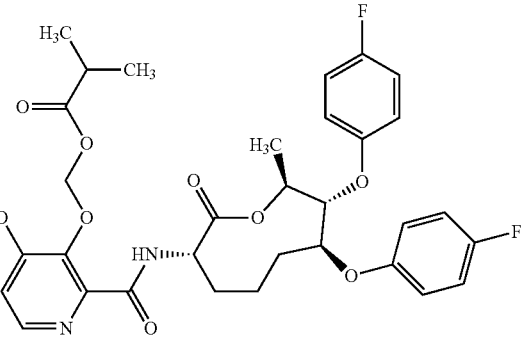 | 17B |
| F50 | 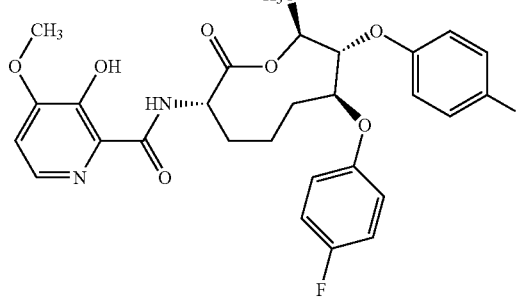 | 16A |
| F51 | 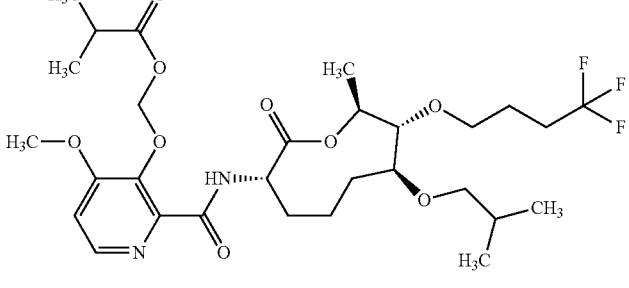 | 17B |
| F52 | 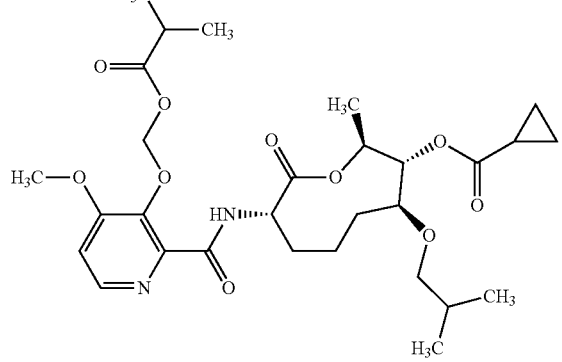 | 17B |

TABLE 1-continued

Structure and Preparation Method for F Series Compounds

| Compound Number | Structure | Prepared According to Example |
|---|---|---|
| F53 | 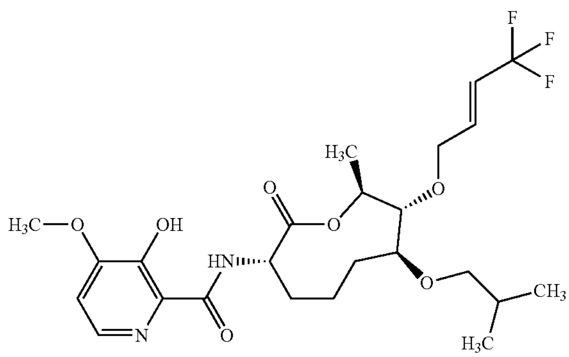 [SMILES: COc1ccnc(C(=O)N[C@H]2CCC[C@H](OCC(C)C)[C@@H](OC/C=C/C(F)(F)F)[C@H](C)OC2=O)c1O] | 16A |
| F54 | 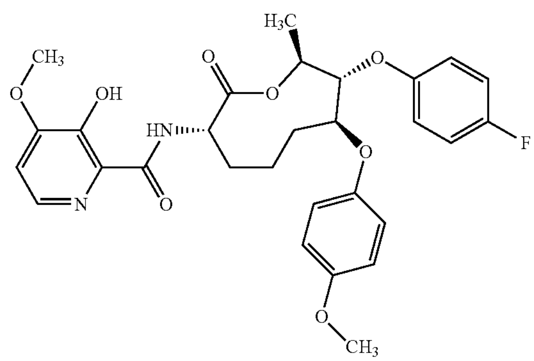 [SMILES: COc1ccc(O[C@H]2CCC[C@H](NC(=O)c3nccc(OC)c3O)C(=O)O[C@@H](C)[C@@H]2Oc2ccc(F)cc2)cc1] | 16A |
| F55 | 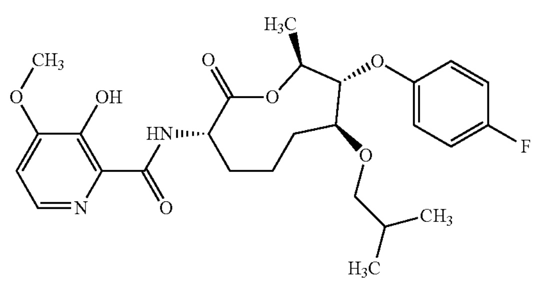 [SMILES: COc1ccnc(C(=O)N[C@H]2CCC[C@H](OCC(C)C)[C@@H](Oc3ccc(F)cc3)[C@H](C)OC2=O)c1O] | 16A |
| F56 | 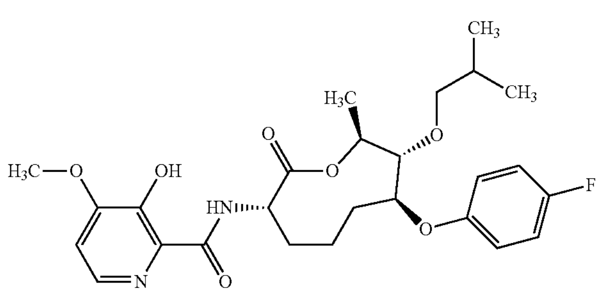 [SMILES: COc1ccnc(C(=O)N[C@H]2CCC[C@H](Oc3ccc(F)cc3)[C@@H](OCC(C)C)[C@H](C)OC2=O)c1O] | 16A |

TABLE 1-continued

Structure and Preparation Method for F Series Compounds

| Compound Number | Structure | Prepared According to Example |
|---|---|---|
| F57 | 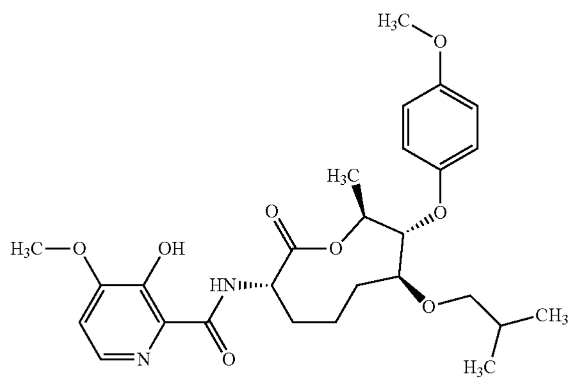 [SMILES: COc1ccc(O[C@H]2[C@H](C)OC(=O)[C@@H](NC(=O)c3nccc(OC)c3O)CCC[C@@H]2OCC(C)C)cc1] | 16A |
| F58 | 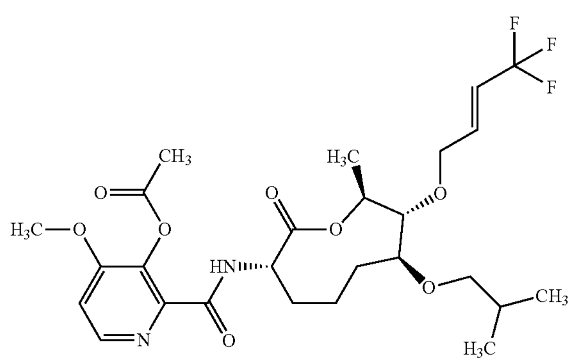 [SMILES: COc1ccnc(C(=O)N[C@H]2CCC[C@H](OCC(C)C)[C@@H](OC/C=C/C(F)(F)F)[C@H](C)OC2=O)c1OC(C)=O] | 17C |
| F59 | 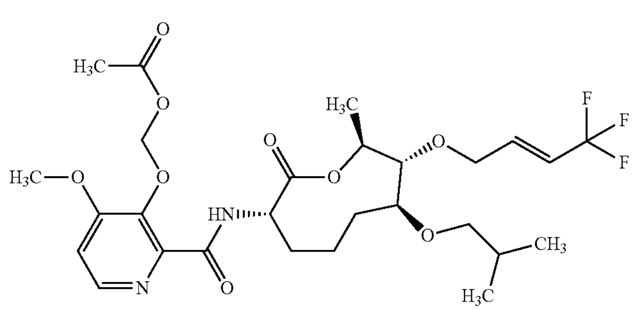 [SMILES: COc1ccnc(C(=O)N[C@H]2CCC[C@H](OCC(C)C)[C@@H](OC/C=C/C(F)(F)F)[C@H](C)OC2=O)c1OCOC(C)=O] | 17A |

TABLE 1-continued

Structure and Preparation Method for F Series Compounds

| Compound Number | Structure | Prepared According to Example |
|---|---|---|
| F60 | 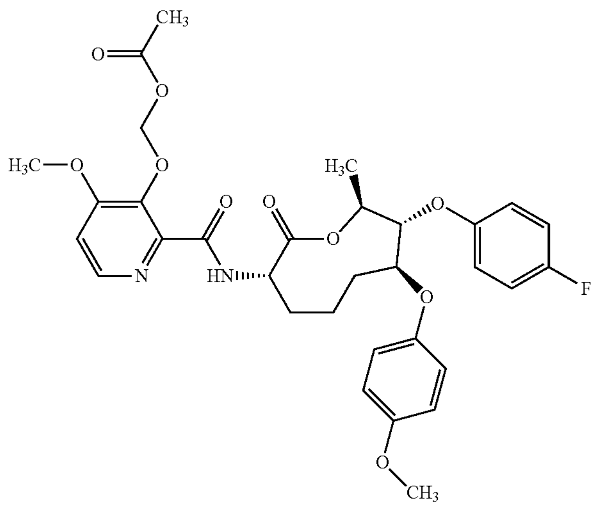 [SMILES: COc1ccc(O[C@H]2CCC[C@H](NC(=O)c3nccc(OC)c3OCOC(C)=O)C(=O)O[C@@H](C)[C@@H]2Oc2ccc(F)cc2)cc1] | 17A |
| F61 | 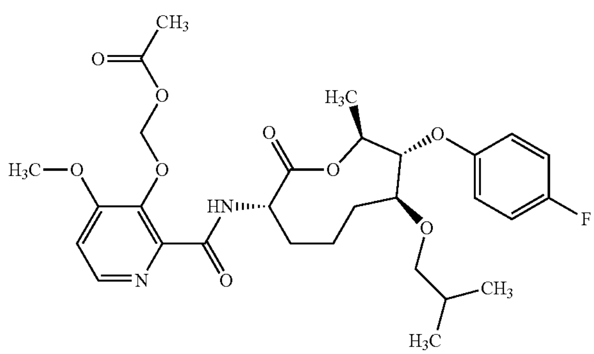 [SMILES: COc1ccnc(C(=O)N[C@H]2CCC[C@H](OCC(C)C)[C@@H](Oc3ccc(F)cc3)[C@H](C)OC2=O)c1OCOC(C)=O] | 17A |
| F62 | 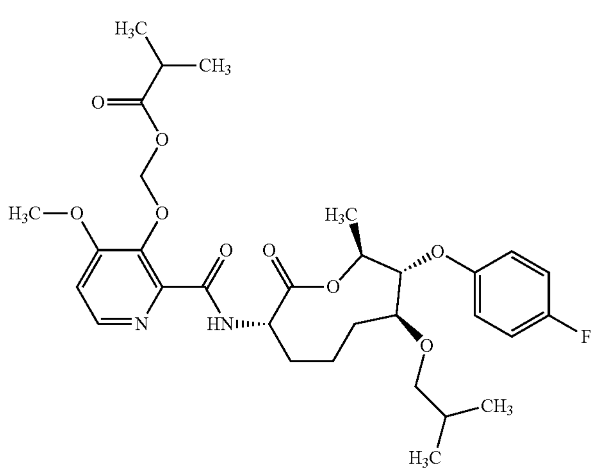 [SMILES: COc1ccnc(C(=O)N[C@H]2CCC[C@H](OCC(C)C)[C@@H](Oc3ccc(F)cc3)[C@H](C)OC2=O)c1OCOC(=O)C(C)C] | 17B |

TABLE 1-continued

Structure and Preparation Method for F Series Compounds

| Compound Number | Structure | Prepared According to Example |
|---|---|---|
| F63 | 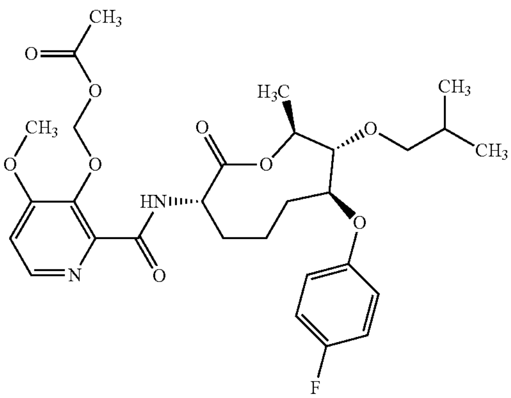 [SMILES: COc1ccnc(C(=O)N[C@H]2CCC[C@H](Oc3ccc(F)cc3)[C@@H](OCC(C)C)[C@H](C)OC2=O)c1OCOC(C)=O] | 17A |
| F64 | 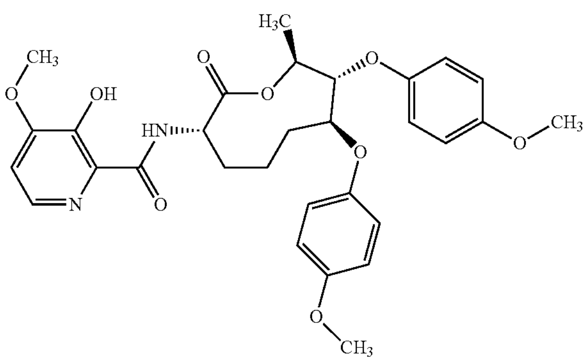 [SMILES: COc1ccc(O[C@H]2[C@H](C)OC(=O)[C@@H](NC(=O)c3nccc(OC)c3O)CCC[C@@H]2Oc2ccc(OC)cc2)cc1] | 16A |
| F65 | 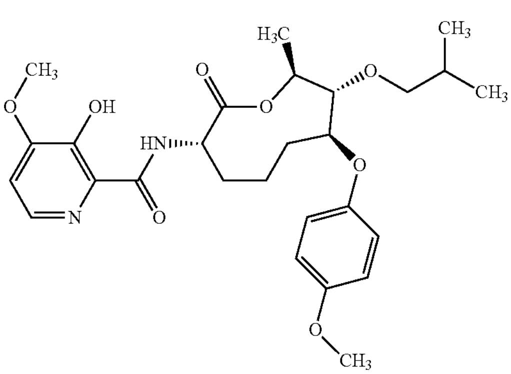 [SMILES: COc1ccc(O[C@H]2CCC[C@H](NC(=O)c3nccc(OC)c3O)C(=O)O[C@@H](C)[C@@H]2OCC(C)C)cc1] | 16A |

TABLE 1-continued

Structure and Preparation Method for F Series Compounds

| Compound Number | Structure | Prepared According to Example |
|---|---|---|
| F66 | 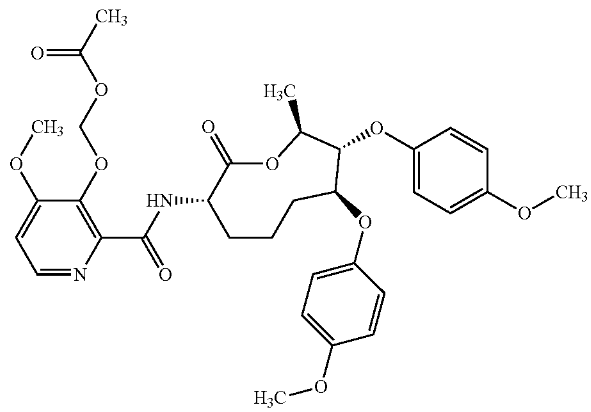 [SMILES: COc1ccc(O[C@H]2[C@H](C)OC(=O)[C@@H](NC(=O)c3nccc(OC)c3OCOC(C)=O)CCC[C@@H]2Oc2ccc(OC)cc2)cc1] | 17A |
| F67 | 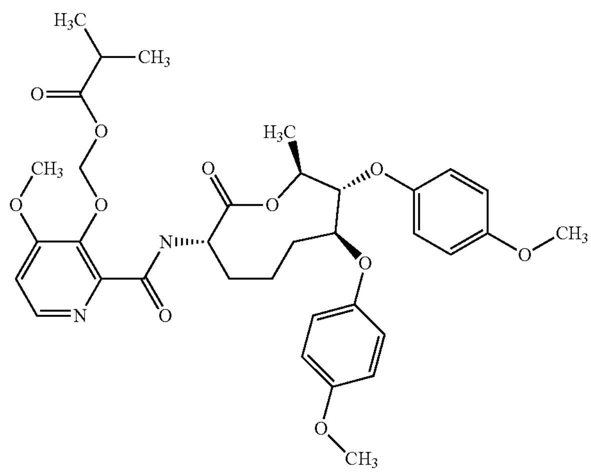 [SMILES: COc1ccc(O[C@H]2[C@H](C)OC(=O)[C@@H](NC(=O)c3nccc(OC)c3OCOC(=O)C(C)C)CCC[C@@H]2Oc2ccc(OC)cc2)cc1] | 17B |
| F68 | 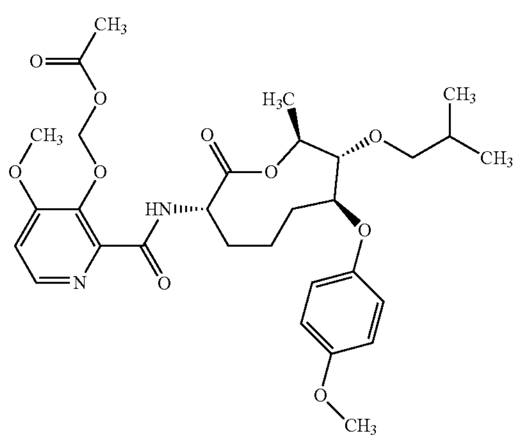 [SMILES: COc1ccc(O[C@H]2CCC[C@H](NC(=O)c3nccc(OC)c3OCOC(C)=O)C(=O)O[C@@H](C)[C@@H]2OCC(C)C)cc1] | 17A |

TABLE 1-continued

Structure and Preparation Method for F Series Compounds

| Compound Number | Structure | Prepared According to Example |
|---|---|---|
| F69 | 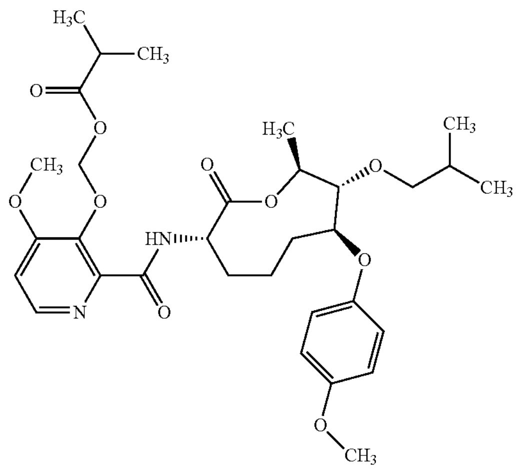 [SMILES: COc1ccc(O[C@H]2CCC[C@H](NC(=O)c3nccc(OC)c3OCOC(=O)C(C)C)C(=O)O[C@@H](C)[C@@H]2OCC(C)C)cc1] | 17B |
| F70 | 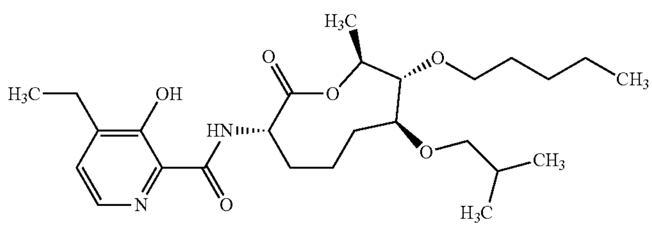 [SMILES: CCCCCO[C@H]1[C@H](C)OC(=O)[C@@H](NC(=O)c2nccc(CC)c2O)CCC[C@@H]1OCC(C)C] | 16A |
| F71 | 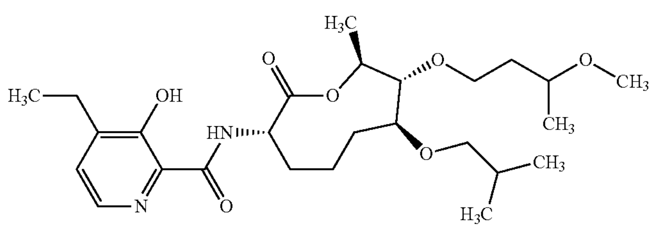 [SMILES: CCc1ccnc(C(=O)N[C@H]2CCC[C@H](OCC(C)C)[C@@H](OCCC(C)OC)[C@H](C)OC2=O)c1O] | 16A |
| F72 | 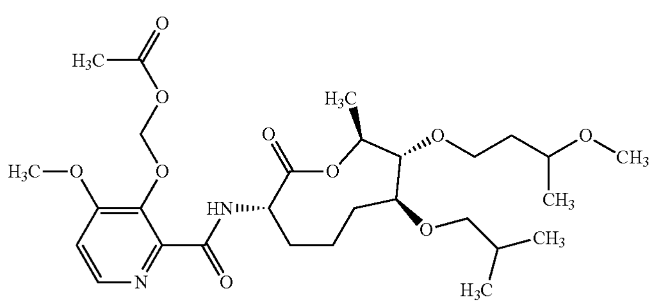 | 17A |
| F73 | 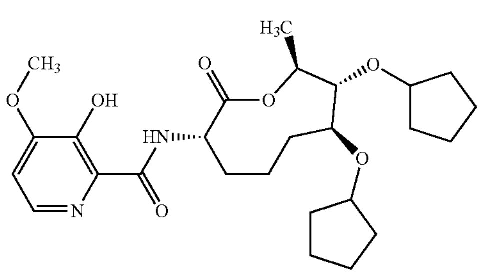 [SMILES: COc1ccnc(C(=O)N[C@H]2CCC[C@H](OC3CCCC3)[C@@H](OC3CCCC3)[C@H](C)OC2=O)c1O] | 16A |

TABLE 1-continued

Structure and Preparation Method for F Series Compounds

| Compound Number | Structure | Prepared According to Example |
|---|---|---|
| F74 | 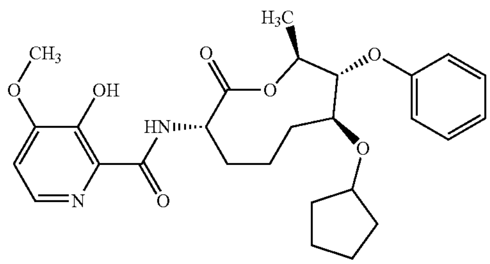 [SMILES: COc1ccnc(C(=O)N[C@H]2CCC[C@H](OC3CCCC3)[C@@H](Oc3ccccc3)[C@H](C)OC2=O)c1O] | 16A |
| F75 | 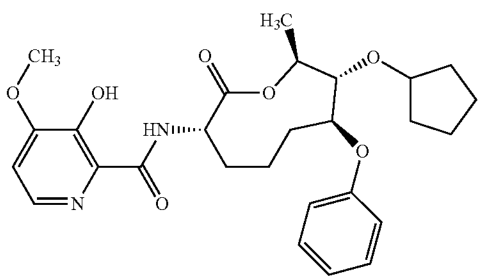 [SMILES: COc1ccnc(C(=O)N[C@H]2CCC[C@H](Oc3ccccc3)[C@@H](OC3CCCC3)[C@H](C)OC2=O)c1O] | 16A |
| F76 | 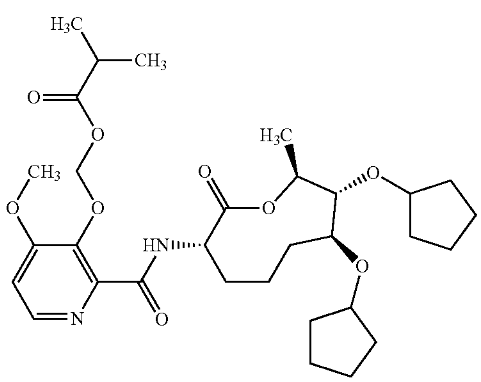 [SMILES: COc1ccnc(C(=O)N[C@H]2CCC[C@H](OC3CCCC3)[C@@H](OC3CCCC3)[C@H](C)OC2=O)c1OCOC(=O)C(C)C] | 17B |
| F77 | 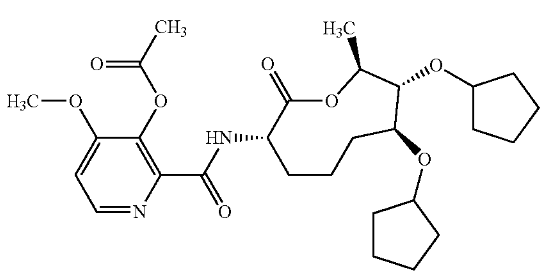 [SMILES: COc1ccnc(C(=O)N[C@H]2CCC[C@H](OC3CCCC3)[C@@H](OC3CCCC3)[C@H](C)OC2=O)c1OC(C)=O] | 17C |

TABLE 1-continued

Structure and Preparation Method for F Series Compounds

| Compound Number | Structure | Prepared According to Example |
|---|---|---|
| F78 | 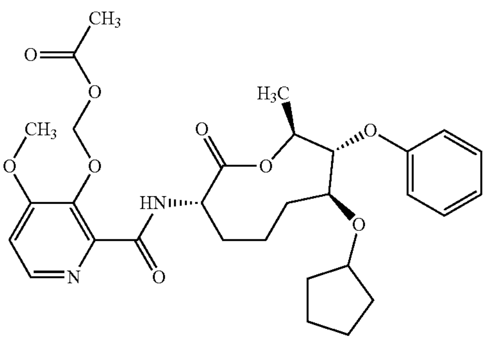 [SMILES: COc1ccnc(C(=O)N[C@H]2CCC[C@H](OC3CCCC3)[C@@H](Oc3ccccc3)[C@H](C)OC2=O)c1OCOC(C)=O] | 17A |
| F79 | 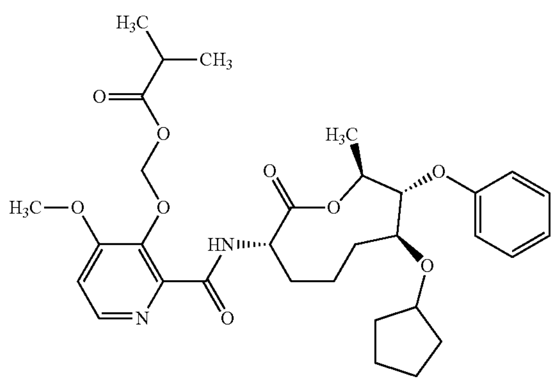 [SMILES: COc1ccnc(C(=O)N[C@H]2CCC[C@H](OC3CCCC3)[C@@H](Oc3ccccc3)[C@H](C)OC2=O)c1OCOC(=O)C(C)C] | 17B |
| F80 | 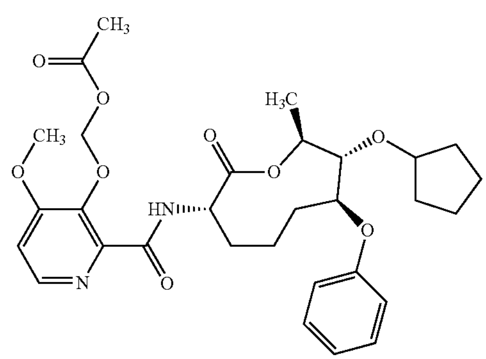 [SMILES: COc1ccnc(C(=O)N[C@H]2CCC[C@H](Oc3ccccc3)[C@@H](OC3CCCC3)[C@H](C)OC2=O)c1OCOC(C)=O] | 17A |
| F81 | 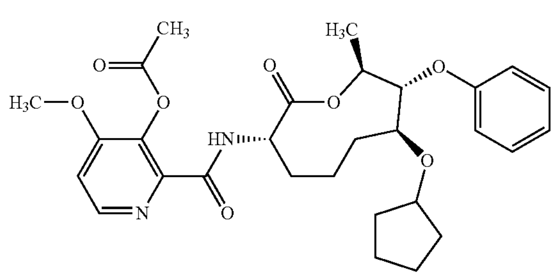 [SMILES: COc1ccnc(C(=O)N[C@H]2CCC[C@H](OC3CCCC3)[C@@H](Oc3ccccc3)[C@H](C)OC2=O)c1OC(C)=O] | 17C |

TABLE 1-continued

Structure and Preparation Method for F Series Compounds

| Compound Number | Structure | Prepared According to Example |
|---|---|---|
| F82 | 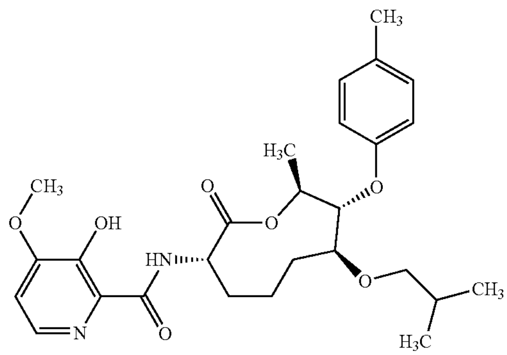 [SMILES: COc1ccnc(C(=O)N[C@H]2CCC[C@H](OCC(C)C)[C@@H](Oc3ccc(C)cc3)[C@H](C)OC2=O)c1O] | 16A |
| F83 | 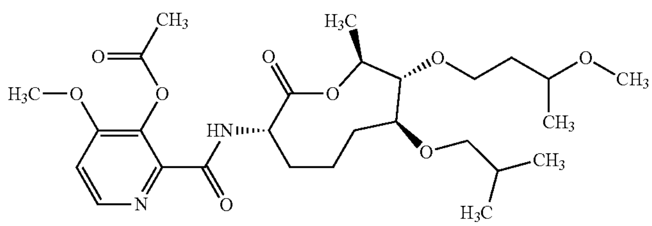 | 17C |
| F84 | 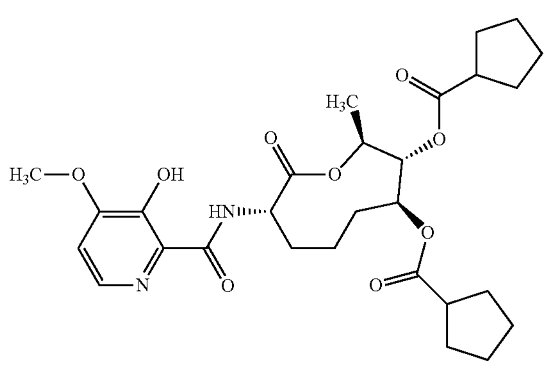 [SMILES: COc1ccnc(C(=O)N[C@H]2CCC[C@H](OC(=O)C3CCCC3)[C@@H](OC(=O)C3CCCC3)[C@H](C)OC2=O)c1O] | 16A |
| F85 | 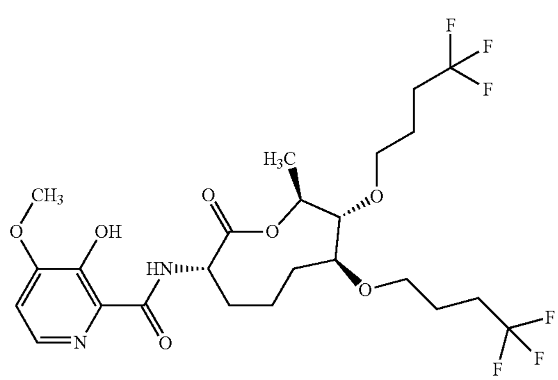 [SMILES: COc1ccnc(C(=O)N[C@H]2CCC[C@H](OCCCC(F)(F)F)[C@@H](OCCCC(F)(F)F)[C@H](C)OC2=O)c1O] | 16A |

TABLE 1-continued

Structure and Preparation Method for F Series Compounds

| Compound Number | Structure | Prepared According to Example |
|---|---|---|
| F86 | 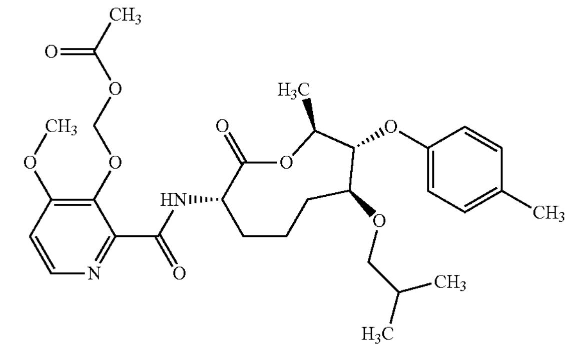 [SMILES: COc1ccnc(C(=O)N[C@H]2CCC[C@H](OCC(C)C)[C@@H](Oc3ccc(C)cc3)[C@H](C)OC2=O)c1OCOC(C)=O] | 17A |
| F87 | 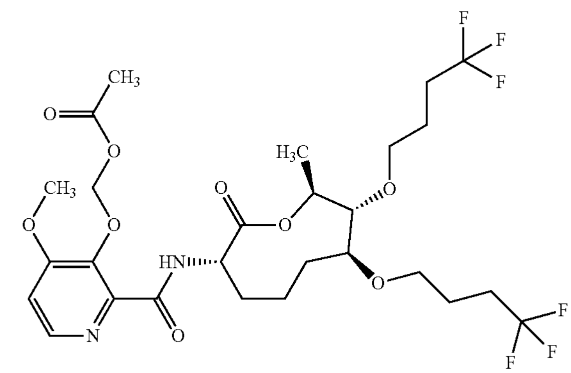 [SMILES: COc1ccnc(C(=O)N[C@H]2CCC[C@H](OCCCC(F)(F)F)[C@@H](OCCCC(F)(F)F)[C@H](C)OC2=O)c1OCOC(C)=O] | 17A |
| F88 | 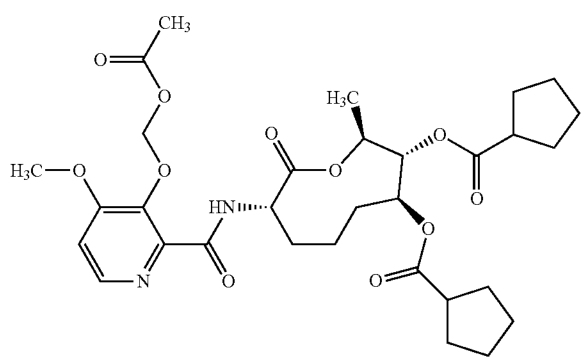 [SMILES: COc1ccnc(C(=O)N[C@H]2CCC[C@H](OC(=O)C3CCCC3)[C@@H](OC(=O)C3CCCC3)[C@H](C)OC2=O)c1OCOC(C)=O] | 17A |
| F89 | 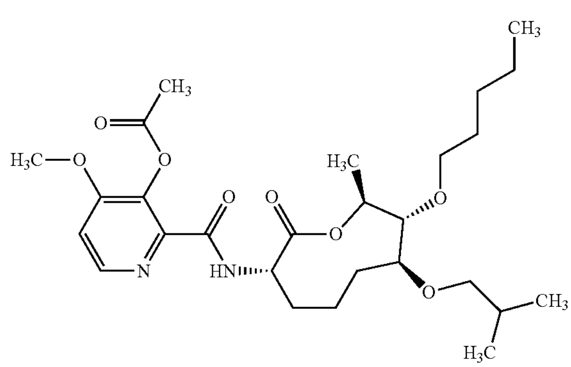 [SMILES: CCCCCO[C@H]1[C@H](C)OC(=O)[C@@H](NC(=O)c2nccc(OC)c2OC(C)=O)CCC[C@@H]1OCC(C)C] | 17C |

TABLE 1-continued

Structure and Preparation Method for F Series Compounds

| Compound Number | Structure | Prepared According to Example |
|---|---|---|
| F90 | 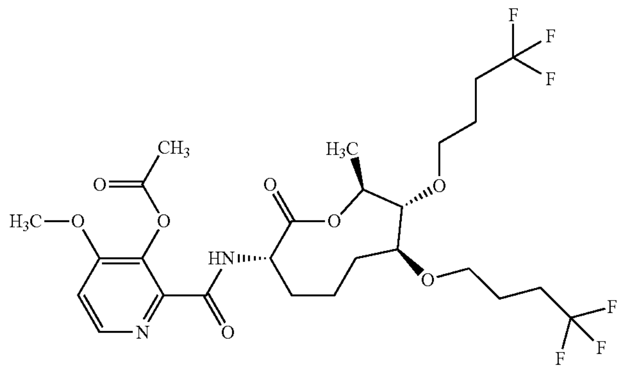 [SMILES: COc1ccnc(C(=O)N[C@H]2CCC[C@H](OCCCC(F)(F)F)[C@@H](OCCCC(F)(F)F)[C@H](C)OC2=O)c1OC(C)=O] | 17C |
| F91 | 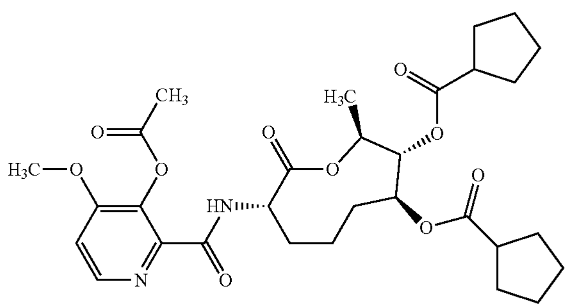 [SMILES: COc1ccnc(C(=O)N[C@H]2CCC[C@H](OC(=O)C3CCCC3)[C@@H](OC(=O)C3CCCC3)[C@H](C)OC2=O)c1OC(C)=O] | 17C |
| F92 | 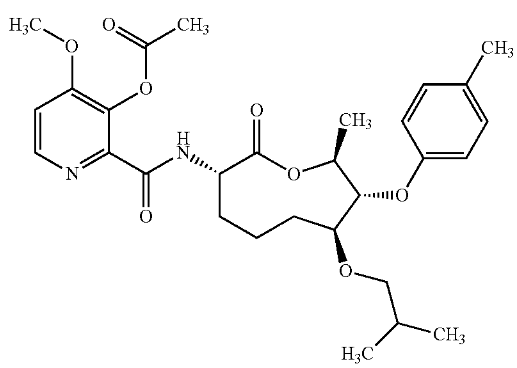 [SMILES: COc1ccnc(C(=O)N[C@H]2CCC[C@H](OCC(C)C)[C@@H](Oc3ccc(C)cc3)[C@H](C)OC2=O)c1OC(C)=O] | 17C |
| F93 | 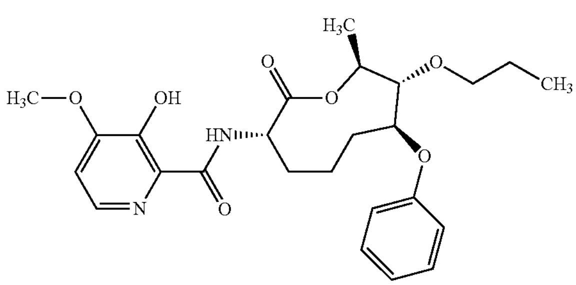 [SMILES: CCCO[C@H]1[C@H](C)OC(=O)[C@@H](NC(=O)c2nccc(OC)c2O)CCC[C@@H]1Oc1ccccc1] | 16A |

TABLE 1-continued

Structure and Preparation Method for F Series Compounds

| Compound Number | Structure | Prepared According to Example |
|---|---|---|
| F94 | 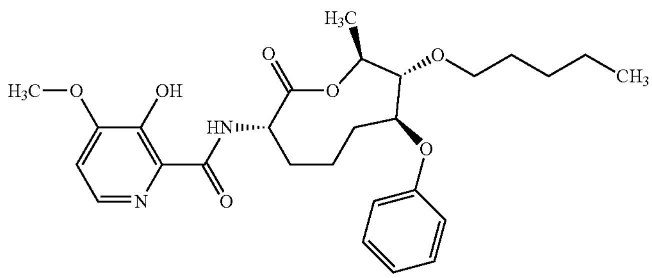 [SMILES: CCCCCO[C@H]1[C@H](C)OC(=O)[C@@H](NC(=O)c2nccc(OC)c2O)CCC[C@@H]1Oc1ccccc1] | 16A |
| F95 | 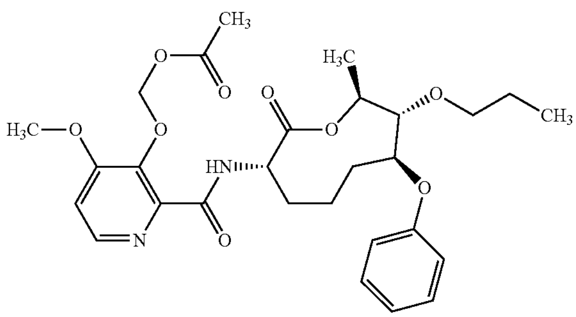 [SMILES: CCCO[C@H]1[C@H](C)OC(=O)[C@@H](NC(=O)c2nccc(OC)c2OCOC(C)=O)CCC[C@@H]1Oc1ccccc1] | 17A |
| F96 | 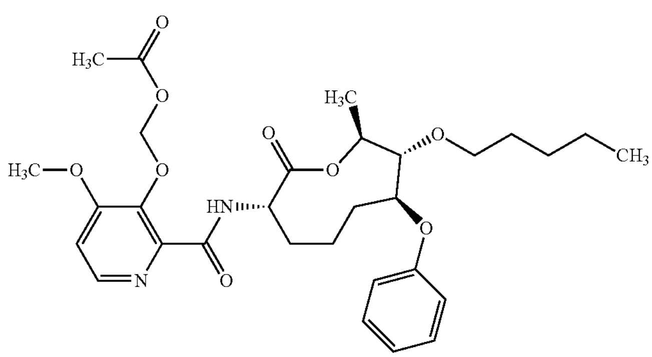 [SMILES: CCCCCO[C@H]1[C@H](C)OC(=O)[C@@H](NC(=O)c2nccc(OC)c2OCOC(C)=O)CCC[C@@H]1Oc1ccccc1] | 17A |
| F97 | 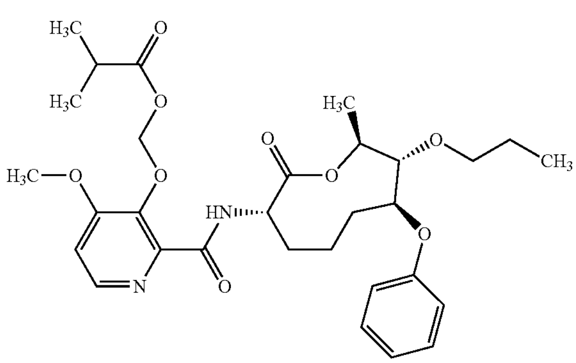 [SMILES: CCCO[C@H]1[C@H](C)OC(=O)[C@@H](NC(=O)c2nccc(OC)c2OCOC(=O)C(C)C)CCC[C@@H]1Oc1ccccc1] | 17B |

TABLE 1-continued

Structure and Preparation Method for F Series Compounds

| Compound Number | Structure | Prepared According to Example |
|---|---|---|
| F98 | 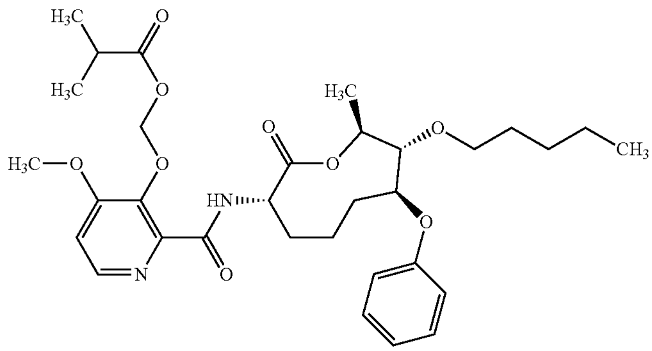 [SMILES: CCCCCO[C@H]1[C@H](C)OC(=O)[C@@H](NC(=O)c2nccc(OC)c2OCOC(=O)C(C)C)CCC[C@@H]1Oc1ccccc1] | 17B |
| F99 | 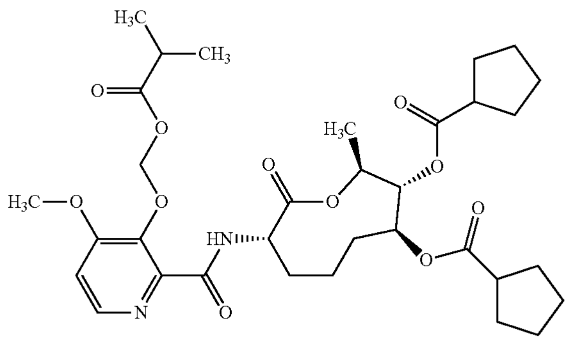 [SMILES: COc1ccnc(C(=O)N[C@H]2CCC[C@H](OC(=O)C3CCCC3)[C@@H](OC(=O)C3CCCC3)[C@H](C)OC2=O)c1OCOC(=O)C(C)C] | 17B |
| F100 | 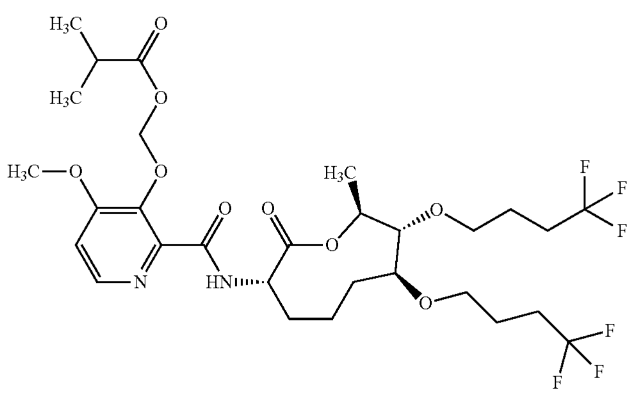 [SMILES: COc1ccnc(C(=O)N[C@H]2CCC[C@H](OCCCC(F)(F)F)[C@@H](OCCCC(F)(F)F)[C@H](C)OC2=O)c1OCOC(=O)C(C)C] | 17B |
| F101 | 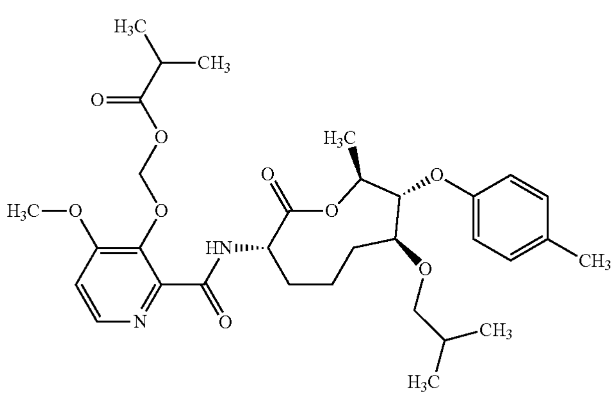 | 17B |

TABLE 1-continued

Structure and Preparation Method for F Series Compounds

| Compound Number | Structure | Prepared According to Example |
|---|---|---|
| F102 | 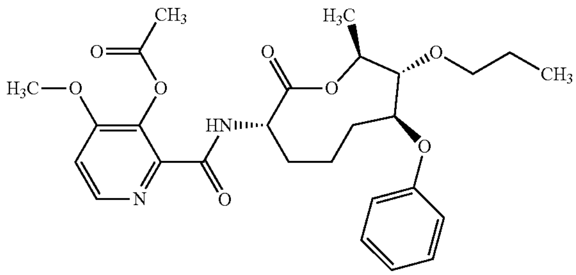 [SMILES: CCCO[C@H]1[C@H](C)OC(=O)[C@@H](NC(=O)c2nccc(OC)c2OC(C)=O)CCC[C@@H]1Oc1ccccc1] | 17C |
| F103 | 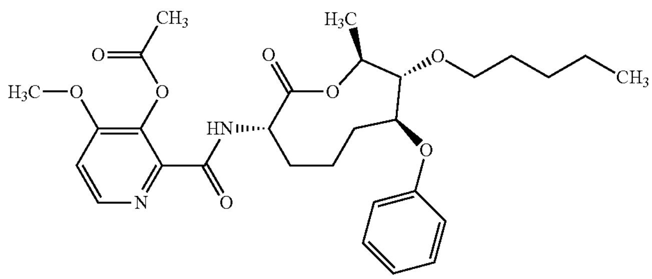 [SMILES: CCCCCO[C@H]1[C@H](C)OC(=O)[C@@H](NC(=O)c2nccc(OC)c2OC(C)=O)CCC[C@@H]1Oc1ccccc1] | 17C |
| F104 | 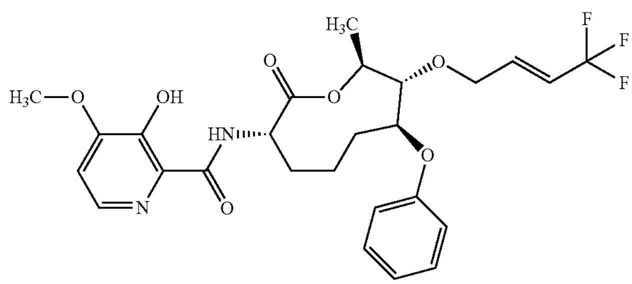 [SMILES: COc1ccnc(C(=O)N[C@H]2CCC[C@H](Oc3ccccc3)[C@@H](OC/C=C/C(F)(F)F)[C@H](C)OC2=O)c1O] | 16A |
| F105 | 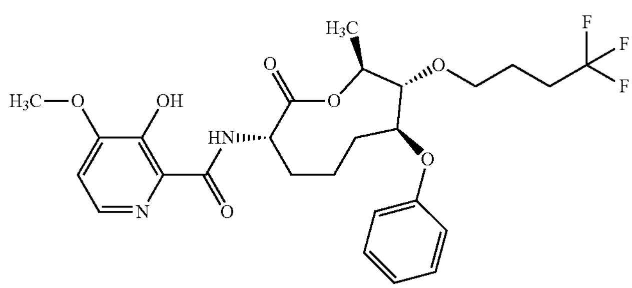 [SMILES: COc1ccnc(C(=O)N[C@H]2CCC[C@H](Oc3ccccc3)[C@@H](OCCCC(F)(F)F)[C@H](C)OC2=O)c1O] | 16A |
| F106 | 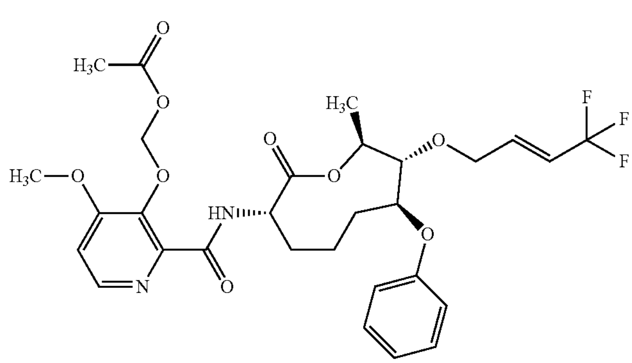 [SMILES: COc1ccnc(C(=O)N[C@H]2CCC[C@H](Oc3ccccc3)[C@@H](OC/C=C/C(F)(F)F)[C@H](C)OC2=O)c1OCOC(C)=O] | 17A |

TABLE 1-continued

Structure and Preparation Method for F Series Compounds

| Compound Number | Structure | Prepared According to Example |
|---|---|---|
| F107 | 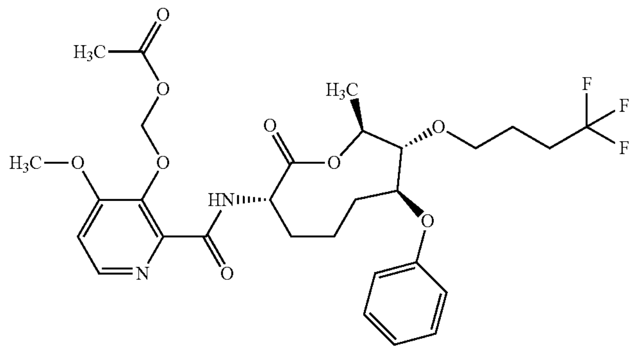 [SMILES: COc1ccnc(C(=O)N[C@H]2CCC[C@H](Oc3ccccc3)[C@@H](OCCCC(F)(F)F)[C@H](C)OC2=O)c1OCOC(C)=O] | 17A |
| F108 | 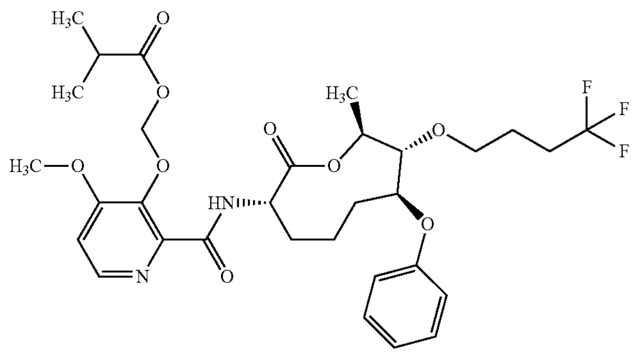 [SMILES: COc1ccnc(C(=O)N[C@H]2CCC[C@H](Oc3ccccc3)[C@@H](OCCCC(F)(F)F)[C@H](C)OC2=O)c1OCOC(=O)C(C)C] | 17B |
| F109 | 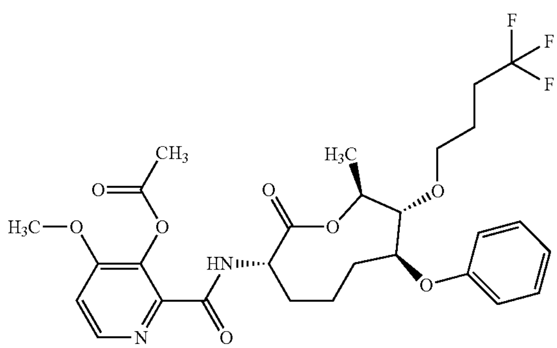 [SMILES: COc1ccnc(C(=O)N[C@H]2CCC[C@H](Oc3ccccc3)[C@@H](OCCCC(F)(F)F)[C@H](C)OC2=O)c1OC(C)=O] | 17C |
| F110 | 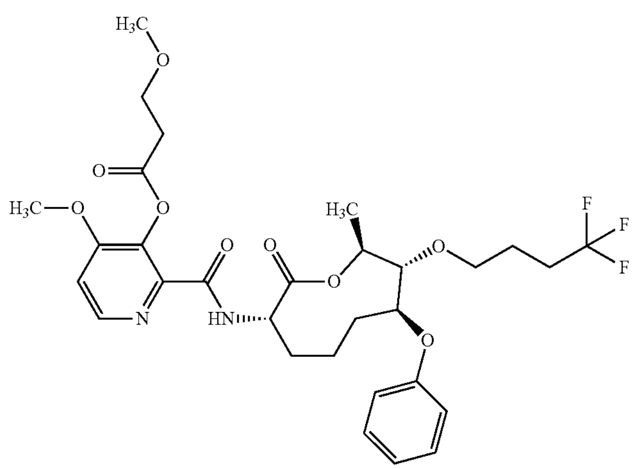 [SMILES: COCCC(=O)Oc1c(OC)ccnc1C(=O)N[C@H]1CCC[C@H](Oc2ccccc2)[C@@H](OCCCC(F)(F)F)[C@H](C)OC1=O] | 17D |

TABLE 1-continued

Structure and Preparation Method for F Series Compounds

| Compound Number | Structure | Prepared According to Example |
|---|---|---|
| F111 | 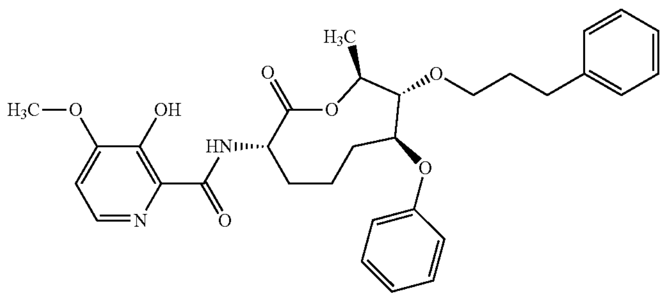 [SMILES: COc1ccnc(C(=O)N[C@H]2CCC[C@H](Oc3ccccc3)[C@@H](OCCCc3ccccc3)[C@H](C)OC2=O)c1O] | 16A |
| F112 | 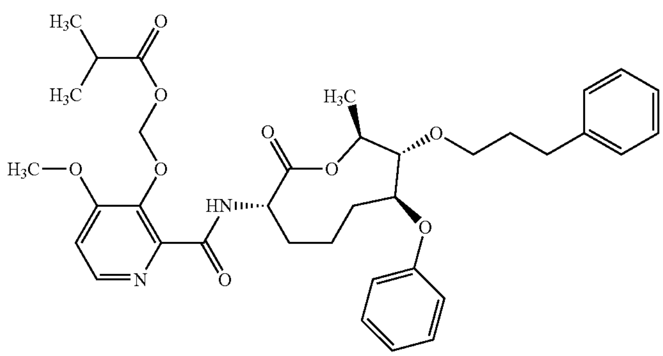 [SMILES: COc1ccnc(C(=O)N[C@H]2CCC[C@H](Oc3ccccc3)[C@@H](OCCCc3ccccc3)[C@H](C)OC2=O)c1OCOC(=O)C(C)C] | 17B |
| F113 | 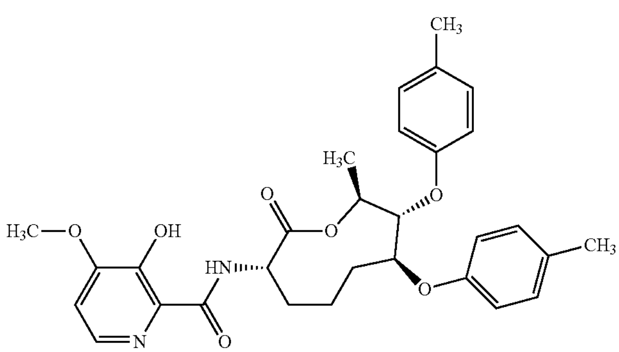 | 16A |
| F114 | 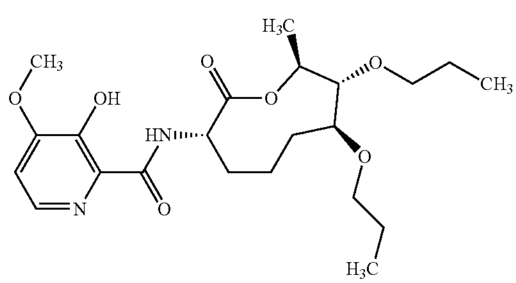 [SMILES: CCCO[C@H]1[C@H](C)OC(=O)[C@@H](NC(=O)c2nccc(OC)c2O)CCC[C@@H]1OCCC] | 16A |

TABLE 1-continued

Structure and Preparation Method for F Series Compounds

| Compound Number | Structure | Prepared According to Example |
|---|---|---|
| F115 | 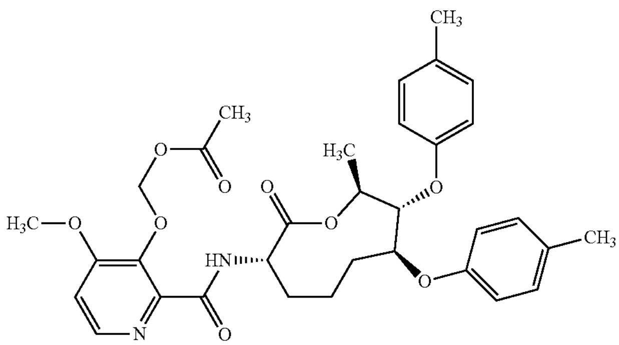 | 17A |
| F116 | 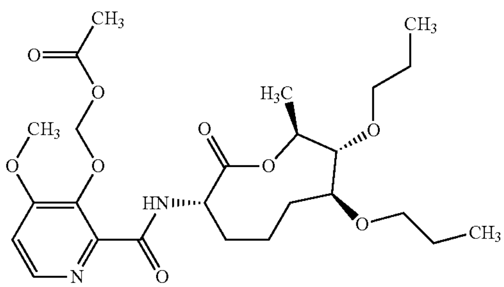 [SMILES: CCCO[C@H]1[C@H](C)OC(=O)[C@@H](NC(=O)c2nccc(OC)c2OCOC(C)=O)CCC[C@@H]1OCCC] | 17A |
| F117 | 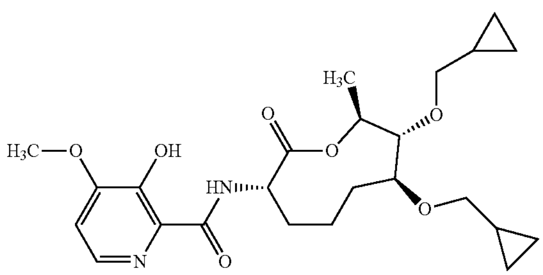 [SMILES: COc1ccnc(C(=O)N[C@H]2CCC[C@H](OCC3CC3)[C@@H](OCC3CC3)[C@H](C)OC2=O)c1O] | 16A |
| F118 | 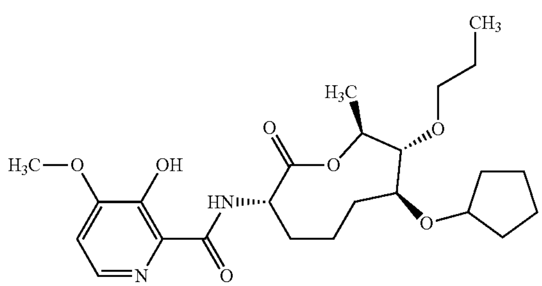 [SMILES: CCCO[C@H]1[C@H](C)OC(=O)[C@@H](NC(=O)c2nccc(OC)c2O)CCC[C@@H]1OC1CCCC1] | 16A |
| F119 | 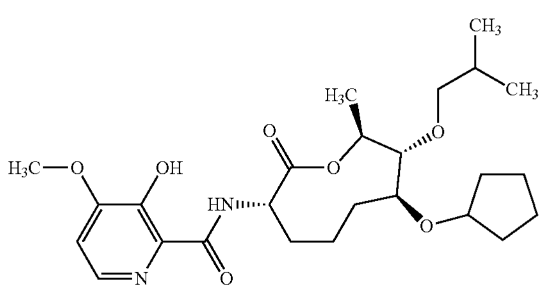 [SMILES: COc1ccnc(C(=O)N[C@H]2CCC[C@H](OC3CCCC3)[C@@H](OCC(C)C)[C@H](C)OC2=O)c1O] | 16A |

TABLE 1-continued

Structure and Preparation Method for F Series Compounds

| Compound Number | Structure | Prepared According to Example |
|---|---|---|
| F120 | 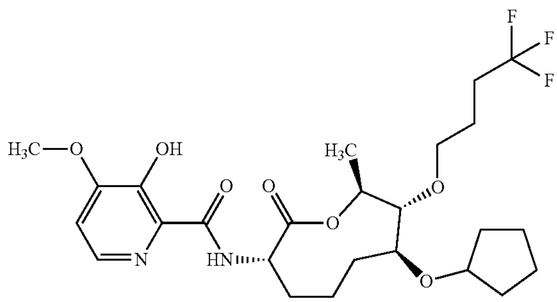 [SMILES: COc1ccnc(C(=O)N[C@H]2CCC[C@H](OC3CCCC3)[C@@H](OCCCC(F)(F)F)[C@H](C)OC2=O)c1O] | 16A |
| F121 | 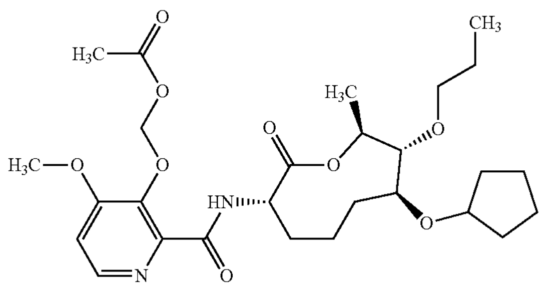 [SMILES: CCCO[C@H]1[C@H](C)OC(=O)[C@@H](NC(=O)c2nccc(OC)c2OCOC(C)=O)CCC[C@@H]1OC1CCCC1] | 17A |
| F122 | 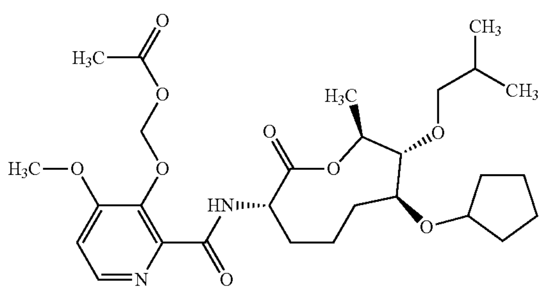 [SMILES: COc1ccnc(C(=O)N[C@H]2CCC[C@H](OC3CCCC3)[C@@H](OCC(C)C)[C@H](C)OC2=O)c1OCOC(C)=O] | 17A |
| F123 | 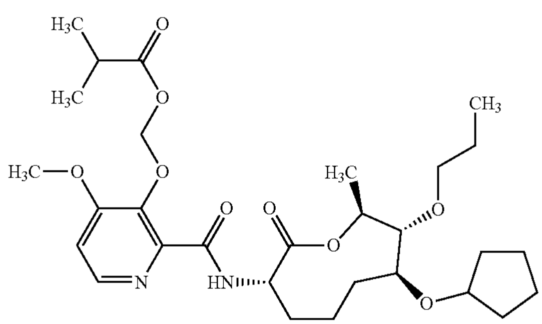 [SMILES: CCCO[C@H]1[C@H](C)OC(=O)[C@@H](NC(=O)c2nccc(OC)c2OCOC(=O)C(C)C)CCC[C@@H]1OC1CCCC1] | 17B |
| F124 | 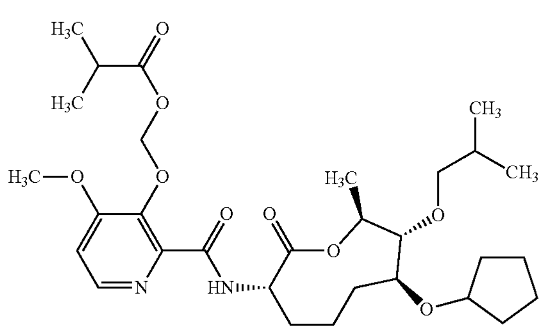 [SMILES: COc1ccnc(C(=O)N[C@H]2CCC[C@H](OC3CCCC3)[C@@H](OCC(C)C)[C@H](C)OC2=O)c1OCOC(=O)C(C)C] | 17B |

TABLE 1-continued

Structure and Preparation Method for F Series Compounds

| Compound Number | Structure | Prepared According to Example |
|---|---|---|
| F125 | 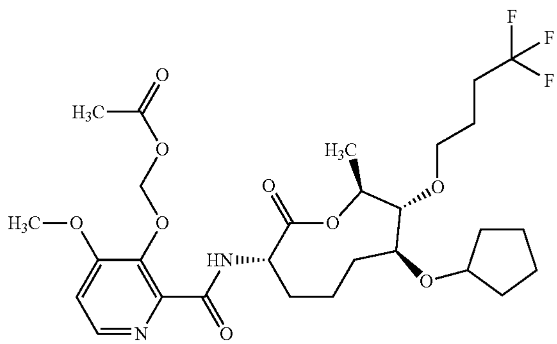 [SMILES: COc1ccnc(C(=O)N[C@H]2CCC[C@H](OC3CCCC3)[C@@H](OCCCC(F)(F)F)[C@H](C)OC2=O)c1OCOC(C)=O] | 17A |
| F126 | 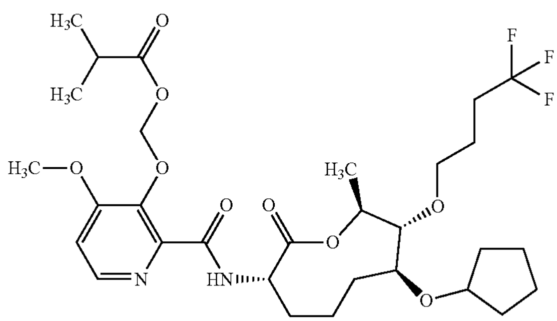 [SMILES: COc1ccnc(C(=O)N[C@H]2CCC[C@H](OC3CCCC3)[C@@H](OCCCC(F)(F)F)[C@H](C)OC2=O)c1OCOC(=O)C(C)C] | 17B |
| F127 | 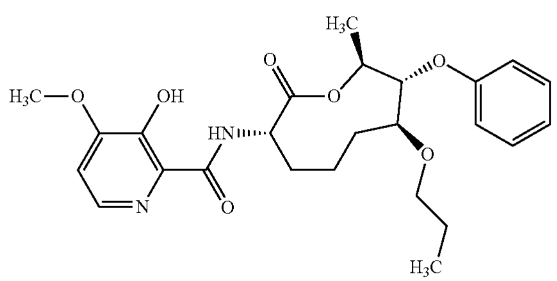 [SMILES: CCCO[C@H]1CCC[C@H](NC(=O)c2nccc(OC)c2O)C(=O)O[C@@H](C)[C@@H]1Oc1ccccc1] | 16A |
| F128 | 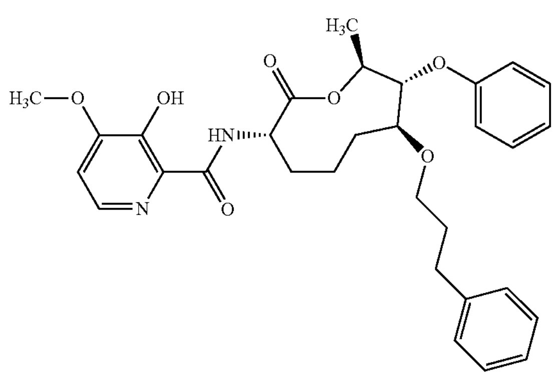 [SMILES: COc1ccnc(C(=O)N[C@H]2CCC[C@H](OCCCc3ccccc3)[C@@H](Oc3ccccc3)[C@H](C)OC2=O)c1O] | 16A |

TABLE 1-continued

Structure and Preparation Method for F Series Compounds

| Compound Number | Structure | Prepared According to Example |
|---|---|---|
| F129 | 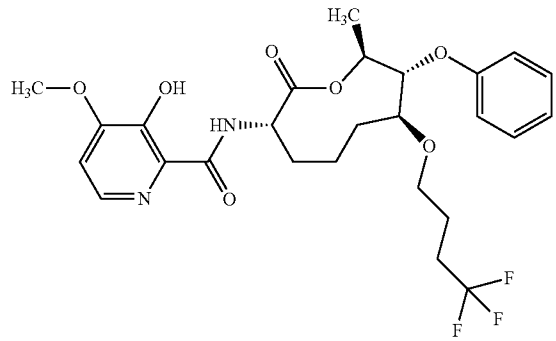 [SMILES: COc1ccnc(C(=O)N[C@H]2CCC[C@H](OCCCC(F)(F)F)[C@@H](Oc3ccccc3)[C@H](C)OC2=O)c1O] | 16A |
| F130 | 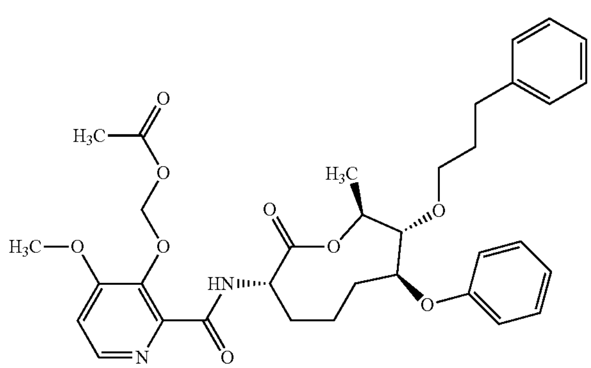 [SMILES: COc1ccnc(C(=O)N[C@H]2CCC[C@H](Oc3ccccc3)[C@@H](OCCCc3ccccc3)[C@H](C)OC2=O)c1OCOC(C)=O] | 17A |
| F131 | 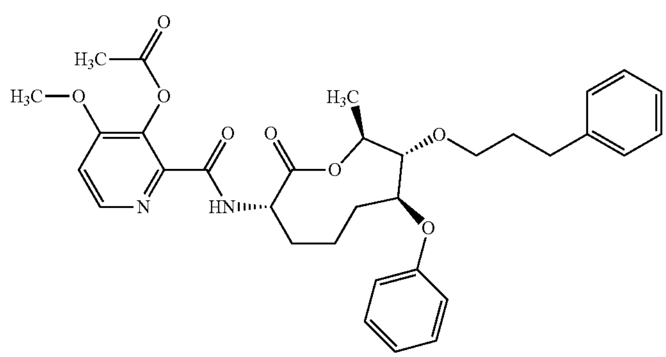 [SMILES: COc1ccnc(C(=O)N[C@H]2CCC[C@H](Oc3ccccc3)[C@@H](OCCCc3ccccc3)[C@H](C)OC2=O)c1OC(C)=O] | 17C |
| F132 | 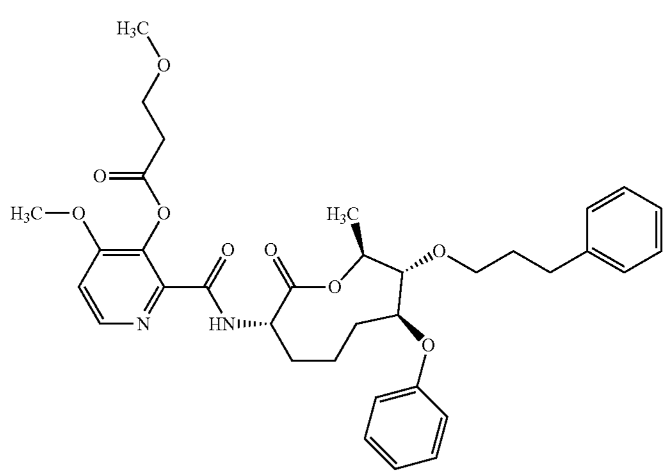 [SMILES: COCCC(=O)Oc1c(OC)ccnc1C(=O)N[C@H]1CCC[C@H](Oc2ccccc2)[C@@H](OCCCc2ccccc2)[C@H](C)OC1=O] | 17D |

TABLE 1-continued

Structure and Preparation Method for F Series Compounds

| Compound Number | Structure | Prepared According to Example |
|---|---|---|
| F133 | 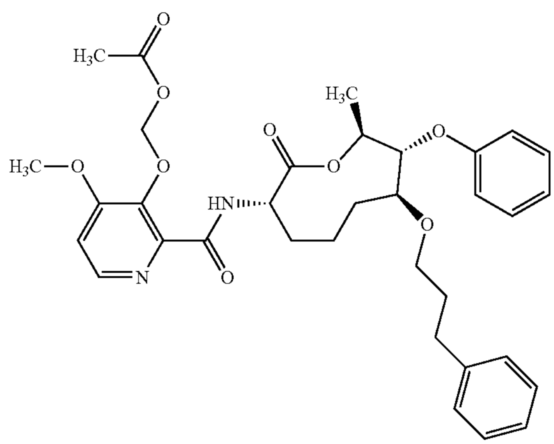 [SMILES: COc1ccnc(C(=O)N[C@H]2CCC[C@H](OCCCc3ccccc3)[C@@H](Oc3ccccc3)[C@H](C)OC2=O)c1OCOC(C)=O] | 17A |
| F134 | 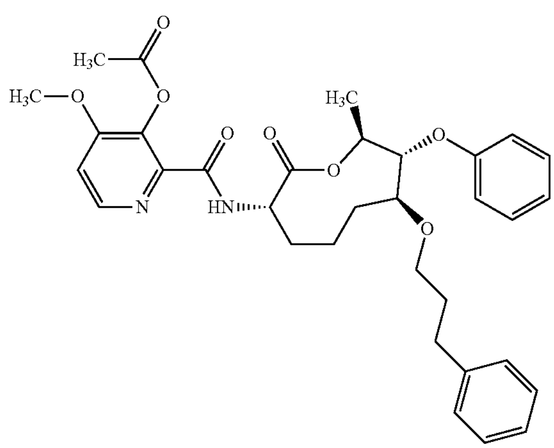 [SMILES: COc1ccnc(C(=O)N[C@H]2CCC[C@H](OCCCc3ccccc3)[C@@H](Oc3ccccc3)[C@H](C)OC2=O)c1OC(C)=O] | 17C |
| F135 | 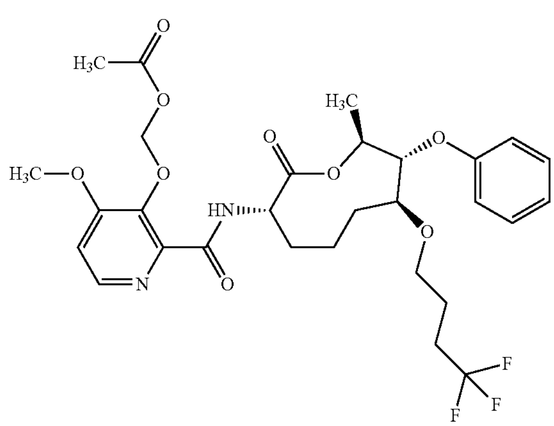 [SMILES: COc1ccnc(C(=O)N[C@H]2CCC[C@H](OCCCC(F)(F)F)[C@@H](Oc3ccccc3)[C@H](C)OC2=O)c1OCOC(C)=O] | 17A |

TABLE 1-continued
Structure and Preparation Method for F Series Compounds
| Compound Number | Structure | Prepared According to Example |
|---|---|---|
| F136 | 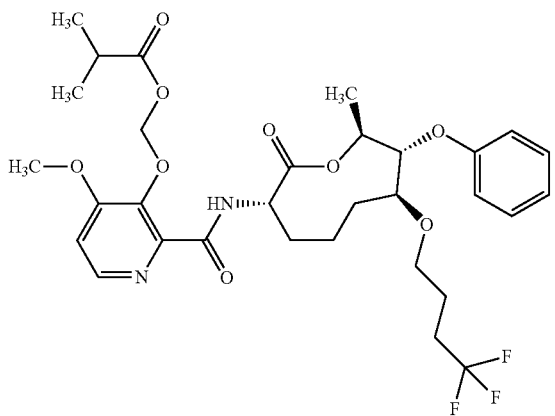 [SMILES: COc1ccnc(C(=O)N[C@H]2CCC[C@H](OCCCC(F)(F)F)[C@@H](Oc3ccccc3)[C@H](C)OC2=O)c1OCOC(=O)C(C)C] | 17B |
| F137 | 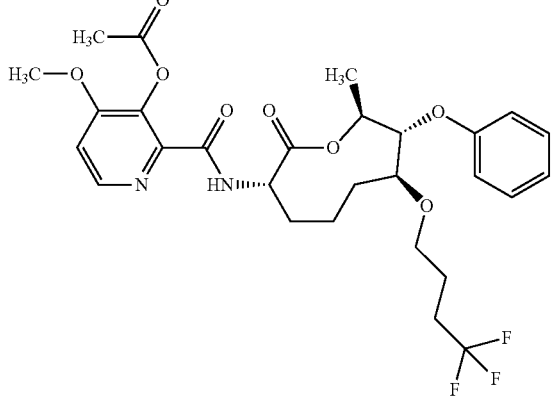 | 17C |
| F138 | 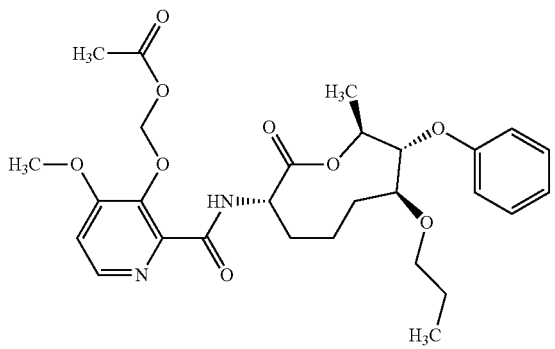 [SMILES: CCCO[C@H]1CCC[C@H](NC(=O)c2nccc(OC)c2OCOC(C)=O)C(=O)O[C@@H](C)[C@@H]1Oc1ccccc1] | 17A |

TABLE 1-continued

Structure and Preparation Method for F Series Compounds

| Compound Number | Structure | Prepared According to Example |
|---|---|---|
| F139 | 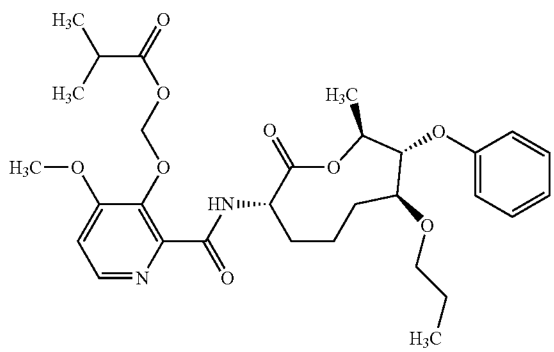 [SMILES: CCCO[C@H]1CCC[C@H](NC(=O)c2nccc(OC)c2OCOC(=O)C(C)C)C(=O)O[C@@H](C)[C@@H]1Oc1ccccc1] | 17B |
| F140 | 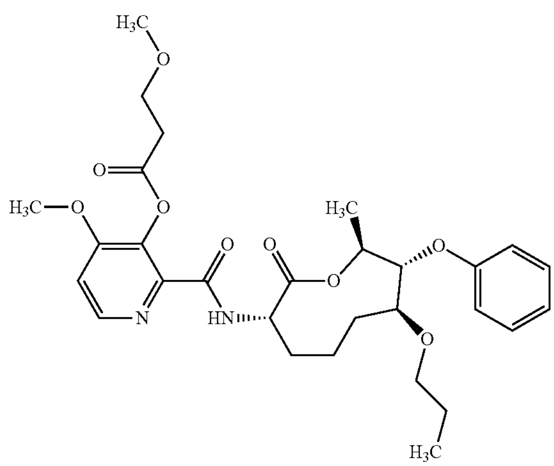 [SMILES: CCCO[C@H]1CCC[C@H](NC(=O)c2nccc(OC)c2OC(=O)CCOC)C(=O)O[C@@H](C)[C@@H]1Oc1ccccc1] | 17D |
| F141 | 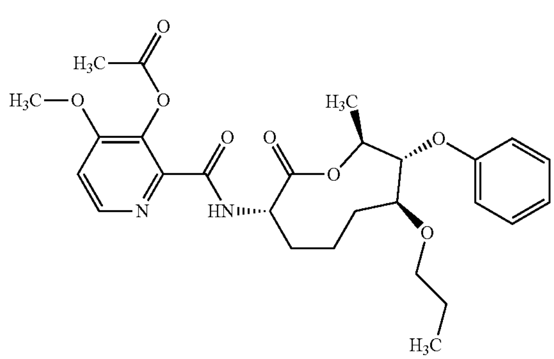 [SMILES: CCCO[C@H]1CCC[C@H](NC(=O)c2nccc(OC)c2OC(C)=O)C(=O)O[C@@H](C)[C@@H]1Oc1ccccc1] | 17C |
| F142 | 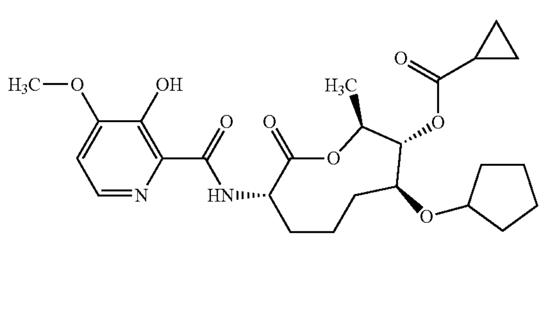 [SMILES: COc1ccnc(C(=O)N[C@H]2CCC[C@H](OC3CCCC3)[C@@H](OC(=O)C3CC3)[C@H](C)OC2=O)c1O] | 16A |

TABLE 1-continued

Structure and Preparation Method for F Series Compounds

| Compound Number | Structure | Prepared According to Example |
|---|---|---|
| F143 | 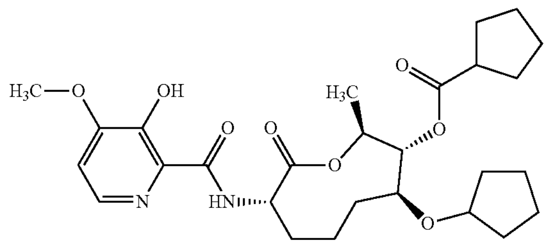 [SMILES: COc1ccnc(C(=O)N[C@H]2CCC[C@H](OC3CCCC3)[C@@H](OC(=O)C3CCCC3)[C@H](C)OC2=O)c1O] | 16A |
| F144 | 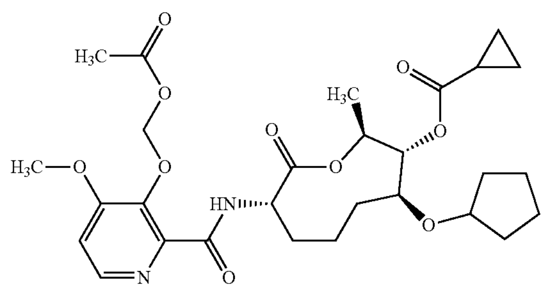 [SMILES: COc1ccnc(C(=O)N[C@H]2CCC[C@H](OC3CCCC3)[C@@H](OC(=O)C3CC3)[C@H](C)OC2=O)c1OCOC(C)=O] | 17A |
| F145 | 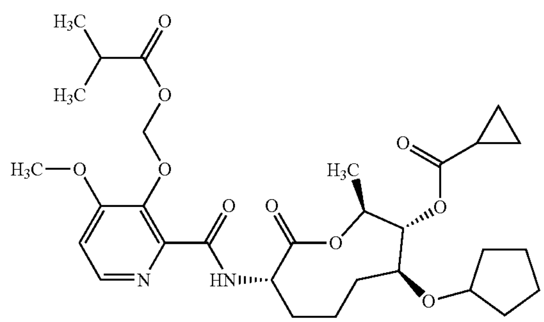 [SMILES: COc1ccnc(C(=O)N[C@H]2CCC[C@H](OC3CCCC3)[C@@H](OC(=O)C3CC3)[C@H](C)OC2=O)c1OCOC(=O)C(C)C] | 17B |
| F146 | 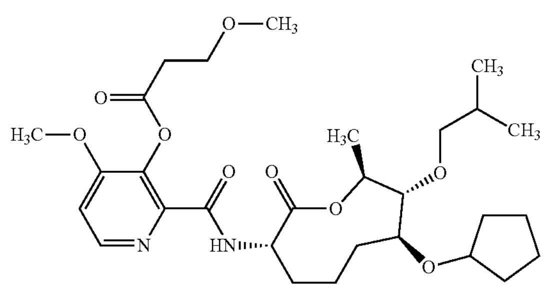 [SMILES: COCCC(=O)Oc1c(OC)ccnc1C(=O)N[C@H]1CCC[C@H](OC2CCCC2)[C@@H](OCC(C)C)[C@H](C)OC1=O] | 17D |
| F147 | 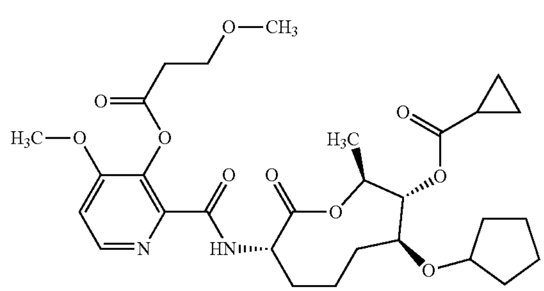 [SMILES: COCCC(=O)Oc1c(OC)ccnc1C(=O)N[C@H]1CCC[C@H](OC2CCCC2)[C@@H](OC(=O)C2CC2)[C@H](C)OC1=O] | 17D |

TABLE 1-continued

Structure and Preparation Method for F Series Compounds

| Compound Number | Structure | Prepared According to Example |
|---|---|---|
| F148 | 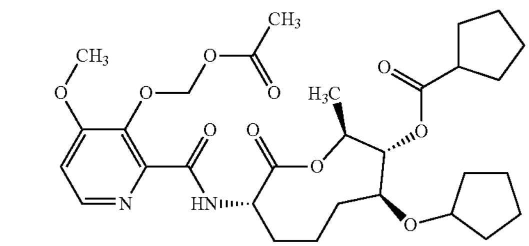 [SMILES: COc1ccnc(C(=O)N[C@H]2CCC[C@H](OC3CCCC3)[C@@H](OC(=O)C3CCCC3)[C@H](C)OC2=O)c1OCOC(C)=O] | 17A |
| F149 | 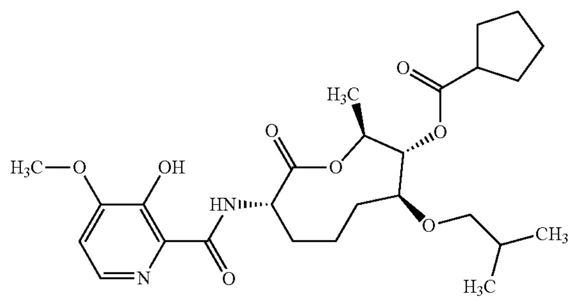 [SMILES: COc1ccnc(C(=O)N[C@H]2CCC[C@H](OCC(C)C)[C@@H](OC(=O)C3CCCC3)[C@H](C)OC2=O)c1O] | 16A |
| F150 | 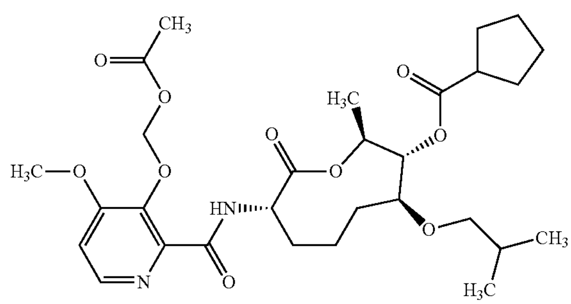 [SMILES: COc1ccnc(C(=O)N[C@H]2CCC[C@H](OCC(C)C)[C@@H](OC(=O)C3CCCC3)[C@H](C)OC2=O)c1OCOC(C)=O] | 17A |
| F151 | 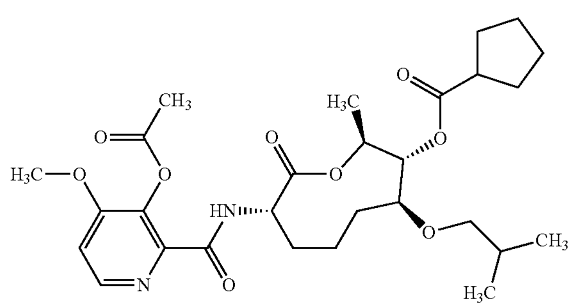 [SMILES: COc1ccnc(C(=O)N[C@H]2CCC[C@H](OCC(C)C)[C@@H](OC(=O)C3CCCC3)[C@H](C)OC2=O)c1OC(C)=O] | 17C |
| F152 | 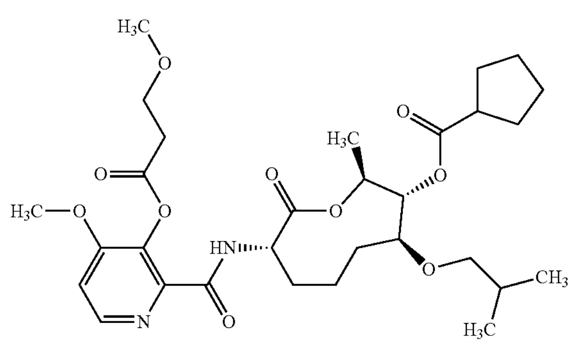 [SMILES: COCCC(=O)Oc1c(OC)ccnc1C(=O)N[C@H]1CCC[C@H](OCC(C)C)[C@@H](OC(=O)C2CCCC2)[C@H](C)OC1=O] | 17D |

TABLE 1-continued

Structure and Preparation Method for F Series Compounds

| Compound Number | Structure | Prepared According to Example |
|---|---|---|
| F153 | 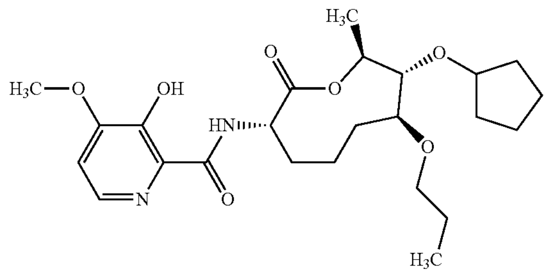 [SMILES: CCCO[C@H]1CCC[C@H](NC(=O)c2nccc(OC)c2O)C(=O)O[C@@H](C)[C@@H]1OC1CCCC1] | 16A |
| F154 | 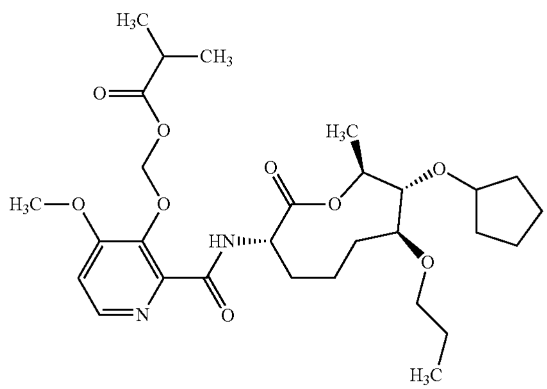 [SMILES: CCCO[C@H]1CCC[C@H](NC(=O)c2nccc(OC)c2OCOC(=O)C(C)C)C(=O)O[C@@H](C)[C@@H]1OC1CCCC1] | 17B |
| F155 | 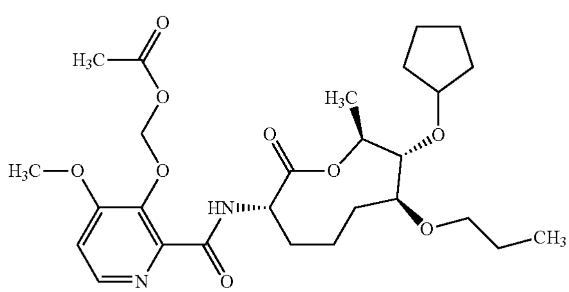 [SMILES: CCCO[C@H]1CCC[C@H](NC(=O)c2nccc(OC)c2OCOC(C)=O)C(=O)O[C@@H](C)[C@@H]1OC1CCCC1] | 17A |
| F156 | 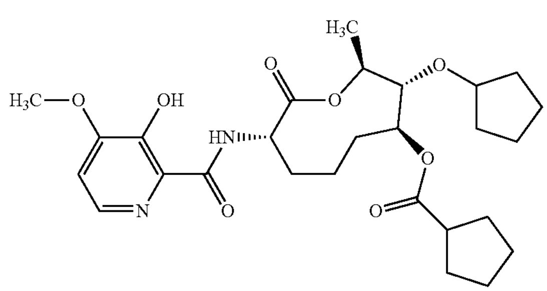 [SMILES: COc1ccnc(C(=O)N[C@H]2CCC[C@H](OC(=O)C3CCCC3)[C@@H](OC3CCCC3)[C@H](C)OC2=O)c1O] | 16A |

TABLE 1-continued

Structure and Preparation Method for F Series Compounds

| Compound Number | Structure | Prepared According to Example |
|---|---|---|
| F157 | 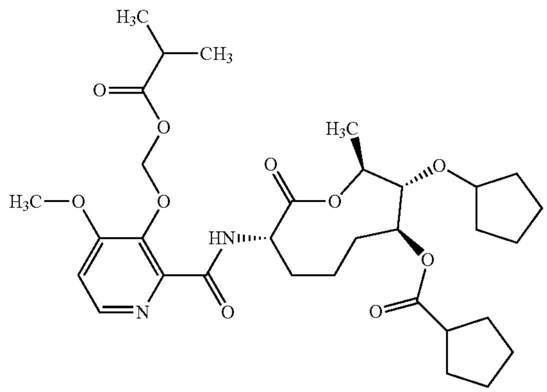 [SMILES: COc1ccnc(C(=O)N[C@H]2CCC[C@H](OC(=O)C3CCCC3)[C@@H](OC3CCCC3)[C@H](C)OC2=O)c1OCOC(=O)C(C)C] | 17B |
| F158 | 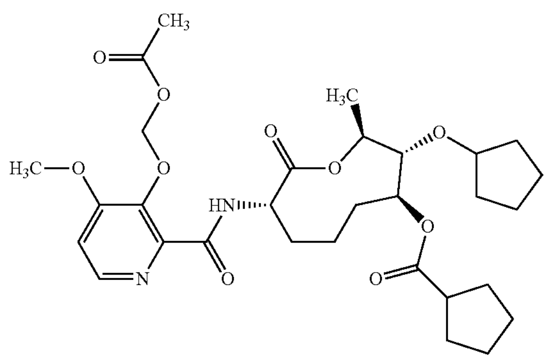 [SMILES: COc1ccnc(C(=O)N[C@H]2CCC[C@H](OC(=O)C3CCCC3)[C@@H](OC3CCCC3)[C@H](C)OC2=O)c1OCOC(C)=O] | 17A |
| F159 | 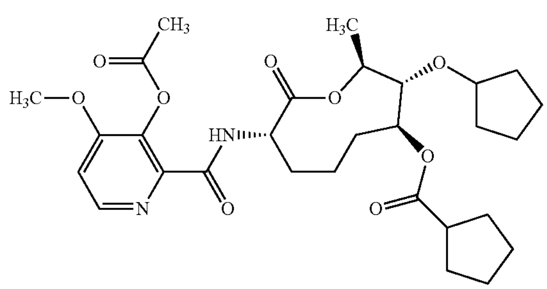 [SMILES: COc1ccnc(C(=O)N[C@H]2CCC[C@H](OC(=O)C3CCCC3)[C@@H](OC3CCCC3)[C@H](C)OC2=O)c1OC(C)=O] | 17C |
| F160 | 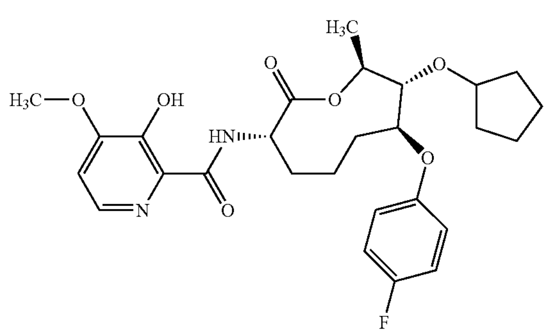 [SMILES: COc1ccnc(C(=O)N[C@H]2CCC[C@H](Oc3ccc(F)cc3)[C@@H](OC3CCCC3)[C@H](C)OC2=O)c1O] | 16A |

TABLE 1-continued

Structure and Preparation Method for F Series Compounds

| Compound Number | Structure | Prepared According to Example |
|---|---|---|
| F161 | 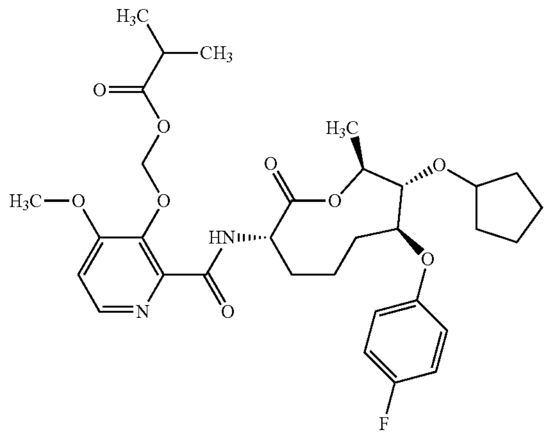 [SMILES: COc1ccnc(C(=O)N[C@H]2CCC[C@H](Oc3ccc(F)cc3)[C@@H](OC3CCCC3)[C@H](C)OC2=O)c1OCOC(=O)C(C)C] | 17B |
| F162 | 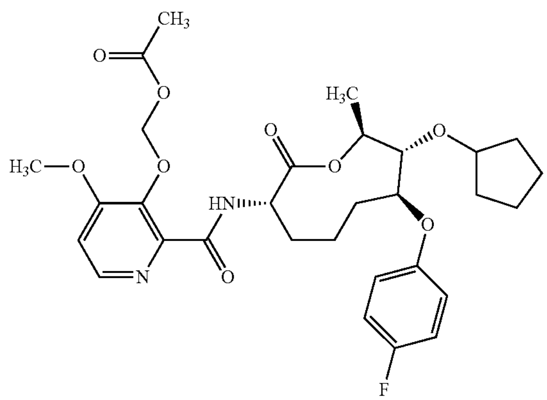 [SMILES: COc1ccnc(C(=O)N[C@H]2CCC[C@H](Oc3ccc(F)cc3)[C@@H](OC3CCCC3)[C@H](C)OC2=O)c1OCOC(C)=O] | 17A |
| F163 | 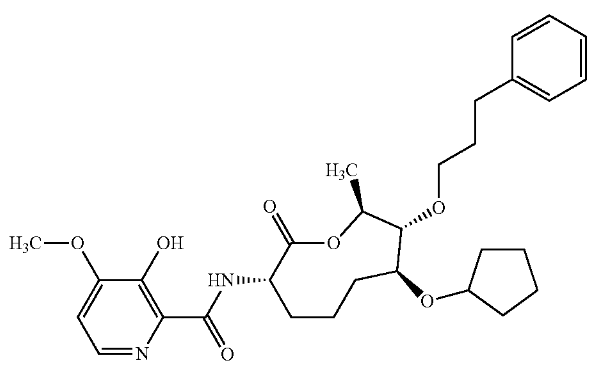 [SMILES: COc1ccnc(C(=O)N[C@H]2CCC[C@H](OC3CCCC3)[C@@H](OCCCc3ccccc3)[C@H](C)OC2=O)c1O] | 16A |
| F164 | 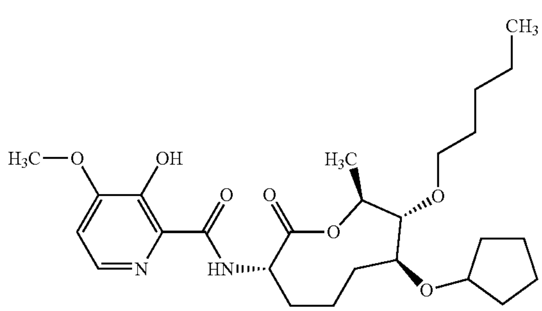 [SMILES: CCCCCO[C@H]1[C@H](C)OC(=O)[C@@H](NC(=O)c2nccc(OC)c2O)CCC[C@@H]1OC1CCCC1] | 16A |

TABLE 1-continued

Structure and Preparation Method for F Series Compounds

| Compound Number | Structure | Prepared According to Example |
|---|---|---|
| F165 | 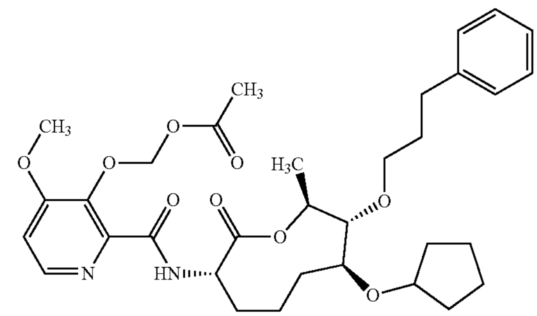 [SMILES: COc1ccnc(C(=O)N[C@H]2CCC[C@H](OC3CCCC3)[C@@H](OCCCc3ccccc3)[C@H](C)OC2=O)c1OCOC(C)=O] | 17A |
| F166 | 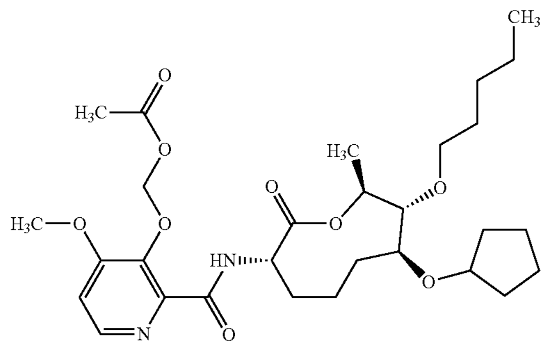 [SMILES: CCCCCO[C@H]1[C@H](C)OC(=O)[C@@H](NC(=O)c2nccc(OC)c2OCOC(C)=O)CCC[C@@H]1OC1CCCC1] | 17A |
| F167 | 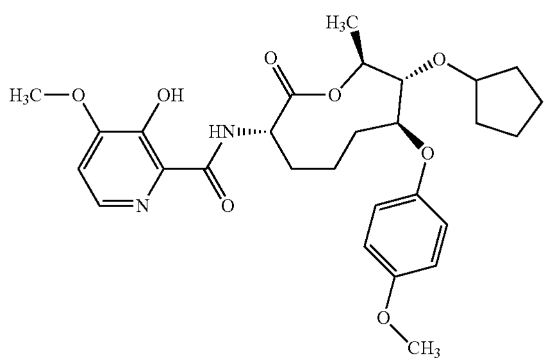 [SMILES: COc1ccc(O[C@H]2CCC[C@H](NC(=O)c3nccc(OC)c3O)C(=O)O[C@@H](C)[C@@H]2OC2CCCC2)cc1] | 16A |
| F168 | 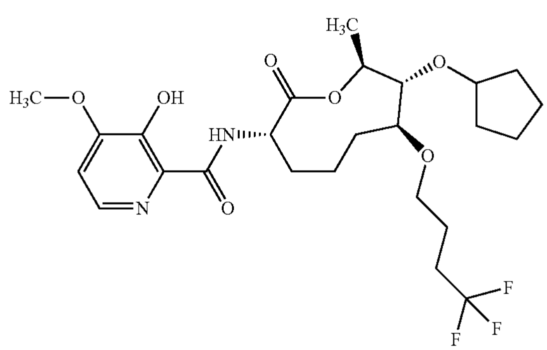 [SMILES: COc1ccnc(C(=O)N[C@H]2CCC[C@H](OCCCC(F)(F)F)[C@@H](OC3CCCC3)[C@H](C)OC2=O)c1O] | 16A |

TABLE 1-continued

Structure and Preparation Method for F Series Compounds

| Compound Number | Structure | Prepared According to Example |
|---|---|---|
| F169 | 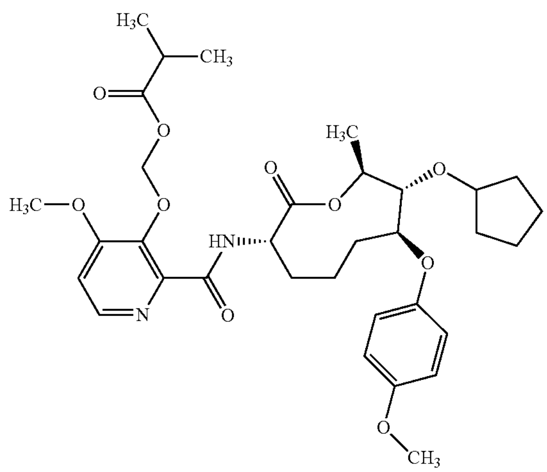 [SMILES: COc1ccc(O[C@H]2CCC[C@H](NC(=O)c3nccc(OC)c3OCOC(=O)C(C)C)C(=O)O[C@@H](C)[C@@H]2OC2CCCC2)cc1] | 17B |
| F170 | 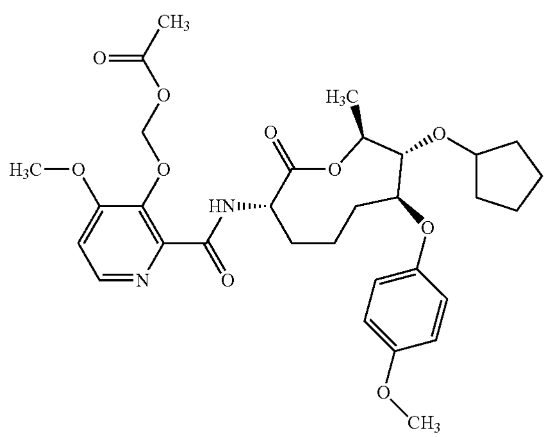 [SMILES: COc1ccc(O[C@H]2CCC[C@H](NC(=O)c3nccc(OC)c3OCOC(C)=O)C(=O)O[C@@H](C)[C@@H]2OC2CCCC2)cc1] | 17A |
| F171 | 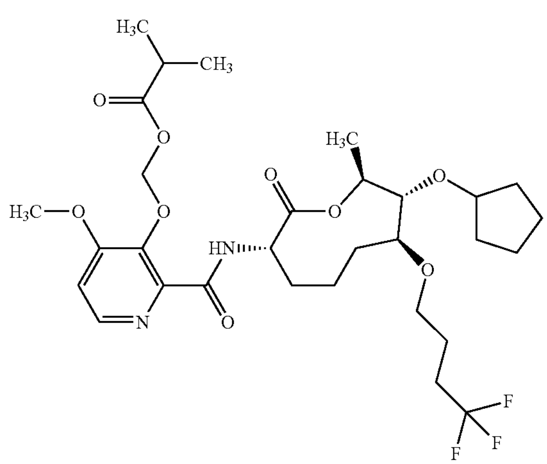 [SMILES: COc1ccnc(C(=O)N[C@H]2CCC[C@H](OCCCC(F)(F)F)[C@@H](OC3CCCC3)[C@H](C)OC2=O)c1OCOC(=O)C(C)C] | 17B |

TABLE 1-continued

Structure and Preparation Method for F Series Compounds

| Compound Number | Structure | Prepared According to Example |
|---|---|---|
| F172 | 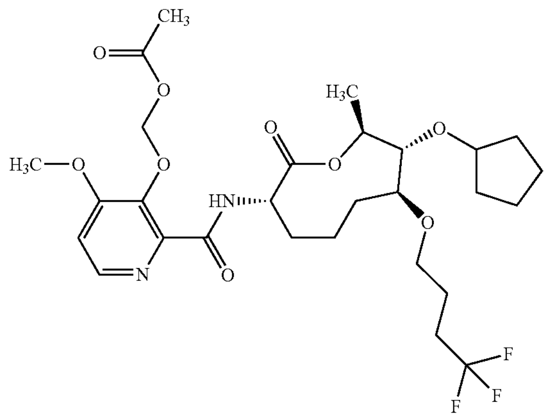 [SMILES: COc1ccnc(C(=O)N[C@H]2CCC[C@H](OCCCC(F)(F)F)[C@@H](OC3CCCC3)[C@H](C)OC2=O)c1OCOC(C)=O] | 17A |
| F173 | 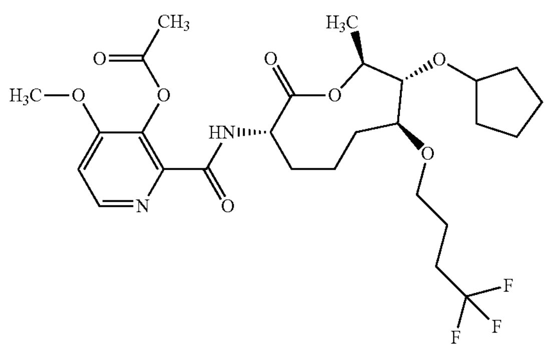 [SMILES: COc1ccnc(C(=O)N[C@H]2CCC[C@H](OCCCC(F)(F)F)[C@@H](OC3CCCC3)[C@H](C)OC2=O)c1OC(C)=O] | 17C |
| F174 | 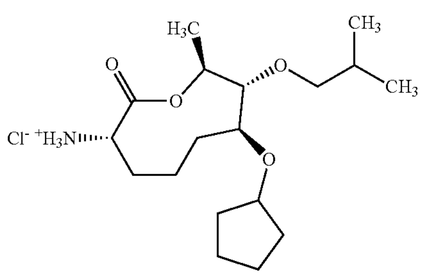 [SMILES: [Cl-] ; CC(C)CO[C@H]1[C@H](C)OC(=O)[C@@H]([NH3+])CCC[C@@H]1OC1CCCC1] | 13, 13F (1-3) |
| F175 | 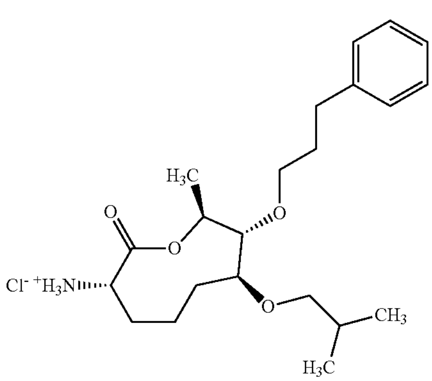 [SMILES: [Cl-] ; CC(C)CO[C@H]1CCC[C@H]([NH3+])C(=O)O[C@@H](C)[C@@H]1OCCCc1ccccc1] | 13, 13F (1-3) |

TABLE 1-continued

Structure and Preparation Method for F Series Compounds

| Compound Number | Structure | Prepared According to Example |
|---|---|---|
| F176 | 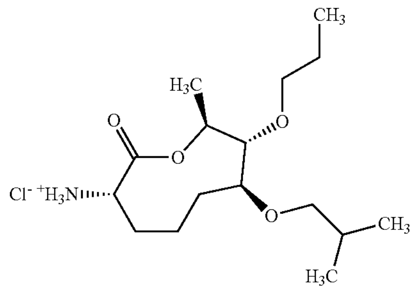 [SMILES: [Cl-] ; CCCO[C@H]1[C@H](C)OC(=O)[C@@H]([NH3+])CCC[C@@H]1OCC(C)C] | 13, 13F (1-3) |
| F177 | 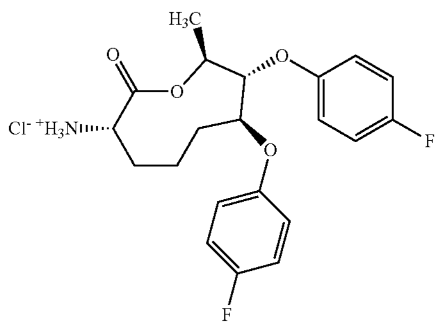 [SMILES: [Cl-] ; C[C@@H]1OC(=O)[C@@H]([NH3+])CCC[C@H](Oc2ccc(F)cc2)[C@H]1Oc1ccc(F)cc1] | 12, 12C (1-2) |
| F178 | 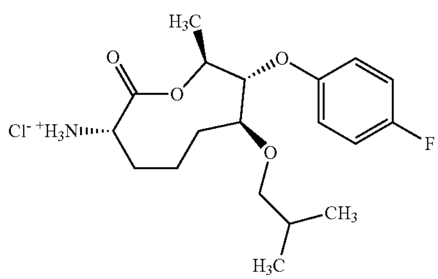 [SMILES: [Cl-] ; CC(C)CO[C@H]1CCC[C@H]([NH3+])C(=O)O[C@@H](C)[C@@H]1Oc1ccc(F)cc1] | 12, 12B (1-3) |
| F179 | 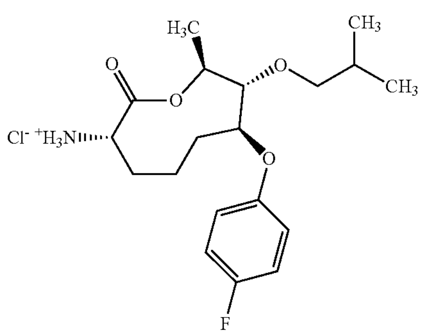 [SMILES: [Cl-] ; CC(C)CO[C@H]1[C@H](C)OC(=O)[C@@H]([NH3+])CCC[C@@H]1Oc1ccc(F)cc1] | 12, 12B (1-3) |
| F180 | 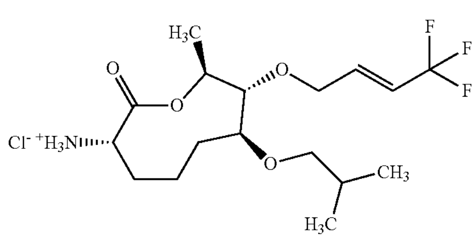 [SMILES: [Cl-] ; CC(C)CO[C@H]1CCC[C@H]([NH3+])C(=O)O[C@@H](C)[C@@H]1OC/C=C/C(F)(F)F] | 13, 13B (1) |

TABLE 1-continued

Structure and Preparation Method for F Series Compounds

| Compound Number | Structure | Prepared According to Example |
|---|---|---|
| F181 | 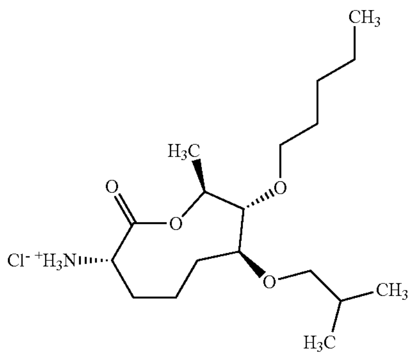 [SMILES: [Cl-] ; CCCCCO[C@H]1[C@H](C)OC(=O)[C@@H]([NH3+])CCC[C@@H]1OCC(C)C] | 13, 13B (1) and 13F (1, 3) |
| F182 | 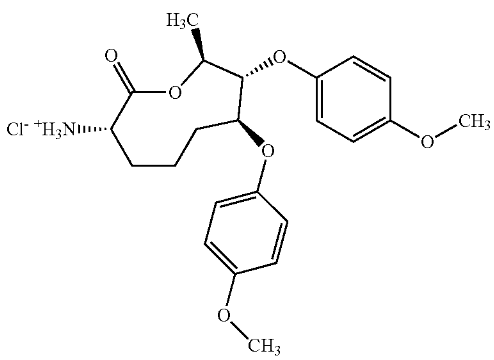 [SMILES: [Cl-] ; COc1ccc(O[C@H]2[C@H](C)OC(=O)[C@@H]([NH3+])CCC[C@@H]2Oc2ccc(OC)cc2)cc1] | 12, 12C (1-2) |
| F183 | 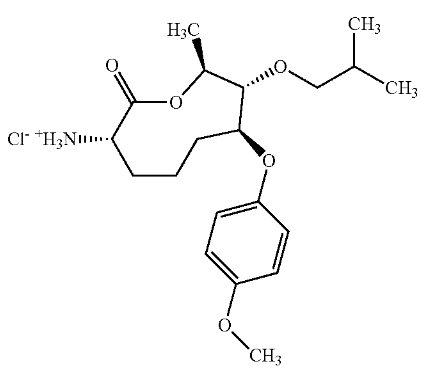 [SMILES: [Cl-] ; COc1ccc(O[C@H]2CCC[C@H]([NH3+])C(=O)O[C@@H](C)[C@@H]2OCC(C)C)cc1] | 12, 12B (1-3) |
| F184 | 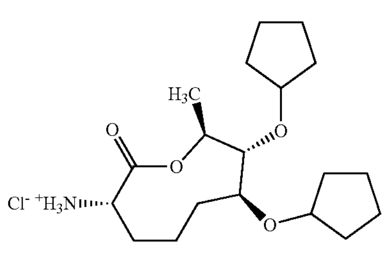 [SMILES: [Cl-] ; C[C@@H]1OC(=O)[C@@H]([NH3+])CCC[C@H](OC2CCCC2)[C@H]1OC1CCCC1] | 13, 13F (1-3) or 13A (1-2) |

TABLE 1-continued

Structure and Preparation Method for F Series Compounds

| Compound Number | Structure | Prepared According to Example |
|---|---|---|
| F185 | 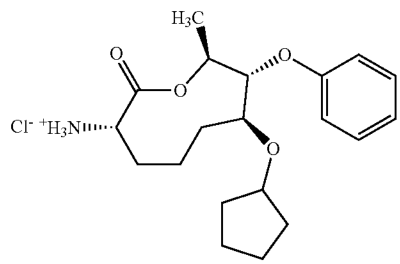 [SMILES: [Cl-] ; C[C@@H]1OC(=O)[C@@H]([NH3+])CCC[C@H](OC2CCCC2)[C@H]1Oc1ccccc1] | 13, 13C (1-3) |
| F186 | 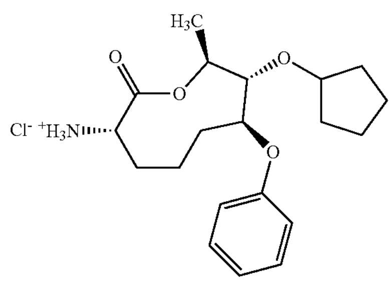 [SMILES: [Cl-] ; C[C@@H]1OC(=O)[C@@H]([NH3+])CCC[C@H](Oc2ccccc2)[C@H]1OC1CCCC1] | 13, 13B (1-3) |
| F187 | 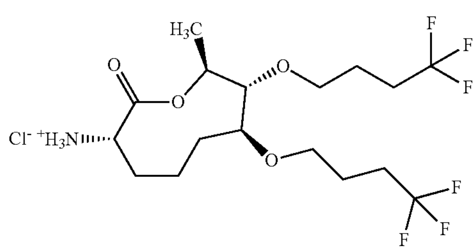 [SMILES: [Cl-] ; C[C@@H]1OC(=O)[C@@H]([NH3+])CCC[C@H](OCCCC(F)(F)F)[C@H]1OCCCC(F)(F)F] | 13, 13A (1-2) |
| F188 | 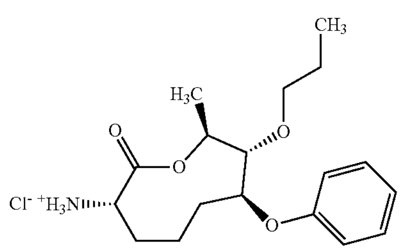 [SMILES: [Cl-] ; CCCO[C@H]1[C@H](C)OC(=O)[C@@H]([NH3+])CCC[C@@H]1Oc1ccccc1] | 12, 12B (1-3) |
| F189 | 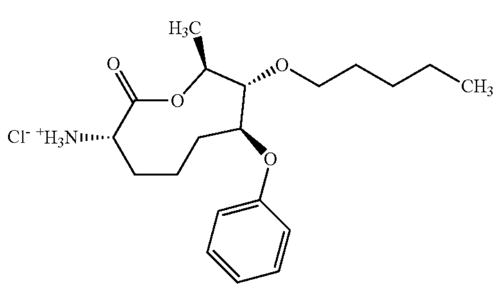 [SMILES: [Cl-] ; CCCCCO[C@H]1[C@H](C)OC(=O)[C@@H]([NH3+])CCC[C@@H]1Oc1ccccc1] | 12, 12B (1-3) |

TABLE 1-continued

Structure and Preparation Method for F Series Compounds

| Compound Number | Structure | Prepared According to Example |
|---|---|---|
| F190 | 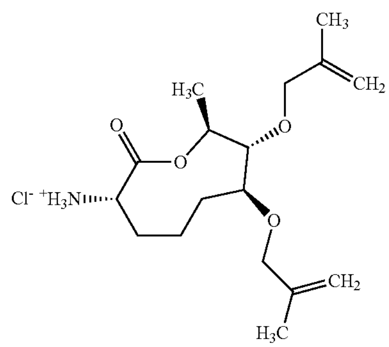 [SMILES: [Cl-] ; C=C(C)CO[C@H]1[C@H](C)OC(=O)[C@@H]([NH3+])CCC[C@@H]1OCC(=C)C] | 13, 13A (2) |
| F191 | 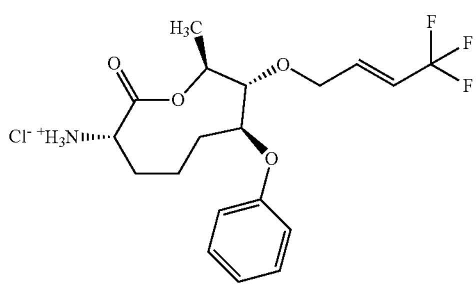 [SMILES: [Cl-] ; C[C@@H]1OC(=O)[C@@H]([NH3+])CCC[C@H](Oc2ccccc2)[C@H]1OC/C=C/C(F)(F)F] | 12, 12B (1, 3) |
| F192 | 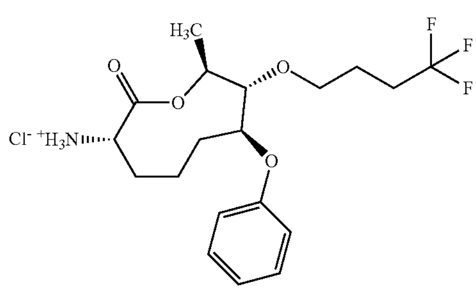 [SMILES: [Cl-] ; C[C@@H]1OC(=O)[C@@H]([NH3+])CCC[C@H](Oc2ccccc2)[C@H]1OCCCC(F)(F)F] | 12, 12B (1-3) |
| F193 | 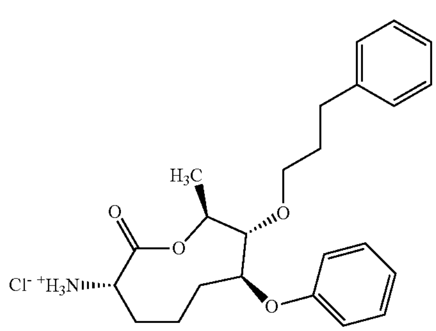 [SMILES: [Cl-] ; C[C@@H]1OC(=O)[C@@H]([NH3+])CCC[C@H](Oc2ccccc2)[C@H]1OCCCc1ccccc1] | 12, 12B (1-3) |

TABLE 1-continued

Structure and Preparation Method for F Series Compounds

| Compound Number | Structure | Prepared According to Example |
|---|---|---|
| F194 | 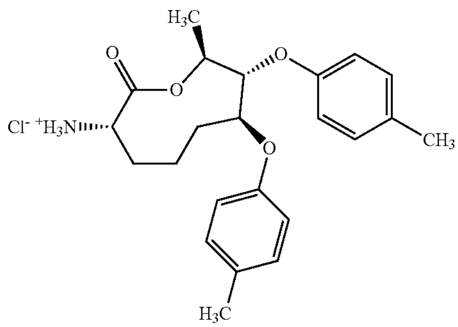 [SMILES: [Cl-] ; Cc1ccc(O[C@H]2[C@H](C)OC(=O)[C@@H]([NH3+])CCC[C@@H]2Oc2ccc(C)cc2)cc1] | 12, 12A |
| F195 | 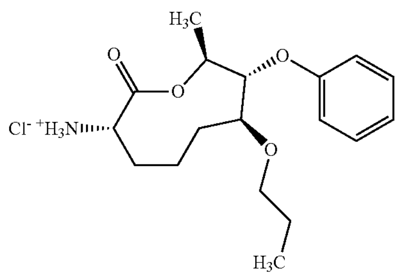 [SMILES: [Cl-] ; CCCO[C@H]1CCC[C@H]([NH3+])C(=O)O[C@@H](C)[C@@H]1Oc1ccccc1] | 12, 12B (1-3) |
| F196 | 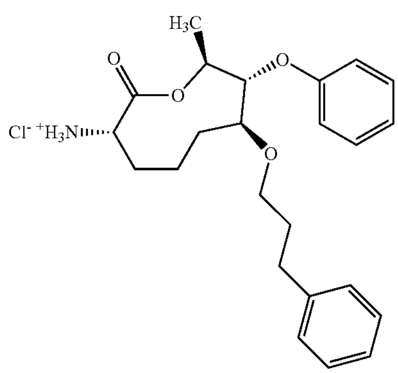 [SMILES: [Cl-] ; C[C@@H]1OC(=O)[C@@H]([NH3+])CCC[C@H](OCCCc2ccccc2)[C@H]1Oc1ccccc1] | 12, 12B (1-3) |
| F197 | 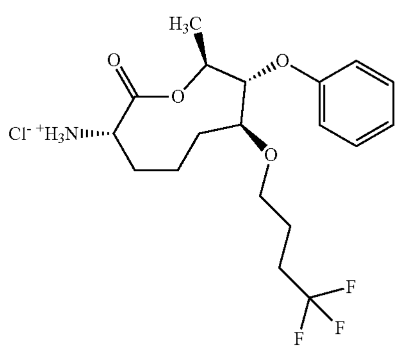 [SMILES: [Cl-] ; C[C@@H]1OC(=O)[C@@H]([NH3+])CCC[C@H](OCCCC(F)(F)F)[C@H]1Oc1ccccc1] | 12, 12B (1-3) |

TABLE 1-continued

Structure and Preparation Method for F Series Compounds

| Compound Number | Structure | Prepared According to Example |
|---|---|---|
| F198 | 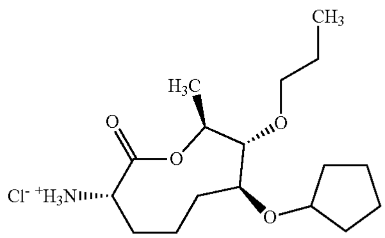 [SMILES: [Cl-] ; CCCO[C@H]1[C@H](C)OC(=O)[C@@H]([NH3+])CCC[C@@H]1OC1CCCC1] | 13, 13F (1-3) |
| F199 | 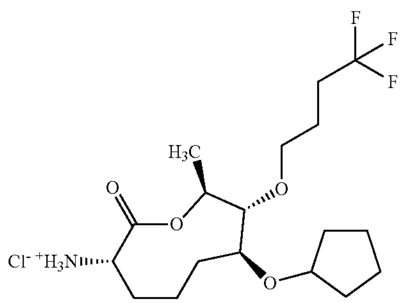 [SMILES: [Cl-] ; C[C@@H]1OC(=O)[C@@H]([NH3+])CCC[C@H](OC2CCCC2)[C@H]1OCCCC(F)(F)F] | 13, 13F (1-3) |
| F200 | 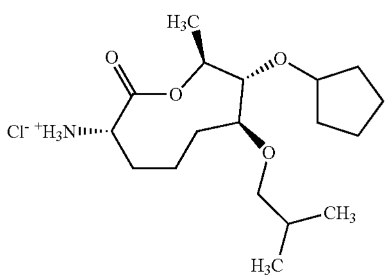 [SMILES: [Cl-] ; CC(C)CO[C@H]1CCC[C@H]([NH3+])C(=O)O[C@@H](C)[C@@H]1OC1CCCC1] | 13, 13G (1-3) |
| F201 | 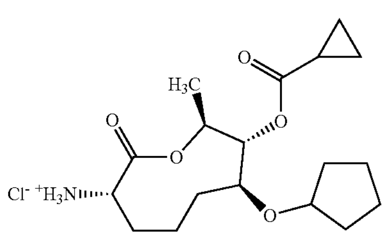 [SMILES: [Cl-] ; C[C@@H]1OC(=O)[C@@H]([NH3+])CCC[C@H](OC2CCCC2)[C@H]1OC(=O)C1CC1] | 13, 13B (1) and 13D (1-2) |
| F202 | 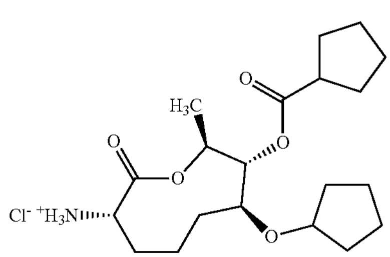 [SMILES: [Cl-] ; C[C@@H]1OC(=O)[C@@H]([NH3+])CCC[C@H](OC2CCCC2)[C@H]1OC(=O)C1CCCC1] | 13, 13B (1) and 13D (1-2) |

TABLE 1-continued

Structure and Preparation Method for F Series Compounds

| Compound Number | Structure | Prepared According to Example |
|---|---|---|
| F203 | 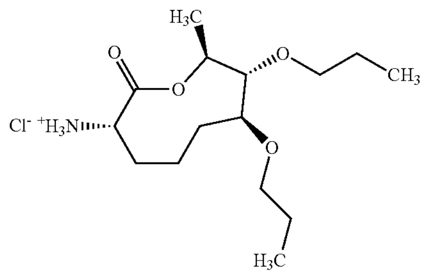 [SMILES: [Cl-] ; CCCO[C@H]1[C@H](C)OC(=O)[C@@H]([NH3+])CCC[C@@H]1OCCC] | 13, 13A (1-2) |
| F204 | 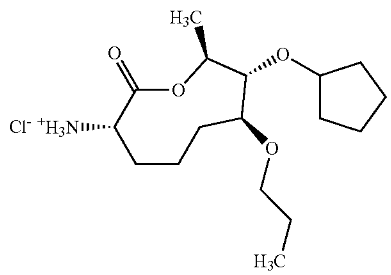 [SMILES: [Cl-] ; CCCO[C@H]1CCC[C@H]([NH3+])C(=O)O[C@@H](C)[C@@H]1OC1CCCC1] | 13, 13G (1-3) |
| F205 | 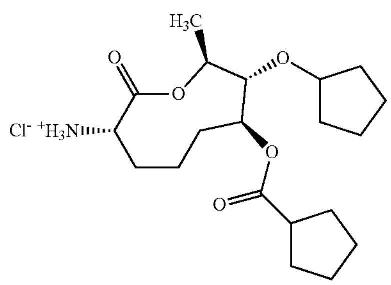 [SMILES: [Cl-] ; C[C@@H]1OC(=O)[C@@H]([NH3+])CCC[C@H](OC(=O)C2CCCC2)[C@H]1OC1CCCC1] | 13, 13B (1) and 13D (1-2) |
| F206 | 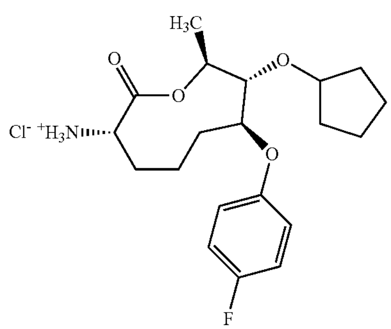 [SMILES: [Cl-] ; C[C@@H]1OC(=O)[C@@H]([NH3+])CCC[C@H](Oc2ccc(F)cc2)[C@H]1OC1CCCC1] | 12, 12B (1-3) |
| F207 | 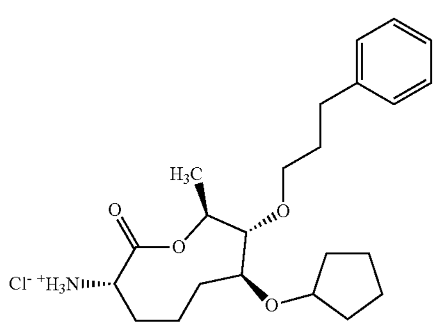 [SMILES: [Cl-] ; C[C@@H]1OC(=O)[C@@H]([NH3+])CCC[C@H](OC2CCCC2)[C@H]1OCCCc1ccccc1] | 13, 13F (1-3) |

TABLE 1-continued

Structure and Preparation Method for F Series Compounds

| Compound Number | Structure | Prepared According to Example |
|---|---|---|
| F208 | 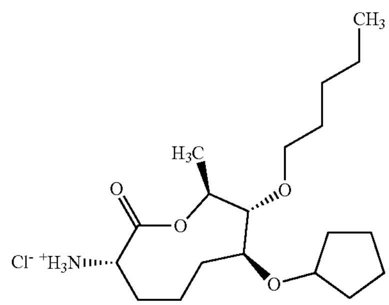 [SMILES: [Cl-] ; CCCCCO[C@H]1[C@H](C)OC(=O)[C@@H]([NH3+])CCC[C@@H]1OC1CCCC1] | 13, 13F (1-3) |
| F209 | 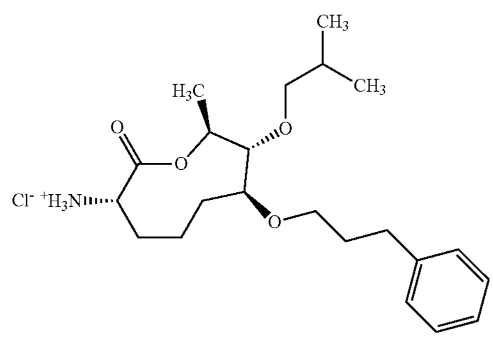 [SMILES: [Cl-] ; CC(C)CO[C@H]1[C@H](C)OC(=O)[C@@H]([NH3+])CCC[C@@H]1OCCCc1ccccc1] | 13, 13G (1-3) |
| F210 | 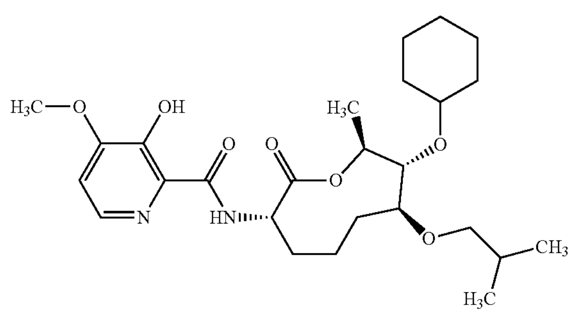 [SMILES: COc1ccnc(C(=O)N[C@H]2CCC[C@H](OCC(C)C)[C@@H](OC3CCCCC3)[C@H](C)OC2=O)c1O] | 16A |
| F211 | 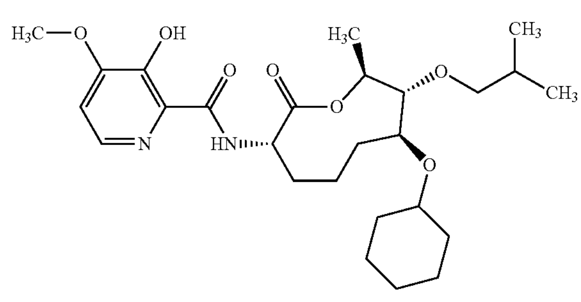 [SMILES: COc1ccnc(C(=O)N[C@H]2CCC[C@H](OC3CCCCC3)[C@@H](OCC(C)C)[C@H](C)OC2=O)c1O] | 16A |

TABLE 1-continued

Structure and Preparation Method for F Series Compounds

| Compound Number | Structure | Prepared According to Example |
|---|---|---|
| F212 | 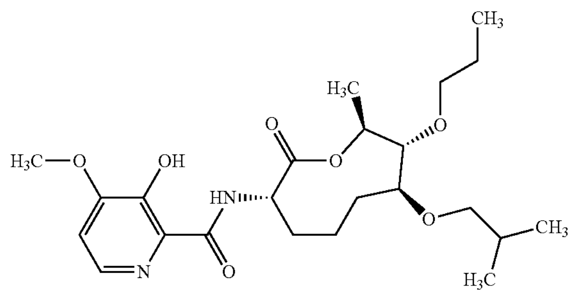 [SMILES: CCCO[C@H]1[C@H](C)OC(=O)[C@@H](NC(=O)c2nccc(OC)c2O)CCC[C@@H]1OCC(C)C] | 16A |
| F213 | 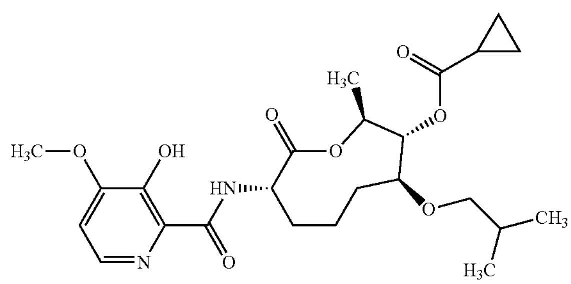 [SMILES: COc1ccnc(C(=O)N[C@H]2CCC[C@H](OCC(C)C)[C@@H](OC(=O)C3CC3)[C@H](C)OC2=O)c1O] | 16A |
| F214 | 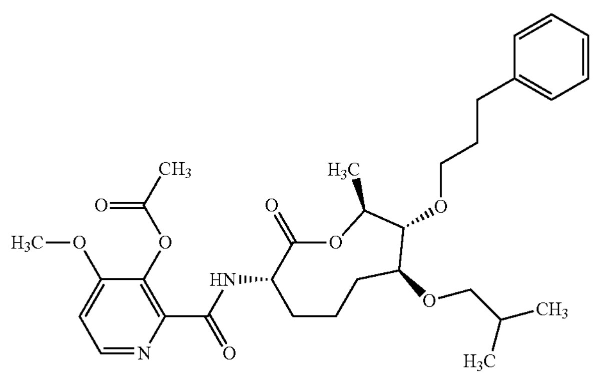 [SMILES: COc1ccnc(C(=O)N[C@H]2CCC[C@H](OCC(C)C)[C@@H](OCCCc3ccccc3)[C@H](C)OC2=O)c1OC(C)=O] | 17C |
| F215 | 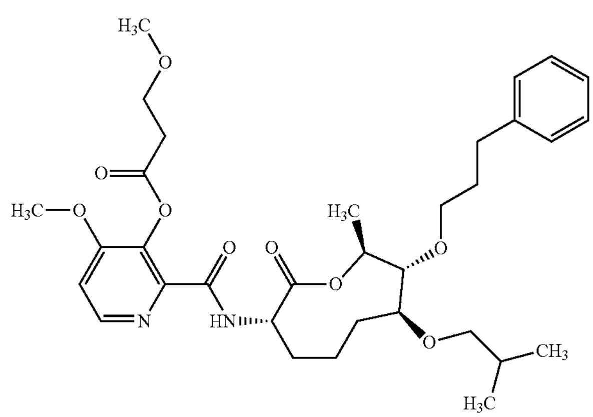 [SMILES: COCCC(=O)Oc1c(OC)ccnc1C(=O)N[C@H]1CCC[C@H](OCC(C)C)[C@@H](OCCCc2ccccc2)[C@H](C)OC1=O] | 17D |

TABLE 1-continued

Structure and Preparation Method for F Series Compounds

| Compound Number | Structure | Prepared According to Example |
|---|---|---|
| F216 | 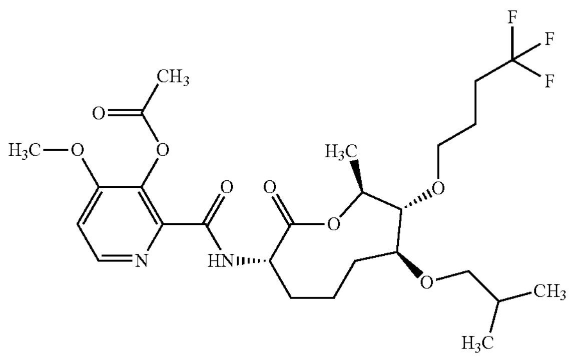 [SMILES: COc1ccnc(C(=O)N[C@H]2CCC[C@H](OCC(C)C)[C@@H](OCCCC(F)(F)F)[C@H](C)OC2=O)c1OC(C)=O] | 17C |
| F217 | 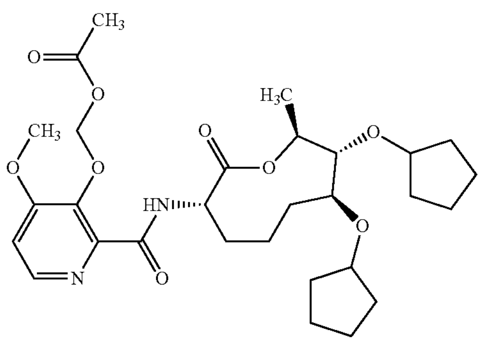 [SMILES: COc1ccnc(C(=O)N[C@H]2CCC[C@H](OC3CCCC3)[C@@H](OC3CCCC3)[C@H](C)OC2=O)c1OCOC(C)=O] | 17A |
| F218 | 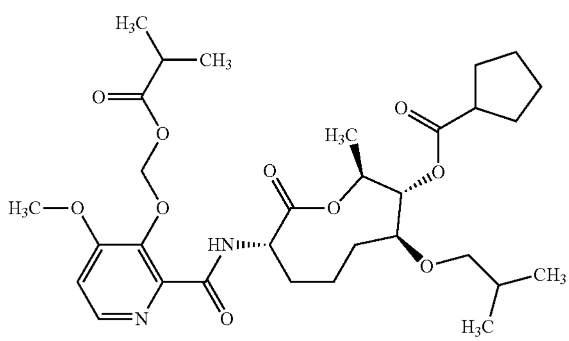 [SMILES: COc1ccnc(C(=O)N[C@H]2CCC[C@H](OCC(C)C)[C@@H](OC(=O)C3CCCC3)[C@H](C)OC2=O)c1OCOC(=O)C(C)C] | 17B |
| F219 | 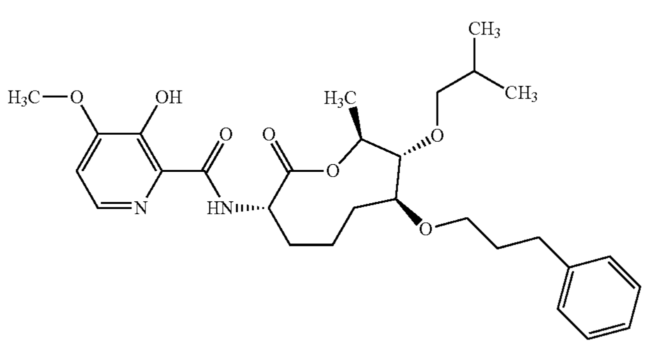 [SMILES: COc1ccnc(C(=O)N[C@H]2CCC[C@H](OCCCc3ccccc3)[C@@H](OCC(C)C)[C@H](C)OC2=O)c1O] | 16A |

TABLE 1-continued

Structure and Preparation Method for F Series Compounds

| Compound Number | Structure | Prepared According to Example |
|---|---|---|
| F220 | 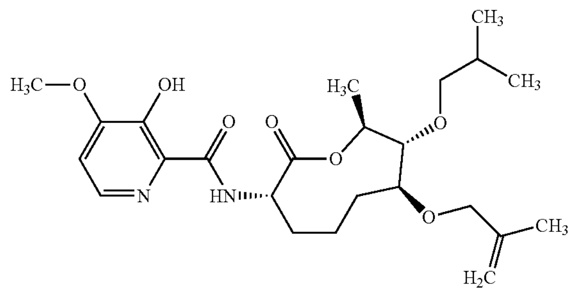 [SMILES: C=C(C)CO[C@H]1CCC[C@H](NC(=O)c2nccc(OC)c2O)C(=O)O[C@@H](C)[C@@H]1OCC(C)C] | 16A |
| F221 | 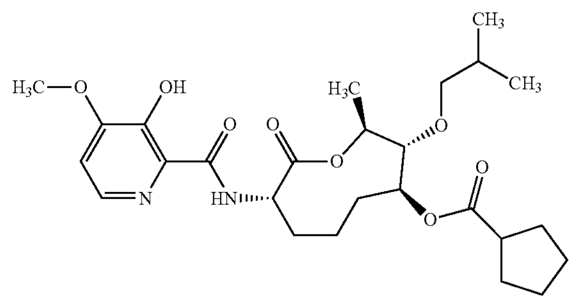 [SMILES: COc1ccnc(C(=O)N[C@H]2CCC[C@H](OC(=O)C3CCCC3)[C@@H](OCC(C)C)[C@H](C)OC2=O)c1O] | 16A |
| F222 | 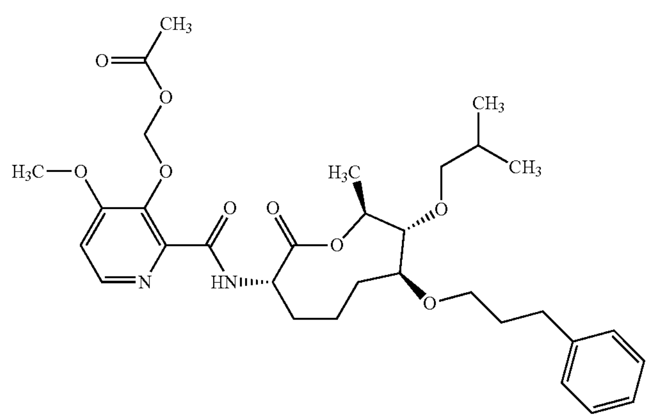 [SMILES: COc1ccnc(C(=O)N[C@H]2CCC[C@H](OCCCc3ccccc3)[C@@H](OCC(C)C)[C@H](C)OC2=O)c1OCOC(C)=O] | 17A |
| F223 | 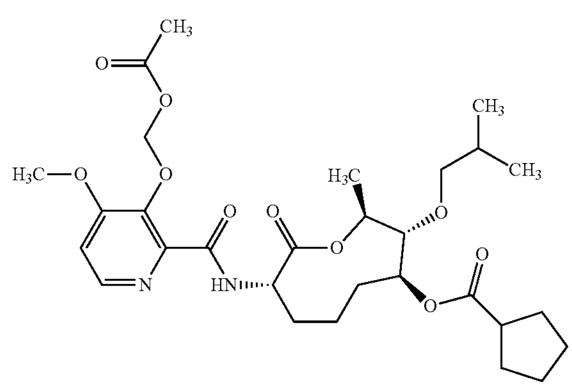 [SMILES: COc1ccnc(C(=O)N[C@H]2CCC[C@H](OC(=O)C3CCCC3)[C@@H](OCC(C)C)[C@H](C)OC2=O)c1OCOC(C)=O] | 17A |

TABLE 1-continued

Structure and Preparation Method for F Series Compounds

| Compound Number | Structure | Prepared According to Example |
|---|---|---|
| F224 | 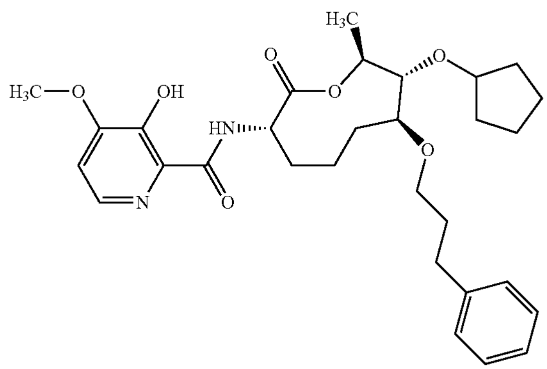 [SMILES: COc1ccnc(C(=O)N[C@H]2CCC[C@H](OCCCc3ccccc3)[C@@H](OC3CCCC3)[C@H](C)OC2=O)c1O] | 16A |
| F225 | 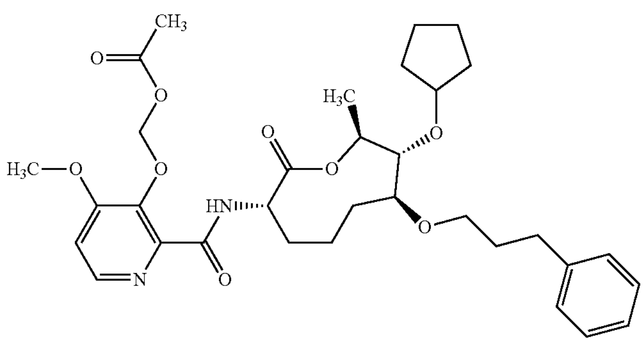 [SMILES: COc1ccnc(C(=O)N[C@H]2CCC[C@H](OCCCc3ccccc3)[C@@H](OC3CCCC3)[C@H](C)OC2=O)c1OCOC(C)=O] | 17A |
| F226 | 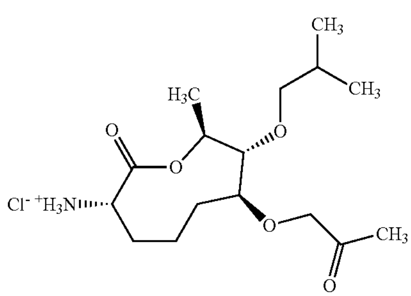 [SMILES: [Cl-] ; CC(=O)CO[C@H]1CCC[C@H]([NH3+])C(=O)O[C@@H](C)[C@@H]1OCC(C)C] | 13, 13B (1) and 13F (1, 3) |
| F227 | 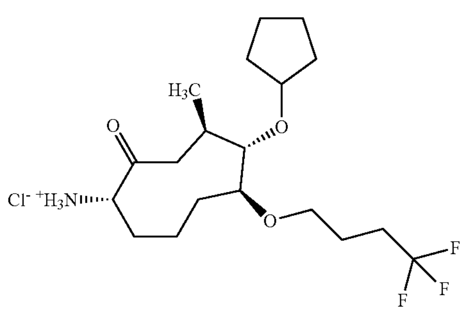 [SMILES: [Cl-] ; C[C@@H]1CC(=O)[C@@H]([NH3+])CCC[C@H](OCCCC(F)(F)F)[C@H]1OC1CCCC1] | 13, 13G (1-3) |

TABLE 1-continued

Structure and Preparation Method for F Series Compounds

| Compound Number | Structure | Prepared According to Example |
|---|---|---|
| F228 | 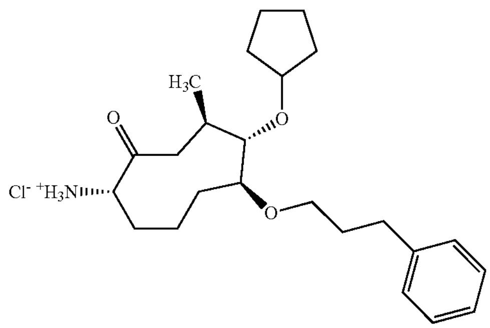 [SMILES: [Cl-] ; C[C@@H]1CC(=O)[C@@H]([NH3+])CCC[C@H](OCCCc2ccccc2)[C@H]1OC1CCCC1] | 13, 13G (1-3) |
| F229 | 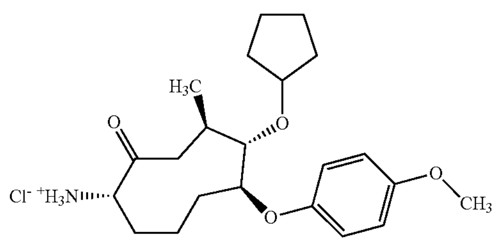 [SMILES: [Cl-] ; COc1ccc(O[C@H]2CCC[C@H]([NH3+])C(=O)C[C@@H](C)[C@@H]2OC2CCCC2)cc1] | 12, 12B (1-3) |
| F230 | 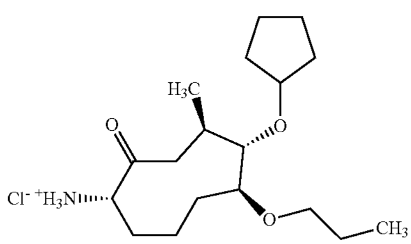 [SMILES: [Cl-] ; CCCO[C@H]1CCC[C@H]([NH3+])C(=O)C[C@@H](C)[C@@H]1OC1CCCC1] | 13, 13G (1-3) |
| F231 | 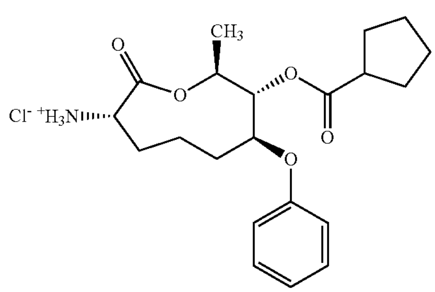 [SMILES: [Cl-] ; C[C@@H]1OC(=O)[C@@H]([NH3+])CCC[C@H](Oc2ccccc2)[C@H]1OC(=O)C1CCCC1] | 12, 13D (1-2) |
| F232 | 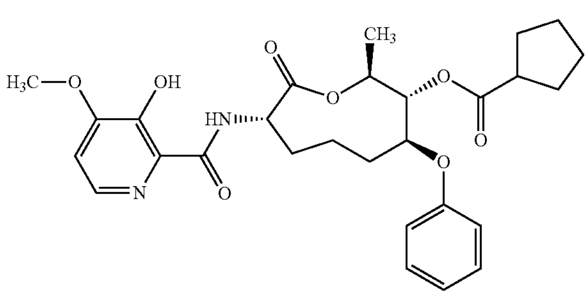 [SMILES: COc1ccnc(C(=O)N[C@H]2CCC[C@H](Oc3ccccc3)[C@@H](OC(=O)C3CCCC3)[C@H](C)OC2=O)c1O] | 16A |

TABLE 1-continued

Structure and Preparation Method for F Series Compounds

| Compound Number | Structure | Prepared According to Example |
|---|---|---|
| F233 | 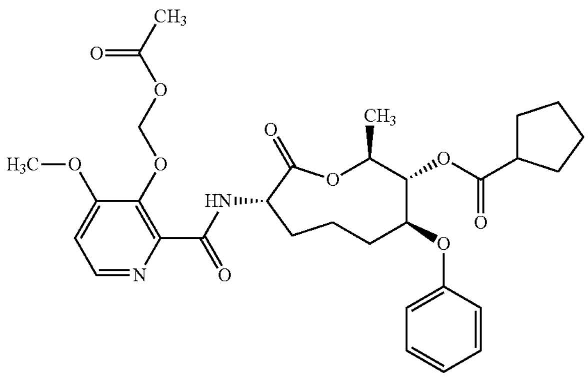 [SMILES: COc1ccnc(C(=O)N[C@H]2CCC[C@H](Oc3ccccc3)[C@@H](OC(=O)C3CCCC3)[C@H](C)OC2=O)c1OCOC(C)=O] | 17A |
| F234 | 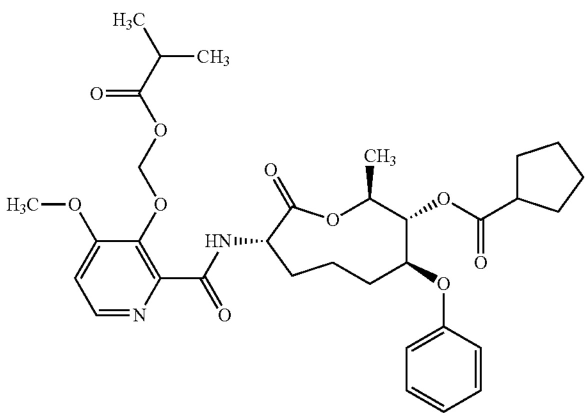 [SMILES: COc1ccnc(C(=O)N[C@H]2CCC[C@H](Oc3ccccc3)[C@@H](OC(=O)C3CCCC3)[C@H](C)OC2=O)c1OCOC(=O)C(C)C] | 17B |
| F235 | 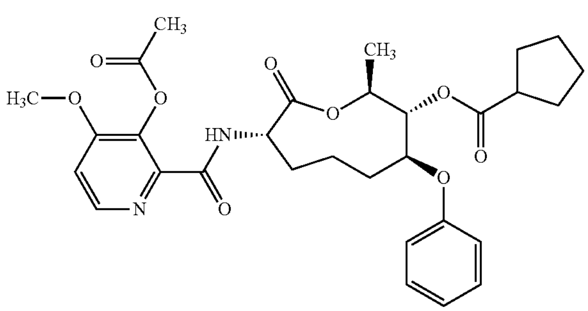 [SMILES: COc1ccnc(C(=O)N[C@H]2CCC[C@H](Oc3ccccc3)[C@@H](OC(=O)C3CCCC3)[C@H](C)OC2=O)c1OC(C)=O] | 17C |
| F236 | 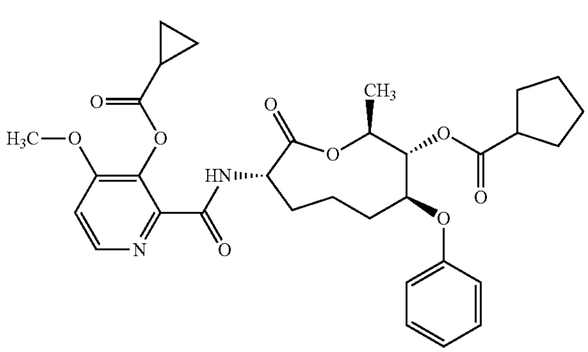 [SMILES: COc1ccnc(C(=O)N[C@H]2CCC[C@H](Oc3ccccc3)[C@@H](OC(=O)C3CCCC3)[C@H](C)OC2=O)c1OC(=O)C1CC1] | 17C |

TABLE 1-continued
Structure and Preparation Method for F Series Compounds
| Compound Number | Structure | Prepared According to Example |
|---|---|---|
| F237 | 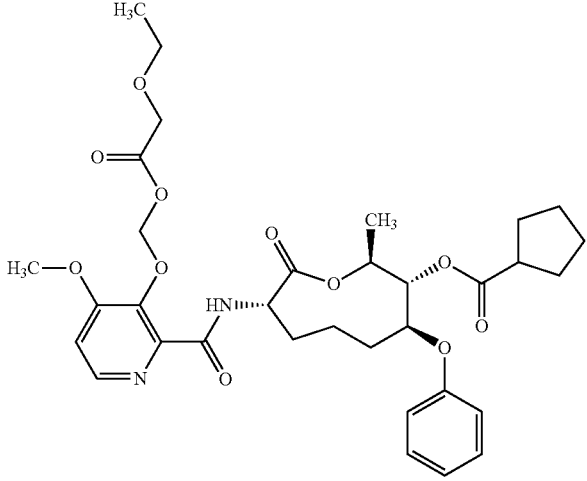 [SMILES: CCOCC(=O)OCOc1c(OC)ccnc1C(=O)N[C@H]1CCC[C@H](Oc2ccccc2)[C@@H](OC(=O)C2CCCC2)[C@H](C)OC1=O] | 17B |
| F238 | 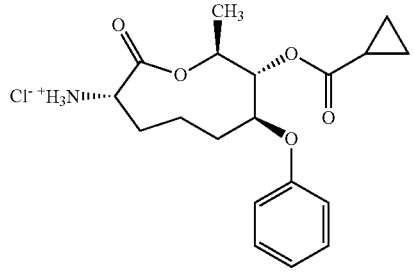 [SMILES: [Cl-] ; C[C@@H]1OC(=O)[C@@H]([NH3+])CCC[C@H](Oc2ccccc2)[C@H]1OC(=O)C1CC1] | 12, 13D (1-2) |
| F239 | 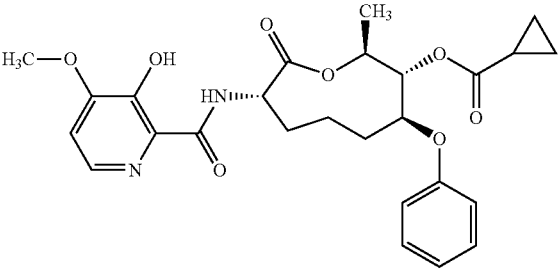 [SMILES: COc1ccnc(C(=O)N[C@H]2CCC[C@H](Oc3ccccc3)[C@@H](OC(=O)C3CC3)[C@H](C)OC2=O)c1O] | 16A |
| F240 | 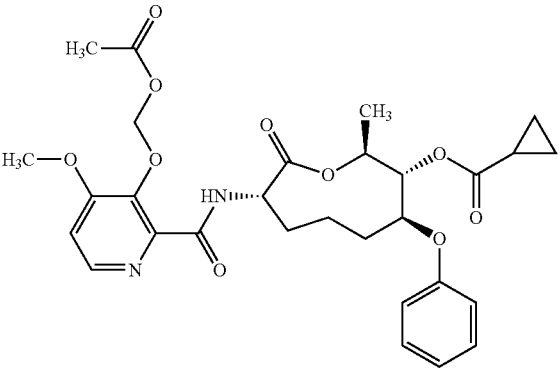 [SMILES: COc1ccnc(C(=O)N[C@H]2CCC[C@H](Oc3ccccc3)[C@@H](OC(=O)C3CC3)[C@H](C)OC2=O)c1OCOC(C)=O] | 17A |

TABLE 1-continued

Structure and Preparation Method for F Series Compounds

| Compound Number | Structure | Prepared According to Example |
|---|---|---|
| F241 | 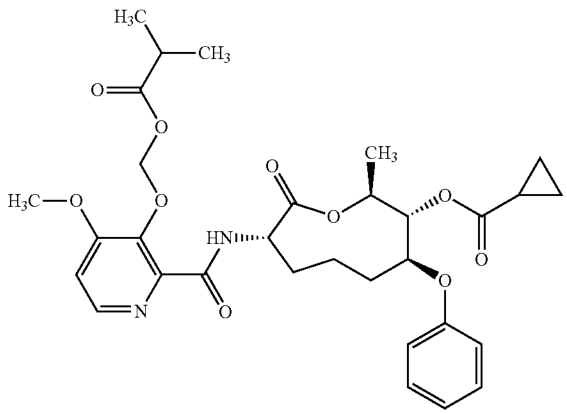 [SMILES: COc1ccnc(C(=O)N[C@H]2CCC[C@H](Oc3ccccc3)[C@@H](OC(=O)C3CC3)[C@H](C)OC2=O)c1OCOC(=O)C(C)C] | 17B |
| F242 | 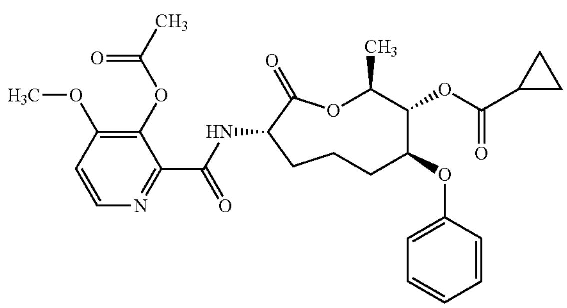 [SMILES: COc1ccnc(C(=O)N[C@H]2CCC[C@H](Oc3ccccc3)[C@@H](OC(=O)C3CC3)[C@H](C)OC2=O)c1OC(C)=O] | 17C |
| F243 | 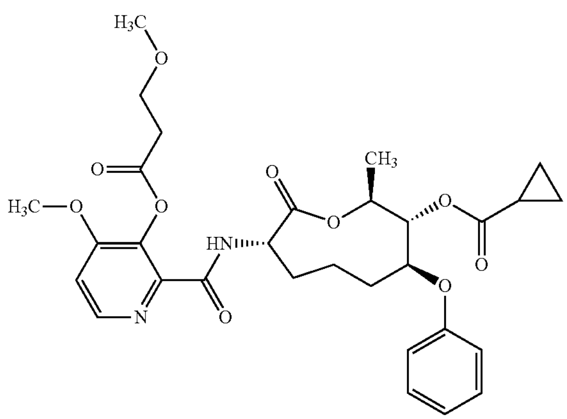 [SMILES: COCCC(=O)Oc1c(OC)ccnc1C(=O)N[C@H]1CCC[C@H](Oc2ccccc2)[C@@H](OC(=O)C2CC2)[C@H](C)OC1=O] | 17D |
| F244 | 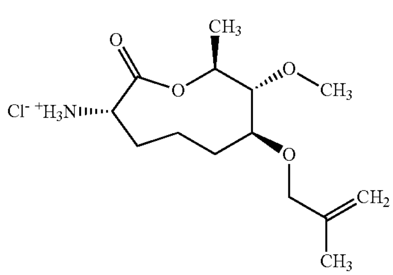 [SMILES: [Cl-] ; C=C(C)CO[C@H]1CCC[C@H]([NH3+])C(=O)O[C@@H](C)[C@@H]1OC] | 13, 23, 12A |

TABLE 1-continued

Structure and Preparation Method for F Series Compounds

| Compound Number | Structure | Prepared According to Example |
|---|---|---|
| F245 | 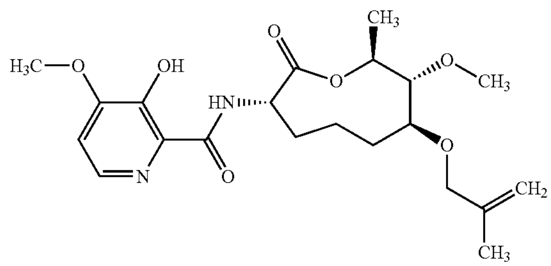 [SMILES: C=C(C)CO[C@H]1CCC[C@H](NC(=O)c2nccc(OC)c2O)C(=O)O[C@@H](C)[C@@H]1OC] | 16A |
| F246 | 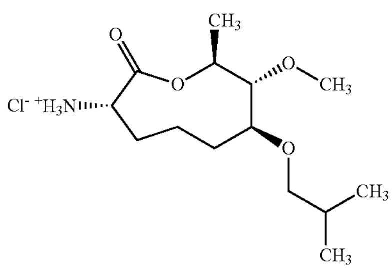 | 13, 23, 13B (1, 3) |
| F247 | 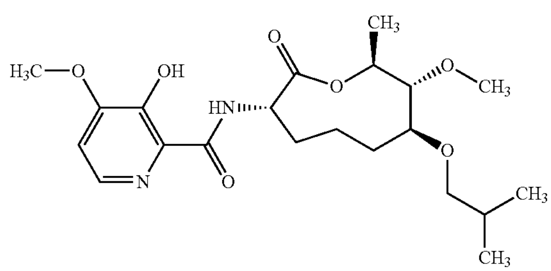 [SMILES: COc1ccnc(C(=O)N[C@H]2CCC[C@H](OCC(C)C)[C@@H](OC)[C@H](C)OC2=O)c1O] | 16A |
| F248 | 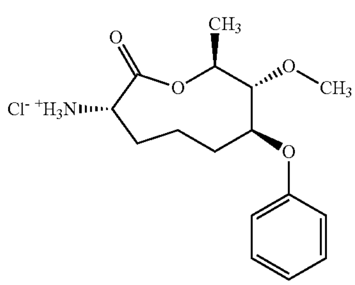 [SMILES: [Cl-] ; CO[C@H]1[C@H](C)OC(=O)[C@@H]([NH3+])CCC[C@@H]1Oc1ccccc1] | 12, 23, 12A |
| F249 | 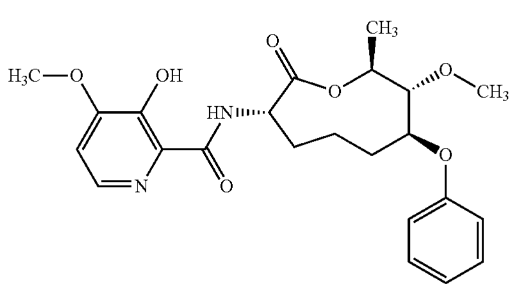 [SMILES: COc1ccnc(C(=O)N[C@H]2CCC[C@H](Oc3ccccc3)[C@@H](OC)[C@H](C)OC2=O)c1O] | 16A |

TABLE 1-continued

Structure and Preparation Method for F Series Compounds

| Compound Number | Structure | Prepared According to Example |
|---|---|---|
| F250 | 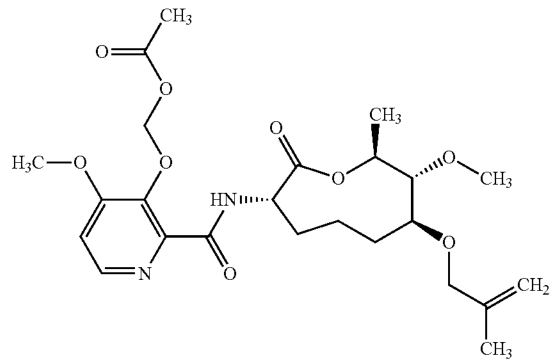 [SMILES: C=C(C)CO[C@H]1CCC[C@H](NC(=O)c2nccc(OC)c2OCOC(C)=O)C(=O)O[C@@H](C)[C@@H]1OC] | 17A |
| F251 | 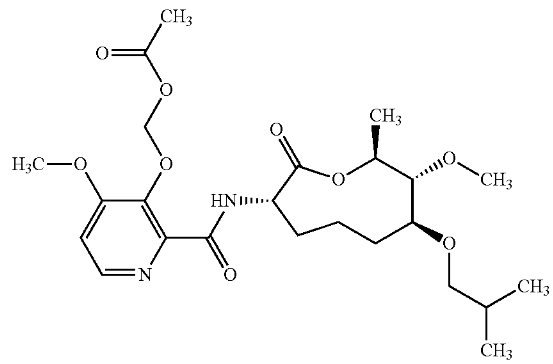 [SMILES: COc1ccnc(C(=O)N[C@H]2CCC[C@H](OCC(C)C)[C@@H](OC)[C@H](C)OC2=O)c1OCOC(C)=O] | 17A |
| F252 | 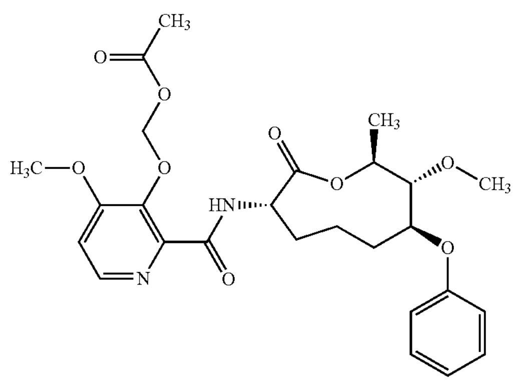 [SMILES: COc1ccnc(C(=O)N[C@H]2CCC[C@H](Oc3ccccc3)[C@@H](OC)[C@H](C)OC2=O)c1OCOC(C)=O] | 17A |
| F253 | 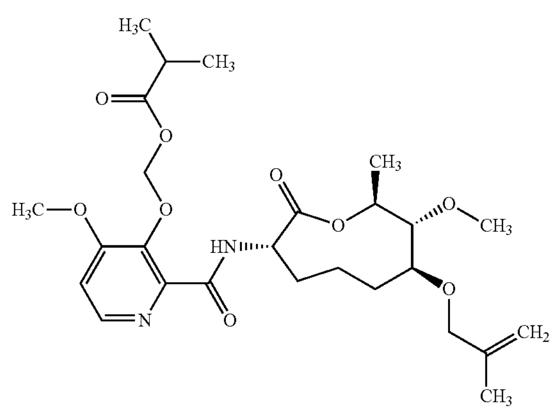 [SMILES: C=C(C)CO[C@H]1CCC[C@H](NC(=O)c2nccc(OC)c2OCOC(=O)C(C)C)C(=O)O[C@@H](C)[C@@H]1OC] | 17B |

TABLE 1-continued
Structure and Preparation Method for F Series Compounds
| Compound Number | Structure | Prepared According to Example |
|---|---|---|
| F254 | 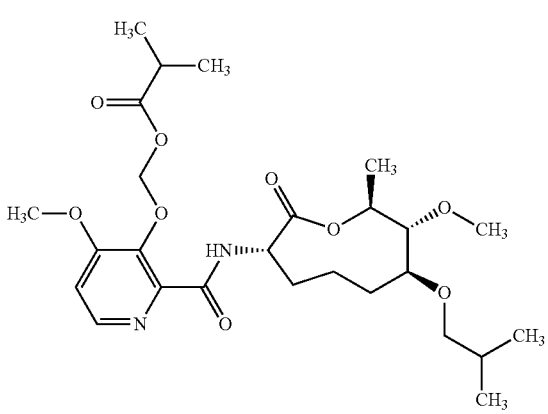 [SMILES: COc1ccnc(C(=O)N[C@H]2CCC[C@H](OCC(C)C)[C@@H](OC)[C@H](C)OC2=O)c1OCOC(=O)C(C)C] | 17B |
| F255 | 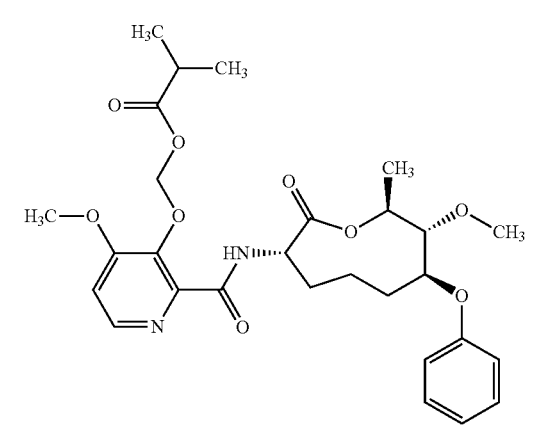 [SMILES: COc1ccnc(C(=O)N[C@H]2CCC[C@H](Oc3ccccc3)[C@@H](OC)[C@H](C)OC2=O)c1OCOC(=O)C(C)C] | 17B |
| F256 | 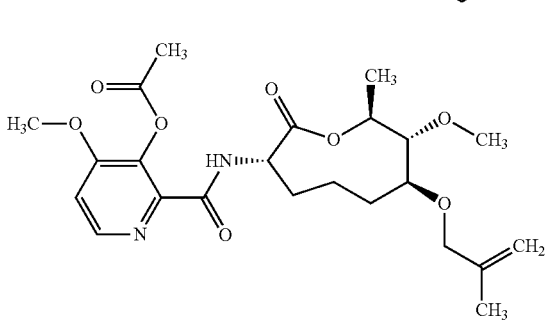 | 17C |
| F257 | 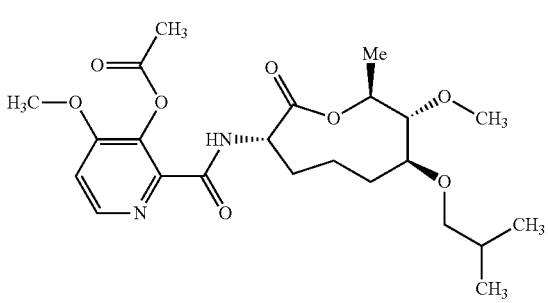 [SMILES: COc1ccnc(C(=O)N[C@H]2CCC[C@H](OCC(C)C)[C@@H](OC)[C@H](C)OC2=O)c1OC(C)=O] | 17C |

TABLE 1-continued

Structure and Preparation Method for F Series Compounds

| Compound Number | Structure | Prepared According to Example |
|---|---|---|
| F258 | 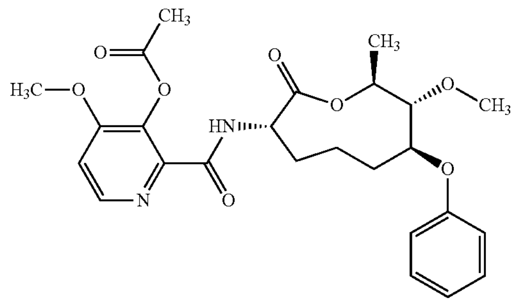 [SMILES: COc1ccnc(C(=O)N[C@H]2CCC[C@H](Oc3ccccc3)[C@@H](OC)[C@H](C)OC2=O)c1OC(C)=O] | 17C |
| F259 | 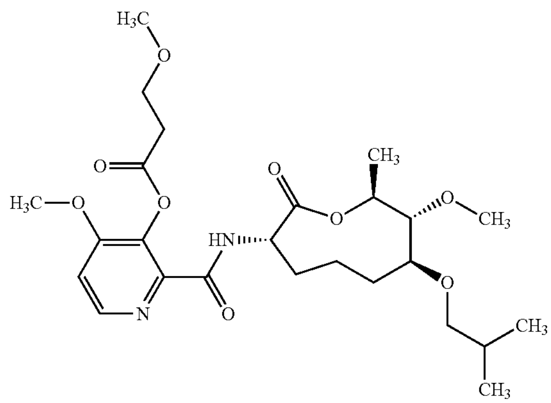 [SMILES: COCCC(=O)Oc1c(OC)ccnc1C(=O)N[C@H]1CCC[C@H](OCC(C)C)[C@@H](OC)[C@H](C)OC1=O] | 17D |
| F260 | 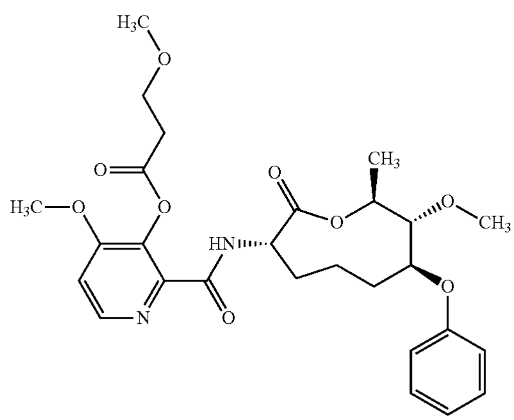 [SMILES: COCCC(=O)Oc1c(OC)ccnc1C(=O)N[C@H]1CCC[C@H](Oc2ccccc2)[C@@H](OC)[C@H](C)OC1=O] | 17D |
| F261 | 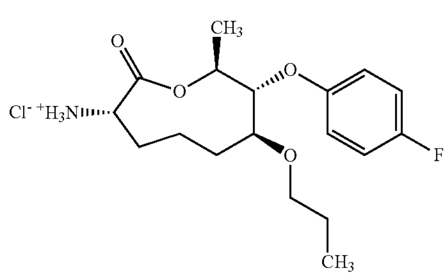 [SMILES: [Cl-] ; CCCO[C@H]1CCC[C@H]([NH3+])C(=O)O[C@@H](C)[C@@H]1Oc1ccc(F)cc1] | 12, 12B (1-3) |

TABLE 1-continued

Structure and Preparation Method for F Series Compounds

| Compound Number | Structure | Prepared According to Example |
|---|---|---|
| F262 | 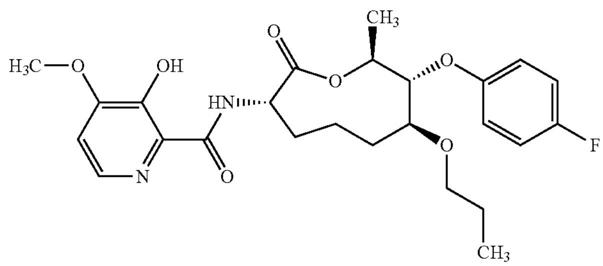 [SMILES: CCCO[C@H]1CCC[C@H](NC(=O)c2nccc(OC)c2O)C(=O)O[C@@H](C)[C@@H]1Oc1ccc(F)cc1] | 16A |
| F263 | 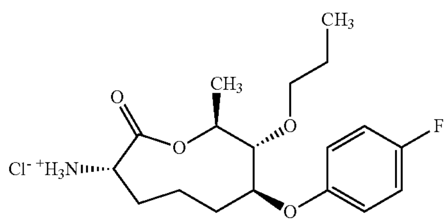 [SMILES: [Cl-] ; CCCO[C@H]1[C@H](C)OC(=O)[C@@H]([NH3+])CCC[C@@H]1Oc1ccc(F)cc1] | 12, 12B (1-3) |
| F264 | 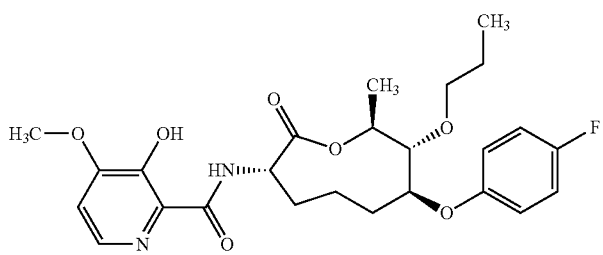 [SMILES: CCCO[C@H]1[C@H](C)OC(=O)[C@@H](NC(=O)c2nccc(OC)c2O)CCC[C@@H]1Oc1ccc(F)cc1] | 16A |
| F265 | 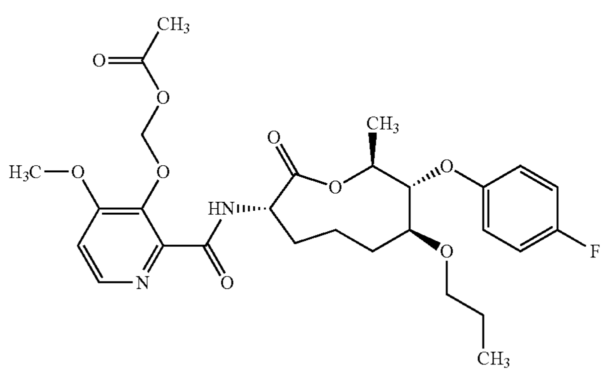 [SMILES: CCCO[C@H]1CCC[C@H](NC(=O)c2nccc(OC)c2OCOC(C)=O)C(=O)O[C@@H](C)[C@@H]1Oc1ccc(F)cc1] | 17A |
| F266 | 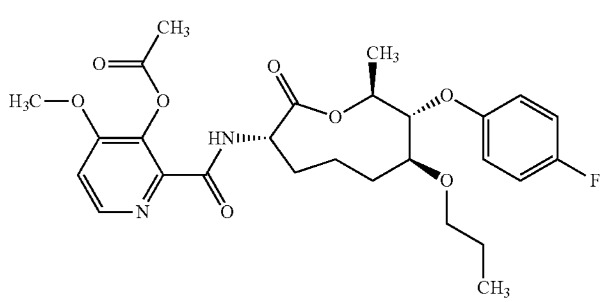 [SMILES: CCCO[C@H]1CCC[C@H](NC(=O)c2nccc(OC)c2OC(C)=O)C(=O)O[C@@H](C)[C@@H]1Oc1ccc(F)cc1] | 17C |

TABLE 1-continued

Structure and Preparation Method for F Series Compounds

| Compound Number | Structure | Prepared According to Example |
|---|---|---|
| F267 | 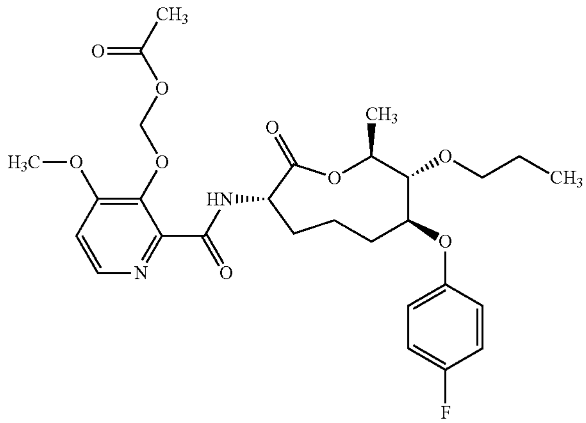 [SMILES: CCCO[C@H]1[C@H](C)OC(=O)[C@@H](NC(=O)c2nccc(OC)c2OCOC(C)=O)CCC[C@@H]1Oc1ccc(F)cc1] | 17A |
| F268 | 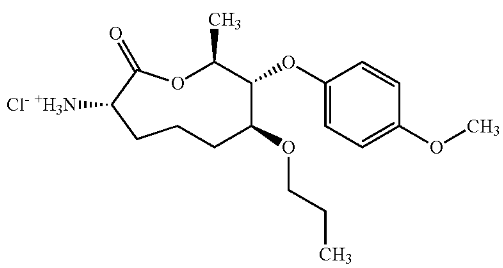 [SMILES: [Cl-] ; CCCO[C@H]1CCC[C@H]([NH3+])C(=O)O[C@@H](C)[C@@H]1Oc1ccc(OC)cc1] | 12, 12B (1-3) |
| F269 | 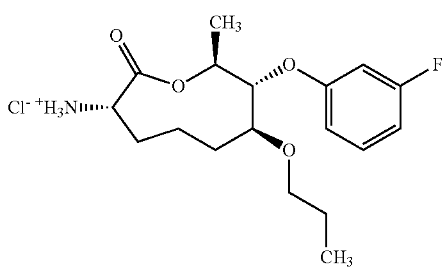 [SMILES: [Cl-] ; CCCO[C@H]1CCC[C@H]([NH3+])C(=O)O[C@@H](C)[C@@H]1Oc1cccc(F)c1] | 20, 12B (1-3) |
| F270 | 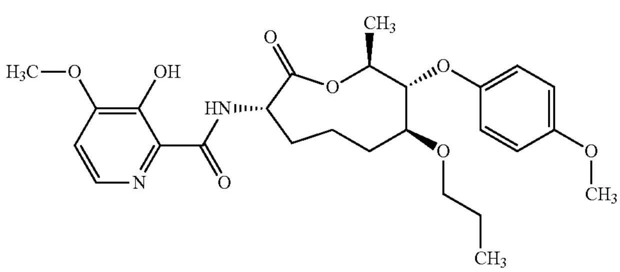 | 16A |
| F271 | 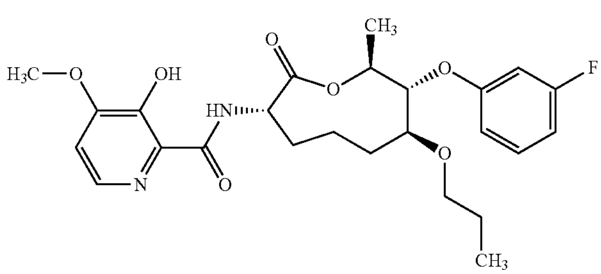 [SMILES: CCCO[C@H]1CCC[C@H](NC(=O)c2nccc(OC)c2O)C(=O)O[C@@H](C)[C@@H]1Oc1cccc(F)c1] | 16A |

TABLE 1-continued
Structure and Preparation Method for F Series Compounds
| Compound Number | Structure | Prepared According to Example |
|---|---|---|
| F272 | 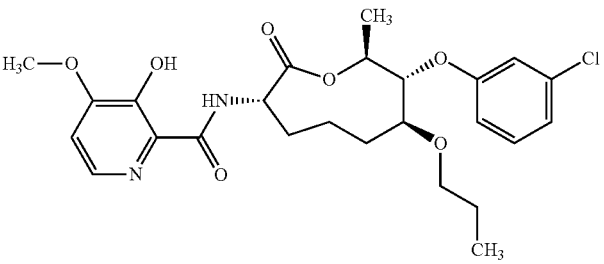 [SMILES: CCCO[C@H]1CCC[C@H](NC(=O)c2nccc(OC)c2O)C(=O)O[C@@H](C)[C@@H]1Oc1cccc(Cl)c1] | 16A |
| F273 | 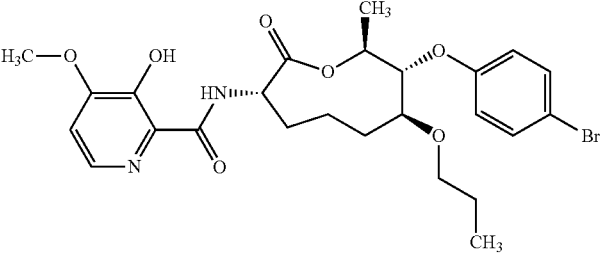 [SMILES: CCCO[C@H]1CCC[C@H](NC(=O)c2nccc(OC)c2O)C(=O)O[C@@H](C)[C@@H]1Oc1ccc(Br)cc1] | 16A |
| F274 | 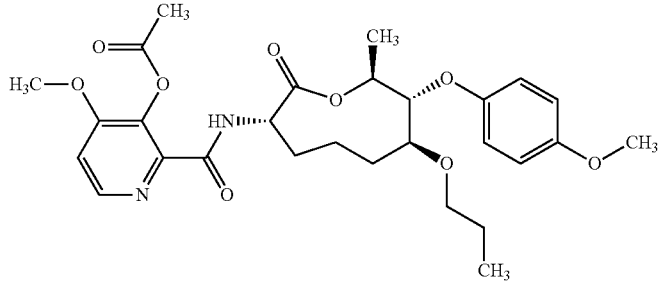 | 17C |
| F275 | 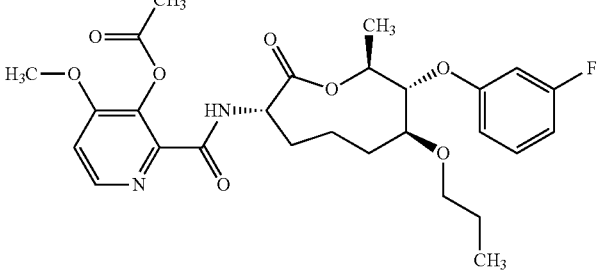 | 17C |
| F276 | 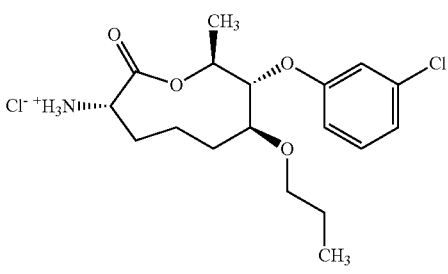 [SMILES: [Cl-] ; CCCO[C@H]1CCC[C@H]([NH3+])C(=O)O[C@@H](C)[C@@H]1Oc1cccc(Cl)c1] | 12, 12B (1-3) |

TABLE 1-continued

Structure and Preparation Method for F Series Compounds

| Compound Number | Structure | Prepared According to Example |
|---|---|---|
| F277 | 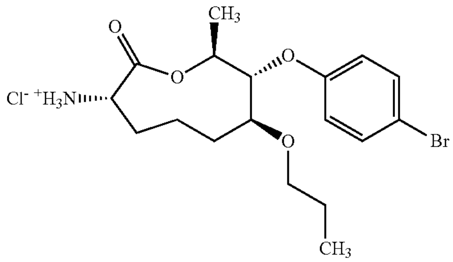 [SMILES: [Cl-] ; CCCO[C@H]1CCC[C@H]([NH3+])C(=O)O[C@@H](C)[C@@H]1Oc1ccc(Br)cc1] | 12, 12B (1-2), 21, 12A |
| F278 | 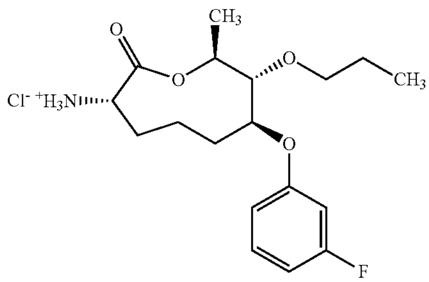 [SMILES: [Cl-] ; CCCO[C@H]1[C@H](C)OC(=O)[C@@H]([NH3+])CCC[C@@H]1Oc1cccc(F)c1] | 20, 12B (1-3) |
| F279 | 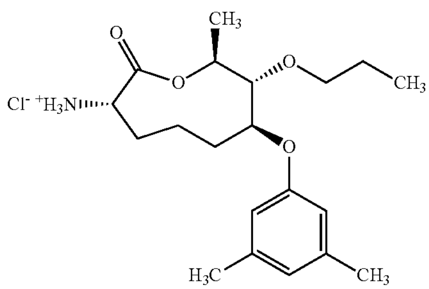 [SMILES: [Cl-] ; CCCO[C@H]1[C@H](C)OC(=O)[C@@H]([NH3+])CCC[C@@H]1Oc1cc(C)cc(C)c1] | 12, 12B (1-3) |
| F280 | 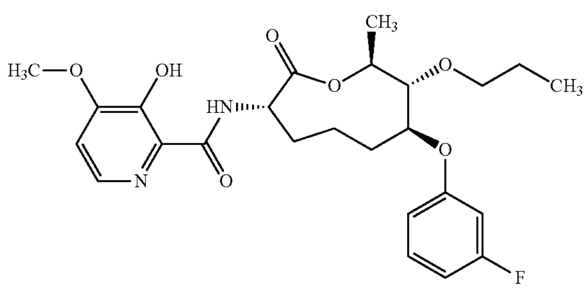 [SMILES: CCCO[C@H]1[C@H](C)OC(=O)[C@@H](NC(=O)c2nccc(OC)c2O)CCC[C@@H]1Oc1cccc(F)c1] | 16A |
| F281 | 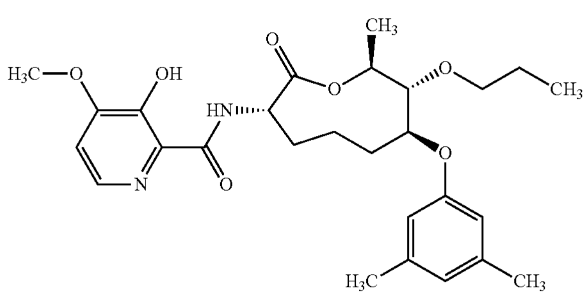 [SMILES: CCCO[C@H]1[C@H](C)OC(=O)[C@@H](NC(=O)c2nccc(OC)c2O)CCC[C@@H]1Oc1cc(C)cc(C)c1] | 16A |

TABLE 1-continued

Structure and Preparation Method for F Series Compounds

| Compound Number | Structure | Prepared According to Example |
|---|---|---|
| F282 | 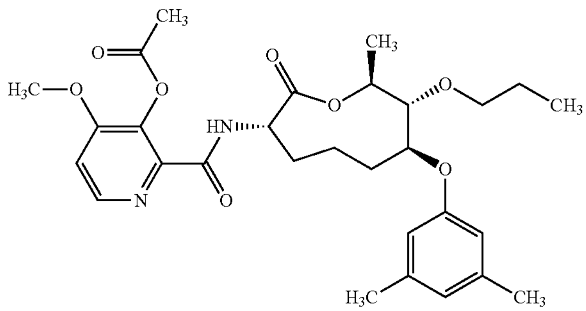 [SMILES: CCCO[C@H]1[C@H](C)OC(=O)[C@@H](NC(=O)c2nccc(OC)c2OC(C)=O)CCC[C@@H]1Oc1cc(C)cc(C)c1] | 17C |
| F283 | 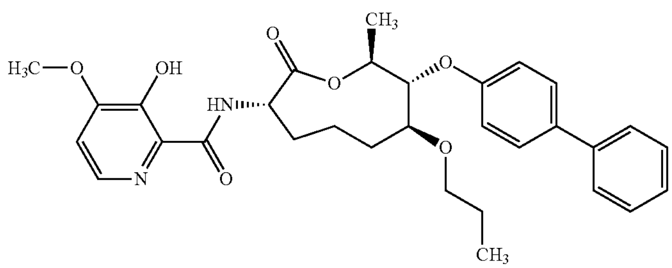 [SMILES: CCCO[C@H]1CCC[C@H](NC(=O)c2nccc(OC)c2O)C(=O)O[C@@H](C)[C@@H]1Oc1ccc(-c2ccccc2)cc1] | 16A |
| F284 | 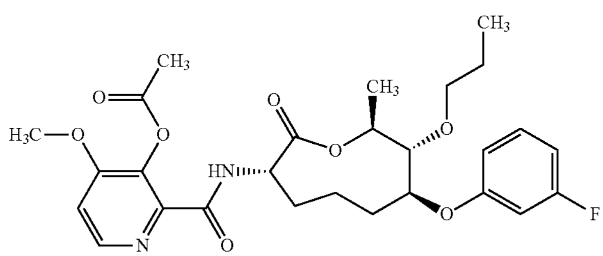 [SMILES: CCCO[C@H]1[C@H](C)OC(=O)[C@@H](NC(=O)c2nccc(OC)c2OC(C)=O)CCC[C@@H]1Oc1cccc(F)c1] | 17C |
| F285 | 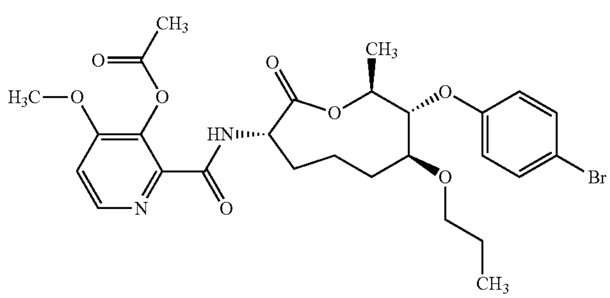 [SMILES: CCCO[C@H]1CCC[C@H](NC(=O)c2nccc(OC)c2OC(C)=O)C(=O)O[C@@H](C)[C@@H]1Oc1ccc(Br)cc1] | 17C |
| F286 | 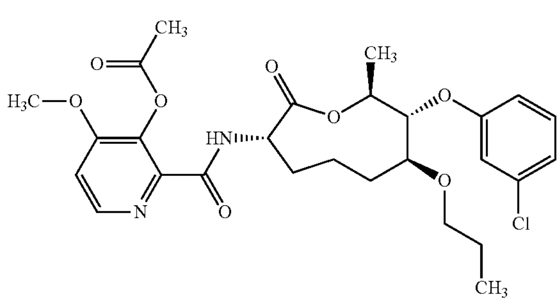 [SMILES: CCCO[C@H]1CCC[C@H](NC(=O)c2nccc(OC)c2OC(C)=O)C(=O)O[C@@H](C)[C@@H]1Oc1cccc(Cl)c1] | 17C |

TABLE 1-continued

Structure and Preparation Method for F Series Compounds

| Compound Number | Structure | Prepared According to Example |
|---|---|---|
| F287 | 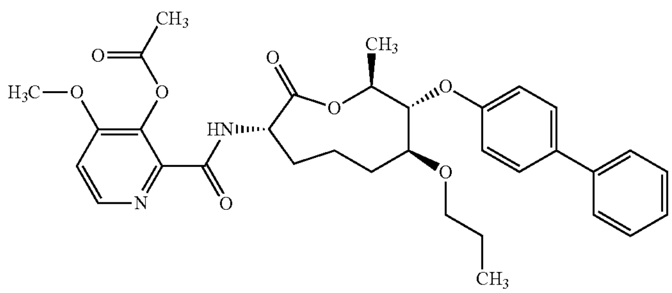 [SMILES: CCCO[C@H]1CCC[C@H](NC(=O)c2nccc(OC)c2OC(C)=O)C(=O)O[C@@H](C)[C@@H]1Oc1ccc(-c2ccccc2)cc1] | 17C |
| F288 | 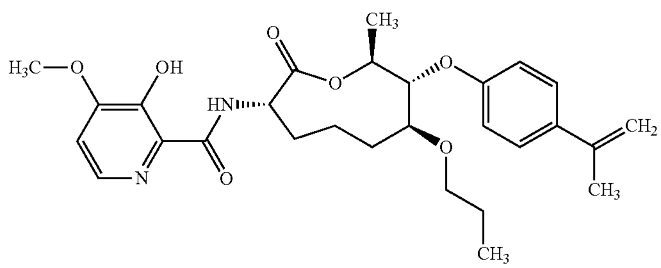 [SMILES: C=C(C)c1ccc(O[C@H]2[C@H](C)OC(=O)[C@@H](NC(=O)c3nccc(OC)c3O)CCC[C@@H]2OCCC)cc1] | 16A |
| F289 | 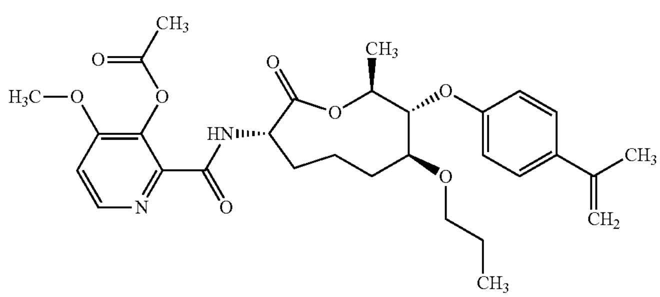 [SMILES: C=C(C)c1ccc(O[C@H]2[C@H](C)OC(=O)[C@@H](NC(=O)c3nccc(OC)c3OC(C)=O)CCC[C@@H]2OCCC)cc1] | 17C |
| F290 | 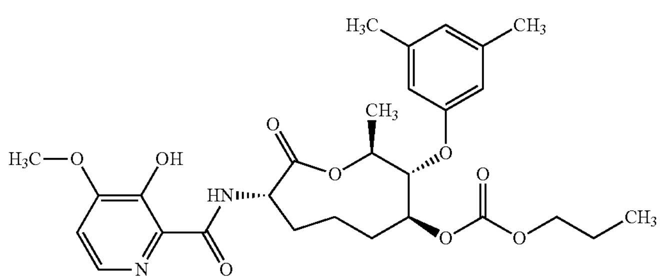 [SMILES: CCCOC(=O)O[C@H]1CCC[C@H](NC(=O)c2nccc(OC)c2O)C(=O)O[C@@H](C)[C@@H]1Oc1cc(C)cc(C)c1] | 16A |
| F291 | 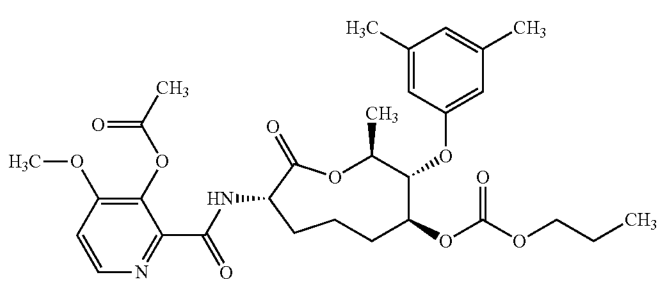 [SMILES: CCCOC(=O)O[C@H]1CCC[C@H](NC(=O)c2nccc(OC)c2OC(C)=O)C(=O)O[C@@H](C)[C@@H]1Oc1cc(C)cc(C)c1] | 17C |

TABLE 1-continued

Structure and Preparation Method for F Series Compounds

| Compound Number | Structure | Prepared According to Example |
|---|---|---|
| F292 | 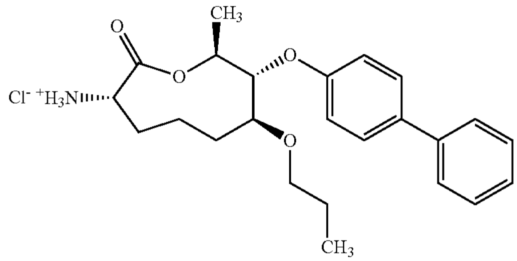 [SMILES: [Cl-] ; CCCO[C@H]1CCC[C@H]([NH3+])C(=O)O[C@@H](C)[C@@H]1Oc1ccc(-c2ccccc2)cc1] | 12, 12B (1-2), 21, 22 12A |
| F293 | 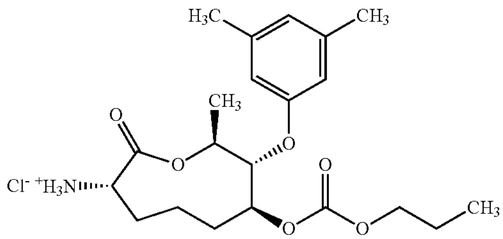 [SMILES: [Cl-] ; CCCOC(=O)O[C@H]1CCC[C@H]([NH3+])C(=O)O[C@@H](C)[C@@H]1Oc1cc(C)cc(C)c1] | 12, 12B (1-3) |
| F294 | 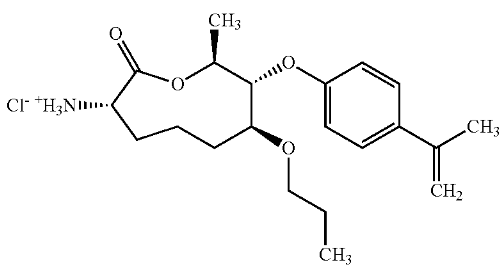 [SMILES: [Cl-] ; C=C(C)c1ccc(O[C@H]2[C@H](C)OC(=O)[C@@H]([NH3+])CCC[C@@H]2OCCC)cc1] | 12, 12B (1-2), 21, 22 12A |

TABLE 2

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| F1 | White Crystalline Solid | — | — | HRMS-ESI (m/z) [M + Na]⁺ calcd for $C_{19}H_{33}NNaO_8$, 426.2102; found, 426.2098 | ¹H NMR (CDCl₃) δ 4.84 (dd, J = 10.0, 7.4 Hz, 1H), 4.72 (dq, J = 9.1, 6.3 Hz, 1H), 3.59-3.41 (m, 2H), 2.70-2.58 (m, 1H), 2.42-2.27 (m, 1H), 2.12-2.00 (m, 1H), 1.96-1.63 (m, 3H), 1.59-1.46 (m, 18H), 1.42 (d, J = 6.3 Hz, 3H) | ¹³C NMR (CDCl₃) δ 170.82, 152.88, 82.85, 73.79, 73.28, 57.70, 35.10, 30.87, 29.22, 27.95, 19.98, 18.06 |
| F2 | White Foam | — | — | ESI-MS m/z 356.5 ([M + H]⁺) | ¹H NMR (CDCl₃) δ 8.74 (s, 3H), 7.20 (dd, J = 15.3, 7.6 Hz, 4H), 7.01 (d, J = 8.0 Hz, 2H), 6.92 (dt, J = 14.2, 7.3 Hz, 2H), 6.81 (d, J = 8.0 Hz, 2H), 1.90-1.64 (m, 3H), 5.08 (t, J = 7.0 Hz, 1H), 4.60 (t, J = 8.1 Hz, 1H), 4.50 (br s, 1H), 4.16 (br s, 1H), 2.57 (br s, 1H), | ¹³C NMR (CDCl₃) δ 170.00, 159.33, 157.42, 129.47, 129.46, 121.76, 121.59, 116.69, 116.48, 82.15, 81.87, 73.49, 52.29, 30.92, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 2.30 (br s, 1H), 1.38 (d, J = 5.7 Hz, 3H), 1.13 (d, J = 10.0 Hz, 1H) | 28.28, 18.11, 17.88 |
| F3 | White Solid | — | — | HRMS-ESI (m/z) [M + H]⁺ calcd for C₁₉H₃₀NO₄, 336.2169; found, 336.2173 | ¹H NMR (CDCl₃) δ 8.73 (br s, 3H), 7.28-7.21 (m, 2H), 7.04 (d, J = 7.9 Hz, 2H), 6.94 (t, J = 7.3 Hz, 1H), 4.98 (dq, J = 12.7, 6.1 Hz, 1H), 4.37 (dd, J = 9.3, 7.4 Hz, 1H), 4.11 (t, J = 8.3 Hz, 1H), 3.70 (s, 1H), 3.22 (dd, J = 8.7, 6.6 Hz, 1H), 3.03 (dd, J = 8.7, 6.2 Hz, 1H), 2.58 (s, 1H), 2.28-2.15 (m, 1H), 1.90-1.59 (m, 4H), 1.34 (d, J = 6.3 Hz, 3H), 0.98 (d, J = 9.3 Hz, 1H), 0.77 (d, J = 6.7 Hz, 3H), 0.72 (d, J = 6.7 Hz, 3H) | ¹³C NMR (CDCl₃) δ 170.08, 159.50, 129.35, 121.39, 116.34, 82.82, 82.50, 76.39, 73.64, 52.28, 31.07, 28.67, 27.87, 19.33, 19.18, 18.00, 17.87 |
| F4 | White Solid | — | — | HRMS-ESI (m/z) [M + H]⁺ calcd for C₁₉H₃₀NO₄, 336.2169; found, 336.2167 | ¹H NMR (CDCl₃) δ 8.65 (br s, 3H), 7.25 (t, J = 7.9 Hz, 2H), 7.00-6.84 (m, 3H), 4.93-4.68 (m, 1H), 4.34 (br s, 1H), 4.09 (br s, 1H), 3.61-3.46 (m, 2H), 3.36 (dd, J = 8.5, 6.7 Hz, 1H), 2.49 (br s, 1H), 1.89-1.51 (m, 4H), 1.43 (d, J = 6.0 Hz, 3H), 1.05-0.87 (m, 1H), 0.82 (d, J = 6.7 Hz, 3H), 0.78 (d, J = 6.7 Hz, 3H) | ¹³C NMR (CDCl₃) δ 170.02, 157.44, 129.50, 121.27, 116.49, 83.14, 82.78, 80.70, 73.85, 52.21, 30.85, 28.97, 28.16, 19.37, 19.27, 17.91, 17.76 |
| F5 | Colorless Solid | — | — | ESIMS m/z 404.2 ([M + H]⁺) | ¹H NMR (CDCl₃) δ 8.65 (bs, 3H), 7.02-6.86 (m, 4H), 6.82-6.67 (m, 4H), 5.07-4.96 (m, 1H), 4.44 (dd, J = 9.4, 7.3 Hz, 1H), 4.34-4.26 (m, 1H), 4.21-4.08 (m, 1H), 3.70 (s, 3H), 3.38-3.04 (m, 1H), 2.63-2.51 (m, 1H), 2.30-2.13 (m, 1H), 1.85-1.69 (m, 2H), 1.37 (d, J = 6.3 Hz, 3H), 1.10-0.98 (m, 1H) | ¹³C NMR (CDCl₃) δ 170.11, 157.86 (d, J = 239.9 Hz), 155.67 (d, J = 2.0 Hz), 154.77, 151.39, 118.40, 117.88 (d, J = 8.1 Hz), 115.97 (d, J = 23.0 Hz), 114.74, 83.58, 83.43, 73.46, 55.72, 52.40, 31.01, 28.32, 18.19, 18.02; ¹⁹F NMR (CDCl₃) δ −122.33 |
| F6 | Chalky White Solid | 188-230 | — | ESIMS m/z 316.6 ([M + H]⁺) | ¹H NMR (CDCl₃) δ 8.69 (s, 2H), 4.75 (s, 1H), 4.00 (s, 1H), 3.60 (dd, J = 8.6, 6.2 Hz, 1H), 3.36-3.28 (m, 3H), 3.28-3.20 (m, 1H), 3.09 (dd, J = 8.6, 6.3 Hz, 1H), 2.51 (s, 1H), 2.13 (s, 1H), 1.88-1.52 (m, 6H), 1.39 (d, J = 6.2 Hz, 3H), 0.96-0.85 (m, 12H) | — |
| F7 | White Solid | 199-202 | 3395, 2947, 2093, | HRMS-ESI (m/z) [M + H]⁺ | ¹H NMR (CD₃OD) δ 7.07-6.94 (m, 2H), 6.90-6.71 (m, 2H), | ¹³C NMR (CD₃OD) δ 169.76, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | 1745, 1506 | calcd for C$_{20}$H$_{32}$NO$_5$, 366.2275; found, 366.2275 | 5.01 (dq, J = 9.4, 6.4 Hz, 1H), 4.32 (dd, J = 9.5, 7.3 Hz, 1H), 3.98 (dd, J = 10.8, 7.5 Hz, 1H), 3.74 (s, 3H), 3.64-3.48 (m, 1H), 3.30-3.27 (m, 1H), 3.08 (dd, J = 8.8, 6.1 Hz, 1H), 2.40-2.18 (m, 2H), 1.89-1.71 (m, 2H), 1.65 (dq, J = 13.2, 6.6 Hz, 1H), 1.56-1.42 (m, 1H), 1.36 (d, J = 6.4 Hz, 3H), 0.95 (dd, J = 11.5, 7.3 Hz, 1H), 0.78 (dd, J = 16.4, 6.7 Hz, 6H) | 154.43, 153.69, 117.00, 114.06, 82.99, 82.91, 76.03, 73.61, 54.67, 51.40, 30.61, 28.58, 27.32, 18.35, 18.23, 17.41, 17.02 |
| F8 | White Solid | — | — | ESIMS m/z 356.3 ([M + H]$^+$) | — | — |
| F9 | White Solid | — | — | ESIMS m/z 356 ([M + H]$^+$) | $^1$H NMR (CD$_3$OD) δ 5.11 (dd, J = 9.7, 7.9 Hz, 1H), 4.99 (dq, J = 9.7, 6.3 Hz, 1H), 3.99 (dd, J = 10.8, 7.5 Hz, 1H), 3.46 (ddd, J = 7.4, 5.1, 1.8 Hz, 1H), 3.37-3.32 (m, 1H), 3.02 (dd, J = 8.7, 6.5 Hz, 1H), 2.87-2.73 (m, 1H), 2.37-2.20 (m, 2H), 1.99-1.55 (m, 12H), 1.55-1.41 (m, 1H), 1.27 (d, J = 6.3 Hz, 3H), 0.92 (dtd, J = 15.1, 4.8, 2.4 Hz, 1H), 0.86 (dd, J = 6.7, 1.2 Hz, 6H) | $^{13}$C NMR (CD$_3$OD) δ 177.44, 171.22, 82.37, 77.16, 76.44, 73.86, 52.81, 45.17, 31.99, 31.11, 30.86, 30.01, 28.36, 26.78, 26.69, 19.77, 19.72, 18.51, 17.57 |
| F10 | White Solid | 231-235 | 2944, 2870, 2106, 1742, 1727, 1225 | HRMS-ESI (m/z) [M + Na]$^+$ calcd for C$_{17}$H$_{29}$NNaO$_5$, 350.1938; found, 350.1937 | $^1$H NMR (CD$_3$OD) δ 5.13 (dd, J = 9.8, 7.8 Hz, 1H), 5.08-4.96 (m, 1H), 4.01 (dd, J = 10.7, 7.5 Hz, 1H), 3.49 (ddd, J = 7.6, 5.2, 1.8 Hz, 1H), 3.38 (dd, J = 8.8, 6.0 Hz, 1H), 3.05 (dd, J = 8.8, 6.7 Hz, 1H), 2.44-2.20 (m, 2H), 1.86-1.61 (m, 4H), 1.59-1.42 (m, 1H), 1.30 (d, J = 6.3 Hz, 3H), 1.02-0.90 (m, 5H), 0.90 (dd, J = 6.6, 2.3 Hz, 6H) | $^{13}$C NMR (CD$_3$OD) δ 174.56, 169.88, 81.00, 75.96, 75.24, 72.42, 51.38, 30.64, 28.52, 27.12, 18.29, 18.21, 17.08, 16.01, 12.23, 7.69, 7.57 |
| F11 | White Solid | 236-240 | 2943, 2900, 2872, 2109, 1743, 1453, 1253 | — | $^1$H NMR (CD$_3$OD) δ 4.87-4.75 (m, 1H), 3.97-3.80 (m, 2H), 3.71 (dt, J = 9.3, 6.2 Hz, 1H), 3.43-3.35 (m, 3H), 3.14 (dd, J = 8.7, 6.0 Hz, 1H), 2.33-2.12 (m, 4H), 1.89-1.72 (m, 3H), 1.68 (dq, J = 9.5, 4.6 Hz, 2H), 1.52-1.35 (m, 4H), 0.93 (dd, J = 6.7, 3.7 Hz, 6H), 0.85 (dt, J = 16.3, 4.8 Hz, 1H) | $^{13}$C NMR (CD$_3$OD) δ 169.81, 83.65, 83.58, 75.37, 73.68, 71.34, 51.39, 30.56, 30.21 (q, J = 28.7 Hz), 28.74, 26.95, 22.90-22.61 (m), 18.51, 18.39, 17.35, 16.81; $^{19}$F NMR (CD$_3$OD) δ −69.61 (t, J = 11.3 Hz) |
| F12 | Flaky Brown Solid | — | 3455, 2951, 2870, 1732, | HRMS-ESI (m/z) [M + H]$^+$ calcd for | $^1$H NMR (CD$_3$OD) δ 5.21 (dd, J = 9.7, 8.0 Hz, 1H), 5.14 (dq, J = 9.7, 6.2 Hz, 1H), | $^{13}$C NMR (CD$_3$OD) δ 175.65, 169.83, 74.39, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | 1184, 1144 | $C_{21}H_{34}NO_6$, 396.2381; found, 396.2372 | 5.03 (ddd, J = 7.7, 5.4, 2.2 Hz, 1H), 4.03 (t, J = 9.1 Hz, 1H), 2.73 (dtt, J = 24.0, 8.7, 6.9 Hz, 2H), 2.30 (dt, J = 13.9, 7.1 Hz, 1H), 2.21-2.08 (m, 1H), 1.95-1.54 (m, 18H), 1.48 (q, J = 12.6, 12.1 Hz, 1H), 1.30 (d, J = 6.2 Hz, 3H), 1.15 (ddt, J = 16.3, 7.6, 2.4 Hz, 1H) | 73.59, 72.07, 51.35, 43.64, 43.52, 30.54, 29.57, 29.53, 29.44, 28.72, 25.31, 25.25, 17.29, 16.10 |
| F13 | Greasy White Solid | — | 2955, 2873, 1748, 1223, 1103 | HRMS-ESI (m/z) [M + H]⁺ calcd for $C_{18}H_{36}NO_5$, 346.2588; found, 346.2596 | — | ¹³C NMR (CD₃OD) δ 169.78, 169.75, 85.14, 83.88, 83.69, 83.42, 75.56, 75.48, 75.46, 73.85, 73.66, 73.09, 60.22, 51.39, 32.19, 30.53, 28.75, 28.72, 27.28, 27.26, 27.17, 19.04, 18.44, 18.41, 17.39, 16.77, 16.63, 12.88 |
| F14 | White Foam | — | 3373, 2923, 2853, 1740, 1650, 1575, 1527, 1448, 1441 | ESIMS m/z 463.3 ([M + H]⁺); HRMS-ESI (m/z) [M + H]⁺ calcd for $C_{24}H_{34}N_2O_7$, 463.2433; found, 463.2439 | ¹H NMR (CDCl₃) δ 12.08 (s, 1H), 8.47 (d, J = 8.1 Hz, 1H), 7.99 (d, J = 5.1 Hz, 1H), 6.87 (d, J = 5.2 Hz, 1H), 4.97 (dq, J = 2.8, 1.4 Hz, 2H), 4.87 (dq, J = 4.7, 2.2 Hz, 2H), 4.90-4.82 (m, 1H), 4.60 (dt, J = 10.8, 7.6 Hz, 1H), 4.28 (d, J = 11.7 Hz, 1H), 4.05 (d, J = 11.7 Hz, 1H), 3.97 (d, J = 12.4 Hz, 1H), 3.94 (s, 3H), 3.85 (d, J = 11.6 Hz, 1H), 3.57-3.42 (m, 2H), 2.38 (dtd, J = 13.7, 7.1, 6.7, 1.8 Hz, 1H), 2.09-2.20 (m, 1H), 1.79-1.74 (m, 6H), 1.75-1.66 (m, 1H), 1.61-1.54 (m, 2H), 1.49-1.37 (m, 3H), 0.90-0.80 (m, 1H); | ¹³CNMR (CDCl₃) δ 172.12, 168.78, 155.47, 148.84, 142.56, 142.50, 140.65, 130.50, 112.25, 112.12, 109.60, 83.77, 83.62, 73.30, 73.24, 56.20, 51.43, 33.42, 29.54, 28.08, 19.93, 19.81, 18.40, 18.12 |
| F15 | Colorless Oil | — | 3377, 2924, 2854, 1745, 1676, 1502 | HRMS-ESI (m/z) [M + H]⁺ calcd for $C_{27}H_{39}N_2O_9$, 535.2650; found, 535.2644 | ¹H NMR (CDCl₃) δ 8.32 (d, J = 8.1 Hz, 1H), 8.28 (dd, J = 5.3, 1.8 Hz, 1H), 6.95 (d, J = 5.3 Hz, 1H), 5.74 (d, J = 1.7 Hz, 2H), 4.97 (s, 2H), 4.87 (d, J = 2.6 Hz, 2H), 4.85-4.79 (m, 1H), 4.61 (dt, J = 10.1, 7.6 Hz, 1H), 4.28 (d, J = 11.7 Hz, 1H), 4.05 (d, J = 11.7 Hz, 1H), 3.95 (d, J = 12.1 Hz, 1H), 3.91 (s, 3H), 3.85 (d, J = 11.6 Hz, 1H), 3.51-3.45 (m, 2H), 2.38 (dt, J = 13.6, 6.8 Hz, 1H), | ¹³CNMR (CDCl₃) δ 172.59, 170.26, 162.96, 160.25, 145.72, 143.95, 142.46, 142.40, 142.38, 112.08, 111.94, 109.61, 89.50, 83.69, 83.56, 73.07, 72.88, 56.18, 51.62, 33.35, 29.41, 28.01, 20.86, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 2.21-2.08 (m, 1H), 2.07 (s, 3H), 1.75 (s, 6H), 1.74-1.61 (m, 1H), 1.56 (d, J = 3.6 Hz, 1H), 1.42 (d, J = 6.5 Hz, 3H), 1.40-1.29 (m, 1H), 1.03-0.79 (m, 1H) | 19.79, 19.68, 18.33, 17.97 |
| F16 | Colorless Oil | — | 3377, 2974, 2934, 1744, 1677, 1503, 1455 | HRMS-ESI (m/z) [M + H]$^+$ calcd for C$_{27}$H$_{39}$N$_2$O$_9$, 563.2963; found, 563.2974 | $^1$H NMR (CDCl$_3$) δ 8.37 (d, J = 8.0 Hz, 1H), 8.27 (d, J = 5.1 Hz, 1H), 6.94 (d, J = 5.3 Hz, 1H), 5.79-5.74 (m, 2H), 4.97 (s, 2H), 4.89-4.81 (m, 1H), 4.87-4.79 (s, 2H), 4.61 (q, J = 8.0 Hz, 1H), 4.27 (d, J = 11.6 Hz, 1H), 4.04 (d, J = 11.7 Hz, 1H), 3.96 (d, J = 12.0 Hz, 1H), 3.89 (s, 3H), 3.85 (d, J = 11.7 Hz, 1H), 3.55-3.41 (m, 2H), 2.55 (p, J = 7.0 Hz, 1H), 2.38 (dt, J = 13.5, 6.7 Hz, 1H), 2.21-2.06 (m, 1H), 1.75 (s, 6H), 1.73-1.59 (m, 1H), 1.56 (m, 1H), 1.41 (d, J = 6.3 Hz, 3H), 1.41-1.27 (m, 1H), 1.14 (d, J = 7.0 Hz, 6H), 0.96 (dd, J = 15.0, 7.1 Hz, 1H) | $^{13}$CNMR (CDCl$_3$) δ 176.24, 172.60, 162.94, 160.23, 145.59, 144.19, 142.47, 142.42, 142.06, 112.08, 111.95, 109.54, 89.89, 83.71, 83.58, 73.08, 72.88, 56.13, 51.62, 33.85, 33.38, 29.69, 29.41, 28.02, 19.80, 19.69, 18.67, 18.34, 17.98 |
| F17 | Colorless Oil | — | 3378, 2954, 2873, 1772, 1744, 1679, 1508 | HRMS-ESI (m/z) [M + H]$^+$ calcd for C$_{26}$H$_{39}$N$_2$O$_8$, 507.2705; found, 507.2701 | $^1$HNMR (CDCl$_3$) δ 8.59-8.46 (m, 1H), 8.33 (d, J = 5.4 Hz, 1H), 7.00 (d, J = 5.5 Hz, 1H), 4.97 (s, 1H), 4.87 (s, 1H), 4.80 (dq, J = 9.2, 6.4 Hz, 1H), 4.59 (ddd, J = 10.8, 8.4, 7.2 Hz, 1H), 3.95 (d, J = 12.0 Hz, 1H), 3.90 (s, 3H), 3.84 (d, J = 12.0 Hz, 1H), 3.63 (dd, J = 8.6, 6.1 Hz, 1H), 3.47-3.32 (m, 3H), 2.40 (s, 3H), 2.39-2.30 (m, 1H), 2.11 (dddd, J = 15.7, 10.2, 8.1, 5.1 Hz, 1H), 1.83 (dt, J = 13.3, 6.6 Hz, 1H), 1.76 (t, J = 1.1 Hz, 3H), 1.73-1.59 (m, 2H), 1.39 (d, J = 6.3 Hz, 3H), 1.36-1.26 (m, 1H), 0.95 (dt, J = 7.4, 2.1 Hz, 1H), 0.91 (d, J = 6.7 Hz, 3H), 0.89 (d, J = 6.8 Hz, 3H) | $^{13}$CNMR (CDCl$_3$) δ 172.52, 168.91, 162.38, 159.43, 146.69, 142.52, 141.42, 137.48, 112.13, 109.78, 83.82, 83.68, 80.67, 73.25, 73.12, 56.29, 51.35, 33.63, 29.12, 28.05, 20.76, 19.72, 19.54, 19.38, 18.30, 17.93 |
| F18 | White Solid | 73-77 | 2935, 1744, 1679, 1508 | HRMS-ESI (m/z) [M + H]$^+$ calcd for C$_{28}$H$_{43}$N$_2$O$_9$, 551.2963; found, 551.2968 | $^1$H NMR (CDCl$_3$) δ 8.53-8.46 (m, 1H), 8.32 (d, J = 5.4 Hz, 1H), 6.99 (d, J = 5.5 Hz, 1H), 4.77 (dq, J = 9.6, 6.4 Hz, 1H), 4.58 (ddd, J = 10.7, 8.4, 7.3 Hz, 1H), 4.01 (ddd, J = 8.0, 5.5, 3.4 Hz, 1H), 3.89 (s, 3H), 3.81 (t, J = 6.6 Hz, | $^{13}$C NMR (CDCl$_3$) δ 172.56, 169.39, 162.31, 159.41, 146.73, 141.44, 137.31, 109.77, 83.74, 81.75, 79.15, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 2H), 3.77 (dt, J = 8.8, 6.6 Hz, 1H), 3.54 (dt, J = 8.7, 6.8 Hz, 1H), 3.44-3.38 (m, 1H), 3.40 (s, 3H), 3.30 (dd, J = 9.6, 7.3 Hz, 1H), 2.98 (t, J = 6.6 Hz, 2H), 2.40-2.28 (m, 1H), 2.14-1.99 (m, 1H), 1.78-1.46 (m, 12H), 1.38 (d, J = 6.3 Hz, 3H), 1.35-1.26 (m, 1H), 0.92 (t, J = 7.4 Hz, 3H), 0.90-0.83 (m, 1H) | 75.80, 73.15, 67.56, 58.77, 56.30, 51.31, 34.61, 33.68, 33.51, 31.88, 28.42, 23.64, 23.52, 23.33, 18.49, 17.81, 10.65 |
| F19 | Off-White Foam | — | — | HRMS-ESI (m/z) [M + H]⁺ calcd for $C_{28}H_{30}N_2O_7$, 506.2053; found, 506.2053 | ¹H NMR (CDCl₃) δ 12.04 (s, 1H), 8.48 (d, J = 8.1 Hz, 1H), 7.99 (d, J = 5.2 Hz, 1H), 7.30-7.13 (m, 4H), 7.11-7.01 (m, 2H), 7.01-6.88 (m, 2H), 6.88-6.79 (m, 3H), 5.15 (dq, J = 9.5, 6.4 Hz, 1H), 4.76-4.60 (m, 2H), 4.60-4.45 (m, 1H), 3.93 (s, 3H), 2.41 (dt, J = 13.7, 7.0 Hz, 1H), 2.36-2.18 (m, 1H), 1.99-1.84 (m, 1H), 1.77 (dt, J = 16.0, 7.8 Hz, 1H), 1.46-1.34 (m, 4H), 1.18 (dd, J = 16.1, 7.8 Hz, 1H) | ¹³C NMR (CDCl₃) δ 171.93, 168.73, 159.50, 157.55, 155.38, 148.76, 140.57, 130.32, 129.46, 129.45, 121.68, 121.59, 116.90, 116.54, 109.54, 82.38, 82.30, 72.71, 56.09, 51.26, 33.22, 28.18, 18.29, 18.20 |
| F20 | White Solid | — | — | HRMS-ESI (m/z) [M + H]⁺ calcd for $C_{31}H_{35}N_2O_9$, 579.2337; found, 578.2234 | ¹H NMR (CDCl₃) δ 8.33 (d, J = 8.0 Hz, 1H), 8.28 (d, J = 5.4 Hz, 1H), 7.26-7.16 (m, 5H), 7.10-7.02 (m, 2H), 6.99-6.88 (m, 3H), 6.88-6.81 (m, 2H), 5.74 (s, 2H), 5.13 (dq, J = 9.5, 6.4 Hz, 1H), 4.75-4.62 (m, 2H), 4.57-4.49 (m, 1H), 3.91 (s, 3H), 2.42 (dt, J = 13.6, 7.1 Hz, 1H), 2.36-2.21 (m, 1H), 2.07 (s, 3H), 1.98-1.87 (m, 1H), 1.74 (dq, J = 15.5, 7.8 Hz, 1H), 1.63 (s, 1H), 1.42 (d, J = 6.4 Hz, 3H), 1.40-1.28 (m, 1H), 1.19 (dd, J = 16.1, 7.7 Hz, 1H) | ¹³C NMR (CDCl₃) δ 172.54, 170.30, 163.02, 160.29, 159.53, 157.59, 145.74, 144.06, 142.29, 129.42, 121.62, 121.52, 116.91, 116.54, 109.66, 89.53, 82.44, 82.38, 72.44, 56.20, 51.61, 33.29, 28.27, 20.89, 18.37, 18.19 |
| F21 | Hard White Foam | 94-95 | — | HRMS-ESI (m/z) [M + Na]⁺ calcd for $C_{24}H_{38}N_2O_7Na$, 489.2571; found, 489.2567 | ¹H NMR (CDCl₃) δ 12.09 (d, J = 0.4 Hz, 1H), 8.47 (d, J = 8.2 Hz, 1H), 7.99 (d, J = 5.2 Hz, 1H), 6.86 (d, J = 5.2 Hz, 1H), 4.81 (pd, J = 6.3, 2.0 Hz, 1H), 4.58 (dt, J = 10.8, 7.6 Hz, 1H), 3.94 (s, 3H), 3.62 (dd, J = 8.6, 6.2 Hz, 1H), 3.42-3.31 (m, 3H), 3.28 (dd, J = 8.7, 6.5 Hz, 1H), 3.12 (dd, J = 8.7, 6.3 Hz, 1H), 2.37 (dt, J = 13.8, 6.5 Hz, 1H), | ¹³C NMR (CDCl₃) δ 172.05, 168.65, 155.34, 148.72, 140.51, 130.42, 109.46, 84.19, 83.70, 80.50, 75.84, 73.34, 56.07, 51.31, 33.34, 29.09, 28.90, 27.63, 19.57, 19.54, 19.39, 18.24, 18.00 |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 2.24-2.06 (m, 1H), 1.82 (dpd, J = 13.2, 6.6, 3.5 Hz, 2H), 1.75-1.58 (m, 2H), 1.45-1.30 (m, 4H), 0.96-0.86 (m, 13H) | |
| F22 | Hard White Foam | 47-52 | 3348, 3029, 2941, 2875, 1743, 1649, 1576, 1528, 1497, 1481, 1450, 1327, 1242, 1216, 1059, 800 | HRMS-ESI (m/z) [M + H]$^+$ calcd for C$_{30}$H$_{35}$N$_2$O$_7$, 535.2439; found, 535.2433 | $^1$H NMR (CDCl$_3$) δ 12.09 (d, J = 3.1 Hz, 1H), 8.49 (d, J = 8.0 Hz, 1H), 7.97 (d, J = 5.2 Hz, 1H), 7.42-7.19 (m, 10H), 6.84 (dd, J = 5.1, 1.5 Hz, 1H), 4.96-4.80 (m, 2H), 4.69 (d, J = 10.9 Hz, 1H), 4.66-4.53 (m, 2H), 4.53-4.44 (m, 1H), 3.91 (d, J = 2.3 Hz, 3H), 3.66 (d, J = 7.6 Hz, 2H), 2.38 (dt, J = 13.6, 6.7 Hz, 1H), 2.30-2.11 (m, 1H), 1.88-1.61 (m, 2H), 1.49-1.32 (m, 4H), 1.01 (dd, J = 16.1, 7.3 Hz, 1H) | $^{13}$C NMR (CDCl$_3$) δ 172.03, 168.72, 155.35, 148.74, 140.57, 138.41, 138.33, 130.37, 128.43, 128.40, 127.96, 127.83, 127.75, 127.69, 109.54, 83.89, 83.64, 75.75, 73.13, 71.22, 56.09, 51.33, 33.27, 27.96, 18.35, 18.13 |
| F23 | Hard White Foam | 58-64 | 3364, 2940, 1744, 1649, 1527, 1481, 1327, 1240, 1207, 1059, 1030, 752, 549 | HRMS-ESI (m/z) [M + H]$^+$ calcd for C$_{29}$H$_{33}$N$_2$O$_7$, 521.2282; found, 521.2274 | $^1$H NMR (CDCl$_3$) δ 12.06 (s, 1H), 8.58-8.37 (m, 1H), 7.98 (d, J = 5.2 Hz, 1H), 7.31-7.19 (m, 5H), 7.14-7.05 (m, 4H), 7.04-6.94 (m, 1H), 6.85 (d, J = 5.2 Hz, 1H), 5.04 (dq, J = 9.6, 6.4 Hz, 1H), 4.62 (dt, J = 10.8, 7.6 Hz, 1H), 4.57-4.47 (m, 2H), 4.42 (d, J = 11.5 Hz, 1H), 3.92 (s, 3H), 3.79-3.69 (m, 1H), 2.41 (dt, J = 13.8, 6.6 Hz, 1H), 2.31-2.13 (m, 1H), 1.98-1.63 (m, 2H), 1.51-1.30 (m, 4H), 1.09 (dd, J = 16.2, 7.3 Hz, 1H) | $^{13}$C NMR (CDCl$_3$) δ 171.98, 168.71, 159.50, 155.37, 148.75, 140.57, 138.13, 130.34, 129.51, 128.21, 127.82, 127.56, 121.45, 116.34, 109.54, 82.57, 82.49, 72.84, 71.68, 56.09, 51.32, 33.31, 28.16, 18.41, 18.11 |
| F24 | Hard White Foam | 56-62 | 3367, 3030, 2240, 1743, 1649, 1596, 1327, 1240, 1211, 1061, 728, 695 | HRMS-ESI (m/z) [M + H]$^+$ calcd for C$_{29}$H$_{33}$N$_2$O$_7$, 521.2282; found, 521.2282 | $^1$H NMR (CDCl$_3$) δ 12.06 (s, 1H), 8.47 (d, J = 8.1 Hz, 1H), 8.08-7.89 (m, 1H), 7.38-7.16 (m, 7H), 7.03-6.91 (m, 3H), 6.85 (d, J = 5.2 Hz, 1H), 4.97 (dq, J = 9.6, 6.4 Hz, 1H), 4.84 (d, J = 10.8 Hz, 1H), 4.75-4.57 (m, 2H), 4.50 (t J = 5.4 Hz, 1H), 3.93 (s, 3H), 3.85 (dd, J = 9.6, 7.2 Hz, 1H), 2.37 (dt, J = 13.6, 7.0 Hz, 1H), 2.29-2.12 (m, 1H), 1.94-1.78 (m, 1H), 1.68 (h, J = 8.0 Hz, 1H), 1.48 (d, J = 6.4 Hz, 3H), 1.44-1.29 (m, 1H), 1.09 (dd, J = 16.1, 7.8 Hz, 1H) | $^{13}$C NMR (CDCl$_3$) δ 171.95, 168.71, 157.40, 155.37, 148.75, 140.56, 137.91, 130.34, 129.63, 128.36, 128.23, 127.82, 121.48, 116.70, 109.52, 83.13, 82.91, 75.62, 72.85, 56.09, 51.25, 33.19, 28.29, 18.23, 18.15 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| F25 | Off-White Foam | — | — | HRMS-ESI (m/z) [M + H]⁺ calcd for $C_{26}H_{35}N_2O_7$, 487.2437; found, 487.2439 | ¹H NMR (CDCl₃) δ 12.06 (s, 1H), 8.48 (d, J = 8.1 Hz, 1H), 7.99 (d, J = 5.2 Hz, 1H), 7.31-7.23 (m, 2H), 7.08 (d, J = 7.8 Hz, 2H), 6.95 (t, J = 7.3 Hz, 1H), 6.87 (d, J = 5.2 Hz, 1H), 5.03 (dq, J = 9.6, 6.4 Hz, 1H), 4.62 (dt, J = 10.8, 7.7 Hz, 1H), 4.44 (dd, J = 9.6, 7.3 Hz, 1H), 3.94 (s, 3H), 3.55 (t, J = 5.5 Hz, 1H), 3.24 (dd, J = 8.7, 6.6 Hz, 1H), 3.06 (dd, J = 8.7, 6.2 Hz, 1H), 2.41 (dt, J = 13.8, 6.6 Hz, 1H), 2.31-2.13 (m, 1H), 1.88-1.60 (m, 3H), 1.51-1.38 (m, 1H), 1.36 (d, J = 6.4 Hz, 3H), 1.04 (dd, J = 16.1, 7.3 Hz, 1H), 0.79 (d, J = 6.7 Hz, 3H), 0.74 (d, J = 6.7 Hz, 3H) | ¹³C NMR (CDCl₃) δ 172.00, 168.68, 159.66, 155.37, 148.74, 140.54, 130.37, 129.33, 121.31, 116.41, 109.50, 83.06, 82.76, 76.41, 72.88, 56.08, 51.31, 33.37, 28.71, 27.88, 19.36, 19.21, 18.29, 18.11 |
| F26 | — | — | — | HRMS-ESI (m/z) [M + Na]⁺ calcd for $C_{29}H_{38}N_2NaO_9$, 581.2470; found, 581.2457 | ¹H NMR (CDCl₃) δ 8.33 (d, J = 8.0 Hz, 1H), 8.28 (d, J = 5.4 Hz, 1H), 7.32-7.22 (m, 2H), 7.13-7.02 (m, 2H), 6.99-6.91 (m, 2H), 5.74 (s, 2H), 5.01 (dq, J = 9.6, 6.4 Hz, 1H), 4.64 (dt, J = 10.8, 7.6 Hz, 1H), 4.43 (dd, J = 9.6, 7.3 Hz, 1H), 3.91 (s, 3H), 3.54 (t, J = 5.5 Hz, 1H), 3.24 (dd, J = 8.8, 6.6 Hz, 1H), 3.06 (dd, J = 8.8, 6.2 Hz, 1H), 2.42 (dt, J = 13.7, 6.7 Hz, 1H) 2.28-2.12 (m, 1H) 2.07 (s, 3H), 1.85-1.56 (m, 3H), 1.45-1.29 (m, 4H), 1.04 (dd, J = 16.1, 7.5 Hz, 1H), 0.79 (d, J = 6.7 Hz, 3H), 0.73 (d, J = 6.7 Hz, 3H) | ¹³C NMR (CDCl₃) δ 172.62, 170.29, 162.98, 160.28, 159.70, 145.73, 144.03, 142.38, 129.31, 121.25, 116.42, 109.62 89.54, 83.14, 82.82, 76.39, 72.61, 56.19, 51.65, 33.45, 28.70, 27.95, 20.88, 19.36, 19.21, 18.36, 18.10 |
| F27 | White Foam | — | — | HRMS-ESI (m/z) [M + H]⁺ calcd for $C_{26}H_{35}N_2O_7$, 487.2439; found, 487.2438 | ¹H NMR (CDCl₃) δ 12.06 (d, J = 0.5 Hz, 1H), 8.47 (d, J = 8.1 Hz, 1H), 7.98 (d, J = 5.2 Hz, 1H), 7.33-7.20 (m, 2H), 7.01-6.89 (m, 3H), 6.86 (d, J = 5.2 Hz, 1H), 4.93 (dq, J = 9.7, 6.4 Hz, 1H), 4.63 (dt, J = 10.8, 7.6 Hz, 1H), 4.39 (t, J = 5.4 Hz, 1H), 3.94 (s, 3H), 3.64 (dd, J = 9.6, 7.2 Hz, 1H), 3.57 (dd, J = 8.6, 6.2 Hz, 1H), 3.40 (dd, J = 8.6, 6.6 Hz, 1H), 2.36 (dt, J = 13.6, 7.0 Hz, 1H), 2.17 (tdd, J = 13.4, | ¹³C NMR (CDCl₃) δ 171.96, 168.68, 157.54, 155.35, 148.72, 140.53, 130.35, 129.49, 121.28, 116.66, 109.48, 83.35, 83.07, 80.68, 73.10, 56.07, 51.24, 33.20, 28.99, 28.17, 19.38, 19.28, 18.19, 18.01 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 6.4, 4.0 Hz, 1H), 1.89-1.55 (m, 3H), 1.47 (d, J = 6.4 Hz, 3H), 1.35 (q, J = 11.8, 11.4 Hz, 1H), 1.05 (dd, J = 16.1, 7.8 Hz, 1H), 0.83 (d, J = 6.7 Hz, 3H), 0.79 (d, J = 6.7 Hz, 3H) | |
| F28 | White Powder | 135-137 | — | HRMS-ESI (m/z) [M + H]⁺ calcd for $C_{29}H_{39}N_2O_9$, 559.2650; found, 559.2652 | ¹H NMR (CDCl₃) δ 8.31 (d, J = 8.0 Hz, 1H), 8.27 (d, J = 5.4 Hz, 1H), 7.30-7.24 (m, 2H), 6.98-6.89 (m, 4H), 5.74 (s, 2H), 4.91 (dq, J = 9.7, 6.4 Hz, 1H), 4.65 (dt, J = 10.7, 7.6 Hz, 1H), 4.38 (t, J = 5.5 Hz, 1H), 3.90 (s, 3H), 3.63 (dd, J = 9.6, 7.2 Hz, 1H), 3.57 (dd, J = 8.6, 6.3 Hz, 1H), 3.40 (dd, J = 8.6, 6.7 Hz, 1H), 2.37 (dt, J = 13.6, 7.0 Hz, 1H), 2.24-2.09 (m, 1H), 2.07 (s, 3H), 1.87-1.56 (m, 3H), 1.46 (d, J = 6.4 Hz, 3H), 1.30 (dd, J = 23.8, 10.8 Hz, 1H), 1.04 (dd, J = 16.1, 7.8 Hz, 1H), 0.83 (d, J = 6.7 Hz, 3H), 0.79 (d, J = 6.7 Hz, 3H) | ¹³C NMR (CDCl₃) δ 172.58, 170.28, 162.99, 160.27, 157.60, 145.73, 144.00, 142.36, 129.47, 121.22, 116.68, 109.62, 89.53, 83.41, 83.16, 80.68, 72.83, 56.19, 51.58, 33.30, 29.00, 28.26, 20.88, 19.39, 19.29, 18.26, 18.00 |
| F29 | Sticky Yellow Solid | — | 3378, 2954, 2872, 1745, 1676, 1577, 1503, 1463, 1367, 1201, 1097, 1058, 1003, 967, 912, 728 | HRMS-ESI (m/z) [M + H]⁺ calcd for $C_{27}H_{43}N_2O_9$, 539.2963; found, 539.2957 | ¹H NMR (CDCl₃) δ 8.32 (d, J = 8.0 Hz, 1H), 8.27 (dd, J = 5.3, 2.9 Hz, 1H), 6.95 (d, J = 5.4 Hz, 1H), 5.74 (d, J = 2.6 Hz, 2H), 4.80 (t, J = 6.5 Hz, 1H), 4.60 (dt, J = 10.4, 7.8 Hz, 1H), 3.91 (s, 3H), 3.62 (dd, J = 8.6, 6.2 Hz, 1H), 3.42-3.31 (m, 3H), 3.28 (dd, J = 8.6, 6.5 Hz, 1H), 3.12 (dd, J = 8.6, 6.3 Hz, 1H), 2.37 (dt, J = 13.6, 6.7 Hz, 1H), 2.21-2.09 (m, 1H), 2.07 (s, 3H), 1.82 (dtd, J = 13.0, 6.6, 3.6 Hz, 2H), 1.75-1.55 (m, 2H), 1.39 (d, J = 6.4 Hz, 3H), 1.35-1.21 (m, 1H), 0.97-0.85 (m, 13H) | ¹³C NMR (CDCl₃) δ 172.64, 170.25, 162.95, 160.24, 145.72, 143.94, 142.40, 109.60, 89.50, 84.24, 83.71, 80.46, 75.78, 73.03, 56.17, 51.62, 33.38, 29.06, 28.87, 27.67, 20.85, 19.55, 19.52, 19.37, 18.28, 17.97 |
| F30 | Fluffy Light Yellow Solid | 42-52 | 3376, 3030, 2939, 2875, 1745, 1675, 1577, 1497, 1453, 1369, 1313, 1200, 1095, 1058, 1002, | HRMS-ESI (m/z) [M + H]⁺ calcd for $C_{33}H_{39}N_2O_9$, 607.2650; found, 607.2648 | ¹H NMR (CDCl₃) δ 8.32 (d, J = 8.0 Hz, 1H), 8.27 (d, J = 5.4 Hz, 1H), 7.40-7.23 (m, 10H), 6.94 (d, J = 5.4 Hz, 1H), 5.74 (s, 2H), 4.94-4.80 (m, 2H), 4.69 (d, J = 10.9 Hz, 1H), 4.67-4.57 (m, 2H), 4.49 (d, J = 11.4 Hz, 1H), 3.89 (s, 3H), 3.70-3.60 (m, 2H), 2.40 (dt, J = 13.5, 6.8 Hz, 1H), 2.20 (dddd, J = 15.2, | ¹³C NMR (CDCl₃) δ 172.62, 170.29, 163.01, 160.28, 145.77, 143.99, 142.40, 138.44, 138.37, 128.41, 128.38, 127.95, 127.82, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | 965, 828, 736, 697 | | 12.4, 9.5, 4.4 Hz, 1H), 2.07 (s, 3H), 1.86-1.62 (m, 2H), 1.43 (d, J = 6.4 Hz, 3H), 1.40-1.29 (m, 1H), 1.08-0.95 (m, 1H) | 127.71, 127.65, 109.66, 89.53, 83.96, 83.72, 75.75, 72.86, 71.20, 56.21, 51.66, 33.37, 28.03, 20.90, 18.41, 18.10 |
| F31 | Fluffy White Solid | 49-55 | 3380, 2941, 2877, 1748, 1676, 1585, 1492, 1368, 1200, 1130, 1030, 1002, 966, 829, 752, 694 | HRMS-ESI (m/z) [M + H]⁺ calcd for $C_{32}H_{37}N_2O_9$, 593.2494; found, 593.2499 | ¹H NMR (CDCl₃) δ 8.33 (d, J = 8.0 Hz, 1H), 8.27 (d, J = 5.4 Hz, 1H), 7.33-7.18 (m, 5H), 7.14-7.05 (m, 4H), 7.05-6.85 (m, 2H), 5.74 (s, 2H), 5.02 (dq, J = 9.6, 6.4 Hz, 1H), 4.64 (dt, J = 10.8, 7.5 Hz, 1H), 4.58-4.47 (m, 2H), 4.47-4.36 (m, 1H), 3.90 (s, 3H), 3.78-3.66 (m, 1H), 2.42 (dt, J = 13.7, 6.7 Hz, 1H), 2.29-2.13 (m, 1H), 2.07 (s, 3H), 1.89-1.64 (m, 2H), 1.44-1.30 (m, 4H), 1.08 (dd, J = 16.1, 7.5 Hz, 1H) | ¹³C NMR (CDCl₃) δ 172.59, 170.30, 163.01, 160.29, 159.53, 145.75, 144.03, 142.34, 138.17, 129.49, 128.19, 127.81, 127.52, 121.39, 116.34, 109.66, 89.53, 82.62, 82.56, 72.57, 71.65, 56.21, 51.66, 33.39, 28.22, 20.89, 18.47, 18.09 |
| F32 | Fluffy White Solid | — | 3379, 2941, 1747, 1676, 1584, 1493, 1454, 1200, 1061, 1002, 966, 829, 753, 695 | HRMS-ESI (m/z) [M + H]⁺ calcd for $C_{32}H_{37}N_2O_9$, 593.2494; found, 593.2498 | ¹H NMR (CDCl₃) δ 8.31 (d, J = 8.0 Hz, 1H), 8.27 (d, J = 5.4 Hz, 1H), 7.37-7.17 (m, 7H), 7.02-6.88 (m, 4H), 5.74 (s, 2H), 4.95 (dq, J = 9.6, 6.3 Hz, 1H), 4.85 (d, J = 10.7 Hz, 1H), 4.74-4.61 (m, 2H), 4.49 (t, J = 5.5 Hz, 1H), 3.90 (s, 3H), 3.85 (dd, J = 9.6, 7.2 Hz, 1H), 2.38 (dt, J = 13.6, 7.0 Hz, 1H), 2.26-2.11 (m, 1H), 2.07 (s, 3H), 1.91-1.77 (m, 1H), 1.66 (dd, J = 16.1, 7.8 Hz, 1H), 1.47 (d, J = 6.4 Hz, 3H), 1.37-1.23 (m, 1H), 1.08 (dd, J = 16.1, 7.8 Hz, 1H) | ¹³C NMR (CDCl₃) δ 172.55, 170.29, 163.01, 160.27, 157.45, 145.75, 144.01, 142.34, 137.96, 129.60, 128.34, 128.22, 127.79, 121.41, 116.71, 109.65, 89.52, 83.22, 83.00, 75.63, 72.58, 56.20, 51.59, 33.27, 28.37, 20.89, 18.30, 18.14 |
| F33 | White Solid | — | — | HRMS-ESI (m/z) [M + Na]⁺ calcd for $C_{25}H_{38}N_2NaO_7$, 501.2571; found, 501.2586 | ¹H NMR (CDCl₃) δ 12.16-12.07 (m, 1H), 8.48 (d, J = 8.1 Hz, 1H), 7.98 (d, J = 5.2 Hz, 1H), 6.86 (d, J = 5.2 Hz, 1H), 4.76 (dq, J = 9.7, 6.4 Hz, 1H), 4.58 (dt, J = 10.8, 7.7 Hz, 1H), 4.31 (d, J = 3.3 Hz, 1H), 3.94 (s, 3H), 3.54-3.42 (m, 1H), 3.32 (t, J = 5.6 Hz, 1H), 3.24 (dd, J = 8.6, 7.0 Hz, 1H), 3.15 (dd, J = 8.6, 6.0 Hz, 1H), 2.36 (dt, J = 13.7, 6.6 Hz, 1H), | ¹³C NMR (CDCl₃) δ 172.10, 168.64, 155.33, 148.70, 140.50, 130.41, 109.45, 84.23, 83.14, 81.18, 75.92, 73.51, 56.06, 51.33, 33.31, 32.94, 32.31, 28.90, 27.59, 23.26, 23.19, 19.63, 19.48, 18.27, 18.13 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 2.25-2.08 (m, 1H), 1.90-1.50 (m, 11H), 1.44-1.30 (m, 4H), 0.92 (dd, J = 6.7, 4.8 Hz, 7H) | |
| F34 | Clear Tacky Solid | — | — | HRMS-ESI (m/z) [M + H]⁺ calcd for C₃₁H₄₃N₂O₉, 587.2963; found, 587.3065 | ¹H NMR (CDCl₃) δ 8.39 (d, J = 8.0 Hz, 1H), 8.27 (d, J = 5.4 Hz, 1H), 7.34-7.22 (m, 2H), 7.08 (d, J = 8.0 Hz, 2H), 6.95 (t, J = 6.5 Hz, 2H), 5.84-5.71 (m, 2H), 5.01 (dq, J = 9.6, 6.4 Hz, 1H), 4.64 (dt, J = 10.7, 7.6 Hz, 1H), 4.43 (dd, J = 9.6, 7.3 Hz, 1H), 3.89 (s, 3H), 3.54 (t, J = 5.6 Hz, 1H), 3.24 (dd, J = 8.7, 6.6 Hz, 1H), 3.06 (dd, J = 8.7, 6.3 Hz, 1H), 2.55 (p, J = 7.0 Hz, 1H), 2.42 (dt, J = 13.6, 6.7 Hz, 1H), 2.20 (dp, J = 15.7, 5.1 Hz, 1H), 1.86-1.61 (m, 3H), 1.45-1.31 (m, 4H), 1.14 (d, J = 7.0 Hz, 6H), 1.04 (dd, J = 16.1, 7.5 Hz, 1H), 0.79 (d, J = 6.7 Hz, 3H), 0.73 (d, J = 6.7 Hz, 3H) | ¹³C NMR (CDCl₃) δ 176.25, 172.60, 162.96, 160.25, 159.70, 145.59, 144.23, 142.03, 129.31, 121.25, 116.42, 109.57, 89.88, 83.14, 82.82, 76.38, 72.59, 56.14, 51.65, 33.85, 33.44, 28.70, 27.94, 19.36, 19.21, 18.68, 18.36, 18.09 |
| F35 | Clear Tacky Solid | — | — | HRMS-ESI (m/z) [M + H]⁺ calcd for C₃₁H₄₃N₂O₉, 587.2963; found, 587.2952 | ¹H NMR (CDCl₃) δ 8.37 (d, J = 8.1 Hz, 1H), 8.26 (d, J = 5.4 Hz, 1H), 7.35-7.22 (m, 2H), 7.01-6.87 (m, 4H), 5.83-5.67 (m, 2H), 4.91 (dq, J = 9.7, 6.4 Hz, 1H), 4.65 (dt, J = 10.7, 7.6 Hz, 1H), 4.38 (t, J = 5.4 Hz, 1H), 3.88 (s, 3H), 3.63 (dd, J = 9.6, 7.2 Hz, 1H), 3.57 (dd, J = 8.7, 6.3 Hz, 1H), 3.40 (dd, J = 8.7, 6.7 Hz, 1H), 2.55 (p, J = 7.0 Hz, 1H), 2.36 (dt, J = 13.6, 7.0 Hz, 1H), 2.23-2.08 (m, 1H), 1.90-1.56 (m, 3H), 1.46 (d, J = 6.4 Hz, 3H), 1.36-1.27 (m, 1H), 1.14 (d, J = 7.0 Hz, 6H), 1.05 (dd, J = 16.1, 7.9 Hz, 1H), 0.83 (d, J = 6.7 Hz, 3H), 0.79 (d, J = 6.7 Hz, 3H) | ¹³C NMR (CDCl₃) δ 176.25, 172.57, 162.97, 160.25, 157.60, 145.59, 144.22, 142.02, 129.47, 121.22, 116.67, 109.55, 89.90, 83.41, 83.16, 80.68, 72.81, 56.13, 51.57, 33.86, 33.31, 28.99, 28.25, 19.39, 19.29, 18.68, 18.27, 18.00 |
| F36 | Clear Tacky Solid | — | — | HRMS-ESI (m/z) [M + Na]⁺ calcd for C₃₃H₃₈N₂NaO₉, 629.2470; found, 629.2460 | ¹H NMR (CDCl₃) δ 8.39 (d, J = 8.0 Hz, 1H), 8.27 (d, J = 5.4 Hz, 1H), 7.29-7.15 (m, 4H), 7.10-7.03 (m, 2H), 6.98-6.88 (m, 3H), 6.88-6.82 (m, 2H), 5.81-5.74 (m, 2H), 5.13 (dq, J = 9.6, 6.4 Hz, 1H), | ¹³C NMR (CDCl₃) δ 176.26, 172.53, 162.99, 160.26, 159.53, 157.59, 145.60, 144.26, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 4.67 (ddd, J = 9.6, 7.6, 3.1 Hz, 2H), 4.56-4.51 (m, 1H), 3.88 (s, 3H), 2.55 (p, J = 7.0 Hz, 1H), 2.42 (dt, J = 13.6, 7.1 Hz, 1H), 2.35-2.21 (m, 1H), 1.98-1.85 (m, 1H), 1.74 (dt, J = 24.4, 8.1 Hz, 1H), 1.42 (d, J = 6.4 Hz, 3H), 1.36 (d, J = 13.1 Hz, 1H), 1.22-1.17 (m, 1H), 1.14 (d, J = 7.0 Hz, 6H) | 141.95, 129.43, 129.41, 121.61, 121.52, 116.90, 116.54, 109.60, 89.87, 82.45, 82.38, 72.42, 56.15, 51.60, 33.86, 33.29, 28.26, 18.69, 18.37, 18.18 |
| F37 | Clear Tacky Solid | — | — | HRMS-ESI (m/z) [M + Na]$^+$ calcd for C$_{29}$H$_{46}$N$_2$NaO$_9$, 589.3096; found, 589.3090 | $^1$H NMR (CDCl$_3$) δ 8.37 (d, J = 8.1 Hz, 1H), 8.27 (d, J = 5.3 Hz, 1H), 6.94 (d, J = 5.4 Hz, 1H), 5.83-5.72 (m, 2H), 4.79 (dq, J = 12.6, 6.2 Hz, 1H), 4.60 (dt, J = 10.7, 7.6 Hz, 1H), 3.89 (s, 3H), 3.62 (dd, J = 8.6, 6.2 Hz, 1H), 3.41-3.31 (m, 3H), 3.28 (dd, J = 8.6, 6.5 Hz, 1H), 3.12 (dd, J = 8.6, 6.3 Hz, 1H), 2.55 (p, J = 7.0 Hz, 1H), 2.37 (dt, J = 13.5, 6.7 Hz, 1H), 2.12 (ddt, J = 10.7, 8.2, 5.6 Hz, 1H), 1.90-1.54 (m, 4H), 1.39 (d, J = 6.4 Hz, 3H), 1.38-1.27 (m, 1H), 1.14 (d, J = 7.0 Hz, 6H), 0.90 (t, J = 7.0 Hz, 13H) | $^{13}$C NMR (CDCl$_3$) δ 176.24, 172.65, 162.93, 160.24, 145.58, 144.19, 142.10, 109.52, 89.91, 84.26, 83.74, 80.49, 75.81, 73.04, 56.12, 51.63, 33.85, 33.43, 29.08, 28.88, 27.69, 19.57, 19.54, 19.53, 19.39, 18.67, 18.29, 17.98 |
| F38 | Clear Tacky Solid | — | — | HRMS-ESI (m/z) [M + Na]$^+$ calcd for C$_{30}$H$_{46}$N$_2$NaO$_9$, 601.3096; found, 601.3105 | $^1$NMR (CDCl$_3$) δ 8.37 (d, J = 8.1 Hz, 1H), 8.27 (d, J = 5.4 Hz, 1H), 6.94 (d, J = 5.4 Hz, 1H), 5.83-5.72 (m, 2H), 4.74 (dq, J = 9.6, 6.4 Hz, 1H), 4.60 (dt, J = 10.8, 7.6 Hz, 1H), 4.38-4.27 (m, 1H), 3.89 (s, 3H), 3.46 (dd, J = 9.6, 7.0 Hz, 1H), 3.31 (t, J = 5.5 Hz, 1H), 3.24 (dd, J = 8.6, 7.0 Hz, 1H), 3.14 (dd, J = 8.7, 6.0 Hz, 1H), 2.55 (hept, J = 7.0 Hz, 1H), 2.37 (dt, J = 13.6, 6.7 Hz, 1H), 2.17-2.06 (m, 1H), 1.90-1.47 (m, 11H), 1.38 (d, J = 6.4 Hz, 3H), 1.32 (d, J = 11.3 Hz, 1H), 1.14 (d, J = 7.0 Hz, 6H), 0.92 (d, J = 4.5 Hz, 3H), 0.91 (d, J = 4.6 Hz, 3H), 0.88 (d, J = 7.5 Hz, 1H) | $^{13}$C NMR (CDCl$_3$) δ 176.23, 172.71, 162.92, 160.23, 145.58, 144.18, 142.12, 109.51, 89.90, 84.31, 83.13, 81.25, 75.91, 73.22, 56.12, 51.65, 33.85, 33.42, 32.95, 32.31, 28.89, 27.68, 23.26, 23.18, 19.63, 19.49, 18.67, 18.34, 18.13 |
| F39 | Clear Tacky Solid | — | — | HRMS-ESI (m/z) [M + H]$^+$ calcd for C$_{28}$H$_{43}$N$_2$O$_9$, | $^1$H NMR (CDCl$_3$) δ 8.32 (d, J = 8.1 Hz, 1H), 8.27 (d, J = 5.4 Hz, 1H), 6.94 (d, J = 5.4 Hz, 1H), 5.74 (s, | $^{13}$C NMR (CDCl$_3$) δ 172.73, 170.27, 162.95, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | 551.2963; found, 551.2962 | 2H), 4.74 (dq, J = 9.6, 6.4 Hz, 1H), 4.60 (dt, J = 10.8, 7.5 Hz, 1H), 4.31 (p, J = 5.3, 4.6 Hz, 1H), 3.91 (s, 3H), 3.46 (dd, J = 9.6, 7.0 Hz, 1H), 3.31 (t, J = 5.5 Hz, 1H), 3.24 (dd, J = 8.6, 6.9 Hz, 1H), 3.14 (dd, J = 8.7, 6.0 Hz, 1H), 2.37 (dt, J = 13.6, 6.7 Hz, 1H), 2.07 (s, 4H), 1.89-1.46 (m, 11H), 1.38 (d, J = 6.4 Hz, 3H), 1.32 (d, J = 11.3 Hz, 1H), 0.92 (dd, J = 6.7, 4.6 Hz, 7H) | 160.26, 145.72, 143.97, 142.46, 109.57, 89.55, 84.31, 83.13, 81.25, 75.91, 73.24, 56.18, 51.66, 33.42, 32.95, 32.31, 28.89, 27.68, 23.26, 23.19, 20.87, 19.64, 19.49, 18.34, 18.13 |
| F40 | colorless semi solid | — | 3367, 2949, 2870, 1742, 1650, 1528 | HRMS-ESI (m/z) [M + Na]⁺ calcd for $C_{29}H_{40}N_2NaO_7$, 551.2728; found, 551.2734 | ¹H NMR (CDCl₃) δ 12.09 (s, 1H), 8.47 (d, J = 8.2 Hz, 1H), 7.99 (d, J = 5.2 Hz, 1H), 7.33-7.23 (m, 2H), 7.23-7.13 (m, 3H), 6.87 (d, J = 5.3 Hz, 1H), 4.86-4.77 (m, 1H), 4.58 (dt, J = 10.8, 7.6 Hz, 1H), 3.94 (s, 3H), 3.85 (dt, J = 9.1, 6.4 Hz, 1H), 3.64 (dt, J = 9.1, 6.5 Hz, 1H), 3.43-3.32 (m, 2H), 3.27 (dd, J = 8.7, 6.6 Hz, 1H), 3.10 (dd, J = 8.7, 6.2 Hz, 1H), 2.68 (td, J = 7.6, 3.9 Hz, 2H), 2.43-2.30 (m, 1H), 2.21-2.08 (m, 1H), 1.96-1.84 (m, 2H), 1.78 (dq, J = 13.1, 6.5 Hz, 1H), 1.72-1.62 (m, 2H), 1.43-1.33 (m, 4H), 0.95-0.90 (m, 1H), 0.89 (dd, J = 6.7, 3.0 Hz, 6H) | ¹³C NMR (CDCl₃) δ 172.04, 168.62, 155.38, 148.73, 142.02, 140.49, 130.36, 128.35, 128.32, 125.77, 109.45, 84.16, 83.85, 75.83, 73.19, 73.00, 56.08, 51.31, 33.31, 32.51, 32.00, 28.86, 27.62, 19.54, 19.48, 18.21, 18.02 |
| F41 | White Solid | 108-114 | 3370, 2955, 2874, 1744, 1651, 1530, 1263 | HRMS-ESI (m/z) [M + Na]⁺ calcd for $C_{24}H_{35}F_3N_2NaO_7$, 543.2289; found, 543.2291 | ¹H NMR (CDCl₃) δ 12.07 (s, 1H), 8.47 (d, J = 8.2 Hz, 1H), 7.99 (d, J = 5.2 Hz, 1H), 6.87 (d, J = 5.2 Hz, 1H), 4.80 (dq, J = 9.1, 6.3 Hz, 1H), 4.58 (dt, J = 10.7, 7.6 Hz, 1H), 3.94 (s, 3H), 3.86 (dt, J = 9.2, 6.1 Hz, 1H), 3.68 (dt, J = 9.2, 6.3 Hz, 1H), 3.43-3.31 (m, 2H), 3.28 (dd, J = 8.7, 6.7 Hz, 1H), 3.09 (dd, J = 8.6, 6.1 Hz, 1H), 2.44-2.29 (m, 1H), 2.26-2.09 (m, 3H), 1.86-1.75 (m, 3H), 1.71-1.58 (m, 3H), 1.39 (d, J = 6.4 Hz, 3H), 0.97-0.85 (m, 7H) | ¹³C NMR (CDCl₃) δ 171.99, 168.60, 155.45, 148.77, 140.45, δ 133.17-125.57 (m), 109.46, 83.99, 83.96, 75.65, 72.93, 71.69, 56.10, 51.31, 33.25, 30.90 (q, J = 28.9 Hz), 28.88, 27.39, 23.07 (q, J = 2.4 Hz), 19.54, 19.46, 18.16, 17.96 |
| F42 | White Solid | 167-169 | 3387, 2955, 2877, 1772, 1735, | HRMS-ESI (m/z) [M + H]⁺ calcd for $C_{26}H_{37}N_2O_9$, | ¹H NMR (CDCl₃) δ 8.50 (d, J = 8.3 Hz, 1H), 8.33 (d, J = 5.5 Hz, 1H), 7.00 (d, J = 5.4 Hz, 1H), 5.13 (dd, | ¹³C NMR (CDCl₃) δ 173.90, 172.61, 168.93, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | 1679, 1508, 1168 | 521.2494; found, 521.2505 | J = 9.8, 7.8 Hz, 1H), 4.95 (dq, J = 9.8, 6.4 Hz, 1H), 4.63 (dt, J = 10.6, 7.7 Hz, 1H), 3.91 (s, 3H), 3.37 (ddd, J = 7.6, 5.3, 1.9 Hz, 1H), 3.30 (dd, J = 8.8, 6.1 Hz, 1H), 2.98 (dd, J = 8.8, 6.8 Hz, 1H), 2.40 (s, 3H), 2.43-2.33 (m, 1H), 2.22-2.02 (m, 1H), 1.84-1.56 (m, 4H), 1.40-1.29 (m, 1H), 1.28 (d, J = 6.4 Hz, 3H), 1.07-0.95 (m, 3H), 0.91-0.81 (m, 8H) | 162.36, 159.45, 146.66, 141.39, 137.52, 109.80, 81.19, 76.33, 75.64, 71.49, 56.29, 51.33, 33.64, 28.63, 28.12, 20.76, 19.32, 19.26, 18.03, 17.20, 12.88, 8.45, 8.38 |
| F43 | Colorless Semi-Solid | — | 3389, 2950, 2870, 1750, 1678, 1503, 1202 | HRMS-ESI (m/z) [M + H]⁺ calcd for $C_{32}H_{45}N_2O_9$, 601.3120; found, 601.3136 | ¹H NMR (CDCl₃) δ 8.31 (d, J = 8.0 Hz, 1H), 8.28 (d, J = 5.3 Hz, 1H), 7.31-7.23 (m, 2H), 7.22-7.14 (m, 3H), 6.94 (d, J = 5.4 Hz, 1H), 5.74 (s, 2H), 4.84-4.75 (m, 1H), 4.60 (dt, J = 10.7, 7.6 Hz, 1H), 3.91 (s, 3H), 3.85 (dt, J = 9.1, 6.4 Hz, 1H), 3.64 (dt, J = 9.2, 6.5 Hz, 1H), 3.41-3.31 (m, 2H), 3.27 (dd, J = 8.8, 6.6 Hz, 1H), 3.09 (dd, J = 8.7, 6.3 Hz, 1H), 2.75-2.62 (m, 2H), 2.37 (dt, J = 13.5, 6.9 Hz, 1H), 2.17-2.07 (m, 1H), 2.07 (s, 3H), 1.94-1.83 (m, 2H), 1.78 (dt, J = 13.2, 6.7 Hz, 1H), 1.70-1.58 (m, 2H), 1.40 (d, J = 6.3 Hz, 3H), 1.32 (q, J = 11.0 Hz, 1H), 0.95-0.89 (m, 1H), 0.89 (dd, J = 6.7, 2.9 Hz, 6H) | ¹³C NMR (CDCl₃) δ 172.68, 170.31, 162.97, 160.27, 145.73, 144.00, 142.44, 142.06, 128.36, 128.33, 125.77, 109.58, 99.98, 89.57, 84.25, 83.91, 75.82, 73.01, 72.93, 56.18, 51.63, 33.43, 32.52, 32.02, 28.86, 27.70, 20.89, 19.54, 19.49, 18.28, 18.01 |
| F44 | Colorless Semi-Solid | — | 3382, 2954, 2875, 1750, 1678, 1504, 1203 | HRMS-ESI (m/z) [M + H]⁺ calcd for $C_{27}H_{40}F_3N_2O_9$, 593.2680; found, 593.2697 | ¹H NMR (CDCl₃) δ 8.31 (d, J = 8.1 Hz, 1H), 8.28 (d, J = 5.4 Hz, 1H), 6.95 (d, J = 5.4 Hz, 1H), 5.74 (s, 2H), 4.78 (dq, J = 9.3, 6.4 Hz, 1H), 4.60 (dt, J = 10.8, 7.6 Hz, 1H), 3.91 (s, 3H), 3.85 (dt, J = 9.3, 6.1 Hz, 1H), 3.67 (dt, J = 9.3, 6.1 Hz, 1H), 3.42-3.30 (m, 2H), 3.27 (dd, J = 8.7, 6.6 Hz, 1H), 3.09 (dd, J = 8.6, 6.1 Hz, 1H), 2.47-2.32 (m, 1H), 2.28-2.09 (m, 3H), 2.07 (s, 3H), 1.87-1.77 (m, 3H), 1.71-1.61 (m, 2H), 1.38 (d, J = 6.3 Hz, 3H), 1.37-1.23 (m, 1H), 0.91 (dd, J = 6.8, 1.8 Hz, 6H), 0.89-0.85 (m, 1H) | ¹³C NMR (CDCl₃) δ 172.63, 170.31, 162.98, 160.27, 145.73, 144.01, 142.39, 109.60, 89.55, 84.07, 84.01, 75.63, 72.67, 71.68, 56.19, 51.61, 30.91 (q, J = 29.1 Hz), 28.87, 27.47, 23.09, 23.06, 20.89, 19.54, 19.46, 18.22, 17.95; ¹⁹F NMR (CDCl₃) δ −66.38−−66.51 (m) |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| F45 | Colorless Semi-Solid | — | 3376, 2956, 2873, 1745, 1676, 1502, 1236 | HRMS-ESI (m/z) [M + Na]$^+$ calcd for C$_{26}$H$_{40}$N$_2$NaO$_9$, 547.2626; found, 547.2624 | $^1$H NMR (CDCl$_3$) δ 8.32 (d, J = 8.0 Hz, 1H), 8.27 (dd, J = 5.5, 1.5 Hz, 1H), 6.95 (d, J = 5.4 Hz, 1H), 5.75-5.72 (m, 2H), 4.78 (p, J = 6.8 Hz, 1H), 4.60 (dt, J = 11.0, 7.6 Hz, 1H), 3.91 (s, 3H), 3.78 (dt, J = 9.4, 6.6 Hz, 1H), 3.62-3.52 (m, 1H), 3.41-3.32 (m, 2H), 3.29 (dd, J = 8.7, 6.5 Hz, 1H), 3.16-3.10 (m, 1H), 2.37 (dt, J = 13.5, 6.8 Hz, 1H), 2.18-2.09 (m, 1H), 2.07 (s, 3H), 1.82 (hept, J = 6.6 Hz, 1H), 1.71-1.53 (m, 4H), 1.40 (d, J = 6.5 Hz, 3H), 1.38-1.22 (m, 1H), 0.97-0.85 (m, 10H) | $^{13}$C NMR (CDCl$_3$) δ 172.63, 170.24, 162.95, 160.24, 145.72, 143.93, 142.41, 109.60, 89.49, 84.22, 83.76, 75.90, 75.39, 72.99, 56.17, 51.62, 33.40, 28.85, 27.75, 23.50, 20.85, 19.50, 19.47, 18.27, 17.88, 10.67 |
| F46 | Colorless Semi-Solid | — | 3378, 2954, 2873, 1732, 1676, 1501, 1163 | HRMS-ESI (m/z) [M + Na]$^+$ calcd for C$_{27}$H$_{38}$N$_2$NaO$_{10}$, 573.2419; found, 573.2415 | $^1$H NMR (CDCl$_3$) δ 8.37-8.23 (m, 2H), 6.95 (d, J = 5.4 Hz, 1H), 5.74 (s, 2H), 5.15 (dd, J = 9.8, 7.8 Hz, 1H), 4.96 (dq, J = 9.6, 6.4 Hz, 1H), 4.63 (dt, J = 10.7, 7.5 Hz, 1H), 3.91 (s, 3H), 3.38 (ddt, J = 7.6, 5.4, 3.0 Hz, 1H), 3.30 (dd, J = 8.8, 6.1 Hz, 1H), 2.98 (dd, J = 8.8, 6.8 Hz, 1H), 2.40 (dt, J = 13.8, 7.3 Hz, 1H), 2.15 (dddd, J = 15.8, 10.1, 8.0, 5.4 Hz, 1H), 2.07 (s, 3H), 1.77 (dt, J = 13.3, 6.7 Hz, 2H), 1.72-1.56 (m, 2H), 1.43-1.32 (m, 1H), 1.29 (d, J = 6.4 Hz, 3H), 1.08-0.99 (m, 3H), 0.90-0.84 (m, 8H) | $^{13}$C NMR (CDCl$_3$) δ 173.90, 172.72, 170.32, 162.96, 160.29, 145.69, 144.10, 142.34, 109.61, 89.58, 76.33, 75.67, 71.49, 56.19, 51.64, 33.41, 28.65, 28.13, 20.88, 19.32, 19.27, 18.08, 17.23, 12.89, 8.44, 8.37 |
| F47 | Yellow-Semi Solid | — | 3375, 2956, 2874, 1772, 1744, 1679, 1508, 1198 | HRMS-ESI (m/z) [M + H]$^+$ calcd for C$_{25}$H$_{39}$N$_2$O$_8$, 495.2701; found, 495.2713 | $^1$H NMR (CDCl$_3$) δ 8.56-8.48 (m, 1H), 8.33 (d, J = 5.4 Hz, 1H), 7.00 (d, J = 5.5 Hz, 1H), 4.78 (t, J = 7.7 Hz, 1H), 4.59 (dt, J = 10.7, 7.7 Hz, 1H), 3.91 (s, 3H), 3.77 (dt, J = 8.8, 6.5 Hz, 1H), 3.56 (dt, J = 8.9, 6.8 Hz, 1H), 3.42-3.31 (m, 2H), 3.28 (dd, J = 8.8, 6.4 Hz, 1H), 3.12 (dd, J = 8.8, 6.3 Hz, 1H), 2.40 (s, 3H), 2.38-2.26 (m, 1H), 2.17-2.05 (m, 1H), 1.81 (dt, J = 13.2, 6.6 Hz, 1H), 1.72-1.56 (m, 3H), 1.38 (d, J = 6.4 Hz, 3H), 1.36-1.19 (m, 2H), 1.02-0.81 (m, 10H) | $^{13}$C NMR (CDCl$_3$) δ 172.55, 168.92, 162.38, 159.42, 146.69, 141.43, 137.47, 109.77, 84.25, 83.77, 75.95, 75.44, 73.04, 56.28, 51.35, 28.86, 27.77, 23.52, 20.76, 19.52, 19.49, 18.23, 17.87, 10.68 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| F48 | White Solid | — | — | ESIMS m/z 616.2 ([M + H]⁺) | ¹H NMR (CDCl₃) δ 8.33 (d, J = 7.9 Hz, 1H), 8.28 (d, J = 5.4 Hz, 1H), 7.03-6.87 (m, 7H), 6.82-6.75 (m, 2H), 5.74 (s, 2H), 5.10 (dq, J = 9.7, 6.4 Hz, 1H), 4.68 (dt, J = 10.7, 7.5 Hz, 1H), 4.53 (dd, J = 9.6, 7.4 Hz, 1H), 4.40 (ddd, J = 7.3, 5.2, 1.8 Hz, 1H), 3.91 (s, 3H), 2.43 (dt, J = 13.8, 7.0 Hz, 1H), 2.29-2.16 (m, 1H), 2.07 (s, 3H), 1.95-1.81 (m, 1H), 1.81-1.68 (m, 1H), 1.42 (d, J = 6.4 Hz, 3H), 1.41-1.28 (m, 1H), 1.23-1.10 (m, 1H) | ¹⁹F NMR (CDCl₃) δ–122.28, –122.60 |
| F49 | White Solid | — | — | ESIM m/z 643.2 ([M + H]⁺) | ¹H NMR (CDCl₃) δ 8.38 (d, J = 8.0 Hz, 1H), 8.27 (d, J = 5.3 Hz, 1H), 7.03-6.86 (m, 7H), 6.82-6.76 (m, 2H), 5.80-5.74 (m, 2H), 5.10 (dq, J = 9.5, 6.3 Hz, 1H), 4.68 (dt, J = 10.8, 7.6 Hz, 1H), 4.53 (dd, J = 9.6, 7.3 Hz, 1H), 4.40 (ddd, J = 7.3, 5.2, 1.8 Hz, 1H), 3.89 (s, 3H), 2.55 (p, J = 7.0 Hz, 1H), 2.42 (dt, J = 13.9, 7.1 Hz, 1H), 2.22 (dddd, J = 15.8, 10.3, 7.9, 5.2 Hz, 1H), 1.94-1.82 (m, 1H), 1.80-1.67 (m, 1H), 1.42 (d, J = 6.4 Hz, 3H), 1.40-1.33 (m, 1H), 1.33-1.26 (m, 1H), 1.14 (d, J = 7.0 Hz, 6H) | ¹⁹F NMR (CDCl₃) δ–122.29, –122.61 |
| F50 | White Solid | 89-91 | 3364, 2918, 1745, 1649, 1502, 1200 | HRMS ESI (m/z) calcd for C₂₈H₂₈F₂N₂O₇, 542.1865; found, 542.1872 | ¹H NMR (CDCl₃) δ 12.04 (s, 1H), 8.49 (d, J = 8.1 Hz, 1H), 7.98 (d, J = 5.2 Hz, 1H), 7.05-6.75 (m, 9H), 5.11 (dq, J = 9.6, 6.3 Hz, 1H), 4.67 (dt, J = 10.8, 7.6 Hz, 1H), 4.54 (dd, J = 9.5, 7.4 Hz, 1H), 4.41 (ddd, J = 7.1, 5.2, 1.8 Hz, 1H), 3.93 (s, 3H), 2.42 (dt, J = 13.7, 7.2 Hz, 1H), 2.31-2.16 (m, 1H), 1.96-1.82 (m, 1H), 1.85-1.68 (m, 1H), 1.47-1.36 (m, 1H), 1.43 (d, J = 6.3 Hz, 3H), 1.16 (ddt, J = 15.9, 7.6, 1.8 Hz, 1H) | ¹³C NMR (CDCl₃) δ 171.92, 168.81, 157.81 (d, J = 239.9 Hz), 155.66 (d, J = 2.0 Hz), 155.44, 154.63 (d, J = 208.1 Hz), 153.60 (d, J = 2.0 Hz), 148.82, 140.65, 130.31, 118.35 (d, J = 8.0 Hz), 117.77 (d, J = 8.2 Hz), 116.05 (d, J = 6.3 Hz), 115.82 (d, J = 6.6 Hz), 109.63, 83.67, 83.43, 72.51, 56.14, 51.27, 33.22, 28.20, 18.33, 18.23 |
| F51 | Colorless Oil | — | 3376, 2954, 2875, 1746, 1679, 1504, | HRMS-ESI (m/z) [M + H]⁺ calcd for C₂₉H₄₄F₃N₂O₉, 621.2993; | ¹H NMR (CDCl₃) δ 8.37 (d, J = 8.0 Hz, 1H), 8.27 (d, J = 5.3 Hz, 1H), 6.94 (d, J = 5.4 Hz, 1H), 5.85-5.67 (m, 2H), | ¹³C NMR (CDCl₃) δ 176.27, 172.62, 162.95, 160.26, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | 1253, 1100, 833 | found, 621.3003 | 4.78 (dq, J = 9.2, 6.3 Hz, 1H), 4.60 (dt, J = 10.8, 7.6 Hz, 1H), 3.89 (s, 3H), 3.87-3.81 (m, 1H), 3.68 (dt, J = 9.2, 6.3 Hz, 1H), 3.41-3.31 (m, 2H), 3.28 (dd, J = 8.7, 6.6 Hz, 1H), 3.09 (dd, J = 8.7, 6.2 Hz, 1H), 2.55 (hept, J = 7.0 Hz, 1H), 2.37 (dtd, J = 13.6, 6.6, 1.7 Hz, 1H), 2.26-2.06 (m, 3H), 1.86-1.76 (m, 3H), 1.75-1.56 (m, 2H), 1.38 (d, J = 6.3 Hz, 3H), 1.35-1.25 (m, 1H), 1.14 (d, J = 7.0 Hz, 6H), 0.91 (dd, J = 6.7, 1.8 Hz, 6H), 0.93-0.86 (m, 1H) | 145.60, 144.23, 142.05, 109.54, 89.92, 84.08, 84.02, 75.63, 72.65, 71.69, 56.14, 51.61, 33.86, 33.39, 30.91 (q, J = 28.7 Hz), 28.88, 27.47, 23.08 (q, J = 2.4 Hz), 19.55, 19.47, 18.69, 18.23, 17.95; ¹⁹F NMR (CDCl₃) δ −66.43 (t, J = 11.0 Hz) |
| F52 | Colorless Oil | — | 3379, 2955, 2874, 1736, 1678, 1503, 1383, 1315, 1165, 1094, 1027, 973 | HRMS-ESI (m/z) [M + H]⁺ calcd for C₂₉H₄₃N₂O₁₀, 579.2912; found, 579.2922 | ¹H NMR (CDCl₃) δ 8.36 (d, J = 7.9 Hz, 1H), 8.27 (d, J = 5.3 Hz, 1H), 6.95 (d, J = 5.3 Hz, 1H), 5.81-5.72 (m, 2H), 5.15 (dd, J = 9.8, 7.8 Hz, 1H), 4.96 (dq, J = 9.7, 6.4 Hz, 1H), 4.63 (dt, J = 10.6, 7.5 Hz, 1H), 3.89 (s, 3H), 3.38 (ddd, J = 7.6, 5.4, 1.9 Hz, 1H), 3.31 (dd, J = 8.8, 6.1 Hz, 1H), 2.99 (dd, J = 8.8, 6.8 Hz, 1H), 2.55 (hept, J = 7.0 Hz, 1H), 2.44-2.29 (m, 1H), 2.23-2.05 (m, 1H), 1.84-1.56 (m, 4H), 1.44-1.29 (m, 1H), 1.29 (d, J = 6.4 Hz, 3H), 1.14 (d, J = 7.0 Hz, 6H), 1.07-0.98 (m, 3H), 0.92-0.83 (m, 8H) | ¹³C NMR (CDCl₃) δ 176.29, 173.90, 172.72, 162.92, 160.26, 145.55, 144.31, 141.99, 109.53, 89.94, 81.20, 76.32, 75.66, 71.46, 56.13, 51.63, 33.86, 33.40, 28.64, 28.11, 19.32, 19.27, 18.69, 18.07, 17.22, 12.88, 8.45, 8.38 |
| F53 | Colorless Semi-Solid | — | — | HRMS-ESI (m/z) [M + H]⁺ calcd for C₂₄H₃₄F₃N₂O₇, 519.2313; found, 519.2324 | ¹H NMR (CDCl₃) δ 12.07 (s, 1H), 8.48 (d, J = 8.2 Hz, 1H), 7.98 (d, J = 5.2 Hz, 1H), 6.87 (d, J = 5.2 Hz, 1H), 6.43 (dtt, J = 13.6, 4.0, 2.0 Hz, 1H), 5.90 (dqt, J = 15.3, 6.6, 2.2 Hz, 1H), 4.86 (dq, J = 9.4, 6.3 Hz, 1H), 4.60 (dt, J = 10.7, 7.6 Hz, 1H), 4.54-4.45 (m, 1H), 4.34-4.25 (m, 1H), 3.94 (s, 3H), 3.46 (dd, J = 9.4, 7.2 Hz, 1H), 3.44-3.36 (m, 1H), 3.28 (dd, J = 8.7, 6.6 Hz, 1H), 3.09 (dd, J = 8.7, 6.1 Hz, 1H), 2.44-2.31 (m, 1H), 2.24-2.09 (m, 1H), 1.88-1.75 (m, 1H), 1.75-1.59 (m, 2H), 1.41 (d, J = 6.3 Hz, 3H), | ¹³C NMR (CDCl₃) δ 171.97, 168.68, 155.36, 148.73, 140.55, 136.86 (q, J = 6.3 Hz), 130.35, 123.14 (q, J = 269.1 Hz), 118.09 (q, J = 34.1 Hz), 109.50, 84.27, 83.94, 75.68, 72.65, 71.03, 56.08, 51.26, 33.26, 28.84, 27.44, 19.49, 19.40, 18.16, 17.96; ¹⁹F NMR (CDCl₃) δ −64.24 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1.40-1.30 (m, 1H), 0.98-0.93 (m, 1H), 0.90 (dd, J = 6.7, 3.3 Hz, 6H) | |
| F54 | Colorless Oil | — | 3369, 2946, 1747, 1651, 1504, 1203 | HRMS-ESI (m/z) [M]⁺ calcd for $C_{29}H_{31}FN_2O_8$, 554.2064; found, 554.2074 | ¹H NMR (CDCl₃) δ 12.03 (s, 1H), 8.47 (d, J = 8.1 Hz, 1H), 7.99 (d, J = 5.2 Hz, 1H), 7.07-7.01 (m, 2H), 6.98-6.90 (m, 2H), 6.87 (d, J = 5.2 Hz, 1H), 6.84-6.74 (m, 4H), 5.11 (dq, J = 9.6, 6.4 Hz, 1H), 4.66 (dt, J = 10.8, 7.7 Hz, 1H), 4.53 (dd, J = 9.6, 7.4 Hz, 1H), 4.36 (ddd, J = 7.2, 5.2, 1.8 Hz, 1H), 3.94 (s, 3H), 3.74 (s, 3H), 2.42 (dt, J = 13.8, 7.3 Hz, 1H), 2.24 (dddd, J = 15.8, 10.3, 8.0, 5.1 Hz, 1H), 1.96-1.84 (m, 1H), 1.84-1.72 (m, 1H), 1.44-1.34 (m, 1H), 1.43 (d, J = 6.4 Hz, 3H), 1.12 (ddt, J = 16.2, 7.8, 1.8 Hz, 1H) | ¹³C NMR (CDCl₃) δ 172.01, 168.85, 157.85 (d, J = 239.3 Hz), 155.90 (d, J = 2.2 Hz), 155.52, 154.80, 151.52, 148.89, 140.70, 130.44, 118.68, 117.96 (d, J = 7.9 Hz), 115.95 (d, J = 23.0 Hz), 114.74, 109.67, 84.07, 83.69, 72.67, 56.23, 55.78, 51.36, 33.39, 28.18, 18.44, 18.35; ¹⁹F NMR (CDCl₃) δ −122.66 |
| F55 | Colorless Solid | 65-67 | 2953, 2873, 1746, 1651, 1503, 1201 | HRMS-ESI (m/z) [M]⁺ calcd for $C_{26}H_{33}FN_2O_7$, 504.2272; found, 504.2282 | ¹H NMR (CDCl₃) δ 12.06 (s, 1H), 8.48 (d, J = 8.1 Hz, 1H), 7.99 (d, J = 5.1 Hz, 1H), 7.07-7.01 (m, 2H), 6.99-6.92 (m, 2H), 6.87 (d, J = 5.2 Hz, 1H), 5.02 (dq, J = 9.6, 6.4 Hz, 1H), 4.62 (dt, J = 10.7, 7.6 Hz, 1H), 4.32 (dd, J = 9.6, 7.3 Hz, 1H), 3.94 (s, 3H), 3.54 (ddd, J = 7.1, 5.2, 1.7 Hz, 1H), 3.25 (dd, J = 8.7, 6.6 Hz, 1H), 3.05 (dd, J = 8.7, 6.1 Hz, 1H), 2.47-2.35 (m, 1H), 2.22 (dddd, J = 15.8, 10.0, 8.4, 5.3 Hz, 1H), 1.83-1.64 (m, 3H), 1.50-1.39 (m, 1H), 1.36 (d, J = 6.4 Hz, 3H), 1.03 (ddt, J = 16.0, 6.7, 1.9 Hz, 1H), 0.80 (d, J = 6.7 Hz, 3H), 0.76 (d, J = 6.7 Hz, 3H) | ¹³C NMR (CDCl₃) δ 171.95, 168.69, 157.52 (d, J = 238.6 Hz), 156.33, 155.87 (d, J = 2.2 Hz), 155.35, 148.73, 140.54, 130.32, 117.56 (d, J = 8.0 Hz), 115.63 (d, J = 23.0 Hz), 109.51, 83.79, 83.04, 76.24, 72.70, 56.07, 51.28, 33.30, 28.71, 27.69, 19.37, 19.23, 18.24, 18.12; ¹⁹F NMR (CDCl₃) δ −123.24 |
| F56 | Off-White Solid | 131-133 | 3369, 2954, 1743, 1650, 1503, 1202 | HRMS-ESI (m/z) [M]⁺ calcd for $C_{26}H_{33}FN_2O_7$, 504.2272; found, 504.2294 | ¹H NMR (CDCl₃) δ 12.05 (s, 1H), 8.46 (d, J = 8.2 Hz, 1H), 7.98 (d, J = 5.2 Hz, 1H), 7.00-6.92 (m, 2H), 6.91-6.84 (m, 3H), 4.92 (dq, J = 9.6, 6.4 Hz, 1H), 4.63 (dt, J = 10.7, 7.6 Hz, 1H), 4.27 (ddd, J = 7.1, 5.3, 1.8 Hz, 1H), 3.94 (s, 3H), 3.65-3.52 (m, 2H), 3.41 (dd, J = 8.6, 6.6 Hz, 1H), 2.43-2.31 (m, 1H), 2.12 (dddd, J = 15.8, 10.2, 7.9, 5.3 Hz, 1H), | ¹³C NMR (CDCl₃) δ 171.92, 168.69, 157.56 (d, J = 239.2 Hz), 155.36, 153.66 (d, J = 2.5 Hz), 148.73, 140.54, 130.34, 117.95 (d, J = 7.8 Hz), 115.89 (d, J = 23.3 Hz), 109.50, 84.24, 83.32, 80.79, 73.06, 56.08, 51.22, 33.22, 29.03, 28.18, 19.39, 19.31, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 1.88-1.60 (m, 3H), 1.47 (d, J = 6.3 Hz, 3H), 1.42-1.29 (m, 1H), 1.04 (ddt, J = 16.1, 7.8, 1.9 Hz, 1H), 0.85 (d, J = 6.7 Hz, 3H), 0.81 (d, J = 6.7 Hz, 3H) | 18.19, 17.96; $^{19}$F NMR (CDCl$_3$) δ −122.87 |
| F57 | Flaky White Solid | — | 3366, 2953, 2872, 1745, 1506, 1208 | HRMS-ESI (m/z) [M + Na]$^+$ calcd for C$_{27}$H$_{36}$N$_2$NaO$_8$, 539.2364; found, 539.2365 | $^1$H NMR (CDCl$_3$) δ 12.07 (d, J = 0.6 Hz, 1H), 8.48 (d, J = 8.2 Hz, 1H), 8.00 (d, J = 5.1 Hz, 1H), 7.09-6.98 (m, 2H), 6.87 (d, J = 5.2 Hz, 1H), 6.84-6.78 (m, 2H), 5.01 (dq, J = 9.5, 6.4 Hz, 1H), 4.61 (dt, J = 10.8, 7.6 Hz, 1H), 4.29 (dd, J = 9.6, 7.2 Hz, 1H), 3.95 (s, 3H), 3.78 (s, 3H), 3.54 (ddd, J = 7.2, 5.2, 1.7 Hz, 1H), 3.25 (dd, J = 8.8, 6.7 Hz, 1H), 3.09 (dd, J = 8.8, 6.2 Hz, 1H), 2.50-2.34 (m, 1H), 2.28-2.12 (m, 1H), 1.84-1.66 (m, 3H), 1.49-1.38 (m, 1H), 1.37 (d, J = 6.4 Hz, 3H), 1.03 (dd, J = 16.1, 6.9 Hz, 1H), 0.80 (dd, J = 18.7, 6.7 Hz, 6H) | $^{13}$C NMR (CDCl$_3$) δ 171.99, 168.66, 155.36, 154.19, 153.96, 148.74, 140.53, 130.38, 117.54, 114.42, 109.48, 83.93, 83.07, 76.38, 72.97, 56.08, 55.69, 51.30, 33.38, 28.74, 27.79, 19.42, 19.28, 18.27, 18.18 |
| F58 | Purple Semi-Solid | — | 3381, 2956, 2875, 1773, 1745, 1680, 1510, 1119 | HRMS-ESI (m/z) [M + Na]$^+$ calcd for C$_{26}$H$_{35}$F$_3$N$_2$NaO$_8$, 583.2238; found, 583.2244 | $^1$H NMR (CDCl$_3$) δ 8.57-8.47 (m, 1H), 8.34 (d, J = 5.4 Hz, 1H), 7.01 (d, J = 5.5 Hz, 1H), 6.56-6.36 (m, 1H), 5.99-5.79 (m, 1H), 4.91-4.73 (m, 1H), 4.66-4.54 (m, 1H), 4.53-4.40 (m, 1H), 4.34-4.15 (m, 1H), 3.91 (s, 3H), 3.50-3.35 (m, 2H), 3.28 (dd, J = 8.7, 6.6 Hz, 1H), 3.08 (dd, J = 8.7, 6.2 Hz, 1H), 2.40 (s, 3H), 2.38-2.31 (m, 1H), 2.23-2.06 (m, 1H), 1.80 (dp, J = 13.2, 6.7 Hz, 1H), 1.69-1.59 (m, 3H), 1.38 (d, J = 6.3 Hz, 3H), 1.36-1.26 (m, 1H), 0.89 (dd, J = 6.6, 2.6 Hz, 6H) | $^{13}$C NMR (CDCl$_3$) δ 172.46, 168.91, 162.40, 159.44, 146.69, 141.37, 137.50, 136.91, 118.22, 117.88, 109.81, 84.33, 84.01, 75.68, 72.39, 71.02, 56.29, 51.31, 33.57, 28.82, 27.54, 20.75, 19.48, 19.40, 18.18, 17.93; $^{19}$F NMR (CDCl$_3$) δ −64.22 |
| F59 | Light Yellow Semi-Solid | — | 3381, 2955, 2875, 1748, 1678, 1504, 1310, 1115 | HRMS-ESI (m/z) [M + Na]$^+$ calcd for C$_{27}$H$_{37}$F$_3$N$_2$O$_9$, 613.2343; found, 613.2349 | $^1$H NMR (CDCl$_3$) δ 8.31 (d, J = 8.0 Hz, 1H), 8.28 (d, J = 5.3 Hz, 1H), 6.95 (d, J = 5.5 Hz, 1H), 6.42 (ddq, J = 15.7, 4.0, 2.1 Hz, 1H), 5.95-5.84 (m, 1H), 5.74 (s, 2H), 4.84 (dq, J = 9.3, 6.3 Hz, 1H), 4.61 (dt, J = 10.8, 7.6 Hz, 1H), 4.55-4.44 (m, 1H), 4.29 (dt, J = 15.3, 4.1 Hz, 1H), 3.91 (s, 3H), 3.45 (dd, J = 9.5, 7.2 Hz, 1H), 3.41-3.35 (m, | $^{13}$C NMR (CDCl$_3$) δ 172.59, 170.31, 162.99, 160.28, 145.74, 144.02, 142.37, 136.93, 117.89, 109.61, 89.55, 84.35, 84.02, 76.70, 75.67, 72.38, 71.03, 56.19, 51.60, 33.36, 28.83, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1H), 3.28 (dd, J = 8.7, 6.6 Hz, 1H), 3.08 (dd, J = 8.7, 6.2 Hz, 1H), 2.38 (dt, J = 13.5, 6.7 Hz, 1H), 2.21-2.10 (m, 1H), 2.08 (s, 3H), 1.80 (dt, J = 13.2, 6.6 Hz, 1H), 1.71-1.60 (m, 2H), 1.39 (d, J = 6.3 Hz, 3H), 1.37-1.29 (m, 1H), 0.98-0.88 (m, J = 7.3 Hz, 1H), 0.90 (dd, J = 6.7, 3.0 Hz, 6H) | 27.52, 20.89, 19.49, 19.41, 18.23, 17.95; ¹⁹F NMR (CDCl$_3$) δ −64.23 (p, J = 3.3 Hz) |
| F60 | Yellow Oil | — | 3384, 2946, 1751, 1677, 1502, 1200, 1035 | HRMS-ESI (m/z) [M]$^+$ calcd for C$_{32}$H$_{35}$FN$_2$O$_{10}$, 626.2276; found, 626.2306 | ¹H NMR (CDCl$_3$) δ 8.32 (d, J = 8.0 Hz, 1H), 8.28 (d, J = 5.4 Hz, 1H), 7.07-7.01 (m, 2H), 6.97-6.89 (m, 3H), 6.83-6.73 (m, 4H), 5.74 (s, 2H), 5.09 (dq, J = 9.5, 6.4 Hz, 1H), 4.67 (dt, J = 10.8, 7.6 Hz, 1H), 4.52 (dd, J = 9.6, 7.4 Hz, 1H), 4.35 (ddd, J = 7.2, 5.2, 1.8 Hz, 1H), 3.91 (s, 3H), 3.74 (s, 3H), 2.42 (dt, J = 13.8, 7.0 Hz, 1H), 2.30-2.15 (m, 1H), 2.07 (s, 3H), 1.96-1.82 (m, 1H), 1.82-1.68 (m, 1H), 1.42 (d, J = 6.4 Hz, 3H), 1.41-1.31 (m, 1H), 1.11 (ddt, J = 16.2, 8.2, 1.8 Hz, 1H) | ¹³C NMR (CDCl$_3$) δ 172.61, 170.42, 163.14, 160.42, 157.82 (d, J = 239.1 Hz), 155.93 (d, J = 2.7 Hz), 154.76, 151.58, 145.86, 144.19, 142.40, 118.68, 117.96 (d, J = 8.0 Hz), 115.92 (d, J = 23.0 Hz), 114.73, 109.80, 89.65, 84.15, 83.75, 72.40, 56.33, 55.77, 51.72, 33.45, 28.26, 21.01, 18.51, 18.34; ¹⁹F NMR (CDCl$_3$) δ−122.77 |
| F61 | Yellow Oil | — | 3384, 2954, 1750, 1678, 1503, 1200 | HRMS-ESI (m/z) [M]$^+$ calcd for C$_{29}$H$_{37}$FN$_2$O$_9$, 576.2483; found 576.2508 | ¹H NMR (CDCl$_3$) δ 8.33 (d, J = 8.0 Hz, 1H), 8.28 (d, J = 5.4 Hz, 1H), 7.06-7.00 (m, 2H), 6.99-6.92 (m, 3H), 5.74 (s, 2H), 5.00 (dq, J = 9.6, 6.4 Hz, 1H), 4.63 (dt, J = 10.8, 7.6 Hz, 1H), 4.31 (dd, J = 9.6, 7.3 Hz, 1H), 3.91 (s, 3H), 3.53 (ddd, J = 7.2, 5.2, 1.7 Hz, 1H), 3.25 (dd, J = 8.8, 6.6 Hz, 1H), 3.04 (dd, J = 8.8, 6.2 Hz, 1H), 2.47-2.32 (m, 1H), 2.20 (dddd, J = 15.6, 10.4, 8.3, 5.3 Hz, 1H), 2.07 (s, 3H), 1.83-1.61 (m, 3H), 1.43-1.33 (m, 1H), 1.35 (d, J = 6.4 Hz, 3H), 1.02 (ddt, J = 16.0, 7.2, 1.9 Hz, 1H), 0.80 (d, J = 6.7 Hz, 3H), 0.75 (d, J = 6.7 Hz, 3H) | ¹³C NMR (CDCl$_3$) δ 172.57, 170.29, 162.99, 160.28, 157.51 (d, J = 238.8 Hz), 155.91 (d, J = 2.2 Hz), 145.73, 144.03, 142.35, 117.56 (d, J = 8.0 Hz), 115.62 (d, J = 22.9 Hz), 109.65, 89.52, 83.86, 83.13, 76.24, 72.44, 56.20, 51.64, 33.39, 28.72, 27.78, 20.87, 19.37, 19.23, 18.32, 18.12; ¹⁹F NMR (CDCl$_3$) δ−123.37 |
| F62 | Yellow Oil | — | 3381, 2954, 1747, 1678, | HRMS-ESI (m/z) [M]$^+$ calcd for | ¹H NMR (CDCl$_3$) δ 8.38 (d, J = 8.0 Hz, 1H), 8.27 (d, J = 5.4 Hz, 1H), | ¹³C NMR (CDCl$_3$) δ 176.26, 172.57, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | 1503, 1201 | $C_{31}H_{41}FN_2O_9$, 604.2796; found, 604.2811 | 7.06-7.01 (m, 2H), 6.98-6.92 (m, 3H), 5.80-5.73 (m, 2H), 5.00 (dq, J = 9.6, 6.4 Hz, 1H), 4.63 (dt, J = 10.8, 7.6 Hz, 1H), 4.31 (dd, J = 9.6, 7.3 Hz, 1H), 3.89 (s, 3H), 3.53 (ddd, J = 7.1, 5.2, 1.7 Hz, 1H), 3.25 (dd, J = 8.8, 6.6 Hz, 1H), 3.04 (dd, J = 8.8, 6.2 Hz, 1H), 2.54 (h, J = 7.0 Hz, 1H), 2.46-2.36 (m, 1H), 2.20 (dddd, J = 11.3, 10.0, 8.4, 5.2 Hz, 1H), 1.85-1.59 (m, 3H), 1.43-1.33 (m, 1H), 1.35 (d, J = 6.4 Hz, 3H), 1.14 (d, J = 7.0 Hz, 6H), 1.03 (ddt, J = 16.5, 7.7, 2.1 Hz, 1H), 0.80 (d, J = 6.7 Hz, 3H), 0.75 (d, J = 6.7 Hz, 3H); | 162.96, 160.26, 157.51 (d, J = 238.8 Hz), 155.91 (d, J = 2.2 Hz), 145.59, 144.25, 142.02, 117.57 (d, J = 8.0 Hz), 115.62 (d, J = 23.1 Hz), 109.58, 89.88, 83.87, 83.13, 76.25, 72.43, 56.14, 51.63, 33.86, 33.41, 28.72, 27.78, 19.37, 19.24, 18.68, 18.33, 18.12; $^{19}$F NMR (CDCl$_3$) δ−123.38 |
| F63 | Off-White Solid | 139-141 | 3371, 2959, 1747, 1676, 1503, 1202 | HRMS-ESI (m/z) [M]$^+$ calcd for $C_{29}H_{37}FN_2O_9$, 576.2483; found, 576.2489 | $^1$H NMR (CDCl$_3$) δ 8.31 (d, J = 8.0 Hz, 1H), 8.27 (d, J = 5.4 Hz, 1H), 7.00-6.90 (m, 3H), 6.92-6.84 (m, 2H), 5.74 (s, 2H), 4.89 (dq, J = 9.7, 6.4 Hz, 1H), 4.65 (dt, J = 10.8, 7.6 Hz, 1H), 4.26 (ddd, J = 7.2, 5.3, 1.7 Hz, 1H), 3.91 (s, 3H), 3.67-3.49 (m, 2H), 3.40 (dd, J = 8.6, 6.6 Hz, 1H), 2.42-2.29 (m, 1H), 2.07 (s, 3H), 1.88-1.55 (m, 3H), 1.45 (d, J = 6.4 Hz, 3H), 1.37-1.22 (m, 2H), 1.03 (ddt, J = 16.0, 7.8, 1.8 Hz, 1H), 0.84 (d, J = 6.7 Hz, 3H), 0.81 (d, J = 6.7 Hz, 3H) | $^{13}$C NMR (CDCl$_3$) δ 172.54, 170.28, 163.00, 160.27, 157.54 (d, J = 239.0 Hz), 153.71 (d, J = 2.2 Hz), 145.73, 144.01, 142.34, 117.96 (d, J = 8.0 Hz), 115.86 (d, J = 23.1 Hz), 109.63, 89.52, 84.32, 83.38, 80.77, 72.79, 56.19, 51.56, 33.30, 29.02, 28.26, 20.88, 19.39, 19.31, 18.25, 17.95; $^{19}$F NMR (CDCl$_3$) δ−122.98 |
| F64 | Colorless Solid | 84-86 | 3366, 2949, 1649, 1505, 1212 | HRMS-ESI (m/z) [M]$^+$ calcd for $C_{30}H_{34}N_2O_9$, 566.2264; found, 566.2281 | $^1$H NMR (CDCl$_3$) δ 12.05 (s, 1H), 8.48 (d, J = 8.1 Hz, 1H), 7.98 (d, J = 5.2 Hz, 1H), 7.07-6.98 (m, 2H), 6.89-6.71 (m, 7H), 5.09 (dq, J = 9.6, 6.4 Hz, 1H), 4.65 (dt, J = 10.8, 7.6 Hz, 1H), 4.50 (dd, J = 9.5, 7.3 Hz, 1H), 4.36 (ddd, J = 7.2, 5.1, 1.7 Hz, 1H), 3.93 (s, 3H), 3.75 (s, 3H), 3.73 (s, 3H), 2.41 (dt, J = 13.8, 7.0 Hz, 1H), 2.29-2.14 (m, 1H), 1.97-1.83 (m, 1H), 1.83-1.69 (m, 1H), 1.45 (d, J = 6.4 Hz, 3H), 1.45-1.34 (m, 1H), 1.10 (ddt, J = 16.4, 7.9, 1.8 Hz, 1H) | $^{13}$C NMR (CDCl$_3$) δ 171.90, 168.71, 155.36, 154.60, 154.43, 153.86, 151.58, 148.75, 140.56, 130.31, 118.65, 117.80, 114.58, 114.53, 109.54 84.08, 83.63, 72.76, 56.08, 55.64, 51.24, 33.27, 28.06, 18.31, 18.27, 14.21 |
| F65 | Colorless Solid | 70-72 | 3367, 2953, 1742, | HRMS-ESI (m/z) [M]$^+$ | $^1$H NMR (CDCl$_3$) δ 12.07 (s, 1H), 8.47 (d, J = 8.1 Hz, 1H), | $^{13}$C NMR (CDCl$_3$) δ 171.95, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | 1649, 1504, 1213 | calcd for $C_{27}H_{36}N_2O_8$, 516.2472; found, 516.2483 | 7.97 (d, J = 5.2 Hz, 1H), 6.92-6.80 (m, 5H), 4.91 (dq, J = 9.6, 6.3 Hz, 1H), 4.63 (dt, J = 10.8, 7.6 Hz, 1H), 4.23 (ddd, J = 7.0, 5.1, 1.7 Hz, 1H), 3.93 (s, 3H), 3.76 (s, 3H), 3.66-3.56 (m, 2H), 3.41 (dd, J = 8.6, 6.6 Hz, 1H), 2.36 (dt, J = 13.6, 7.3 Hz, 1H), 2.12 (dddd, J = 15.8, 10.3, 7.9, 5.1 Hz, 1H), 1.88-1.74 (m, 2H), 1.76-1.59 (m, 1H), 1.47 (d, J = 6.4 Hz, 3H), 1.40-1.28 (m, 1H), 0.98 (ddt, J = 16.2, 8.1, 1.7 Hz, 1H), 0.87 (d, J = 6.6 Hz, 3H), 0.84 (d, J = 6.7 Hz, 3H) | 168.68, 155.33, 154.36, 151.44, 148.71, 140.53, 130.33, 118.25, 114.62, 109.50, 84.59, 83.30, 80.75, 73.11, 56.07, 55.65, 51.23, 33.24, 29.06, 28.03, 19.45, 19.36, 18.20, 18.00 |
| F66 | Yellow Oil | — | 3384, 2959, 1750, 1677, 1504, 1203, 1036 | ESIMS (m/z) 640.3 ([M + 2H]⁺) | ¹H NMR (CDCl₃) δ 8.33 (d, J = 8.0 Hz, 1H), 8.27 (d, J = 5.3 Hz, 1H), 7.07-6.99 (m, 2H), 6.95 (d, J = 5.4 Hz, 1H), 6.86-6.72 (m, 6H), 5.74 (s, 2H), 5.08 (dq, J = 9.5, 6.3 Hz, 1H), 4.67 (dt, J = 10.7, 7.6 Hz, 1H), 4.49 (dd, J = 9.6, 7.3 Hz, 1H), 4.35 (ddd, J = 7.3, 5.2, 1.7 Hz, 1H), 3.90 (s, 3H), 3.75 (s, 3H), 3.73 (s, 3H), 2.42 (dt, J = 13.8, 7.0 Hz, 1H), 2.22 (dddd, J = 15.8, 10.3, 8.0, 5.3 Hz, 1H), 2.07 (s, 3H), 1.94-1.82 (m, 1H), 1.82-1.68 (m, 1H), 1.43 (d, J = 6.4 Hz, 3H), 1.40-1.28 (m, 1H), 1.10 (ddt, J = 16.2, 7.9, 1.9 Hz, 1H) | ¹³C NMR (CDCl₃) δ 172.52, 170.30, 163.01, 160.28, 154.56, 154.39, 153.90, 151.63, 145.74, 144.03, 142.29, 118.68, 117.80, 114.56, 114.52, 109.67, 89.51, 84.18, 83.70, 72.50, 56.20, 55.66, 51.60, 33.35, 28.13, 20.89, 18.39, 18.26 |
| F67 | Yellow Oil | — | 3375, 2944, 1747, 1678, 1505, 1214, 1036 | HRMS-ESI (m/z) [M]⁺ calcd for $C_{35}H_{42}N_2O_{11}$, 666.2789; found, 666.2793 | ¹H NMR (CDCl₃) δ 8.38 (d, J = 8.0 Hz, 1H), 8.27 (d, J = 5.3 Hz, 1H), 7.07-6.99 (m, 2H), 6.94 (d, J = 5.4 Hz, 1H), 6.86-6.73 (m, 6H), 5.80-5.74 (m, 2H), 5.08 (dq, J = 9.5, 6.4 Hz, 1H), 4.67 (dt, J = 10.7, 7.6 Hz, 1H), 4.49 (dd, J = 9.6, 7.4 Hz, 1H), 4.35 (ddd, J = 7.2, 5.1, 1.7 Hz, 1H), 3.89 (s, 3H), 3.75 (s, 3H), 3.74 (s, 3H), 2.62-2.47 (m, 1H), 2.42 (dt, J = 13.8, 7.0 Hz, 1H), 2.22 (dddd, J = 15.7, 9.9, 7.9, 5.2 Hz, 1H), 1.95-1.82 (m, 1H), 1.81-1.69 (m, 1H), 1.43 (d, J = 6.4 Hz, 3H), 1.43-1.29 (m, | ¹³C NMR (CDCl₃) δ 176.27, 172.52, 162.98, 160.26, 154.57, 154.39, 153.91, 151.64, 145.60, 144.26, 141.97, 118.68, 117.81, 114.56, 114.52, 109.59, 89.88, 84.19, 83.71, 72.49, 56.15, 55.65, 51.59, 33.86, 33.37, 28.14, 18.69, 18.40, 18.27 |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 1H), 1.14 (d, J = 7.0 Hz, 6H), 1.13-1.04 (m, 1H) | |
| F68 | White Solid | 118-120 | 3376, 2956, 1751, 1679, 1506, | ESIMS m/z 589.3 ([M + H]$^+$) | $^1$H NMR (CDCl$_3$) δ 8.31 (d, J = 8.0 Hz, 1H), 8.27 (d, J = 5.3 Hz, 1H), 6.94 (d, J = 5.4 Hz, 1H), 6.91-6.86 (m, 2H), 6.85-6.78 (m, 2H), 5.74 (s, 2H), 4.89 (dq, J = 9.6, 6.3 Hz, 1H), 4.65 (dt, J = 10.8, 7.6 Hz, 1H), 4.23 (ddd, J = 7.0, 5.2, 1.7 Hz, 1H), 3.90 (s, 3H), 3.77 (s, 3H), 3.68-3.55 (m, 2H), 3.41 (dd, J = 8.7, 6.6 Hz, 1H), 2.37 (dt, J = 13.7, 7.0 Hz, 1H), 2.16-2.07 (m, 1H), 2.07 (s, 3H), 1.80 (dtt, J = 13.3, 8.5, 4.6 Hz, 2H), 1.73-1.55 (m, 1H), 1.45 (d, J = 6.3 Hz, 3H), 1.35-1.22 (m, 1H), 0.98 (ddt, J = 16.1, 7.9, 1.7 Hz, 1H), 0.87 (d, J = 6.7 Hz, 3H), 0.83 (d, J = 6.7 Hz, 3H) | $^{13}$C NMR (CDCl$_3$) δ 172.56, 170.28, 162.99, 160.26, 154.33, 151.50, 145.73, 143.99, 142.35, 118.27, 114.60, 109.63, 89.52, 84.69, 83.36, 80.75, 72.84, 56.19, 55.65, 51.57, 33.35, 29.06, 28.09, 20.88, 19.45, 19.36, 18.26, 18.00 |
| F69 | Yellow Oil | — | 3383, 2956, 1747, 1678, 1506, 1216 | HRMS-ESI (m/z) [M]$^+$ calcd for C$_{32}$H$_{44}$N$_2$O$_{10}$, 616.2996; found, 616.3006 | $^1$H NMR (CDCl$_3$) δ 8.36 (d, J = 8.0 Hz, 1H), 8.26 (d, J = 5.4 Hz, 1H), 6.93 (d, J = 5.4 Hz, 1H), 6.91-6.86 (m, 2H), 6.85-6.79 (m, 2H), 5.80-5.74 (m, 2H), 4.89 (dq, J = 9.6, 6.3 Hz, 1H), 4.64 (dt, J = 10.7, 7.6 Hz, 1H), 4.27-4.19 (m, 1H), 3.88 (s, 3H), 3.77 (s, 3H), 3.64-3.57 (m, 2H), 3.41 (dd, J = 8.7, 6.6 Hz, 1H), 2.55 (hept, J = 7.0 Hz, 1H), 2.37 (dt, J = 13.7, 7.0 Hz, 1H), 2.10 (dddd, J = 15.7, 10.2, 8.0, 5.1 Hz, 1H), 1.87-1.73 (m, 2H), 1.72-1.57 (m, 1H), 1.45 (d, J = 6.3 Hz, 3H), 1.35-1.22 (m, 1H), 1.14 (d, J = 7.0 Hz, 6H), 0.98 (ddt, J = 16.2, 7.6, 1.7 Hz, 1H), 0.87 (d, J = 6.7 Hz, 3H), 0.83 (d, J = 6.7 Hz, 3H) | $^{13}$C NMR (CDCl$_3$) δ 176.24, 172.55, 162.96, 160.24, 154.32, 151.50, 145.59, 144.20, 142.01, 118.26, 114.60, 109.56, 89.89, 84.69, 83.36, 80.75, 72.83, 56.14, 55.65, 51.56, 33.85, 33.36, 29.06, 28.09, 19.45, 19.36, 18.68, 18.27, 17.99 |
| F70 | White Semi-Solid | — | 3367, 2955, 2872, 1744, 1650, 1529 | HRMS-ESI (m/z) [M + H]$^+$ calcd for C$_{25}$H$_{41}$N$_2$O$_7$, 481.2908; found, 481.2922 | $^1$H NMR (CDCl$_3$) δ 12.09 (s, 1H), 8.47 (d, J = 8.0 Hz, 1H), 7.99 (d, J = 5.2 Hz, 1H), 6.87 (d, J = 5.2 Hz, 1H), 4.79 (dp, J = 9.6, 6.1 Hz, 1H), 4.58 (dt, J = 10.8, 7.6 Hz, 1H), 3.94 (s, 3H), 3.81 (dt, J = 9.0, 6.6 Hz, 1H), 3.60 (dt, J = 8.9, 6.7 Hz, 1H), | $^{13}$C NMR (CDCl$_3$) δ 172.05, 168.65, 155.34, 148.71, 140.51, 130.41, 109.45, 84.17, 83.78, 75.97, 73.89, 73.30, 56.07, 51.30, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 3.43-3.33 (m, 2H), 3.28 (dd, J = 8.7, 6.5 Hz, 1H), 3.13 (dd, J = 8.7, 6.3 Hz, 1H), 2.44-2.32 (m, 1H), 2.21-2.07 (m, 1H), 1.81 (dq, J = 13.2, 6.6 Hz, 1H), 1.75-1.63 (m, 2H), 1.61-1.51 (m, 2H), 1.41 (t, J = 6.5 Hz, 3H), 1.39-1.24 (m, 4H), 1.00-0.80 (m, 11H) | 33.35, 30.06, 28.88, 28.39, 27.69, 22.57, 19.54, 19.48, 18.22, 17.91, 14.05 |
| F71 | Colorless Semi-Solid | — | 3365, 2953, 2873, 1744, 1650, 1529, 1482 | HRMS-ESI (m/z) [M + H]⁺ calcd for $C_{25}H_{41}N_2O_8$, 497.2857; found, 497.2864 | ¹H NMR (CDCl₃) δ 12.09 (s, 1H), 8.47 (d, J = 8.2 Hz, 1H), 7.99 (d, J = 5.2 Hz, 1H), 6.87 (d, J = 5.3 Hz, 1H), 4.80 (ddd, J = 8.5, 6.2, 2.4 Hz, 1H), 4.58 (dt, J = 10.7, 7.7 Hz, 1H), 3.94 (s, 3H) 3.93-3.81 (m 1H), 3.79-3.63 (m, 1H), 3.52-3.23 (m, 7H), 3.13 (dt, J = 8.7, 6.3 Hz, 1H), 2.41-2.32 (m, 1H), 2.21-2.05 (m, 1H), 1.92-1.60 (m, 5H), 1.47-1.36 (m, 4H), 1.15 (dd, J = 6.1, 2.1 Hz, 3H), 0.96-0.86 (m, 7H) | ¹³C NMR (CDCl₃) δ 172.06, 168.65, 155.35, 148.72, 140.51, 130.40, 109.46, 84.10, 83.90, 83.84, 75.86, 74.16, 73.68, 73.20, 73.13, 70.40, 70.09, 56.08, 56.01, 55.96, 51.30, 37.38, 37.28, 33.33, 28.88, 27.65, 19.54, 19.48, 19.15, 19.12, 18.21, 17.97, 17.93 |
| F72 | Colorless Semi-Solid | — | 3377, 2952, 2873, 1747, 1678, 1504, 1202, 1099 | HRMS-ESI (m/z) [M + H]⁺ calcd for $C_{28}H_{45}N_2O_{10}$, 569.3069; found, 569.3093 | ¹H NMR (CDCl₃) δ 8.31 (d, J = 8.2 Hz, 1H), 8.28 (d, J = 5.4 Hz, 1H), 6.95 (d, J = 5.3 Hz, 1H), 5.74 (s, 2H), 4.78 (dqt, J = 10.4, 6.5, 3.3 Hz, 1H), 4.60 (dt, J = 10.7, 7.6 Hz, 1H), 3.91 (s, 3H), 3.89-3.80 (m, 1H), 3.77-3.71 (m, 1H), 3.66 (dt, J = 9.2, 6.6 Hz, 1H), 3.50-3.24 (m, 8H), 3.12 (dt, J = 8.8, 6.3 Hz, 1H), 2.43-2.33 (m, 1H), 2.19-2.09 (m, 1H), 2.07 (s, 3H), 1.88-1.73 (m, 2H), 1.72-1.55 (m, 5H), 1.35-1.28 (m, 1H), 1.15 (dd, J = 6.1, 2.1 Hz, 3H), 0.92 (dd, J = 6.7, 1.9 Hz, 6H), 0.89-0.81 (m, 1H) | ¹³C NMR (CDCl₃) δ 172.67, 170.30, 162.96, 160.26, 145.74, 143.99, 142.42, 109.58, 89.55, 84.18, 83.95, 83.89, 75.84, 74.17, 73.70, 72.93, 72.86, 70.39, 70.08, 56.18, 56.00, 55.96, 51.63, 37.38, 37.28, 33.42, 28.87, 27.72, 20.88, 19.55, 19.49, 19.14, 19.12, 18.27, 17.96, 17.92 |
| F73 | White Solid | 61-63 | 3368, 2954, 1743, 1650, 1529, 1265 | HRMS-ESI (m/z) [M]⁺ calcd for $C_{26}H_{38}N_2O_7$, 490.2679; found, 490.2708 | ¹H NMR (CDCl₃) δ 12.09 (s, 1H), 8.50 (d, J = 8.2 Hz, 1H), 7.96 (d, J = 5.3 Hz, 1H), 6.86 (d, J = 5.2 Hz, 1H), 4.74 (dp, J = 12.9, 6.4 Hz, 1H), 4.58 (dt, J = 10.8, 7.6 Hz, 1H), 4.37-4.29 (m, 1H), 4.06-3.97 (m, 1H), 3.94 (s, 3H), 3.46-3.32 (m, 2H), 2.42-2.27 (m, 1H), 2.09 (dtd, J = 17.1, | ¹³C NMR (CDCl₃) δ 172.10, 168.62, 155.22, 148.60, 140.46, 130.28, 109.42, 83.24, 81.67, 80.96, 78.88, 73.66, 55.99, 51.27, 33.50, 33.24, 32.73, 32.41, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 7.8, 6.0, 3.2 Hz, 1H), 1.86-1.44 (m, 19H), 1.40 (d, J = 6.4 Hz, 3H), 0.90 (dd, J = 16.2, 7.2 Hz, 1H) | 31.68, 23.69, 23.46, 23.38, 23.31, 23.28, 18.50, 18.06 |
| F74 | White Solid | 91-93 | 3365, 2953, 1745, 1650, 1529, 1492, 1209 | HRMS-ESI (m/z) [M]$^+$ calcd for $C_{27}H_{34}N_2O_7$, 498.2366; found, 498.2355 | $^1$H NMR (CDCl$_3$) δ 12.08 (s, 1H), 8.50 (d, J = 8.0 Hz, 1H), 7.98 (d, J = 5.2 Hz, 1H), 7.30-7.21 (m, 2H), 7.11-7.03 (m, 2H), 6.98-6.90 (m, 1H), 6.86 (d, J = 5.2 Hz, 1H), 5.02 (dq, J = 9.7, 6.5 Hz, 1H), 4.62 (dt, J = 10.8, 7.6 Hz, 1H), 4.40 (dd, J = 9.5, 7.3 Hz, 1H), 3.99-3.92 (m, 1H), 3.93 (s, 3H), 3.66-3.58 (m, 1H), 2.47-2.31 (m, 1H), 2.25-2.09 (m, 1H), 1.91-1.37 (m, 9H), 1.36 (d, J = 6.3 Hz, 3H), 1.33-1.17 (m, 2H), 1.04 (dd, J = 16.1, 7.3 Hz, 1H) | $^{13}$C NMR (CDCl$_3$) δ 172.01, 168.68, 159.76, 155.33, 148.71, 140.53, 130.32, 129.26, 121.18, 116.23, 109.50, 82.55, 80.49, 79.68, 72.93, 56.06, 51.31, 33.37, 33.33, 31.76, 28.45, 23.40, 22.96, 18.55, 18.12 |
| F75 | White Solid | 68-70 | 3368, 2954, 1744, 1650, 1530, 1482, 1241 | HRMS-ESI (m/z) [M]$^+$ calcd for $C_{27}H_{34}N_2O_7$, 498.2366; found, 498.2360 | $^1$H NMR (CDCl$_3$) δ 12.07 (s, 1H), 8.48 (d, J = 8.1 Hz, 1H), 7.97 (d, J = 5.2 Hz, 1H), 7.31-7.22 (m, 2H), 6.98-6.89 (m, 3H), 6.85 (d, J = 5.2 Hz, 1H), 4.89 (dq, J = 9.6, 6.4 Hz, 1H), 4.63 (dt, J = 10.8, 7.6 Hz, 1H), 4.38-4.30 (m, 1H), 4.27 (tt, J = 5.3, 3.6 Hz, 1H), 3.93 (s, 3H), 3.74 (dd, J = 9.6, 7.1 Hz, 1H), 2.41-2.28 (m, 1H), 2.25-2.09 (m, 1H), 1.90-1.76 (m, 1H), 1.76-1.48 (m, 8H), 1.46 (d, J = 6.4 Hz, 3H), 1.44-1.28 (m, 2H), 1.03 (ddt, J = 16.2, 7.9, 1.8 Hz, 1H) | $^{13}$C NMR (CDCl$_3$) δ 172.02, 168.69, 157.57, 155.33, 148.71, 140.53, 130.33, 129.50, 121.21, 116.52, 109.50, 83.74, 82.77, 80.97, 73.29, 56.06, 51.27, 33.16, 32.89, 32.42, 28.09, 23.11, 18.22, 18.09 |
| F76 | Thick Yellow Oil | — | 3379, 2954, 1745, 1678, 1504, 1209 | HRMS-ESI (m/z) [M]$^+$ calcd for $C_{31}H_{46}N_2O_9$, 590.3203; found, 590.3216 | $^1$H NMR (CDCl$_3$) δ 8.38 (d, J = 8.1 Hz, 1H), 8.26 (d, J = 5.4 Hz, 1H), 6.94 (d, J = 5.4 Hz, 1H), 5.81-5.73 (m, 2H), 4.73 (dq, J = 8.7, 6.4 Hz, 1H), 4.60 (dt, J = 10.7, 7.5 Hz, 1H), 4.33 (ddd, J = 7.9, 4.2, 2.2 Hz, 1H), 4.02 (qd, J = 5.6, 4.1 Hz, 1H), 3.89 (s, 3H), 3.46-3.36 (m, 2H), 2.55 (hept, J = 7.0 Hz, 1H), 2.37 (dtd, J = 13.6, 6.8, 1.7 Hz, 1H), 2.16-2.01 (m, 1H), 1.85-1.44 (m, 18H), 1.38 (d, J = 6.4 Hz, 3H), 1.32 (dt, J = 10.8, | $^{13}$C NMR (CDCl$_3$) δ 176.21, 172.75, 162.92, 160.23, 145.58, 144.18, 142.09, 109.52, 89.90, 83.28, 81.82, 81.08, 78.94, 73.43, 56.12, 51.65, 33.84, 33.53, 33.47, 32.78, 32.44, 31.74, 28.39, 23.71, 23.41, 23.34, 23.31, 18.66, 18.60, 18.09 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 2.3 Hz, 1H), 1.14 (d, J = 7.0 Hz, 6H), 0.90 (ddt, J = 16.3, 7.5, 1.9 Hz, 1H) | |
| F77 | White Solid | 73-75 | 3379, 2953, 1772, 1679, 1508, 1198 | HRMS-ESI (m/z) [M]⁺ calcd for $C_{28}H_{40}N_2O_8$, 532.2785; found, 532.2807 | ¹H NMR (CDCl₃) δ 8.53 (d, J = 7.8 Hz, 1H), 8.32 (d, J = 5.4 Hz, 1H), 7.00 (d, J = 5.5 Hz, 1H), 4.72 (dq, J = 8.1, 6.2 Hz, 1H), 4.58 (ddd, J = 10.8, 8.4, 7.3 Hz, 1H), 4.32 (qd, J = 5.0, 3.3 Hz, 1H), 4.01 (qd, J = 5.4, 3.6 Hz, 1H), 3.90 (s, 3H), 3.46-3.34 (m, 2H), 2.40 (s, 3H), 2.39-2.30 (m, 1H), 2.14-2.01 (m, 1H), 1.85-1.43 (m, 18H), 1.37 (d, J = 6.4 Hz, 3H), 1.34-1.26 (m, 1H), 0.95-0.83 (m, 1H) | ¹³C NMR (CDCl₃) δ 172.65, 168.87, 162.37, 159.42, 146.68, 141.43, 137.47, 109.78, 83.30, 81.85, 81.07, 78.97, 73.46, 56.28, 51.38, 33.67, 33.52, 32.80, 32.45, 31.75, 28.41, 23.72, 23.41, 23.34, 23.31, 20.74, 18.57, 18.08 |
| F78 | Pale Yellow Oil | — | 3375, 2951, 1749, 1677, 1493, 1201 | HRMS-ESI (m/z) [M]⁺ calcd for $C_{30}H_{38}N_2O_9$, 570.2577; found, 570.2584 | ¹H NMR (CDCl₃) δ 8.33 (d, J = 8.0 Hz, 1H), 8.28 (d, J = 5.3 Hz, 1H), 7.30-7.22 (m, 2H), 7.10-7.04 (m, 2H), 6.98-6.90 (m, 2H), 5.77-5.71 (m, 2H), 5.00 (dq, J = 9.6, 6.4 Hz, 1H), 4.64 (dt, J = 10.8, 7.6 Hz, 1H), 4.39 (dd, J = 9.6, 7.4 Hz, 1H), 3.95 (tt, J = 5.4, 3.4 Hz, 1H), 3.91 (s, 3H), 3.61 (ddd, J = 7.2, 5.2, 1.8 Hz, 1H), 2.42 (dtd, J = 13.6, 6.8, 1.6 Hz, 1H), 2.25-2.09 (m, 1H), 2.07 (s, 3H), 1.86-1.49 (m, 5H), 1.49-1.35 (m, 5H), 1.34 (d, J = 6.4 Hz, 3H), 1.35-1.29 (m, 1H), 1.03 (ddt, J = 15.9, 7.6, 2.0 Hz, 1H) | ¹³C NMR (CDCl₃) δ 172.65, 170.30, 162.98, 160.28, 159.80, 145.73, 144.03, 142.37, 129.25, 121.13, 116.25, 109.62, 89.55, 82.62, 80.59, 79.69, 72.70, 56.19, 51.66, 33.47, 33.36, 31.77, 28.55, 23.40, 22.97, 20.88, 18.63, 18.12 |
| F79 | Pale Yellow Oil | — | 3375, 2944, 1745, 1676, 1492, 1205 | ESIMS m/z 599.3 ([M + H]⁺) | ¹H NMR (CDCl₃) δ 8.38 (d, J = 8.1 Hz, 1H), 8.27 (d, J = 5.3 Hz, 1H), 7.30-7.23 (m, 2H), 7.10-7.03 (m, 2H), 6.97-6.91 (m, 2H), 5.81-5.73 (m, 2H), 5.01 (dq, J = 9.6, 6.4 Hz, 1H), 4.63 (dt, J = 10.8, 7.6 Hz, 1H), 4.39 (dd, J = 9.6, 7.4 Hz, 1H), 3.95 (tt, J = 5.4, 3.4 Hz, 1H), 3.89 (s, 3H), 3.61 (ddd, J = 7.2, 5.2, 1.8 Hz, 1H), 2.55 (hept, J = 7.0 Hz, 1H), 2.42 (dtd, J = 13.6, 6.8, 1.6 Hz, 1H), 2.24-2.09 (m, 1H), 1.85-1.49 (m, 5H), 1.49-1.35 (m, 5H), 1.34 (d, J = 6.4 Hz, 3H), 1.34-1.28 (m, 1H), 1.14 | ¹³C NMR (CDCl₃) δ 176.26, 172.64, 162.95, 160.26, 159.80, 145.59, 144.24, 142.04, 129.25, 121.13, 116.25, 109.56, 89.90, 82.64, 80.59, 79.68, 72.68, 56.14, 51.65, 33.86, 33.48, 33.37, 31.77, 28.55, 23.40, 22.97, 18.68, 18.63, 18.12 |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | (d, J = 7.1 Hz, 6H), 1.04 (ddt, J = 15.9, 7.5, 1.9 Hz, 1H) | |
| F80 | White Solid | 148-149 | 3373, 2952, 1749, 1677, 1494, 1202 | HRMS-ESI (m/z) [M]$^+$ calcd for C$_{30}$H$_{38}$N$_2$O$_9$, 570.2577; found, 570.2577 | $^1$H NMR (CDCl$_3$) δ 8.31 (d, J = 8.1 Hz, 1H), 8.27 (d, J = 5.3 Hz, 1H), 7.31-7.23 (m, 2H), 6.99-6.89 (m, 4H), 5.74 (s, 2H), 4.87 (dq, J = 9.6, 6.4 Hz, 1H), 4.65 (dt, J = 10.8, 7.6 Hz, 1H), 4.33 (ddd, J = 7.0, 5.2, 1.7 Hz, 1H), 4.26 (td, J = 5.3, 2.8 Hz, 1H), 3.90 (s, 3H), 3.74 (dd, J = 9.6, 7.1 Hz, 1H), 2.36 (dt, J = 13.7, 7.0 Hz, 1H), 2.24-2.09 (m, 1H), 2.07 (s, 3H), 1.89-1.75 (m, 1H), 1.75-1.45 (m, 7H), 1.45 (d, J = 6.4 Hz, 3H), 1.45-1.36 (m, 2H), 1.35-1.25 (m, 1H), 1.03 (ddt, J = 16.0, 7.7, 1.8 Hz, 1H) | $^{13}$C NMR (CDCl$_3$) δ 172.64, 170.29, 162.99, 160.26, 157.62, 145.73, 143.99, 142.36, 129.48, 121.16, 116.55, 109.62, 89.52, 83.74, 82.87, 81.03, 73.03, 56.19, 51.61, 33.28, 32.89, 32.42, 28.16, 23.11, 20.88, 18.29, 18.09 |
| F81 | Thick Colorless Oil | — | 3373, 2952, 1746, 1679, 1493, 1198 | HRMS-ESI (m/z) [M]$^+$ calcd for C$_{29}$H$_{36}$N$_2$O$_8$, 540.2472; found, 540.2464 | $^1$H NMR (CDCl$_3$) δ 8.53 (d, J = 8.4 Hz, 1H), 8.34 (d, J = 5.4 Hz, 1H), 7.30-7.22 (m, 2H), 7.09-7.03 (m, 2H), 7.00 (d, J = 5.5 Hz, 1H), 6.97-6.92 (m, 1H), 5.00 (dq, J = 9.7, 6.4 Hz, 1H), 4.68-4.57 (m, 1H), 4.37 (dd, J = 9.7, 7.4 Hz, 1H), 3.98-3.92 (m, 1H), 3.91 (s, 3H), 3.60 (ddd, J = 7.3, 5.2, 1.8 Hz, 1H), 2.40 (s, 3H), 2.24-2.07 (m, 1H), 1.83-1.49 (m, 6H), 1.49-1.34 (m, 5H), 1.33 (d, J = 6.4 Hz, 3H), 1.34-1.28 (m, 1H); 1.07-0.99 (m, 1H) | $^{13}$C NMR (CDCl$_3$) δ 172.53, 168.90, 162.40, 159.79, 159.45, 146.69, 141.41, 137.52, 129.26, 121.13, 116.26, 109.81, 82.62, 80.60, 79.70, 72.71, 56.29, 51.37, 33.36, 31.77, 28.57, 23.40, 22.96, 20.75, 18.59, 18.10, 14.21 |
| F82 | Colorless Semi-Solid | — | 3367, 2954, 2872, 1744, 1650, 1508, 1207 | HRMS-ESI (m/z) [M + Na]$^+$ calcd for C$_{27}$H$_{36}$N$_2$NaO$_7$, 523.2415; found, 523.2409 | $^1$H NMR (600 MHz, CDCl$_3$) δ 12.06 (s, 1H), 8.48 (d, J = 8.1 Hz, 1H), 8.00 (d, J = 5.2 Hz, 1H), 7.06 (d, J = 8.6 Hz, 2H), 6.98 (d, J = 8.6 Hz, 2H), 6.87 (d, J = 5.3 Hz, 1H), 5.01 (dq, J = 9.5, 6.4 Hz, 1H), 4.61 (dt, J = 10.8, 7.7 Hz, 1H), 4.37 (dd, J = 9.6, 7.3 Hz, 1H), 3.94 (s, 3H), 3.54 (ddd, J = 7.2, 5.3, 1.7 Hz, 1H), 3.24 (dd, J = 8.8, 6.6 Hz, 1H), 3.08 (dd, J = 8.8, 6.2 Hz, 1H), 2.41 (dt, J = 13.7, 6.6 Hz, 1H), 2.29 (s, 3H), 2.27-2.16 (m, 1H), 1.87-1.66 (m, 3H), 1.47-1.37 (m, 1H), 1.35 (d, | $^{13}$C NMR (151 MHz, CDCl$_3$) δ 172.00, 168.67, 157.65, 155.37, 148.75, 140.53, 130.57, 130.39, 129.79, 116.32, 109.49, 83.12, 83.04, 76.45, 73.00, 56.08, 51.31, 33.39, 28.73, 27.90, 20.50, 19.40, 19.25, 18.29, 18.12 |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | J = 6.4 Hz, 3H), 1.07-0.99 (m, 1H), 0.81 (d, J = 6.7 Hz, 3H), 0.76 (d, J = 6.7 Hz, 3H) | |
| F83 | Brownish Semi-Solid | — | 3380, 2952, 2873, 1771, 1743, 1677, 1506, 1195 | HRMS-ESI (m/z) [M + H]$^+$ calcd for C$_{27}$H$_{43}$N$_2$O$_9$, 539.2963; found, 539.2984 | $^1$H NMR (CDCl$_3$) δ 8.52 (d, J = 8.9 Hz, 1H), 8.33 (d, J = 5.3 Hz, 1H), 7.00 (d, J = 5.2 Hz, 1H), 4.77 (ddd, J = 8.8, 6.0, 2.5 Hz, 1H), 4.59 (dt, J = 10.6, 7.8 Hz, 1H), 3.90 (s, 3H), 3.89-3.79 (m, 1H), 3.76-3.61 (m, 1H), 3.49-3.21 (m, 7H), 3.12 (dt, J = 8.8, 6.3 Hz, 1H), 2.40 (s, 3H), 2.38-2.30 (m, 1H), 2.17-2.02 (m, 1H), 1.91-1.48 (m, 5H), 1.42-1.35 (m, 3H), 1.30 (dtd, J = 13.8, 11.5, 2.0 Hz, 1H), 1.15 (dd, J = 6.1, 2.0 Hz, 3H), 0.95-0.88 (m, 6H), 0.87 (d, J = 7.7 Hz, 1H) | $^{13}$C NMR (CDCl$_3$) δ 172.54, 168.91, 162.38, 159.43, 146.69, 141.40, 137.48, 109.79, 84.19, 84.17, 84.11, 83.93, 83.87, 75.85, 74.17, 73.69, 72.93, 72.87, 70.38, 70.06, 56.29, 56.00, 55.95, 51.35, 37.38, 37.28, 33.61, 28.86, 27.73, 20.75, 19.54, 19.49, 19.14, 19.12, 18.23, 17.94, 17.90 |
| F84 | White Solid | — | 3367, 2954, 2871, 1737, 1650, 1529, 1157 | HRMS-ESI (m/z) [M + H]$^+$ calcd for C$_{28}$H$_{39}$N$_2$O$_9$, 547.2650; found, 547.2637 | $^1$H NMR (CDCl$_3$) δ 12.01 (s, 1H), 8.46 (d, J = 8.1 Hz, 1H), 7.99 (d, J = 5.2 Hz, 1H), 6.87 (d, J = 5.2 Hz, 1H), 5.28 (dd, J = 9.8, 8.1 Hz, 1H), 5.12-5.04 (m, 1H), 5.01 (ddd, J = 7.8, 5.4, 2.2 Hz, 1H), 4.66 (dt, J = 10.8, 7.6 Hz, 1H), 3.94 (s, 3H), 2.77-2.58 (m, 2H), 2.47-2.35 (m, 1H), 2.16 (dddd, J = 15.9, 10.1, 7.8, 5.4 Hz, 1H), 1.93-1.79 (m, 5H), 1.78-1.63 (m, 9H), 1.62-1.51 (m, 4H), 1.49-1.35 (m, 1H), 1.31 (d, J = 6.4 Hz, 3H), 1.19 (ddt, J = 16.4, 7.9, 2.3 Hz, 1H) | $^{13}$C NMR (CDCl$_3$) δ 175.81, 175.51, 171.83, 168.69, 155.37, 148.73, 140.56, 130.28, 109.52, 74.66, 73.70, 71.42, 56.09, 51.16, 43.87, 43.78, 33.12, 30.09, 30.00, 29.94, 29.80, 29.16, 25.77, 25.70, 18.11, 17.24 |
| F85 | White Solid | — | 3368, 2946, 2882, 1744, 1650, 1530, 1451, 1253 | HRMS-ESI (m/z) [M + H]$^+$ calcd for C$_{24}$H$_{33}$F$_6$N$_2$O$_7$, 575.2186; found, 575.2191 | $^1$H NMR (CDCl$_3$) δ 12.05 (s, 1H), 8.46 (d, J = 8.1 Hz, 1H), 7.99 (d, J = 5.2 Hz, 1H), 6.87 (d, J = 5.2 Hz, 1H), 4.80 (pd, J = 6.3, 1.9 Hz, 1H), 4.59 (dt, J = 10.8, 7.6 Hz, 1H), 3.94 (s, 3H), 3.80 (dt, J = 9.3, 6.1 Hz, 1H), 3.69 (dt, J = 9.3, 6.2 Hz, 1H), 3.58 (dt, J = 9.4, 6.4 Hz, 1H), 3.42-3.34 (m, 3H), 2.45-2.32 (m, 1H), 2.29-2.05 (m, 5H), 1.87-1.77 (m, 4H), 1.70-1.61 (m, 2H), 1.47-1.33 (m, 4H), 0.94 (dd, J = 16.2, 7.3 Hz, 1H) | $^{13}$C NMR (CDCl$_3$) δ 171.93, 168.69, 155.38, 148.75, 140.55, 130.34, 128.55, 125.80, 109.50, 84.14, 83.94, 72.86, 71.82, 66.89, 56.09, 51.23, 33.22, 30.77 (qd, J = 28.8, 1.3 Hz), 27.52, 22.96 (dd, J = 19.1, 3.0 Hz), 18.11, 17.90; $^{19}$F NMR (CDCl$_3$) δ |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| F86 | Colorless Semi-Solid | — | 2954, 1751, 1678, 1508 | HRMS-ESI (m/z) [M + H]⁺ calcd for $C_{30}H_{41}N_2O_9$, 573.2807; found, 573.2792 | ¹H NMR (CDCl₃) δ 8.32 (d, J = 8.1 Hz, 1H), 8.28 (d, J = 5.3 Hz, 1H), 7.06 (d, J = 8.5 Hz, 2H), 6.97 (d, J = 8.6 Hz, 2H), 6.95 (d, J = 5.4 Hz, 1H), 5.74 (s, 2H), 4.99 (dq, J = 9.6, 6.4 Hz, 1H), 4.63 (dt, J = 10.7, 7.6 Hz, 1H), 4.36 (dd, J = 9.6, 7.3 Hz, 1H), 3.91 (s, 3H), 3.53 (ddd, J = 7.1, 5.2, 1.7 Hz, 1H), 3.24 (dd, J = 8.8, 6.6 Hz, 1H), 3.08 (dd, J = 8.8, 6.2 Hz, 1H), 2.41 (dt, J = 13.8, 6.6 Hz, 1H), 2.29 (s, 3H), 2.24-2.13 (m, 1H), 2.07 (s, 3H), 1.86-1.65 (m, 3H), 1.43-1.35 (m, 1H), 1.34 (d, J = 6.5 Hz, 3H), 1.03 (dd, J = 16.1, 7.4 Hz, 1H), 0.78 (dd, J = 19.4, 6.7 Hz, 6H) | −66.37 (dt, J = 25.5, 11.2 Hz) ¹³C NMR (CDCl₃) δ 172.62, 170.31, 162.97, 160.28, 157.69, 145.73, 144.03, 142.38, 130.51, 129.77, 116.32, 109.61, 89.55, 83.18, 83.12, 76.42, 72.73, 56.19, 51.65, 33.46, 28.72, 27.96, 20.89, 20.50, 19.40, 19.26, 18.35, 18.12 |
| F87 | Colorless Semi-Solid | — | 2948, 1751, 1679, 1505, 1335 | HRMS-ESI (m/z) [M + H]⁺ calcd for $C_{27}H_{37}F_6N_2O_9$, 647.2398; found, 647.2414 | ¹H NMR (CDCl₃) δ 8.31 (d, J = 8.1 Hz, 1H), 8.28 (d, J = 5.3 Hz, 1H), 6.95 (d, J = 5.4 Hz, 1H), 5.74 (s, 2H), 4.83-4.74 (m, 1H), 4.61 (dt, J = 10.8, 7.5 Hz, 1H), 3.91 (s, 3H), 3.80 (dt, J = 9.3, 6.2 Hz, 1H), 3.68 (dt, J = 9.2, 6.1 Hz, 1H), 3.58 (dt, J = 9.3, 6.3 Hz, 1H), 3.42-3.33 (m, 3H), 2.42-2.34 (m, 1H), 2.26-2.05 (m, 6H), 2.07 (s, 3H), 1.88-1.78 (m, 4H), 1.71-1.60 (m, 1H), 1.38 (d, J = 6.3 Hz, 3H), 1.36-1.22 (m, 1H), 0.99-0.88 (m, 1H) | ¹³C NMR (CDCl₃) δ 172.55, 170.31, 163.00 160.28, 145.74, 144.03, 142.34, 109.62, 89.53, 84.21, 83.99, 72.59, 71.80, 66.87, 56.19, 51.57, 33.29, 30.78 (qd, J = 28.9, 2.1 Hz), 27.60, 23.25-22.60 (m), 20.88, 18.18, 17.89; ¹⁹F NMR CDCl₃) δ −66.38 (dt, J = 26.8, 11.1 Hz) |
| F88 | Colorless Semi-Solid | — | 2956, 2871, 1737, 1678, 1503, 1157 | HRMS-ESI (m/z) [M + H]⁺ calcd for $C_{31}H_{43}N_2O_{11}$, 619.2861; found, 619.2855 | ¹H NMR (CDCl₃) δ 8.32 (d, J = 7.9 Hz, 1H), 8.27 (d, J = 5.3 Hz, 1H), 6.95 (d, J = 5.4 Hz, 1H), 5.74 (s, 2H), 5.27 (dd, J = 9.8, 8.1 Hz, 1H), 5.12-4.95 (m, 2H), 4.67 (dt, J = 10.8, 7.6 Hz, 1H), 3.91 (s, 3H), 2.68 (dtt, J = 10.3, 8.6, 7.0 Hz, 2H), 2.41 (dt, J = 13.8, 7.1 Hz, 1H), 2.20-2.09 (m, 1H), 2.07 (s, 3H), 1.96-1.79 (m, 5H), 1.79-1.64 (m, 9H), 1.61-1.49 (m, 4H), 1.43-1.32 (m, 1H), | ¹³C NMR (CDCl₃) δ 175.85, 175.51, 172.43, 170.31, 162.99, 160.28, 145.72, 144.07, 142.22, 109.65, 89.53, 74.77, 73.79, 71.13, 56.20, 51.51, 43.89, 43.79, 33.18, 30.08, 30.01, 29.93, 29.80, 29.22, 25.77, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 1.29 (d, J = 6.4 Hz, 3H), 1.18 (ddt, J = 16.2, 7.9, 2.2 Hz, 1H) | 25.70, 20.88, 18.18, 17.24 |
| F89 | Yellow Oil | — | 3376, 2954, 2872, 1772, 1744, 1679, 1508, 1197 | HRMS-ESI (m/z) [M + H]$^+$ calcd for C$_{27}$H$_{43}$N$_2$O$_8$, 523.3014; found, 523.3055 | $^1$H NMR (CDCl$_3$) δ 8.52 (d, J = 8.2 Hz, 1H), 8.33 (d, J = 5.4 Hz, 1H), 7.00 (d, J = 5.5 Hz, 1H), 4.77 (ddq, J = 9.0, 6.2, 3.6 Hz, 1H), 4.67-4.50 (m, 1H), 3.90 (s, 3H), 3.80 (dt, J = 9.0, 6.5 Hz, 1H), 3.59 (dt, J = 8.9, 6.7 Hz, 1H), 3.42-3.21 (m, 3H), 3.12 (dd, J = 8.8, 6.3 Hz, 1H), 2.40 (s, 3H), 2.37-2.29 (m, 1H), 2.21-2.01 (m, 1H), 1.82 (dt, J = 13.1, 6.6 Hz, 2H), 1.69-1.55 (m, 3H), 1.43-1.19 (m, 8H), 1.00-0.78 (m, 10H) | $^{13}$C NMR (CDCl$_3$) δ 172.54, 168.91, 162.38, 159.42, 146.69, 141.42, 137.47, 109.78, 84.25, 83.82, 75.96, 73.87, 73.03, 56.28, 51.35, 33.64, 30.06, 28.86, 28.39, 27.78, 22.56, 20.75, 19.53, 19.48, 18.24, 17.88, 14.05 |
| F90 | Yellow Semi-Solid | — | 3379, 2946, 2881, 1772, 1744, 1508, 1147 | HRMS-ESI (m/z) [M + H]$^+$ calcd for C$_{26}$H$_{35}$F$_6$N$_2$O$_8$, 617.2292; found, 617.2297 | $^1$H NMR (CDCl$_3$) δ 8.49 (d, J = 8.2 Hz, 1H), 8.33 (d, J = 5.5 Hz, 1H), 7.00 (d, J = 5.5 Hz, 1H), 4.78 (dq, J = 8.4, 6.1 Hz, 1H), 4.59 (dt, J = 10.8, 7.7 Hz, 1H), 3.91 (s, 3H), 3.80 (dt, J = 9.3, 6.1 Hz, 1H), 3.68 (dt, J = 9.3, 6.2 Hz, 1H), 3.57 (dt, J = 9.3, 6.3 Hz, 1H), 3.43-3.19 (m, 3H), 2.40 (s, 3H), 2.40-2.27 (m, 1H), 2.23-1.97 (m, 5H), 1.88-1.67 (m, 4H), 1.67-1.49 (m, 2H), 1.37 (d, J = 6.3 Hz, 3H), 1.34-1.15 (m, 1H), 0.99-0.86 (m, 1H) | $^{13}$C NMR (CDCl$_3$) δ 172.43, 168.92, 162.43, 159.45, 146.70, 141.35, 137.51, 128.55, 109.83, 84.20, 83.98, 72.60, 71.79, 66.88, 56.30, 51.29, 33.51, 30.78 (qd, J = 29.3, 28.8, 1.4 Hz), 27.61, 22.94 (dt, J = 19.7, 2.9 Hz), 20.75, 18.13, 17.87; $^{19}$F NMR (CDCl$_3$) δ-66.38 (dt, J = 25.0, 11.1 Hz) |
| F91 | Colorless Semi-Solid | — | 3375, 2953, 2871, 1735, 1677, 1507, 1157 | HRMS-ESI (m/z) [M + H]$^+$ calcd for C$_{30}$H$_{41}$N$_2$O$_{10}$, 589.2756; found, 589.2769 | $^1$H NMR (CDCl$_3$) δ 8.49 (d, J = 8.2 Hz, 1H), 8.33 (d, J = 5.4 Hz, 1H), 7.01 (d, J = 5.5 Hz, 1H), 5.25 (dd, J = 9.8, 8.1 Hz, 1H), 5.11-4.92 (m, 2H), 4.66 (dt, J = 10.7, 7.7 Hz, 1H), 3.91 (s, 3H), 2.82-2.57 (m, 2H), 2.42-2.34 (m, 1H), 2.40 (s, 3H), 2.19-2.06 (m, 1H), 1.93-1.49 (m, 18H), 1.42-1.31 (m, 1H), 1.27 (dd, J = 12.1, 6.8 Hz, 3H), 1.17 (ddt, J = 16.1, 7.7, 2.3 Hz, 1H) | $^{13}$C NMR (CDCl$_3$) δ 175.83, 175.51, 172.31, 168.91, 162.42, 159.45, 146.69, 141.26, 137.52, 109.85, 74.74, 73.77, 71.15, 56.30, 51.21, 43.87, 43.78, 30.08, 30.00, 29.94, 29.79, 29.25, 25.77, 25.75, 25.69, 20.75, 18.14, 17.22 |
| F92 | Light Yellow Semi-Solid | — | 3376, 2954, 2872, 1770, | HRMS-ESI (m/z) [M + H]$^+$ calcd for | $^1$H NMR (CDCl$_3$) δ 8.53 (d, J = 8.5 Hz, 1H), 8.34 (d, J = 5.4 Hz, 1H), | $^{13}$C NMR (CDCl$_3$) δ 172.50, 168.92, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | 1744, 1506, 1195 | $C_{29}H_{39}N_2O_8$, 543.2701; found, 543.2698 | 7.09-7.02 (m, 2H), 7.03-6.94 (m, 3H), 4.99 (dq, J = 9.6, 6.4 Hz, 1H), 4.62 (dt, J = 10.7, 7.7 Hz, 1H), 4.34 (dd, J = 9.7, 7.3 Hz, 1H), 3.91 (s, 3H), 3.52 (ddd, J = 7.1, 5.2, 1.7 Hz, 1H), 3.23 (dd, J = 8.8, 6.6 Hz, 1H), 3.12-3.00 (m, 1H), 2.40 (s, 3H), 2.40-2.30 (m, 1H), 2.29 (s, 3H), 2.24-2.09 (m, 1H), 1.72 (ddt, J = 13.2, 9.5, 6.7 Hz, 3H), 1.62-1.53 (m, 1H), 1.37-1.28 (m, 3H), 1.07-0.96 (m, 1H), 0.85-0.71 (m, 6H) | 162.39, 159.43, 157.67, 146.70, 141.39, 137.50, 130.50, 129.76, 116.33, 109.80, 83.18, 83.10, 76.43, 72.73, 56.29, 51.36, 33.66, 28.71, 27.97, 20.75, 20.50, 19.39, 19.25, 18.31, 18.09 |
| F93 | White Foam | — | — | HRMS-ESI (m/z) [M + Na]⁺ calcd for $C_{33}H_{43}NNaO_8$, 604.2881; found, 604.2874 | ¹H NMR (CDCl₃) δ 7.37-7.25 (m, 10H), 5.89 (dd, J = 18.1, 10.3 Hz, 1H), 5.60 (t, J = 10.2 Hz, 1H), 5.02 (d, J = 10.9 Hz, 1H), 4.95-4.81 (m, 1H), 4.66-4.48 (m, 3H), 4.43 (d, J = 11.6 Hz, 1H), 4.08 (t, J = 9.2 Hz, 1H), 3.41 (t, J = 9.0 Hz, 1H), 3.14 (q, J = 12.0 Hz, 1H), 2.37 (dd, J = 12.3, 7.4 Hz, 1H), 1.49 (s, 18H), 1.33 (d, J = 6.3 Hz, 3H) | ¹³C NMR (CDCl₃) δ 170.26, 152.74, 138.49, 138.31, 135.57, 128.54, 128.32, 128.30, 128.23, 127.69, 127.56, 127.44, 83.80, 82.89, 77.68, 75.28, 74.28, 70.89, 56.96, 33.02, 27.97, 19.17 |
| F94 | White Foam | — | — | HRMS-ESI (m/z) [M + H]⁺ calcd for $C_{27}H_{37}N_2O_7$, 501.2595; found, 501.2603 | ¹H NMR (CDCl₃) δ 12.10-12.02 (m, 1H), 8.47 (d, J = 8.1 Hz, 1H), 7.98 (dd, J = 5.2, 0.9 Hz, 1H), 7.32-7.24 (m, 2H), 6.93 (dddd, J = 12.2, 9.6, 8.3, 4.1 Hz, 3H), 6.86 (d, J = 5.2 Hz, 1H), 4.91 (tq, J = 9.0, 6.4 Hz, 1H), 4.63 (dtd, J = 11.4, 7.7, 3.9 Hz, 1H), 4.40 (dt, J = 18.8, 5.4 Hz, 1H), 3.93 (s, 3H), 3.86-3.71 (m, 1H), 3.63 (dt, J = 9.0, 6.7 Hz, 2H), 2.35 (dq, J = 14.9, 7.4 Hz, 1H), 2.30-2.10 (m, 1H), 1.89-1.75 (m, 1H), 1.67-1.55 (m, 1H), 1.55-1.42 (m, 5H), 1.40-1.28 (m, 1H), 1.28-1.17 (m, 3H), 1.05 (dd, J = 16.1, 7.8 Hz, 1H), 0.87 (t, J = 7.5 Hz, 1H), 0.83-0.77 (m, 2H), 0.69 (t, J = 7.4 Hz, 1H) | ¹³C NMR (CDCl₃) δ 171.97, 168.69, 157.62 155.35, 148.73, 140.54, 130.35, 129.50, 121.29, 116.63, 109.49, 83.40, 83.03, 73.98, 73.04, 56.07, 51.24 33.22, 29.95, 28.24, 22.44, 18.21, 17.93, 13.96, 9.42, 9.21 |
| F95 | Tacky White Foam | — | — | HRMS-ESI (m/z) [M + H]⁺ calcd for | ¹H NMR (CDCl₃) δ 8.31 (d, J = 8.0 Hz, 1H), 8.27 (d, J = 5.4 Hz, 1H), | ¹³C NMR (CDCl₃) δ 172.57, 170.27, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | $C_{28}H_{37}N_2O_9$, 545.2494; found, 545.2506 | 7.32-7.22 (m, 2H), 7.02-6.86 (m, 4H), 5.74 (s, 2H), 4.91 (dq, J = 9.7, 6.4 Hz, 1H), 4.65 (dt, J = 10.7, 7.6 Hz, 1H), 4.37 (t, J = 5.5 Hz, 1H), 3.90 (s, 3H), 3.73 (dt, J = 8.9, 6.5 Hz, 1H), 3.68-3.52 (m, 2H), 2.37 (dt, J = 13.6, 7.0 Hz, 1H), 2.25-2.09 (m, 1H), 2.07 (s, 3H), 1.85-1.76 (m, 1H), 1.64 (dq, J = 15.4, 7.5 Hz, 1H), 1.56-1.41 (m, 5H), 1.37-1.26 (m, 1H), 1.05 (dd, J = 16.1, 7.8 Hz, 1H), 0.83 (t, J = 7.4 Hz, 3H) | 163.00, 160.27, 157.68, 145.74, 143.99, 142.35, 129.48, 121.25, 116.69, 109.64, 89.51, 83.41, 83.19, 75.57, 72.77, 56.19, 51.58, 33.29, 28.32, 23.43, 20.88, 18.27, 17.92, 10.60 |
| F96 | Tacky White Foam | — | — | HRMS-ESI (m/z) [M + Na]⁺ calcd for $C_{30}H_{40}N_2NaO_9$, 595.2626; found, 595.2659 | ¹H NMR (CDCl₃) δ 8.31 (d, J = 8.0 Hz, 1H), 8.27 (dd, J = 5.4, 0.8 Hz, 1H), 7.31-7.22 (m, 2H), 6.98-6.84 (m, 4H), 5.74 (s, 2H), 4.96-4.82 (m, 1H), 4.65 (dtd, J = 11.4, 7.6, 4.0 Hz, 1H), 4.39 (dt, J = 18.7, 5.4 Hz, 1H), 3.90 (s, 3H), 3.85-3.70 (m, 1H), 3.62 (ddd, J = 9.0, 7.0, 5.1 Hz, 2H), 2.36 (dq, J = 14.3, 7.3 Hz, 1H), 2.28-2.10 (m, 1H), 2.07 (s, 3H), 1.89-1.75 (m, 1H), 1.64 (ddt, J = 15.0, 11.7, 7.4 Hz, 1H), 1.54-1.42 (m, 5H), 1.36-1.27 (m, 1H), 1.26 (s, 3H), 1.10-0.99 (m, 1H), 0.86 (t, J = 7.5 Hz, 1H), 0.83-0.76 (m, 2H), 0.69 (t, J = 7.4 Hz, 1H) | ¹³C NMR (CDCl₃) δ 172.57, 170.27, 162.99, 160.26, 157.67, 145.73, 143.99, 142.35, 129.47, 121.23, 116.64, 109.63, 89.51, 83.45, 83.12, 73.95, 72.76, 56.19, 51.58, 33.29, 29.95, 28.24, 25.30, 22.43, 20.87, 18.28, 17.92, 13.96, 9.41, 9.20 |
| F97 | Tacky White Foam | — | — | HRMS-ESI (m/z) [M + H]⁺ calcd for $C_{30}H_{41}N_2O_9$, 573.2807; found, 573.2795 | ¹H NMR (CDCl₃) δ 8.37 (d, J = 8.1 Hz, 1H), 8.26 (d, J = 5.4 Hz, 1H), 7.32-7.20 (m, 2H), 6.99-6.88 (m, 4H), 5.81-5.72 (m, 2H), 4.91 (dq, J = 9.6, 6.4 Hz, 1H), 4.65 (dt, J = 10.7, 7.6 Hz, 1H), 4.37 (t, J = 5.4 Hz, 1H), 3.88 (s, 3H), 3.73 (dt, J = 8.9, 6.5 Hz, 1H), 3.67-3.53 (m, 2H), 2.55 (p, J = 7.0 Hz, 1H), 2.37 (dt, J = 13.6, 7.0 Hz, 1H), 2.16 (dddd, J = 15.7, 10.1, 6.4, 4.0 Hz, 1H), 1.88-1.78 (m, 1H), 1.63 (tt, J = 16.0, 8.2 Hz, 1H) 1.55-1.41 (m, 5H), 1.36-1.23 (m, 1H), 1.14 (d, J = 7.0 Hz, 6H), 1.05 (dd, J = 16.1, 7.8 Hz, 1H), | ¹³C NMR (CDCl₃) δ 176.24, 172.56, 162.97, 160.24, 157.68, 145.60, 144.20, 142.01, 129.48, 121.24, 116.68, 109.57, 89.87, 83.41, 83.19, 75.57, 72.75, 56.14, 51.57, 33.85, 33.30, 28.31, 23.43, 18.67, 18.27, 17.92, 10.59 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| F98 | Tacky White Foam | — | — | HRMS-ESI (m/z) [M + H]⁺ calcd for $C_{32}H_{45}N_2O_9$, 601.3120; found, 601.3131 | ¹H NMR (CDCl₃) δ 8.37 (d, J = 8.1 Hz, 1H), 8.26 (dd, J = 5.4, 0.9 Hz, 1H), 7.31-7.20 (m, 2H), 6.99-6.84 (m, 4H), 5.83-5.73 (m, 2H), 4.96-4.80 (m, 1H), 4.64 (dtd, J = 11.3, 7.6, 3.9 Hz, 1H), 4.39 (dt, J = 18.7, 5.5 Hz, 1H), 3.88 (s, 3H), 3.84-3.72 (m, 1H), 3.62 (ddd, J = 9.0, 6.9, 5.4 Hz, 2H), 2.62-2.47 (m, 1H), 2.36 (dq, J = 14.3, 7.3 Hz, 1H), 2.26-2.08 (m, 1H), 1.88-1.74 (m, 1H), 1.64 (ddt, J = 14.8, 11.5, 7.3 Hz, 1H), 1.53-1.40 (m, 5H), 1.36-1.26 (m, 1H), 1.23 (td, J = 8.2, 6.7, 4.6 Hz, 3H), 1.14 (d, J = 7.0 Hz, 6H), 1.10-1.00 (m, 1H), 0.86 (t, J = 7.5 Hz, 1H), 0.83-0.76 (m, 2H), 0.69 (t, J = 7.4 Hz, 1H) 0.83 (t, J = 7.4 Hz, 3H), | ¹³C NMR (CDCl₃) δ 176.24, 172.57, 162.97, 160.24, 157.67, 145.60, 144.20, 142.02, 129.47, 121.22, 116.63, 109.58, 89.87, 83.46, 83.11, 73.95, 72.75, 56.14, 51.57, 33.85, 33.30, 29.95, 28.33, 28.24, 25.32, 25.30, 22.43, 18.68, 18.28, 17.92, 13.96, 9.41, 9.20 |
| F99 | Yellow Semi-Solid | — | 3376, 2955, 2872, 1738, 1679, 1504, 1157 | HRMS-ESI (m/z) [M + H]⁺ calcd for $C_{33}H_{47}N_2O_{11}$, 647.3174; found 647.3187 | ¹H NMR (CDCl₃) δ 8.37 (d, J = 8.0 Hz, 1H), 8.27 (d, J = 5.3 Hz, 1H), 6.94 (d, J = 5.4 Hz, 1H), 5.81-5.72 (m, 2H), 5.27 (dd, J = 9.8, 8.1 Hz, 1H), 5.11-4.95 (m, 2H), 4.66 (dt, J = 10.8, 7.6 Hz, 1H), 3.89 (s, 3H), 2.74-2.62 (m, 2H), 2.55 (p, J = 7.0 Hz, 1H), 2.40 (dt, J = 13.8, 7.1 Hz, 1H), 2.22-2.04 (m, 1H), 1.96-1.79 (m, 6H), 1.78-1.67 (m, 8H), 1.60-1.50 (m, 5H), 1.45-1.34 (m, 1H), 1.29 (d, J = 6.3 Hz, 3H), 1.14 (d, J = 7.0 Hz, 6H) | ¹³C NMR (CDCl₃) δ 176.28, 175.84, 175.51, 172.42, 162.97, 160.26, 145.58, 144.27, 141.89, 109.60, 89.87, 74.78, 73.79, 71.11, 56.14, 51.51, 43.89, 43.79, 33.86, 33.17, 30.08, 30.00, 29.93, 29.79, 29.21, 25.77, 25.75, 25.70, 18.68, 18.18, 17.24 |
| F100 | Colorless Semi-Solid | — | 3382, 2943, 2880, 1746, 1678, 1504, 1253, 1103 | HRMS-ESI (m/z) [M + H]⁺ calcd for $C_{29}H_{41}F_6N_2O_9$, 675.2711; found, 675.2713 | ¹H NMR (CDCl₃) δ 8.36 (d, J = 8.0 Hz, 1H), 8.27 (d, J = 5.3 Hz, 1H), 6.94 (d, J = 5.4 Hz, 1H), 5.84-5.72 (m, 2H), 4.78 (pd, J = 6.4, 2.2 Hz, 1H), 4.60 (dt, J = 10.7, 10.7, 7.5 Hz, 1H), 3.89 (s, 3H), 3.80 (dt, J = 9.3, 6.1 Hz, 1H), 3.68 (dt, J = 9.1, 6.2 Hz, 1H), 3.58 (dt, J = 9.1, 6.3 Hz, 1H), 3.42-3.31 (m, 3H), 2.55 (p, J = 7.0 Hz, 1H), 2.42-2.32 (m, 1H), 2.26-2.06 (m, 5H), 1.86-1.79 (m, 4H), 1.72-1.58 (m, 2H), | ¹³C NMR (CDCl₃) δ 176.28, 172.55, 163.00, 160.28, 145.63, 144.24, 142.01, 127.21 (q, J = 276.0 Hz), 109.61, 89.89, 84.22, 84.01, 72.59, 71.81, 66.87, 56.16, 51.58, 33.87, 33.30, 30.79 (qd, J = 28.7, 2.1 Hz), 27.60, 22.97 (dd, J = 19.7, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1.39 (d, J = 6.3 Hz, 3H), 1.35-1.28 (m, 1H), 1.14 (d, J = 7.0 Hz, 6H), 1.00-0.88 (m, 1H) | 2.9 Hz), 18.68, 18.20, 17.90; ¹⁹F NMR (CDCl₃) δ-66.40 (dt, J = 25.3, 11.2 Hz) |
| F101 | Colorless Semi-Solid | — | 3377, 2954, 2874, 1745, 1677, 1506, 1205 | HRMS-ESI (m/z) [M + H]⁺ calcd for C₃₂H₄₅N₂O₉, 601.3120; found, 601.3105 | ¹H NMR (CDCl₃) δ 8.38 (d, J = 8.0 Hz, 1H), 8.27 (d, J = 5.3 Hz, 1H), 7.06 (d, J = 8.4 Hz, 2H), 6.98 (d, J = 8.6 Hz, 2H), 6.94 (d, J = 5.4 Hz, 1H), 5.87-5.69 (m, 2H), 4.99 (dq, J = 9.6, 6.4 Hz, 1H), 4.63 (dt, J = 10.8, 7.5 Hz, 1H), 4.36 (dd, J = 9.6, 7.3 Hz, 1H), 3.89 (s, 3H), 3.53 (ddd, J = 7.2, 5.2, 1.7 Hz, 1H), 3.24 (dd, J = 8.8, 6.7 Hz, 1H), 3.08 (dd, J = 8.8, 6.2 Hz, 1H), 2.55 (p, J = 7.0 Hz, 1H), 2.48-2.35 (m, 1H), 2.29 (s, 3H), 2.19 (dddd, J = 15.7, 10.3, 8.3, 5.3 Hz, 1H), 1.77-1.61 (m, 3H), 1.42-1.27 (m, 4H), 1.14 (d, J = 7.0 Hz, 6H), 1.07-0.96 (m, 1H), 0.78 (dd, J = 19.4, 6.7 Hz, 6H) | ¹³C NMR (CDCl₃) δ 176.26, 172.61, 162.95, 160.25, 157.69, 145.60, 144.22, 142.03, 130.49, 129.76, 116.32, 116.29, 109.57, 89.88, 83.18, 83.11, 76.41, 72.70, 56.14, 51.64, 33.85, 33.44, 28.71, 27.94, 20.50, 19.40, 19.25, 18.68, 18.36, 18.11 |
| F102 | White Foam | — | — | HRMS-ESI (m/z) [M + Na]⁺ calcd for C₂₇H₃₄N₂NaO₉, 537.2207; found, 537.2210 | ¹H NMR (CDCl₃) δ 8.52 (d, J = 6.7 Hz, 1H), 8.32 (d, J = 5.4 Hz, 1H), 7.27 (t, J = 7.9 Hz, 2H), 6.99 (d, J = 5.5 Hz, 1H), 6.95 (t, J = 8.7 Hz, 3H), 4.96-4.84 (m, 1H), 4.64 (dt, J = 10.5, 7.9 Hz, 1H), 4.36 (t, J = 5.5 Hz, 1H), 3.89 (s, 3H), 3.73 (dt, J = 8.7, 6.5 Hz, 1H), 3.67-3.51 (m, 2H), 2.47-2.26 (m, 4H), 2.23-2.07 (m, 1H), 1.86-1.74 (m, 1H), 1.62 (dq, J = 16.4, 9.0, 8.4 Hz, 1H), 1.55-1.40 (m, 5H), 1.33-1.23 (m, 1H), 1.04 (dd, J = 16.0, 7.7 Hz, 1H), 0.83 (t, J = 7.4 Hz, 3H) | ¹³C NMR (CDCl₃) δ 172.45, 168.89, 162.42, 159.44, 157.68, 146.70, 141.35, 137.49, 129.48, 121.25, 116.68, 109.83, 83.40, 83.20, 75.57, 72.78, 56.29, 51.30, 33.50, 28.34, 23.43, 20.74, 18.24, 17.90, 10.59 |
| F103 | White Foam | — | — | HRMS-ESI (m/z) [M + Na]⁺ calcd for C₂₉H₃₈N₂NaO₉, 560.2966; found, 560.2954 | ¹H NMR (CDCl₃) δ 8.52 (d, J = 6.6 Hz, 1H), 8.32 (d, J = 5.4 Hz, 1H), 7.32-7.23 (m, 1H), 7.00 (d, J = 5.5 Hz, 1H), 6.97-6.85 (m, 3H), 4.88 (dtd, J = 9.5, 6.4, 3.2 Hz, 1H), 4.63 (ddq, J = 11.6, 8.0, 4.1 Hz, 1H), 4.39 (dt, J = 18.8, 18.8, 5.5 Hz, 1H), 3.90 (s, 3H), 3.77 (ddt, J = 13.0, 8.9, 6.7 Hz, 1H), | ¹³C NMR (CDCl₃) δ 172.45, 168.89, 162.42, 159.44, 157.67, 146.69, 141.36, 137.50, 129.47, 121.23, 116.64, 109.82, 83.44, 83.13, 73.95, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 3.66-3.57 (m, 2H), 2.40 (s, 4H), 2.27-2.07 (m, 1H), 1.86-1.71 (m, 1H), 1.69-1.56 (m, 1H), 1.46 (dd, J = 13.0, 13.0, 5.7 Hz, 5H), 1.31-1.17 (m, 5H), 1.10-0.94 (m, 1H), 0.86 (t, J = 7.5 Hz, 1H), 0.83-0.76 (m, 2H), 0.68 (t, J = 7.4 Hz, 1H) | 72.77, 56.28, 51.29, 33.51, 29.95, 28.24, 25.30, 22.43, 20.74, 17.89, 13.95, 9.19 |
| F104 | White Foam | — | — | HRMS-ESI (m/z) [M + H]⁺ calcd for $C_{26}H_{30}F_3N_2O_7$, 540.2032; found 540.2038 | ¹H NMR (CDCl₃) δ 12.04 (d, J = 0.5 Hz, 1H), 8.46 (d, J = 8.1 Hz, 1H), 7.98 (d, J = 5.2 Hz, 1H), 7.31-7.24 (m, 2H), 7.03-6.94 (m, 1H), 6.91 (dd, J = 8.7, 1.0 Hz, 2H), 6.87 (d, J = 5.2 Hz, 1H), 6.33 (ddq, J = 15.7, 4.2, 2.1 Hz, 1H), 5.89-5.74 (m, 1H), 4.98 (dq, J = 9.6, 6.4 Hz, 1H), 4.64 (dt, J = 10.7, 7.6 Hz, 1H), 4.51-4.39 (m, 2H), 4.35-4.24 (m, 1H), 3.94 (s, 3H), 3.74 (dd, J = 9.6, 7.2 Hz, 1H), 2.37 (dt, J = 13.6, 7.1 Hz, 1H), 2.20 (tdd, J = 13.3, 6.3, 3.9 Hz, 1H), 1.90-1.75 (m, 1H), 1.73-1.62 (m, 1H), 1.47 (d, J = 6.4 Hz, 3H), 1.43-1.31 (m, 1H), 1.09 (dd, J = 16.2, 7.8 Hz, 1H) | ¹³C NMR (CDCl₃) δ 171.88, 168.72, 157.08, 155.37, 148.74, 140.56, 6.39 (q, J = 6.4 Hz), 130.29, 129.66, 125.64 (q, J = 269.1 Hz), 121.67, 118.43 (q, J = 34.1 Hz), 116.55, 109.53, 83.80, 82.70, 72.39, 71.00, 56.08, 51.20, 33.12, 28.16, 18.17, 17.98 |
| F105 | White Solid | — | — | HRMS-ESI (m/z) [M + Na]⁺ calcd for $C_{26}H_{31}F_3N_2NaO_7$, 563.1976; found, 563.2009 | ¹H NMR (CDCl₃) δ 12.04 (s, 1H), 8.46 (d, J = 8.1 Hz, 1H), 7.98 (d, J = 5.2 Hz, 1H), 7.32-7.28 (m, 1H), 6.97 (t, J = 7.4 Hz, 1H), 6.93-6.89 (m, 2H), 6.87 (d, J = 5.2 Hz, 1H), 4.93 (dq, J = 9.6, 6.4 Hz, 1H), 4.64 (dt, J = 10.7, 7.6 Hz, 1H), 4.38 (t, J = 5.5 Hz, 1H), 3.94 (s, 3H), 3.80 (dt, J = 9.1, 6.1 Hz, 1H), 3.71 (dt, J = 9.2, 5.9 Hz, 1H), 3.65 (dd, J = 9.6, 7.2 Hz, 1H), 2.36 (dt, J = 13.7, 7.0 Hz, 1H), 2.27-2.13 (m, 1H), 2.03 (dddd, J = 29.6, 14.8, 11.3, 6.9, 3.3 Hz, 2H), 1.90-1.76 (m, 1H), 1.76-1.59 (m, 4H), 1.46 (d, J = 6.4 Hz, 3H), 1.42-1.29 (m, 1H), 1.07 (dd, J = 16.1, 7.8 Hz, 1H) | ¹³C NMR (CDCl₃) δ 171.93, 168.70, 157.30, 155.37, 148.74, 140.55, 130.31, 129.61, 127.14 (q, J = 276.0 Hz), 121.45, 116.31, 109.51, 83.63, 82.48, 72.70, 71.85, 56.08, 51.22, 33.17, 30.54 (q, J = 28.9 Hz), 28.25, 22.93 (q, J = 2.7 Hz), 18.16, 17.93 |
| F106 | Clear Tacky Solid | — | — | HRMS-ESI (m/z) [M + H]⁺ calcd for $C_{29}H_{34}F_3N_2O_9$, | ¹H NMR (CDCl₃) δ 8.32 (d, J = 8.0 Hz, 1H), 8.27 (d, J = 5.4 Hz, 1H), 7.31-7.23 (m, 2H), | ¹³C NMR (CDCl₃) δ 172.48, 170.28, 163.02, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | 611.2211 found 611.2213 | 7.01-6.87 (m, 4H), 6.32 (ddq, J = 15.7, 4.1, 2.1 Hz, 1H), 5.88-5.75 (m, 1H), 5.74 (s, 2H), 4.96 (dq, J = 9.7, 6.4 Hz, 1H), 4.66 (dt, J = 10.7, 7.6 Hz, 1H), 4.51-4.37 (m, 2H), 4.33-4.24 (m, 1H), 3.91 (s, 3H), 3.73 (dd, J = 9.6, 7.2 Hz, 1H), 2.37 (dt, J = 13.6, 13.6, 7.0 Hz, 1H), 2.28-2.11 (m, 1H), 2.07 (s, 3H), 1.80 (s, 1H), 1.64 (dq, J = 15.5, 7.7 Hz, 1H), 1.46 (d, J = 6.4 Hz, 3H), 1.32 (q, J = 11.1 HZ, 1H), 1.08 (dd, J = 16.2, 7.7 Hz, 1H) | 160.28, 157.14, 145.74, 144.01, 142.27, 136.45 (q, J = 6.4 Hz), 129.62, 122.98 (q, J = 269.2 Hz), 121.60, 118.36 (q, J = 34.1 Hz), 116.56, 109.67, 89.48, 83.87, 82.77, 72.12, 70.99, 56.19, 51.55, 33.17, 28.23, 20.86, 18.24, 17.96 |
| F107 | Off-White Solid | — | — | HRMS-ESI (m/z) [M + H]⁺ calcd for $C_{29}H_{36}F_3N_2O_9$, 613.2367; found, 613.2398 | ¹H NMR (CDCl₃) δ 8.31 (d, J = 8.0 Hz, 1H), 8.27 (d, J = 5.4 Hz, 1H), 7.34-7.20 (m, 2H), 7.01-6.88 (m, 4H), 5.74 (s, 2H), 4.91 (dq, J = 9.6, 6.4 Hz, 1H), 4.65 (dt, J = 10.7, 7.6 Hz, 1H), 4.37 (t, J = 5.5 Hz, 1H), 3.91 (s, 3H), 3.79 (dt, J = 9.1, 6.1 Hz, 1H), 3.71 (dt, J = 9.2, 5.9 Hz, 1H), 3.64 (dd, J = 9.6, 7.3 Hz, 1H), 2.37 (dt, J = 13.7, 7.0 Hz, 1H), 2.26-2.12 (m, 1H), 2.10-1.89 (m, 5H), 1.85-1.61 (m, 4H), 1.44 (d, J = 6.4 Hz, 3H), 1.31 (q, J = 11.1 Hz, 1H), 1.07 (dd, J = 16.1, 7.8 Hz, 1H) | ¹³C NMR (CDCl₃) δ 172.54, 170.28, 163.01, 160.28, 157.36, 145.73, 144.01, 142.30, 129.59, 127.15 (q, J = 276.0 Hz), 121.38, 116.32, 109.65, 89.51, 83.68, 82.56, 72.42, 71.83, 56.19, 51.56, 33.24, 30.69 (q, J = 29.0 Hz), 28.33, 22.93 (q, J = 2.9 Hz), 20.87, 18.24, 17.92 |
| F108 | Clear Tacky Solid | — | — | HRMS-ESI (m/z) [M + H]⁺ calcd for $C_{31}H_{40}F_3N_2O_9$, 641.2680; found, 641.2686 | ¹H NMR (CDCl₃) δ 8.37 (d, J = 8.0 Hz, 1H), 8.26 (d, J = 5.4 Hz, 1H), 7.32-7.21 (m, 2H), 7.00-6.87 (m, 4H), 5.77 (d, J = 1.5 Hz, 2H), 4.91 (dq, J = 9.6, 6.4 Hz, 1H), 4.65 (dt, J = 10.7, 7.6 Hz, 1H), 4.37 (t, J = 5.5 Hz, 1H), 3.89 (s, 3H), 3.75 (ddt, J = 33.0, 9.2, 6.0 Hz, 2H), 3.64 (dd, J = 9.6, 7.3 Hz, 1H), 2.55 (hept, J = 7.0 Hz, 1H), 2.36 (dt, J = 13.6, 7.0 Hz, 1H), 2.24-2.10 (m, 1H), 2.02 (ddddt, J = 29.4, 15.3, 11.0, 7.5, 3.4 Hz, 2H), 1.85-1.62 (m, 4H), 1.44 (d, J = 6.4 Hz, 3H), 1.40-1.24 (m, 1H), 1.14 (d, J = 7.0 Hz, 6H), 1.07 (dd, J = 16.1, 7.8 Hz, 1H) | ¹³C NMR (CDCl₃) δ 176.25, 172.53, 162.98, 160.26, 157.36, 145.60, 144.23, 141.97, 129.58, 127.15 (q, J = 276.1 Hz), 121.38, 116.32, 109.58, 89.87, 83.69, 82.56, 72.40, 71.83, 56.14, 51.56, 33.85, 33.25, 30.69 (q, J = 29.0 Hz), 28.32, 22.93 (q, J = 2.9 Hz), 18.67, 18.24, 17.92 |
| F109 | White Foam | — | — | HRMS-ESI (m/z) | ¹H NMR (CDCl₃) δ 8.52 (d, J = 7.6 Hz, | ¹³C NMR (CDCl₃) δ |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | [M + H]$^+$ calcd for C$_{28}$H$_{34}$F$_3$N$_2$O$_8$, 583.2262; found, 583.2270 | 1H), 8.32 (d, J = 5.4 Hz, 1H), 7.32-7.22 (m, 2H), 7.00 (d, J = 5.5 Hz, 1H), 6.98-6.93 (m, 1H), 6.91 (dd, J = 8.7, 1.0 Hz, 2H), 4.91 (dq, J = 9.6, 6.4 Hz, 1H), 4.64 (dt, J = 10.7, 7.6 Hz, 1H), 4.41-4.33 (m, 1H), 3.90 (s, 3H), 3.74 (ddt, J = 33.5, 9.2, 6.0 Hz, 2H), 3.62 (dd, J = 9.6, 7.2 Hz, 1H), 2.40 (s, 3H), 2.35 (dt, J = 13.5, 7.0 Hz, 1H), 2.16 (dddd, J = 15.8, 10.1, 6.2, 3.8 Hz, 1H), 2.10-1.88 (m, 2H), 1.82-1.59 (m, 4H), 1.43 (d, J = 6.4 Hz, 3H), 1.34-1.23 (m, 1H), 1.06 (dd, J = 16.1, 7.7 Hz, 1H) | 172.42, 168.89, 162.44, 159.45, 157.36, 146.70, 141.32, 137.51, 129.59, 127.15 (q, J = 276.0 Hz), 121.39, 116.32, 109.85, 83.67, 82.56, 72.43, 71.82, 56.29, 51.28, 33.46, 30.69 (q, J = 28.9 Hz), 28.36, 22.93 (q, J = 3.0 Hz), 20.74, 18.20, 17.90 |
| F110 | White Foam | — | — | HRMS-ESI (m/z) [M + H]$^+$ calcd for C$_{30}$H$_{38}$F$_3$N$_2$O$_9$, 627.2524; found, 627.2539 | $^1$H NMR (CDCl$_3$) δ 8.50 (d, J = 7.2 Hz, 1H), 8.32 (d, J = 5.4 Hz, 1H), 7.32-7.20 (m, 2H), 7.01-6.93 (m, 2H), 6.90 (dd, J = 8.7, 1.0 Hz, 2H), 4.90 (dq, J = 9.6, 6.4 Hz, 1H), 4.63 (dt, J = 10.7, 7.6 Hz, 1H), 4.37 (t, J = 5.4 Hz, 1H), 3.89 (s, 3H), 3.85-3.75 (m, 3H), 3.74-3.66 (m, 1H), 3.62 (dd, J = 9.6, 7.2 Hz, 1H), 3.41 (s, 3H), 2.98 (t, J = 6.6 Hz, 2H), 2.33 (dt, J = 13.7, 7.0 Hz, 1H), 2.23-1.88 (m, 3H), 1.81-1.54 (m, 4H), 1.43 (d, J = 6.4 Hz, 3H), 1.37-1.20 (m, 1H), 1.06 (dd, J = 16.1, 7.7 Hz, 1H) | $^{13}$C NMR (CDCl$_3$) δ 172.42, 169.42, 162.39, 159.45, 157.36, 146.76, 141.35, 137.36, 129.59, 127.15 (q, J = 276.0 Hz), 121.39, 116.31, 109.85, 83.67, 82.56, 72.42, 71.82, 67.57, 58.78, 56.32, 51.26, 34.62, 33.45, 30.68 (q, J = 28.9 Hz), 28.34, 22.92 (q, J = 3.0 Hz), 18.21, 17.89 |
| F111 | White Foam | — | — | HRMS-ESI (m/z) [M + H]$^+$ calcd for C$_{31}$H$_{37}$N$_2$O$_7$, 549.2595; found, 549.2610 | $^1$H NMR (CDCl$_3$) δ 12.06 (s, 1H), 8.47 (d, J = 8.1 Hz, 1H), 7.98 (d, J = 5.2 Hz, 1H), 7.31-7.17 (m, 4H), 7.17-7.11 (m, 1H), 7.11-7.04 (m, 2H), 7.00-6.89 (m, 3H), 6.86 (d, J = 5.2 Hz, 1H), 4.94 (dq, J = 9.6, 6.4 Hz, 1H), 4.63 (dt, J = 10.7, 7.7 Hz, 1H), 4.41 (t, J = 5.5 Hz, 1H), 3.93 (s, 3H), 3.79 (dt, J = 9.1, 6.3 Hz, 1H), 3.72-3.62 (m, 2H), 2.66-2.52 (m, 2H), 2.36 (dt, J = 13.6, 7.0 Hz, 1H), 2.26-2.11 (m, 1H), 1.88-1.75 (m, 3H), 1.66 (t, J = 6.8 Hz, 1H), 1.48 (d, J = 6.4 Hz, 3H), 1.35 (q, J = 11.0 Hz, 1H), | $^{13}$C NMR (CDCl$_3$) δ 171.98, 168.70, 157.51, 155.36, 148.74, 141.91, 140.55, 130.35, 129.56, 128.35, 128.27, 125.71, 121.33, 116.57, 109.51, 83.51, 82.81, 73.09, 72.99, 56.08, 51.26, 33.20, 32.32, 31.87, 28.20, 18.20, 18.01 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| F112 | Off-White Foam | — | — | HRMS-ESI (m/z) [M + H]⁺ calcd for $C_{36}H_{45}N_2O_9$, 649.3120; found, 649.3133 | ¹H NMR (CDCl₃) δ 8.37 (d, J = 8.0 Hz, 1H), 8.26 (d, J = 5.3 Hz, 1H), 7.30-7.18 (m, 4H), 7.18-7.11 (m, 1H), 7.11-7.04 (m, 2H), 7.01-6.88 (m, 4H), 5.81-5.73 (m, 2H), 4.92 (dq, J = 9.6, 6.4 Hz, 1H), 4.65 (dt, J = 10.7, 7.6 Hz, 1H), 4.40 (t, J = 5.5 Hz, 1H), 3.88 (s, 3H), 3.79 (dt, J = 9.1, 6.3 Hz, 1H), 3.66 (ddd, J = 12.6, 9.4, 6.7 Hz, 2H), 2.62-2.47 (m, 3H), 2.36 (dt, J = 13.6, 7.0 Hz, 1H), 2.23-2.10 (m, 1H), 1.88-1.71 (m, 4H), 1.63 (dq, J = 15.7, 7.8 Hz, 1H), 1.47 (d, J = 6.4 Hz, 3H), 1.37-1.23 (m, 1H), 1.14 (d, J = 7.0 Hz, 6H), 1.06 (dd, J = 16.1, 7.8 Hz, 1H) | ¹³C NMR (CDCl₃) δ 176.26, 172.58, 162.98, 160.25, 157.57, 145.61, 144.21, 142.02, 141.94, 129.54, 128.34, 128.26, 125.69, 121.27, 116.57, 109.58, 89.88, 83.57, 82.89, 73.08, 72.70, 56.14, 51.58, 33.86, 33.28, 32.32, 31.88, 28.28, 18.69, 18.27, 18.00 |
| F113 | White Solid | — | 3369, 2941, 1745, 1650, 1529 | HRMS-ESI (m/z) [M + H]⁺ calcd for $C_{30}H_{35}N_2O_7$, 535.2439; found, 535.2432 | 1H NMR (CDCl₃) δ 12.04 (s, 1H), 8.47 (d, J = 8.1 Hz, 1H), 7.99 (d, J = 5.2 Hz, 1H), 7.08-6.94 (m, 6H), 6.87 (d, J = 5.1 Hz, 1H), 6.78 (d, J = 8.5 Hz, 2H), 5.12 (dq, J = 9.6, 6.5 Hz, 1H), 4.78-4.52 (m, 2H), 4.46 (ddd, J = 7.2, 5.3, 1.7 Hz, 1H), 3.94 (s, 3H), 2.41 (dt, J = 13.7, 7.1 Hz, 1H), 2.26 (d, J = 7.0 Hz, 7H), 1.91 (q, J = 11.4, 9.2 Hz, 1H), 1.76 (dq, J = 15.4, 7.7 Hz, 1H), 1.43 (d, J = 6.5 Hz, 3H), 1.42-1.38 (m, 1H), 1.19-0.99 (m, 1H) | ¹³C NMR (CDCl₃) δ 171.92, 168.69, 157.54, 155.43, 155.37, 148.74, 140.55, 131.00, 130.92, 130.32, 129.89, 117.08, 116.46, 109.50, 82.88, 82.70, 72.81, 56.08, 51.24, 33.25, 28.05, 20.52, 20.50, 18.27, 18.20 |
| F114 | White Solid | — | 3370, 2960, 2938, 2876, 1743, 1650, 1529, 1265 | HRMS-ESI (m/z) [M + H]⁺ calcd for $C_{22}H_{35}N_2O_7$, 439.2439; found, 439.2461 | ¹H NMR (CDCl₃) δ 12.09 (s, 1H), 8.48 (d, J = 8.2 Hz, 1H), 7.98 (d, J = 5.2 Hz, 1H), 6.87 (d, J = 5.2 Hz, 1H), 4.80 (pd, J = 6.3, 2.1 Hz, 1H), 4.66-4.38 (m, 1H), 3.94 (s, 3H), 3.78 (dt, J = 9.0, 6.5 Hz, 1H), 3.54 (ddt, J = 30.9, 9.0, 6.6 Hz, 2H), 3.43-3.25 (m, 3H), 2.37 (dddd, J = 13.6, 8.0, 6.3, 2.0 Hz, 1H), 2.24-2.06 (m, 1H), 1.75-1.52 (m, 6H), 1.44-1.31 (m, 4H), 0.98-0.81 (m, 7H) | ¹³C NMR (CDCl₃) δ 172.04, 168.65, 155.34, 148.71, 140.52, 130.40, 109.46, 84.16, 83.76, 75.50, 73.30, 70.92, 56.07, 51.30, 33.36, 27.90, 23.53, 23.36, 18.24, 17.91, 10.78, 10.70 |
| F115 | White Solid | — | 3377, 2943, 1751, 1678, | HRMS-ESI (m/z) [M + H]⁺ calcd for | ¹H NMR (CDCl₃) δ 8.32 (d, J = 8.0 Hz, 1H), 8.28 (d, J = 5.3 Hz, 1H), | ¹³C NMR (CDCl₃) δ 172.54, 170.31, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | 1506, 1202 | $C_{33}H_{39}N_2O_9$, 607.2650; found, 607.2672 | 7.10-6.92 (m, 7H), 6.77 (d, J = 8.6 Hz, 2H), 5.74 (s, 2H), 5.10 (dq, J = 9.6, 6.3 Hz, 1H), 4.67 (dt, J = 10.7, 7.6 Hz, 1H), 4.58 (dd, J = 9.5, 7.3 Hz, 1H), 4.49-4.40 (m, 1H), 3.91 (s, 3H), 2.41 (dt, J = 13.7, 7.1 Hz, 1H), 2.26 (s, 3H), 2.25 (s, 3H), 2.24-2.19 (m, 1H), 2.07 (s, 3H), 1.96-1.83 (m, 1H), 1.75 (d, J = 8.0 Hz, 1H), 1.41 (d, J = 6.4 Hz, 3H), 1.39-1.24 (m, 1H), 1.13 (dd, J = 16.0, 7.6 Hz, 1H) | 162.99, 160.28, 157.59, 155.49, 145.73, 144.05, 142.30, 130.94, 130.86, 129.87, 117.09, 116.47, 109.63, 89.54, 82.98, 82.77, 72.54, 56.19, 51.59, 33.32, 28.14, 20.89, 20.50, 18.35, 18.20 |
| F116 | Colorless Semi-Solid | — | 3377, 2960, 2937, 2876, 1745, 1676, 1503, 1236 | HRMS-ESI (m/z) [M + Na]⁺ calcd for $C_{25}H_{38}N_2NaO_9$, 533.2470; found, 533.2488 | ¹H NMR (CDCl₃) δ 8.32 (d, J = 8.1 Hz, 1H), 8.27 (d, J = 5.4 Hz, 1H), 6.95 (d, J = 5.4 Hz, 1H), 5.74 (s, 2H), 4.79 (ddq, J = 13.6, 6.6, 4.4, 3.2 Hz, 1H), 4.60 (dt, J = 10.7, 7.6 Hz, 1H), 3.91 (s, 3H), 3.77 (dt, J = 8.9, 6.5 Hz, 1H), 3.58 (dt, J = 9.0, 6.7 Hz, 1H), 3.50 (dt, J = 9.0, 6.6 Hz, 1H), 3.42-3.22 (m, 3H), 2.38 (dtd, J = 13.7, 6.7, 1.7 Hz, 1H), 2.16-2.08 (m, 1H), 2.07 (s, 3H), 1.73-1.50 (m, 6H), 1.39 (d, J = 6.3 Hz, 3H), 1.36-1.26 (m, 1H), 0.97-0.85 (m, 7H) | ¹³C NMR (CDCl₃) δ 172.66, 170.29, 162.97, 160.26, 145.75, 143.97, 142.41, 109.61, 89.53, 84.24, 83.81, 75.48, 73.01, 70.89, 56.19, 51.63, 33.43, 27.96, 23.52, 23.36, 20.88, 18.30, 17.90, 10.78, 10.70 |
| F117 | Off-White Amorphous Solid | — | — | HRMS FAB (m/z) [M]⁺ calcd for $C_{24}H_{34}N_2O_7$, 462.2378; found, 462.2366 | ¹H NMR (CDCl₃) δ 12.08 (s, 1H), 8.47 (d, J = 8.2 Hz, 1H), 7.98 (d, J = 5.1 Hz, 1H), 6.87 (d, J = 5.2 Hz, 1H), 4.88-4.78 (m, 1H), 4.59 (dt, J = 10.7, 7.5 Hz, 1H), 3.94 (s, 3H), 3.79-3.60 (m, 2H), 3.53-3.47 (m, 1H), 3.47-3.39 (m, 2H), 3.39-3.24 (m, 2H), 2.42-2.31 (m, 1H), 2.19-2.06 (m, 1H), 1.76-1.59 (m, 2H), 1.43 (d, J = 6.4 Hz, 3H), 1.41-1.32 (m, 1H), 1.15-1.00 (m, 2H), 0.98-0.89 (m, 1H), 0.60-0.49 (m, 4H), 0.27-0.16 (m, 4H) | ¹³CNMR (CDCl₃) δ 172.0, 168.7, 155.3, 148.7, 140.5, 130.4, 109.5, 84.1, 83.4, 78.7, 74.0, 73.2, 56.1, 51.3, 33.3, 28.0, 18.3, 17.9, 11.1, 11.0, 3.1, 3.1, 2.9, 2.9 |
| F118 | White Solid | 119-121 | 3694, 3369, 2958, 2873, 1739, 1650, 1576, 1528 | HRMS-ESI (m/z) [M + H]⁺ calcd for $C_{24}H_{37}N_2O_7$, 465.2595; found, 465.2601 | ¹H NMR (CDCl₃) δ 12.09 (s, 1H), 8.47 (d, J = 8.2 Hz, 1H), 7.99 (d, J = 5.2 Hz, 1H), 6.86 (d, J = 5.2 Hz, 1H), 4.80 (dq, J = 9.6, 6.4 Hz, 1H), 4.58 (dt, J = 10.7, 7.7 Hz, 1H), 4.07-3.97 (m, 1H), 3.94 (s, 3H), 3.78 (dt, J = 8.8, 6.6 Hz, | ¹³CNMR (CDCl₃) δ 172.07, 168.64, 155.33, 148.70, 140.50, 130.39, 109.45, 83.72, 81.67, 79.20, 75.84, 73.46, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1H), 3.55 (dt, J = 8.7, 6.9 Hz, 1H), 3.42 (ddd, J = 7.1, 5.1, 1.7 Hz, 1H), 3.32 (dd, J = 9.5, 7.4 Hz, 1H), 2.37 (dtd, J = 13.7, 7.2, 6.5, 1.9 Hz, 1H), 2.09 (dddd, J = 15.5, 10.0, 8.2, 5.0 Hz, 1H), 1.79-1.47 (m, 13H), 1.41 (d, J = 6.4 Hz, 3H), 0.93 (t, J = 7.4 Hz, 3H), 0.90-0.85 (m, 1H) | 56.06, 51.31, 33.53, 33.39, 31.90, 28.37, 23.65, 23.52, 23.34, 18.47, 17.85, 10.66 |
| F119 | Colorless Clear Solid | 99-100 | 3368, 2957, 2871, 1744, 1650, 1529 | ESIMS m/z 479.4 ([M + H]⁺); HRMS-ESI (m/z) [M + H]⁺ calcd for C₂₅H₃₉N₂O₇, 479.2752; found, 479.2766 | ¹H NMR (CDCl₃) δ 12.09 (s, 1H), 8.47 (d, J = 8.2 Hz, 1H), 7.98 (d, J = 5.2 Hz, 1H), 6.86 (d, J = 5.2 Hz, 1H), 4.81 (dq, J = 9.5, 6.4 Hz, 1H), 4.58 (dt, J = 10.8, 7.6 Hz, 1H), 4.01 (dtd, J = 7.2, 3.7, 1.2 Hz, 1H), 3.94 (s, 3H), 3.65 (dd, J = 8.5, 5.9 Hz, 1H), 3.44 (ddd, J = 7.2, 5.3, 1.7 Hz, 1H), 3.32 (ddd, J = 9.5, 7.2, 3.1 Hz, 2H), 2.37 (dtd, J = 13.9, 7.1, 6.6, 1.8 Hz, 1H), 2.17-2.05 (m, 1H), 1.90-1.77 (m, 1H), 1.77-1.57 (m, 10H), 1.57-1.46 (m, 2H), 1.40 (d, J = 6.4 Hz, 3H), 0.93 (d, J = 6.6 Hz, 3H), 0.90 (d, J = 6.7 Hz, 3H) | ¹³CNMR (CDCl₃) δ 172.07, 168.64, 155.33, 148.71, 140.50, 130.40, 109.45, 83.71, 81.71, 80.94, 79.17, 73.52, 56.06, 51.31, 33.57, 33.38, 31.89, 29.17, 28.37, 23.67, 23.38, 19.60, 19.40, 18.48, 17.93 |
| F120 | White Solid | 43-48 | 3368, 2946, 2873, 1743, 1650, 1576, 1527 | ESIMS m/z 533.3 ([M + H]⁺); HRMS-ESI (m/z) [M + H]⁺ calcd for C₂₅H₃₆F₃N₂O₇, 533.2469; found, 533.2474 | ¹H NMR (CDCl₃) δ 12.07 (s, 1H), 8.46 (d, J = 8.1 Hz, 1H), 7.99 (d, J = 5.2 Hz, 1H), 6.87 (d, J = 5.2 Hz, 1H), 4.80 (dq, J = 9.5, 6.4 Hz, 1H), 4.58 (dt, J = 10.8, 7.6 Hz, 1H), 4.04-3.96 (m, 1H), 3.94 (s, 3H), 3.87 (dt, J = 9.0, 6.0 Hz, 1H), 3.65 (dt, J = 9.1, 6.3 Hz, 1H), 3.46-3.38 (m, 1H), 3.33 (dd, J = 9.5, 7.3 Hz, 1H), 2.37 (dtd, J = 13.7, 7.0, 6.1, 2.2 Hz, 1H), 2.27-2.04 (m, 3H), 1.82 (dq, J = 8.2, 6.3 Hz, 2H), 1.77-1.47 (m, 10H), 1.39 (d, J = 6.4 Hz, 4H), 0.91 (ddt, J = 15.6, 6.0, 1.9 Hz, 1H) | ¹³CNMR (CDCl₃) δ 172.03, 168.66, 155.35, 148.73, 140.52, 130.36, 127.20 (q, J = 276.2 Hz), 109.48, 83.97, 81.53, 79.02, 73.11, 72.07, 56.07, 51.29, 33.55, 33.35, 31.87, 30.90 (q, J = 28.9 Hz), 28.21, 23.63, 23.35, 23.06 (q, J = 2.8 Hz), 18.44, 17.90 |
| F121 | Colorless Oil | — | 3377, 2936, 2874, 1744, 1676, 1501 | HRMS-ESI (m/z) [M + H]⁺ calcd for C₂₇H₄₁N₂O₉, 537.2807; found, 537.2817 | ¹H NMR (CDCl₃) δ 8.31 (d, J = 8.2 Hz, 1H), 8.27 (d, J = 5.5 Hz, 1H), 6.95 (d, J = 5.5 Hz, 1H), 5.74 (s, 2H), 4.77 (ddt, J = 12.4, 7.5, 3.7 Hz, 1H), 4.66-4.55 (m, 1H), 4.06-3.97 (m, 1H), 3.91 (s, 3H), 3.78 (t, J = 7.6, 7.1 Hz, | ¹³CNMR (CDCl₃) δ 172.69, 170.29, 162.96, 160.26, 145.72, 143.98, 142.43, 109.57, 89.56, 83.77, 81.76, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 1H), 3.55 (td, J = 8.6, 8.0, 6.3 Hz, 1H), 3.47-3.37 (m, 1H), 3.35 (dd, J = 9.5, 7.7 Hz, 1H), 2.38 (dt, J = 13.7, 6.8 Hz, 1H), 2.07 (s, 3H), 1.79-1.44 (m, 14H), 1.39 (dd, J = 6.5, 1.5 Hz, 3H), 0.93 (t, J = 7.5 Hz, 3H), 0.89-0.82 (m, 1H) | 79.17, 75.83, 73.19, 56.18, 51.63, 33.53, 33.50, 31.90, 28.44, 23.65, 23.53, 23.34, 20.87, 18.53, 17.84, 10.66 |
| F122 | Colorless Oil | — | 3377, 2954, 2871, 1745, 1676, 1503 | HRMS-ESI (m/z) [M + H]$^+$ calcd for C$_{27}$H$_{43}$N$_2$O$_9$, 551.2963; found, 551.2966 | $^1$H NMR (CDCl$_3$) δ 8.31 (d, J = 8.1 Hz, 1H), 8.27 (d, J = 5.2 Hz, 1H), 6.95 (d, J = 5.4 Hz, 1H), 5.74 (s, 2H), 4.79 (dq, J = 9.2, 6.5 Hz, 1H), 4.60 (dt, J = 10.7, 7.7 Hz, 1H), 4.01 (p, J = 4.2 Hz, 1H), 3.91 (s, 3H), 3.65 (dd, J = 8.4, 6.0 Hz, 1H), 3.43 (t, J = 6.1 Hz, 1H), 3.35-3.28 (m, 2H), 2.37 (dt, J = 13.6, 6.7 Hz, 1H), 2.07 (s, 3H), 1.92-1.75 (m, 2H), 1.65-1.58 (m, 9H), 1.55-1.44 (m, 2H), 1.39 (d, J = 6.4 Hz, 3H), 0.92 (d, J = 6.7 Hz, 3H), 0.90 (d, J = 6.6 Hz, 3H), 0.89-0.83 (m, 1H) | $^{13}$CNMR (CDCl$_3$) δ 172.79, 170.38, 163.06, 160.37, 145.83, 144.08, 142.52, 109.69, 89.65, 83.85, 81.89, 81.04, 79.23, 73.35, 56.28, 51.74, 33.67, 33.58, 31.99, 29.27, 28.53, 23.77, 23.48, 20.97, 19.71, 19.50, 18.65, 18.03 |
| F123 | Colorless Oil | — | 3375, 2957, 2920, 2851, 1744, 1677, 1503 | HRMS-ESI (m/z) [M + H]$^+$ calcd for C$_{29}$H$_{45}$N$_2$O$_9$, 565.3120; found, 565.3131 | $^1$H NMR (CDCl$_3$) δ 8.36 (d, J = 8.1 Hz, 1H), 8.27 (d, J = 5.4 Hz, 1H), 6.94 (d, J = 5.5 Hz, 1H), 5.81-5.72 (m, 2H), 4.78 (dq, J = 10.2, 6.5 Hz, 1H), 4.60 (dt, J = 11.1, 7.5 Hz, 1H), 4.06-3.96 (m, 1H), 3.88 (s, 3H), 3.78 (dt, J = 9.4, 6.6 Hz, 1H), 3.55 (dt, J = 9.3, 7.0 Hz, 1H), 3.41 (ddd, J = 7.8, 5.3, 2.0 Hz, 1H), 3.32 (dd, J = 9.6, 7.3 Hz, 1H), 2.54 (hept, J = 6.7 Hz, 1H), 2.43-2.31 (m, 1H), 2.15-2.00 (m, 1H), 1.81-1.44 (m, 12H), 1.39 (d, J = 6.3 Hz, 2H), 1.36-1.23 (m, 2H), 1.12 (d, J = 8.2 Hz, 6H), 0.92 (t, J = 7.3 Hz, 3H), 0.90-0.83 (m, 1H) | $^{13}$CNMR (CDCl$_3$) δ 176.36, 172.80, 163.05, 160.36, 145.71, 144.31, 142.20, 109.64, 90.03, 83.89, 81.88, 79.28, 75.95, 73.29, 56.25, 51.74, 33.97, 33.64, 33.62, 32.02, 28.55, 23.77, 23.65, 23.46, 18.80, 18.66, 17.96, 14.24, 10.78 |
| F124 | Colorless Oil | — | 3377, 2954, 2972, 1744, 1677, 1502 | HRMS-ESI (m/z) [M + H]$^+$ calcd for C$_{30}$H$_{47}$N$_2$O$_9$, 579.3276; found, 579.3287 | $^1$H NMR (CDCl$_3$) δ 8.37 (d, J = 8.1 Hz, 1H), 8.26 (d, J = 5.3 Hz, 1H), 6.94 (d, J = 5.4 Hz, 1H), 5.81-5.72 (m, 2H), 4.79 (dt, J = 9.7, 6.3 Hz, 1H), 4.60 (dt, J = 11.1, 7.7 Hz, 1H), 4.06-3.96 (m, 1H), 3.88 (s, 3H), 3.65 (dd, J = 8.5, 6.0 Hz, 1H), 3.43 (td, J = 5.5, | $^{13}$CNMR (CDCl$_3$) δ 176.37, 172.81, 163.06, 160.36, 145.71, 144.32, 142.21, 109.64, 90.04, 83.88, 81.92, 81.06, 79.25, 73.36, 56.25, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 2.8 Hz, 1H), 3.38-3.26 (m, 2H), 2.54 (h, J = 7.1 Hz, 1H), 2.37 (dt, J = 13.6, 6.8 Hz, 1H), 2.15-2.01 (m, 1H), 1.89-1.77 (m, 1H), 1.77-1.57 (m, 9H), 1.56-1.47 (m, 1H), 1.39 (d, J = 6.3 Hz, 3H), 1.36-1.29 (m, 1H), 1.14 (d, J = 7.0, 1.6 Hz, 6H), 0.92 (d, J = 6.7 Hz, 3H), 0.90 (d, J = 6.7 Hz, 3H), 0.88-0.81 (m, 1H) | 51.76, 33.97, 33.69, 33.61, 32.01, 29.29, 28.55, 23.79, 23.50, 19.73, 19.53, 18.80, 18.68, 18.05, 7.44 |
| F125 | White Waxy Solid | 34-39 | 3375, 2953, 1749, 1677, 1504 | HRMS-ESI (m/z) [M + H]⁺ calcd for $C_{28}H_{40}F_3N_2O_9$, 605.2680; found, 605.2688 | ¹H NMR (CDCl₃) δ 8.31 (d, J = 8.1 Hz, 1H), 8.28 (d, J = 5.4 Hz, 1H), 6.95 (d, J = 5.4 Hz, 1H), 5.74 (s, 2H), 4.77 (dq, J = 9.5, 6.4 Hz, 1H), 4.60 (dt, J = 10.6, 7.6 Hz, 1H), 4.00 (ddt, J = 9.1, 5.6, 3.4 Hz, 1H), 3.91 (s, 3H), 3.87 (dt, J = 9.1, 6.1 Hz, 1H), 3.65 (dt, J = 9.0, 6.4 Hz, 1H), 3.41 (ddd, J = 7.2, 5.1, 1.8 Hz, 1H), 3.32 (dd, J = 9.5, 7.4 Hz, 1H), 2.37 (dt, J = 12.4, 4.5 Hz, 1H), 2.26-2.09 (m, 2H), 2.07 (s, 3H), 1.86-1.77 (m, 2H), 1.77-1.49 (m, 11H), 1.37 (d, J = 6.3 Hz, 3H), 1.36-1.27 (m, 1H), 0.98-0.81 (m, 1H) | ¹³CNMR (CDCl₃) δ 172.79, 170.42, 163.11, 160.41, 145.86, 144.13, 142.51, 127.35 (d, J = 275.9 Hz), 109.74, 89.68, 84.15, 81.74, 79.12, 72.98, 72.19, 56.32, 51.75, 33.67, 33.57, 32.00, 31.04 (d, J = 28.9 Hz), 28.40, 23.77, 23.48, 23.20 (d, J = 2.6 Hz), 21.01, 18.64, 18.03 |
| F126 | Colorless Oil | — | 3386, 2925, 1745, 1677, 1503 | HRMS-ESI (m/z) [M + H]⁺ calcd for $C_{30}H_{44}F_3N_2O_9$, 633.2993; found, 633.3007 | ¹H NMR (CDCl₃) δ 8.36 (d, J = 8.1 Hz, 1H), 8.27 (d, J = 5.3 Hz, 1H), 6.94 (d, J = 5.4 Hz, 1H), 5.81-5.72 (m, 2H), 4.78 (dq, J = 9.5, 6.4 Hz, 1H), 4.60 (dt, J = 10.7, 7.6 Hz, 1H), 4.07-3.93 (m, 1H), 3.89 (s, 3H), 3.88-3.83 (m, 1H), 3.65 (dt, J = 9.0, 6.3 Hz, 1H), 3.41 (ddd, J = 7.0, 5.1, 1.7 Hz, 1H), 3.32 (dd, J = 9.5, 7.3 Hz, 1H), 2.55 (hept, J = 7.1 Hz, 1H), 2.43-2.31 (m, 1H), 2.26-2.13 (m, 2H), 2.13-2.02 (m, 1H), 1.87-1.76 (m, 2H), 1.77-1.46 (m, 10H), 1.37 (d, J = 6.2 Hz, 3H), 1.32 (ddd, J = 13.5, 8.1, 2.7 Hz, 1H), 1.14 (d, J = 7.0 Hz, 6H), 0.93-0.81 (m, 1H) | ¹³CNMR (CDCl₃) δ 176.39, 172.77, 163.09, 160.38, 145.72, 144.35, 142.17, 127.35 (q, J = 276.1 Hz), 109.67, 90.04, 84.16, 81.74, 79.11, 72.96, 72.19, 56.26, 51.75, 33.99, 33.67, 33.58, 32.00, 31.04 (q, J = 29.1 Hz), 29.84, 28.40, 23.77, 23.49, 23.20 (q, J = 3.0 Hz), 18.81, 18.64, 18.03 |
| F127 | Off-White Solid | — | — | HRMS-ESI (m/z) [M + H]⁺ calcd for $C_{25}H_{33}N_2O_7$, | ¹H NMR (CDCl₃) δ 12.12-12.02 (m, 1H), 8.48 (d, J = 8.1 Hz, 1H), 7.99 (d, J = 5.2 Hz, 1H), | ¹³C NMR (CDCl₃) δ 171.99, 168.68, 159.70, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | 473.2282; found, 473.2278 | 7.29-7.25 (m, 2H), 7.09 (dd, J = 8.8, 1.0 Hz, 2H), 7.00-6.92 (m, 1H), 6.87 (d, J = 5.2 Hz, 1H), 5.03 (dq, J = 9.6, 6.4 Hz, 1H), 4.62 (dt, J = 10.8, 7.6 Hz, 1H), 4.42 (dd, J = 9.6, 7.3 Hz, 1H), 3.94 (s, 3H), 3.57 (ddd, J = 7.0, 5.3, 1.6 Hz, 1H), 3.45 (dt, J = 9.0, 6.6 Hz, 1H), 3.25 (dt, J = 9.0, 6.5 Hz, 1H), 2.42 (ddd, J = 13.9, 10.0, 4.4 Hz, 1H) 2.32-2.13 (m, 1H), 1.77 (dq, J = 10.2, 6.5, 5.2 Hz, 2H), 1.50-1.39 (m, 3H), 1.37 (d, J = 6.4 Hz, 3H), 1.06 (dd, J = 16.1, 7.2 Hz, 1H), 0.77 (t, J = 7.4 Hz, 3H) | 155.36, 148.74, 140.54, 130.36, 129.35, 121.35, 116.48, 109.50, 82.98, 82.91, 72.86, 71.40, 56.08, 51.31, 33.37, 28.11, 23.16, 18.32, 18.11, 10.54 |
| F128 | White Foam | — | — | HRMS-ESI (m/z) [M + H]⁺ calcd for $C_{31}H_{37}N_2O_7$, 549.2595; found, 549.2602 | ¹H NMR (CDCl₃) δ 12.06 (d, J = 0.5 Hz, 1H), 8.49 (d, J = 8.1 Hz, 1H), 7.99 (d, J = 5.2 Hz, 1H), 7.31-7.20 (m, 4H), 7.19-7.07 (m, 3H), 7.06-7.01 (m, 2H), 6.99-6.92 (m, 1H), 6.87 (d, J = 5.2 Hz, 1H), 5.04 (dq, J = 9.6, 6.4 Hz, 1H), 4.63 (dt, J = 10.8, 7.6 Hz, 1H), 4.47 (dd, J = 9.6, 7.4 Hz, 1H), 3.94 (s, 3H), 3.61-3.49 (m, 2H), 3.27 (dt, J = 9.2, 6.2 Hz, 1H), 2.55-2.46 (m, 2H), 2.42 (dt, J = 13.7, 6.7 Hz, 1H), 2.27-2.13 (m, 1H), 1.88-1.67 (m, 4H), 1.49-1.39 (m, 1H), 1.37 (d, J = 6.4 Hz, 3H), 1.05 (dd, J = 16.1, 7.5 Hz, 1H) | ¹³C NMR (CDCl₃) δ 171.98, 168.69, 159.66, 155.37, 148.75, 142.00, 140.55, 130.36, 129.43, 128.41, 128.21, 125.65, 121.40, 116.35, 109.51, 83.12, 82.54, 72.86, 68.59, 56.09, 51.30, 33.37, 32.17, 31.54, 28.01, 18.31, 18.10 |
| F129 | White Crystalline Solid | — | — | HRMS-ESI (m/z) [M + H]⁺ calcd for $C_{26}H_{32}F_3N_2O_7$, 541.2156; found, 541.2158 | ¹H NMR (CDCl₃) δ 12.05 (d, J = 0.5 Hz, 1H), 8.48 (d, J = 8.1 Hz, 1H), 8.00 (d, J = 5.2 Hz, 1H), 7.28 (dd, J = 8.4, 7.0 Hz, 2H), 7.04 (dd, J = 8.8, 0.9 Hz, 2H), 7.00-6.93 (m, 1H), 6.87 (d, J = 5.2 Hz, 1H), 5.04 (dq, J = 9.6, 6.4 Hz, 1H), 4.64 (dt, J = 10.8, 7.6 Hz, 1H), 4.46 (dd, J = 9.6, 7.4 Hz, 1H), 3.94 (s, 3H), 3.56 (td, J = 6.1, 5.3, 3.5 Hz, 2H), 3.28 (dt, J = 9.1, 6.0 Hz, 1H), 2.42 (dt, J = 13.8, 6.7 Hz, 1H), 2.19 (dddd, J = 15.8, 10.1, 8.2, 5.3 Hz, 1H), 1.96-1.70 (m, 4H), 1.66-1.58 (m, 2H), 1.50-1.40 (m, 1H), 1.38 (d, J = 6.4 Hz, | ¹³C NMR (CDCl₃) δ 171.93, 168.70, 159.35, 155.38, 148.75, 140.55, 130.33, 129.46, 127.18 (q, J = 276.1 Hz), 121.52, 116.03, 109.52, 83.40, 82.07, 72.69, 67.61, 56.08, 51.25, 33.29, 30.43 (q, J = 28.9 Hz), 28.00, 22.59 (q, J = 2.9 Hz), 18.25, 18.02 |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 3H), 1.08 (dd, J = 16.2, 7.5 Hz, 1H) | |
| F130 | Clear Tacky Solid | — | — | HRMS-ESI (m/z) [M + H]$^+$ calcd for C$_{34}$H$_{41}$N$_2$O$_9$, 621.2807; found, 621.2809 | $^1$H NMR (CDCl$_3$) δ 8.31 (d, J = 8.0 Hz, 1H), 8.27 (d, J = 5.4 Hz, 1H), 7.30-7.24 (m, 2H), 7.21 (t, J = 7.2 Hz, 2H), 7.14 (dd, J = 8.5, 6.0 Hz, 1H), 7.08 (d, J = 7.0 Hz, 2H), 7.00-6.89 (m, 4H), 5.74 (s, 2H), 4.92 (dq, J = 9.7, 6.3 Hz, 1H), 4.65 (dt, J = 10.7, 7.6 Hz, 1H), 4.40 (t, J = 5.6 Hz, 1H), 3.90 (s, 3H), 3.79 (dt, J = 9.1, 6.3 Hz, 1H), 3.74-3.59 (m, 2H), 2.63-2.52 (m, 2H), 2.36 (dt, J = 13.7, 7.0 Hz, 1H), 2.27-2.10 (m, 1H), 2.07 (s, 3H), 1.81 (dd, J = 14.4, 5.6 Hz, 3H), 1.64 (dt, J = 15.5, 7.6 Hz, 1H), 1.46 (d, J = 6.4 Hz, 3H), 1.37-1.23 (m, 1H), 1.06 (dd, J = 16.0, 7.7 Hz, 1H) | $^{13}$C NMR (CDCl$_3$) δ 172.59, 170.29, 163.01, 160.27, 157.57, 145.75, 144.00, 142.35, 141.94, 129.54, 128.34, 128.26, 125.69, 121.27, 116.58, 109.65, 89.52, 83.56, 82.89, 73.07, 72.71, 56.20, 51.59, 33.27, 32.32, 31.88, 28.28, 20.89, 18.27, 18.01 |
| F131 | White Foam | — | — | HRMS-ESI (m/z) [M + H]$^+$ calcd for C$_{33}$H$_{39}$N$_2$O$_8$, 591.2701; found, 591.2706 | $^1$H NMR (CDCl$_3$) δ 8.52 (d, J = 7.4 Hz, 1H), 8.32 (d, J = 5.4 Hz, 1H), 7.30-7.11 (m, 5H), 7.10-7.04 (m, 2H), 7.00-6.89 (m, 4H), 4.92 (dq, J = 9.7, 6.3 Hz, 1H), 4.64 (dt, J = 10.7, 7.7 Hz, 1H), 4.39 (t, J = 5.5 Hz, 1H), 3.88 (s, 3H), 3.79 (dt, J = 9.1, 6.3 Hz, 1H), 3.70-3.59 (m, 2H), 2.62-2.52 (m, 2H), 2.40 (s, 3H), 2.38-2.28 (m, 1H), 2.23-2.09 (m, 1H), 1.86-1.75 (m, 3H), 1.61 (dq, J = 15.6, 7.6 Hz, 1H), 1.45 (d, J = 6.4 Hz, 3H), 1.28 (q, J = 11.1 Hz, 1H), 1.05 (dd, J = 16.1, 7.8 Hz, 1H) | $^{13}$C NMR (CDCl$_3$) δ 172.47, 168.90, 162.44, 159.45, 157.57, 146.72, 141.94, 141.35, 137.51, 129.55, 128.35, 128.27, 125.70, 121.28, 116.58, 109.85, 83.56, 82.90, 73.07, 72.73, 56.30, 51.31, 33.50, 32.33, 31.89, 28.31, 20.77, 18.24, 17.99 |
| F132 | Clear Tacky Solid | — | — | HRMS-ESI (m/z) [M + H]$^+$ calcd for C$_{35}$H$_{43}$N$_2$O$_9$, 635.2963; found, 635.2977 | $^1$H NMR (CDCl$_3$) δ 8.50 (d, J = 7.2 Hz, 1H), 8.32 (d, J = 5.4 Hz, 1H), 7.30-7.12 (m, 5H), 7.11-7.05 (m, 2H), 7.00-6.88 (m, 4H), 4.92 (dq, J = 9.7, 6.4 Hz, 1H), 4.63 (dt, J = 10.6, 7.7 Hz, 1H), 4.39 (t, J = 5.5 Hz, 1H), 3.88 (s, 3H), 3.85-3.74 (m, 3H), 3.72-3.57 (m, 2H), 3.41 (s, 3H), 2.98 (t, J = 6.6 Hz, 2H), 2.61-2.53 (m, 2H), 2.33 (dt, J = 13.7, 7.0 Hz, 1H), 2.24-2.08 (m, 1H), 1.83-1.75 (m, 3H), 1.61 (dq, J = 16.1, | $^{13}$C NMR (CDCl$_3$) δ 172.47, 169.44, 162.39, 159.45, 157.57, 146.77, 141.94, 141.39, 137.36, 129.54, 128.35, 128.26, 125.70, 121.28, 116.58, 109.84, 83.56, 82.90, 73.06, 72.70, 67.59, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 7.7 Hz, 1H), 1.45 (d, J = 6.4 Hz, 3H), 1.35-1.20 (m, 1H), 1.05 (dd, J = 16.1, 7.8 Hz, 1H) | 58.80, 56.33, 51.29, 34.64, 33.49, 32.32, 31.88, 28.29, 18.24, 17.99 |
| F133 | White Foam | — | — | HRMS-ESI (m/z) [M + H]$^+$ calcd for C$_{34}$H$_{41}$N$_2$O$_9$, 621.2807; found, 621.2809 | $^1$H NMR (CDCl$_3$) δ 8.33 (d, J = 8.0 Hz, 1H), 8.28 (d, J = 5.4 Hz, 1H), 7.32-7.26 (m, 2H), 7.22 (ddd, J = 7.5, 6.4, 1.2 Hz, 2H), 7.17-7.07 (m, 3H), 7.06-7.01 (m, 2H), 6.99-6.93 (m, 2H), 5.74 (s, 2H), 5.02 (dq, J = 9.6, 6.4 Hz, 1H), 4.65 (dt, J = 10.7, 7.6 Hz, 1H), 4.46 (dd, J = 9.6, 7.4 Hz, 1H), 3.90 (s, 3H), 3.61-3.48 (m, 2H), 3.26 (dt, J = 9.2, 6.2 Hz, 1H), 2.54-2.47 (m, 2H), 2.43 (dt, J = 13.6, 6.8 Hz, 1H), 2.26-2.10 (m, 1H), 2.07 (s, 3H), 1.86-1.65 (m, 4H), 1.45-1.30 (m, 4H), 1.05 (dd, J = 16.1, 7.6 Hz, 1H) | $^{13}$C NMR (CDCl$_3$) δ 172.60, 170.30, 163.00, 160.28, 159.70, 145.74, 144.03, 142.36, 142.03, 129.41, 128.42, 128.20, 125.63, 121.35, 116.35, 109.65, 89.53, 83.20, 82.60, 72.59, 68.54, 56.20, 51.65, 33.43, 32.17, 31.55, 28.08, 20.89, 18.38, 18.10 |
| F134 | White Foam | — | — | HRMS-ESI (m/z) [M + H]$^+$ calcd for C$_{33}$H$_{39}$N$_2$O$_8$, 591.2701; found, 591.2705 | $^1$H NMR (CDCl$_3$) δ 8.54 (d, J = 7.4 Hz, 1H), 8.33 (d, J = 5.4 Hz, 1H), 7.30-7.20 (m, 4H), 7.17-7.06 (m, 3H), 7.06-6.92 (m, 4H), 5.01 (dq, J = 9.6, 6.4 Hz, 1H), 4.64 (dt, J = 10.7, 7.6 Hz, 1H), 4.44 (dd, J = 9.6, 7.4 Hz, 1H), 3.89 (s, 3H), 3.61-3.47 (m, 2H), 3.25 (dt, J = 9.2, 6.2 Hz, 1H), 2.54-2.47 (m, 2H), 2.40 (s, 4H), 2.25-2.11 (m, 1H), 1.80-1.68 (m, 4H), 1.41-1.29 (m, 4H), 1.04 (dd, J = 16.1, 7.5 Hz, 1H) | $^{13}$C NMR (CDCl$_3$) δ 172.48, 168.91, 162.43, 159.69, 159.46, 146.71, 142.02, 141.38, 137.52, 129.41, 128.42, 128.21, 125.64, 121.36, 116.36, 109.85, 83.20, 82.60, 72.61, 68.55, 56.30, 51.37, 33.66, 32.17, 31.54, 28.09, 20.76, 18.35, 18.08 |
| F135 | White Foam | — | — | HRMS-ESI (m/z) [M + H]$^+$ calcd for C$_{29}$H$_{36}$F$_3$N$_2$O$_9$, 613.2367; found, 613.2378 | $^1$H NMR (CDCl$_3$) δ 8.33 (d, J = 8.0 Hz, 1H), 8.28 (d, J = 5.4 Hz, 1H), 7.32-7.24 (m, 2H), 7.08-7.00 (m, 2H), 6.99-6.92 (m, 2H), 5.74 (s, 2H), 5.02 (dq, J = 9.6, 6.4 Hz, 1H), 4.65 (dt, J = 10.7, 7.6 Hz, 1H), 4.45 (dd, J = 9.6, 7.4 Hz, 1H), 3.91 (s, 3H), 3.57 (dt, J = 10.7, 5.7 Hz, 2H), 3.27 (dt, J = 9.2, 6.0 Hz, 1H), 2.43 (dt, J = 13.6, 6.8 Hz, 1H), 2.26-2.11 (m, 1H), 2.07 (s, 3H), 1.87 (dtt, J = 22.6, 11.3, 3.2 Hz, 2H), | $^{13}$C NMR (CDCl$_3$) δ 172.54, 170.30, 163.00, 160.28, 159.38, 145.74, 144.03, 142.31, 129.44, 127.19 (q, J = 276.1 Hz), 121.46, 116.03, 109.66, 89.50, 83.46, 82.12, 72.41, 67.56, 56.19, 51.60, 33.34, 30.43 (q, J = 28.8 Hz), |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1.80-1.67 (m, 2H), 1.62 (ddd, J = 14.0, 7.8, 6.4 Hz, 2H), 1.45-1.32 (m, 4H), 1.08 (dd, J = 16.1, 7.6 Hz, 1H) | 28.05, 22.58 (q, J = 2.8 Hz), 20.87, 18.32, 18.01 |
| F136 | White Foam | — | — | HRMS-ESI (m/z) [M + H]⁺ calcd for C$_{31}$H$_{40}$F$_3$N$_2$O$_8$, 641.2680; found, 641.2687 | ¹H NMR (CDCl$_3$) δ 8.39 (d, J = 8.0 Hz, 1H), 8.27 (d, J = 5.4 Hz, 1H), 7.31-7.24 (m, 2H), 7.07-7.00 (m, 2H), 7.00-6.92 (m, 2H), 5.80-5.73 (m, 2H), 5.02 (dq, J = 9.6, 6.4 Hz, 1H), 4.65 (dt, J = 10.7, 7.6 Hz, 1H), 4.45 (dd, J = 9.6, 7.4 Hz, 1H), 3.89 (s, 3H), 3.57 (dt, J = 10.8, 5.7 Hz, 2H), 3.27 (dt, J = 9.1, 6.0 Hz, 1H), 2.55 (hept, J = 7.0 Hz, 1H), 2.42 (dt, J = 13.7, 6.8 Hz, 1H), 2.27-2.07 (m, 1H), 1.87 (dddd, J = 22.2, 11.1, 7.8, 3.1 Hz, 2H), 1.78-1.57 (m, 4H), 1.36 (d, J = 6.4 Hz, 4H), 1.14 (d, J = 7.0 Hz, 6H), 1.08 (dd, J = 16.2, 7.6 Hz, 1H) | ¹³C NMR (CDCl$_3$) δ 176.25, 172.53, 162.98, 160.25, 159.39, 145.60, 144.23, 141.97, 129.43, 127.19 (q, J = 276.1 Hz), 121.45, 116.03, 109.60, 89.86, 83.47, 82.13, 72.39, 67.56, 56.14, 51.59, 33.85, 33.34, 30.43 (q, J = 28.8 Hz), 28.04, 22.58 (q, J = Hz), 18.67, 18.32, 18.01 |
| F137 | White Foam | — | — | HRMS-ESI (m/z) [M + H]⁺ calcd for C$_{28}$H$_{34}$F$_3$N$_2$O$_8$, 583.2262; found, 583.2272 | ¹H NMR (CDCl$_3$) δ 8.54 (d, J = 7.7 Hz, 1H), 8.33 (d, J = 5.4 Hz, 1H), 7.32-7.22 (m, 2H), 7.05-6.99 (m, 3H), 6.99-6.93 (m, 1H), 5.01 (dq, J = 9.6, 6.4 Hz, 1H), 4.64 (dt, J = 10.7, 7.6 Hz, 1H), 4.43 (dd, J = 9.6, 7.4 Hz, 1H), 3.90 (s, 3H), 3.56 (dt, J = 10.7, 5.7 Hz, 2H), 3.26 (dt, J = 9.1, 6.0 Hz, 1H), 2.40 (s, 4H), 2.22-2.10 (m, 1H), 1.85 (dtdd, J = 22.1, 11.0, 7.6, 3.1 Hz, 2H), 1.77-1.56 (m, 4H), 1.35 (d, J = 6.4 Hz, 4H), 1.07 (dd, J = 16.2, 7.5 Hz, 1H) | ¹³C NMR (CDCl$_3$) δ 172.42, 168.90, 162.43, 159.46, 159.38, 146.71, 141.33, 137.52, 129.44, 127.19 (q, J = 276.1 Hz), 121.46, 116.03, 109.86, 83.46, 82.11, 72.42, 67.57, 56.29, 51.32, 33.56, 30.43 (q, J = 28.8 Hz), 28.07, 22.57 (q, J = 2.9 Hz), 20.74, 18.28, 18.00 |
| F138 | Clear Tacky Solid | — | — | HRMS-ESI (m/z) [M + H]⁺ calcd for C$_{28}$H$_{37}$N$_2$O$_9$, 545.2494; found, 545.2511 | ¹H NMR (CDCl$_3$) δ 8.33 (d, J = 8.0 Hz, 1H), 8.28 (d, J = 5.4 Hz, 1H), 7.27 (t, J = 8.0 Hz, 2H), 7.09 (d, J = 7.9 Hz, 2H), 7.00-6.91 (m, 2H), 5.74 (s, 2H), 5.01 (dq, J = 9.6, 6.4 Hz, 1H), 4.64 (dt, J = 10.7, 7.6 Hz, 1H), 4.41 (dd, J = 9.6, 7.3 Hz, 1H), 3.91 (s, 3H), 3.56 (t, J = 5.5 Hz, 1H), 3.45 (dt, J = 9.0, 6.6 Hz, 1H), 3.24 (dt, J = 9.0, 6.5 Hz, 1H), 2.42 (dt, J = 13.8, 6.6 Hz, 1H), 2.19 (ddd, J = 15.7, | ¹³C NMR (CDCl$_3$) δ 172.60, 170.28, 162.99, 160.27, 159.72, 145.73, 144.01, 142.35, 129.32, 121.30, 116.48, 109.64, 89.52, 83.04, 82.96, 72.58, 71.36, 56.19, 51.65, 33.42, 28.17, 23.15, 20.87, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 8.9, 4.5 Hz, 1H), 2.07 (s, 3H), 1.82-1.64 (m, 2H), 1.50-1.32 (m, 6H), 1.05 (dd, J = 16.1, 7.3 Hz, 1H), 0.77 (t, J = 7.4 Hz, 3H) | 18.38, 18.10, 10.54 |
| F139 | Clear Tacky Oil | — | — | HRMS-ESI (m/z) [M + H]$^+$ calcd for C$_{30}$H$_{41}$N$_2$O$_9$, 573.2807; found, 573.2819 | $^1$H NMR (CDCl$_3$) δ 8.39 (d, J = 8.0 Hz, 1H), 8.27 (d, J = 5.4 Hz, 1H), 7.31-7.22 (m, 2H), 7.12-7.05 (m, 2H), 7.00-6.91 (m, 2H), 5.81-5.73 (m, 2H), 5.01 (dq, J = 9.6, 6.4 Hz, 1H), 4.64 (dt, J = 10.8, 7.6 Hz, 1H), 4.42 (dd, J = 9.6, 7.3 Hz, 1H), 3.88 (s, 3H), 3.56 (ddd, J = 7.0, 5.2, 1.5 Hz, 1H), 3.50-3.41 (m, 1H), 3.24 (dt, J = 9.0, 6.5 Hz, 1H), 2.55 (hept, J = 7.0 Hz, 1H), 2.42 (dt, J = 13.9, 6.6 Hz, 1H), 2.27-2.12 (m, 1H), 1.74 (ddd, J = 15.3, 11.6, 7.7 Hz, 2H), 1.48-1.32 (m, 6H), 1.14 (d, J = 7.0 Hz, 6H), 1.05 (dd, J = 16.1, 7.3 Hz, 1H), 0.77 (t, J = 7.4 Hz, 3H) | $^{13}$C NMR (CDCl$_3$) δ 176.24, 172.59, 162.96, 160.25, 159.73, 145.59, 144.22, 142.01, 129.32, 121.29, 116.48, 109.58, 89.87, 83.04, 82.97, 72.56, 71.35, 56.14, 51.64, 33.84, 33.42, 28.17, 23.15, 18.67, 18.39, 18.10, 10.54 |
| F140 | White Foam | — | — | HRMS-ESI (m/z) [M + H]$^+$ calcd for C$_{29}$H$_{39}$N$_2$O$_9$, 559.2650; found, 559.2666 | $^1$H NMR (CDCl$_3$) δ 8.51 (d, J = 7.1 Hz, 1H), 8.33 (d, J = 5.4 Hz, 1H), 7.31-7.23 (m, 2H), 7.10-7.03 (m, 2H), 6.99 (d, J = 5.5 Hz, 1H), 6.98-6.92 (m, 1H), 5.01 (dq, J = 9.7, 6.4 Hz, 1H), 4.62 (dt, J = 10.7, 7.7 Hz, 1H), 4.40 (dd, J = 9.6, 7.3 Hz, 1H), 3.89 (s, 3H), 3.81 (t, J = 6.6 Hz, 2H), 3.55 (dd, J = 8.9, 3.5 Hz, 1H), 3.49-3.35 (m, 4H), 3.23 (dt, J = 9.0, 6.5 Hz, 1H), 2.98 (t, J = 6.6 Hz, 2H), 2.38 (dt, J = 13.8, 6.4 Hz, 1H), 2.18 (ddt, J = 15.6, 8.5, 5.0 Hz, 1H), 1.71 (dq, J = 18.0, 7.7, 7.0 Hz, 2H), 1.49-1.27 (m, 6H), 1.04 (dd, J = 16.1, 7.2 Hz, 1H), 0.76 (t, J = 7.4 Hz, 3H) | $^{13}$C NMR (CDCl$_3$) δ 172.49, 169.43, 162.37, 159.72, 159.45, 146.76, 141.40, 137.35, 129.33, 121.30, 116.48, 109.84, 83.04, 82.96, 72.58, 71.36, 67.56, 58.77, 56.32, 51.35, 34.61, 33.61, 28.17, 23.14, 18.35, 18.08, 10.53 |
| F141 | White Foam | — | — | HRMS-ESI (m/z) [M + H]$^+$ calcd for C$_{27}$H$_{35}$N$_2$O$_8$, 515.2388; found, 515.2397 | $^1$H NMR (CDCl$_3$) δ 8.54 (d, J = 7.7 Hz, 1H), 8.33 (d, J = 5.4 Hz, 1H), 7.30-7.24 (m, 2H), 7.08 (dd, J = 8.8, 1.0 Hz, 2H), 7.00 (d, J = 5.5 Hz, 1H), 6.98-6.92 (m, 1H), 5.01 (dq, J = 9.7, 6.4 Hz, 1H), 4.63 (dt, J = 10.7, | $^{13}$C NMR (CDCl$_3$) δ 172.49, 168.90, 162.41, 159.72, 159.44, 146.71, 141.37, 137.50, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 7.5 Hz, 1H), 4.40 (dd, J = 9.6, 7.3 Hz, 1H), 3.90 (s, 3H), 3.55 (ddd, J = 7.0, 5.2, 1.5 Hz, 1H), 3.45 (dt, J = 9.0, 6.6 Hz, 1H), 3.23 (dt, J = 9.0, 6.5 Hz, 1H), 2.39 (s, 4H), 2.26-2.12 (m, 1H), 1.81-1.66 (m, 2H), 1.49-1.29 (m, 6H), 1.04 (dd, J = 16.1, 7.2 Hz, 1H), 0.76 (t, J = 7.4 Hz, 3H) | 129.33, 121.30, 116.49, 109.84, 83.05, 82.96, 72.60, 71.38, 56.29, 51.37, 33.64, 28.19, 23.14, 20.74, 18.35, 18.09, 10.53 |
| F142 | White Solid | 69-72 | 3364, 2946, 1733, 1649, 1527 | HRMS-ESI (m/z) [M + H]⁺ calcd for $C_{25}H_{35}N_2O_8$, 491.2388; found, 491.2393 | ¹H NMR (CDCl₃) δ 12.06 (s, 1H), 8.44 (d, J = 8.0 Hz, 1H), 7.99 (d, J = 5.2 Hz, 1H), 6.87 (d, J = 5.3 Hz, 1H), 5.07 (dd, J = 9.8, 7.7 Hz, 1H), 4.98 (dq, J = 9.8, 6.3 Hz, 1H), 4.61 (dt, J = 10.7, 7.6 Hz, 1H), 3.96-3.90 (m, 1H), 3.94 (s, 3H), 3.45 (ddd, J = 7.5, 5.4, 2.0 Hz, 1H), 2.40 (dtd, J = 13.4, 7.1, 1.4 Hz, 1H), 2.13 (dddd, J = 15.7, 10.0, 7.8, 5.4 Hz, 1H), 1.92-1.35 (m, 13H), 1.30 (d, J = 6.2 Hz, 3H), 1.12-1.00 (m, 3H), 0.93-0.84 (m, 2H) | ¹³C NMR (CDCl₃) δ 173.89, 172.14, 168.65, 155.36, 148.74, 140.50, 130.35, 109.48, 79.51, 78.43, 75.63, 71.82, 56.08, 51.34, 33.32, 33.21, 32.01, 28.73, 23.44, 23.15, 18.22, 17.32, 12.79, 8.46, 8.42 |
| F143 | White Solid | 124-125 | 3376, 2950, 2870, 1734, 1652, 1527 | HRMS-ESI (m/z) [M + H]⁺ calcd for $C_{27}H_{39}N_2O_8$, 519.2701; found, 519.2709 | ¹H NMR (CDCl₃) δ 12.06 (s, 1H), 8.44 (d, J = 8.0 Hz, 1H), 7.99 (d, J = 5.2 Hz, 1H), 6.87 (d, J = 5.2 Hz, 1H), 5.09 (dd, J = 9.7, 7.7 Hz, 1H), 4.97 (dq, J = 9.7, 6.3 Hz, 1H), 4.62 (dt, J = 10.7, 7.6 Hz, 1H), 3.94 (s, 3H), 3.93-3.88 (m, 1H), 3.46 (ddd, J = 7.5, 5.4, 1.9 Hz, 1H), 2.74 (p, J = 8.0 Hz, 1H), 2.40 (ddd, J = 12.4, 7.5, 6.1 Hz, 1H), 2.22-2.07 (m, 1H), 2.01-1.34 (m, 19H), 1.28 (d, J = 6.3 Hz, 3H), 1.02 (ddt, J = 16.2, 7.9, 2.1 Hz, 1H) | ¹³C NMR (CDCl₃) δ 175.57, 172.14, 168.65, 155.36, 148.74, 140.49, 130.35, 109.48, 79.38, 78.55, 75.37, 71.87, 56.07, 51.32, 43.98, 33.30, 33.27, 32.08, 30.31, 29.74, 28.54, 25.82, 25.73, 23.49, 23.27, 18.20, 17.32 |
| F144 | White Solid | 39-43 | 3380, 2953, 1735, 1678, 1503 | HRMS-ESI (m/z) [M + H]⁺ calcd for $C_{28}H_{39}N_2O_{10}$, 563.2599; found, 563.2605 | ¹H NMR (CDCl₃) δ 8.30 (d, J = 7.9 Hz, 1H), 8.27 (d, J = 5.3 Hz, 1H), 6.96 (d, J = 5.4 Hz, 1H), 5.73 (s, 2H), 5.06 (dd, J = 9.8, 7.7 Hz, 1H), 4.96 (dq, J = 9.7, 6.3 Hz, 1H), 4.62 (dt, J = 10.8, 7.5 Hz, 1H), 3.96-3.92 (m, 1H), 3.91 (s, 3H), 3.44 (ddd, J = 7.6, 5.4, 2.0 Hz, 1H), 2.40 (dt, J = 13.4, 6.4 Hz, 1H), 2.21-2.09 (m, 1H), 2.07 (s, 3H), | ¹³C NMR (CDCl₃)δ 173.86, 172.72, 170.27, 162.94, 160.27, 145.68, 144.03, 142.28, 109.62, 89.52, 79.47, 78.48, 75.71, 71.51, 56.18, 51.67, 33.36, 33.18, 31.99, 29.68, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1.81-1.44 (m, 10H), 1.36 (dtd, J = 12.9, 11.2, 1.6 Hz, 1H), 1.29 (d, J = 6.2 Hz, 3H), 1.09-0.98 (m, 3H), 0.93-0.79 (m, 3H) | 28.82, 23.43, 23.14, 20.85, 18.30, 17.30, 12.78, 8.42 |
| F145 | White Solid | 48-51 | 3379, 2946, 2875, 17334, 1676, 1503 | HRMS-ESI (m/z) [M + H]⁺ calcd for $C_{30}H_{43}N_2O_{10}$, 591.2912; found, 591.2918 | ¹H NMR (CDCl₃) δ 8.35 (d, J = 8.0 Hz, 1H), 8.27 (d, J = 5.4 Hz, 1H), 6.94 (d, J = 5.4 Hz, 1H), 5.80-5.72 (m, 2H), 5.06 (dd, J = 9.8, 7.7 Hz, 1H), 4.96 (dq, J = 9.7, 6.2 Hz, 1H), 4.62 (dt, J = 10.7, 7.5 Hz, 1H), 3.95-3.88 (m, 1H), 3.89 (s, 3H), 3.44 (ddd, J = 7.6, 5.5, 2.0 Hz, 1H), 2.55 (hept, J = 7.0 Hz, 1H), 2.40 (dtd, J = 13.4, 7.2, 1.5 Hz, 1H), 2.20-2.04 (m, 1H), 1.81-1.44 (m, 11H), 1.44-1.31 (m, 1H), 1.29 (d, J = 6.2 Hz, 3H), 1.14 (d, J = 7.0 Hz, 6H), 1.08-0.97 (m, 3H), 0.92-0.85 (m, 2H) | ¹³C NMR (CDCl₃) δ 176.25, 173.86, 172.73, 162.92, 160.25, 145.55, 144.26, 141.97, 109.55, 89.90, 79.47, 78.48, 75.72, 71.51, 56.13, 53.44, 51.67, 33.83, 33.38, 33.19, 32.00, 28.84, 23.43, 23.14, 18.66, 18.31, 17.31, 12.78, 8.42, 8.37 |
| F146 | White Solid | 144-145 | 2955, 1770, 1745, 1680, 1509 | HRMS-ESI (m/z) [M + H]⁺ calcd for $C_{29}H_{45}N_2O_9$, 565.3120; found, 565.3124 | ¹H NMR (CDCl₃) δ 8.54-8.47 (m, 1H), 8.32 (d, J = 5.4 Hz, 1H), 6.99 (d, J = 5.5 Hz, 1H), 4.78 (dq, J = 9.5, 6.3 Hz, 1H), 4.58 (ddd, J = 10.7, 8.5, 7.3 Hz, 1H), 4.00 (ddt, J = 6.6, 4.2, 2.6 Hz, 1H), 3.89 (s, 3H), 3.81 (t, J = 6.6 Hz, 2H), 3.65 (dd, J = 8.5, 5.9 Hz, 1H), 3.45-3.41 (m, 1H), 3.40 (s, 3H), 3.30 (dt, J = 9.7, 7.4 Hz, 2H), 2.98 (t, J = 6.6 Hz, 2H), 2.40-2.28 (m, 1H), 2.07 (dddd, J = 15.7, 10.0, 8.3, 5.1 Hz, 1H), 1.83 (dt, J = 13.2, 6.7 Hz, 1H), 1.76-1.45 (m, 10H), 1.38 (d, J = 6.4 Hz, 3H), 1.35-1.25 (m, 1H), 0.92 (d, J = 6.6 Hz, 3H), 0.90 (d, J = 6.6 Hz, 3H; 0.90-0.85 (m, 1H) | ¹³C NMR (CDCl₃) δ 172.56, 169.39, 162.31, 159.41, 146.72, 141.43, 137.30, 109.77, 83.72, 81.78, 80.91, 79.11, 73.22, 67.56, 58.76, 56.30, 51.32, 34.61, 33.66, 33.55, 31.87, 29.15, 28.41, 23.65, 23.36, 19.59, 19.39, 18.50, 17.90 |
| F147 | White Solid | 44-47 | 3379, 2951, 1735, 1679, 1508 | HRMS-ESI (m/z) [M + H]⁺ calcd for $C_{29}H_{41}N_2O_{10}$, 577.2756; found, 577.2761 | ¹H NMR (CDCl₃) δ 8.52-8.45 (m, 1H), 8.32 (d, J = 5.4 Hz, 1H), 7.00 (d, J = 5.5 Hz, 1H), 5.05 (dd, J = 9.8, 7.7 Hz, 1H), 4.95 (dq, J = 9.8, 6.3 Hz, 1H), 4.61 (dt, J = 10.6, 7.6 Hz, 1H), 3.92 (dq, J = 5.1, 2.7, 2.1 Hz, 1H), 3.89 (s, 3H), 3.81 (t, J = 6.5 Hz, 2H), 3.44 (dq, J = 5.8, 3.6, 2.8 Hz, 1H), | ¹³C NMR (CDCl₃) δ 173.85, 172.61, 169.40, 162.30, 159.44, 146.71, 141.38, 137.34, 109.82, 79.47, 78.48, 75.69, 71.51, 67.55, 58.76, 56.31, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 3.40 (s, 3H), 2.98 (t, J = 6.6 Hz, 2H), 2.42-2.31 (m, 1H), 2.11 (dddd, J = 15.7, 9.9, 8.2, 4.1 Hz, 1H), 1.82-1.42 (m, 10H), 1.41-1.30 (m, 1H), 1.27 (d, J = 6.3 Hz, 3H), 1.06-0.97 (m, 3H), 0.91-0.82 (m, 3H) | 51.34, 34.61, 33.61, 33.18, 31.99, 28.82, 23.43, 23.14, 18.27, 17.28, 12.77, 8.42, 8.37 |
| F148 | White Solid | 48-51 | 3371, 2952, 2871, 1737, 1676, 1504 | HRMS-ESI (m/z) [M + H]$^+$ calcd for C$_{30}$H$_{43}$N$_2$O$_{10}$, 591.2912; found, 591.2936 | $^1$H NMR (CDCl$_3$) δ 8.30 (d, J = 8.0 Hz, 1H), 8.27 (d, J = 5.3 Hz, 1H), 6.96 (d, J = 5.4 Hz, 1H), 5.74 (s, 2H), 5.08 (dd, J = 9.8, 7.7 Hz, 1H), 4.95 (dq, J = 9.7, 6.3 Hz, 1H), 4.63 (dt, J = 10.8, 7.5 Hz, 1H), 3.95-3.85 (m, 1H), 3.91 (s, 3H), 3.45 (ddd, J = 7.6, 5.4, 1.9 Hz, 1H), 2.73 (p, J = 8.0 Hz, 1H), 2.46-2.34 (m, 1H), 2.21-2.09 (m, 1H), 2.07 (s, 3H), 1.99-1.44 (m, 18H), 1.43-1.30 (m, 1H), 1.27 (d, J = 6.4 Hz, 3H), 1.02 (ddt, J = 16.1, 7.9, 2.3 Hz, 1H) | $^{13}$C NMR (CDCl$_3$) δ 175.52, 172.72, 170.26, 162.94, 160.27, 145.68, 144.05, 142.28, 109.62, 89.53, 79.33, 78.60, 75.44, 71.55, 56.18, 51.65, 43.97, 33.36, 33.25, 32.06, 30.29, 29.72, 28.63, 25.80, 25.74, 23.48, 23.26, 20.85, 18.28, 17.31 |
| F149 | White Foam | — | 3368, 2954, 2871, 1737, 1528 | HRMS-ESI (m/z) [M + H]$^+$ calcd for C$_{26}$H$_{39}$N$_2$O$_8$, 507.2701; found, 507.2717 | $^1$H NMR (CDCl$_3$) δ 12.06 (s, 1H), 8.44 (d, J = 8.1 Hz, 1H), 7.99 (d, J = 5.1 Hz, 1H), 6.87 (d, J = 5.2 Hz, 1H), 5.17 (dd, J = 9.7, 7.8 Hz, 1H), 4.97 (dq, J = 9.7, 6.4 Hz, 1H), 4.62 (dt, J = 10.9, 7.6 Hz, 1H), 3.94 (s, 3H), 3.39 (ddd, J = 7.6, 5.3, 1.9 Hz, 1H), 3.27 (dd, J = 8.7, 6.3 Hz, 1H), 2.98 (dd, J = 8.7, 6.6 Hz, 1H), 2.74 (p, J = 8.0 Hz, 1H), 2.47-2.33 (m, 1H), 2.26-2.10 (m, 1H), 1.96-1.64 (m, 9H), 1.64-1.52 (m, 2H), 1.41 (dtd, J = 13.2, 11.6, 1.6 Hz, 1H), 1.29 (d, J = 6.4 Hz, 3H), 1.01 (ddt, J = 16.3, 8.0, 2.0 Hz, 1H), 0.85 (d, J = 6.7 Hz, 6H) | $^{13}$C NMR (CDCl$_3$) δ 175.59, 172.12, 168.66, 155.37, 148.75, 140.50, 130.36, 109.48, 81.11, 76.14, 75.26, 71.77, 56.08, 51.28, 43.97, 33.30, 30.13, 29.77, 28.69, 27.73, 25.82, 25.72, 19.37, 19.33, 17.95, 17.26 |
| F150 | White Foam | — | 3379, 2954, 2872, 1739, 1503 | HRMS-ESI (m/z) [M + Na]$^+$ calcd for C$_{29}$H$_{42}$N$_2$NaO$_{10}$, 601.2732; found, 01.2758 | $^1$H NMR (CDCl$_3$) δ 8.30 (d, J = 7.8 Hz, 1H), 8.27 (d, J = 5.3 Hz, 1H), 6.95 (d, J = 5.4 Hz, 1H), 5.74 (s, 2H), 5.16 (dd, J = 9.8, 7.8 Hz, 1H), 4.95 (dq, J = 9.8, 6.4 Hz, 1H), 4.64 (dt, J = 10.8, 7.6 Hz, 1H), 3.91 (s, 3H), 3.37 (ddd, J = 7.5, 5.3, 1.9 Hz, 1H), 3.27 (dd, J = 8.7, 6.3 Hz, 1H), 2.97 (dd, J = 8.7, 6.6 Hz, 1H), 2.73 (p, J = 7.9 Hz, | $^{13}$C NMR (CDCl$_3$) δ 175.56, 172.74, 170.33, 162.95, 160.29, 145.68, 144.11, 142.32, 109.60, 89.59, 81.19, 76.12, 75.36, 71.49, 56.19, 51.62, 43.98, 33.39, 30.13, 29.76, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1H), 2.41 (dt, J = 13.8, 7.1 Hz, 1H), 2.24-2.09 (m, 1H), 2.08 (s, 3H), 1.95-1.61 (m, 11H), 1.42-1.29 (m, 1H), 1.27 (d, J = 6.4 Hz, 3H), 1.07-0.96 (m, 1H), 0.85 (d, J = 6.7 Hz, 6H) | 28.69, 27.84, 25.82, 25.72, 20.89, 19.37, 19.34, 18.04, 17.27 |
| F151 | White Foam | — | 3379, 2955, 2872, 1738 | HRMS-ESI (m/z) [M + H]⁺ calcd for $C_{28}H_{41}N_2O_9$, 549.2807; found, 549.2832 | ¹H NMR (CDCl₃) δ 8.50 (d, J = 8.2 Hz, 1H), 8.33 (d, J = 5.4 Hz, 1H), 7.00 (d, J = 5.5 Hz, 1H), 5.14 (dd, J = 9.8, 7.8 Hz, 1H), 4.99-4.91 (m, 1H), 4.63 (dt, J = 10.8, 7.7 Hz, 1H), 3.91 (s, 3H), 3.39-3.35 (m, 1H), 3.26 (dd, J = 8.7, 6.2 Hz, 1H), 2.96 (dd, J = 8.7, 6.6 Hz, 1H), 2.77-2.69 (m, 1H), 2.42-2.35 (m, 1H), 2.40 (s, 3H), 2.23-2.08 (m, 1H), 1.97-1.60 (m, 11H), 1.38-1.27 (m, 1H), 1.26 (d, J = 6.4 Hz, 3H), 1.00 (dd, J = 15.7, 7.7 Hz, 1H), 0.85 (dd, J = 6.7, 2.6 Hz, 6H) | ¹³C NMR (CDCl₃) δ 175.57, 172.62, 168.93, 162.36, 159.45, 146.66, 141.39, 137.52, 109.80, 81.19, 76.13, 75.34, 71.50, 56.29, 51.33, 43.98, 33.62, 30.13, 29.76, 28.68, 27.86, 25.82, 25.72, 20.76, 19.37, 19.33, 18.0, 17.24 |
| F152 | White Foam | — | 3378, 2954, 2872, 1738 | HRMS-ESI (m/z) [M + H]⁺ calcd for $C_{30}H_{45}N_2O_{10}$, 593.3069; found, 593.3077 | ¹H NMR (CDCl₃) δ 8.47 (s, 1H), 8.33 (d, J = 5.4 Hz, 1H), 6.99 (d, J = 5.4 Hz, 1H), 5.14 (dd, J = 9.8, 7.8 Hz, 1H), 4.94 (dq, J = 9.7, 6.3 Hz, 1H), 4.62 (dt, J = 10.8, 7.7 Hz, 1H), 3.90 (s, 3H), 3.81 (t, J = 6.6 Hz, 2H), 3.41 (s, 3H), 3.37 (ddd, J = 7.5, 5.2, 1.9 Hz, 1H), 3.26 (dd, J = 8.7, 6.3 Hz, 1H), 3.01-2.94 (m, 2H), 2.73 (p, J = 7.9 Hz, 1H), 2.37 (dt, J = 13.6, 7.0 Hz, 1H), 2.23-2.06 (m, 1H), 1.96-1.50 (m, 12H), 1.39-1.29 (m, 1H), 1.26 (d, J = 6.3 Hz, 3H), 1.05-0.95 (m, 1H), 0.85 (d, J = 6.7 Hz, 6H) | ¹³C NMR (CDCl₃) δ 175.58, 172.63, 169.47, 162.32, 159.46, 146.71, 141.42, 137.38, 109.79, 81.19, 76.12, 75.33, 71.49, 67.57, 58.80, 56.32, 51.31, 43.98, 34.62, 33.62, 30.13, 29.76, 28.68, 27.83, 25.82, 25.72, 19.37, 19.33, 18.00, 17.23 |
| F153 | White Foam | — | 3368, 2958, 2874, 1742, 1529 | HRMS-ESI (m/z) [M + H]⁺ calcd for $C_{24}H_{37}N_2O_7$, 465.2595; found, 465.2617 | ¹H NMR (CDCl₃) δ 12.09 (s, 1H), 8.48 (d, J = 8.2 Hz, 1H), 7.98 (d, J = 5.2 Hz, 1H), 6.86 (d, J = 5.2 Hz, 1H), 4.76 (dq, J = 9.6, 6.4 Hz, 1H), 4.58 (ddd, J = 10.8, 8.2, 7.3 Hz, 1H), 4.30 (td, J = 5.3, 2.8 Hz, 1H), 3.52-3.41 (m, 2H), 3.36-3.24 (m, 2H), 2.37 (dtd, J = 13.5, 7.0, 6.5, 1.9 Hz, 1H), 2.14 (dddd, J = 15.8, 10.1, 8.3, 5.3 Hz, 1H), 1.86-1.46 (m, 12H), 1.42-1.33 (m, | ¹³C NMR (CDCl₃) δ 172.11, 168.64, 155.34, 148.71, 140.52, 130.41, 109.45, 84.20, 83.37, 81.33, 73.54, 70.92, 56.07, 51.33, 33.33, 32.92, 32.39, 27.79, 23.34, 23.26, 23.22, 18.27, 18.11, 10.78 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1H), 1.39 (d, J = 6.4 Hz, 3H), 0.93 (t, J = 7.4 Hz, 3H), 0.94-0.88 (m, 1H) | |
| F154 | White Foam | — | 3379, 2959, 2875, 1746, 1504 | HRMS-ESI (m/z) [M + H]⁺ calcd for C₂₉H₄₅N₂O₉, 565.3120; found, 565.3134 | ¹H NMR (CDCl₃) δ 8.37 (d, J = 8.1 Hz, 1H), 8.27 (d, J = 5.3 Hz, 1H), 6.93 (d, J = 5.4 Hz, 1H), 5.83-5.69 (m, 2H), 4.74 (dq, J = 9.7, 6.5 Hz, 1H), 4.60 (dt, J = 10.8, 7.6 Hz, 1H), 4.34-4.24 (m, 1H), 3.89 (s, 3H), 3.51-3.41 (m, 2H), 3.36-3.26 (m, 2H), 2.55 (hept, J = 7.0 Hz, 1H), 2.37 (dt, J = 14.0, 6.8 Hz, 1H), 2.18-2.04 (m, 1H), 1.85-1.44 (m, 12H), 1.38 (d, J = 6.4 Hz, 3H), 1.37-1.25 (m, 1H), 1.14 (d, J = 7.0 Hz, 6H), 0.93 (t, J = 7.4 Hz, 3H), 0.93-0.88 (m, 1H) | ¹³C NMR (CDCl₃) δ 176.27, 172.73, 162.93, 160.25, 145.59, 144.21, 142.11, 109.51, 89.94, 84.28, 83.36, 81.40, 73.25, 70.90, 56.13, 51.66, 33.86, 33.43, 32.93, 32.39, 27.88, 23.34, 23.26, 23.22, 18.68, 18.34, 18.10, 10.78 |
| F155 | White Foam | — | 3380, 2958, 2874, 1746, 1678 | HRMS-ESI (m/z) [M + H]⁺ calcd for C₂₇H₄₁N₂O₉, 537.2807; found, 537.2824 | ¹H NMR (CDCl₃) δ 8.32 (d, J = 8.0 Hz, 1H), 8.27 (d, J = 5.3 Hz, 1H), 6.94 (d, J = 5.4 Hz, 1H), 5.74 (s, 2H), 4.74 (dq, J = 9.6, 6.4 Hz, 1H), 4.60 (dt, J = 10.8, 7.6 Hz, 1H), 4.30 (h, J = 3.4 Hz, 1H), 3.91 (s, 3H), 3.53-3.41 (m, 2H), 3.38-3.24 (m, 2H), 2.38 (ddd, J = 13.7, 7.0, 5.3 Hz, 1H), 2.19-2.09 (m, 1H), 2.07 (s, 3H), 1.86-1.44 (m, 12H), 1.38 (d, J = 6.4 Hz, 3H), 1.36-1.29 (m, 1H), 0.93 (t, J = 7.4 Hz, 3H), 0.91-0.79 (m, 1H) | ¹³C NMR (CDCl₃) δ 172.74, 170.31, 162.96, 160.27, 145.73, 143.99, 142.45, 109.57, 89.57, 84.28, 83.36, 81.39, 73.27, 70.90, 56.18, 51.66, 33.42, 32.93, 32.39, 27.87, 23.34, 23.26, 23.21, 20.89, 18.34, 18.10, 10.78 |
| F156 | White Foam | — | 3367, 2952, 2871, 1732, 1530 | HRMS-ESI (m/z) [M + H]⁺ calcd for C₂₇H₃₉N₂O₈, 519.2701; found, 519.2719 | ¹H NMR (CDCl₃) δ 12.04 (s, 1H), 8.50 (d, J = 8.2 Hz, 1H), 7.99 (dd, J = 5.2, 1.4 Hz, 1H), 6.87 (d, J = 5.2 Hz, 1H), 4.94-4.81 (m, 2H), 4.61 (dt, J = 10.9, 7.6 Hz, 1H), 4.15-4.07 (m, 1H), 3.58 (dd, J = 9.5, 7.4 Hz, 1H), 2.74 (p, J = 8.1 Hz, 1H), 2.36 (dt, J = 13.8, 7.0 Hz, 1H), 2.22-2.07 (m, 1H), 1.94 (m, 1H), 1.86 (q, J = 7.2 Hz, 2H), 1.81-1.46 (m, 15H), 1.46-1.32 (m, 1H), 1.43 (d, J = 6.4 Hz, 3H), 1.10 (dd, J = 16.2, 7.2 Hz, 1H) | ¹³C NMR (CDCl₃) δ 175.77, 171.84, 168.67, 155.33, 148.69, 140.57, 130.34, 109.49, 83.35, 80.01, 77.66, 73.39, 56.08, 51.27, 44.07, 33.12, 32.91, 32.35, 30.55, 29.51, 29.31, 25.82, 25.77, 23.13, 23.11, 18.41, 18.00 |
| F157 | white foam | — | 3380, 2948, 2872, 1744, 1678 | HRMS-ESI (m/z) [M + H]⁺ calcd for C₃₂H₄₇N₂O₁₀, | ¹H NMR (CDCl₃) δ 8.40 (d, J = 8.1 Hz, 1H), 8.27 (d, J = 5.4 Hz, 1H), 6.94 (d, J = 5.4 Hz, 1H), | ¹³C NMR (CDCl₃) δ 176.25, 175.79, 172.44, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | 619.3225; found, 619.3256 | 5.83-5.70 (m, 2H), 4.89-4.82 (m, 2H), 4.62 (dt, J = 10.8, 7.6 Hz, 1H), 4.17-4.03 (m, J = 4.1 Hz, 1H), 3.89 (s, 3H), 3.58 (dd, J = 9.5, 7.3 Hz, 1H), 2.80-2.66 (m, 1H), 2.54 (hept, J = 7.0 Hz, 1H), 2.36 (dt, J = 13.8, 6.8 Hz, 1H), 2.19-2.05 (m, 1H), 2.01-1.89 (m, 1H), 1.86 (td, J = 7.9, 7.5, 5.8 Hz, 2H), 1.79-1.46 (m, 14H), 1.41 (d, J = 6.4 Hz, 3H), 1.39-1.26 (m, 2H), 1.14 (d, J = 7.0 Hz, 6H), 1.13-1.01 (m, 1H) | 162.96, 160.24, 145.63, 144.15, 142.01, 109.56, 89.87, 83.33, 80.07, 77.81, 73.10, 56.14, 51.60, 44.09, 33.86, 33.21, 32.91, 32.36, 30.55, 29.51, 29.33, 25.82, 25.77, 23.13, 23.11, 18.68, 18.46, 17.99 |
| F158 | white foam | — | 3360, 2951, 2871, 1732, 1677 | HRMS-ESI (m/z) [M + H]⁺ calcd for C₃₀H₄₃N₂O₁₀, 591.2912; found, 591.2941 | ¹H NMR (CDCl₃) δ 8.34 (d, J = 8.1 Hz, 1H), 8.27 (d, J = 5.3 Hz, 1H), 6.95 (d, J = 5.4 Hz, 1H), 5.74 (s, 2H), 4.89-4.82 (m, 2H), 4.62 (dt, J = 10.8, 7.7 Hz, 1H), 4.10 (p, J = 4.6 Hz, 1H), 3.91 (s, 3H), 3.58 (dd, J = 9.5, 7.3 Hz, 1H), 2.79-2.67 (m, 1H), 2.42-2.29 (m, 1H), 2.19-2.08 (m, 1H), 2.07 (s, 3H), 1.99-1.89 (m, 1H), 1.86 (td, J = 8.0, 7.5, 5.7 Hz, 2H), 1.80-1.46 (m, 15H), 1.41 (d, J = 6.4 Hz, 3H), 1.34 (q, J = 11.5 Hz, 1H), 1.09 (ddt, J = 16.0, 7.2, 2.4 Hz, 1H) | ¹³C NMR (CDCl₃) δ 175.80, 172.45, 170.29, 162.99, 160.25, 145.76, 143.94, 142.34, 109.62, 89.51, 83.33, 80.07, 77.79, 73.12, 56.19, 51.61, 44.09, 33.19, 32.91, 32.36, 30.55, 29.51, 29.35, 25.82, 25.77, 23.13, 23.11, 20.89, 18.46, 17.99 |
| F159 | white foam | — | 3350, 2951, 2871, 1731, 1676 | HRMS-ESI (m/z) [M + H]⁺ calcd for C₂₉H₄₁N₂O₉, 561.2807; found, 561.2834 | ¹H NMR (CDCl₃) δ 8.55 (d, J = 8.1 Hz, 1H), 8.33 (d, J = 5.4 Hz, 1H), 7.00 (d, J = 5.4 Hz, 1H), 4.92-4.77 (m, 2H), 4.61 (ddd, J = 10.8, 8.4, 7.1 Hz, 1H), 4.14-4.01 (m, 1H), 3.91 (s, 3H), 3.56 (dd, J = 9.5, 7.3 Hz, 1H), 2.79-2.65 (m, 1H), 2.40 (s, 3H), 2.38-2.25 (m, 1H), 2.11 (ddt, J = 16.3, 10.0, 7.4 Hz 1H), 2.00-1.89 (m, 1H), 1.85 (td, J = 7.5, 5.6 Hz, 2H), 1.79-1.45 (m, 15H), 1.40 (d, J = 6.4 Hz, 3H), 1.37-1.26 (m, 1H), 1.15-1.02 (m, 1H) | ¹³C NMR (CDCl₃) δ 175.79, 172.32, 168.90, 162.42, 159.41, 146.72, 141.33, 137.47, 109.82, 83.32, 80.07, 77.74, 73.12, 56.29, 51.34, 44.08, 33.39, 32.92, 32.35, 30.55, 29.51, 29.39, 25.82, 25.76, 23.13, 23.11, 20.75, 18.43, 17.97 |
| F160 | White Foam | — | 3370, 2952, 1743, 1503 | HRMS-ESI (m/z) [M + H]⁺ calcd for C₂₇H₃₄FN₂O₇, 517.2345; found, 517.2364 | ¹H NMR (CDCl₃) δ 12.05 (d, J = 0.6 Hz, 1H), 8.46 (d, J = 8.1 Hz, 1H), 7.99 (d, J = 5.2 Hz, 1H), 7.02-6.92 (m, 2H), 6.92-6.76 (m, 3H), 4.87 (dq, J = 9.7, 6.4 Hz, 1H), 4.63 (dt, J = 10.8, | ¹³C NMR (CDCl₃) δ 172.00, 168.68, 155.36, 148.73, 140.55, 130.34, 117.87, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 7.7 Hz, 1H), 4.31-4.17 (m, 2H), 3.94 (s, 3H), 3.72 (dd, J = 9.6, 7.1 Hz, 1H), 2.37 (dt, J = 13.7, 6.9 Hz, 1H), 2.14-2.09 (m, 1H), 1.89-1.76 (m, 1H), 1.76-1.50 (m, 9H), 1.46 (d, J = 6.4 Hz, 3H), 1.41-1.27 (m, 1H), 1.09-0.97 (m, 1H) | 117.79, 116.02, 115.79, 109.49, 83.97, 83.86, 80.93, 73.28, 56.09, 51.24, 33.21, 32.85, 32.47, 28.07, 23.13, 23.11, 18.21, 18.06 |
| F161 | White Foam | — | 3375, 2946, 1746, 1503 | HRMS-ESI (m/z) [M + H]$^+$ calcd for C$_{32}$H$_{42}$FN$_2$O$_9$, 617.2869; found, 617.2887 | $^1$H NMR (CDCl$_3$) δ 8.37 (d, J = 8.0 Hz, 1H), 8.26 (d, J = 5.3 Hz, 1H), 7.03-6.91 (m, 3H), 6.91-6.81 (m, 2H), 5.88-5.65 (m, 2H), 4.85 (dq, J = 9.6, 6.4 Hz, 1H), 4.64 (dt, J = 10.8, 7.6 Hz, 1H), 4.31-4.18 (m, 2H), 3.71 (dd, J = 9.6, 7.1 Hz, 1H), 2.55 (hept, J = 7.0 Hz, 1H), 2.44-2.29 (m, 1H), 2.18-2.01 (m, 1H), 1.87-1.49 (m, 10H), 1.45 (d, J = 6.4 Hz, 3H), 1.36-1.25 (m, 1H), 1.14 (d, J = 7.0 Hz, 6H), 1.02 (dd, J = 16.0, 7.6 Hz, 1H) | $^{13}$C NMR (CDCl$_3$) δ 176.27, 172.61, 162.97, 160.25, 156.31, 153.74, 153.72, 145.60, 144.22, 142.00, 117.87, 117.79, 115.99, 115.76, 109.56, 89.89, 84.05, 83.84, 81.00, 72.98, 56.14, 51.58, 33.86, 33.29, 32.85, 32.47, 28.15, 23.12, 23.11, 18.68, 18.28, 18.05 |
| F162 | White Foam | — | 3375, 2952, 1749, 1503 | HRMS-ESI (m/z) [M + H]$^+$ calcd for C$_{30}$H$_{38}$FN$_2$O$_9$, 589.2556; found, 589.2572 | $^1$H NMR (CDCl$_3$) δ 8.31 (d, J = 8.0 Hz, 1H), 8.27 (d, J = 5.4 Hz, 1H), 7.04-6.92 (m, 3H), 6.92-6.82 (m, 2H), 5.74 (s, 2H), 4.85 (dq, J = 9.7, 6.4 Hz, 1H), 4.64 (dt, J = 10.8, 7.6 Hz, 1H), 4.32-4.18 (m, 2H), 3.91 (s, 3H), 3.71 (dd, J = 9.6, 7.1 Hz, 1H), 2.44-2.30 (m, 1H), ), 2.15-2.05 (m, 1H), 2.07 (s, 3H), 1.87-1.47 (m, 10H), 1.45 (d, J = 6.4 Hz, 3H), 1.36-1.26 (m, 1H), 1.06-0.95 (m, 1H) | $^{13}$C NMR (CDCl$_3$) δ 172.62, 170.31, 162.99, 160.27, 156.31, 153.73, 153.71, 145.74, 144.00, 142.34, 117.88, 117.80, 115.99, 115.76, 109.62, 89.52, 84.05, 83.84, 80.99, 73.00, 56.19, 51.58, 33.28, 32.85, 32.47, 28.15, 23.12, 23.11, 20.89, 18.28, 18.05 |
| F163 | Colorless Oil | — | 3365, 2939, 2869, 1742, 1649, 1576, 1527, 1450 | HRMS-ESI (m/z) [M + H]$^+$ calcd for C$_{30}$H$_{41}$N$_2$O$_7$, 541.2908; found, 541.2915 | $^1$H NMR (CDCl$_3$) δ 12.09 (s, 1H), 8.48 (d, J = 8.1 Hz, 1H), 7.98 (d, J = 5.2 Hz, 1H), 7.33-7.23 (m, 2H), 7.19 (d, J = 7.3 Hz, 3H), 6.86 (d, J = 5.2 Hz, 1H), 4.81 (dq, J = 9.5, 6.4 Hz, 1H), 4.58 (dt, J = 10.7, 7.6 Hz, 1H), 3.99 (dq, J = 7.6, 3.3, 2.4 Hz, 1H), | $^{13}$C NMR (CDCl$_3$) δ 172.07, 168.65, 155.35, 148.73, 141.98, 140.51, 130.38, 128.34, 128.32, 125.80, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 3.93 (s, 3H), 3.85 (dt, J = 8.9, 6.5 Hz, 1H), 3.63 (dt, J = 8.9, 6.7 Hz, 1H), 3.43 (ddd, J = 7.1, 5.2, 1.7 Hz, 1H), 3.33 (dd, J = 9.5, 7.3 Hz, 1H), 2.78-2.59 (m, 2H), 2.36 (dtd, J = 13.6, 7.1, 6.4, 1.9 Hz, 1H), 2.09 (dddd, J = 15.8, 9.9, 8.3, 5.1 Hz, 1H), 2.02-1.80 (m, 2H), 1.77-1.45 (m, 10H), 1.41 (d, J = 6.3 Hz, 3H), 1.40-1.32 (m, 1H), 0.94-0.87 (m, 1H) | 109.47, 83.89, 81.67, 79.14, 73.55, 73.37, 56.07, 51.32, 33.53, 33.38, 32.55, 32.04, 31.88, 28.35, 23.64, 23.36, 18.49, 17.96 |
| F164 | Colorless Oil | — | 3367, 2735, 2871, 1746, 1650, 1522, 1487 | HRMS-ESI (m/z) [M + H]⁺ calcd for C$_{26}$H$_{41}$N$_2$O$_7$, 493.2908; found, 493.2921 | ¹H NMR (CDCl$_3$) δ 12.09 (s, 1H), 8.47 (d, J = 8.0 Hz, 1H), 7.99 (d, J = 5.2 Hz, 1H), 6.86 (d, J = 5.2 Hz, 1H), 4.79 (dqd, J = 9.0, 6.4, 3.3 Hz, 1H), 4.58 (dt, J = 10.7, 7.4 Hz, 1H), 4.01 (dq, J = 6.4, 2.2 Hz, 1H), 3.94 (s, 3H), 3.81 (dt, J = 8.8, 6.6 Hz, 1H), 3.68-3.54 (m, 1H), 3.48-3.38 (m, 1H), 3.38-3.27 (m, 1H), 2.37 (dtd, J = 13.8, 7.2, 6.6, 2.0 Hz, 1H), 2.09 (dddd, J = 15.7, 10.1, 8.4, 5.1 Hz, 1H), 1.80-1.46 (m, 11H), 1.40 (d, J = 6.4 Hz, 3H), 1.37-1.29 (m, 4H), 0.96-0.81 (m, 6H) | ¹³C NMR (CDCl$_3$) δ 172.07, 168.64, 155.3, 148.70, 140.50, 130.39, 109.45, 83.77, 81.66, 79.19, 74.32, 73.45, 56.06, 51.30, 33.53, 33.40, 33.35, 31.91, 30.07, 28.37, 23.66, 23.36, 22.60, 18.47, 17.85, 14.04 |
| F165 | Colorless Oil | — | 3377, 2941, 2868, 1744, 1676, 1499 | HRMS-ESI (m/z) [M + H]⁺ calcd for C$_{33}$H$_{45}$N$_2$O$_9$, 613.3120; found, 613.3119 | ¹H NMR (CDCl$_3$) δ 8.31 (d, J = 8.1 Hz, 1H), 8.27 (d, J = 5.4 Hz, 1H), 7.33-7.24 (m, 2H), 7.19 (d, J = 7.3 Hz, 3H), 6.94 (d, J = 5.4 Hz, 1H), 5.74 (s, 2H), 4.79 (dq, J = 9.6, 6.4 Hz, 1H), 4.60 (dt, J = 10.7, 7.5 Hz, 1H), 3.99 (dq, J = 5.7, 3.6 Hz, 1H), 3.90 (s, 3H), 3.85 (dt, J = 9.0, 6.4 Hz, 1H), 3.63 (dt, J = 8.8, 6.7 Hz, 1H), 3.42 (ddd, J = 7.2, 5.2, 1.7 Hz, 1H), 3.32 (dd, J = 9.6, 7.3 Hz, 1H), 2.77-2.59 (m, 2H), 2.43-2.31 (m, 1H), 2.14-2.07 (m, 1H), 2.07 (s, 3H), 1.98-1.80 (m, 3H), 1.77-1.43 (m, 9H), 1.40 (d, J = 6.4 Hz, 3H), 1.37-1.27 (m, 1H), 0.94-0.83 (m, 1H) | ¹³C NMR (CDCl$_3$) δ 172.69, 170.28, 162.97, 160.27, 145.74, 143.98, 142.41, 142.00, 128.34, 128.32, 125.79, 109.61, 89.54, 83.93, 81.75, 79.11, 73.53, 73.09, 56.19, 51.64, 33.51, 33.47, 32.55, 32.04, 31.88, 28.42, 23.63, 23.35, 20.88, 18.55, 17.95 |
| F166 | Colorless Oil | — | 3377, 2974, 2934, 1744, 1677, | HRMS-ESI (m/z) [M + H]⁺ calcd for C$_{29}$H$_{45}$N$_2$O$_9$, | ¹H NMR (CDCl$_3$) δ 8.31 (d, J = 7.9 Hz, 1H), 8.27 (d, J = 5.4 Hz, 1H), 6.95 (d J = 5.4 Hz, 1H), 5.74 (s, | ¹³C NMR (CDCl$_3$) δ 172.69, 170.27, 162.96, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | 1502, 1455 | 565.3120; found, 565.3120 | 2H), 4.77 (dqd, J = 9.9, 6.4, 3.7 Hz, 1H), 4.60 (dt, J = 10.6, 7.6 Hz, 1H), 4.01 (dtd, J = 7.4, 3.7, 1.5 Hz, 1H), 3.91 (s, 3H), 3.80 (dt, J = 8.8, 6.6 Hz, 1H), 3.58 (dt, J = 8.7, 6.8 Hz, 1H), 3.45-3.38 (m, 1H), 3.31 (dd, J = 9.6, 7.4 Hz, 1H), 2.43-2.31 (m, 1H), 2.14-2.01 (m, 1H), 2.07 (s, 3H), 1.81-1.46 (m, 11H), 1.38 (d, J = 6.2 Hz, 3H), 1.33 (dtt, J = 10.5, 4.2, 2.3 Hz, 5H), 0.93-0.84 (m, 5H) | 160.26, 145.72, 143.97, 142.43, 109.58, 89.55, 83.82, 81.75, 79.15, 74.29, 73.17, 56.18, 51.63, 33.52, 33.49, 31.91, 30.08, 28.44, 28.37, 23.65, 23.36, 22.59, 20.87, 18.53, 17.84, 14.03 |
| F167 | White Foam | — | 3366, 2950, 1742, 1505 | HRMS-ESI (m/z) [M + H]⁺ calcd for C₂₈H₃₇N₂O₈, 529.2544; found, 529.2544 | ¹H NMR (CDCl₃) δ 12.07 (d, J = 0.7 Hz, 1H), 8.46 (d, J = 8.2 Hz, 1H), 7.98 (d, J = 5.2 Hz, 1H), 6.96-6.64 (m, 5H), 4.86 (dq, J = 9.7, 6.4 Hz, 1H), 4.62 (dt, J = 10.8, 7.7 Hz, 1H), 4.30 (tt, J = 5.5, 3.6 Hz, 1H), 4.19 (ddd, J = 7.1, 5.2, 1.7 Hz, 1H), 3.94 (s, 3H), 3.77 (s, 3H), 3.72 (dd, J = 9.6, 7.1 Hz, 1H), 2.37 (dt, J = 13.7, 7.0 Hz, 1H), 2.17-2.08 (m, 1H), 1.90-1.48 (m, 10H), 1.46 (d, J = 6.5 Hz, 3H), 1.33 (dt, J = 13.5, 11.4 Hz, 1H), 1.03-0.92 (m, 1H) | ¹³C NMR (CDCl₃) δ 172.02, 168.67, 155.35, 154.32, 151.48, 148.72, 140.53, 130.36, 118.14, 114.63, 109.48, 84.40, 83.80, 80.93, 73.32, 56.08, 55.66, 51.25, 33.26, 32.93, 32.47, 27.91, 23.15, 18.23, 18.09 |
| F168 | White Foam | — | 3367, 2946, 1742, 1528 | HRMS-ESI (m/z) [M + H]⁺ calcd for C₂₅H₃₆F₃N₂O₇, 533.2469; found, 533.2472 | ¹H NMR (CDCl₃) δ 12.07 (d, J = 0.7 Hz, 1H), 8.47 (d, J = 8.1 Hz, 1H), 7.99 (d, J = 5.2 Hz, 1H), 6.87 (d, J = 5.2 Hz, 1H), 4.76 (dq, J = 9.5, 6.4 Hz, 1H), 4.64-4.53 (m, 1H), 4.24 (td, J = 5.3, 2.9 Hz, 1H), 3.61-3.52 (m, 1H), 3.47-3.39 (m, 2H), 3.35-3.31 (m, 1H), 2.38 (dt, J = 13.7, 6.8 Hz, 1H), 2.31-2.03 (m, 3H), 1.89-1.78 (m, 2H), 1.75-1.52 (m, 10H), 1.41-1.33 (m, 1H), 1.40 (d, J = 6.4 Hz, 3H), 0.94 (ddt, J = 16.2, 7.6, 1.9 Hz, 1H) | ¹³C NMR (CDCl₃) δ 172.05, 168.66, 155.35, 148.72, 140.53, 130.38, 128.62, 125.87, 109.47, 84.27, 83.46, 81.20, 73.50, 67.14, 56.08, 51.28, 33.25, 32.85, 32.40, 31.29, 31.00, 30.71, 30.43, 27.72, 23.23, 23.20, 22.88, 22.86, 22.83, 22.80, 18.21, 18.05 |
| F169 | White Foam | — | 3378, 2947, 1745, 1504 | HRMS-ESI (m/z) [M + H]⁺ calcd for C₃₃H₄₅N₂O₁₀, 629.3069; found, 629.3075 | ¹H NMR (CDCl₃) δ 8.36 (d, J = 8.0 Hz, 1H), 8.26 (d, J = 5.4 Hz, 1H), 6.93 (d, J = 5.4 Hz, 1H), 6.91-6.85 (m, 2H), 6.85-6.77 (m, 2H), 4.84 (dq, J = 9.6, 6.4 Hz, 1H), 4.64 (dt, J = 10.8, 7.6 Hz, 1H), | ¹³C NMR (CDCl₃) δ 176.27, 172.63, 162.96, 160.25, 154.27, 151.54, 145.60, 144.21, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 4.30 (tt, J = 5.5, 3.7 Hz, 1H), 4.18 (ddd, J = 7.1, 5.2, 1.7 Hz, 1H), 3.89 (s, 3H), 3.77 (s, 3H), 3.71 (dd, J = 9.6, 7.1 Hz, 1H), 2.55 (hept, J = 7.0 Hz, 1H), 2.37 (dt, J = 13.7, 7.0 Hz, 1H), 2.17-2.06 (m, 1H), 1.87-1.47 (m, 10H), 1.44 (d, J = 6.4 Hz, 3H), 1.35-1.23 (m, 1H), 1.14 (d, J = 7.0 Hz, 6H), 1.03-0.89 (m, 1H) | 142.03, 118.15, 114.61, 109.54, 89.90, 84.49, 83.78, 81.00, 73.02, 56.13, 55.66, 51.58, 33.86, 33.35, 32.93, 32.47, 27.99, 23.14, 18.68, 18.30, 18.08 |
| F170 | White Foam | — | 3379, 2949, 1748, 1677, 1504 | HRMS-ESI (m/z) [M + H]$^+$ calcd for C$_{31}$H$_{41}$N$_2$O$_{10}$, 601.2756; found, 601.2763 | $^1$H NMR (CDCl$_3$) δ 8.31 (d, J = 8.1 Hz, 1H), 8.27 (d, J = 5.3 Hz, 1H), 6.94 (d, J = 5.4 Hz, 1H), 6.92-6.85 (m, 2H), 6.85-6.77 (m, 2H), 5.74 (s, 2H), 4.84 (dq, J = 9.6, 6.4 Hz, 1H), 4.64 (dt, J = 10.8, 7.6 Hz, 1H), 4.30 (tt, J = 5.5, 3.7 Hz, 1H), 4.18 (ddd, J = 7.0, 5.2, 1.7 Hz, 1H), 3.91 (s, 3H), 3.77 (s, 3H), 3.71 (dd, J = 9.6, 7.1 Hz, 1H), 2.37 (dt, J = 13.6, 7.0 Hz, 1H), 2.12 (ddd, J = 10.7, 8.2, 5.4 Hz, 1H), 2.07 (s, 3H), 1.89-1.47 (m, 10H), 1.44 (d, J = 6.4 Hz, 3H), 1.35-1.21 (m, 1H), 0.97 (dd, J = 16.1, 7.8 Hz, 1H) | $^{13}$C NMR (CDCl$_3$) δ 172.64, 170.31, 162.98, 160.26, 154.28, 151.54, 145.73, 144.00, 142.37, 118.15, 114.61, 109.60, 89.54, 84.49, 83.79, 80.99, 73.04, 56.19, 55.66, 51.59, 33.35, 32.93, 32.47, 27.99, 23.14, 20.89, 18.30, 18.08 |
| F171 | Colorless Oil | — | 3380, 2946, 2876, 1745, 1676 | HRMS-ESI (m/z) [M + H]$^+$ calcd for C$_{30}$H$_{44}$F$_3$N$_2$O$_9$, 633.2993; found, 633.3010 | $^1$H NMR (CDCl$_3$) δ 8.37 (d, J = 8.0 Hz, 1H), 8.27 (d, J = 5.4 Hz, 1H), 6.93 (d, J = 5.4 Hz, 1H), 5.81-5.71 (m, 2H), 4.74 (dq, J = 9.5, 6.4 Hz, 1H), 4.60 (dt, J = 10.8, 7.5 Hz, 1H), 4.28-4.20 (m, 1H), 3.89 (s, 3H), 3.60-3.51 (m, 1H), 3.46-3.38 (m, 2H), 3.32 (ddd, J = 7.1, 5.3, 1.6 Hz, 1H), 2.55 (hept, J = 7.0 Hz, 1H), 2.38 (dt, J = 13.7, 6.8 Hz, 1H), 2.30-2.01 (m, 3H), 1.92-1.48 (m, 12H), 1.39 (d, J = 6.4 Hz, 3H), 1.36-1.30 (m, 1H), 1.14 (d, J = 7.0 Hz, 6H), 0.94 (ddt, J = 16.2, 7.7, 2.1 Hz, 1H) | $^{13}$C NMR (CDCl$_3$) δ 176.27, 172.66, 162.95, 160.24, 145.60, 144.21, 142.06, 128.63, 125.89, 109.54, 89.90, 84.34, 83.43, 81.26, 73.21, 67.13, 56.14, 51.62, 33.86, 33.34, 32.86, 32.40, 31.01, 30.73, 27.81, 23.23, 23.20, 22.86, 22.83, 18.68, 18.28, 18.04 |
| F172 | Colorless Oil | — | 3381, 2949, 2874, 1747, 1677 | HRMS-ESI (m/z) [M + H]$^+$ calcd for C$_{28}$H$_{40}$F$_3$N$_2$O$_9$, 605.2680; found, 605.2686 | $^1$H NMR (CDCl$_3$) δ 8.32 (d, J = 8.0 Hz, 1H), 8.27 (d, J = 5.3 Hz, 1H), 6.95 (d, J = 5.4 Hz, 1H), 5.74 (s, 2H), 4.74 (dq, J = 9.5, 6.4 Hz, 1H), 4.66-4.54 (m, 1H), | $^{13}$C NMR (CDCl$_3$) δ 172.67, 170.31, 162.98, 160.26, 145.74, 143.99, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 4.24 (td, J = 5.2, 3.4 Hz, 1H), 3.91 (s, 3H), 3.61-3.51 (m, 1H), 3.47-3.39 (m, 2H), 3.32 (ddd, J = 7.1, 5.4, 1.7 Hz, 1H), 2.38 (dt, J = 13.7, 6.9 Hz, 1H), 2.31-2.08 (m, 3H), 2.07 (s, 3H), 1.92-1.46 (m, 12H), 1.39 (d, J = 6.4 Hz, 3H), 1.33 (dt, J = 11.0, 1.8 Hz, 1H), 0.93 (ddt, J = 16.1, 7.6, 1.8 Hz, 1H) | 142.40, 128.63, 125.89, 109.60, 89.54, 84.33, 83.44, 81.26, 73.23, 67.13, 56.19, 51.62, 33.33, 32.86, 32.40, 31.30, 31.01, 30.73, 30.44, 27.81, 23.23, 23.20, 22.89, 22.86, 22.83, 22.80, 20.89, 18.28, 18.04 |
| F173 | Colorless Oil | — | 3379, 2949, 1772, 1743, 1678 | HRMS-ESI (m/z) [M + H]⁺ calcd for $C_{27}H_{38}F_3N_2O_8$, 575.2575; found, 575.2588 | ¹H NMR (CDCl₃) δ 8.53 (d, J = 8.4 Hz, 1H), 8.33 (d, J = 5.4 Hz, 1H), 7.00 (d, J = 5.5 Hz, 1H), 4.73 (dq, J = 9.6, 6.4 Hz, 1H), 4.59 (ddd, J = 10.8, 8.4, 7.2 Hz, 1H), 4.26-4.22 (m, 1H), 3.91 (s, 3H), 3.61-3.50 (m, 1H), 3.45-3.39 (m, 2H), 3.32 (ddd, J = 7.1, 5.3, 1.6 Hz, 1H), 2.40 (s, 3H), 2.41-2.33 (m, 1H), 2.30-2.02 (m, 3H), 1.91-1.47 (m, 12H), 1.37 (d, J = 6.4 Hz, 3H), 1.36-1.27 (m, 1H), 0.93 (ddt, J = 16.0, 7.5, 2.0 Hz, 1H) | ¹³C NMR (CDCl₃) δ 172.55, 168.92, 162.40, 159.43, 146.70, 141.40, 137.49, 128.62, 125.88, 109.80, 84.33, 83.43, 81.26, 73.24, 67.14, 56.29, 51.35, 33.53, 32.87, 32.40, 31.30, 31.01, 30.72, 30.44, 27.84, 23.23, 23.19, 22.88, 22.85, 22.82, 22.79, 20.75, 18.23, 18.02 |
| F174 | Off-White Solid | — | — | ESIMS m/z 328.3 ([M + H]⁺) | — | — |
| F175 | White Solid | — | 2959, 2936, 2878, 1751, 1207 | HRMS-ESI (m/z) [M + H]⁺ calcd for $C_{15}H_{30}NO_4$, 288.2169; found, 288.2167 | ¹H NMR (CDCl₃) δ 8.69 (br s, 3H), 4.74 (t, J = 7.2 Hz, 1H), 4.01-3.97 (m, 1H), 3.75 (dt, J = 8.9, 6.5 Hz, 1H), 3.51 (ddt, J = 29.8, 9.0, 6.6 Hz, 2H), 3.35-3.15 (m, 3H), 2.56-2.45 (m, 1H), 2.11 (s, 1H), 1.75-1.47 (m, 7H), 1.39 (d, J = 6.2 Hz, 3H), 0.92 (td, J = 7.4, 1.8 Hz, 6H), 0.86-0.71 (m, 1H) | ¹³C NMR (CDCl₃) δ 169.99, 83.91, 83.53, 75.52, 74.21, 70.90, 52.10, 31.28, 27.87, 23.49, 23.33, 17.81, 17.77, 10.76, 10.67 |
| F176 | White Solid | 226-229 | 2958, 2873, 2110, 1743, 1455, 1226 | HRMS-ESI (m/z) [M + Na]⁺ calcd for $C_{16}H_{31}NNaO_4$, 324.2145; found, 324.2156 | ¹H NMR (400 MHz, CD₃OD) δ 4.78 (pd, J = 6.3, 2.1 Hz, 1H), 3.93 (dd, J = 10.7, 7.4 Hz, 1H), 3.78 (dt, J = 8.9, 6.5 Hz, 1H), 3.58 (dt, J = 8.8, 6.6 Hz, 1H), 3.38-3.33 (m, 3H), 3.15 (dd, J = 8.7, 6.2 Hz, 1H), 2.33-2.13 (m, 2H), 1.81 (dp, J = 13.3, 6.7 Hz, 1H), 1.68 (tt, J = 9.8, 4.7 Hz, 2H), 1.62-1.52 (m, 2H), 1.51-1.42 (m, 1H), 1.41 (d, J = 6.3 Hz, 3H), | ¹³C NMR (101 MHz, CD₃OD) δ 169.68, 83.82, 83.37, 75.79, 75.26, 74.00, 51.45, 30.62, 28.75, 27.26, 23.24, 18.86, 18.80, 17.50, 17.17, 10.02 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 0.98-0.86 (m, 9H), 0.84 (dt, J = 16.9, 5.0 Hz, 1H) | |
| F177 | White Foamy Solid | — | 3349, 1635, 1502, 1203 | HRMS-ESI (m/z) [M + H]⁺ calcd for $C_{21}H_{23}F_2NO_4$, 392.1668; found, 392.1664 | ¹H NMR (CDCl₃) δ 8.70 (bs, 3H), 6.99-6.82 (m, 6H), 6.79-6.68 (m, 2H), 5.10-4.97 (m, 1H), 4.48-4.40 (m, 1H), 4.39-4.32 (m, 1H), 4.26-4.09 (m, 1H), 2.67-2.47 (m, 1H), 2.29-2.11 (m, 1H), 1.92-1.66 (m, 3H), 1.37 (d, J = 5.9 Hz, 3H), 1.18-1.04 (m, 1H) | ¹³C NMR (CDCl₃) δ 170.06, 157.87 (d, J = 240.2 Hz), 155.46 (d, J = 2.0 Hz), 154.48 (d, J = 199.0 Hz), 153.49 (d, J = 2.0 Hz), 118.13 (d, J = 8.0 Hz), 117.72 (d, J = 8.1 Hz), 116.14 (d, J = 4.9 Hz), 115.92 (d, J = 4.6 Hz), 83.27, 83.09, 73.33, 52.43, 30.95, 28.65, 18.17, 18.06 |
| F178 | White Solid | — | — | ESIMS m/z 354.2 ([M + H]⁺) | ¹H NMR (CDCl₃) δ 8.71 (bs, 3H), 7.04-6.87 (m, 4H), 5.01-4.89 (m, 1H), 4.25 (dd, J = 9.5, 7.2 Hz, 1H), 4.16-4.03 (m, 1H), 3.54-3.46 (m, 1H), 3.22 (dd, J = 8.7, 6.5 Hz, 1H), 3.02 (dd, J = 8.7, 6.1 Hz, 1H), 2.63-2.51 (m, 1H), 2.29-2.10 (m, 1H), 1.89-1.72 (m, 1H), 1.74-1.59 (m, 3H), 1.33 (d, J = 6.3 Hz, 3H), 1.02-0.90 (m, 1H), 0.79 (d, J = 6.7 Hz, 3H), 0.74 (d, J = 6.7 Hz, 3H) | ¹⁹F NMR (CDCl₃) δ -122.97 |
| F179 | White Solid | — | — | ESIMS m/z 354.2 ([M + H]⁺) | ¹H NMR (CDCl₃) δ 8.64 (bs, 3H), 7.30-7.23 (m, 1H), 7.22-7.13 (m, 1H), 6.98-6.90 (m, 1H), 6.87-6.80 (m, 1H), 4.87-4.76 (m, 1H), 4.27-4.17 (m, 1H), 4.16-4.01 (m, 1H), 3.57-3.47 (m, 2H), 3.36 (dd, J = 8.7, 6.5 Hz, 1H), 2.89 (t, J = 7.6 Hz, 1H), 2.71 (t, J = 7.6 Hz, 1H), 2.59-2.39 (m, 1H), 2.18-1.99 (m, 1H), 1.80-1.56 (m, 3H), 1.42 (d, J = 6.0 Hz, 3H), 0.83 (d, J = 6.6 Hz, 3H), 0.79 (d, J = 6.7 Hz, 3H) | ¹⁹F NMR (CDCl₃) δ -122.79 |
| F180 | White Solid | 236-240 | 2957, 2878, 1742, 1458, 1108 | HRMS-ESI (m/z) [M + Na]⁺ calcd for $C_{17}H_{28}F_3NNaO_4$, 390.1863; found, 390.1874 | ¹H NMR (CD₃OD) δ 6.50 (dtd, J = 15.7, 4.0, 2.0 Hz, 1H), 5.98 (dqt, J = 15.5, 6.6, 2.1 Hz, 1H), 4.48 (ddt, J = 15.7, 6.6, 3.2 Hz, 1H), 4.41-4.29 (m, 1H), 3.93 (dd, J = 10.7, 7.4 Hz, 1H), 3.55-3.40 (m, 2H), 3.37-3.32 (m, 2H), 3.14 (dd, J = 8.7, 6.0 Hz, 1H), 2.24 (dtd, J = 18.3, 9.1, 4.6 Hz, 2H), 1.80 (dp, J = 13.2, 6.7 Hz, 1H), 1.69 (tt, J = 9.8, 4.5 Hz, | ¹³C NMR (CD₃OD) δ 170.03, 137.51, 117.43, 117.09, 83.80, 83.59, 75.48, 73.41, 70.70, 51.45, 30.77, 28.68, 27.05, 18.45, 18.34, 17.37, 16.72; ¹⁹F NMR (CD₃OD) δ -65.82 (dt, J = 8.4, 2.5 Hz) |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 2H), 1.57-1.44 (m, 1H), 1.42 (d, J = 6.4 Hz, 3H), 0.91 (dd, J = 6.7, 4.4 Hz, 6H), 0.86 (t, J = 4.7 Hz, 1H) | |
| F181 | White Solid | — | 2933, 2859, 1743, 1456 | HRMS-ESI (m/z) [M + H]$^+$ calcd for C$_{18}$H$_{36}$NO$_4$, 330.2639; found, 330.2643 | $^1$H NMR (CD$_3$OD) δ 4.78 (pd, J = 6.3, 2.0 Hz, 1H), 3.93 (dd, J = 10.8, 7.4 Hz, 1H), 3.80 (dt, J = 8.9, 6.5 Hz, 1H), 3.62 (dt, J = 8.9, 6.6 Hz, 1H), 3.39-3.32 (m, 2H), 3.15 (dd, J = 8.7, 6.1 Hz, 1H), 2.31-2.14 (m 2H), 1.81 (dp, J = 13.2, 6.6 Hz, 1H), 1.68 (tt, J = 9.8, 4.6 Hz, 2H), 1.62-1.49 (m, 2H), 1.48-1.38 (m, 2H), 1.41 (d, J = 6.4 Hz, 3H), 1.40-1.28 (m, 4H), 0.97-0.86 (m, 9H), 0.87-0.79 (m, 1H) | $^{13}$C NMR (CD$_3$OD) δ 169.83, 83.87, 83.43, 75.59, 73.84, 73.39, 51.40, 30.57, 29.73, 28.75, 28.19, 27.18, 22.19, 18.50, 18.43, 17.41, 16.77, 12.98 |
| F182 | Colorless Solid | — | — | ESIMS m/z 416.3 ([M + H]$^+$) | $^1$H NMR (CDCl$_3$) δ 8.65 (bs, 3H), 7.04-6.92 (m, 1H), 6.83-6.66 (m, 6H), 5.11-4.92 (m, 1H), 4.46-4.36 (m, 1H), 4.36-4.25 (m, 1H), 4.23-4.07 (m, 1H), 3.73 (s, 3H), 3.71 (s, 3H), 2.68-2.47 (m, 1H), 2.31-2.11 (m, 1H), 1.90-1.65 (m, 3H), 1.38 (d, J = 6.2 Hz, 3H), 1.13-0.95 (m, 1H) | $^{13}$C NMR (CDCl$_3$) δ 170.03, 154.57, 154.46, 153.68, 151.51, 118.44, 117.74, 114.59, 114.52, 83.69, 83.42, 73.48, 55.61, 52.33, 30.93, 28.23, 18.17, 17.94 |
| F183 | White Solid | 198-200 | — | — | $^1$H NMR (CDCl$_3$) δ 8.64 (bs, 3H), 6.92-6.71 (m, 4H), 4.90-4.72 (m, 1H), 4.24-4.15 (m, 1H), 4.15-4.02 (m, 1H), 3.76 (s, 3H), 3.62-3.49 (m, 2H), 3.37 (dd, J = 8.7, 6.6 Hz, 1H), 2.57-2.41 (m, 1H), 2.20-2.02 (m, 1H), 1.84-1.54 (m, 4H), 1.43 (d, J = 6.2 Hz, 3H), 0.96-0.85 (m, 1H), 0.85 (d, J = 6.7 Hz, 3H), 0.82 (d, J = 6.7 Hz, 3H) | $^{13}$C NMR (CDCl$_3$) δ 170.03, 154.32, 151.36, 118.02, 114.64, 84.25, 83.13, 80.78, 73.79, 55.65, 52.21, 30.86, 29.03, 28.04, 19.43, 19.33, 17.89, 17.78 |
| F184 | White Solid | 246-248 | 3432, 2957, 1750 | HRMS-ESI (m/z) [M + H]$^+$ calcd for C$_{19}$H$_{33}$NO$_4$, 340.2482; found, 340.2485 | $^1$H NMR (CDCl$_3$) δ 8.68 (bs, 3H), 4.67 (dq, J = 11.2, 5.1, 3.8 Hz, 1H), 4.35-4.26 (m, 1H), 4.06-3.93 (m, 2H), 3.41-3.30 (m, 2H), 2.60-2.42 (m, 1H), 2.18-2.00 (m, 1H), 1.86-1.43 (m, 19H), 1.37 (d, J = 6.3 Hz, 3H), 0.89-0.74 (m, 1H) | $^{13}$C NMR (CDCl$_3$) δ 170.18, 83.36, 81.60, 80.77, 78.96, 74.53, 52.20, 33.54, 32.75, 32.43, 31.70, 31.07, 28.20, 23.72, 23.40, 23.32, 23.29, 18.06, 18.01 |
| F185 | White Solid | 195-197 | 3389, 2925, 1749, 1588, 1492, | HRMS-ESI (m/z) [M + H]$^+$ calcd for C$_{20}$H$_{29}$NO$_4$, | $^1$H NMR (CDCl$_3$) δ 8.73 (bs, 3H), 7.31-7.21 (m, 2H), 7.06-6.99 (m, 2H), 6.98-6.91 (m, 1H), | $^{13}$C NMR (CDCl$_3$) δ 170.07, 159.61, 129.30, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | 1223 | 348.2169; found, 348.2181 | 5.04-4.90 (m, 1H), 4.33 (dd, J = 9.5, 7.3 Hz, 1H), 4.14-4.01 (m, 1H), 3.95-3.89 (m, 1H), 3.62-3.55 (m, 1H), 2.64-2.46 (m, 1H), 2.26-2.09 (m, 1H), 2.08-1.37 (m, 11H), 1.33 (d, J = 6.3 Hz, 3H), 1.03-0.89 (m, 1H) | 121.29, 116.19, 82.30, 80.25, 79.73, 73.83, 52.21, 33.35, 31.72, 31.13, 28.43, 23.38, 22.94, 18.08, 18.03 |
| F186 | White Solid | 243-245 | 3367, 2954, 1750, 1597, 1493, 1236 | HRMS-ESI (m/z) [M + H]⁺ calcd for C₂₀H₂₉NO₄, 348.2169; found, 348.2137 | ¹H NMR (CDCl₃) δ 8.64 (bs, 3H), 7.29-7.21 (m, 2H), 6.97-6.85 (m, 3H), 4.87-4.73 (m, 1H), 4.33-4.26 (m, 1H), 4.26-4.19 (m, 1H), 4.12-3.98 (m, 1H), 3.73-3.61 (m, 2H), 2.58-2.41 (m, 1H), 2.23-2.04 (m, 1H), 1.90-1.45 (m, 10H), 1.42 (d, J = 6.4 Hz, 3H), 0.92 (dd, J = 15.8, 7.2 Hz, 1H) | — |
| F187 | White Solid | — | 2945, 2888, 2109, 1741, 1251, 1142 | HRMS-ESI (m/z) [M + H]⁺ calcd for C₁₇H₂₈F₆NO₄, 424.1917; found, 424.1917 | ¹H NMR (CD₃OD) δ 4.86-4.74 (m, 1H), 3.95 (dd, J = 10.7, 7.4 Hz, 1H), 3.82 (dt, J = 9.3, 6.1 Hz, 1H), 3.72 (dt, J = 9.3, 6.2 Hz, 1H), 3.64 (dt, J = 9.3, 6.3 Hz, 1H), 3.46-3.37 (m, 3H), 2.34-2.15 (m, 5H), 1.87-1.74 (m, 4H), 1.73-1.62 (m, 2H), 1.52-1.33 (m, 2H), 1.42 (d, J = 6.4 Hz, 3H), 0.87 (dt, J = 15.3, 4.6 Hz, 1H) | ¹³C NMR (CD₃OD) δ 169.74, 83.68, 83.52, 73.67, 71.42, 66.57, 51.36, 30.49, 30.29, 30.00, 27.01, 22.65 (dd, J = 17.9, 3.2 Hz), 17.25, 16.76; ¹⁹F NMR (CD₃OD) δ −68.04 (q, J = 11.4 Hz) |
| F188 | White Solid | — | — | HRMS-ESI (m/z) [M + H]⁺ calcd for C₁₈H₂₈NO₄, 322.2013; found, 322.2012 | ¹H NMR (CDCl₃) δ 8.65 (s, 3H), 7.32-7.14 (m, 2H), 7.00-6.82 (m, 3H), 4.89-4.77 (m, 1H), 4.38-4.29 (m, 1H), 4.10 (t, J = 8.5 Hz, 1H), 3.76-3.64 (m, 1H), 3.56 (ddd, J = 12.4, 9.3, 6.8 Hz, 2H), 2.50 (t, J = 12.8 Hz, 1H), 2.26-2.03 (m, 1H), 1.69 (tt, J = 16.1, 9.9 Hz, 3H), 1.48 (qd, J = 6.8, 2.4 Hz, 2H), 1.42 (d, J = 6.3 Hz, 3H), 0.96 (dd, J = 15.9, 6.8 Hz, 1H), 0.81 (t, J = 7.4 Hz, 3H) | ¹³C NMR (CDCl₃) δ 170.04, 157.52, 129.50, 121.28, 116.50, 83.15, 82.81, 75.59, 73.74, 52.19, 30.81, 28.23, 23.40, 17.81, 17.77, 10.58 |
| F189 | White Solid | — | — | HRMS-ESI (m/z) [M + H]⁺ calcd for C₂₀H₃₂NO₄, 350.2326; found, 350.2319 | ¹H NMR (CDCl₃) δ 8.63 (s, 3H), 7.28-7.19 (m, 2H), 7.03-6.77 (m, 3H), 4.83 (dd, J = 9.6, 6.3 Hz, 1H), 4.34 (dt, J = 10.9, 5.4 Hz, 1H), 4.09 (s, 1H), 3.73 (dd, J = 8.9, 6.4 Hz, 1H), 3.64-3.44 (m, 2H), 2.49 (s, 1H), 2.31-2.02 (m, 1H), 1.81-1.50 (m, 3H), 1.43 (p, J = 7.4 Hz, | ¹³C NMR (CDCl₃) δ 170.05, 157.51, 129.50, 121.26, 116.46, 83.18, 82.75, 73.99, 73.75, 52.19, 30.81, 29.92, 28.22, 28.21, 22.42, 18.19, 17.80, 13.95. |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 5H), 1.30-1.08 (m, 3H), 1.01-0.88 (m, 1H), 0.84 (t, J = 7.4 Hz, 1H), 0.82-0.77 (m, 2H), 0.67 (t, J = 7.4 Hz, 1H) | |
| F190 | White Solid | — | — | Ammonium Salt: ESIMS m/z 311.3 ([M + H]$^+$) | — | — |
| F191 | White Solid | — | — | HRMS-ESI (m/z) [M + H]$^+$ calcd for C$_{19}$H$_{25}$F$_3$NO$_4$, 388.1730; found, 388.1738 | $^1$H NMR (CDCl$_3$) δ 7.32-7.23 (m, 2H), 6.98 (t, J = 7.3 Hz, 1H), 6.89 (d, J = 8.1 Hz, 2H), 6.32 (dt, J = 15.8, 2.0 Hz, 1H), 5.89-5.71 (m, 1H), 4.94 (dd, J = 9.4, 6.4 Hz, 1H), 4.42 (d, J = 15.9 Hz, 2H), 4.34-4.20 (m, 1H), 4.01 (t, J = 8.7 Hz, 1H), 3.78-3.59 (m, 1H), 3.31-1.85 (m, 5H), 1.84-1.50 (m, 3H), 1.46 (d, J = 6.3 Hz, 3H), 0.99 (dd, J = 16.4, 6.4 Hz, 1H) | $^{13}$C NMR (CDCl$_3$) δ 169.76, 156.89, 136.21 (q, J = 6.3 Hz), 129.66, 122.88 (q, J = 269.0 Hz), 121.76, 118.52 (q, J = 34.0 Hz), 116.41, 83.47, 82.35, 73.29, 70.99, 51.73, 30.69, 28.06, 17.78, 17.64 |
| F192 | White Solid | — | — | HRMS-ESI (m/z) [M + H]$^+$ calcd for C$_{19}$H$_{27}$F$_3$NO$_4$, 390.1187; found, 390.1889 | $^1$H NMR (CDCl$_3$) δ 7.27 (dd, J = 8.5, 7.4 Hz, 2H), 6.97 (t, J = 7.4 Hz, 1H), 6.92-6.84 (m, 2H), 4.88 (dt, J = 9.5, 6.3 Hz, 1H), 4.42-4.30 (m, 1H), 3.99 (dd, J = 10.4, 7.6 Hz, 1H), 3.86-3.65 (m, 2H), 3.60 (dd, J = 9.5, 7.3 Hz, 1H), 2.47 (dt, J = 13.6, 6.8 Hz, 1H), 2.19 (dt, J = 15.7, 7.0 Hz, 1H), 2.01 (dddd, J = 29.9, 14.5, 7.2, 3.2 Hz, 2H), 1.80-1.60 (m, 4H), 1.56 (q, J = 11.5 Hz, 1H), 1.45 (d, J = 6.4 Hz, 3H), 0.98 (dd, J = 16.1, 7.1 Hz, 1H) | $^{13}$C NMR (CDCl$_3$) δ 169.81, 157.11, 129.61, 127.07 (q, J = 276.1 Hz), 121.53, 116.17, 83.33, 82.14, 73.59, 71.85, 51.73, 30.73, 30.58 (q, J = 28.7 Hz), 28.12, 22.84 (q, J = 2.7 Hz), 17.72, 17.62 |
| F193 | White Solid | — | — | HRMS-ESI (m/z) [M + H]$^+$ calcd for C$_{24}$H$_{32}$NO$_4$, 398.2326; found, 398.2324 | $^1$H NMR (CDCl$_3$) δ 8.66 (s, 3H), 7.28-7.16 (m, 4H), 7.16-7.10 (m, 1H), 7.09-7.01 (m, 2H), 6.93 (t, J = 7.3 Hz, 1H), 6.88 (d, J = 8.0 Hz, 2H), 4.86 (s, 1H), 4.36 (s, 1H), 4.10 (s, 1H), 3.86-3.72 (m, 1H), 3.67-3.53 (m, 2H), 2.54 (q, J = 13.1, 10.3 Hz, 3H), 2.18 (s, 1H), 1.77 (dq, J = 15.2, 8.5, 7.5 Hz, 5H), 1.44 (d, J = 4.9 Hz, 3H), 0.98 (d, J = 9.1 Hz, 1H) | $^{13}$C NMR (CDCl$_3$) δ 170.06, 157.40, 141.85, 129.57, 128.33, 128.27, 125.73, 121.32, 116.39, 83.31, 82.52, 73.72, 73.12, 67.10, 32.30, 31.85, 30.84, 28.21, 17.92, 17.79 |
| F194 | White Solid | — | 2923, 1750, 1507, 1223 | HRMS-ESI (m/z) [M + H]$^+$ calcd for C$_{23}$H$_{30}$NO$_4$, | $^1$H NMR (CDCl$_3$) δ 8.69 (s, 3H), 7.00 (dd, J = 12.5, 8.0 Hz, 4H), 6.92 (d, J = 8.2 Hz, 2H), 6.72 (d, J = 8.1 Hz, | $^{13}$C NMR (CDCl$_3$) δ 170.01, 157.38, 155.35, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | 384.2169; found, 384.2172 | 2H), 5.04 (br s, 1H), 4.51 (t, J = 8.0 Hz, 1H), 4.41 (d, J = 8.4 Hz, 1H), 4.22-3.99 (m, 1H), 3.82-3.74 (m, 1H), 3.70 (s, 3H), 2.55 (s, 1H), 2.24 (d, J = 8.9 Hz, 6H), 1.41-1.32 (m, 3H), 1.07 (d, J = 14.0 Hz, 1H) | 130.96, 130.94, 129.91, 129.89, 116.84, 116.38, 82.46, 82.43, 73.59, 72.26, 71.12, 61.69, 59.45, 52.31, 42.91, 30.95, 28.17, 20.49, 18.12, 17.87 |
| F195 | White Solid | — | — | HRMS-ESI (m/z) [M + H]⁺ calcd for C₁₈H₂₈NO₄, 322.2013; found, 322.2019 | ¹H NMR (CDCl₃) δ 8.70 (s, 3H), 7.31-7.18 (m, 2H), 7.05 (d, J = 7.8 Hz, 2H), 6.95 (t, J = 7.3 Hz, 1H), 4.97 (dt, J = 12.8, 6.4 Hz, 1H), 4.36 (dd, J = 9.4, 7.3 Hz, 1H), 4.16-4.04 (m, 1H), 3.60-3.48 (m, 1H), 3.43 (dt, J = 8.9, 6.6 Hz, 1H), 3.21 (dt, J = 9.0, 6.5 Hz, 1H), 2.65-2.47 (m, 1H), 2.21 (dd, J = 15.1, 5.7 Hz, 1H), 1.77 (dd, J = 41.7, 9.2 Hz, 3H), 1.41 (h, J = 7.4 Hz, 2H), 1.34 (d, J = 6.4 Hz, 3H), 0.99 (dd, J = 15.3, 5.1 Hz, 1H), 0.75 (t, J = 7.4 Hz, 3H) | ¹³C NMR (CDCl₃) δ 170.13, 159.55, 129.36, 121.43, 116.41, 82.76, 82.67, 73.60, 71.39, 52.31, 31.03, 28.13, 23.12, 18.01, 17.91, 10.53 |
| F196 | Off-White Solid | — | — | HRMS-ESI (m/z) [M + H]⁺ calcd for C₂₄H₃₂NO₄, 398.2326; found, 398.2332 | ¹H NMR (CDCl₃) δ 8.71 (s, 3H), 7.24 (td, J = 8.9, 7.3 Hz, 4H), 7.17-7.11 (m, 1H), 7.08-6.98 (m, 4H), 6.95 (t, J = 7.3 Hz, 1H), 4.98 (dq, J = 12.5, 6.0 Hz, 1H), 4.46-4.33 (m, 1H), 4.12 (s, 1H), 3.51 (ddd, J = 12.1, 9.6, 5.9 Hz, 2H), 3.22 (dt, J = 9.1, 6.1 Hz, 1H), 3.03-2.52 (m, 2H), 2.52-2.41 (m, 2H), 2.33-2.11 (m, 1H), 1.70 (dq, J = 12.8, 6.2 Hz, 4H), 1.34 (d, J = 6.3 Hz, 3H), 0.98 (d, J = 16.2 Hz, 1H) | ¹³C NMR (CDCl₃) δ 170.13, 159.51, 141.94, 129.45, 128.39, 128.23, 125.67, 121.50, 116.28, 82.91, 82.28, 73.64, 68.59, 52.30, 32.14, 31.51, 31.05, 27.99, 18.01, 17.90 |
| F197 | White Solid | — | — | HRMS-ESI (m/z) [M + H]⁺ calcd for C₁₉H₂₇F₃NO₄, 390.1187; found, 390.1892 | ¹H NMR (CDCl₃) δ 8.72 (s, 3H), 7.31-7.21 (m, 2H), 6.97 (dd, J = 15.9, 7.9 Hz, 3H), 5.03-4.93 (m, 1H), 4.39 (t, J = 8.2 Hz, 1H), 4.14 (s, 1H), 3.54 (s, 2H), 3.35-3.14 (m, 1H), 2.59 (s, 1H), 2.30-2.04 (m, 1H), 1.97-1.76 (m, 3H), 1.71 (s, 2H), 1.61 (p, J = 7.6, 7.0 Hz, 2H), 1.36 (d, J = 6.0 Hz, 3H), 1.11-0.94 (m, 1H) | ¹³C NMR (CDCl₃) δ 170.10, 159.18, 129.49, 127.14 qd, J = 276.1 Hz), 121.66, 115.96, 83.18, 81.84, 73.48, 67.63, 52.32, 30.99, 30.38 (q, J = 28.9 Hz), 28.09, 22.55 (q, J = 2.8 Hz), 17.94, 17.88 |
| F198 | White Solid | — | — | ESIMS m/z 314.3 ([M + H]⁺) | — | — |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| F199 | White Solid | — | — | ESIMS m/z 382.3 ([M + H]$^+$) | — | — |
| F200 | White Solid | — | — | HRMS-ESI (m/z) [M + H]$^+$ calcd for C$_{18}$H$_{34}$NO$_4$, 328.2482, 328.2492 | $^1$H NMR (CDCl$_3$) δ 8.67 (s, 3H), 4.69 (dq, J = 12.5, 6.0 Hz, 1H), 4.29 (s, 1H), 4.02 (s, 1H), 3.41 (dd, J = 9.4, 7.0 Hz, 1H), 3.32-3.24 (m, 1H), 3.24-3.17 (m, 1H), 3.12 (dd, J = 8.6, 6.0 Hz, 1H), 2.51 (s, 1H), 2.20-2.06 (m, 1H), 1.89-1.46 (m, 12H), 1.37 (d, J = 6.3 Hz, 3H), 0.90 (dd, J = 6.7, 4.2 Hz, 6H), 0.82 (d, J = 14.6 Hz, 1H) | $^{13}$C NMR (CDCl$_3$) δ 170.12, 84.08, 83.15, 80.97, 75.84, 74.26, 52.26, 32.92, 32.27, 31.05, 28.88, 27.51, 23.24, 23.16, 19.62, 19.46, 18.05, 17.85 |
| F201 | White Solid | — | — | ESIMS m/z 340.3 ([M + H]$^+$) | — | — |
| F202 | White Solid | — | — | ESIMS m/z 368.3 ([M + H]$^+$) | — | — |
| F203 | White Solid | — | 2959, 2936, 2878, 1751, 1207 | HRMS-ESI (m/z) [M + H]$^+$ calcd for C$_{15}$H$_{30}$NO$_4$, 288.2169; found, 288.2167 | $^1$H NMR (CDCl$_3$) δ 8.69 (br s, 3H), 4.74 (t, J = 7.2 Hz, 1H), 4.01-3.97 (m, 1H), 3.75 (dt, J = 8.9, 6.5 Hz, 1H), 3.51 (ddt, J = 29.8, 9.0, 6.6 Hz, 2H), 3.35-3.15 (m 3H) 2.56-2.45 (m, 1H) 2.11 (s, 1H), 1.75-1.47 (m, 7H), 1.39 (d, J = 6.2 Hz, 3H), 0.92 (td, J = 7.4, 1.8 Hz, 6H), 0.86-0.71 (m, 1H) | $^{13}$C NMR (CDCl$_3$) δ 169.99, 83.91, 83.53, 75.52, 74.21, 70.90, 52.10, 31.28, 27.87, 23.49, 23.33, 17.81, 17.77, 10.76, 10.67 |
| F204 | White Solid | — | — | ESIMS m/z 314 ([M + H]$^+$) | $^1$H NMR (CD$_3$OD) δ 4.72 (dq, J = 9.4, 6.3 Hz, 1H), 4.32 (td, J = 4.8, 2.6 Hz, 1H), 3.94 (dd, J = 10.6, 7.0 Hz, 1H), 3.52 (dt, J = 8.8, 6.7 Hz, 1H) 3.44 (dd, J = 9.4, 6.9 Hz, 1H), 3.36-3.24 (m, 2H), 2.36-2.13 (m, 2H), 1.88-1.76 (m, 1H), 1.76-1.42 (m, 12H), 1.39 (d, J = 6.4 Hz, 3H), 0.94 (t, J = 7.4 Hz, 3H), 0.84 (dt, J = 15.9, 4.3 Hz, 1H) | $^{13}$C NMR (CD$_3$OD) δ 171.27, 85.26, 84.55, 82.36, 75.48, 71.88, 52.90, 33.91, 33.32, 31.94, 28.66, 24.48, 24.27, 24.25, 18.90, 18.48, 11.24 |
| F205 | White Solid | — | — | ESIMS m/z 368 ([M + H]$^+$) | $^1$H NMR (CD$_3$OD) δ 4.91-4.84 (m, 1H), 4.78 (ddd, J = 7.8, 6.0, 2.1 Hz, 1H), 4.21-4.11 (m, 1H), 3.97 (dd, J = 10.8, 7.1 Hz, 1H), 3.62 (dd, J = 9.4, 7.4 Hz, 1H), 2.78 (ddd, J = 15.6, 8.5, 7.2 Hz, 1H), 2.27 (dtd, J = 13.9, 7.0, 1.9 Hz, 1H), 2.17-2.04 (m, 1H), 2.00-1.90 (m, 1H), 1.90-1.79 (m, 2H), 1.79-1.45 (m, 16H), 1.44 (d, J = 6.5 Hz, 3H), 1.16-1.03 (m, 1H) | — |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| F206 | White Solid | — | 3398, 2924, 1749, 1503 | ESIMS m/z 366 ([M + H]⁺) | ¹H NMR (CD$_3$OD) δ 7.04-6.89 (m, 4H), 4.32-4.26 (m, 2H), 3.99 (dd, J = 10.7, 7.2 Hz, 1H), 3.77-3.63 (m, 2H), 2.34-2.10 (m, 2H), 1.88-1.39 (m, 11H), 1.47 (d, J = 6.4 Hz, 3H), 0.98 (dd, J = 16.4, 7.6 Hz, 1H) | — |
| F207 | White Solid | — | — | ESIMS m/z 390.4 ([M + H]⁺) | — | — |
| F208 | White Solid | — | — | ESIMS m/z 342.3 ([M + H]⁺) | — | — |
| F209 | White Solid | — | — | ESIMS m/z 378.3 ([M + H]⁺) | — | — |
| F210 | White Solid | — | — | ESIMS m/z 493.1 ([M + H]⁺), m/z 515.2 ([M + Na]⁺) | ¹H NMR (CDCl$_3$) δ 12.09 (s, 1H), 8.48 (d, J = 8.1 Hz, 1H), 7.99 (d, J = 5.2 Hz, 1H), 6.86 (d, J = 5.2 Hz, 1H), 4.77 (dq, J = 9.7, 6.4 Hz, 1H), 4.58 (dt, J = 10.8, 7.7 Hz, 1H), 3.94 (s, 3H), 3.69-3.58 (m, 1H), 3.54 (dd, J = 9.6, 7.0 Hz, 1H), 3.34 (t, J = 5.6 Hz, 1H), 3.27 (dd, J = 8.6, 6.7 Hz, 1H), 3.12 (dd, J = 8.6, 6.2 Hz, 1H), 2.36 (dd, J = 13.4, 6.5 Hz, 1H), 2.23-2.07 (m, 1H), 1.98 (dd, J = 13.6, 8.8 Hz, 2H), 1.89-1.59 (m, 5H), 1.55 (d, J = 9.7 Hz, 1H), 1.45-1.31 (m, 4H), 1.31-1.10 (m, 5H), 0.92 (d, J = 6.7 Hz, 7H) | ¹³C NMR (CDCl$_3$) δ 172.09, 168.65, 155.34, 148.72, 140.51, 130.43, 109.45, 84.71, 80.34, 79.29, 75.87, 73.45, 56.07, 51.32, 33.52, 33.35, 32.69, 28.93, 27.45, 25.76, 24.55, 24.45, 19.63, 19.54, 18.27, 18.25 |
| F211 | White Solid | — | — | ESIMS m/z 493.1 ([M + H]⁺), m/z 515.2 ([M + Na]) | ¹H NMR (CDCl$_3$) δ 12.09 (s, 1H), 8.46 (d, J = 8.1 Hz, 1H), 7.99 (d, J = 5.2 Hz, 1H), 6.86 (d, J = 5.2 Hz, 1H), 4.80 (dq, J = 9.8, 6.5 Hz, 1H), 4.58 (dt, J = 10.8, 7.6 Hz, 1H), 3.94 (s, 3H), 3.69 (dd, J = 8.5, 6.0 Hz, 1H), 3.60-3.43 (m, 1H), 3.34 (ddd, J = 8.4, 7.2, 3.9 Hz, 3H), 2.37 (dt, J = 14.0, 7.0 Hz, 1H), 2.04 (ddd, J = 21.2, 9.4, 5.0 Hz, 1H), 1.91 (t, J = 8.8 Hz, 1H), 1.83 (dt, J = 13.0, 6.6 Hz, 2H), 1.78-1.63 (m, 4H), 1.60 (s, 1H), 1.41 (d, J = 6.4 Hz, 3H), 1.38-1.12 (m, 7H), 0.91 (dd, J = 9.5, 6.7 Hz, 6H) | ¹³C NMR (CDCl$_3$) δ 172.09, 168.65, 155.36, 148.74, 140.50, 130.43, 109.46, 83.81, 80.99, 76.00, 73.61, 56.07, 51.32, 33.78, 33.43, 32.32, 29.18, 29.13, 25.78, 24.43, 24.24, 19.63, 19.45, 18.50, 17.93 |
| F212 | White Solid | 109-111 | 3368, 2956, 2874, 1743, 1650, | HRMS-ESI (m/z) [M + Na]⁺ calcd for C$_{23}$H$_{36}$N$_2$NaO$_7$, | ¹H NMR (CDCl$_3$) δ 12.09 (s, 1H), 8.47 (d, J = 8.1 Hz, 1H), 7.99 (d, J = 5.2 Hz, 1H), 6.87 (d, J = 5.1 Hz, | ¹³C NMR (CDCl$_3$) δ 172.05, 168.64, 155.34, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | 1528, 1100 | 475.2415; found, 475.2419 | 1H), 4.89-4.67 (m, 1H), 4.58 (dt, J = 10.8, 7.6 Hz, 1H), 3.94 (s, 3H), 3.83-3.69 (m, 1H), 3.57 (dt, J = 8.8, 6.7 Hz, 1H), 3.41-3.32 (m, 2H), 3.29 (dd, J = 8.7, 6.5 Hz, 1H), 3.13 (dd, J = 8.7, 6.3 Hz, 1H), 2.43-2.29 (m, 1H), 2.23-2.04 (m, 1H), 1.82 (hept, J = 6.6 Hz, 1H), 1.73-1.61 (m, 2H), 1.62-1.52 (m, 3H), 1.41 (d, J = 6.4 Hz, 3H), 1.40-1.31 (m, 1H), 0.97-0.84 (m, 9H) | 148.72, 140.51, 130.40, 109.45, 84.17, 83.73, 75.95, 75.45, 73.30, 56.07, 51.30, 33.35, 28.87, 27.69, 23.51, 19.53, 19.48, 18.22, 17.91, 10.69 |
| F213 | White Solid | 63-66 | 3367, 2954, 2872, 1734, 1528, 1166 | HRMS-ESI (m/z) [M + Na]⁺ calcd for C₂₄H₃₄N₂NaO₈, 501.2207; found, 501.2209 | ¹H NMR (CDCl₃) δ 12.06 (s, 1H), 8.44 (d, J = 8.0 Hz, 1H), 7.99 (d, J = 5.2 Hz, 1H), 6.87 (d, J = 5.3 Hz, 1H), 5.16 (dd, J = 9.7, 7.8 Hz, 1H), 4.97 (dq, J = 9.8, 6.4 Hz, 1H), 4.62 (dt, J = 10.7, 7.6 Hz, 1H), 3.94 (s, 3H), 3.39 (ddd, J = 7.6, 5.3, 1.9 Hz, 1H), 3.31 (dd, J = 8.8, 6.1 Hz, 1H), 2.99 (dd, J = 8.8, 6.8 Hz, 1H), 2.40 (ddd, J = 13.8, 7.6, 6.2 Hz, 1H), 2.17 (dddd, J = 15.7, 10.1, 7.9, 5.3 Hz, 1H), 1.86-1.60 (m, 4H), 1.47-1.33 (m, 1H), 1.30 (d, J = 6.4 Hz, 3H), 1.07-0.96 (m, 3H), 0.92-0.81 (m, 8H) | ¹³C NMR (CDCl₃) δ 173.91, 172.11, 168.65, 155.37, 148.76, 140.50, 130.36, 109.48, 81.12, 76.34, 75.56, 71.77, 56.08, 51.29, 33.33, 28.64, 28.00, 19.31, 19.26, 17.98, 17.22, 12.87, 8.48, 8.40 |
| F214 | Colorless Oil | — | 2949, 2871, 1772, 1743, 1679, 1507, 1197 | HRMS-ESI (m/z) [M + Na]⁺ calcd for C₃₁H₄₂N₂NaO₈, 593.2833; found, 593.2832 | ¹H NMR (CDCl₃) δ 8.53 (s, 1H), 8.33 (d, J = 5.5 Hz, 1H), 7.31-7.27 (m, 2H), 7.22-7.15 (m, 3H), 7.00 (d, J = 5.5Hz, 1H), 4.85-4.73 (m, 1H), 4.59 (dt, J = 10.8, 7.7 Hz, 1H), 3.91 (s, 3H), 3.84 (dt, J = 9.1, 6.4 Hz, 1H), 3.63 (dt, J = 9.1, 6.5 Hz, 1H), 3.41-3.31 (m, 2H), 3.26 (dd, J = 8.7, 6.6 Hz, 1H), 3.09 (dd, J = 8.8, 6.3 Hz, 1H), 2.68 (td, J = 7.6, 4.3 Hz, 2H), 2.40 (s, 3H), 2.39-2.27 (m, 1H), 2.19-2.04 (m, 1H), 1.90 (dtd, J = 8.6, 6.7, 1.8 Hz, 2H), 1.78 (dt, J = 13.2, 6.6 Hz, 1H), 1.68-1.59 (m, 2H), 1.39 (d, J = 6.3 Hz, 3H), 1.36-1.24 (m, 2H), 0.88 (dd, J = 6.7, 2.5 Hz, 6H) | ¹³C NMR (CDCl₃) δ 172.55, 162.38, 159.43, 146.69, 142.05, 141.43, 137.48, 128.35, 128.32, 125.76, 109.77, 84.25, 83.89, 75.83, 73.00, 72.93, 56.28, 51.35, 33.63, 32.52, 32.01, 28.84, 27.71, 20.75, 19.54, 19.49, 18.24, 17.98 |
| F215 | Colorless Semi-Solid | — | 2948, 1769, 1743, | HRMS-ESI (m/z) [M + H]⁺ | ¹H NMR (CDCl₃) δ 8.50 (s, 1H), 8.33 (d, J = 5.4 Hz, 1H), | ¹³C NMR (CDCl₃) δ 172.55, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | 1679, 1507, 1106 | calcd for $C_{33}H_{47}N_2O_9$, 615.3276; found, 615.3298 | 7.32-7.24 (m, 2H), 7.24-7.10 (m, 3H), 6.99 (d, J = 5.5 Hz, 1H), 4.87-4.71 (m, 1H), 4.58 (dt, J = 10.8, 7.8 Hz, 1H), 3.90 (s, 3H), 3.87-3.74 (m, 3H), 3.74-3.54 (m, 1H), 3.41 (s, 3H), 3.37-3.27 (m, 2H), 3.27-3.20 (m, 1H), 3.09 (dd, J = 8.7, 6.3 Hz, 1H), 2.98 (t, J = 6.6 Hz, 2H), 2.68 (td, J = 7.8, 4.3 Hz, 2H), 2.40-2.27 (m, 1H), 2.18-2.04 (m, 1H), 1.95-1.84 (m, 2H), 1.78 (dt, J = 13.2, 6.6 Hz, 1H), 1.69-1.57 (m, 2H), 1.39 (d, J = 6.3 Hz, 3H), 1.36-1.18 (m, 2H), 0.88 (dd, J = 6.6, 2.6 Hz, 6H) | 169.44, 162.33, 159.44, 146.74, 142.05, 141.47, 137.33, 128.35, 128.32, 125.76, 109.76, 84.24, 83.90, 75.82, 72.99, 72.91, 67.58, 58.80, 56.31, 51.33, 34.62, 33.62, 32.52, 32.01, 29.71, 28.85, 27.70, 19.54, 19.49, 18.24, 17.99 |
| F216 | White Solid | — | 2954, 2874, 1772, 1744, 1679, 1508, 1198 | HRMS-ESI (m/z) [M + H]⁺ calcd for $C_{26}H_{38}F_3N_2O_8$, 563.2575; found, 563.2587 | ¹H NMR (CDCl₃) δ 8.52 (d, J = 10.1 Hz, 1H), 8.33 (d, J = 5.5 Hz, 1H), 7.00 (d, J = 5.4 Hz, 1H), 4.84-4.71 (m, 1H), 4.59 (dt, J = 10.7, 7.7 Hz, 1H), 3.91 (s, 3H), 3.85 (dt, J = 9.3, 6.1 Hz, 1H), 3.67 (dt, J = 9.4, 6.1 Hz, 1H), 3.39-3.29 (m, 2H), 3.27 (dd, J = 8.7, 6.7 Hz, 1H), 3.08 (dd, J = 8.7, 6.2 Hz, 1H), 2.40 (s, 3H), 2.34 (dd, J = 13.8, 6.7 Hz, 1H), 2.25-2.05 (m, 3H), 1.87-1.75 (m, 3H), 1.71-1.59 (m, 2H), 1.37 (d, J = 6.4 Hz, 3H), 1.34-1.22 (m, 1H), 0.91 (dd, J = 6.7, 1.3 Hz, 6H), 0.91-0.83 (m, 1H) | ¹³C NMR (CDCl₃) δ 172.51, 168.92, 162.40, 159.44, 146.69, 141.39, 137.49, 109.79, 84.07, 83.99, 75.64, 72.68, 71.67, 56.29, 51.33, 33.59, 31.05, 30.76, 28.87, 27.48, 23.1-23.00 (m), 20.76, 19.54, 19.47, 18.18, 17.93; ¹⁹F NMR (CDCl₃) δ −66.43 (t, J = 10.9 Hz) |
| F217 | Yellow Oil | — | 3380, 2952, 1745, 1677, 1504, 1202 | HRMS-ESI (m/z) [M]⁺ calcd for $C_{29}H_{42}N_2O_9$, 562.2890; found, 562.2908 | ¹H NMR (CDCl₃) δ 8.32 (d, J = 8.1 Hz, 1H), 8.27 (d, J = 5.3 Hz, 1H), 6.95 (d, J = 5.4 Hz, 1H), 5.74 (s, 2H), 4.73 (dq, J = 8.9, 6.5 Hz, 1H), 4.60 (dt, J = 10.8, 7.6 Hz, 1H), 4.33 (qd, J = 5.1, 4.7, 3.4 Hz, 1H), 4.02 (qd, J = 5.4, 3.8 Hz, 1H), 3.91 (s, 3H), 3.46-3.36 (m, 2H), 2.37 (dtd, J = 13.5, 6.7, 1.6 Hz, 1H), 2.15-2.06 (m, 1H), 2.07 (s, 3H), 1.84-1.43 (m, 18H), 1.38 (d, J = 6.4 Hz, 3H), 1.32 (dt, J = 10.8, 2.3 Hz, 1H), 0.90 (ddt, J = 15.8, 7.4, 1.8 Hz, 1H) | ¹³C NMR (CDCl₃) δ 172.74, 170.23, 162.94, 160.25, 145.71, 143.94, 142.41, 109.59, 89.52, 83.27, 81.81, 81.07, 78.94, 73.44, 56.17, 51.65, 33.52, 33.45, 32.77, 32.43, 31.73, 28.38, 23.71, 23.40, 23.33, 23.30, 20.85, 18.59, 18.08 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| F218 | White Foam | — | 3377, 2955, 1740, 1679 | HRMS-ESI (m/z) [M + H]⁺ calcd for $C_{31}H_{47}N_2O_{10}$, 607.3225; found, 607.3241 | ¹H NMR (CDCl₃) δ 8.35 (d, J = 8.0 Hz, 1H), 8.27 (d, J = 5.3 Hz, 1H), 6.94 (d, J = 5.4 Hz, 1H), 5.82-5.70 (m, 2H), 5.16 (dd, J = 9.8, 7.8 Hz, 1H), 4.95 (dq, J = 9.8, 6.5 Hz, 1H), 4.63 (dt, J = 10.9, 7.6 Hz, 1H), 3.89 (s, 3H), 3.37 (ddd, J = 7.5, 5.3, 1.9 Hz, 1H), 3.27 (dd, J = 8.6, 6.3 Hz, 1H), 3.01-2.93 (m, 1H), 2.73 (p, J = 7.9 Hz, 1H), 2.55 (p, J = 7.0 Hz, 1H), 2.40 (dt, J = 13.7, 7.0 Hz, 1H), 2.22-2.10 (m, 1H), 1.95-1.41 (m, 11H), 1.36 (q, J = 11.7 Hz, 1H), 1.26 (d, J = 7.9, 3H), 1.14 (d, J = 6.9 Hz, 6H), 1.07-0.96 (m, 1H), 0.85 (d, J = 6.7 Hz, 6H) | ¹³C NMR (CDCl₃) δ 176.29, 175.57, 172.73, 162.93, 160.26, 145.55, 141.99, 109.54, 89.93, 81.19, 76.12, 75.36, 71.47, 56.13, 51.63, 43.98, 33.86, 33.38, 30.13, 29.76, 28.69, 27.84, 25.82, 25.72, 19.37, 19.34, 18.68, 18.04, 17.26 |
| F219 | Colorless Oil | — | 3367, 2949, 2870, 1742, 1649, 1526, 1497 | HRMS-ESI (m/z) [M + H]⁺ calcd for $C_{29}H_{41}N_2O_7$, 529.2908; found, 529.2912 | ¹HNMR (CDCl₃) δ 12.09 (s, 1H), 8.48 (d, J = 8.2 Hz, 1H), 7.98 (d, J = 5.1 Hz, 1H), 7.34-7.24 (m, 2H), 7.24-7.15 (m, 3H), 6.86 (d, J = 5.2 Hz, 1H), 4.82 (dtd, J = 12.7, 6.3, 2.0 Hz, 1H), 4.59 (dt, J = 10.8, 7.6 Hz, 1H), 3.94 (s, 3H), 3.63 (dd, J = 8.7, 6.2 Hz, 1H), 3.56 (dt, J = 9.1, 6.4 Hz, 1H), 3.43-3.33 (m, 4H), 2.70 (dd, J = 8.8, 6.7 Hz, 2H), 2.37 (dtd, J = 13.7, 6.8, 1.6 Hz, 1H), 2.19-2.05 (m, 1H), 1.97-1.78 (m, 3H), 1.78-1.59 (m, 2H), 1.42 (d, J = 6.3 Hz, 3H), 1.40-1.31 (m, 1H), 0.91 (d, J = 6.6 Hz, 3H), 0.89 (d, J = 6.7 Hz, 3H), 0.90-0.87 (m, 1H) | ¹³CNMR (CDCl₃) δ 172.03, 168.66, 155.34, 148.72, 142.00, 140.52, 130.40, 128.40, 128.34, 125.80, 109.47, 84.30, 83.75, 80.69, 73.35, 68.34, 56.08, 51.31, 49.34, 33.35, 32.53, 31.81, 29.11, 27.88, 19.54, 19.49, 19.43, 18.26, 17.99 |
| F220 | White Solid | | 3366, 2954, 2872, 1742, 1649, 1526 | HRMS-ESI (m/z) [M + H]⁺ calcd for $C_{24}H_{37}N_2O_7$, 465.2605; found, 465.2595 | ¹H NMR (CDCl₃) δ 12.09 (s, 1H), 8.48 (d, J = 8.2 Hz, 1H), 7.99 (d, J = 5.2 Hz, 1H), 6.87 (d, J = 5.2 Hz, 1H), 4.98 (s, 1H), 4.87 (t, J = 1.8 Hz, 1H), 4.86-4.77 (m, 1H), 4.59 (dt, J = 10.7, 7.6 Hz, 1H), 3.96 (d, J = 11.7 Hz, 1H), 3.94 (s, 3H), 3.85 (d, J = 12.0 Hz, 1H), 3.64 (dd, J = 8.6, 6.1 Hz, 1H), 3.48-3.33 (m, 3H), 2.37 (dtd, J = 13.8, 7.1, 6.7, 1.8 Hz, 1H), 2.23-2.05 (m, 1H), 1.83 (dq, J = 13.8, 6.9 Hz, | ¹³CNMR (CDCl₃) δ 172.03, 168.65, 155.34, 148.71, 142.48, 140.51, 130.38, 112.11, 109.46, 83.78, 83.60, 80.67, 73.37, 73.25, 56.07, 51.31, 33.30, 29.11, 27.97, 19.71, 19.53, 19.38, 18.28, 17.96 |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 1H), 1.76 (s, 3H), 1.76-1.63 (m, 2H), 1.42 (d, J = 6.4 Hz, 3H), 1.39-1.32 (m, 1H), 0.99-0.93 (m, 1H), 0.92 (d, J = 6.7 Hz, 3H), 0.90 (d, J = 6.7 Hz, 3H); | |
| F221 | White Solid | 129-130 | 3384, 2954, 2871, 1735, 1655, 1526, 1447 | HRMS-ESI (m/z) [M + H]$^+$ calcd for C$_{26}$H$_{39}$N$_2$O$_8$, 507.2712; found, 507.2701 | $^1$H NMR (CDCl$_3$) δ 12.04 (s, 1H), 8.49 (d, J = 8.2 Hz, 1H), 7.99 (d, J = 5.2 Hz, 1H), 6.87 (d, J = 5.2 Hz, 1H), 4.99-4.84 (m, 2H), 4.61 (ddd, J = 10.8, 8.2, 7.2 Hz, 1H), 3.94 (s, 3H), 3.50 (dd, J = 9.5, 7.6 Hz, 1H), 3.43-3.32 (m, 2H), 2.80-2.66 (m, 1H), 2.36 (dtd, J = 13.5, 7.2, 1.4 Hz, 1H), 2.14 (dddd, J = 15.9, 10.0, 7.8, 5.5 Hz, 1H), 1.98-1.54 (m, 11H), 1.44 (d, J = 6.4 Hz, 3H), 1.42-1.33 (m, 1H), 1.10 (ddt, J = 16.3, 7.4, 2.2 Hz, 1H), 0.88 (d, J = 7.0 Hz, 3H), 0.86 (d, J = 6.9 Hz, 3H) | $^{13}$CNMR (CDCl$_3$) δ 175.71, 171.76, 168.68, 155.33, 148.69, 140.57, 130.32, 109.50, 82.23, 80.27, 77.63, 73.12, 56.08, 51.21, 44.09, 33.16, 30.24, 29.76, 29.13, 29.01, 25.80, 25.79, 19.36, 19.29, 18.32, 17.90 |
| F222 | Colorless Oil | — | 3380, 2951, 2871, 1748, 1678, 1502 | HRMS-ESI (m/z) [M + H]$^+$ calcd for C$_{32}$H$_{45}$N$_2$O$_9$, 601.3127; found, 601.3120 | $^1$HNMR (CDCl$_3$) δ 8.32 (d, J = 8.0 Hz, 1H), 8.27 (d, J = 5.4 Hz, 1H), 7.33-7.25 (m, 2H), 7.23-7.12 (m, 3H), 6.94 (d, J = 5.4 Hz, 1H), 5.74 (s, 2H), 4.79 (ddd, J = 10.7, 6.7, 3.7 Hz, 1H), 4.61 (dt, J = 10.8, 7.5 Hz, 1H), 3.90 (s, 3H), 3.63 (dd, J = 8.7, 6.1 Hz, 1H), 3.56 (dt, J = 9.1, 6.4 Hz, 1H), 3.43-3.30 (m, 4H), 2.70 (dd, J = 8.8, 6.7 Hz, 2H), 2.46-2.30 (m, 1H), 2.10 (dd, J = 5.3, 3.1 Hz, 1H), 2.07 (s, 3H), 1.94-1.78 (m, 4H), 1.78-1.57 (m, 1H), 1.40 (d, J = 6.3 Hz, 3H), 1.38-1.26 (m, 1H), 0.96-0.93 (m, 1H), 0.91 (d, J = 7.2 Hz, 3H), 0.89 (d, J = 6.9 Hz, 3H) | $^{13}$CNMR (CDCl$_3$) δ 172.63, 170.27, 162.98, 160.27, 145.74, 143.98, 142.41, 142.01, 128.40, 128.34, 128.31, 125.77, 109.61, 89.54, 84.37, 83.79, 80.67, 73.07, 68.29, 56.19, 51.63, 33.42, 32.53, 31.80, 29.10, 27.94, 20.88, 19.55, 19.43, 18.32, 17.98 |
| F223 | White Solid | 35-39 | 3379, 2954, 2872, 1732, 1677, 1502 | HRMS-ESI (m/z) [M + H]$^+$ calcd for C$_{29}$H$_{43}$N$_2$O$_{10}$, 579.2910; found, 579.2912 | $^1$HNMR (CDCl$_3$) δ 8.34 (d, J = 8.1 Hz, 1H), 8.27 (d, J = 5.4 Hz, 1H), 6.96 (d, J = 5.4 Hz, 1H), 5.74 (s, 2H), 4.97-4.84 (m, 2H), 4.63 (dt, J = 10.7, 7.5 Hz, 1H), 3.91 (s, 3H), 3.49 (dd, J = 9.6, 7.5 Hz, 1H), 3.44-3.30 (m, 2H), 2.81-2.67 (m, 1H), 2.43-2.29 (m, 1H), 2.20-2.09 (m, | $^{13}$CNMR (CDCl$_3$) δ 175.70, 172.35, 170.23, 162.98, 160.23, 145.75, 143.90, 142.28, 109.66, 89.44, 82.25, 80.23, 77.72, 72.81, 56.19, 51.52, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1H), 2.08 (s, 3H), 2.00-1.54 (m, 11H), 1.42 (d, J = 6.4 Hz, 3H), 1.40-1.29 (m, 1H), 1.09 (ddt, J = 16.5, 7.8, 2.2 Hz, 1H), 0.88 (d, J = 6.3 Hz, 3H), 0.86 (d, J = 6.6 Hz, 3H) | 44.07, 33.19, 30.21, 29.73, 29.17, 28.98, 25.77, 25.76, 20.85, 19.34, 19.27, 18.36, 17.87 |
| F224 | Colorless Oil | — | 3368, 2934, 1743, 1529 | HRMS-ESI (m/z) [M + H]⁺ calcd for C₃₀H₄₁N₂O₇, 541.2908; found, 541.2919 | ¹H NMR (CDCl₃) δ 12.09 (s, 1H), 8.48 (d, J = 8.1 Hz, 1H), 7.98 (d, J = 5.2 Hz, 1H), 7.33-7.23 (m, 2H), 7.23-7.15 (m, 3H), 6.86 (d, J = 5.2 Hz, 1H), 4.76 (dq, J = 9.6, 6.4 Hz, 1H), 4.59 (dt, J = 10.8, 7.6 Hz, 1H), 4.37-4.26 (m, 1H), 3.93 (s, 3H), 3.55 (dt, J = 9.1, 6.6 Hz, 1H), 3.48 (dd, J = 9.6, 7.1 Hz, 1H), 3.40-3.28 (m, 2H), 2.80-2.61 (m, 2H), 2.41-2.32 (m, 1H), 2.16-2.05 (m, 1H), 1.98-1.86 (m, 2H), 1.86-1.46 (m, 10H), 1.40 (d, J = 6.5 Hz, 3H), 1.38-1.29 (m, 1H), 0.96-0.86 (m, 1H) | ¹³C NMR (CDCl₃) δ 172.09, 168.66, 155.33, 148.70, 141.98, 140.53, 130.38, 128.38, 128.34, 125.81, 109.48, 84.32, 83.39, 81.26, 73.54, 68.41, 56.07, 51.33, 33.31, 32.94, 32.53, 32.41, 31.77, 27.82, 23.30, 23.24, 18.29, 18.11 |
| F225 | Colorless Oil | — | 3378, 2939, 2868, 1748, 1678 | HRMS-ESI (m/z) [M + H]⁺ calcd for C₃₃H₄₅N₂O₉, 613.3120; found, 613.3133 | ¹H NMR (CDCl₃) δ 8.33 (d, J = 8.0 Hz, 1H), 8.27 (d, J = 5.3 Hz, 1H), 7.33-7.23 (m, 2H), 7.23-7.13 (m, 3H), 6.94 (d, J = 5.4 Hz, 1H), 5.74 (s, 2H), 4.74 (dq, J = 9.5, 6.4 Hz, 1H), 4.61 (dt, J = 10.7, 7.5 Hz, 1H), 4.36-4.26 (m, 1H), 3.90 (s, 3H), 3.55 (dt, J = 9.0, 6.6 Hz, 1H), 3.48 (dd, J = 9.6, 7.0 Hz, 1H), 3.41-3.27 (m, 2H), 2.80-2.61 (m, 2H), 2.45-2.31 (m, 1H), 2.19-2.08 (m, 1H), 2.07 (s, 3H), 1.98-1.85 (m, 2H), 1.85-1.45 (m, 10H), 1.39 (d, J = 6.4 Hz, 3H), 1.37-1.28 (m, 1H), 0.96-0.87 (m, 1H) | ¹³C NMR (CDCl₃) δ 172.69, 170.26, 162.97, 160.26, 145.73, 143.96, 142.41, 142.01, 128.38, 128.32, 125.78, 109.62, 89.52, 84.39, 83.36, 81.32, 73.25, 68.37, 56.19, 51.66, 33.40, 32.94, 32.52, 32.40, 31.76, 27.91, 23.29, 23.23, 20.88, 18.36, 18.10 |
| F226 | White Solid | — | — | ESIMS m/z 314.3 ([M + H]⁺) | — | — |
| F227 | Colorless Oil | — | — | ESIMS m/z 382 ([M + H]⁺) | ¹H NMR (CD₃OD) δ 4.64 (dq, J = 9.4, 6.4 Hz, 1H), 4.23-4.18 (m, 1H), 3.85 (dd, J = 10.7, 7.3 Hz, 1H), 3.59-3.50 (m, 1H), 3.39-3.29 (m, 2H), 3.27-3.22 (m, 1H), 2.27-2.05 (m, 4H), 1.77-1.67 (m, 3H), 1.66-1.33 (m, 10H), 1.31 (d, J = 6.4 Hz, | ¹³C NMR (CD₃OD) δ 173.78, 132.81, 130.07, 87.79, 87.15, 84.79, 78.03, 70.65, 55.37, 36.36, 35.85, 34.59, 34.42, 34.30, 34.02, 33.73, 31.08, 26.75, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 3H), 0.84-0.70 (m, 1H) | 26.56, 26.53, 26.50, 26.47, 21.30, 20.91 |
| F228 | White Foam | — | — | ESIMS m/z 390 ([M + H]$^+$) | $^1$H NMR (CD$_3$OD) δ 7.30-7.22 (m, 2H), 7.21-7.12 (m, 3H), 4.73 (dq, J = 9.5, 6.4 Hz, 1H), 4.37-4.32 (m, 1H), 3.94 (dd, J = 10.7, 7.3 Hz, 1H), 3.58 (dt, J = 9.0, 6.6 Hz, 1H), 3.47 (dd, J = 9.5, 7.0 Hz, 1H), 3.41-3.32 (m, 2H), 2.79-2.61 (m, 2H), 2.34-2.10 (m, 2H), 1.97-1.76 (m, 3H), 1.76-1.42 (m, 10H), 1.40 (d, J = 6.4 Hz, 3H), 0.85 (dt, J = 16.3, 4.3 Hz, 1H) | $^{13}$C NMR (CD$_3$OD) δ 171.31, 143.33, 129.70, 129.61, 127.05, 85.41, 84.67, 82.45, 75.52, 69.77, 68.43, 53.38, 34.14, 33.86, 33.60, 33.36, 32.37, 29.05, 24.51, 24.48, 19.36, 18.90 |
| F229 | Colorless Oil | — | — | ESIMS m/z 378.3 ([M + H]$^+$) | $^1$H NMR (CD$_3$OD) δ 6.92-6.80 (m, 4H), 4.86-4.80 (m, 1H), 4.31 (tt, J = 5.3, 3.5 Hz, 1H), 4.23 (ddd, J = 7.1, 5.3, 1.7 Hz, 1H), 3.98 (dd, J = 10.8, 7.5 Hz, 1H), 3.74 (s, 3H), 3.75-3.71 (m, 1H), 2.26 (dt, J = 13.7, 7.1 Hz, 1H), 2.20-2.12 (m, 1H), 1.90-1.48 (m, 10H), 1.46 (d, J = 6.4 Hz, 3H), 1.45-1.35 (m, 1H), 0.93 (ddt, J = 16.2, 7.7, 1.7 Hz, 1H) | $^{13}$C NMR (CD$_3$OD) δ 171.23, 155.86, 152.78, 118.77, 115.77, 85.04, 84.67, 82.11, 75.39, 68.18, 56.17, 52.86, 33.86, 33.47, 31.91, 28.98, 24.19, 24.13, 18.85, 18.43 |
| F230 | White Foam | — | — | ESIMS m/z 314.4 ([M + H]$^+$) | $^1$H NMR (CD$_3$OD) δ 4.72 (dq, J = 9.4, 6.3 Hz, 1H), 4.32 (td, J = 4.8, 2.6 Hz, 1H), 3.94 (dd, J = 10.6, 7.0 Hz, 1H), 3.52 (dt, J = 8.8, 6.7 Hz, 1H), 3.44 (dd, J = 9.4, 6.9 Hz, 1H), 3.36-3.24 (m, 2H), 2.36-2.13 (m, 2H), 1.88-1.76 (m, 1H), 1.76-1.42 (m, 12H), 1.39 (d, J = 6.4 Hz, 3H), 0.94 (t, J = 7.4 Hz, 3H), 0.84 (dt, J = 15.9, 4.3 Hz, 1H) | $^{13}$C NMR (CD$_3$OD) δ 171.27, 85.26, 84.55, 82.36, 75.48, 71.88, 52.90, 33.91, 33.32, 31.94, 28.66, 24.48, 24.27, 24.25, 18.90, 18.48, 11.24 |
| F231 | White Solid | — | — | HRMS-ESI (m/z) [M + ]$^+$ calcd for C$_{21}$H$_{30}$NO$_5$, 376.2118; found, 376.2122 | $^1$H NMR (CDCl$_3$) δ 7.24 (t, J = 8.0 Hz, 2H), 6.94 (t, J = 7.4 Hz, 1H), 6.89-6.79 (m, 2H), 5.35 (dd, J = 9.5, 8.1 Hz, 1H), 5.06 (dq, J = 12.7, 6.3 Hz, 1H), 4.48-4.30 (m, 1H), 4.06 (dd, J = 10.3, 7.7 Hz, 1H), 2.56 (ddd, J = 19.5, 9.7, 3.9 Hz, 5H), 1.93-1.40 (m, 12H), 1.33 (d, J = 6.3 Hz, 3H), 1.13 (dd, J = 16.0, 7.1 Hz, 1H) | $^{13}$C NMR (CDCl$_3$) δ 175.68, 169.87, 157.60, 129.49, 121.56, 116.40, 79.58, 74.57, 72.42, 51.82, 43.68, 30.80, 29.80, 29.70, 28.60, 25.67, 25.58, 17.51, 17.11 |
| F232 | White Tacky Solid | — | — | HRMS-ESI (m/z) [M + H]$^+$ calcd for | $^1$H NMR (CDCl$_3$) δ 12.03 (s, 1H), 8.45 (d, J = 8.0 Hz, 1H), 7.98 (d, J = 5.2 Hz, 1H), | $^{13}$C NMR (CDCl$_3$) δ 175.59, 172.07, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | $C_{28}H_{35}N_2O_8$, 527.2388; found, 527.2400 | 7.27-7.22 (m, 2H), 6.98-6.92 (m, 1H), 6.89-6.84 (m, 3H), 5.40 (dd, J = 9.7, 7.9 Hz, 1H), 5.11 (dq, J = 9.8, 6.4 Hz, 1H), 4.68 (dt, J = 10.7, 7.6 Hz, 1H), 4.41 (ddd, J = 7.5, 5.4, 1.8 Hz, 1H), 3.94 (s, 3H), 2.59 (ddd, J = 15.6, 8.3, 7.1 Hz, 1H), 2.41 (dt, J = 13.7, 7.1 Hz, 1H), 2.32-2.18 (m, 1H), 2.02-1.86 (m, 1H), 1.80-1.37 (m, 10H), 1.34 (d, J = 6.4 Hz, 3H), 1.27-1.14 (m, 1H) | 168.71, 157.75, 155.38, 148.76, 140.54, 130.29, 129.50, 121.51, 116.50, 109.53, 79.77, 74.85, 71.48, 56.09, 51.27, 43.73, 33.16, 29.84, 29.73, 28.81, 25.71, 25.62, 18.02, 17.30 |
| F233 | White Foam | — | — | HRMS-ESI (m/z) [M + H]⁺ calcd for $C_{31}H_{38}N_2O_{10}$, 599.2599; found, 599.2600 | ¹H NMR (CDCl₃) δ 8.31 (d, J = 7.8 Hz, 1H), 8.27 (d, J = 5.4 Hz, 1H), 7.25 (dd, J = 8.7, 7.4 Hz, 2H), 6.97-6.91 (m, 2H), 6.87 (dd, J = 8.7, 0.9 Hz, 2H), 5.74 (s, 2H), 5.38 (dd, J = 9.8, 7.9 Hz, 1H), 5.09 (dq, J = 9.8, 6.4 Hz, 1H), 4.69 (dt, J = 10.7, 7.5 Hz, 1H), 4.39 (ddd, J = 7.5, 5.4, 1.8 Hz, 1H), 3.91 (s, 3H), 2.59 (ddd, J = 15.6, 8.3, 7.1 Hz, 1H), 2.41 (dt, J = 13.7, 7.1 Hz, 1H), 2.30-2.15 (m, 1H), 2.07 (s, 3H), 2.00-1.86 (m, 1H), 1.85-1.43 (m, 9H), 1.42-1.30 (m, 4H), 1.27-1.15 (m, 1H) | ¹³C NMR (CDCl₃) δ 175.57, 172.67, 170.30, 162.99, 160.30, 157.81, 145.70, 144.10, 142.24, 129.47, 121.44, 116.50, 109.66, 89.54, 79.80, 74.95, 71.18, 56.20, 51.63, 43.74, 33.22, 29.84, 29.73, 28.95, 25.70, 25.61, 20.88, 18.12, 17.30 |
| F234 | White Foam | — | — | HRMS-ESI (m/z) [M + H]⁺ calcd for $C_{33}H_{43}N_2O_{10}$, 627.2912; found, 627.2919 | ¹H NMR (CDCl₃) δ 8.36 (d, J = 7.9 Hz, 1H), 8.26 (d, J = 5.4 Hz, 1H), 7.30-7.20 (m, 2H), 6.99-6.91 (m, 2H), 6.87 (d, J = 7.8 Hz, 2H), 5.77 (d, J = 1.2 Hz, 2H), 5.39 (dd, J = 9.7, 7.9 Hz, 1H), 5.09 (dq, J = 9.9, 6.4 Hz, 1H), 4.68 (dt, J = 10.7, 7.5 Hz, 1H), 4.40 (dd, J = 6.7, 4.8 Hz, 1H), 3.89 (s, 3H), 2.56 (tt, J = 14.0, 7.2 Hz, 2H), 2.41 (dt, J = 13.8, 7.1 Hz, 1H), 2.31-2.17 (m, 1H), 2.01-1.85 (m, 1H), 1.80-1.46 (m, 9H), 1.43-1.28 (m, 4H), 1.22 (dd, J = 16.1, 7.5 Hz, 1H), 1.15 (d, J = 7.0 Hz, 6H) | ¹³C NMR (CDCl₃) δ 176.27, 175.58, 172.67, 162.97, 160.27, 157.81, 145.56, 144.31, 141.91, 129.46, 121.43, 116.50, 109.60, 89.89, 79.80, 74.96, 71.16, 56.14, 51.63, 43.74, 33.85, 33.23, 29.84, 29.72, 28.94, 25.70, 25.61, 18.68, 18.12, 17.30 |
| F235 | White Foam | — | — | HRMS-ESI (m/z) [M + H]⁺ calcd for $C_{30}H_{37}N_2O_9$, 569.2429; found, 569.2427 | ¹H NMR (CDCl₃) δ 8.51 (d, J = 7.6 Hz, 1H), 8.33 (d, J = 5.4 Hz, 1H), 7.28-7.19 (m, 2H), 7.00 (d, J = 5.5 Hz, 1H), 6.94 (t, J = 7.4 Hz, 1H), 6.89-6.82 (m, 2H), 5.37 (dd, J = 9.8, 7.9 Hz, | ¹³C NMR (CDCl₃) δ 175.57, 172.56, 168.89, 162.42, 159.47, 157.81, 146.67, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1H), 5.09 (dq, J = 9.9, 6.4 Hz, 1H), 4.68 (dt, J = 10.6, 7.7 Hz, 1H), 4.39 (ddd, J = 7.5, 5.5, 1.7 Hz, 1H), 3.90 (s, 3H), 2.64-2.52 (m, 1H), 2.40 (s, 4H), 2.30-2.16 (m, 1H), 1.98-1.83 (m, 1H), 1.78-1.45 (m, 9H), 1.39-1.28 (m, 4H), 1.24-1.13 (m, 1H) | 141.32, 137.55, 129.47, 121.44, 116.50, 109.86, 79.80, 74.94, 71.21, 56.30, 51.34, 43.74, 33.48, 29.84, 29.73, 28.99, 25.70, 25.61, 20.75, 18.09, 17.28 |
| F236 | White Foam | — | — | HRMS-ESI (m/z) [M + H]⁺ calcd for $C_{32}H_{39}N_2O_9$, 595.2650; found, 595.2657 | ¹H NMR (CDCl₃) δ 8.47 (d, J = 8.0 Hz, 1H), 8.32 (d, J = 5.4 Hz, 1H), 7.26-7.20 (m, 2H), 6.99 (d, J = 5.5 Hz, 1H), 6.94 (t, J = 7.3 Hz, 1H), 6.86 (d, J = 7.8 Hz, 2H), 5.37 (dd, J = 9.8, 7.9 Hz, 1H), 5.08 (dq, J = 9.8, 6.4 Hz, 1H), 4.72 (dt, J = 10.6, 7.7 Hz, 1H), 4.39 (ddd, J = 7.5, 5.4, 1.7 Hz, 1H), 3.90 (s, 3H), 2.66-2.53 (m, 1H), 2.40 (dt, J = 13.9, 7.2 Hz, 1H), 2.31-2.15 (m, 1H), 2.02-1.84 (m, 2H), 1.79-1.46 (m, 9H), 1.32 (t, J = 6.9 Hz, 4H), 1.27-1.16 (m, 3H), 1.07 (dq, J = 7.2, 3.7 Hz, 2H) | ¹³C NMR (CDCl₃) δ 175.58, 172.64, 172.46, 162.36, 159.52, 157.82, 146.58, 141.70, 137.51, 129.46, 121.43, 116.51, 109.75, 79.82, 74.96, 71.15, 56.32, 51.25, 43.74, 33.56, 29.84, 29.73, 29.00, 25.70, 25.61, 18.10, 17.28, 13.00, 9.32 |
| F237 | White Foam | — | — | HRMS-ESI (m/z) [M + H]⁺ calcd for $C_{33}H_{43}N_2O_{11}$, 643.2861; found, 643.2874 | ¹H NMR (CDCl₃) δ 8.32 (d, J = 7.9 Hz, 1H), 8.27 (d, J = 5.4 Hz, 1H), 7.25 (dd, J = 8.6, 7.4 Hz, 2H), 6.98-6.91 (m, 2H), 6.90-6.83 (m, 2H), 5.82 (s, 2H), 5.39 (dd, J = 9.8, 7.9 Hz, 1H), 5.09 (dq, J = 9.8, 6.4 Hz, 1H), 4.67 (dt, J = 10.7, 7.5 Hz, 1H), 4.39 (ddd, J = 7.5, 5.4, 1.8 Hz, 1H), 4.10 (s, 2H), 3.90 (s, 3H), 3.60 (q, J = 7.0 Hz, 2H), 2.59 (ddd, J = 15.6, 8.3, 7.1 Hz, 1H), 2.40 (dt, J = 13.8, 7.1 Hz, 1H), 2.32-2.16 (m, 1H), 2.01-1.85 (m, 1H), 1.80-1.46 (m, 9H), 1.43-1.30 (m, 4H), 1.23 (t, J = 7.0 Hz, 4H) | ¹³C NMR (CDCl₃) δ 175.58, 172.64, 170.09, 162.94, 160.20, 157.80, 145.75, 144.05, 142.10, 129.47, 121.44, 116.50, 109.76, 89.53, 79.80, 74.95, 71.20, 67.79, 67.19, 56.23, 51.62, 43.74, 33.22, 29.84, 29.73, 28.94, 25.70, 25.61, 18.11, 17.30, 15.02 |
| F238 | White Solid | — | — | HRMS-ESI (m/z) [M + H]⁺ calcd for $C_{19}H_{26}NO_5$, 348.1805; found, 348.1807 | ¹H NMR (CDCl₃) δ 7.26 (t, J = 7.9 Hz, 2H), 6.96 (t, J = 7.3 Hz, 1H), 6.87 (d, J = 8.1 Hz, 2H), 5.34 (dd, J = 9.4, 8.1 Hz, 1H), 5.06 (dt, J = 12.7, 6.3 Hz, 1H), 4.47-4.32 (m, 1H), 4.01 (dd, J = 10.3, 7.6 Hz, 1H), 2.39 (ddt, J = 100.3, 15.5, 7.2 Hz, 5H), 1.94-1.67 (m, 2H), | ¹³C NMR (CDCl₃) δ 174.04, 169.82, 157.67, 129.50, 121.67, 116.61, 79.54, 74.92, 72.49, 51.72, 30.78, 28.74, 17.49, 17.05, 12.75, 8.63, 8.55 |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 1.61 (q, J = 11.4 Hz, 1H), 1.49 (tt, J = 8.1, 4.6 Hz, 1H), 1.35 (d, J = 6.3 Hz, 3H), 1.13 (dd, J = 16.1, 6.9 Hz, 1H), 0.98-0.69 (m, 4H) | |
| F239 | White Foam | — | — | HRMS-ESI m/z [M + H]$^+$ calcd for C$_{26}$H$_{31}$N$_2$O$_8$, 499.2075; found, 499.2077 | $^1$H NMR (CDCl$_3$) δ 12.03 (s, 1H), 8.45 (d, J = 8.0 Hz, 1H), 7.99 (d, J = 5.2 Hz, 1H), 7.33-7.17 (m, 2H), 7.01-6.93 (m, 1H), 6.92-6.84 (m, 3H), 5.38 (dd, J = 9.7, 7.8 Hz, 1H), 5.11 (dq, J = 9.8, 6.4 Hz, 1H), 4.67 (dt, J = 10.7, 7.6 Hz, 1H), 4.41 (ddd, J = 7.6, 5.5, 1.9 Hz, 1H), 3.94 (s, 3H), 2.41 (dt, J = 13.7, 7.1 Hz, 1H), 2.33-2.19 (m, 1H), 2.01-1.86 (m, 1H), 1.75 (dt, J = 15.5, 7.7 Hz, 1H), 1.55-1.44 (m, 1H), 1.41 (d, J = 12.9 Hz, 1H), 1.35 (d, J = 6.4 Hz, 3H), 1.28-1.17 (m, 1H), 0.99-0.72 (m, 4H) | $^{13}$C NMR (CDCl$_3$) δ 173.88, 172.07, 168.70, 157.85, 155.39, 148.77, 140.54, 130.31, 129.49, 121.56, 116.69, 109.53, 79.72, 75.19, 71.52, 56.09, 51.29, 33.16, 28.97, 18.04, 17.25, 12.81, 8.58, 8.50 |
| F240 | White Foam | — | — | HRMS-ESI m/z [M + H]$^+$ calcd for C$_{29}$H$_{35}$N$_2$O$_{10}$, 571.2286; found, 571.2298 | $^1$H NMR (CDCl$_3$) δ 8.31 (d, J = 7.9 Hz, 1H), 8.27 (d, J = 5.4 Hz, 1H), 7.30-7.21 (m, 2H), 6.99-6.92 (m, 2H), 6.92-6.87 (m, 2H), 5.74 (s, 2H), 5.37 (dd, J = 9.7, 7.9 Hz, 1H), 5.09 (dq, J = 9.8, 6.4 Hz, 1H), 4.68 (dt, J = 10.7, 7.5 Hz, 1H), 4.40 (ddd, J = 7.6, 5.6, 1.8 Hz, 1H), 3.91 (s, 3H), 2.41 (dt, J = 13.7, 7.1 Hz, 1H), 2.31-2.17 (m, 1H), 2.07 (s, 3H), 1.99-1.85 (m, 1H), 1.72 (dq, J = 15.7, 7.8 Hz, 1H), 1.49 (tt, J = 8.0, 4.6 Hz, 1H), 1.34 (d, J = 6.4 Hz, 4H), 1.29-1.16 (m, 1H), 0.97-0.70 (m, 4H) | $^{13}$C NMR (CDCl$_3$) δ 173.86, 172.66, 170.29, 162.99, 160.29, 157.90, 145.71, 144.08, 142.24, 129.46, 121.50, 116.69, 109.68, 89.52, 79.76, 75.29, 71.22, 56.20, 51.65, 33.20, 29.11, 20.87, 18.14, 17.25, 12.81, 8.53, 8.46 |
| F241 | White Foam | — | — | HRMS-ESI (m/z) [M + H]$^+$ calcd for C$_{31}$H$_{39}$N$_2$O$_{10}$, 599.2599; found, 599.2596 | $^1$H NMR (CDCl$_3$) δ 8.36 (d, J = 7.9 Hz, 1H), 8.26 (d, J = 5.4 Hz, 1H), 7.29-7.21 (m, 2H), 6.99-6.92 (m, 2H), 6.89 (dd, J = 8.7, 1.0 Hz, 2H), 5.77 (d, J = 1.3 Hz, 2H), 5.37 (dd, J = 9.8, 7.8 Hz, 1H), 5.09 (dq, J = 9.8, 6.4 Hz, 1H), 4.68 (dt, J = 10.7, 7.5 Hz, 1H), 4.40 (ddd, J = 7.6, 5.6, 1.8 Hz, 1H), 3.89 (s, 3H), 2.55 (hept, J = 7.0 Hz, 1H), 2.41 (dt, J = 13.7, 7.1 Hz, 1H), 2.24 (ddt, J = 13.2, 9.5, 7.5 Hz, 1H), 2.00-1.83 (m, 1H), | $^{13}$C NMR (CDCl$_3$) δ 176.26, 173.87, 172.66, 162.97, 160.27, 157.91, 145.57, 144.30, 141.91, 129.46, 121.49, 116.68, 109.61, 89.88, 79.75, 75.29, 71.21, 56.15, 51.65, 33.85, 33.21, 29.11, 18.68, 18.14, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 1.72 (dq, J = 15.7, 7.9 Hz, 1H), 1.55-1.45 (m, 1H), 1.34 (d, J = 6.4 Hz, 4H), 1.22 (ddd, J = 19.3, 7.3, 5.1 Hz, 1H), 1.14 (d, J = 7.0 Hz, 6H), 0.96-0.71 (m, 4H) | 17.25, 12.81, 8.53, 8.46 |
| F242 | White Foam | — | — | HRMS-ESI (m/z) [M + H]$^+$ calcd for C$_{28}$H$_{33}$N$_2$O$_9$, 541.2181; found, 541.2185 | $^1$H NMR (CDCl$_3$) δ 8.51 (d, J = 7.6 Hz, 1H), 8.33 (d, J = 5.4 Hz, 1H), 7.29-7.22 (m, 2H), 7.00 (d, J = 5.5 Hz, 1H), 6.95 (t, J = 7.3 Hz, 1H), 6.88 (d, J = 8.0 Hz, 2H), 5.35 (dd, J = 9.7, 7.8 Hz, 1H), 5.08 (dq, J = 9.8, 6.4 Hz, 1H), 4.67 (dt, J = 10.5, 7.7 Hz, 1H), 4.44-4.34 (m, 1H), 3.90 (s, 3H), 2.40 (s, 4H), 2.32-2.16 (m, 1H), 1.96-1.82 (m, 1H), 1.71 (dt, J = 15.5, 8.0 Hz, 1H), 1.48 (tt, J = 8.1, 4.6 Hz, 1H), 1.34 (t, J = 7.6 Hz, 4H), 1.27-1.15 (m, 1H), 0.97-0.69 (m, 4H) | 13CC NMR (CDCl$_3$) δ 173.86, 172.56, 168.89, 162.41, 159.47, 157.91, 146.68, 141.32, 137.55, 129.46, 121.50, 116.68, 109.86, 79.75, 75.28, 71.25, 56.30, 51.36, 33.46, 29.16, 20.74, 18.11, 17.23, 12.80, 8.53, 8.47 |
| F243 | White Foam | — | — | HRMS-ESI (m/z) [M + H]$^+$ calcd for C$_{30}$H$_{37}$N$_2$O$_{10}$, 585.2443; found, 585.2447 | $^1$H NMR (CDCl$_3$) δ 8.49 (d, J = 7.1 Hz, 1H), 8.32 (d, J = 5.4 Hz, 1H), 7.30-7.22 (m, 2H), 6.99 (d, J = 5.5 Hz, 1H), 6.98-6.93 (m, 1H), 6.91-6.86 (m, 2H), 5.35 (dd, J = 9.8, 7.8 Hz, 1H), 5.08 (dq, J = 9.8, 6.4 Hz, 1H), 4.67 (dt, J = 10.6, 7.6 Hz, 1H), 4.39 (ddd, J = 7.6, 5.6, 1.8 Hz, 1H), 3.89 (s, 3H), 3.81 (t, J = 6.6 Hz, 2H), 3.41 (s, 3H), 2.98 (t, J = 6.6 Hz, 2H), 2.38 (dt, J = 13.8, 7.1 Hz, 1H), 2.23 (ddt, J = 13.3, 9.5, 7.5 Hz, 1H), 1.96-1.83 (m, 1H), 1.70 (dq, J = 15.6, 7.8 Hz, 1H), 1.48 (tt, J = 8.0, 4.6 Hz, 1H), 1.40-1.27 (m, 4H), 1.21 (ddd, J = 16.0, 6.2, 2.2 Hz, 1H), 0.96-0.70 (m, 4H) | $^{13}$C NMR (CDCl$_3$) δ 173.87, 172.55, 169.43, 162.36, 159.47, 157.90, 146.73, 141.34, 137.39, 129.46, 121.50, 116.68, 109.87, 79.77, 75.27, 71.22, 67.57, 58.78, 56.33, 51.33, 34.63, 33.45, 29.12, 18.11, 17.22, 12.80, 8.53, 8.46 |
| F244 | White Solid | — | — | HRMS-ESI (m/z) [M + H]$^+$ calcd for C$_{14}$H$_{26}$NO$_4$, 272.1862; found, 272.1856 | $^1$H NMR (CDCl$_3$) δ 8.61 (s, 3H), 3.56-3.51 (m, 1H), 2.59-2.47 (m, 1H), 2.20-1.98 (m, 1H), 1.70 (d, J = 45.2 Hz, 4H), 1.57 (d, J = 3.2 Hz, 1H), 1.40 (d, J = 6.2 Hz, 3H), 0.96-0.78 (m, 1H), 4.87-4.82 (m, 0H), 4.97 (s, 1H), 4.87 (s, 1H), 4.73 (dq, J = 12.4, 6.0 Hz, 1H), 4.11-4.01 (m, 1H), 3.95 (d, J = 12.1 Hz, | $^{13}$C NMR (CDCl$_3$) δ 170.09, 142.36, 112.26, 85.41, 82.94, 73.77, 72.99, 61.47, 52.24, 30.89, 29.38, 27.77, 19.55, 17.66 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1H), 3.84 (d, J = 12.1 Hz, 1H), 3.57 (s, 3H), 3.47-3.34 (m, 1H), 3.29-3.21 (m, 1H) | |
| F245 | Off-White Foam | — | — | HRMS-ESI (m/z) [M + Na]⁺ calcd for $C_{21}H_{30}N_2NaO_7$, 445.1945; found, 445.1961 | ¹H NMR (CDCl₃) δ 12.07 (dd, J = 4.6, 0.5 Hz, 1H), 8.47 (d, J = 8.1 Hz, 1H), 7.99 (d, J = 5.2 Hz, 1H), 6.87 (d, J = 5.2 Hz, 1H), 4.99 (dd, J = 2.0, 0.9 Hz, 1H), 4.91-4.86 (m, 1H), 4.80 (dq, J = 9.5, 6.4 Hz, 1H), 4.59 (dt, J = 10.8, 7.6 Hz, 1H), 3.98 (d, J = 12.1 Hz, 1H), 3.94 (s, 3H), 3.87 (d, J = 12.1 Hz, 1H), 3.59 (s, 3H), 3.42 (ddd, J = 7.0, 5.2, 1.7 Hz, 1H), 3.32 (dd, J = 9.5, 7.4 Hz, 1H), 2.38 (ddd, J = 13.9, 10.1, 4.2 Hz, 1H), 2.24-2.06 (m, 1H), 1.78 (s, 2H), 1.73-1.63 (m, 2H), 1.59 (d, J = 2.3 Hz, 1H), 1.47-1.33 (m, 4H), 1.01-0.89 (m, 1H) | ¹³C NMR (CDCl₃) δ 171.97, 168.66, 155.34, 148.72, 142.47, 140.51, 130.38, 112.18, 109.48, 85.65, 83.14, 73.10, 73.07, 61.48, 56.06, 51.28, 33.33, 27.87, 19.56, 18.24, 17.74 |
| F246 | White Solid | — | — | HRMS-ESI (m/z) [M + Na]⁺ calcd for $C_{14}H_{27}NNaO_4$, 296.1832; found, 296.1832 | ¹H NMR (CDCl₃) δ 8.67 (s, 3H), 4.73 (dq, J = 12.7, 6.2 Hz, 1H), 4.11-3.96 (m, 1H), 3.55 (s, 3H), 3.35-3.17 (m, 3H), 3.11 (dd, J = 8.7, 6.4 Hz, 1H), 2.52 (d, J = 6.8 Hz, 1H), 2.12 (dd, J = 15.4, 5.7 Hz, 1H), 1.79 (ddd, J = 28.0, 13.9, 8.7 Hz, 2H), 1.61 (d, J = 7.3 Hz, 2H), 1.39 (d, J = 6.3 Hz, 3H), 0.92 (d, J = 2.7 Hz, 3H), 0.90 (d, J = 2.7 Hz, 3H), 0.87-0.76 (m, 1H) | ¹³C NMR (CDCl₃) δ 170.05, 85.36, 83.85, 75.84, 73.76, 61.34, 52.22, 31.02, 28.83, 27.72, 19.46, 19.45, 17.79, 17.71 |
| F247 | Off-White Solid | — | — | HRMS-ESI (m/z) [M + Na]⁺ calcd for $C_{21}H_{32}N_2NaO_7$, 447.2102; found, 447.2115 | ¹H NMR (CDCl₃) δ 12.09 (s, 1H), 8.47 (d, J = 8.1 Hz, 1H), 7.99 (d, J = 5.2 Hz, 1H), 6.87 (d, J = 5.2 Hz, 1H), 4.79 (dq, J = 9.3, 6.4 Hz, 1H), 4.59 (dt, J = 10.8, 7.7 Hz, 1H), 3.94 (s, 3H), 3.58 (s, 3H), 3.38-3.22 (m, 3H), 3.14 (dd, J = 8.7, 6.4 Hz, 1H), 2.37 (dt, J = 13.9, 6.3 Hz, 1H), 2.22-2.06 (m, 1H), 1.84 (dp, J = 13.2, 6.6 Hz, 1H), 1.69 (dd, J = 13.1, 6.0 Hz, 2H), 1.47-1.28 (m, 4H), 0.93 (d, J = 2.7 Hz, 3H), 0.92 (d, J = 2.7 Hz, 3H), 0.89 (d, J = 7.3 Hz, 1H) | ¹³C NMR (CDCl₃) δ 172.00, 168.65, 155.34, 148.72, 140.51, 130.39, 109.47, 85.55, 84.03, 75.91, 73.06, 61.37, 56.06, 51.29, 33.34, 28.85, 27.75, 19.48, 19.46, 18.20, 17.79 |
| F248 | White Solid | — | — | HRMS-ESI (m/z) [M + H]⁺ calcd for $C_{16}H_{24}NO_4$, | ¹H NMR (CDCl₃) δ 8.66 (s, 3H), 7.34-7.20 (m, 2H), 7.02-6.84 (m, 3H), 4.83 (dd, J = 9.4, 6.3 Hz, | ¹³C NMR (CDCl₃) δ 170.01, 157.46, 129.57, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | 294.1700; found, 294.1716 | 1H), 4.38-4.25 (m, 1H), 4.11 (s, 1H), 3.58-3.41 (m, 4H), 2.50 (s, 1H), 2.29-2.06 (m, 1H), 1.68 (dd, J = 23.6, 12.8 Hz, 3H), 1.43 (d, J = 6.2 Hz, 3H), 0.97 (dd, J = 15.6, 6.7 Hz, 1H) | 121.36, 116.47, 84.83, 82.64, 73.53, 61.41, 52.20, 30.82, 28.31, 17.78, 17.73 |
| F249 | White Foam | — | — | HRMS-ESI (m/z) [M + Na]⁺ calcd for $C_{23}H_{28}N_2NaO_7$, 467.1789; found, 467.1810 | ¹H NMR (CDCl₃) δ 12.06 (d, J = 0.5 Hz, 1H), 8.46 (d, J = 8.1 Hz, 1H), 7.98 (d, J = 5.2 Hz, 1H), 7.28 (dd, J = 8.2, 7.3 Hz, 2H), 7.01-6.90 (m, 3H), 6.86 (d, J = 5.2 Hz, 1H), 4.91 (dq, J = 9.6, 6.4 Hz, 1H), 4.64 (dt, J = 10.7, 7.7 Hz, 1H), 4.40-4.32 (m, 1H), 3.94 (s, 3H), 3.56 (s, 4H), 2.37 (dt, J = 13.6, 7.1 Hz, 1H), 2.19 (dddd, J = 15.8, 10.1, 8.0, 5.4 Hz, 1H), 1.90-1.76 (m, 1H), 1.75-1.58 (m, 1H), 1.47 (d, J = 6.4 Hz, 3H), 1.41-1.29 (m, 1H), 1.06 (dd, J = 16.1, 7.8 Hz, 1H) | ¹³C NMR (CDCl₃) δ 171.92, 168.69, 157.57, 155.36, 148.74, 140.54, 130.35, 129.56, 121.38, 116.64, 109.50, 85.04, 82.96, 72.83, 61.43, 56.07, 51.23, 33.21, 28.29, 18.20, 17.82 |
| F250 | White Foam | — | — | HRMS-ESI (m/z) [M + H]⁺ calcd for $C_{24}H_{35}N_2O_9$, 495.2337; found, 495.2368 | ¹H NMR (CDCl₃) δ 8.31 (d, J = 8.0 Hz, 1H), 8.28 (d, J = 5.4 Hz, 1H), 6.95 (d, J = 5.4 Hz, 1H), 5.74 (s, 2H), 5.01-4.97 (m, 1H), 4.91-4.86 (m, 1H), 4.78 (dq, J = 9.5, 6.4 Hz, 1H), 4.61 (dt, J = 10.8, 7.6 Hz, 1H), 3.98 (d, J = 12.1 Hz, 1H), 3.91 (s, 3H), 3.87 (d, J = 12.1 Hz, 1H), 3.59 (s, 3H) 3.41 (td, J = 6.1, 5.1, 1.7 Hz, 1H), 3.31 (dd, J = 9.5, 7.3 Hz, 1H), 2.45-2.32 (m, 1H), 2.07 (s, 4H), 1.77 (s, 2H), 1.68 (dq, J = 15.1, 8.4 Hz, 2H), 1.59 (d, J = 2.8 Hz, 1H), 1.40 (d, J = 6.4 Hz, 4H), 0.93 (ddd, J = 14.3, 7.4, 2.3 Hz, 1H) | ¹³C NMR (CDCl₃) δ 172.58, 170.25, 162.95, 160.25, 145.73, 143.96, 142.50, 142.39, 112.15, 109.61, 89.51, 85.69, 83.21, 73.03, 72.82, 61.46, 56.18, 51.60, 33.40, 29.37, 27.92, 20.86, 19.56, 18.29, 17.73 |
| F251 | White Foam | — | — | HRMS-ESI (m/z) [M + Na]⁺ calcd for $C_{24}H_{36}N_2NaO_9$, 519.2313; found, 519.2336 | ¹H NMR (CDCl₃) δ 8.31 (d, J = 8.0 Hz, 1H), 8.27 (d, J = 5.4 Hz, 1H), 6.95 (d, J = 5.4 Hz, 1H), 5.74 (s, 2H), 4.77 (dq, J = 9.3, 6.4 Hz, 1H), 4.61 (dt, J = 10.8, 7.5 Hz, 1H), 3.91 (s, 3H), 3.58 (s, 3H), 3.30 (ddt, J = 11.6, 9.3, 6.4 Hz, 3H), 3.13 (dd, J = 8.8, 6.4 Hz, 1H), 2.38 (dt, J = 13.8, 6.7 Hz, 1H), 2.07 (s, 4H), 1.89-1.77 (m, 1H), 1.75-1.58 (m, 2H), 1.44-1.30 (m, 4H), 0.93 (d, | ¹³C NMR (CDCl₃) δ 172.61, 170.25, 162.95, 160.25, 145.72, 143.96, 142.41, 109.60, 89.52, 85.59, 84.11, 75.88, 72.78, 61.35, 56.18, 51.61, 33.42, 28.84, 27.81, 20.86, 19.48, 19.46, 18.26, 17.77 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | J = 2.9 Hz, 3H), 0.92 (d, J = 2.9 Hz, 3H), 0.88 (d, J = 7.4 Hz, 1H) | |
| F252 | White Foam | — | — | HRMS-ESI (m/z) [M + Na]⁺ calcd for $C_{26}H_{32}N_2NaO_9$, 540.2032; found, 540.2042 | ¹H NMR (CDCl₃) δ 8.31 (d, J = 8.0 Hz, 1H), 8.27 (d, J = 5.4 Hz, 1H), 7.31-7.24 (m, 2H), 6.98-6.92 (m, 4H), 5.74 (s, 2H), 4.89 (dq, J = 9.6, 6.4 Hz, 1H), 4.66 (dt, J = 10.7, 7.6 Hz, 1H), 4.40-4.32 (m, 1H), 3.90 (s, 3H), 3.55 (s, 4H), 2.37 (dt, J = 13.6, 7.1 Hz, 1H), 2.17 (ddddd, J = 15.9, 13.3, 10.3, 8.1, 2.7 Hz, 1H), 2.07 (s, 3H), 1.88-1.76 (m, 1H), 1.64 (dq, J = 15.5, 7.7 Hz, 1H), 1.45 (d, J = 6.4 Hz, 3H), 1.37-1.25 (m, 1H), 1.05 (dd, J = 16.1, 7.8 Hz, 1H) | ¹³C NMR (CDCl₃) δ 172.53, 170.27, 163.00, 160.27, 157.62, 145.74, 144.00, 142.34, 129.53, 121.32, 116.65, 109.64, 89.51, 85.09, 83.05, 72.54, 61.42, 56.19, 51.57, 33.28, 28.36, 20.88, 18.27, 17.81 |
| F253 | White Foam | — | — | HRMS-ESI (m/z) [M + Na]⁺ calcd for $C_{26}H_{38}N_2NaO_9$, 545.2470; found, 545.2500 | ¹H NMR (CDCl₃) δ 8.37 (d, J = 8.0 Hz, 1H), 8.27 (d, J = 5.4 Hz, 1H), 6.94 (d, J = 5.4 Hz, 1H), 5.81-5.73 (m, 2H), 5.01-4.96 (m, 1H), 4.91-4.86 (m, 1H), 4.78 (dq, J = 9.5, 6.4 Hz, 1H), 4.61 (dt, J = 10.7, 7.6 Hz, 1H), 3.98 (d, J = 12.1 Hz, 1H), 3.89 (s, 4H), 3.59 (s, 3H), 3.41 (ddd, J = 6.9, 5.2, 1.7 Hz, 1H), 3.31 (dd, J = 9.5, 7.3 Hz, 1H), 2.55 (hept, J = 7.0 Hz, 1H), 2.43-2.32 (m, 1H), 2.12 (dddd, J = 15.8, 13.7, 6.9, 4.2 Hz, 1H), 1.77 (s, 2H), 1.68 (dq, J = 15.1, 8.3 Hz, 2H), 1.59 (d, J = 2.7 Hz, 1H), 1.41 (d, J = 6.4 Hz, 3H), 1.39-1.28 (m, 1H), 1.15 (s, 3H), 1.14 (s, 3H), 1.02-0.88 (m, 1H) | ¹³C NMR (CDCl₃) δ 176.22, 172.58, 162.94, 160.24, 145.59, 144.19, 142.50, 142.06, 112.14, 109.54, 89.88, 85.70, 83.22, 73.03, 72.81, 61.46, 56.13, 51.60, 33.84, 33.42, 29.37, 27.92, 19.57, 18.67, 18.30, 17.73 |
| F254 | White Foam | — | — | HRMS-ESI (m/z) [M + Na]⁺ calcd for $C_{26}H_{40}N_2NaO_9$, 547.2626; found, 547.2648 | ¹H NMR (CDCl₃) δ 8.37 (d, J = 8.1 Hz, 1H), 8.27 (d, J = 5.4 Hz, 1H), 6.94 (d, J = 5.4 Hz, 1H), 5.81-5.73 (m, 2H), 4.77 (dq, J = 9.3, 6.4 Hz, 1H), 4.61 (dt, J = 10.8, 7.5 Hz, 1H), 3.89 (s, 3H), 3.58 (s, 3H), 3.30 (ddt, J = 11.7, 9.3, 6.4 Hz, 3H), 3.13 (dd, J = 8.8, 6.4 Hz, 1H), 2.55 (hept, J = 7.0 Hz, 1H), 2.37 (dt, J = 13.8, 6.7 Hz, 1H), 2.12 (dddd, J = 15.7, 10.1, 8.3, 5.2 Hz, 1H), | ¹³C NMR (CDCl₃) δ 176.22, 172.60, 162.93, 160.24, 145.59, 144.18, 142.08, 109.53, 89.89, 85.60, 84.11, 75.88, 72.76, 61.35, 56.12, 51.61, 33.84, 33.44, 28.84, 27.82, 19.48, 19.47, 18.67, 18.27, 17.77 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1.91-1.76 (m, 1H), 1.75-1.56 (m, 2H), 1.40 (d, J = 6.4 Hz, 3H), 1.38-1.27 (m, 1H), 1.14 (d, J = 7.0 Hz, 6H), 0.93 (d, J = 3.0 Hz, 3H), 0.92 (d, J = 3.0 Hz, 3H), 0.89 (dt, J = 7.8, 1.9 Hz, 1H) | |
| F255 | White Foam | — | — | HRMS-ESI (m/z) [M + Na]⁺ calcd for C₂₈H₃₆N₂NaO₉, 567.2313; found, 567.2346 | ¹H NMR (CDCl₃) δ 8.37 (d, J = 8.0 Hz, 1H), 8.26 (d, J = 5.4 Hz, 1H), 7.33-7.23 (m, 2H), 7.01-6.91 (m, 4H), 5.81-5.73 (m, 2H), 4.89 (dq, J = 9.6, 6.4 Hz, 1H), 4.65 (dt, J = 10.7, 7.6 Hz, 1H), 4.39-4.32 (m, 1H), 3.88 (s, 3H), 3.55 (s, 4H), 2.55 (hept, J = 7.0 Hz, 1H), 2.37 (dt, J = 13.6, 7.0 Hz, 1H), 2.17 (dddd, J = 15.7, 10.1, 8.0, 5.4 Hz, 1H), 1.87-1.78 (m, 1H), 1.64 (dq, J = 15.5, 7.7 Hz, 1H), 1.45 (d, J = 6.4 Hz, 3H), 1.37-1.28 (m, 1H), 1.14 (d, J = 7.0 Hz, 6H), 1.06 (dd, J = 16.1, 7.8 Hz, 1H) | ¹³C NMR (CDCl₃) δ 176.23, 172.53, 162.97, 160.25, 157.63, 145.60, 144.22, 142.01, 129.53, 121.32, 116.65, 109.58, 89.88, 85.09, 83.05, 72.53, 61.42, 56.14, 51.57, 33.86, 33.29, 28.36, 18.68, 18.28, 17.81 |
| F256 | White Foam | — | — | HRMS-ESI (m/z) [M + H]⁺ calcd for C₂₃H₃₃N₂O₈, 465.2231; found, 465.2246 | ¹H NMR (CDCl₃) δ 8.52 (d, J = 6.9 Hz, 1H), 8.33 (d, J = 5.4 Hz, 1H), 7.00 (d, J = 5.5 Hz, 1H), 5.00-4.96 (m, 1H), 4.90-4.86 (m, 1H), 4.77 (dq, J = 9.5, 6.4 Hz, 1H), 4.60 (dt, J = 10.7, 7.7 Hz, 1H), 3.98 (d, J = 12.1 Hz, 5H), 3.58 (s, 3H), 3.41 (ddd, J = 7.0, 5.2, 1.7 Hz, 1H), 3.29 (dd, J = 9.5, 7.3 Hz, 1H), 2.40 (s, 4H), 2.11 (dddd, J = 15.7, 10.1, 8.5, 5.3 Hz, 1H), 1.77 (s, 2H), 1.72-1.61 (m, 2H), 1.59 (d, J = 3.0 Hz, 1H), 1.39 (d, J = 6.4 Hz, 3H), 1.32 (qd, J = 10.9, 5.2 Hz, 1H), 0.97-0.87 (m, 1H) | ¹³C NMR (CDCl₃) δ 172.46, 168.86, 162.38, 159.43, 146.69, 142.49, 141.38, 137.48, 112.19, 109.81, 85.67, 83.21, 73.04, 72.84, 61.46, 56.28, 51.33, 29.37, 27.93, 20.73, 19.57, 18.26, 17.72 |
| F257 | White Foam | — | — | HRMS-ESI (m/z) [M + H]⁺ calcd for C₂₃H₃₅N₂O₈, 467.2388; found, 467.2414 | ¹H NMR (CDCl₃) δ 8.52 (d, J = 7.2 Hz, 1H), 8.32 (d, J = 5.4 Hz, 1H), 7.00 (d, J = 5.5 Hz, 1H), 4.76 (dq, J = 9.4, 6.4 Hz, 1H), 4.59 (dt, J = 10.7, 7.6 Hz, 1H), 3.90 (s, 3H), 3.57 (s, 3H), 3.35-3.22 (m, 3H), 3.13 (dd, J = 8.8, 6.4 Hz, 1H), 2.40 (s, 4H), 2.11 (tdd, J = 13.8, 6.6, 4.1 Hz, 1H), 1.83 (dp, J = 13.2, 6.6 Hz, 1H), 1.71-1.58 (m, 2H), 1.38 (d, J = 6.4 Hz, 3H), 1.36-1.24 (m, | ¹³C NMR (CDCl₃) δ 172.48, 168.85, 162.37, 159.42, 146.69, 141.39, 137.47, 109.80, 85.57, 84.10, 75.89, 72.79, 61.33, 56.27, 51.33, 33.62, 28.83, 27.83, 20.73, 19.47, 18.22, 17.75 |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 1H), 0.93 (d, J = 3.4 Hz, 3H), 0.91 (d, J = 3.4 Hz, 3H), 0.87 (d, J = 7.4 Hz, 1H) | |
| F258 | White Foam | — | — | HRMS-ESI (m/z) [M + H]$^+$ calcd for C$_{25}$H$_{31}$N$_2$O$_8$, 487.2075; found, 487.2095 | $^1$H NMR (CDCl$_3$) δ 8.52 (d, J = 6.9 Hz, 1H), 8.32 (d, J = 5.4 Hz, 1H), 7.31-7.25 (m, 2H), 7.01-6.93 (m, 4H), 4.88 (dq, J = 9.6, 6.4 Hz, 1H), 4.64 (dt, J = 10.7, 7.6 Hz, 1H), 4.38-4.31 (m, 1H), 3.89 (s, 3H), 3.55 (s, 3H), 3.54-3.50 (m, 1H), 2.40 (s, 3H), 2.39-2.30 (m, 1H), 2.22-2.09 (m, 1H), 1.86-1.74 (m, 1H), 1.62 (dq, J = 15.3, 7.8 Hz, 1H), 1.44 (d, J = 6.4 Hz, 3H), 1.35-1.21 (m, 1H), 1.04 (dd, J = 16.1, 7.8 Hz, 1H) | $^{13}$C NMR (CDCl$_3$) δ 172.41, 168.88, 162.43, 159.45, 157.63, 146.71, 141.34, 137.51, 129.54, 121.33, 116.65, 109.84, 85.07, 83.05, 72.56, 61.42, 56.30, 51.29, 33.50, 28.39, 20.75, 18.24, 17.80 |
| F259 | White Foam | — | — | HRMS-ESI (m/z) [M + H]$^+$ calcd for C$_{25}$H$_{39}$N$_2$O$_9$, 511.2681; found, 511.2650 | $^1$H NMR (CDCl$_3$) δ 8.49 (s, 1H), 8.33 (d, J = 5.5 Hz, 1H), 7.00 (d, J = 5.5 Hz, 1H), 4.76 (dq, J = 9.4, 6.4 Hz, 1H), 4.58 (dt, J = 10.7, 7.8 Hz, 1H), 3.90 (s, 3H), 3.81 (t, J = 6.6 Hz, 2H), 3.57 (s, 3H), 3.41 (s, 3H), 3.35-3.23 (m, 3H), 3.13 (dd, J = 8.8, 6.4 Hz, 1H), 2.99 (t, J = 6.6 Hz, 2H), 2.34 (dt, J = 13.8, 6.6 Hz, 1H), 2.19-2.02 (m, 1H) 1.83 (dp, J = 13.2, 6.6 Hz, 1H), 1.70-1.61 (m, 2H), 1.38 (d, J = 6.4 Hz, 3H), 1.36-1.24 (m, 1H), 0.93 (d, J = 3.4 Hz, 3H), 0.91 (d, J = 3.4 Hz, 3H), 0.87 (d, J = 7.4 Hz, 1H) | $^{13}$C NMR (CDCl$_3$) δ 172.51, 169.44, 162.33, 159.43, 146.74, 141.43, 137.32, 109.77, 85.57, 84.11, 75.89, 72.79, 67.57, 61.37, 58.80, 56.32, 51.31, 34.61, 33.63, 28.83, 27.79, 19.48, 18.22, 17.76 |
| F260 | White Foam | — | — | HRMS-ESI (m/z) [M + H]$^+$ calcd for C$_{27}$H$_{35}$N$_2$O$_9$, 531.2350; found, 531.2337 | $^1$H NMR (CDCl$_3$) δ 8.50 (s, 1H), 8.33 (d, J = 5.4 Hz, 1H), 7.30-7.26 (m, 2H), 7.02-6.91 (m, 4H), 4.88 (dq, J = 9.7, 6.4 Hz, 1H), 4.64 (dt, J = 10.6, 7.8 Hz, 1H), 4.35 (t, J = 5.5 Hz, 1H), 3.90 (s, 3H), 3.81 (t, J = 6.6 Hz, 2H), 3.55 (s, 4H), 3.41 (s, 3H), 2.99 (t, J = 6.6 Hz, 2H), 2.34 (dt, J = 13.7, 7.1 Hz, 1H), 2.23-2.09 (m, 1H), 1.85-1.74 (m, 1H), 1.60 (dd, J = 15.4, 8.5 Hz, 1H), 1.44 (d, J = 6.4 Hz, 3H), 1.28 (q, J = 11.3 Hz, 1H), 1.04 (dd, J = 16.1, 7.8 Hz, 1H) | $^{13}$C NMR (CDCl$_3$) δ 172.42, 169.44, 162.37, 159.44, 157.60, 146.75, 141.36, 137.34, 129.53, 121.33, 116.65, 109.81, 85.04, 83.05, 72.54, 67.57, 61.43, 58.80, 56.32, 51.25, 34.61, 33.48, 28.33, 18.22, 17.78 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| F261 | White Solid | — | IR (Thin Film) 3449, 2950, 2900, 1743, 1713, 1504, 1203 | HRMS-ESI (m/z) [M]⁺ calcd for $C_{18}H_{26}FNO_4$, 339.1846; found, 339.1851 | — | ¹⁹F NMR (CDCl₃) δ −122.90 |
| F262 | Fluffy White Solid | — | — | HRMS-ESI (m/z) [M]⁺ calcd for $C_{25}H_{31}FN_2O_7$, 490.2115; found, 490.2114 | 1H NMR (CDCl₃) δ 12.06 (d, J = 0.6 Hz, 1H), 8.48 (dd, J = 8.1, 4.4 Hz, 1H), 7.98 (dd, J = 5.2, 4.4 Hz, 1H), 7.10-6.83 (m, 5H), 5.02 (dq, J = 9.6, 6.4 Hz, 1H), 4.62 (ddd, J = 10.8, 8.0, 7.2 Hz, 1H), 4.35-4.22 (m, 1H), 3.93 (s, 3H), 3.55 (ddd, J = 7.3, 5.3, 1.8 Hz, 1H), 3.46 (dt, J = 9.0, 6.6 Hz, 1H), 3.23 (dt, J = 9.0, 6.5 Hz, 1H), 2.47-2.31 (m, 1H), 2.29-2.09 (m, 1H), 1.87-1.68 (m, 2H), 1.58-1.39 (m, 3H), 1.37 (d, J = 6.4 Hz, 3H), 1.04 (ddt, J = 16.1, 6.6, 2.0 Hz, 1H), 0.79 (t, J = 7.4 Hz, 3H) | ¹⁹F NMR (CDCl₃) δ −123.15 |
| F263 | White Solid | — | — | ESIMS m/z 340 ([M + H]⁺) | — | — |
| F264 | White Solid | — | — | HRMS-ESI (m/z) [M]⁺ calcd for $C_{25}H_{31}FN_2O_7$, 490.2116; found, 490.2115 | ¹H NMR (CDCl₃) δ 12.05 (d, J = 0.6 Hz, 1H), 8.46 (d, J = 8.2 Hz, 1H), 7.98 (d, J = 5.2 Hz, 1H), 7.02-6.83 (m, 5H), 4.91 (dq, J = 9.6, 6.4 Hz, 1H), 4.63 (ddd, J = 10.8, 8.2, 7.2 Hz, 1H), 4.26 (ddd, J = 7.1, 5.2, 1.8 Hz, 1H), 3.94 (s, 3H), 3.72 (dt, J = 9.0, 6.5 Hz, 1H), 3.66-3.55 (m, 2H), 2.37 (ddd, J = 12.7, 7.6, 6.4 Hz, 1H), 2.20-2.02 (m, 1H), 1.89-1.75 (m, 1H), 1.74-1.59 (m, 1H), 1.61-1.44 (m, 5H), 1.43-1.27 (m, 1H), 1.04 (ddt, J = 16.1, 7.8, 1.8 Hz, 1H), 0.85 (t, J = 7.4 Hz, 3H) | ¹³C NMR (CDCl₃) δ 171.93, 168.69, 158.77, 155.36, 153.76 (d, J = 2.5 Hz), 148.73, 140.55, 130.33, 118.01 (d, J = 7.9 Hz), 115.89 (d, J = 22.9 Hz), 109.50, 84.31, 83.33, 75.69, 73.01, 56.08, 51.21, 33.22, 28.24, 23.45, 18.19, 17.88, 10.61 |
| F265 | Colorless Semi Solid | — | — | HRMS-ESI (m/z) [M]⁺calcd for $C_{28}H_{35}FN_2O_9$, 562.2327; found, 562.2330 | ¹H NMR (CDCl₃) δ 8.33 (d, J = 8.0 Hz, 1H), 8.28 (d, J = 5.3 Hz, 1H), 7.09-6.85 (m, 5H), 5.74 (s, 2H), 5.00 (dq, J = 9.7, 6.4 Hz, 1H), 4.64 (dq, J = 10.8, 7.9 Hz, 1H), 4.29 (dd, J = 9.6, 7.3 Hz, 1H), 3.91 (s, 3H), 3.54 (ddd, J = 7.2, 5.3, 1.8 Hz, 1H), 3.46 (dt, J = 9.0, 6.6 Hz, 1H), 3.22 (dt, J = 8.9, 6.4 Hz, | ¹⁹F NMR (CDCl₃) δ −123.28 |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | | 1H), 2.42 (dtd, J = 13.5, 6.8, 6.2, 2.0 Hz, 1H), 2.20 (dddd, J = 15.9, 10.3, 8.4, 5.4 Hz, 1H), 2.07 (s, 3H), 1.82-1.69 (m, 2H), 1.48-1.38 (m, 3H), 1.35 (d, J = 6.4 Hz, 3H), 1.09-0.97 (m, 1H), 0.78 (t, J = 7.4 Hz, 3H) | |
| F266 | Colorless Semi Solid | — | — | HRMS-ESI (m/z) [M]$^+$ calcd for C$_{27}$H$_{33}$FN$_2$O$_8$, 532.2221; found, 532.2227 | $^1$H NMR (CDCl$_3$) δ 8.53 (d, J = 8.4 Hz, 1H), 8.33 (dd, J = 5.5, 4.3 Hz, 1H), 7.09-6.84 (m, 5H), 4.99 (dq, J = 9.6, 6.4 Hz, 1H), 4.62 (ddd, J = 10.7, 8.4, 7.2 Hz, 1H), 4.27 (dd, J = 9.6, 7.3 Hz, 1H), 3.91 (s, 3H), 3.53 (ddd, J = 7.1, 5.3, 1.8 Hz, 1H), 3.45 (dt, J = 9.0, 6.6 Hz, 1H), 3.22 (dt, J = 9.0, 6.5 Hz, 1H), 2.40 (s, 3H), 2.45-2.32 (m, 1H), 2.26-2.11 (m, 1H), 1.79-1.61 (m, 2H), 1.49-1.39 (m, 2H), 1.41-1.30 (m, 1H), 1.34 (d, J = 6.4 Hz, 3H), 1.08-0.96 (m, 1H), 0.78 (t, J = 7.4 Hz, 3H) | $^{19}$F NMR (CDCl$_3$) δ −123.29 |
| F267 | White Solid | — | — | HRMS-ESI (m/z) [M]+calcd for C$_{28}$H$_{35}$FN$_2$O$_9$, 562.2327; found, 562.2335 | $^1$H NMR (600 MHz, CDCl$_3$) δ 8.31 (d, J = 8.0 Hz, 1H), 8.27 (d, J = 5.4 Hz, 1H), 6.99-6.92 (m, 3H), 6.92-6.85 (m, 2H), 5.74 (s, 2H), 4.89 (dq, J = 9.6, 6.4 Hz, 1H), 4.65 (dt, J = 10.7, 7.6 Hz, 1H), 4.25 (ddd, J = 7.2, 5.3, 1.8 Hz, 1H), 3.91 (s, 3H), 3.72 (dt, J = 9.0, 6.5 Hz, 1H), 3.64-3.54 (m, 2H), 2.42-2.34 (m, 1H), 2.15-2.08 (m, 1H), 2.07 (s, 3H), 1.81 (dddd, J = 15.1, 11.9, 7.7, 1.6 Hz, 1H), 1.70-1.60 (m, 1H), 1.57-1.47 (m, 2H), 1.45 (d, J = 6.4 Hz, 3H), 1.31 (dddd, J = 13.4, 12.0, 10.7, 1.4 Hz, 1H), 1.04 (ddt, J = 16.4, 8.0, 1.8 Hz, 1H), 0.84 (t, J = 7.4 Hz, 3H) | $^{19}$F NMR (CDCl$_3$) δ −122.93 |
| F268 | White Solid | — | — | ESIMS m/z 352 ([M + H]$^+$) | — | — |
| F269 | White Solid | — | — | ESIMS m/z 340 ([M + H]$^+$) | — | — |
| F270 | White Solid | — | — | HRMS-ESI (m/z) [M]+calcd for C$_{26}$H$_{34}$N$_2$O$_8$, 502.2315; found, 502.2317 | $^1$H NMR (600 MHz, CDCl$_3$) δ 12.06 (d, J = 0.7 Hz, 1H), 8.48 (d, J = 8.2 Hz, 1H), 7.99 (d, J = 5.2 Hz, 1H), 7.06-7.00 (m, 2H), 6.93-6.84 (m, 1H), | $^{13}$C NMR (151 MHz, CDCl$_3$) δ 171.99, 168.68, 155.37, 154.24, 154.00, |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 6.85-6.78 (m, 2H), 5.01 (dq, J = 9.6, 6.4 Hz, 1H), 4.66-4.57 (m, 1H), 4.27 (dd, J = 9.6, 7.3 Hz, 1H), 3.94 (s, 3H), 3.78 (s, 3H), 3.55 (ddd, J = 7.2, 5.2, 1.7 Hz, 1H), 3.46 (dt, J = 9.0, 6.6 Hz, 1H), 3.27 (dt, J = 9.0, 6.5 Hz, 1H), 2.45-2.35 (m, 1H), 2.21 (dddd, J = 15.7, 10.1, 8.3, 5.2 Hz, 1H), 1.76 (dddd, J = 14.8, 10.4, 7.2, 4.9 Hz, 2H), 1.51-1.40 (m, 3H), 1.38 (d, J = 6.4 Hz, 3H), 1.04 (ddt, J = 16.1, 7.4, 1.9 Hz, 1H), 0.81 (t, J = 7.4 Hz, 3H) | 148.74, 140.54, 130.37, 117.63, 114.44, 109.50, 84.08, 83.02, 72.94, 71.36, 56.08, 55.69, 51.30, 33.37, 28.03, 23.20, 18.30, 18.19, 10.60 |
| F271 | White Solid | — | — | HRMS-ESI (m/z) [M]⁺ calcd for $C_{25}H_{31}FN_2O_7$, 490.2115; found, 490.2123 | ¹H NMR (600 MHz, CDCl₃) δ 12.05 (s, 1H), 8.47 (d, J = 8.1 Hz, 1H), 8.00 (d, J = 5.2 Hz, 1H), 7.21 (td, J = 8.4, 6.8 Hz, 1H), 6.89-6.82 (m, 3H), 6.67 (tdd, J = 8.2, 2.3, 0.9 Hz, 1H), 5.03 (dq, J = 9.6, 6.4 Hz, 1H), 4.62 (dt, J = 10.8, 7.7 Hz, 1H), 4.38 (dd, J = 9.6, 7.3 Hz, 1H), 3.94 (s, 3H), 3.55 (ddd, J = 7.3, 5.2, 1.7 Hz, 1H), 3.46 (dt, J = 9.0, 6.6 Hz, 1H), 3.22 (dt, J = 9.0, 6.4 Hz, 1H), 2.46-2.37 (m, 1H), 2.21 (dddd, J = 15.8, 10.1, 8.2, 5.2 Hz, 1H), 1.76 (dddd, J = 18.3, 12.9, 7.9, 3.7 Hz, 2H), 1.49-1.40 (m, 3H), 1.36 (d, J = 6.4 Hz, 3H), 1.05 (ddt, J = 16.1, 7.4, 1.9 Hz, 1H), 0.78 (t, J = 7.4 Hz, 3H) | ¹⁹F NMR (CDCl₃) δ -111.78 |
| F272 | White Solid | — | — | HRMS-ESI (m/z) [M]⁺ calcd for $C_{25}H_{31}ClN_2O_7$, 506.1820; found, 506.1825 | ¹H NMR (600 MHz, CDCl₃) δ 12.05 (d, J = 0.7 Hz, 1H), 8.47 (d, J = 8.0 Hz, 1H), 7.99 (d, J = 5.2 Hz, 1H), 7.19 (t, J = 8.1 Hz, 1H), 7.14 (t, J = 2.2 Hz, 1H), 6.99-6.91 (m, 2H), 6.87 (d, J = 5.2 Hz, 1H), 5.03 (dq, J = 9.6, 6.4 Hz, 1H), 4.62 (dt, J = 10.8, 7.6 Hz, 1H), 4.37 (dd, J = 9.6, 7.2 Hz, 1H), 3.94 (s, 3H), 3.55 (ddd, J = 7.2, 5.2, 1.8 Hz, 1H), 3.46 (dt, J = 9.0, 6.6 Hz, 1H), 3.21 (dt, J = 9.0, 6.4 Hz, 1H), 2.46-2.36 (m, 1H), 2.21 (dddd, J = 15.8, 10.2, 8.3, 5.2 Hz, 1H), 1.84-1.64 (m, 2H), 1.49-1.42 (m, 3H), 1.36 (d, J = 6.4 Hz, 3H), 1.05 (ddt, J = 16.2, 7.6, 2.0 Hz, | ¹³C NMR (151 MHz, CDCl₃) δ 171.95, 168.69, 160.39, 155.38, 148.76, 140.55, 134.69, 130.35, 130.09, 121.59, 117.06, 114.74, 109.51, 83.28, 82.89, 72.50, 71.26, 56.09, 51.29, 33.32, 27.91, 23.15, 18.29, 18.07, 10.56 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 1H), 0.79 (t, J = 7.4 Hz, 3H) | |
| F273 | White Solid | — | — | HRMS-ESI (m/z) [M]⁺ calcd for $C_{25}H_{31}BrN_2O_7$, 550.1315; found, 550.1320 | ¹H NMR (600 MHz, CDCl₃) δ 12.04 (d, J = 0.7 Hz, 1H), 8.47 (d, J = 8.1 Hz, 1H), 7.99 (d, J = 5.2 Hz, 1H), 7.39-7.33 (m, 2H), 7.01-6.95 (m, 2H), 6.87 (d, J = 5.2 Hz, 1H), 5.02 (dq, J = 9.5, 6.4 Hz, 1H), 4.67-4.58 (m, 1H), 4.34 (dd, J = 9.6, 7.3 Hz, 1H), 3.94 (s, 3H), 3.55 (ddd, J = 7.3, 5.2, 1.8 Hz, 1H), 3.45 (dt, J = 9.1, 6.6 Hz, 1H), 3.22 (dt, J = 9.0, 6.5 Hz, 1H), 2.45-2.36 (m, 1H), 2.21 (dddd, J = 15.8, 10.1, 8.4, 5.3 Hz, 1H), 1.75 (ttd, J = 15.3, 7.2, 5.3 Hz, 2H), 1.51-1.38 (m, 3H), 1.34 (d, J = 6.4 Hz, 3H), 1.04 (ddt, J = 16.2, 7.2, 2.0 Hz, 1H), 0.78 (t, J = 7.4 Hz, 3H) | ¹³C NMR (151 MHz, CDCl₃) δ 171.94, 168.69, 158.88, 155.38, 148.76, 140.55, 132.19, 130.35, 118.27, 113.52, 109.52, 83.35, 82.88, 72.56, 71.30, 56.09, 51.28, 33.32, 27.95, 23.16, 18.28, 18.07, 10.57 |
| F274 | Colorless Semi Solid | — | — | HRMS-ESI (m/z) [M]⁺ calcd for $C_{28}H_{36}N_2O_9$, 544.2421; found, 544.2427 | ¹H NMR (600 MHz, CDCl₃) δ 8.53 (s, 1H), 8.33 (d, J = 5.4 Hz, 1H), 7.06-7.01 (m, 2H), 7.00 (d, J = 5.5 Hz, 1H), 6.85-6.78 (m, 2H), 4.98 (dq, J = 9.5, 6.4 Hz, 1H), 4.67-4.58 (m, 1H), 4.25 (dd, J = 9.6, 7.3 Hz, 1H), 3.90 (s, 3H), 3.77 (s, 3H), 3.54 (ddd, J = 7.2, 5.3, 1.8 Hz, 1H), 3.45 (dt, J = 9.1, 6.7 Hz, 1H), 3.26 (dt, J = 9.1, 6.5 Hz, 1H), 2.39 (s, 3H), 2.39-2.34 (m, 1H), 2.23-2.13 (m, 1H), 1.78-1.66 (m, 2H), 1.51-1.40 (m, 2H), 1.35 (d, J = 6.4 Hz, 3H), 1.38-1.31 (m, 1H), 1.02 (ddt, J = 16.3, 7.7, 2.0 Hz, 1H), 0.80 (t, J = 7.4 Hz, 3H) 7.4 Hz, 3H) | ¹³C NMR (151 MHz, CDCl₃) δ 172.49, 168.90, 162.41, 159.45, 154.21, 154.04, 146.70, 141.40, 137.51, 117.64, 114.43, 109.82, 84.14, 83.10, 72.68, 71.34, 56.29, 55.69, 51.36, 33.67, 28.12, 23.19, 20.75, 18.34, 18.17, 10.59 |
| F275 | Light Yellow Semi Solid | — | — | HRMS-ESI (m/z) [M]⁺ calcd for $C_{27}H_{33}FN_2O_8$, 532.2221; found, 532.2231 | ¹H NMR (600 MHz, CDCl₃) δ 8.53 (s, 1H), 8.34 (d, J = 5.4 Hz, 1H), 7.24-7.16 (m, 1H), 7.01 (d, J = 5.5 Hz, 1H), 6.88-6.80 (m, 2H), 6.66 (tdd, J = 8.3, 2.4, 0.9 Hz, 1H), 5.00 (dq, J = 9.5, 6.4 Hz, 1H), 4.63 (ddd, J = 10.7, 8.4, 7.3 Hz, 1H), 4.38-4.31 (m, 1H), 3.91 (s, 3H), 3.53 (ddd, J = 7.2, 5.3, 1.9 Hz, 1H), 3.45 (dt, J = 9.0, 6.5 Hz, 1H), 3.21 (dt, J = 9.0, 6.5 Hz, 1H), 2.44-2.40 (m, 1H), 2.40 (s, 3H), | ¹⁹F NMR (CDCl₃) δ −111.83 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| | | | | | 2.24-2.12 (m, 1H), 1.79-1.67 (m, 2H), 1.49-1.28 (m, 3H), 1.33 (dd, J = 6.5, 4.6 Hz, 3H), 1.03 (ddt, J = 16.2, 7.7, 2.0 Hz, 1H), 0.77 (t, J = 7.4 Hz, 3H) | |
| F276 | White Solid | — | — | ESIMS m/z 356 ([M + H]⁺) | — | — |
| F277 | White Solid | — | — | ESIMS m/z 400 ([M + H]⁺) | — | — |
| F278 | White Solid | — | — | ESIMS m/z 340 ([M + H]⁺) | — | — |
| F279 | White Solid | — | — | ESIMS m/z 350 ([M + H]⁺) | — | — |
| F280 | White Solid | — | — | HRMS-ESI (m/z) [M]⁺ calcd for C$_{25}$H$_{31}$FN$_2$O$_7$, 490.2115; found, 490.2124 | ¹H NMR (600 MHz, CDCl$_3$) δ 12.05 (d, J = 0.7 Hz, 1H), 8.47 (d, J = 8.2 Hz, 1H), 7.99 (d, J = 5.2 Hz, 1H), 7.25-7.17 (m, 1H), 6.89-6.83 (m, 1H), 6.75-6.62 (m, 3H), 4.92 (dq, J = 9.6, 6.3 Hz, 1H), 4.68-4.60 (m, 1H), 4.35 (ddd, J = 7.2, 5.3, 1.8 Hz, 1H), 3.94 (s, 3H), 3.73-3.53 (m, 3H), 2.42-2.33 (m, 1H), 2.18 (dddd, J = 15.8, 10.1, 7.9, 5.3 Hz, 1H), 1.87-1.74 (m, 1H), 1.71-1.61 (m, 1H), 1.56-1.47 (m, 2H), 1.47 (d, J = 6.4 Hz, 3H), 1.43-1.31 (m, 1H), 1.09 (ddt, J = 16.3, 8.0, 1.8 Hz, 1H), 0.82 (t, J = 7.4 Hz, 3H) | ¹⁹F NMR (CDCl$_3$) δ −111.63 |
| F281 | White Solid | — | — | HRMS-ESI (m/z) [M]⁺ calcd for C$_{27}$H$_{36}$N$_2$O$_7$, 500.2523; found, 500.2533 | ¹H NMR (600 MHz, CDCl$_3$) δ 12.07 (d, J = 0.7 Hz, 1H), 8.46 (d, J = 8.2 Hz, 1H), 7.98 (d, J = 5.2 Hz, 1H), 6.86 (d, J = 5.2 Hz, 1H), 6.63-6.55 (m, 3H), 4.91 (dq, J = 9.6, 6.4 Hz, 1H), 4.63 (dt, J = 10.7, 7.7 Hz, 1H), 4.35 (ddd, J = 7.1, 5.2, 1.7 Hz, 1H), 3.94 (s, 3H), 3.74 (dt, J = 9.0, 6.5 Hz, 1H), 3.66-3.55 (m, 2H), 2.40-2.32 (m, 1H), 2.27 (s, 6H), 2.23-2.13 (m, 1H), 1.86-1.77 (m, 1H), 1.71-1.60 (m, 1H), 1.59-1.47 (m, 2H), 1.47 (d, J = 6.4 Hz, 3H), 1.39-1.29 (m, 1H), 1.01 (ddt, J = 16.4, 8.2, 1.7 Hz, 1H), 0.85 (t, J = 7.4 Hz, 3H) | ¹³C NMR (151 MHz, CDCl$_3$) δ 171.96, 168.69, 157.61, 155.36, 148.74, 140.53, 139.22, 130.38, 123.15, 114.49, 109.49, 83.32, 83.10, 75.57, 73.09, 56.08, 51.24, 33.26, 28.13, 23.46, 21.42, 18.18, 17.94, 10.63 |
| F282 | White Solid | — | — | HRMS-ESI (m/z) [M]⁺ calcd for C$_{29}$H$_{38}$N$_2$O$_8$, | ¹H NMR (600 MHz, CDCl$_3$) δ 8.53-8.50 (m, 1H), 8.32 (d, J = 5.4 Hz, 1H), 6.99 (d, J = 5.5 Hz, 1H), | ¹³C NMR (151 MHz, CDCl$_3$) δ 172.45, 168.89, 162.42, |

TABLE 2-continued

Analytical Data for F Series Compounds

| *Cmpd. No. | *Phys. Apps. | *MP | *IR | *Mass. Spec. | *$^1$H NMR | *$^{13}$C NMR; *$^{19}$F NMR |
|---|---|---|---|---|---|---|
| | | | | 542.2628; found, 542.2632 | 6.62-6.55 (m, 3H), 4.88 (dq, J = 9.5, 6.4 Hz, 1H), 4.64 (ddd, J = 10.7, 8.5, 7.4 Hz, 1H), 4.33 (ddd, J = 7.2, 5.3, 1.8 Hz, 1H), 3.89 (s, 3H), 3.74 (dt, J = 9.0, 6.5 Hz, 1H), 3.64-3.54 (m, 2H), 2.40 (s, 3H), 2.34 (dt, J = 13.8, 7.1 Hz, 1H), 2.27 (s, 6H), 2.22-2.10 (m, 1H), 1.82-1.73 (m, 1H), 1.67-1.57 (m, 1H), 1.58-1.45 (m, 2H), 1.44 (d, J = 6.4 Hz, 3H), 1.32-1.22 (m, 1H), 1.00 (ddt, J = 16.3, 8.1, 1.7 Hz, 1H), 0.85 (t, J = 7.4 Hz, 3H) | 159.45, 157.66, 146.70, 141.38, 139.19, 137.51, 123.10, 114.51, 109.82, 83.36, 83.22, 75.55, 72.82, 56.29, 51.29, 33.56, 28.22, 23.47, 21.41, 20.75, 18.22, 17.92, 10.62 |
| F283 | White Solid | — | — | HRMS-ESI (m/z) [M]$^+$ calcd for C$_{31}$H$_{36}$N$_2$O$_7$, 548.2523; found, 548.2520 | $^1$H NMR (600 MHz, CDCl$_3$) δ 12.06 (d, J = 0.6 Hz, 1H), 8.49 (d, J = 8.1 Hz, 1H), 8.03-7.97 (m, 1H), 7.59-7.54 (m, 2H), 7.54-7.48 (m, 2H), 7.45-7.38 (m, 2H), 7.34-7.28 (m, 1H), 7.18-7.11 (m, 2H), 6.89-6.84 (m, 1H), 5.06 (dq, J = 9.6, 6.4 Hz, 1H), 4.64 (dt, J = 10.8, 7.7 Hz, 1H), 4.48-4.39 (m, 1H), 3.94 (s, 3H), 3.63-3.54 (m, 1H), 3.47 (dt, J = 9.0, 6.6 Hz, 1H), 3.27 (dt, J = 9.0, 6.5 Hz, 1H), 2.47-2.35 (m, 1H), 2.23 (dddd, J = 15.8, 10.4, 8.2, 5.3 Hz, 1H), 1.81-1.71 (m, 2H), 1.52-1.42 (m, 3H), 1.40 (d, J = 6.4 Hz, 3H), 1.08 (ddt, J = 16.2, 7.9, 2.0 Hz, 1H), 0.79 (t, J = 7.4 Hz, 3H) | $^{13}$C NMR (151 MHz, CDCl$_3$) δ 172.00, 168.69, 159.28, 155.38, 148.76, 140.78, 140.54, 134.42, 130.38, 128.70, 128.05, 126.76, 126.70, 116.74, 109.50, 83.09, 82.99, 72.83, 71.44, 56.09, 51.32, 33.39, 28.13, 23.19, 18.34, 18.15, 10.58 |
| F284 | White Solid | — | — | HRMS-ESI (m/z) [M]$^+$ calcd for C$_{27}$H$_{33}$FN$_2$O$_8$, 532.2221; found, 532.2230 | $^1$H NMR (CDCl$_3$) δ 8.53 (d, J = 8.3 Hz, 1H), 8.33 (d, J = 5.4 Hz, 1H), 7.26-7.14 (m, 1H), 7.00 (d, J = 5.5 Hz, 1H), 6.75-6.60 (m, 3H), 4.90 (dq, J = 9.6, 6.4 Hz, 1H), 4.64 (ddd, J = 10.7, 8.4, 7.3 Hz, 1H), 4.34 (ddd, J = 7.2, 5.3, 1.8 Hz, 1H), 3.90 (s, 3H), 3.73-3.50 (m, 3H), 2.40 (s, 3H), 2.39-2.30 (m, 1H), 2.20-2.08 (m, 1H), 1.85-1.71 (m, 1H), 1.69-1.56 (m, 1H), 1.54-1.45 (m, 2H), 1.44 (d, J = 6.4 Hz, 3H), 1.37-1.22 (m, 1H), 1.07 (ddt, J = 16.3, 7.9, 2.0 Hz, 1H), 0.82 (t, J = 7.4 Hz, 3H) | $^{19}$F NMR (CDCl$_3$) δ −111.69 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| F285 | White Solid | — | — | HRMS-ESI (m/z) [M]⁺ calcd for $C_{27}H_{33}BrN_2O_8$, 592.1427; found, 592.1420 | ¹H NMR (600 MHz, CDCl₃) δ 8.53 (s, 1H), 8.33 (d, J = 5.5 Hz, 1H), 7.39-7.31 (m, 2H), 7.00 (d, J = 5.4 Hz, 1H), 6.99-6.96 (m, 2H), 4.99 (dq, J = 9.5, 6.4 Hz, 1H), 4.62 (ddd, J = 10.7, 8.3, 7.3 Hz, 1H), 4.35-4.27 (m, 1H), 3.90 (s, 3H), 3.53 (ddd, J = 7.3, 5.3, 1.8 Hz, 1H), 3.44 (dt, J = 9.0, 6.6 Hz, 1H), 3.20 (dt, J = 9.1, 6.5 Hz, 1H), 2.39 (s, 3H), 2.43-2.31 (m, 1H), 2.23-2.09 (m, 1H), 1.71 (qdt, J = 12.6, 5.6, 3.2 Hz, 2H), 1.48-1.33 (m, 3H), 1.32 (d, J = 6.3 Hz, 3H), 1.03 (ddt, J = 16.2, 7.4, 2.0 Hz, 1H), 0.77 (t, J = 7.4 Hz, 3H) | ¹³C NMR (151 MHz, CDCl₃) δ 172.43, 168.89, 162.41, 159.46, 158.91, 146.69, 141.35, 137.53, 132.16, 118.29, 113.46, 109.85, 83.40, 82.94, 72.29, 71.27, 56.30, 51.33, 33.60, 28.04, 23.14, 20.75, 18.31, 18.04, 10.56 |
| F286 | White Solid | — | — | HRMS-ESI (m/z) [M]⁺ calcd for $C_{27}H_{33}ClN_2O_8$, 548.1925; found, 548.1924 | ¹H NMR (CDCl₃) δ 8.53 (d, J = 8.5 Hz, 1H), 8.38-8.30 (m, 1H), 7.18 (t, J = 8.1 Hz, 1H), 7.13 (t, J = 2.2 Hz, 1H), 7.01 (d, J = 5.5 Hz, 1H), 6.95 (dddd, J = 9.8, 7.9, 2.2, 0.9 Hz, 2H), 5.00 (dq, J = 9.7, 6.4 Hz, 1H), 4.70-4.57 (m, 1H), 4.35 (dd, J = 9.7, 7.2 Hz, 1H), 3.91 (s, 3H), 3.59-3.50 (m, 1H), 3.50-3.40 (m, 1H), 3.20 (dt, J = 8.9, 6.5 Hz, 1H), 2.45-2.30 (m, 1H), 2.40 (s, 3H), 2.26-2.11 (m 1H), 1.81-1.65 (m, 2H), 1.53-1.36 (m, 3H), 1.35-1.28 (m, 3H), 1.09-0.96 (m, 1H), 0.78 (t, J = 7.4 Hz, 3H) | ¹³C NMR (CDCl₃) δ 172.45, 168.90, 162.41, 160.42, 159.46, 146.70, 141.37, 137.53, 134.66, 130.07, 121.53, 117.09, 114.72, 109.83, 83.34, 82.97, 72.23, 71.24, 56.30, 51.34, 33.61, 28.01, 23.14, 20.75, 18.32, 18.05, 10.55 |
| F287 | White Solid | — | — | ESIMS m/z 590 ([M − H]⁻) | ¹H NMR (CDCl₃) δ 8.58-8.45 (m, 1H), 8.34 (dd, J = 5.5, 1.4 Hz, 7.60-7.48 1H), (m, 4H), 7.41 (td, J = 8.6, 8.0, 2.0 Hz, 2H), 7.30 (tt, J = 6.8, 1.4 Hz, 1H), 7.19-7.11 (m, 2H), 7.04-6.96 (m, 1H), 5.03 (dq, J = 10.1, 6.4 Hz, 1H), 4.64 (dt, J = 11.1, 7.8 Hz, 1H), 4.43 (dd, J = 9.7, 7.1 Hz, 1H), 3.90 (d, J = 1.4 Hz, 3H), 3.64-3.51 (m, 1H), 3.46 (dt, J = 9.5, 6.6 Hz, 1H), 3.26 (dt, J = 9.4, 6.6 Hz, 1H), 2.40 (s, 3H), 2.43-2.31 (m, 1H), 2.25-2.13 (m, 2H), 1.84-1.67 (m, 2H), 1.48-1.40 (m, 2H), 1.37 (d, J = 6.0 Hz, 3H), | ¹³C NMR (CDCl₃) δ 172.51, 168.91, 162.42, 159.46, 159.32, 146.71, 141.40, 140.80, 137.53, 134.37, 128.70, 128.03, 126.76, 126.68, 116.76, 109.83, 83.16, 83.07, 72.56, 71.41, 56.30, 51.38, 33.67, 28.21, 23.18, 20.76, 18.38, 18.13, 10.57 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| F288 | White Solid | — | — | ESIMS m/z 513.5 ([M + H]⁺) | ¹H NMR (CDCl₃) δ 12.06 (d, J = 0.7 Hz, 1H), 8.48 (d, J = 8.1 Hz, 1H), 8.00 (d, J = 5.2 Hz, 1H), 7.44-7.31 (m, 2H), 7.07-7.00 (m, 2H), 6.93-6.83 (m, 1H), 5.30 (dd, J = 1.6, 0.8 Hz, 1H), 5.09-4.97 (m, 2H), 4.62 (dt, J = 10.8, 7.6 Hz, 1H), 4.48-4.34 (m, 1H), 3.94 (s, 3H), 3.57 (ddd, J = 7.1, 5.3, 1.8 Hz, 1H), 3.45 (dt, J = 9.1, 6.6 Hz, 1H), 3.26 (dt, J = 9.1, 6.5 Hz, 1H), 2.42 (ddd, J = 14.8, 7.2, 5.3 Hz, 1H), 2.29-2.15 (m, 1H) 2.15-2.11 (m, 3H), 1.87-1.71 (m, 2H), 1.52-1.41 (m, 3H), 1.36 (d, J = 6.4 Hz, 3H), 1.11-1.00 (m, 1H), 0.78 (t, J = 7.4 Hz, 3H) | ¹³C NMR (CDCl₃) δ 171.99, 168.68, 159.21, 155.38, 148.75, 142.53, 140.54, 134.37, 130.37, 126.49, 116.08, 110.81, 109.50, 83.03, 82.91, 72.83, 71.43, 56.09, 51.31, 33.38, 28.12, 23.18, 21.90, 18.32, 18.11, 10.57 |
| F289 | White Solid | — | — | ESIMS m/z 555.6 ([M + H]⁺) | ¹H NMR (CDCl₃) δ 8.54 (d, J = 7.9 Hz, 1H), 8.34 (d, J = 5.4 Hz, 1H), 7.53-7.31 (m, 2H), 7.13-6.93 (m, 3H) 5.30 (dd, J = 1.6, 0.9 Hz, 1H), 5.19-4.94 (m, 2H), 4.78-4.57 (m, 1H), 4.48-4.19 (m, 1H), 3.90 (s, 3H), 3.65-3.37 (m, 2H), 3.30-3.17 (m, 1H), 2.40 (s, 3H), 2.45-2.31 (m, 1H), 2.23-2.14 (m, 1H), 2.14-2.05 (m, 3H), 1.71 (ddd, J = 17.7, 9.4, 4.1 Hz, 2H), 1.53-1.30 (m, 3H), 1.34 (d, J = 6.4 Hz, 3H), 1.04 (ddd, J = 16.3, 5.9, 3.8 Hz, 1H), 0.88-0.64 (m, 3H) | ¹³C NMR (151 MHz, CDCl₃) δ 172.49, 168.90, 162.41, 159.46, 159.25, 146.70, 142.55, 141.39, 134.32, 129.33, 126.48, 116.49, 116.09, 110.77, 109.83, 83.09, 82.98, 72.57, 71.41, 56.29, 51.37, 33.66, 28.21, 23.17, 20.75, 18.36, 18.08, 10.56 |
| F290 | White Solid | — | — | ESIMS m/z 545.5 ([M + H]⁺) | ¹H NMR (CDCl₃) δ 12.02 (d, J = 0.6 Hz, 1H), 8.50 (d, J = 8.1 Hz, 1H), 7.99 (d, J = 5.2 Hz, 1H), 6.87 (dd, J = 5.3, 0.6 Hz, 1H), 6.65-6.60 (m, 3H), 5.12 (dq, J = 9.5, 6.4 Hz, 1H), 5.00 (ddd, J = 7.7, 5.5, 2.1 Hz, 1H), 4.66 (ddd, J = 10.8, 8.2, 7.2 Hz, 1H), 4.50 (dd, J = 9.5, 7.7 Hz, 1H), 4.01-3.92 (m, 2H), 3.94 (s, 3H), 2.43 (dtd, J = 13.7, 7.1, 6.7, 2.0 Hz, 1H), 2.28 (s, 6H), 2.26-2.18 (m, 1H), 1.93-1.75 (m, 2H), 1.63-1.43 (m, 3H), 1.41 (d, J = 6.4 Hz, 3H), 1.30 (td, J = 6.8, 6.3, 3.4 Hz, | ¹³C NMR (CDCl₃) δ 171.75, 168.73, 159.07, 155.37, 154.41, 148.74, 140.59, 139.27, 130.29, 123.68, 114.01, 109.54, 80.79, 80.60, 72.57, 69.61, 56.09, 51.22, 33.18, 29.42, 21.89, 21.40, 18.37, 18.04, 10.03 |

TABLE 2-continued

Analytical Data for F Series Compounds

| *Cmpd. No. | *Phys. Apps. | *MP | *IR | *Mass. Spec. | *¹H NMR | *¹³C NMR; *¹⁹F NMR |
|---|---|---|---|---|---|---|
| F291 | Colorless Semi Solid | — | — | HRMS-ESI (m/z) [M]⁺ calcd for $C_{30}H_{38}N_2O_{10}$, 586.2532; found, 586.2526 | 1H), 0.84 (t, J = 7.4 Hz, 3H) ¹H NMR (CDCl₃) δ 8.56 (d, J = 8.4 Hz, 1H), 8.34 (d, J = 5.4 Hz, 1H), 7.01 (d, J = 5.5 Hz, 1H), 6.65-6.59 (m, 3H), 5.16-5.06 (m, 1H), 5.06-4.94 (m, 1H), 4.66 (ddd, J = 10.7, 8.3, 7.1 Hz, 1H), 4.53-4.43 (m, 1H), 3.95 (tdt, J = 4.9, 2.5, 1.0 Hz, 3H), 3.91 (s, 3H), 2.47-2.34 (m, 1H), 2.40 (s, 3H), 2.28 (d, J = 0.8 Hz, 6H), 2.24-2.15 (m, 1H), 1.83-1.75 (m, 1H), 1.59-1.50 (m, 2H), 1.39 (d, J = 6.4 Hz, 3H), 1.31-1.21 (m, 2H), 0.83 (t, J = 7.4 Hz, 3H) | ¹³C NMR (CDCl₃) δ 172.23, 168.89, 162.45, 159.45, 159.09, 154.42, 146.72, 141.28, 139.25, 137.52, 123.64, 114.03, 109.86, 80.86, 80.70, 72.31, 69.59, 56.30, 51.28, 33.46, 29.51, 21.88, 21.40, 20.75, 18.41, 18.02, 10.03 |
| F292 | White Solid | — | — | ESIMS m/z 398 ([M + H]⁺) | — | — |
| F293 | White Solid | — | — | ESIMS m/z 394 ([M + H]⁺) | — | — |
| F294 | White Solid | — | — | ESIMS m/z 362 ([M + H]⁺) | — | — |

*Cmpd. No. - Compound Number
*Phys. App. - Physical Appearance
*MP - Melting Point; ° C.
*IR - Infrared Spectroscopy; Thin Film; cm⁻¹
*¹H NMR were run at 400 MHz unless specified otherwise.
*¹³C NMR were run at 101 MHz unless specified otherwise.
*¹⁹F NMR were run at 376 MHz unless specified otherwise.

TABLE 3

Rating Scale for Results of Biological Evaluation

| Biology Rating Table (% Control) | Rating |
|---|---|
| 80-100 | A |
| More than 0-Less than 80 | B |
| Not Tested | C |
| ≤0 | D |

TABLE 4

Biological Activity - Disease Control in High Volume Applications (100 ppm)

| Compound Number | PUCCRT | | SEPTTR | |
|---|---|---|---|---|
| | 1DP | 3DC | 1DP | 3DC |
| F1 | C | C | C | C |
| F2 | C | C | C | C |
| F3 | C | C | C | C |
| F4 | C | C | C | C |
| F5 | C | C | C | C |
| F6 | C | C | C | C |
| F7 | C | C | C | C |
| F8 | C | C | C | C |
| F9 | C | C | C | C |
| F10 | C | C | C | C |
| F11 | C | C | C | C |
| F12 | C | C | C | C |
| F13 | C | C | C | C |
| F14 | A | A | D | A |
| F15 | A | A | A | A |
| F16 | A | A | A | A |
| F17 | A | A | A | A |
| F18 | A | A | A | A |
| F19 | A | A | A | A |
| F20 | A | A | A | A |
| F21 | A | A | B | B |
| F22 | A | A | A | A |
| F23 | A | A | A | A |
| F24 | A | A | A | A |
| F25 | A | A | A | A |
| F26 | A | A | A | A |
| F27 | A | A | A | A |
| F28 | A | A | A | A |
| F29 | A | A | A | A |

TABLE 4-continued

Biological Activity - Disease Control in High Volume Applications (100 ppm)

| Compound Number | PUCCRT | | SEPTTR | |
|---|---|---|---|---|
| | 1DP | 3DC | 1DP | 3DC |
| F30 | A | A | A | B |
| F31 | A | A | A | A |
| F32 | A | A | A | A |
| F33 | A | A | B | A |
| F34 | A | A | A | A |
| F35 | A | A | A | A |
| F36 | A | A | A | A |
| F37 | A | A | A | A |
| F38 | A | A | A | A |
| F39 | A | A | A | A |
| F40 | A | A | B | B |
| F41 | A | A | B | A |
| F42 | A | A | A | A |
| F43 | A | A | A | A |
| F44 | A | A | A | A |
| F45 | A | A | A | A |
| F46 | A | A | A | A |
| F47 | A | A | A | A |
| F48 | A | A | A | A |
| F49 | A | A | A | A |
| F50 | A | A | A | B |
| F51 | A | A | A | A |
| F52 | A | A | A | A |
| F53 | A | A | A | B |
| F54 | A | A | A | B |
| F55 | A | A | A | A |
| F56 | A | A | A | A |
| F57 | A | A | A | A |
| F58 | A | A | A | A |
| F59 | A | A | A | A |
| F60 | A | A | A | A |
| F61 | A | A | A | A |
| F62 | A | A | A | A |
| F63 | A | A | A | A |
| F64 | B | D | B | B |
| F65 | A | A | A | B |
| F66 | A | A | A | B |
| F67 | A | A | A | B |
| F68 | A | A | A | A |
| F69 | A | A | A | A |
| F70 | B | B | B | B |
| F71 | B | A | B | B |
| F72 | A | A | A | A |
| F73 | A | A | B | A |
| F74 | A | A | A | A |
| F75 | A | A | A | A |
| F76 | A | A | A | A |
| F77 | A | A | A | A |
| F78 | A | A | A | A |
| F79 | A | A | A | A |
| F80 | A | A | A | A |
| F81 | A | A | A | A |
| F82 | B | B | D | B |
| F83 | A | A | A | A |
| F84 | B | B | B | B |
| F85 | D | B | D | B |
| F86 | A | A | A | A |
| F87 | A | A | A | A |
| F88 | A | A | A | A |
| F89 | A | A | A | A |
| F90 | A | A | A | A |
| F91 | A | A | A | A |
| F92 | A | A | A | A |
| F93 | A | A | A | A |
| F94 | B | D | B | B |
| F95 | A | A | A | A |
| F96 | A | A | A | A |
| F97 | A | A | A | A |
| F98 | A | A | A | A |
| F99 | A | A | A | A |
| F100 | A | A | A | A |
| F101 | A | A | A | A |
| F102 | A | A | A | A |
| F103 | A | A | A | A |
| F104 | A | D | A | D |
| F105 | A | D | A | B |
| F106 | A | A | A | A |
| F107 | A | A | A | A |
| F108 | A | A | A | A |
| F109 | A | A | A | A |
| F110 | A | A | A | A |
| F111 | A | D | B | B |
| F112 | A | A | A | A |
| F113 | B | B | D | B |
| F114 | A | A | A | A |
| F115 | A | B | A | B |
| F116 | A | A | A | A |
| F117 | A | A | D | A |
| F118 | A | A | A | B |
| F119 | A | A | A | A |
| F120 | A | A | A | A |
| F121 | A | A | A | A |
| F122 | A | A | A | A |
| F123 | A | A | A | A |
| F124 | A | A | A | A |
| F125 | A | A | A | A |
| F126 | A | A | A | A |
| F127 | A | A | A | A |
| F128 | A | B | A | D |
| F129 | A | A | A | D |
| F130 | A | A | A | A |
| F131 | A | A | A | A |
| F132 | A | A | A | A |
| F133 | A | A | A | A |
| F134 | A | A | A | A |
| F135 | A | A | A | A |
| F136 | A | A | A | A |
| F137 | A | A | A | A |
| F138 | A | A | A | A |
| F139 | A | A | A | A |
| F140 | A | A | A | A |
| F141 | A | A | A | A |
| F142 | A | A | B | A |
| F143 | A | A | A | B |
| F144 | A | A | A | A |
| F145 | A | A | A | A |
| F146 | A | A | A | A |
| F147 | A | A | A | A |
| F148 | A | A | A | A |
| F149 | A | A | A | B |
| F150 | A | A | A | A |
| F151 | A | A | A | A |
| F152 | A | A | A | A |
| F153 | A | A | A | A |
| F154 | A | A | A | A |
| F155 | A | A | A | A |
| F156 | A | A | A | A |
| F157 | A | A | A | A |
| F158 | A | A | A | A |
| F159 | A | A | A | A |
| F160 | A | A | A | A |
| F161 | A | A | A | A |
| F162 | A | B | A | A |
| F163 | A | A | A | B |
| F164 | A | A | A | A |
| F165 | A | A | A | A |
| F166 | A | A | A | A |
| F167 | A | A | A | A |
| F168 | A | A | A | A |
| F169 | A | A | A | A |
| F170 | A | A | A | A |
| F171 | A | A | A | A |
| F172 | A | A | A | A |
| F173 | A | A | A | A |
| F174 | C | C | C | C |
| F175 | C | C | C | C |

TABLE 4-continued

Biological Activity - Disease Control in High Volume Applications (100 ppm)

| Compound Number | PUCCRT 1DP | PUCCRT 3DC | SEPTTR 1DP | SEPTTR 3DC |
|---|---|---|---|---|
| F176 | C | C | C | C |
| F177 | C | C | C | C |
| F178 | C | C | C | C |
| F179 | C | C | C | C |
| F180 | C | C | C | C |
| F181 | C | C | C | C |
| F182 | C | C | C | C |
| F183 | C | C | C | C |
| F184 | C | C | C | C |
| F185 | C | C | C | C |
| F186 | C | C | C | C |
| F187 | C | C | C | C |
| F188 | C | C | C | C |
| F189 | C | C | C | C |
| F190 | C | C | C | C |
| F191 | C | C | C | C |
| F192 | C | C | C | C |
| F193 | C | C | C | C |
| F194 | C | C | C | C |
| F195 | C | C | C | C |
| F196 | C | C | C | C |
| F197 | C | C | C | C |
| F198 | C | C | C | C |
| F199 | C | C | C | C |
| F200 | C | C | C | C |
| F201 | C | C | C | C |
| F202 | C | C | C | C |
| F203 | C | C | C | C |
| F204 | C | C | C | C |
| F205 | C | C | C | C |
| F206 | C | C | C | C |
| F207 | C | C | C | C |
| F208 | C | C | C | C |
| F209 | C | C | C | C |
| F210 | A | A | A | A |
| F211 | A | A | A | A |
| F212 | A | A | B | B |
| F213 | A | A | B | B |
| F214 | A | A | A | A |
| F215 | A | A | A | A |
| F216 | A | A | A | A |
| F217 | A | A | A | A |
| F218 | A | A | A | B |
| F219 | A | A | A | B |
| F220 | A | A | A | A |
| F221 | A | B | A | B |
| F222 | A | A | A | A |
| F223 | A | A | A | A |
| F224 | A | B | B | B |
| F225 | A | A | A | A |
| F226 | C | C | C | C |
| F227 | C | C | C | C |
| F228 | C | C | C | C |
| F229 | C | C | C | C |
| F230 | C | C | C | C |

PUCCRT - Wheat brown rust (*Puccinia triticina*)
SEPTTR - Wheat leaf blotch (*Septoria tritici*)
1DP - 1 Day Protectant
3DC - 3 Day Curative

TABLE 5

Biological Activity - Disease Control in High Volume (100 ppm) and Low Volume Applications ( TABLE 5-continued Biological Activity - Disease Control in High Volume
(100 ppm) and Low Volume Applications (121.5 g/H)

| Compound Number | PUCCRT* | | | | SEPTTR* | | | |
| --- | --- | --- | --- | --- | --- | --- | --- | --- |
| | 1 DP* Rate | | 3 DC* | | 1 DP* Rate | | 3 DC* | |
| | 121.5 g/H* | 100 ppm* | 121.5 g/H* | 100 ppm* | 121.5 g/H* | 100 ppm* | 121.5 g/H* | 100 ppm* |
| F245 | C | A | C | B | C | B | C | A |
| F246 | C | C | C | C | C | C | C | C |
| F247 | C | A | C | A | C | A | C | B |
| F248 | C | C | C | C | C | C | C | C |
| F249 | C | A | C | A | C | B | C | B |
| F250 | B | C | A | C | D | C | B | C |
| F251 | A | C | A | C | D | C | D | C |
| F252 | A | C | A | C | B | C | B | C |
| F253 | A | C | A | C | D | C | D | C |
| F254 | A | C | A | C | D | C | D | C |
| F255 | A | C | A | C | B | C | B | C |
| F256 | B | C | A | C | D | C | B | C |
| F257 | A | C | A | C | A | C | A | C |
| F258 | A | C | A | C | B | C | B | C |
| F259 | A | C | A | C | D | C | A | C |
| F260 | A | C | A | C | B | C | A | C |
| F261 | C | C | C | C | C | C | C | C |
| F262 | C | B | C | A | C | A | C | A |
| F263 | C | C | C | C | C | C | C | C |
| F264 | C | B | C | A | C | A | C | B |
| F265 | A | A | B | A | A | A | C | A |
| F266 | A | C | A | C | A | C | C | C |
| F267 | C | A | C | A | C | A | C | A |
| F268 | C | C | C | C | C | C | C | C |
| F269 | C | C | C | C | C | C | C | C |
| F270 | C | A | C | A | C | A | C | B |
| F271 | C | A | C | A | C | A | C | A |
| F272 | C | A | C | A | C | A | C | A |
| F273 | C | A | C | A | C | A | C | B |
| F274 | A | A | B | A | A | A | A | A |
| F275 | A | A | A | A | A | A | A | A |
| F276 | C | C | C | C | C | C | C | C |
| F277 | C | C | C | C | C | C | C | C |
| F278 | C | C | C | C | C | C | C | C |

TABLE 5-continued

Biological Activity - Disease Control in High Volume (100 ppm) and Low Volume Applications (121.5 g/H)

| | PUCCRT* | | | | SEPTTR* | | | |
|---|---|---|---|---|---|---|---|---|
| | 1 DP* Rate | | 3 DC* | | 1 DP* Rate | | 3 DC* | |
| Compound Number | 121.5 g/H* | 100 ppm* | 121.5 g/H* | 100 ppm* | 121.5 g/H* | 100 ppm* | 121.5 g/H* | 100 ppm* |
| F279 | C | C | C | C | C | C | C | C |
| F280 | C | A | C | B | C | A | C | A |
| F281 | C | A | C | B | C | B | C | B |
| F282 | A | A | A | A | A | A | A | A |
| F283 | C | A | C | B | C | A | C | B |
| F284 | A | A | A | A | A | A | A | A |
| F285 | A | A | A | B | A | A | A | A |
| F286 | A | A | B | A | A | A | A | A |
| F287 | A | A | A | A | A | A | A | A |
| F288 | C | A | C | A | C | A | C | A |
| F289 | A | A | A | A | A | A | A | A |
| F290 | C | A | C | A | C | B | C | B |
| F291 | C | A | C | B | C | A | C | A |
| F292 | C | C | C | C | C | C | C | C |
| F293 | C | C | C | C | C | C | C | C |
| F294 | C | C | C | C | C | C | C | C |

*PUCCRT - Wheat Brown Rust (*Puccinia triticina*)
*SEPTTR - Wheat Leaf Blotch (*Septoria tritici*)
*1 DP - 1 Day Protectant
*3 DC - 3 Day Curative
*g/H - Grams Per Hectare
*ppm - Parts Per Million

TABLE 6

Biological Activity - Disease Control in High Volume Applications (100 ppm)

| Cmpd. No. | ALTESO* | CERCBE* | COLLLA* 1 DP* | ERYSCI* | ERYSGH* | ERYSGT* |
|---|---|---|---|---|---|---|
| F20 | B | A | A | B | B | B |
| F26 | C | A | A | B | C | B |
| F28 | B | A | A | B | A | B |
| F29 | A | A | A | A | A | A |
| F30 | B | B | A | B | B | D |
| F31 | B | A | A | D | B | B |
| F34 | B | A | A | B | B | B |
| F35 | A | A | A | A | A | B |
| F36 | A | A | A | B | B | D |
| F37 | A | A | A | A | A | B |

TABLE 6-continued

Biological Activity - Disease Control in High Volume Applications (100 ppm)

| Cmpd. No. | ALTESO* | CERCBE* | COLLLA* 1 DP* | ERYSCI* | ERYSGH* | ERYSGT* |
|---|---|---|---|---|---|---|
| F38 | A | A | A | A | A | B |
| F39 | A | A | A | A | A | A |
| F78 | C | C | A | C | C | C |
| F130 | A | A | C | A | B | C |
| F132 | A | B | C | B | B | C |
| F134 | B | A | C | B | B | C |
| F138 | A | A | A | B | B | C |
| F139 | A | A | A | B | D | C |
| F140 | A | A | A | D | B | C |
| F141 | A | A | A | B | A | C |
| F154 | A | A | A | A | A | C |
| F155 | A | A | A | A | A | C |
| F165 | A | A | C | B | B | C |
| F166 | A | A | C | A | A | C |
| F169 | A | A | C | A | B | C |
| F170 | A | A | C | B | B | C |
| F171 | A | A | C | A | B | C |
| F172 | A | A | C | A | B | C |
| F173 | A | A | C | B | B | C |
| F217 | C | C | A | C | C | C |
| F237 | B | A | B | D | B | C |
| F241 | B | A | A | D | B | C |
| F242 | D | A | A | D | B | C |
| F250 | B | B | B | D | B | C |
| F251 | B | B | A | D | D | C |
| F252 | B | B | A | D | B | C |
| F253 | B | D | A | D | B | C |
| F254 | B | B | A | D | B | C |
| F255 | B | B | A | D | B | C |

ALTESO - Tomato Early Blight (*Alternaria solani*)
*CERCBE - Leaf Spot of Sugar Beets (*Cercospora beticola*)
*COLLLA - Cucumber Anthracnose (*Glomerella lagenarium*; Anamorph: *Colletotricum lagenarium*)
*ERYSCI - Powdery Mildew of Cucumber (*Erysiphe cichoracearum*)
*ERYSGH - Barley Powdery Mildew (*Blumeria graminis* f.sp. *hordei*; Synonym: *Erysiphe graminis* f.sp. *hordei*)
*ERYSGT - Wheat Powdery Mildew (*Blumeria graminis* f.sp. *tritici*; Synonym: *Erysiphe graminis* f.sp. *tritici*)
*1 DP - 1 Day Protectant

TABLE 7

Biological Activity - Disease Control in High Volume Applications (100 ppm)

| Cmpd. No. | LEPTNO* | PYRIOR* | RHYNSE* | UNCINE* | VENTIN* 1 DP* |
|---|---|---|---|---|---|
| F20 | A | A | A | B | B |
| F26 | A | C | C | B | C |
| F28 | B | A | A | B | A |
| F29 | A | A | C | A | A |
| F30 | A | A | C | B | A |
| F31 | A | A | C | B | C |
| F34 | C | A | C | B | C |
| F35 | C | A | C | A | C |
| F36 | C | A | C | B | C |
| F37 | C | A | C | A | C |
| F38 | C | A | C | A | C |
| F39 | A | A | A | B | A |
| F78 | C | C | C | C | C |
| F130 | C | A | A | B | C |
| F132 | C | B | B | B | C |
| F134 | C | A | A | B | C |
| F138 | C | A | A | B | C |
| F139 | C | A | A | B | C |
| F140 | C | A | A | B | C |
| F141 | A | A | A | B | B |
| F154 | C | A | A | B | C |
| F155 | C | A | B | B | C |
| F165 | C | A | A | B | C |
| F166 | C | A | A | B | C |
| F169 | C | A | A | B | C |
| F170 | C | A | A | B | C |
| F171 | C | A | A | B | C |
| F172 | C | A | A | B | C |
| F173 | C | A | A | B | C |
| F217 | C | C | C | C | C |
| F237 | C | A | D | B | A |
| F241 | C | A | B | B | B |
| F242 | C | A | D | B | B |
| F250 | A | A | B | B | A |
| F251 | A | A | B | B | D |
| F252 | A | A | A | B | B |
| F253 | A | A | B | B | A |
| F254 | A | A | A | B | A |
| F255 | A | A | A | A | A |

*LEPTNO - Wheat Glume Blotch (Leptosphaeria nodorum)
*PYRIOR - Rice Blast (Magnaporthe grisea; Anamorph: *Pyricularia oryzae*)
*RHYNSE - Barley Scald (*Rhyncosporium secalis*)
*UNCINE - Grape Powdery Mildew (*Uncinula necator*)
*VENTIN - Apple Scab (*Venturia inaequalis*)
*1 DP - 1 Day Protectant

TABLE 8

| Biological Activity - Disease Control in High Volume Applications (25 ppm) | | |
|---|---|---|
| Compound | PHAKPA* | |
| Number | 1DP* | 3DC* |
| F20 | A | A |
| F26 | A | A |
| F28 | A | B |
| F29 | A | C |
| F30 | A | B |
| F34 | A | A |
| F35 | A | C |
| F36 | A | A |
| F37 | A | C |
| F38 | A | A |
| F39 | A | A |
| F44 | A | C |
| F45 | A | A |
| F46 | A | C |
| F47 | D | C |
| F59 | A | C |
| F68 | A | C |
| F76 | A | C |
| F77 | A | C |
| F78 | A | A |
| F79 | A | C |
| F80 | A | A |
| F81 | A | C |
| F95 | A | A |
| F130 | A | B |
| F133 | A | B |
| F138 | A | A |
| F139 | A | A |
| F140 | A | A |
| F141 | A | A |
| F154 | A | A |
| F155 | A | A |
| F165 | A | B |
| F166 | A | A |
| F170 | A | B |
| F172 | A | A |
| F217 | A | C |
| F237 | A | D |
| F241 | A | B |
| F242 | A | B |
| F243 | A | B |
| F250 | B | D |
| F251 | A | B |
| F252 | A | B |
| F253 | B | D |
| F254 | A | B |
| F255 | A | B |

*PHAKPA - Asian Soybean Rust (*Phakopsora pachyrhizi*)
*1DP - 1 Day Protectant
*3DC - 3 Day Curative

What is claimed:

1. A compound of Formula I:

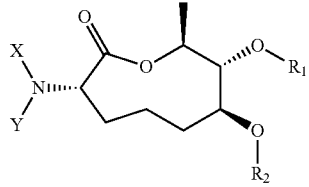

Formula I wherein:
X is H;
Y is Q;
Q is

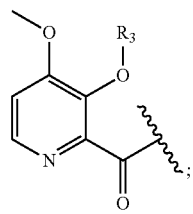

$R_1$ is H, alkyl, alkenyl, aryl, —C(O)$R_4$, each substituted with 0, 1 or multiple $R_4$;
$R_2$ is alkyl, alkenyl, aryl —C(O)$R_4$, each substituted with 0, 1 or multiple $R_4$;
$R_3$ is H, —C(O)$R_6$ or —CH$_2$OC(O)$R_6$;
$R_4$ is alkyl, alkenyl, halo, haloalkyl, alkoxy, or aryl;
$R_5$ is alkyl, alkoxy, benzyl, benzyloxy, each substituted with 0, 1, or multiple $R_7$, wherein each $R_7$ may be substituted with 0, 1, or multiple $R_4$;
$R_6$ is alkyl or alkoxy, each substituted with 0, 1, or multiple $R_4$; and
$R_7$ is alkyl, alkenyl, halo, haloalkyl, alkoxy, aryl, —Si($R_4$)$_3$, —C(O)$R_4$, —S(O)$_n$$R_4$, each substituted with 0, 1, or multiple $R_4$.

2. The compound according to claim 1 wherein $R_1$ is chosen from H, alkyl, alkenyl, aryl, or —C(O)$R_4$, each substituted with 0, 1, or multiple $R_4$, and
wherein $R_2$ is chosen from alkyl, alkenyl, aryl, or —C(O)$R_4$, each substituted with 0, 1, or multiple $R_4$.

3. The compound according to claim 1 wherein $R_1$ and $R_2$ are independently alkyl, alkenyl, aryl, or —C(O)$R_4$, each substituted with 0, 1, or multiple $R_4$.

4. A method for the treatment of plant disease, comprising the steps of:
applying a fungicidally effective amount of at least one of the compounds of claim 1 to at least one surface selected from the group consisting of: at least one surface of a plant, an area adjacent to a plant, soil in contact with a plant, soil adjacent to a plant, seeds, and equipment for use in agriculture.

5. The method of claim 4, wherein the fungicidally effective amount of the compound of Formula I is applied to a surface in the range of about 0.01 g/m$^2$ to about 0.45 g/m$^2$ of the compound of Formula I.

6. The compound of claim 1, wherein the compound is:

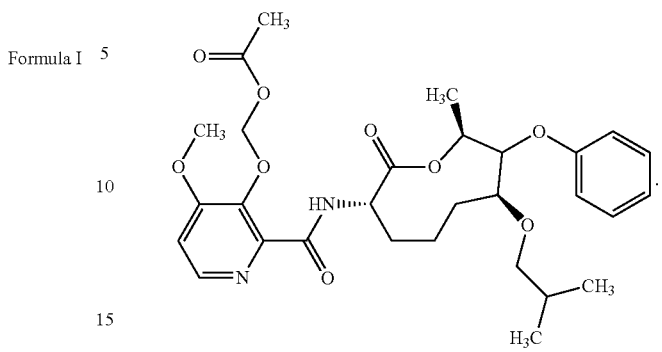

7. A method for the treatment of plant disease, comprising the steps of:
applying a fungicidally effective amount the compound of claim 6 to at least one surface selected from the group consisting of: at least one surface of a plant, an area adjacent to a plant, soil in contact with a plant, soil adjacent to a plant, seeds, and equipment for use in agriculture.

8. The method of claim 7, wherein the fungicidally effective amount of the compound of Formula I is applied to a surface in the range of about 0.01 g/m$^2$ to about 0.45 g/m$^2$ of the compound of Formula I.

9. A compound of Formula I:

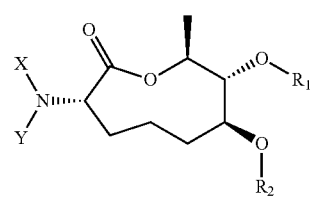

Formula I wherein:
X is H;
Y is Q;
Q is

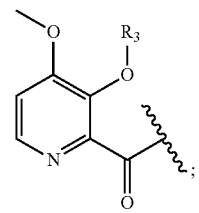

$R_1$ is alkyl, alkenyl, aryl, —C(O)$R_4$, each substituted with 0, 1 or multiple $R_4$;
$R_2$ is H, alkyl, alkenyl, aryl —C(O)$R_4$, each substituted with 0, 1 or multiple $R_4$;
$R_3$ is H, —C(O)$R_6$ or —CH$_2$OC(O)$R_6$;
$R_4$ is alkyl, alkenyl, halo, haloalkyl, alkoxy, or aryl;
$R_5$ is alkyl, alkoxy, benzyl, benzyloxy, each substituted with 0, 1, or multiple $R_7$, wherein each $R_7$ may be substituted with 0, 1, or multiple $R_4$;
$R_6$ is alkyl or alkoxy, each substituted with 0, 1, or multiple $R_4$; and $R_7$ is alkyl, alkenyl, halo, haloalkyl, alkoxy, aryl, —Si$(R_4)_3$, —C(O)$R_4$, —S(O)$_n R_4$, each substituted with 0, 1, or multiple $R_4$.

10. The compound according to claim 9 wherein $R_1$ is chosen from alkyl, alkenyl, aryl, or —C(O)$R_4$, each substituted with 0, 1, or multiple $R_4$, and wherein $R_2$ is chosen from H, alkyl, alkenyl, aryl, or —C(O)$R_4$, each substituted with 0, 1, or multiple $R_4$.

11. A method for the treatment of plant disease, comprising the steps of:
    applying a fungicidally effective amount of at least one of the compounds of claim 9 to at least one surface selected from the group consisting of: at least one surface of a plant, an area adjacent to a plant, soil in contact with a plant, soil adjacent to a plant, seeds, and equipment for use in agriculture.

12. The method of claim 11, wherein the fungicidally effective amount of the compound of Formula I is applied to a surface in the range of about 0.01 g/m$^2$ to about 0.45 g/m$^2$ of the compound of Formula I.

\* \* \* \* \*